US012171755B2

(12) United States Patent
Agarwal et al.

(10) Patent No.: US 12,171,755 B2
(45) Date of Patent: Dec. 24, 2024

(54) PAPD5 INHIBITORS AND METHODS OF USE THEREOF

(71) Applicants: Children's Medical Center Corporation, Boston, MA (US); The Brigham & Women's Hospital, Inc., Boston, MA (US)

(72) Inventors: Suneet Agarwal, Lexington, MA (US); Neha Nagpal, Boston, MA (US); Yick Fong, Cambridge, MA (US)

(73) Assignees: Children's Medical Center Corporation, Boston, MA (US); Brigham & Women's Hospital, Inc., Boston, MA (US)

( * ) Notice: Subject to any disclaimer, the term of this patent is extended or adjusted under 35 U.S.C. 154(b) by 0 days.

(21) Appl. No.: 16/758,804

(22) PCT Filed: Oct. 25, 2018

(86) PCT No.: PCT/US2018/057514
§ 371 (c)(1),
(2) Date: Apr. 23, 2020

(87) PCT Pub. No.: WO2019/084271
PCT Pub. Date: May 2, 2019

(65) Prior Publication Data
US 2021/0177827 A1 Jun. 17, 2021

Related U.S. Application Data

(60) Provisional application No. 62/727,380, filed on Sep. 5, 2018, provisional application No. 62/614,158, filed
(Continued)

(51) Int. Cl.
| | |
|---|---|
| *A61K 31/4706* | (2006.01) |
| *A61K 31/341* | (2006.01) |
| *A61K 31/353* | (2006.01) |
| *A61K 31/381* | (2006.01) |
| *A61K 31/4025* | (2006.01) |
| *A61K 31/404* | (2006.01) |
| *A61K 31/4162* | (2006.01) |
| *A61K 31/4178* | (2006.01) |
| *A61K 31/4188* | (2006.01) |
| *A61K 31/422* | (2006.01) |
| *A61K 31/4245* | (2006.01) |
| *A61K 31/428* | (2006.01) |
| *A61K 31/429* | (2006.01) |
| *A61K 31/433* | (2006.01) |
| *A61K 31/4365* | (2006.01) |
| *A61K 31/437* | (2006.01) |

(Continued)

(52) U.S. Cl.
CPC ........ *A61K 31/4706* (2013.01); *A61K 31/341* (2013.01); *A61K 31/353* (2013.01); *A61K 31/381* (2013.01); *A61K 31/4025* (2013.01); *A61K 31/404* (2013.01); *A61K 31/4162* (2013.01); *A61K 31/4178* (2013.01); *A61K 31/4188* (2013.01); *A61K 31/422* (2013.01); *A61K 31/4245* (2013.01); *A61K 31/428* (2013.01); *A61K 31/429* (2013.01); *A61K 31/433* (2013.01); *A61K 31/4365* (2013.01); *A61K 31/437* (2013.01); *A61K 31/4375* (2013.01); *A61K 31/47* (2013.01); *A61K 31/4709* (2013.01); *A61K 31/472* (2013.01); *A61K 31/473* (2013.01); *A61K 31/4741* (2013.01); *A61K 31/496* (2013.01); *A61K 31/498* (2013.01); *A61K 31/4985* (2013.01); *A61K 31/499* (2013.01); *A61K 31/502* (2013.01); *A61K 31/5025* (2013.01); *A61K 31/506* (2013.01); *A61K 31/517* (2013.01); *A61K 31/519* (2013.01); *A61K 31/52* (2013.01); *A61K 31/53* (2013.01); *A61K 31/5377* (2013.01); *A61K 31/538* (2013.01); *A61K 31/5415* (2013.01); *A61K 31/549* (2013.01); *A61K 31/55* (2013.01); *A61K 31/551* (2013.01); *C12Q 1/66* (2013.01); *G01N 2333/90241* (2013.01); *G01N 2333/91245* (2013.01)

(58) Field of Classification Search
CPC .. A61K 31/55; A61K 31/5377; A61K 31/538; A61K 31/502; A61K 31/4741; A61K 31/437; A61K 31/4375
See application file for complete search history.

(56) References Cited

U.S. PATENT DOCUMENTS

| | | | | | |
|---|---|---|---|---|---|
| 4,343,804 | A | * | 8/1982 | Munson, Jr. ......... | C07D 215/54 546/159 |
| 4,806,537 | A | * | 2/1989 | Roberts ................. | A61K 31/47 514/253.06 |

(Continued)

FOREIGN PATENT DOCUMENTS

| | | | | | |
|---|---|---|---|---|---|
| WO | WO-2007139496 | A1 | * | 12/2007 | ......... C07D 215/54 |
| WO | WO-2008119771 | A2 | * | 10/2008 | ......... C07D 215/54 |

(Continued)

OTHER PUBLICATIONS

Nagpal; Cell Stem Cell 2020, 26, 896-909. https://doi.org/10.1016/j.stem.2020.03.016 (Year: 2020).*
(Continued)

*Primary Examiner* — Daniel R Carcanague
(74) *Attorney, Agent, or Firm* — Fish & Richardson P.C.

(57) ABSTRACT

The disclosure relates to compounds that are, e.g., PAP Associated Domain Containing 5 (PAPD5) inhibitors and methods of use thereof.

16 Claims, 92 Drawing Sheets

Specification includes a Sequence Listing.

Related U.S. Application Data on Jan. 5, 2018, provisional application No. 62/608,327, filed on Dec. 20, 2017, provisional application No. 62/577,107, filed on Oct. 25, 2017.

(51) Int. Cl.

| | | |
|---|---|---|
| A61K 31/4375 | (2006.01) | |
| A61K 31/47 | (2006.01) | |
| A61K 31/4709 | (2006.01) | |
| A61K 31/472 | (2006.01) | |
| A61K 31/473 | (2006.01) | |
| A61K 31/4741 | (2006.01) | |
| A61K 31/496 | (2006.01) | |
| A61K 31/498 | (2006.01) | |
| A61K 31/4985 | (2006.01) | |
| A61K 31/499 | (2006.01) | |
| A61K 31/502 | (2006.01) | |
| A61K 31/5025 | (2006.01) | |
| A61K 31/506 | (2006.01) | |
| A61K 31/517 | (2006.01) | |
| A61K 31/519 | (2006.01) | |
| A61K 31/52 | (2006.01) | |
| A61K 31/53 | (2006.01) | |
| A61K 31/5377 | (2006.01) | |
| A61K 31/538 | (2006.01) | |
| A61K 31/5415 | (2006.01) | |
| A61K 31/549 | (2006.01) | |
| A61K 31/55 | (2006.01) | |
| A61K 31/551 | (2006.01) | |
| C12Q 1/66 | (2006.01) | |

(56) References Cited

U.S. PATENT DOCUMENTS

| | | | | |
|---|---|---|---|---|
| 4,806,549 A * | 2/1989 | Ife | ............ | A61P 1/04 |
| | | | | 546/159 |
| 5,143,920 A * | 9/1992 | Ife | ............ | C07D 215/54 |
| | | | | 546/159 |
| 5,304,121 A | 4/1994 | Sahatjian | | |
| 5,886,026 A | 3/1999 | Hunter et al. | | |
| 6,099,562 A | 8/2000 | Ding et al. | | |
| 6,503,713 B1 | 1/2003 | Rana | | |
| 6,797,692 B1 | 9/2004 | Ikonomidou | | |
| 6,803,031 B2 | 10/2004 | Rabinowitz et al. | | |
| 9,458,153 B2 | 10/2016 | Han et al. | | |
| 9,949,966 B2 | 4/2018 | Han et al. | | |
| 11,220,689 B2 * | 1/2022 | Agarwal | ............ | A61K 31/7052 |
| 2006/0189643 A1 | 8/2006 | Chen et al. | | |
| 2009/0221624 A1 * | 9/2009 | Olivo | ............ | A61K 31/4706 |
| | | | | 514/290 |
| 2009/0226422 A1 * | 9/2009 | Chaudhary | ............ | A61K 45/06 |
| | | | | 424/130.1 |
| 2009/0270450 A1 | 10/2009 | Dakin et al. | | |
| 2011/0053934 A1 * | 3/2011 | Angell | ............ | A61K 31/4353 |
| | | | | 546/160 |
| 2014/0045849 A1 | 2/2014 | McGowan et al. | | |
| 2016/0122344 A1 | 5/2016 | Han et al. | | |
| 2021/0330678 A1 * | 10/2021 | Agarwal | ............ | C12N 5/0636 |
| 2022/0274928 A1 * | 9/2022 | Agarwal | ............ | C07D 215/54 |

FOREIGN PATENT DOCUMENTS

| | | | |
|---|---|---|---|
| WO | WO 2013/103317 | 7/2013 | |
| WO | WO 2015113990 | 8/2015 | |
| WO | WO 2015173164 | 11/2015 | |
| WO | WO 2016107832 | 7/2016 | |
| WO | WO 2016128335 | 8/2016 | |
| WO | WO 2016177655 | 11/2016 | |
| WO | WO 2017017042 | 2/2017 | |
| WO | WO 2017/066712 | 4/2017 | |
| WO | WO 2017066796 | 4/2017 | |
| WO | WO-2017198756 A1 * | 11/2017 | |
| WO | WO 2017216391 | 12/2017 | |
| WO | WO 2018154466 | 8/2018 | |
| WO | WO-2020219729 A1 * | 10/2020 | ........... C07D 215/42 |
| WO | WO-2023086220 A2 * | 5/2023 | |

OTHER PUBLICATIONS

Nagpal; Blood 2018, 132, Suppl. 1 647. https://doi.org/10.1182/blood-2018-99-118800 (Year: 2018).*
Zhang; J Gastrointest Canc 2007, 38, 38-45. https://doi.org/10.1007/s12029-008-9015-1 (Year: 2007).*
Ife; Journal of Medicinal Chemistry 1992, 35, 3413-3422. https://doi.org/10.1021/jm00096a018 (Year: 1992).*
Liu; Molecules 2016, 21, 21. https://doi.org/10.3390/molecules21010021 (Year: 2016).*
EP Extended Search Report in European Appln. No. 18870786.3, dated Feb. 9, 2021, 15 pages.
Ahmadian et al., "Single nucleotide polymorphism analysis by pyrosequencing," Anal. Biochem., 2000, 280:103-110.
Balatsos et al., "Competitive inhibition of human poly (A)-specific ribonuclease (PARN) by synthetic fluoro-pyranosyl nucleosides," Biochemistry, 2009, 48(26):6044-6051.
Balatsos et al., "Inhibition of human poly (A)-specific ribonuclease (PARN) by purine nucleotides: kinetic analysis," Journal of Enzyme Inhibition and Medicinal Chemistry, 2009, 24(2):516-523.
Balatsos et al., "Kinetic and in silico analysis of the slow-binding inhibition of human poly (A)-specific ribonuclease (PARN) by novel nucleoside analogues," Biochimie, 2012, 94(1):214-221.
Balatsos et al., "Modulation of poly (A)-specific ribonuclease (PARN): current knowledge and perspectives," Curr. Med. Chem., 2012, 19(28):4838-4849.
Belloni et al. "IFN-α Inhibits HBV Transcription and Replication in Cell Culture and in Humanized Mice by Targeting the Epigenetic Regulation of the Nuclear cccDNA Minichromosome," J. Clin. Invest., 2012, 122:529-537.
Bernard and Wittwer, "Real-time PCR Technology for Cancer Diagnostics," Clin. Chem., 2002, 48(8):1178-1185.
Bianchi et al., "A Serum Circulating miRNA Diagnostic Test to Identify Asymptomatic High-Risk Individuals With Early Stage Lung Cancer," EMBO Mol. Med., 2011, 3:495-503.
Blackburn et al., "Human telomere biology: A contributory and interactive factor in aging, disease risks, and protection," Science, 2015, 350(6265):1193-1198.
Boitano et al., "Aryl Hydrocarbon Receptor Antagonists Promote the Expansion of Human Hematopoietic Stem Cells," Science, 2010, 329:1345-1348.
Buster et al., "Peginterferon alpha-2b is Safe and Effective in HBeAg-positive Chronic Hepatitis B Patients With Advanced Fibrosis," Hepatology, 2007, 46:388-394.
Chen et al., "Chain termination and inhibition of mammalian poly (A) polymerase by modified ATP analogues." Biochemical Pharmacology, 2010, 79(5):669-677.
Childs et al., "Cellular senescence in aging and age-related disease: from mechanisms to therapy," Nature Medicine, 2015, 21(12):1424-1435.
Codd et al., "Identification of seven loci affecting mean telomere length and their association with disease," Nature Genetics, 2013, 45(4):422-427.
Czarnik, "Encoding Methods for Combinatorial Chemistry," Curr. Opin. Chem. Bio., 1997, 1:60-66.
Diehl et al., "BEAMing: single-molecule PCR on microparticles in water-in-oil emulsions," Nat. Methods, 2006, 3:551-559.
Ekins and Chu, "Microarrays: Their Origins and Applications," Trends in Biotechnology, 1999. 17:217-218.
Fares et al., "Cord Blood Expansion. Pyrimidoindole Derivatives are Agonists of Human Hematopoietic Stem Cell Self-Renewal," Science, 2015, 345:1509-1512.
Fisicaro et al. "Antiviral Intrahepatic T-cell Responses Can Be Restored by Blocking Programmed death-1 Pathway in Chronic Hepatitis B," Gastroenterology, 2010, 138: 682-693.

(56) References Cited

OTHER PUBLICATIONS

Haycock et al., "Leucocyte telomere length and risk of cardiovascular disease: systematic review and meta-analysis," BMJ, 2014, 349:g4227.
Illum, "Is Nose-To-Brain Transport of Drugs in Man a Reality?," J. Pharm, Pharmacol., 2004, 56:3-17.
Illum, "Transport of Drugs From the Nasal Cavity to the Central Nervous System," Eur. J. Pharm. Sci., 2000, 11:1-18.
Janssen et al., "Pegylated Interferon alfa-2b Alone or in Combination With Lamivudine for HBeAg-positive Chronic Hepatitis B: A Randomised Trial," Lancet, 2005, 365:123-129.
Kim et al., "Exosome Cofactors Connect Transcription Termination to RNA Processing by Guiding Terminated Transcripts to the Appropriate Exonuclease within the Nuclear Exosome," Journal of Biological Chemistry, 2016, 291(25):13229-13242.
Kiss et al., "Box H/ACA small ribonucleoproteins," Mol Cell., 2010, 37:597-606.
Kondo et al., "Hepatitis B Surface Antigen Could Contribute to the Immunopathogenesis of Hepatitis B Virus Infection," ISRN Gastroenterology, 2013, Article ID 935295.
Kondo et al., "Recovery of functional cytotoxic T lymphocytes during lamivudine therapy by acquiring multi-specificity," Journal of Medical Virology, 2004, 74:425-433.
Korner and Wahle, "Poly(A) tail shortening by a mammalian poly(A)-specific 3' exoribonuclease," J. Biol. Chem., 1997, 272:10448-10456.
Kumar et al. "Hepatitis B Virus Regulatory HBx Protein Binds to Adaptor Protein IPS-1 and Inhibits the Activation of Beta Interferon," J. Virol., 2011, 85:987-995.
Lambert et al., "Posttranslational N-glycosylation of the hepatitis B virus large envelope protein," Virology Journal, Dec. 1, 2007, 4(1):45.
Lardelli et al., "Biallelic mutations in the 3' exonuclease TOEI cause pontocerebellar hypoplasia and uncover a role in snRNA processing," Nature Genetics, Mar. 2017, 49(3):457-64.
Locarnini, "Molecular virology and the development of resistant mutants: implications for therapy," Seminars in Liver Disease, Feb. 2005, 25(S1): 9-19.
MacBeath et al., "Printing proteins as microarrays for high-throughput function determination," Science, Sep. 8, 2000, 289(5485):1760-3.
Mao et al., "Indoleamine 2, 3-dioxygenase mediates the antiviral effect of gamma interferon against hepatitis B virus in human hepatocyte-derived cells," Journal of Virology, Jan. 15, 2011, 85(2):1048-57.
Mao et al., "Inhibition of hepatitis B virus replication by the host zinc finger antiviral protein," PLoS Pathog, Jul. 11, 2013, 9(7), 19 pages.
Marcellin et al., "Peginterferon alfa-2a alone, lamivudine alone, and the two in combination in patients with HBeAg-negative chronic hepatitis B," New England Journal of Medicine, Sep. 16, 2004, 351(12):1206-17.
Miranda et al., "Nucleic acids within urinary exosomes/microvesicles are potential biomarkers for renal disease," Kidney International, Jul. 2, 2010, 78(2):191-9.
Mitchell et al., "A telomerase component is defective in the human disease dyskeratosis congenita," Nature, Dec. 1999, 402(6761):551-5.
Mueller et al., "A novel orally available small molecule that inhibits hepatitis B virus expression," Journal of Hepatology, Mar. 1, 2018, 68(3):412-20.
Nayersina et al., "HLA A2 restricted cytotoxic T lymphocyte responses to multiple hepatitis B surface antigen epitopes during hepatitis B virus infection," J. Immunol., 1993, 150:4659-4671.
Nordström et al., "Direct analysis of single-nucleotide polymorphism on double-stranded DNA by pyrosequencing," Biotechnology and Applied Biochemistry, Apr. 2000, 31(2):107-12.
Op den Brouw et al., "Hepatitis B virus surface antigen impairs myeloid dendritic cell function: a possible immune escape mechanism of hepatitis B virus," Immunology, Feb. 2009, 126(2):280-9.

PCT International Preliminary Report on Patentability in PCT Appln. No. PCT/US2018/057514, dated Apr. 28, 2020, 7 pages.
PCT International Search Report and Written Opinion in PCT Appln. No. PCT/US2018/057514, dated Mar. 18, 2019, 11 pages.
Quasdorff et al., Control of hepatitis B virus at the level of transcription,: Journal of Viral Hepatitis, Aug. 2010; 17(8):527-36.
Ren et al., "Inhibition of Klenow DNA polymerase and poly (A)-specific ribonuclease by aminoglycosides," RNA, Nov. 2002, 8(11):1393-400.
Schulze et al., "Hepatitis B virus infection initiates with a large surface protein-dependent binding to heparan sulfate proteoglycans," Hepatology, Dec. 2007, 46(6):1759-68.
Shi et al., "Hepatitis B virus suppresses the functional interaction between natural killer cells and plasmacytoid dendritic cells," Journal of Viral Hepatitis. Feb. 2012. 19(2):e26-33.
Son et al., "PARN and TOE1 constitute a 3' end maturation module for nuclear non-coding RNAs." Cell Reports, Apr. 17, 2018, 23(3):888-98.
Taylor et al., "The origin, function, and diagnostic potential of RNA within extracellular vesicles present in human biological fluids," Frontiers in Genetics, Jul. 30, 2013, 4:142, 12 pages.
Thuresson et al., "Inhibition of poly (A) polymerase by aminoglycosides," Biochimie, Oct. 1, 2007, 89(10):1221-7.
Venteicher et al. "A human telomerase holoenzyme protein required for Cajal body localization and telomere synthesis," Science, 2009, 323:644-8.
Vulliamy et al., "Mutations in the telomerase component NHP2 cause the premature ageing syndrome dyskeratosis congenita," Proceedings of the National Academy of Sciences, Jun. 10, 2008, 105(23):8073-8.
Walne et al., "Genetic heterogeneity in autosomal recessive dyskeratosis congenita with one subtype due to mutations in the telomerase-associated protein NOP10," Human Molecular Genetics, Jul. 1, 2007, 16(13):1619-29.
Wieland et al., "Stealth and cunning: hepatitis B and hepatitis C viruses," Journal of Virology, Aug. 1, 2005, 79(15):9369-80.
Woltman et al., "Hepatitis B virus lacks immune activating capacity, but actively inhibits plasmacytoid dendritic cell function," PloS one, Jan. 5, 2011, 6(1), 12 pages.
Yan et al., "Molecular determinants of hepatitis B and D virus entry restriction in mouse sodium taurocholate cotransporting polypeptide," Journal of Virology, Jul. 15, 2013, 87(14):7977-91.
Yang et al., "Detection of tumor cell-specific mRNA and protein in exosome-like microvesicles from blood and saliva," PloS one, Nov. 14, 2014, 9(11), 10 pages.
Zban, Yiqiang, et al. "Telomere length shortening and Alzheimer disease—a Mendelian Randomization Study," JAMA neurology 72.10 (2015): 1202-1203.
Zhao et al., "Association between telomere length and type 2 diabetes mellitus: a meta-analysis," PloS one, Nov. 21, 2013, 8(11):e79993.
Zhou et al., "HBsAg mRNA degradation induced by a dihydroquinolizinone compound depends on the HBV post-transcriptional regulatory element," Antiviral Research, Jan. 1, 2018, 149:191-201.
Boyraz et al., "Posttranscriptional manipulation of TERC reverses molecular hallmarks of telomere disease," The Journal of Clinical Investigation, Sep. 1, 2016, 126(9):3377-82.
Carneiro et al., "Bosutinib therapy ameliorates lung inflammation and fibrosis in experimental silicosis," Frontiers in Physiology, Mar. 15, 2017, 8:159.
Castillo-González et al., "Prediction of telomerase inhibitory activity for acridinic derivatives based on chemical structure," European Journal of Medicinal Chemistry, Dec. 1, 2009, 44(12):4826-40.
EP European Search Report in European Appln. No. 18870786.3, dated Nov. 9, 2020, 18 pages.
Gómez et al., "Discovery of ligands for a novel target, the human telomerase RNA, based on flexible-target virtual screening and NMR," Journal of Medicinal Chemistry, Nov. 27, 2008, 51(22):7205-15.

(56) References Cited

OTHER PUBLICATIONS

Office Action in European Appln. No. 18870786.3, mailed on Mar. 31, 2023, 4 pages.

\* cited by examiner

| Chemical Structure | Cluster | Library | Vendor | Vendor_Reagent_ID | SMILES | InChi | Molecular Weight | PubChem_CID | Chemical_Name | Fold_Change 100μM compound | Fold_Change 33μM compound |
|---|---|---|---|---|---|---|---|---|---|---|---|
|  | 1 | ChemDiv Targeted Diversity Library | ChemDiv | E228-3001 | n1(c(ccc(c2)Br)c2N(C3=O)CCCC(=O)N4CCCC4)c3ccc1 | InChI=1S/C19H20BrN3O2/c1-20-14-7-8-15-17(13-14)23(19(25)16-5-3-11-22(15)16)12-4-6-18(24)21-9-1-2-10-21/h3,5,7-8,11,13H,1-2,4,6,9-10,12H2 | 402.290000000 | 46272920 | 7-bromo-5-(4-oxo-4-pyrrolidin-1-ylbutyl)pyrrolo[1,2-a]quinoxalin-4-one | 1.393369159 | 1.230490654 |
|  | 1 | ChemDiv6 | ChemDiv | E228-1232 | n1(c2c(cccc2)N(C3=O)CCCCC)c3ccc1 | InChI=1/C21H27N3O2/c1-3-5-14-22(4-2)20(25)13-9-16-24-18-11-7-6-10-17(18)23-15-8-12-19(23)21(24)26/h6-8,10-12,15H,3-5,9,13-14,16H2,1-2H3 | 353.457980000 | 16018098 | N-butyl-N-ethyl-4-(4-oxopyrrolo[1,2-a]quinoxalin-5-yl)butanamide | 1.229492119 | 1.083441184 |
|  | 1 | ChemDiv6 | ChemDiv | E228-1001 | N(CCC(=O)Nc1ccc(cc1OC)OC)(c(ccc2)c2)3c(ccc3)C(=O)c3ccc4 | InChI=1/C22H21N3O4/c1-28-15-9-10-16(20(14-15)29-2)23-21(26)11-13-25-18-7-4-3-6-17(18)24-12-5-8-19(24)22(25)27/h3-10,12,14H,11,13H2,1-2H3,(H,23,26) | 391.419840000 | 16018058 | N-(2,4-dimethoxyphenyl)-3-(4-oxopyrrolo[1,2-a]quinoxalin-5-yl)propanamide | 1.238348870 | 1.122059476 |
|  | 1 | ChemDiv6 | ChemDiv | C799-0379 | N1(CCC(O)=O)c2c(cccn2)n3c(ccc3)C1=O | InChI=1S/C13H11N3O3/c17-11(18)5-8-16-12-9(3-1-6-14-12)15-7-2-4-10(15)13(16)19/h1-4,6-7H,5,8H2,(H,17,18) | 257.244740000 | 16011752 | 3-(7-Oxo-2,8,10-triazatricyclo[7.4.0.0²,⁸]trideca-1(13),3,5,9,11-pentaen-8-yl)propionic acid | 1.388671630 | 1.161978050 |
|  | 1 | ChemDiv Targeted Diversity Library | ChemDiv | C200-7014 | C1(=NNC2=S)N2c(c3C(=O)N1CCCC)ccs3 | InChI=1S/C11H12N4OS2/c1-2-3-5-14-9(16)8-7(4-6-18-8)15-10(14)12-13-11(15)17/h4,6H,2-3,5H2,1H3,(H,13,17) | 280.370000000 | 46507135 | 4-butyl-1-thioxo-2,4-dihydrothieno[2,3-e][1,2,4]triazolo[4,3-a]pyrimidin-5(1H)-one | 1.531008935 | 1.172582619 |

FIG. 9

| | | | | | | | |
|---|---|---|---|---|---|---|---|
| ![structure] | 1 | ChemDiv Targeted Diversity Library | ChemDiv | C200-8090 | C1(=NNC2=S)N2c3c(cc(oc3)F)C(=O)N1CCC | InChI=1S/C12H11FN4OS/c1-2-5-16-10(18)8-6-7(13)3-49(8)17-11(16)14-15-12(17)19/h3-4,6H,2,5H2,1H3,(H,15,19) | 278.310000000 | 50743203 | 7-fluoro-4-propyl-1-thioxo-2,4-dihydro[1,2,4]triazolo[4,3-a]quinazolin-5(1H)-one | 1.25561449 | 1.099424444 |
| ![structure] | 1 | ChemDiv Targeted Diversity Library | ChemDiv | L150-1099 | c12c(C(N(C)C(=O)N1C)nc(SCCC(O)=O)n2Cc(cc3)cc3F | InChI=1S/C17H17FN4O4S/c1-20-14-13(15(25)21(2)17(20)26)19-16(27-8-7-12(23)24)22(14)9-10-3-5-11(18)6-4-10/h3-6H,7-9H2,1-2H3,(H,23,24) | 392.410000000 | 45032920 | 3-[[9-(4-fluorobenzyl)-1,3-dimethyl-2,6-dioxo-2,3,6,9-tetrahydro-1H-purin-8-yl]sulfanyl]propanoic acid | 1.25999736 | 1.04975584 |
| ![structure] | 1 | ChemDiv Targeted Diversity Library | ChemDiv | C200-9508 | C1(N(CCCC2C(=O)C2)=Nc(ccs3)c3C(=O)N1c4ccc(ccc4)C | InChI=1S/C19H19N3O3S/c1-12-4-6-14(7-5-12)22-17(23)16-15(8-10-26-16)20-19(22)21-9-2-3-13(11-21)18(24)25/h4-8,10,13H,2-3,9,11H2,1H3,(H,24,25) | 369.450000000 | 50743396 | 1-[3-(4-methylphenyl)-4-oxo-3,4-dihydrothieno[3,2-d]pyrimidin-2-yl]piperidine-3-carboxylic acid | 1.63116037 | 1.207040417 |
| ![structure] | 1 | ChemDiv Targeted Diversity Library | ChemDiv | F201-0117 | N1(Cc(cc(c2)C)c2C(ccn2)c3c(F)cc(F)cc3 | InChI=1S/C13H8FN2O/c14-9-1-2-11(15)12(5-9)17-7-8-3-4-16-6-10(8)13(17)18/h1-6H,7H2 | 246.220000000 | 20930726 | 2-(2,5-difluorophenyl)-1H-pyrrolo[3,4-c]pyridin-3-one | 1.79852223 | 1.076527246 |
| ![structure] | 1 | ChemDiv6 | ChemDiv | E524-1615 | N1(Cc(ccc2)ccc2C(NCCN(CC)CC)=O)c3c(ccn3)n4c(ccc4)C1=O | InChI=1/C24H27N5O2/c1-3-27(4-2)16-14-26-23(30)19-11-9-18(10-12-19)17-29-22-20(7-5-13-25-22)28-15-6-8-21(28)24(29)31/h5-13,15H,3-4,14,16-17H2,1-2H3,(H,26,30) | 417.503470000 | 16018995 | $p$-{[2-(Diethylamino)ethylamino]carbonyl}phenyl}methyl]-2.8.10-triazatricyclo[7.4.0.0$^{2,6}$]trideca-1(13),3,5,9,11-pentaen-7-one | 1.22342911 | 1.115977575 |

FIG. 9 (continued)

| | | | | | | | | |
|---|---|---|---|---|---|---|---|---|
| | ChemDiv Targeted Diversity Library | ChemDiv | C798-1439 | c1(C2=O)n(c3c(cc3)N2Cc(cc4)cc o4C)nc(C(O)=O)n1 | InChI=1S/C18H13ClN4O3/c 1-10-2-7-13-14(8-10)22(9-11)17(24)16-20-15(18(25)26)21-23(13)16/h2-8H,9H2,1H3,(H,25,26) | 368.780000 | 46261177 | 5-(4-chlorobenzyl)-7-methyl-4-oxo-4,5-dihydro[1,2,4]triazolo[1,5-a]quinoxaline-2-carboxylic acid | 1.57927557 | 1.198752819 |
| | ChemDiv Targeted Diversity Library | ChemDiv | P056-0011 | c(C1)(c2)c(CCN1C(C)=O)sc2C(NCCC N3CCCC3=O)=O | InChI=1S/C17H23N3O3S/c 1-12(21)20-9-5-14-13(11-20)10-15(24-14)17(23)18-6-3-8-19-7-2-4-16(19)22/h10H,2-9,11H2,1H3,(H,18,23) | 349.460000 | 53158788 | 5-acetyl-N-{3-(2-oxopyrrolidin-1-yl)propyl]-6,7-dihydro-4H-thieno[3,2-c]pyridine-2-carboxamide | 1.49529675 | 1.041881299 |
| | ChemDiv Targeted Diversity Library | ChemDiv | C797-1259 | c1(C2=O)n(c3c(cc3)F)c1)C(=NN2C C(O)=O)C | InChI=1/C13H10FN3O3/c1-7-15-16(6-12(18)19)13(20)11-5-8-4-9(14)2-3-10(8)17(7)11/h2-5H,6H2,1H3,(H,18,19) | 275.235200 | 16011324 | 2-(8-fluoro-4-methyl-1-oxo-[1,2,4]triazino[4,5-a]indol-2-yl)acetic acid | 1.212599935 | 1.117578308 |
| | ChemDiv Targeted Diversity Library | ChemDiv | M130-0504 | c1(ncnc(c2cccc2 Cp1)N(CC3)CCN3 C(=O)COc(cc4)ccc 4Cl | InChI=1S/C23H23ClN4O2/c 1-17-4-2-3-5-20(17)21-14-22(26-16-25-21)27-10-12-28(13-11-27)23(29)15-30-19-8-6-18(24)7-9-19/h2-9,14,16H,10-13,15H2,1H3 | 422.920000 | 50840967 | 2-(4-chlorophenoxy)-1-[4-[6-(2-methylphenyl)pyrimidin-4-yl]piperazin-1-yl]ethanone | 1.33745739 | 1.089761394 |
| | ChemDiv6 | ChemDiv | E512-0832 | c1(c(CCc(cn(CC(=O)NCc2ccccc2Br)n 3)c13)oc4C(=O)N5 CCCC5)o4C | InChI=1/C24H25BrN4O3/c1-497.384290 15-21-19(32-23(15)24(31)28-10-4-5-11-28)9-8-17-13-29(27-22(17)21)14-20(30)26-12-16-6-2-3-7-18(16)25/h2-9,6-7,13H,4-5,8-12,14H2,1H3,(H,26,30) | 497.384290 | 16018772 | N-[(2-bromophenyl)methyl]-2-[8-methyl-7-(pyrrolidine-1-carbonyl)-4,5-dihydrofuro[2,3-g]indazol-2-yl]acetamide | 1.61646034 | 1.295965154 |

FIG. 9 (continued)

| | | | | | | | |
|---|---|---|---|---|---|---|---|
| 1 | ChemDiv Targeted Diversity Library | ChemDiv | J015-0050 | n(cnn1)(c1)c2cccc(n2)C(=O)Nc(cc3)ccc3N(CC4)CCN4C(=O)c5cccc5F | InChI=1S/C25H22FN7O2/c26-21-5-2-1-4-20(21)25(35)32-14-12-31(13-15-32)19-10-8-18(9-11-19)29-24(34)22-6-3-7-23(30-22)33-16-27-28-17-33/h1-11,16-17H,12-15H2,(H,29,34) | 471.500000000 | 225586987 | N-{4-[4-(2-fluorobenzoyl)piperazin-1-yl]phenyl}-6-(4H-1,2,4-triazol-4-yl)pyridine-2-carboxamide | 1.32659588 | 1.161187156 |
| 1 | ChemDiv Targeted Diversity Library | ChemDiv | L150-1125 | c12c(C(N(C)C(=O)N1C)=O)nc(SCC(O)=O)n2CC | InChI=1S/C11H14N4O4S/c1-4-15-8-7(12-10(15)20-5-6(16)17)9(18)14(3)11(19)13(8)2/h4-5H2,1-3H3,(H,16,17) | 298.320000000 | 45032950 | 2-(9-ethyl-1,3-dimethyl-2,6-dioxopurin-8-yl)sulfanylacetic acid | 1.41880109 | 1.142234332 |
| 1 | ChemDiv Targeted Diversity Library | ChemDiv | L150-1127 | c12c(C(N(C)C(=O)N1C)=O)nc(SCC(O)=O)n2CCc3cccccc3 | InChI=1S/C17H18N4O4S/c1-19-14-13(15(24)20(2)17(19)25)18-16(26-10-12(22)23)21(14)9-8-11-6-4-3-5-7-11/h3-7H,8-10H2,1-2H3,(H,22,23) | 374.420000000 | 45032952 | 2-[1,3-dimethyl-2,6-dioxo-9-(2-phenylethyl)purin-8-yl]sulfanylacetic acid | 1.44686757 | 1.163891092 |
| 1 | ChemDiv Targeted Diversity Library | ChemDiv | Z250-2455 | c12c(scc1c3ccccc3)C(NC(N(CCCC4C(O)=O)C4)=N2)=O | InChI=1S/C18H17N3O3S/c22-16-15-14(13(10-25-15)11-5-2-1-3-6-11)19-18(20-16)21-8-4-7-12(9-21)17(23)24/h1-3,5-6,10,12H,4,7-9H2,(H,23,24)(H,19,20,22) | 355.420000000 | 49668129 | 1-(4-oxo-7-phenyl-3,4-dihydrothieno[3,2-d]pyrimidin-2-yl)piperidine-3-carboxylic acid | 1.5265748 | 1.18996063 |
| 1 | ChemDiv6 | ChemDiv | E942-0223 | N1(CC(C)C)C(=C(NC(=O)NCc(oc2)ccc2Cl)c(c3C1=O)ccc3 | InChI=1/C21H22ClN3O3/c1-14(2)12-25-13-19-6-18(17)20(25)21(27)23-11-15-16(22)10-8-15/h | 383.871280000 | 16023490 | 1-[(4-chlorophenyl)methyl]-3-[2-(2-methylpropyl)-1-oxoisoquinolin-4-yl]urea | 1.36396724 | 1.075523203 |

FIG. 9 (continued)

| | | | | | | | | |
|---|---|---|---|---|---|---|---|---|
| 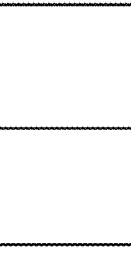 | 1 | NIH Clinical Collection 1 - 2014 | Sequoia Research Products Ltd. | SAM001246686 | NC1CCN(C1)c2nc3n(ccc(C(=O)c(=O))c3cc2F)c4ccc(F)cc4F.Cc1ccc(cc1)S(=O)(=O)O | InChI=1S/C19H15F3N4O3.C7H8O3S/c20-9-1-2-15(13)21)5-9)26-8-14(22)18(24-17(11)26)25-4-3-10(23)7-25;1-6-2-4-7(5-3-6)11(8,9)10/h1-2,5-6,8,10H,3-4,7,23H2;(H,28,29);2- | 576.544220000 | 93858 | TOSUFLOXACIN TOSYLATE | 1.41015801 | 1.297629797 |
| 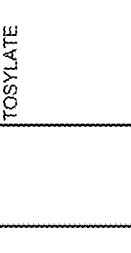 | 1 | ChemDiv Targeted Diversity Library | ChemDiv | L150-1097 | c12c(C(N(C(=O)N1C)=O)nc(SCC(O)=O)n2Cc3ccccc3 | InChI=1S/C16H16N4O4S/c1-18-13-12(14(23)19(2)16(18)24)17-15(25-9-11(21)22)20(13)8-10-6-4-3-5-7-10/h3-7H,8-9H2,1-2H3,(H,21,22) | 360.390000000 | 45032956 | 2-(9-benzyl-1,3-dimethyl-2,6-dioxopurin-8-yl)sulfanylacetic acid | 1.55048774 | 1.163854469 |
| 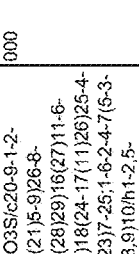 | 1 | Biomol 4 - FDA Approved Drug Library | BIOMOL | DL-453 | c(N1C=C(C(=O)O)C2=O)(c2ccc(F)c3N4CCC(O)CC4)c3CC1C | InChI=1S/C19H21FN2O4/c1-10-2-3-12-16-13(18(24)14(19(25)26)9-22(10)16)8-15(20)17(12)21-6-4-11(23)5-7-21/h8-11,23H,2-7H2,1H3,(H,25,26) | 360.379440000 | 4410 | Nadifloxacin | 1.34035874 | 1.105156951 |
| 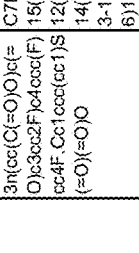 | 1 | ChemDiv Targeted Diversity Library | ChemDiv | C367-0001 | C1(N(C=CC=C1C(O)=O)C2=O)=Nc3c2c4c(CCCC4)s3 | InChI=1S/C15H12N2O3S/c18-14-11-8-4-1-2-6-10(8)21-13(11)16-12-9(15(19)20)5-3-7-17(12)14/h3,5,7H,1-2,4,6H2,(H,19,20) | 300.340000000 | 3264670 | 12-oxo-1,2,3,4-tetrahydro-12H-[1]benzothieno[2,3-d]pyrido[1,2-a]pyrimidine-7-carboxylic acid | 2.037366371 | 1.073502389 |
| 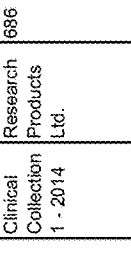 | 2 | Microsource 1 - US Drug Collection | Microsource | 1300037 | [Fe-2](C#N)(C#N)(C#N)(C#N)(C#N)N=O.{Na+}.[Na+] | InChI=1S/5CN.Fe.NO.2Na/c5*1-2;;1-2;;/q;;;;;2*+1;2*+1 | 261.917630000 | 11963579 | Sodium nitroprusside | 1.87152301 | 1.24734419 |

FIG. 9 (continued)

| | | | | | | | | |
|---|---|---|---|---|---|---|---|---|
| | 3 | Microsource 1 - US Drug Collection | Microsource | 1500132 | [C@@H]1(O)[C@@H](O)[C@@H](O)[C@H](OC1S[Au])CO | InChI=1S/C6H12O5S.Au/c7-1-2-3(8)4(9)5(10)6(12)11-2/h2-10,12H,1H2;/q;+1/p-1/t2-,3-,4+,5-,6?;/m1./s1 | 392.180080000 | Aurothioglucose | 2.18447924 | 1.309326072 |
| | 4 | ChemDiv Targeted Diversity Library | ChemDiv | T742-0069 | n1c(c2ccccc2)onc1Cn(ccn3)c3 | InChI=1S/C12H10N4O/c1-2-4-10(5-3-1)12-14-11(15-17-12)8-16-7-6-13-9-16/h1-7,9H,8H2 | 226.240000000 | 53015251 | 3-(1H-imidazol-1-ylmethyl)-5-phenyl-1,2,4-oxadiazole | 1.98398136 | 1.431920781 |
| | 4 | ChemDiv Targeted Diversity Library | ChemDiv | P200-0033 | n1c(Cn(ccn2)c2)onc1c3ccc(cc3)F | InChI=1S/C12H9FN4O/c13-10-3-1-9(2-4-10)12-15-11(18-16-12)7-17-6-5-14-8-17/h1-6,8H,7H2 | 244.230000000 | 36795627 | 3-(4-fluorophenyl)-5-(imidazol-1-ylmethyl)-1,2,4-oxadiazole | 1.98567109 | 1.426186407 |
| | 4 | ChemDiv Targeted Diversity Library | ChemDiv | T742-0007 | n1c(c2ccc(cc2)Cl)onc1Cn(ccn3)c3 | InChI=1S/C12H9ClN4O/c13-10-3-1-9(2-4-10)12-15-11(16-18-12)7-17-6-5-14-8-17/h1-6,8H,7H2 | 260.680000000 | 53015243 | 5-(4-chlorophenyl)-3-(1H-imidazol-1-ylmethyl)-1,2,4-oxadiazole | 1.42657174 | 1.14142633 |
| | 4 | ChemDiv Targeted Diversity Library | ChemDiv | T742-0014 | n1c(c2ccc(cc2)F)onc1Cn(ccn3)c3 | InChI=1S/C12H9FN4O/c13-10-3-1-9(2-4-10)12-15-11(16-18-12)7-17-6-5-14-8-17/h1-6,8H,7H2 | 244.230000000 | 53015246 | 5-(4-fluorophenyl)-3-(1H-imidazol-1-ylmethyl)-1,2,4-oxadiazole | 1.52555831 | 1.178163772 |

| | | | | | | | | |
|---|---|---|---|---|---|---|---|---|
| 4 | ChemDiv Targeted Diversity Library | ChemDiv | P200-0043 | n1c(Cn(ccn2)c2)on c1c(ccc(c3Br)F)c3 | InChI=1S/C12H8BrFN4O/c1 3-9-5-8(1-2-10(9)14)12-16-11(19-17-12)6-18-4-3-15-7-18/h1-5,7H,6H2 | 323.130000 000 | 53164447 | 3-(3-bromo-4-fluorophenyl)-5-(1H-imidazol-1-ylmethyl)-1,2,4-oxadiazole | 1.97962008 | 1.46521575 |
| 4 | ChemDiv Targeted Diversity Library | ChemDiv | P200-0030 | n1c(Cn(ccn2)c2)on c1c(ccc(c34)OCO3 )c4 | InChI=1S/C13H10N4O3/c1-2-10-11(19-8-18-10)5-9(1)13-15-12(20-16-13)6-17-4-3-14-7-17/h1-5,7H,6,8H2 | 270.250000 000 | 53164445 | 3-(1,3-benzodioxol-5-yl)-5-(imidazol-1-ylmethyl)-1,2,4-oxadiazole | 1.71571072 | 1.305289408 |
| 4 | ChemDiv Targeted Diversity Library | ChemDiv | T742-0024 | n1c(Cn(ccn2)c2)no c1c(ccc(c34)OCO3 )c4 | InChI=1S/C13H10N4O3/c1-2-10-11(19-8-18-10)5-9(1)13-15-12(16-20-13)6-17-4-3-14-7-17/h1-5,7H,6,8H2 | 270.250000 000 | 53193097 | 5-(1,3-benzodioxol-5-yl)-3-(1H-imidazol-1-ylmethyl)-1,2,4-oxadiazole | 1.60178465 | 1.213920286 |
| 4 | ChemDiv Targeted Diversity Library | ChemDiv | T742-0003 | n1c(Cn(ccn2)c2)no c1c3cccs3 | InChI=1S/C10H8N4OS/c1-2 8(16-5-1)10-12-9(13-15-10)6-14-4-3-11-7-14/h1-5,7H,6H2 | 232.270000 000 | 53193095 | 3-(1H-imidazol-1-ylmethyl)-5-(2-thienyl)-1,2,4-oxadiazole | 1.529320079 | 1.195386003 |
| 4 | ChemDiv Targeted Diversity Library | ChemDiv | M007-0036 | c(c1C)(nnn1Cc2c(C)oc(c3cccc3)n2) c4onc(c(ccc(c5Br)F)c5)n4 | InChI=1S/C22H16BrFN6O2 /c1-12-19(22-26-20(28-32-22)15-8-9-17(24)16(23)10-15)27-29-30(12)11-18-13(2)31-21(25-18)14-6-4-3-5-7-14/h3-10H,11H2,1-2H3 | 495.310000 000 | 50838085 | 3-(3-bromo-4-fluorophenyl)-5-{5-methyl-1-[(5-methyl-2-phenyl-1,3-oxazol-4-yl)methyl]-1H-1,2,3-triazol-4-yl}-1,2,4-oxadiazole | 1.28193207 | 1.073744027 |

| | | | | | | | |
|---|---|---|---|---|---|---|---|
| 4 | ChemDiv Targeted Diversity Library | ChemDiv | J011-0101 | n(cnn1)(nc(s2)c3cc c(cc3)CNS(=O)(=O )c4cccc(cc4)C)c12 | InChI=1S/C17H15N5O2S2/c1-12-2-8-15(9-3-12)26(23,24)19-10-13-4-6-14(7-5-13)16-21-22-11-18-20-17(22)25-16/h2-9,11,19H,10H2,1H3 | 385.470000000 | 46366641 | 4-methyl-N-[[4-[[1,2,4]triazolo[3,4-b][1,3,4]thiadiazol-6-yl]phenyl]methyl]benzenesulfonamide | 1.238856756 | 1.102924127 |
| 4 | ChemDiv Targeted Diversity Library | ChemDiv | L984-0021 | c1 2c(cnn1c3cccc c3)C(N(Cc4onc(c5c cc(c(OC)c5)OCC)n4)C)=O)C=N2)=O | InChI=1S/C23H20N6O4/c1-3-32-18-10-9-15(11-19(18)31-2)21-26-20(33-27-21)13-28-14-24-22-17(23(28)30)12-25-29(22)16-7-5-4-6-8-16/h4-12,14H,3,13H2,1-2H3 | 444.450000000 | 50838334 | 5-[[3-(4-ethoxy-3-methoxyphenyl)-1,2,4-oxadiazol-5-yl]methyl]-1-phenylpyrazolo[3,4-d]pyrimidin-4-one | 1.24454207 | 1.113684771 |
| 4 | ChemDiv Targeted Diversity Library | ChemDiv | D420-4963 | c1(noc(CCC(=O)N c2sccn2)n1)c3cc(c cc(c4)C)c4nc3O | InChI=1S/C18H15N5O3S/c1-10-2-3-11-9-12(17(25)20-13(11)8-10)16-22-15(26-23-16)5-4-14(24)21-18-19-6-7-27-18/h2-3,6-9H,4-5H2,1H3,(H,20,25)(H,19,21,24) | 381.420000000 | 50748653 | 3-[3-(2-hydroxy-7-methylquinolin-3-yl)-1,2,4-oxadiazol-5-yl]-N-1,3-thiazol-2-ylpropanamide | 1.92595118 | 1.294013364 |
| 4 | ChemDiv Targeted Diversity Library | ChemDiv | L150-0829 | c1(cn(c(cccc2S(=O) (=O)N(C)C)c1c2)C) C(=O)n(ccn3)c3 | InChI=1S/C15H16N4O3S/c1-17(2)23(21,22)11-4-5-14-12(8-11)13(9-18(14)3)15(20)19-7-6-16-10-19/h4-10H,1-3H3 | 332.380000000 | 50820754 | 3-(imidazole-1-carbonyl)-N,N,1-trimethylindole-5-sulfonamide | 1.547 28878 | 1.255737705 |
| 4 | ChemDiv6 | ChemDiv | G751-1260 | n1(C)c(SCC(=C2)N c(c3C2=O)cc(cc3C )C)nnc1c4cccc4 | InChI=1S/C21H20N4OS/c1-13-9-14(2)19-17(10-13)22-16(11-18(19)26)12-27-21-24-23-20(25)(21)3)15-7-5-4-6-8-15/h4-11H,12H2,1-3H3,(H,22,26) | 376.474690000 | 16030364 | 5,7-dimethyl-2-[(4-methyl-5-phenyl-1,2,4-triazol-3-yl)sulfanylmethyl]-1H-quinolin-4-one | 1.2679693 | 1.066410793 |

FIG. 9 (continued)

| Structure | | Source | ID | SMILES | InChI | MW | CID | Name | Value1 | Value2 |
|---|---|---|---|---|---|---|---|---|---|---|
| | 5 | NIH Clinical Collection 1 - 2014 | Sequoia Research Products Ltd. SAM001246737 | COc1ccc(/C=C/C(=O)Nc2ccccc2C(=O)O)cc1OC | InChI=1S/C18H17NO5/c1-23-15-9-7-12(11-16(15)24-2)8-10-17(20)19-14-6-4-3-5-13(14)18(21)22/h3-11H,1-2H3,(H,19,20)(H,21,22)/b10-8+ | 327.331280000 | 5282230 | TRANILAST | 1.40272643 | 1.132855823 |
| | 5 | Biomol 4 - FDA Approved Drug Library | BIOMOL CT110 | c1(NC(=O)/C=C/c2ccc(OC)c(OC)c2)ccccc1C(=O)O | InChI=1S/C18H17NO5/c1-23-15-9-7-12(11-16(15)24-2)8-10-17(20)19-14-6-4-3-5-13(14)18(21)22/h3-11H,1-2H3,(H,19,20)(H,21,22)/b10-8+ | 327.331270000 | 5282230 | Tranilast | 1.201481184 | 1.040272467 |
| | 5 | Microsource 1 - US Drug Collection | Microsource 1505333 | c1(ccccc1NC(=O)/C=C/c(cccc2OC)c2OC)C(O)=O | InChI=1S/C18H17NO5/c1-23-15-9-7-12(11-16(15)24-2)8-10-17(20)19-14-6-4-3-5-13(14)18(21)22/h3-11H,1-2H3,(H,19,20)(H,21,22)/b10-8+ | 327.331280000 | 5282230 | Tranilast | 2.201944253 | 2.092809929 |
| | 5 | ChemDiv6 | ChemDiv 3237-0805 | c1(NC(=O)/C=C\c2)ccc2OC)sc(c(C)c1C(O)=O)C | InChI=1/C17H17NO4S/c1-10-11(2)23-16(15(10)17(20)21)18-14(19)9-6-12-4-7-13(22-3)8-5-12/h4-9H,1-3H3,(H,18,19)(H,20,21)/b9-6+ | 331.386170000 | 760017 | 2-[[(E)-3-(4-methoxyphenyl)prop-2-enoyl]amino]-4,5-dimethylthiophene-3-carboxylic acid | 1.211403934 | 1.0722476 |
| | 5 | ChemDiv6 | ChemDiv 5408-1513 | S(=O)(=O)(Nc(cc1)ccc1OC)c(ccc2c3[C@@]4([H])C@@]([H])(c(cc5)ccc5C(O)=O)N2)[H])C=C4)c3 | InChI=1/C26H24N2O5S/c1-33-19-11-9-18(10-12-19)28-34(31,32)20-13-14-24-22(21)25(27-24)16-5-7-17(8-6-16)26(29)30/h21,29-28H,4H2,1H3,(H,29,30)/t21-,22+,25+/m0/s1 | 476.544160000 | 5322407 | 4-[(3aR,4S,9bS)-8-[(4-methoxyphenyl)sulfamoyl]-3a,4,5,9b-tetrahydro-3H-cyclopenta[c]quinolin-4-yl]benzoic acid | 2.29970297 | 1.31508445 |

FIG. 9 (continued)

| | | | | | | | |
|---|---|---|---|---|---|---|---|
| | ChemDiv6 | ChemDiv | 3681-3709 | C(C(#N)(=C/c(ccc1 c(cc2)ccc2C(O)=O) o1)C(=O)Nc3cccc c3C(O)=O | InChI=1/C22H14N2O6/c23-12-15(20(25)24-18-4-2-1-3-17(18)22(28)29)11-16-9-10-19(30-16)13-5-7-14(8-6-13)21(26)27/h1-11H,(H,24,25)(H,26,27)(H,2 8,29)/b15-11+ | 402.356350 000 | 15991111 | 2-[[(E)-3-[5-(4-carboxyphenyl)fur an-2-yl]-2-cyanoprop-2-enoyl]amino]benz oic acid | 2.57171109 | 1.736683606 |
| | ChemDiv6 | ChemDiv Targeted Diversity Library | L674-0152 | N(c1c2ccc([H])c([H]) c1(=NCc3cccc(O C)c3)C4(N2)CCC( CC4)[H] | InChI=1S/C21H25N3O/c1-25-17-9-7-8-16(14-17)15-22 20-21(12-5-2-6-13-21)24-19-11-4-3-10-18(19)23-20/h3-4,7-11,14,24H,2,5-6,12-13,15H2,1H3,(H,22,23) | 371.910000 000 | 46388991 | N-[(3-methoxyphenyl)m ethyl]spiro[4H-quinoxaline-3,1'-cyclohexane]-2-amine | 1.41683688 | 1.112780858 |
| | ChemDiv6 | ChemDiv Targeted Diversity Library | K261-3098 | S1(=O)(=O)c2c(cc cc2)NC(NCc(ccc(c 34)OCC3)p4)=N1 | InChI=1S/C15H13N3O4S/c 19-23(20)14-4-2-1-3-11(14)17-15(18-23)16-8-10-5-6-12-13(7-10)22-9-21-12/h1-7H,8-9H2,(H2,16,17,18) | 331.350000 000 | 42564787 | N-(1,3-benzodioxol-5-ylmethyl)-1,1-dioxo-4H-1$l^{6},2,4-benzothiadiazin-3-amine | 1.26111032 | 1.123810876 |
| | ChemDiv6 | ChemDiv | 5408-0947 | N1[C@@H](c(cc2) ccc2C(O)=O)[C@ @]([H])(CC=C3)[C @@]3(c(ccccc4OC C)c14)[H] | InChI=1/C21H21NO3/c1-2-25-18-8-4-7-17-15-5-3-6-16(15)19(22-20(17)18)13-9-11-14(12-10-13)21(23)24/h3-5,7-12,15-16,19,22H,2,6H2,1H3,(H,23,24)/t15-,16+,19+/m1/s1 | 335.396340 000 | 6541811 | 4-[(3aS,4R,9bR)-6-ethoxy-3a,4,5,9b-tetrahydro-3H-cyclopenta[c]quin olin-4-yl]benzoic acid | 2.04225212 | 1.264573991 |
| | ChemDiv6 | ChemDiv | C875-0537 | c1(SCc2cccc(OC)c 2)nc(c(cc3)n1CC(= O)Nc4ccc(c(OC)o4 OC)OC)ccn3 | InChI=1/C25H26N4O5S/c1-31-17-7-5-6-16(12-17)15-35-000 25-28-10-11-26-13-20(18)29(25)14-22(30)27-19-8-9-21(32-2)24(34-4)23(19)33-3/h5-13H,14-15H2,1-4H3,(H,27,30) | 494.562730 | 16011818 | 2-[2-[(3-methoxyphenyl)m ethylsulfanyl]imid azo[4,5-c]pyridin-3-yl]-N-(2,3,4-trimethoxyphenyl) acetamide | 1.28622884 | 1.143954857 |

FIG. 9 (continued)

| | | | | | | | |
|---|---|---|---|---|---|---|---|
| 5 | ChemDiv Targeted Diversity Library | ChemDiv | F723-0459 | c(N(C)CCCC)(c1)nc(c2c1C(O)=O)ccc2)NC(=O)c3ccccc3OC | InChI=1S/C23H25N3O4/c1-4-5-12-26(2)21-14-18(23(28)29)17-13-15(10-11-19(17)25-21)24-22(27)16-8-6-7-9-20(16)30-3/h6-11,13-14H,4-5,12H2,1-3H3,(H,24,27)(H,28,29) | 480.390000000 | 1.89475839 | 1.304122304 |
| | | | | | | | 2-[butyl(methyl)amino]-6-[(2-methoxybenzoyl)amino]quinoline-4-carboxylic acid |
| 5 | ChemDiv Targeted Diversity Library | ChemDiv | C716-0659 | S(=O)(=O)(c1ccc(c(Cl)c1)OC)/C2=C\N=C(NC2=O)SCC(=O)Nc3ccccc3C(OC)=O | InChI=1S/C21H18ClN3O7S2/c1-31-16-8-7-12(9-14(16)22)34(29,30)17-10-23-21(25-19(17)27)33-11-18(26)24-15-6-4-3-5-13(15)20(28)32-2/h3-10H,11H2,1-2H3,(H,24,26)(H,23,25,27) | 523.970000000 | 50783959 | 2.10777764 | 1.268498676 |
| | | | | | | | Methyl 2-{[({5-[(3-chloro-4-methoxyphenyl)sulfonyl]-6-oxo-1,6-dihydropyrimidin-2-yl}thio)acetyl]amino}benzoate |
| 5 | ChemDiv6 Targeted Diversity Library | ChemDiv | 7202-4797 | S(=O)(=O)(Nc(ccc(c1C(O)=O)c1)cc2)c(cc3)c(cc3)c(c24)cc3)C(N4CO)=O | InChI=1/C20H16N2O6S/c1-2-22-15-7-9-17(12-4-3-5-13(18(12)15)19(22)24)29(2,7,28)21-11-6-8-16(23)14(10-11)20(25)26/h3-10,21,23H,2H2,1H3,(H,25,26) | 412.415830 | 20878395 | 2.224 | 1.640285714 |
| | | | | | | | 5-{[(1-ethyl-2-oxo-1,2-dihydrobenzo[cd]indol-6-yl)sulfonyl]amino}-2-hydroxybenzoic acid |
| 5 | ChemDiv Targeted Diversity Library | ChemDiv | K781-6023 | c1(ccc(ccN)C(O)=O)N(CC2)CCO2 | InChI=1S/C11H14N2O3/c1-2-9-7-8(11(14)15)1-2-10(9)13-3-5-16-6-4-13/h1-2,7H,3-6,12H2,(H,14,15) | 222.250000000 | 2219634 | 1.35928144 | 1.047625679 |
| | | | | | | | 3-amino-4-morpholin-4-ylbenzoic acid |
| 5 | ChemDiv Targeted Diversity Library | ChemDiv | D727-0650 | N(Cc(coc(c12)OCO1)c2)(C3)C(=O)CC3C(O)=O | InChI=1S/C13H13NO5/c15-12-4-9(13(16)17)6-14(12)5-8-1-2-10-11(3-8)19-7-18-10/h1-3,9H,4-7H2,(H,16,17) | 263.250000000 | 2742111 | 3.90630101 | 3.574600065 |
| | | | | | | | 1-(1,3-benzodioxol-5-ylmethyl)-5-oxopyrrolidine-3-carboxylic acid |

FIG. 9 (continued)

| | | | | | | | |
|---|---|---|---|---|---|---|---|
| 5 | ChemDiv6 | ChemDiv | D278-0132 | n1c(Nc(ccccc2C(O)=O)c2)cc(nc1SC)C(=O)Nc2cccc2C(O)O | InChI=1/C13H13N3O2S/c1-8-6-11(16-13(14-8)19-2)15-10-5-3-4-9(7-10)12(17)18/h3-7H,1-2H3,(H,17,18)(H,14,15,16) | 275.326220000 | 16014846 | 3-{[(6-methyl-2-methylsulfanylpyrimidin-4-yl)amino]benzoic acid | 1.45136587 | 1.179791976 |
| 5 | ChemDiv6 | ChemDiv | C289-0310 | c1(CC(=O)Nc2cc(OC)c(OC)c2)c3c[nH]c1C(O)=O)ccc(Cl)c3 | InChI=1/C19H17ClN2O5/c1-26-11-4-6-12(7-2)15(8-11)21-17(23)9-13-12-7-10(20)3-5-14(12)22-18(13)19(24)25/h3-8,22H,9H2,1-2H3,(H,21,23)(H,24,25) | 388.801670000 | 15989959 | 5-chloro-3-[2-(2,5-dimethoxyanilino)-2-oxoethyl]-1H-indole-2-carboxylic acid | 1.23129252 | 1.076449627 |
| 5 | ChemDiv Targeted Diversity Library | ChemDiv | D562-0973 | c12c(C(CC(=O)N1)c3ccc(c(OCC)c3)OCC(N)=O)sc(C(O)=O)c2c4cccc(F)c4 | InChI=1S/C24H21FN2O6S/c1-2-32-17-9-12(6-7-16(17)33-11-18(26)28)15-10-19(29)27-21-20(13-4-3-5-14(25)8-13)23(24(30)31)34-22(15)21H3-9,15H,2,10-11H2,1H3,(H2,26,28)(H,27,29)(H,30,31) | 484.510000000 | 53003502 | 7-[4-(2-amino-2-oxoethoxy)-3-ethoxyphenyl]-3-(3-fluorophenyl)-5-oxo-4,5,6,7-tetrahydrothieno[3,2-b]pyridine-2-carboxylic acid | 1.26424195 | 1.084213271 |
| 5 | ChemDiv6 | ChemDiv | E796-0187 | N1(N=C(S2)Nc3cc ccc3OC)C2=Nc(cc4C(=O)Nc5cccc(OC)c5)c(cc4)C1=O | InChI=1/C24H19N5O4S/c1-32-16-7-5-6-15(13-16)25-21(30)14-10-11-17-19(12-14)27-24-29(22(17)31)28-23(34-24)26-18-8-3-4-9-20(18)33-2/h3-13H,1-2H3,(H,25,30)(H,26,28) | 473.503750000 | 16022478 | 2-(2-methoxyanilino)-N-(3-methoxyphenyl)-5-oxo-[1,3,4]thiadiazolo[2,3-b]quinazoline-8-carboxamide | 1.30417712 | 1.096193696 |
| 5 | ChemDiv Targeted Diversity Library | ChemDiv | J047-0586 | c1(nnc(SCC(=O)Nc(cccc2C(O)=O)c2)n1c3ccccc3)c4cc(c5o4)cccc5 | InChI=1S/C25H18N4O4S/c30-22(26-18-9-6-8-17(13-18)24(31)32)15-34-25-28-27-23(29(25)19-10-2-1-3-11 19)21-14-16-7-4-5-12-20(16)33-21/h1-14H,15H2,(H,26,30)(H,31,32) | 470.510000000 | 18773540 | 3-[{2-[[5-(1-benzofuran-2-yl)-4-phenyl-1,2,4-triazol-3-yl]sulfanyl]acetyl}amino]benzoic acid | 1.32649639 | 1.098168215 |

| | | | | | | | | |
|---|---|---|---|---|---|---|---|---|
| | 5 | ChemDiv Targeted Diversity Library | ChemDiv | G818-0017 | c1(c(ncnc1Nc2ccc(c(OC)c2)OC)sc3C(O)=O)c3C | InChI=1S/C16H15N3O4S/c1-8-12-14(17-7-18-15(12)24)13(8)16(20)21)19-9-4-5-10(22-2)11(6-9)23-3/h4-7H,1-3H3,(H,17,18,19) | 345.380000 000 | 28855768 | 4-(3,4-dimethoxyanilino)-5-methylthieno[2,3-d]pyrimidine-6-carboxylic acid | 2.9559194 | 1.588581024 |
| | 5 | ChemDiv Targeted Diversity Library | ChemDiv | G311-0530 | S(=O)(=O)(c1ccc(c1)OC)Nc(c(Oc2cccc2)cc(c3N4C)N(C)C(C4=O)=O)c3 | InChI=1S/C23H21N3O6S/c1-25-19-13-18(24-33(29,30)17-11-9-15(31-3)10-12-17)21(32-16-7-5-4-6-8-16)14-20(19)26(2)23(28)22(25)27/h4-14,24H,1-3H3 | 467.500000 000 | 50793132 | N-(1,4-dimethyl-2,3-dioxo-7-phenoxy-1,2,3,4-tetrahydroquinoxalin-6-yl)-4-methoxybenzene sulfonamide | 1.303066922 | 1.081546167 |
| | 5 | ChemDiv6 | ChemDiv | 8011-6852 | c1(c2c(ccc(c2)OC(F)(F)F)ncc1C(OCC)=O)Nc3ccccc3C(O)=O | InChI=1/C20H15F3N2O5/c1-2-29-19(28)14-10-24-15-8-7-13(15)17(14)25-16-6-4-3-5-12(16)18(26)27/h3-10H,2H2,1H3,(H,24,25)(H,26,27) | 420.338700 000 | 10435478 | 2-{[3-ethoxycarbonyl-6-(trifluoromethoxy)quinolin-4-yl]amino}benzoic acid | 1.522690092 | 1.189524190 |
| | 5 | ChemDiv6 | ChemDiv | D103-1622 | S(=O)(=O)(c1ccc(c1)N([H])C(=O)C(O)(cc(C)cc2C)cc2C3Nc4onc(C)c12)22(28)24-16-5-7-17(8-6-16)33(29,30)26-23-14(3)15(4)25-32-23/h5-11,26H,1-4H3,(H,24,28) | InChI=1/C23H21N3O6S/c1-12-9-13(2)21-18(27)11-20(31-19)(21)10- | 467.494330 000 | 16013427 | N-{4-[(3,4-dimethyl-1,2-oxazol-5-yl)sulfamoyl]phenyl}-5,7-dimethyl-4-oxochromene-2-carboxamide | 1.777372226 | 1.315823775 |
| | 5 | ChemDiv6 | ChemDiv | 5849-3295 | C(=O)(c1ccccc1C(O)=O)Nc2ccc(cccn3)c23)Br | InChI=1/C17H11BrN2O3/c1-8-13-7-8-14(15-12(13)6-3-9-19-15)20-16(21)10-4-1-2-5-11(10)17(22)23/h1-9H,(H,20,21)(H,22,23) | 371.184840 000 | 1218429 | 2-{[5-bromoquinolin-8-yl]carbamoyl]benzoic acid | 1.2032913 | 1.041498971 |

| | | | | | | | |
|---|---|---|---|---|---|---|---|
| | ChemDiv6 | ChemDiv | E942-0210 | N1(CC(C)C)C=C(N C(=O)NCc2ccc(OC)c2)c(c3C1=O)ccc3 | InChI=1/C22H25N3O3/c1-15(2)13-25-14-20(18-9-4-5-10-19(18)21(25)26)24-22(27)23-12-16-7-6-8-17(11-16)28-3/h4-11,14-15H,12-13H2,1-3H3,(H2,23,24,27) | 379.452200000 | 16023484 | 1-[(3-methoxyphenyl)methyl]-3-[2-(2-methylpropyl)-1-oxoisoquinolin-4-yl]urea | 1.620737333 | 1.088133641 |
| | ChemDiv6 | ChemDiv | C200-5327 | S(=O)(=O)(c1ccc(c(C)c1)OC)C2=CN=C(NC2=O)SCC(=O)Nc3c(C)occ(F)c3 | InChI=1/C20H17ClFN3O5S 2/c1-11-3-4-12(22)7-15(11)24-18(26)10-31-20-23-9-17(19(27)25-20)32(28,29)13-5-6-16(30-2)14(21)8-13/h3-9H,10H2,1-2H3,(H,24,26)(H,23,25,27) | 497.947480000 | 15988542 | 2-{(5-((3-chloro-4-methoxyphenyl)sulfenyl)-6-oxo-1,6-dihydropyrimidin-2-yl)thio)-N-(5-fluoro-2-methylphenyl)acetamide | 1.362139992 | 1.118006896 |
| | ChemDiv6 | ChemDiv | E157-5454 | c1(nnc(NC(=O)c(cc2OC)ccc(c2OC)OC)s1)S(=O)(=O)N(C)c3cccccc3 | InChI=1/C19H20N4O6S2/c1-23(13-8-6-5-7-9-13)31(25,26)19-22-21-18(30-19)20-17(24)12-10-14(27-2)16(29-4)15(11-12)28-3/h5-11H,1-4H3,(H,20,21,24) | 464.515290000 | 16017357 | 3,4,5-trimethoxy-N-[5-[methyl(phenyl)sulfamoyl]-1,3,4-thiadiazol-2-yl]benzamide | 1.245226930 | 1.110437864 |
| | ChemDiv6 | ChemDiv | E734-0158 | S(=O)(=O)(Nc(cc1)ccc1OC(C(F)(F)F)c(c(C)cc(c23)NC(C(=O)N2)=O)c3 | InChI=1/C16H12F3N3O5S/c1-8-6-11-12(21-15(24)14(23)20-11)7-13(8)28(25,26)22-9-2-4-10(5-3-9)27-16(17,18)19/h2-7,22H,1H3,(H,20,23)(H,21,24) | 415.343780000 | 16021654 | 7-methyl-2,3-dioxo-N-[4-(trifluoromethoxy)phenyl]-1,4-dihydroquinoxaline-6-sulfonamide | 1.300906750 | 1.119892533 |
| | ChemDiv6 | ChemDiv | C660-0019 | c(SCC(O)=O)(c1c2CCC1)c(cc3)c(n2)c3C(=O)Nc4ccc(cc4OC)OC | InChI=1/C23H22N2O5S/c1-29-14-7-9-18(20(11-14)30-2)25-23(28)13-6-8-19(10-13)24-17-5-3-4-15(17)22(16)31-12-21(26)27/h6-11H,3-5,12H2,1-2H3,(H,25,28)(H,26,27) | 438.496170000 | 16009475 | 2-{[6-[(2,4-dimethoxyphenyl)carbamoyl]-2,3-dihydro-1H-cyclopenta[b]quinolin-9-yl]sulfanyl}acetic acid | 1.253103450 | 1.096551724 |

FIG. 9 (continued)

| | | | | | | | | |
|---|---|---|---|---|---|---|---|---|
| 5 | ChemDiv Targeted Diversity Library | ChemDiv | M049-1608 | N1(CC(C)C)c2c(cc cc2)N=C(c(c(cc3) 3C(=O)Nc(cccc(c45) OCCO4)c5)C1=O | InChI=1S/C27H25N3O4/c1-17(2)16-30-22-6-4-3-5-21(22)29-25(27(30)32)18-7-9-19(10-8-18)26(31)28-20-11-12-23-24(15-20)34-14-13-33-23/h3-12,15,17H,13-14,16H2,1-2H3,(H,28,31) | 455.520000 000 | 50838537 | N-(2,3-dihydro-1,4-benzodioxin-6-yl)-4-[4-(2-methylpropyl)-3-oxoquinoxalin-2-yl]benzamide | 1.3385189 | 1.086140396 |
| 5 | ChemDiv6 | ChemDiv | E734-0185 | S(=O)(=O)(c(c(c(C)c c(c12)NC(C(=O)N1 )=O)c2)Nc3c(OC)c c(cc3Cl)OC | InChI=1/C17H17ClN3O6S/c 1-8-4-11-12(20-17(23)16(22)19-11)7-14(8)28(24,25)21-15-10(18)5-9(26-2)6-13(15)27-3/h4-7,21H,1-3H3,(H,19,22)(H,20,23) | 425.843430 000 | 16021662 | N-(2-chloro-4,5-dimethoxyphenyl)-7-methyl-2,3-dioxo-1,4-dihydroquinoxalin e-6-sulfonamide | 1.31694936 | 1.16082704 |
| 5 | ChemDiv6 | ChemDiv | C598-0017 | c(SCC(O)=O)c1c2 CCCC1)c(cc3)c(n2 )cc3C(=O)Nc4ccc( cc4OC)OC | InChI=1/C24H24N2O5S/c1-30-15-8-10-19(21(12-15)31-2)26-24(29)14-7-9-17-20(11-14)25-18-6-4-3-5-16(18)23(17)32-13-22(27)28/h7-12H,3-6,13H2,1-2H3,(H,26,29)(H,27,28) | 452.522750 000 | 16008796 | [(6-{[(2,4-dimethoxyphenyl) amino]carbonyl}-1,2,3,4-tetrahydroacridin-9-yl)thio]acetic acid | 1.27552042 | 1.082065653 |
| 5 | ChemDiv6 | ChemDiv | D205-04472 | n1(nc(n2)NC(=O)c 3cccc(OC)c3)c2nc( c4cccoc4)cc1O | InChI=1/C19H15N5O3/c1-27-14-9-5-8-13(10-14)17(26)21-18-22-19-20-15(11-16(25)24(19)23-18)12-6-3-2-4-7-12/h2-11,25H,1H3,(H,21,23,26) | 361.354100 000 | 6485799 | 3-methoxy-N-(7-oxo-5-phenyl-1H-[1,2,4]triazolo[1,5-a]pyrimidin-2-yl)benzamide | 1.91046993 | 1.329160921 |
| 5 | Microsour ce 1 - US Drug Collection | Microsourc e | 1505982 | c(C(O)=O)(oc(cccc 1)c1c2Cc(c3c(occc 3)cc4C(c(O)=O)c(c4O) c2O,C5(C1C=C1c6cc cc(O)c6)=NCCCN5 C | InChI=1S/C23H16O6.C13H 16N2O/c24-20-16(14-7-3-1-5-12(14)9-18(20)22(26)27)11-17-15-8-4-2-6-13(15)10-19(21(17)25)23(28)29;1-15-9-3-8-14-13(15)7-6-11-4-2-5-12(16)10-11/h1-10,24-25H,11H2,(H,26,27)(H,28,2 | 604.648470 000 | 5281086 | Oxantel pamoate | 1.36211503 | 1.096048376 |

FIG. 9 (continued)

| | | | | | | | |
|---|---|---|---|---|---|---|---|
| 5 | ChemDiv6 | ChemDiv | C716-0323 | S(=O)(=O)c1ccc(c(C)c1)C)C2=CN=C(NC2=O)SCC(=O)Nc(ccc(c34)OCCO3)c4 | InChI=1/C22H21N3O6S2/c1-13-3-5-16(9-14(13)2)33(28,29)19-11-23-22(25-21(19)27)32-12-20(26)24-15-4-6-17-18(10-15)31-8-7-30-17/h3-6,9-11H,7-8,12H2,1-2H3,(H,24,26)(H,23,25,27) | 487.548630000 | 2138664 | N-(2,3-dihydro-1,4-benzodioxin-6-yl)-2-{[5-(3,4-dimethylphenyl)sulfonyl)-6-oxo-1H-pyrimidin-2-yl]sulfanyl}acetamide | 1.23811442 | 1.07252216 |
| 5 | ChemDiv Targeted Diversity Library | ChemDiv | E200-0252 | N1(c2ccc(cc2)OCC)C(=O)NC=C(C(=O)Nc(acc3)ccc3S(N)(=O)=O)C1=O | InChI=1S/C19H18N4O6S/c1-2-29-14-7-5-13(6-8-14)23-18(25)16(11-21-19(23)26)17(24)22-12-3-9-15(10-4-12)30(20,27)28/h3-11H,2H2,1H3,(H,21,26)(H,22,24)(H2,20,27,28) | 430.440000000 | 4302826 | 3-(4-ethoxyphenyl)-2,4-dioxo-N-(4-sulfamoylphenyl)-1H-pyrimidine-5-carboxamide | 1.55307648 | 1.263254744 |
| 5 | ChemDiv6 | ChemDiv | E582-0240 | C1(=C(C(O)c(c(c2)NC1=O)ccc2C(=O)Nc(cc3)ccc3C)S(=O)(=O)c4ccc(cc4)Cl | InChI=1/C23H17ClN2O5S/c1-13-2-7-16(8-3-13)25-22(28)14-4-11-18-19(12-14)26-23(29)21(20(18)27)32(30,31)17-9-5-15(24)6-10-17/h2-12H,1H3,(H,25,28)(H,26,27,29) | 468.909480000 | 54687803 | 3-(4-chlorophenyl)sulfonyl-4-hydroxy-N-(4-methylphenyl)-2-oxo-1H-quinoline-7-carboxamide | 1.22824896 | 1.156256849 |
| 5 | ChemDiv6 | ChemDiv | 6408-0273 | c1(OCC)ccc(ccc1OCc(cc2)ccc2Cl)CN([H])c(cc3)ccc3O | InChI=1/C22H22ClNO3/c1-2-26-22-13-17(14-24-19-8-10-20(25)11-9-19)5-12-21(22)27-15-16-3-6-18(23)7-4-16/h3-13,24-25H,2,14-15H2,1H3 | 383.867980000 | 1017166 | 4-({4-[(4-chlorobenzyl)oxy]-3-ethoxybenzyl)amino}phenol | 1.58515163 | 1.135909763 |
| 5 | ChemDiv Targeted Diversity Library | ChemDiv | 1959-0211 | N1c(ccc(c2)Cl)c2CC3C(CC=C3)C1C(O)=O | InChI=1S/C13H12ClNO2/c1-4-7-4-5-11-10(6-7)8-2-1-3-9(8)12(15-11)13(16)17/h1-2,4-6,8-9,12,15H,3H2,(H,16,17) | 249.700000000 | 609426 | 8-Chloro-3a,4,5,9b-tetrahydro-3H-cyclopenta[c]quinoline-4-carboxylic acid | 2.76450549 | 1.96967033 |

FIG. 9 (continued)

| | | | | | | | | |
|---|---|---|---|---|---|---|---|---|
| 5 | ChemDiv Targeted Diversity Library | ChemDiv | E200-0126 | N1(c2ccc(cc2)C)C(=O)NC=C(C(=O)Nc(cc3)ccc3S(N)(=O)=O)C1=O | InChI=1S/C18H16N4O5S/c1-1-11-2-6-13(7-3-11)22-17(24)15(10-20-18(22)25)16(23)21-12-4-8-14(9-5-12)28(19,26)27/h2-10H,1H3,(H,20,25)(H,21,23)(H2,19,26,27) | 400.420000000 | 5142968 | 3-(4-methylphenyl)-2,4-dioxo-N-(4-sulfamoylphenyl)-1H-pyrimidine-5-carboxamide | 1.302310463 | 1.133373422 |
| 5 | ChemDiv | ChemDiv | C066-4801 | N1(CC(C)C)C=C(NC(=O)NCc2ccc(cc23)OC)Oc(c3C1=O)cccc3 | InChI=1/C23H27N3O4/c1-15(2)13-26-14-20(18-7-5-6-8-19(18)22(26)27)25-23(28)24-12-16-9-10-17(29-3)11-21(16)30-4/h5-11,14-15H,12-13H2,1-4H3,(H2,24,25,28) | 409.478180000 | 15987617 | 1-{[2,4-dimethoxyphenyl)methyl}-3-[2-(2-methylpropyl)-1-oxoisoquinolin-4-yl]urea | 1.50747397 | 1.163755459 |
| 5 | ChemDiv | ChemDiv | 3388-1008 | C1(Nc(ccc(c2C)c)c2)=CC(=O)NC(=O)N1 | InChI=1/C12H13N3O2/c1-7-3-4-9(5-8(7)2)13-10-6-11(16)15-12(17)14-10/h3-6H,1-2H3,(H3,13,14,15,16,17) | 231.250510000 | 7337912 | 6-(3,4-Dimethyl-phenylamino)-1H-pyrimidine-2,4-dione | 1.644223938 | 1.290895564 |
| 5 | ChemDiv | ChemDiv | E734-0048 | S(=O)(=O)(Nc(cccc1C(OCC)=O)c1)c(Cl)cc(c23)NC(C(=O)N2)=O)c3 | InChI=1/C18H17N3O6S/c1-3-27-18(24)11-5-4-6-12(8-11)21-28(25,26)15-9-14-13(7-10(15)2)19-16(22)17(23)20-14/h4-9,21H,3H2,1-2H3,(H,19,22)(H,20,23) | 403.409070000 | 16021588 | ethyl 3-{[(7-methyl-2,3-dioxo-1,4-dihydroquinoxalin-6-yl)sulfonylamino]benzoate | 1.54891245 | 1.2721160892 |
| 5 | ChemDiv Targeted Diversity Library | ChemDiv | C301-4603 | c1(C(=O)Oc(c23)cc(c2)Si(=O)(=O)Nc(co4OC)c3n(cn1)CC | InChI=1S/C19H17N3O5S/c1-3-22-11-20-17-18(22)15-10-14(8-9-16(15)27-19(17)23)28(24,25)21-12-4-6-13(26-2)7-5-12/h4-11,21H,3H2,1-2H3 | 399.430000000 | 15990051 | 1-ethyl-N-(4-methoxyphenyl)-4-oxochromeno[3,4-d]imidazole-8-sulfonamide | 1.36625562 | 1.318889017 |

| | | | | | | | |
|---|---|---|---|---|---|---|---|
| | ChemDiv | D205-0473 | n1(nc(n2)NC(=O)c cc3OC)oc(c3OC)O C)c2nc(c4ccccc4)c c1O | InChI=1/C21H19N5O5/c1-29-15-9-13(10-16(30-2)18(15)31-3)19(28)23-20-17(27)26(21)25-20)12-7-5-4-6-8-12/h4-11,27H,1-3H3,(H,23,25,28) | 421.406050 000 | 16013912 | 3-(4-methoxyphenyl)-6-(3,4,5-trimethoxyphenyl)-2H-pyrazolo[3,4-b]pyridine-4-carboxylic acid | 1.8821318 | 1.308049536 |
| | ChemDiv | E455-0186 | c12c(n[nH]c1c3ccc (cc3)OC)nc(c(cc4O C)cc(c4OC)OC)cc2 C(O)=O | InChI=1/C23H21N3O6/c1-29-14-7-5-12(6-8-14)20-19-15(23(27)28)11-16(24-22(19)26-25-20)13-9-17(30-2)21(32-4)18(10-13)31-3/h5-11H,1-4H3,(H,27,28) | 435.429330 000 | 16018592 | 3,4,5-trimethoxy-N-(7-oxo-5-phenyl-1H-[1,2,4]triazolo[1,5-a]pyrimidin-2-yl)benzamide | 1.346649599 | 1.151985246 |
| | ChemDiv | D205-0477 | n1(nc(n2)NC(=O)c 3ccccc3OC)c2nc(c 4ccccc4)cc1O | InChI=1/C19H15N5O3/c1-27-15-10-6-5-9-13(15)17(26)21-18-22-19-20-14(11-16(25)24(19)23-18)12-7-3-2-4-8-12/h2-11,25H,1H3,(H,21,23,26) | 361.354100 000 | 18777725 | 3-(4-chlorophenyl)sulf onyl-N-(2,5-dimethylphenyl)-4-hydroxy-2-oxo-1H-quinoline-7-carboxamide | 1.55873665 | 1.211429221 |
| | ChemDiv | E582-0267 | C1(=C(O)c(c(c2)N C1=O)ccc2C(=O)N c3cc(C)ccc3C)S(= O)(=O)c4ccc(cc4C )15)27- | InChI=1/C24H19ClN2O5S/c1-13-3-4-14(2)19(11-13)26-23(29)15-5-10-18-20(12-24(30)22(21(18)28)33(31,3 2)17-8-6-16(25)7-9-17/h3-12H,1-2H3,(H,26,29)(H2,27,28,30) | 482.936050 000 | 54687805 | N-(7-hydroxy-5-phenyl[1,2,4]triaz olo[1,5-a]pyrimidin-2-yl)-2-methoxybenzami de | 1.22954823 | 1.184065934 |
| | ChemDiv Targeted Diversity Library | C066-2830 | c1(cc(s2)C(O)=O)c 2c3c(ccc(C)c3)NC 1=O | InChI=1S/C13H9NO3S/c1-6-2-3-9-7(4-6)11-8(12(15)14-9)5-10(18-11)13(16)17/h2-5H,1H3,(H,14,15)(H,16,17) | 259.290000 000 | 3493349 | 8-methyl-4-oxo-5H-thieno[3,2-c]quinoline-2-carboxylic acid | 1.277226659 | 1.068089805 |

| | | | | | | | | |
|---|---|---|---|---|---|---|---|---|
| 5 | ChemDiv Targeted Diversity Library | ChemDiv | L220-0095 | N1(CCc(cct(CNS(C)(=O)=O)c2)c12)C(=O)c3ccc(cc3)OC | InChI=1S/C18H20N2O4S/c1-24-16-7-5-15(6-8-16)18(21)20-10-9-14-4-3-13(11-17(14)20)12-19-25(2,22)23/h3-8,11,19H,9-10,12H2,1-2H3 | 360.440000000 | 53010058 | N-[1-(4-methoxybenzoyl)-2,3-dihydroindol-6-yl]methyl]methanesulfonamide | 1.58538224 | 1.08437458 |
| 5 | LINCS4 Kinase Inhibitor Library | EMD | 218714 | C1=CC=C2C(=C1)C(=C3N2C4=CC=CC=C4C(=O)N3)CC(=O)O | InChI=1S/C17H12N2O3/c20-15(21)9-12-10-5-1-3-7-13(10)19-14-8-4-2-6-11(14)17(22)18-16(12)19/h1-8H,9H2,(H,18,22)(H,20,21) | 292.288780 | | 2-(5-oxo-6H-indolo[1,2-a]quinazolin-7-yl)acetic acid | 1.20460411 | 1.049757407 |
| 5 | ChemDiv6 | ChemDiv | E679-0483 | C(NC(=O)Nc1ccccc1)c(ccccc2)c23)=CN(C3=O)c | InChI=1/C19H19N3O2/c1-3-13-7-6-8-14(11-13)20-19(24)21-17-12-22(2)18(23)16-10-5-4-9-15(16)17/h4-12H,3H2,1-2H3,(H2,20,21,24) | 321.373050 | 16021211 | 1-(3-ethylphenyl)-3-(2-methyl-1-oxoisoquinolin-4-yl)urea | 1.235331485 | 1.069666353 |
| 5 | ChemDiv Targeted Diversity Library | ChemDiv | D300-0106 | C1(=O)N(C)c2c(cc(cc2)COc3ccc(cc4)cccC)CNCCc(cc4)N1C | InChI=1S/C26H28FN3O3/c1-29-22-10-6-20(14-23(22)30(2)26(29)31)17-33-24-11-7-19(15-25(24)32-16-28-13-12-18-4-8-21(27)9-5-18)/h4-11,14-15,28H,12-13,16-17H2,1-3H3 | 485.990000 | 17123367 | 5-{[4-({[2-(4-fluorophenyl)ethyl]amino}methyl)-2-methoxyphenoxy]methyl}-1,3-dimethyl-2H-dihydro-2H-benzimidazol-2-one | 1.21365676 | 1.071860401 |
| 5 | ChemDiv6 | ChemDiv | D103-1154 | c1(nnc(C)s1)N([H])C(=O)C2=CC(c3c(cc(C)cc3)O2)=O | InChI=1/C14H11N3O3S/c1-7-3-4-9-10(18)6-12(20-11(9)5-7)13(19)15-14-17-16-8(2)21-14/h3-6H,1-2H3,(H,15,17,19) | 301.320430 | 4898047 | 7-methyl-N-(5-methyl-1,3,4-thiadiazol-2-yl)-4-oxo-4H-chromene-2-carboxamide | 2.13841706 | 1.459342248 |

FIG. 9 (continued)

| | | | | | | | | |
|---|---|---|---|---|---|---|---|---|
| 5 | ChemDiv Targeted Diversity Library | ChemDiv | F232-0763 | C(C(1ccc(cc2)Cl)(S(c3ccccc3)(=O)=O)=C(O)C(N1Cc(cc(c45)OCO4)c5)=O | InChI=1S/C24H18ClNO6S/c1-25-17-9-7-16(8-10-17)21-23(33(29,30)18-4-2-1-3-5-23)18)22(27)24(28)26(21)13-15-6-11-19-20(12-15)32-14-31-19/h1-12,21,27H,13-14H2 | 483.930000 | 53004596 | 1-(1,3-benzodioxol-5-ylmethyl)-5-(4-chlorophenyl)-3-hydroxy-4-(phenylsulfonyl)-1,5-dihydro-2H-pyrrol-2-one | 1.668948689 | 1.189347462 |
| 5 | ChemDiv Targeted Diversity Library | ChemDiv | F232-0766 | C(C(1ccc(cc2)F)(S(c3ccccc3)(=O)=O)=C(O)C(N1Cc(cc(c45)OCO4)c5)=O | InChI=1S/C24H18FNO6S/c1-25-17-9-7-16(8-10-17)21-23(33(29,30)18-4-2-1-3-5-23)18)22(27)24(28)26(21)13-15-6-11-19-20(12-15)32-14-31-19/h1-12,21,27H,13-14H2 | 467.480000 | 53004597 | 1-(1,3-benzodioxol-5-ylmethyl)-5-(4-fluorophenyl)-3-hydroxy-4-(phenylsulfonyl)-1,5-dihydro-2H-pyrrol-2-one | 1.493129998 | 1.131079967 |
| 5 | SYNthesis med chem Kinase Inhibitor 2 | SYNthesis | SYN-1070 | CC(C)[C@H](CO)Nc1nc(c2c(n1)n(cn2)C(C)C)Nc3ccc(c3)C)C(=O)O | InChI=1S/C20H25ClN6O3/c1-10(2)15(8-28)24-20-25-17(16-18(26-20)27(9-22-16)11(3)4)23-12-5-6-13(19(29)30)14(21)7-12/h5-7,9-11,15,28H,8H2,1-4H3,(H,29,30)/H2,23,24,25,26)/t15-/m0/s1 | 432.903890 | | 2-chloro-4-[[2-[[(2R)-1-hydroxy-3-methylbutan-2-yl]amino]-9-propan-2-ylpurin-6-yl]amino]benzoic acid | 1.328151126 | 1.079096639 |
| 5 | ChemDiv Targeted Diversity Library | ChemDiv | C102-0340 | N1C(=O)C=NN=C1Nc(ccc(c2Cl)C)c2 | InChI=1S/C10H9ClN4O/c1-6-2-3-7(4-8(6)11)13-10-14-9(16)5-12-15-10/h2-5H,1H3,(H2,13,14,15,16) | 236.660000 | 2154009 | 3-[(3-chloro-4-methylphenyl)amino]-1,2,4-triazin-5-ol | 1.536173334 | 1.174072714 |
| 5 | ChemDiv6 | ChemDiv | E783-0238 | c1(C(=O)Oc(c23)cc(c2)S(=O)(=O)Nc4cc(OC)cc(OC)c4)c3n(cn1)C | InChI=1/C19H17N3O6S/c1-22-10-20-17-18(22)15-9-14(4-5-16(15)28-19(17)23)29(24,25)21-11-6-12(26-2)8-13(7-11)27-3/h4-10,21H,1-3H3 | 415.419770 | 160222204 | N-(3,5-dimethoxyphenyl)-1-methyl-4-oxochromeno[3,4-d]imidazole-8-sulfonamide | 1.253920B4 | 1.207404246 |

FIG. 9 (continued)

| | | | | | | | |
|---|---|---|---|---|---|---|---|
| 5 | SYNthesis medchem Kinase Inhibitor 2 | SYNthesis | SYN-1113 | c1cc(cc(c1)C(F)(F)F)/C=C/2\C(=O)NC(=O)S2 | InChI=1S/C11H6F3NO2S/c12-11(13,14)7-3-1-2-6(4-7)5-8-9(16)15-10(17)18-8/h1-5H,(H,15,16,17)/b8-5- | | 273.231040 | | 1.81586074 | 1.207994842 |
| 5 | ChemDiv Targeted Diversity Library | ChemDiv | F083-0377 | N1(c2c(cc(OCO3)c3c2)C(N4)=O)C4=C(SC1=S)C(N([H])[H])=O | InChI=1S/C12H7N3O4S2/c13-9(16)8-10-14-11(17)4-1-6-7(19-3-18-6)2-5(4)15(10)12(20)21-8/h1-2H,3H2,(H2,13,16),(H,14,17) | 321.340000 | 50761579 | 5-oxo-1-thioxo-4,5-dihydro[1,3]dioxolo[4,5-g][1,3]thiazolo[3,4-a]quinazoline-3-carboxamide | 1.88146853 | 1.273776224 |
| 5 | ChemDiv6 | ChemDiv | E942-0168 | N1(CC(C)C)C=C(NC(=O)NCc2ccccc2OCC)c(c3C1=O)cccc3 | InChI=1/C23H27N3O3/c1-4-29-21-12-8-5-9-17(21)13-24-16(2)3)22(27)19-11-7-6-10-18(19)20/h5-12,15-16H,4,13-14H2,1-3H3,(H2,24,25,28) | 393.478780 | 16023478 | 1-[(2-ethoxyphenyl)methyl]-3-[2-(2-methylpropyl)-1-oxoisoquinolin-4-yl]urea | 1.69045403 | 1.11335195 |
| 5 | ChemDiv Targeted Diversity Library | ChemDiv | M060-0336 | c12c(ncnc1SCC(N)=O)c3c(cc(OC)c3)OC)[nH]2 | InChI=1S/C14H14N4O3S/c1-20-9-3-7-8(4-10(9)21-2)18-13-12(7)16-6-17-14(13)22-5-11(15)19/h3-4,6,18H,5H2,1-2H3,(H2,15,19) | 318.360000 | 46395888 | 2-[(7,8-dimethoxy-5H-pyrimido[5,4-b]indol-4-yl)sulfanyl]acetamide | 1.36957071 | 1.192929293 |
| 5 | ChemDiv Targeted Diversity Library | ChemDiv | D538-0179 | s1c(C(C)C)nnc1N([H])C(=O)C2=CC(=O)c(c3O2)cccc3C | InChI=1S/C16H15N3O3S/c1-8(2)15-18-19-16(23-15)17-14(21)12-7-11(20)10-6-4-5-9(3)13(10)22-12/h4-8H,1-3H3,(H,17,19,21) | 329.360000 | 19119117 | 8-methyl-4-oxo-N-(5-propan-2-yl-1,3,4-thiadiazol-2-yl)chromene-2-carboxamide | 1.44352302 | 1.176865885 |

FIG. 9 (continued)

| | | | | | | | | |
|---|---|---|---|---|---|---|---|---|
| 5 | | Gray Kinase Inhibitor-Focused Library | Nathanael Gray Lab | AMY001-009 | Clc1ncn2c(ncn2C(C)Cc(Nc3ccc(C(=O)O)cc3)n1 | InChI=1/C15H14ClN5O2/c1-8(2)21-7-17-11-12(19-15(16)20-13(11)21)18-10-6-3-9(4-6-10)14(22)23/h3-8H,1-2H3,(H,18,19,20) | 331.756960000 | 16746121 | 4-{[(2-chloro-9-propan-2-yl-purin-6-yl)amino]benzoic acid | 1.39279833 | 1.09535036 |
| 5 | | ChemDiv Targeted Diversity Library | ChemDiv | D136-0028 | c12c(ccc(c(c3)nc(c4c3C(O)=O)cccc4)c1)noc2c5ccc(cc5)C | InChI=1S/C24H16N2O3/c1-14-6-8-15(9-7-14)23-19-12-16(10-11-21(19)26-29-23)22-13-18(24(27)28)17-4-2-3-5-20(17)25-22/h2-13H,1H3,(H,27,28) | 380.410000000 | 7454989 | 2-[3-(4-methylphenyl)-2,1-benzoxazol-5-yl]quinoline-4-carboxylic acid | 1.57999053 | 1.120331405 |
| 5 | | ChemDiv Targeted Diversity Library | ChemDiv | F083-0413 | N1(c2cc(c(OCO3)c3c2)C(N4)=O)C4=C(SC1=S)C(NCC)=O | InChI=1S/C15H11N3O4S2/c1-2-3-16-14(20)11-12-17-13(19)7-4-9-10(22-6-21-9)5-8(7)18(12)15(23)24-11/h2,4,5H,1,3,6H2,(H,16,20)(H,17,19) | 361.400000000 | 50761931 | N-allyl-5-oxo-1-thioxo-4,5-dihydro[1,3]dioxolo[4,5-g][1,3]thiazolo[3,4-a]quinazoline-3-carboxamide | 3.11675579 | 1.814282531 |
| 6 | | Microsource 1 - US Drug Collection | Microsource | 15008844 | [Co+1]1(C[C@@H]([C@@H]O)C@H](C2n3cnc4c3ncnc4N)O)O2)(N(C(C(C5(C)CC(N)=O)CCC(N)=O)=O)C(C57C)([NH](C78)=C9C(C8C(N)=O)CCC(C(N)=O)=O)[O-48)(68)82)36(14-17-45(6C)OP(=O)([O-48)(68)82)36(14-17-45(6C)ONCC(OP(=O)([O-48)(68)82)36(14-17-45(6C) | InChI=1S/C62H90N13O14P.C10H12N5O3.Co/c1-29-20-39-40(21-30(29)2)75(28-70-39)57-52(84)53(41(27-76)87-67)89-90(85,86)88-31(3)26-69-49(83)18-19-59(8)37(22-46(66)80)56-62(11)61(10,25-62(11)61(10,25- | 1579.58176 0000 | 16717690 | Coenzyme b12 | 2.1801513 | 2.018335684 |
| 7 | | ChemDiv Targeted Diversity Library | ChemDiv | T636-0444 | n1c(NCc(cc2)ccn2)c3c(nc1C4CC4)CCC3 | InChI=1S/C16H18N4/c1-2-13-14(3-1)19-15(12-4-5-12)20-16(13)18-10-11-6-8-17-9-7-11/h6-9,12H,1-5,10H2,(H,18,19,20) | 266.350000000 | 53192892 | N-(2-cyclopropyl-6,7-dihydro-5H-cyclopenta[d]pyrimidin-4-yl)-N-(4-pyridylmethyl)amine | 1.93576412 | 1.428853495 |

FIG. 9 (continued)

| | | | | | | | | |
|---|---|---|---|---|---|---|---|---|
| 7 | ChemDiv Targeted Diversity Library | ChemDiv | D341-0243 | c1(ncnc2N([H])Cc cc3)ccn3)c2c4c(C CCC4)s1 | InChI=1S/C16H16N4S/c1-2-4-13-12(3-1)14-15/(19-10-20-16(14)21-13)18-9-11-5-7-17-8-6-11/h5-8,10H,1-4,9H2,(H,18,19,20) | 296.400000 | 170113100 | N-(pyridin-4-ylmethyl)-5,6,7,8-tetrahydro[1]benzothieno[2,3-d]pyrimidin-4-amine | 2.27909542 | 1.620932157 |
| 7 | ChemDiv6 | ChemDiv | 2425-4322 | c1(NC(=O)c2ccccc 2C(O)=O)sc(c3c1C (OC)=O)CCCC3 | InChI=1/C18H17NO5S/c1-24-18(23)14-12-8-4-5-9-13(12)25-16(14)19-15(20)10-6-2-3-7-11(10)17(21)22/h2-3,6-7H,4-5,8-9H2,1H3,(H,19,20)(H,21,22) | 359.396270 000 | 1011051 | 2-({[3-(methoxycarbonyl)-4,5,6,7-tetrahydro-1-benzothien-2-yl]amino}carbonyl)benzoic acid | 1.60693591 | 1.199122037 |
| 7 | ChemDiv Targeted Diversity Library | ChemDiv | M467-0616 | S(=O)(=O)(c1ccc(c 2c1CCC2)Nc3onc (c4ccoc4)c3 | InChI=1S/C16H14N2O4S/c1-19-23(20,14-5-4-11-2-1-3-12(11)8-14)18-16-9-15(17-22-16)13-6-7-21-10-13/h4-10,18H,1-3H2 | 330.360000 000 | 53143425 | N-[3-(3-furyl)isoxazol-5-yl]indane-5-sulfonamide | 1.55639176 | 1.132643462 |
| 7 | ChemDiv Targeted Diversity Library | ChemDiv | 8510-0385 | C(=O)(c(ccnn1)c1) Nc2cccc(cccc(C)n3) c23 | InChI=1S/C16H13N3O/c1-11-7-8-12-4-2-6-14(15(12)18-11)19-16(20)13-5-3-9-17-10-13/h2-10H,1H3,(H,19,20) | 263.300000 000 | 6493931 | 6-phenyl-2-(pyridin-3-ylmethylamino)-1H-pyrimidin-4-one | 1.23295038 | 1.084820337 |
| 7 | ChemDiv Targeted Diversity Library | ChemDiv | D306-1230 | N(C(c1ccccc1)=CC (N2)=C2NCc(c ccn3)c3 | InChI=1S/C16H14N4O/c21-15-9-14(13-6-2-1-3-7-13)19-16(20-15)18-11-12-5-4-8-17-10-12/h1-10H,11H2,(H2,18,19,20,21) | 278.320000 000 | 16957576 | 6-phenyl-2-(pyridin-3-ylmethylamino)-1H-pyrimidin-4-one | 1.42633275 | 1.187902753 |

FIG. 9 (continued)

| | | | | | | | | |
|---|---|---|---|---|---|---|---|---|
| | 7 | Gray Kinase Inhibitor-Focused Library | Nathanael Gray Lab | XMD7-1 | Nc1ncc(c2coc(C(=O)N)ccc2)nc1C(=O)c3cccnc3 | InChI=1/S/C17H13N5O2/c18-16-14(15(23)12-5-2-6-20-8-12)22-13(9-21-16)10-3-1-4-11(7-10)17(19)24/h1-9H,(H2,18,21)(H2,19,24) | 319.317420000 | 42628504 | 3-(5-amino-6-(pyridine-3-carbonyl)pyrazin-2-yl)benzamide | 1.42059861 | 1.104430793 |
| | 7 | ChemDiv Targeted Diversity Library | ChemDiv | C301-4299 | n1(nc(n2)CCC)c2nc(C)c(NS(=O)(=O)c(cc3)ccc3C4CCCC4)c1O | InChI=1S/C21H27N5O3S/c1-3-7-18-23-21-22-14(2)19(20(27)26(21)24-18)25-30(28,29)17-12-10-16(11-13-17)15-8-5-4-6-9-15/h10-13,15,25,27H,3-9H2,1-2H3 | 429.550000000 | 22432385 | 4-cyclohexyl-N-(5-methyl-7-oxo-2-propyl-1H-[1,2,4]triazolo[1,5-a]pyrimidin-6-yl)benzenesulfonamide | 1.46497306 | 1.210803182 |
| | 7 | Biomol 4 - FDA Approved Drug Library | BIOMOL | DL-275 | n1nc(Cc2cccnc2)cccc3)c3c1Nc4ccc(Cl)cc4 | InChI=1S/C20H15ClN4/c21-15-5-7-16(8-6-15)23-20-18-4-2-1-3-17(18)19(24-25-20)13-14-9-11-22-12-10-14/h1-12H,13H2,(H,23,25) | 346.812900000 | 151194 | Vatalanib | 1.27536363 | 1.132696831 |
| | 7 | ChemDiv6 | ChemDiv | E010-0082 | c12c(CCc(cn3)c1fnH3)oc(C(=O)NCc4ccccc4)c2C | InChI=1S/C18H17N3O2/c1-11-15-14(8-7-13-10-20-21-16(13)15)23-17(11)18(22)19-9-12-5-3-2-4-6-12/h2-6,10H,7-9H2,1H3,(H,19,22)(H,20,21) | 307.346480000 | 16016780 | N-benzyl-8-methyl-4,5-dihydro-1H-furo[2,3-g]indazole-7-carboxamide | 1.35243847 | 1.09446217 |
| | 7 | ChemDiv Targeted Diversity Library | ChemDiv | G856-6719 | c1(nnc2SCC(=O)Nc3sc(c4c3C(OCC)=O)CCCCC4)n2C(=CC(=O)N1)C | InChI=1S/C20H23N5O4S2/c1-3-29-18(28)16-12-7-5-4-6-8-13(12)31-17(16)21-15(27)10-30-20-24-23-19-22-14(26)9-11(2)25(19)20/h9H,3-8,10H2,1-2H3,(H,21,27)(H,22,23,26) | 461.570000000 | 26842626 | ethyl 2-[[2-{[5-methyl-7-oxo-1H-[1,2,4]triazolo[4,3-a]pyrimidin-3-yl]sulfanyl]acetyl]amino]-5,6,7,8-tetrahydro-4H-cyclohepta[b]thiophene-3- | 1.4142093 | 1.037992045 |

FIG. 9 (continued)

| | | | | | | | |
|---|---|---|---|---|---|---|---|
| 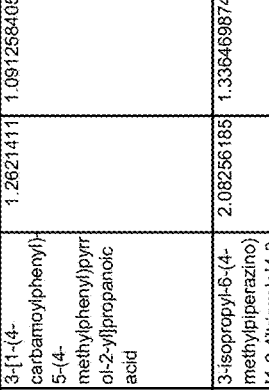 | 7 | ChemDiv6 | ChemDiv | D135-0013 | n1(c(cc2)ccc2C(N)=O)c(CCC(O)=O)cc1c3ccc(cc3)C | InChI=1/C21H20N2O3/c1-14-2-4-15(5-3-14)19-12-10-18(11-13-20(24)25)23(19)17-8-6-16(7-9-17)21(22)26/h2-10,12H,11,13H2,1H3,(H2,2 2,26)(H,24,25) | 348.395090 000 | 935492 | 3-[1-(4-carbamoylphenyl)-5-(4-methylphenyl)pyrrol-2-yl]propanoic acid | 1.2621411 | 1.091258405 |
| 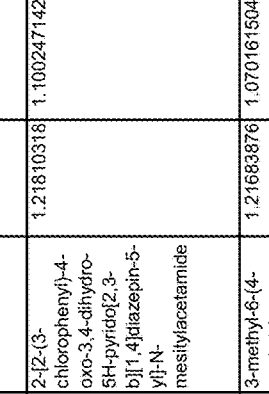 | 8 | ChemDiv Targeted Diversity Library | ChemDiv | Z606-3803 | n12c(ccc(N(CC3)CN3C)n1)nnc2C(C)C | InChI=1S/C13H20N6/c1-10(2)13-15-14-11-4-5-12(16-19(11)13)18-8-6-17(3)7-9-18/h4-5,10H,6-9H2,1-3H3 | 260.340000 000 | 53016942 | 3-isopropyl-6-(4-methylpiperazino)[1,2,4]triazolo[4,3-b]pyridazine | 2.08256185 | 1.336469874 |
| 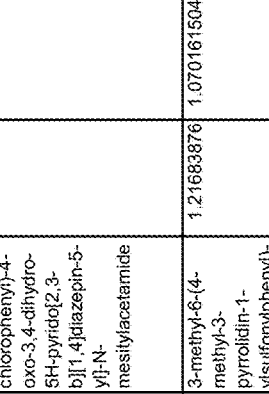 | 8 | ChemDiv Targeted Diversity Library | ChemDiv | L550-2314 | n12c(ccc(N(CC3)CN3c4cccccn4)n1)nc2CCc5onc(c(cc6)ccn6)n5 | InChI=1S/C23H22N10O/c1-2-10-25-18(3-1)31-13-15-32(16-14-31)21-5-4-19-27-28-20(33(19)29-21)6-7-22-26-23(30-34-22)17-8-11-24-12-9-17/h1-5,8-12H,6-7,13-16H2 | 454.500000 000 | 50829543 | 2-[2-(3-chlorophenyl)-4-oxo-3,4-dihydro-5H-pyrido[2,3-b][1,4]diazepin-5-yl]-N-mesitylacetamide | 1.21810318 | 1.100247142 |
| 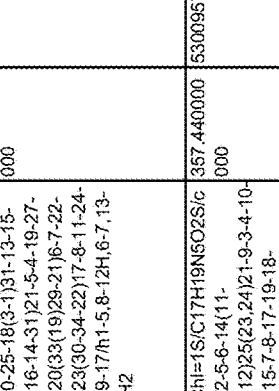 | 8 | ChemDiv Targeted Diversity Library | ChemDiv | J003-0214 | S(=O)(=O)(N1CCCC1)c2c(C)ccc(c2)ccc3n4c(C)nn3)n4 | InChI=1S/C17H19N5O2S/c1-12-5-6-14(11-16(12)25(23,24)21-9-3-4-10-21)15-7-8-17-19-18-13(2)22(17)20-15/h5-8,11H,3-4,9-10H2,1-2H3 | 357.440000 000 | 53009576 | 3-methyl-6-(4-methyl-3-pyrrolidin-1-ylsulfonylphenyl)[1,2,4]triazolo[4,3-b]pyridazine | 1.21683876 | 1.070161504 |
| 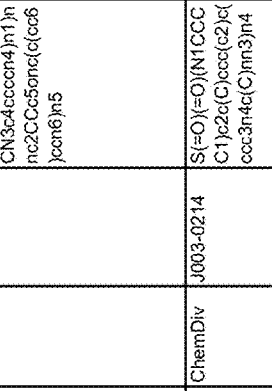 | 8 | Microsource 1 - US Drug Collection | Microsource | 1505305 | C(C(O)=O)(=CN(c1c2cc(c(N(CCN3C)CC3)c1F)CC)C2=O.S(C)(O)(=O)=O | InChI=1S/C17H20FN3O3.CH4O3S/c1-3-20-10-12(17(23)24)16(22)11-8-13(18)15(9-14(11)20)21-6-4-19(2)5-7-21,1-5(2,3)4/h8-10H,3-7H2,1-2H3,(H,23,24);1H3,(H,2,3,4) | 429.463060 000 | 1119525 | Pefloxacine mesylate | 1.21762402 | 1.039556136 |

FIG. 9 (continued)

| | | | | | | | |
|---|---|---|---|---|---|---|---|
| ![structure] | 9 | LINCS4 Kinase Inhibitor Library | MedChem Express | HY-13522 | CN(CC1=CC2=C(S1)C(=NC(=N2)C3=CN=C(C=C3)OC)N4CCOCC4)C5=NC=C(C=N5)C(=O)NO | InChI=1S/C23H24N8O4S/c1-30(23-25-11-15(12-26-23)22(32)29-33)13-16-9-17-19(36-16)21(31-5-7-35-8-6-31)28-20(27-17)14-3-4-18(34-2)24-10-14/h3-4,9-12,33H,5-8,13H2,1-2H3,(H,29,32) | 508.552850000 | | N-hydroxy-2-{[2-(6-methoxypyridin-3-yl)-4-morpholin-4-yl]thieno[3,2-d]pyrimidin-6-yl]methyl-methylamino}pyrimidine-5-carboxamide | 2.52839972 | 1.905373556 |
| ![structure] | 9 | ChemDiv Targeted Diversity Library | ChemDiv | C696-0377 | c1(c2c(cccc2)c(nn1)Cc(cc3)ccn3)N4CCC(CC4)C(OCC)=O | InChI=1S/C22H24N4O2/c1-2-28-22(27)17-9-13-26(14-10-17)21-19-6-4-3-5-18(19)20(24-25-21)15-16-7-11-23-12-8-16/h3-8,11-12,17H,2,9-10,13-15H2,1H3 | 376.460000000 | 20875726 | Ethyl 1-[4-(pyridin-4-ylmethyl)phthalazin-1-yl]piperidine-4-carboxylate | 1.80712366 | 1.307526682 |
| ![structure] | 9 | ChemDiv6 | ChemDiv | E143-0212 | n1(c(cccc2)c2C(N3CCc4cccc4)=O)c3nnc1c5cccc(OC)c5=O | InChI=1/C24H20N4O3/c1-31-20-13-7-11-18(21(20)29)22-25-26-24-27(15-14-16-8-3-2-4-9-16)23(30)17-10-5-6-12-19(17)28(22)24/h2-13,29H,14-15H2,1H3 | 412.440600000 | 16017255 | (1Z)-1-(5-methoxy-6-oxocyclohexa-2,4-dien-1-ylidene)-4-(2-phenylethyl)-2H-[1,2,4]triazolo[4,3-a]quinazolin-5-one | 1.2190984 | 1.173170141 |
| ![structure] | 9 | ChemDiv Targeted Diversity Library | ChemDiv | Z084-0003 | c12c(scc1C(=O)N=CNC2=O | InChI=1S/C7H4N2O3S/c10-5-4-3(7(11)12)1-13-6(4)9-2-8-5/h1-2H,(H,11,12)(H,8,9,10) | 196.190000000 | 52983816 | 4-Oxo-3,4-dihydrothieno[2,3-d]pyrimidine-5-carboxylic acid | 1.31058534 | 1.136487965 |
| ![structure] | 10 | LINCS4 Kinase Inhibitor Library | Haoyuan chemexpress | HY-13022 | C1CCN(CC1)CCOC2=CC=CC(=C2)C3=NNC4=C3C=C(C=C4)C5=NC=NN5 | InChI=1S/C22H24N6O/c1-2-9-28(10-3-1)11-12-29-18-6-4-5-16(13-18)21-19-14-17(22-23-15-24-27-22)7-8-20(19)25-26-21/h4-8,13-15H,1-3,9-12H2,(H,25,26)(H,23,24,27) | 388.465560000 | | 3-[3-(2-piperidin-1-ylethoxy)phenyl]-5-(1H-1,2,4-triazol-5-yl)-1H-indazole | 1.2392866 | 1.075427297 |

FIG. 9 (continued)

| | | | | | | | |
|---|---|---|---|---|---|---|---|
| | 10 | SYNthesis med chem Kinase Inhibitor 2 | SYNthesis | SYN-1028 | c1ccc(c(c1)OCCN2 CCCCC2)c3c4cc(c cc4[nH]n3)c5nc[nH] n5.Cl | InChI=1S/C22H24N6O.ClH/c1-2-9-28(10-3-1)11-12-29-18-6-4-5-16(13-18)21-19-14-17(22-23-15-24-27-22)7-8-20(19)25-26-21/h4-8,13-15H,1-3,9-12H2,(H,25,26)(H,23,24,27);1H | 424.926490000 | | 3-[3-(2-piperidin-1-yl)ethoxy)phenyl]-5-(1H-1,2,4-triazol-5-yl)-1H-indazole chloride | 1.66074265 | 1.144658359 |
| | 10 | ChemDiv Targeted Diversity Library | ChemDiv | C712-0108 | c12c(COc(cccc3C) c13)cc(C(NCCCN4 CCC(CC4)C)=O)s2 | InChI=1S/C22H28N2O2S/c1-15-7-11-24(12-8-15)10-4-9-23-22(25)19-13-17-14-26-18-6-3-5-16(2)20(18)21(17)27-19/h3,5-6,13,15H,4,7-12,14H2,1-2H3 | 384.540000000 | 20877745 | 9-methyl-N-[3-(4-methylpiperidin-1-yl)propyl]-4H-thieno[3,2-c]chromene-2-carboxamide | 1.22794682 | 1.094988494 |
| | 10 | ChemDiv6 | ChemDiv | 41109-2013 | S(=O)(=O)(N(C)C) c1c(C)ccc(c1)c2c3 c(cccc3)c(nn2)Nc(c c4)ccc4OCC(N)=O | InChI=1/C25H25N5O4S/c1-16-8-9-17(14-22(16)35(32,33)30(2)3)24-20-6-4-5-7-21(20)25(29-28-24)27-18-10-12-19(13-11-18)34-15-23(26)31/h4-14H,15H2,1-3H3,(H2,26,31)(H,27,29) | 491.562090000 | 1417297 | 2-[4-(4-[3-(dimethylsulfamoyl)-4-methylphenyl]phthalazin-1-yl]amino)phenoxy]acetamide | 1.56158314 | 1.324308359 |
| | 10 | ChemDiv6 | ChemDiv | C620-0708 | c(c(c1c(C2=O)cccc 1)on3)c34)c2c(cc4 N(C5)CCN5C6C CCCC6)NCCCN(C) C | InChI=1/C29H37N5O2/c1-32(2)14-8-13-30-23-19-24(34-17-15-33(16-18-25(23)28(35)21-11-6-7-12-22(21)29(26)36-31-27)/h6-7,11-12,19-20,30H,3-5,8-10,13-18H2,1-2H3 | 487.636370000 | 16009259 | 3-(4-cyclohexylpiperazin-1-yl)-5-{[3-(dimethylamino)propyl]amino}-6H-anthra[1,9-cd]isoxazol-6-one | 1.20868516 | 1.14628797 |
| | 10 | ChemBridge Focused Kinase-Based Core | ChemBridge | 232333655 | c1([nH]c(n2)c3cccc c3OC(F)F)c2n(nc1 c(cccn4)c4)C | InChI=1S/C17H13F2N5O/c1-24-16-14(13(23-24)10-5-4-000 8-20-9-10)21-15(22-16)11-6-2-3-7-12(11)25-17(18)19/h2-9,17H,1H3,(H,21,22) | 341.322860000 | 46984786 | 5-[2-(difluoromethoxy)phenyl]-1-methyl-3-pyridin-3-yl-2H-imidazo[4,5-c]pyrazole | 1.42541888 | 1.096580847 |

FIG. 9 (continued)

| | | | | | | | | | |
|---|---|---|---|---|---|---|---|---|---|
| 11 | Biomol 4 - FDA Approved Drug Library | BIOMOL | DL-252 | c1(cc(O)c(O)c([N+]([O-])=O)c1)C(=O)c2ccc(C)cc2 | InChI=1S/C14H11NO5/c1-8-2-4-9(5-3-8)13(17)10-6-11(15)(19)20)14(18)12(16)7-10/h2-7,16,18H,1H3 | 273.240830 000 | | Tolcapone | 1.25360058 | 1.042246759 |
| 11 | LINCS4 Kinase Inhibitor Library | MedChem Express | HY-B0183 | C1=C2C3=C(C(=C1O)OC(=O)C4=CC(=C(C(=C43)OC2=O)O)O | InChI=1S/C14H6O8/c15-5-1-3-7-8-4(14(20)22-6(16)10(18)12(8)21-13(3)19)/h19/h1-2,15-18H | 302.192630 000 | 4659569 | Ellagic acid | 1.74373512 | 1.294704615 |
| 11 | LINCS4 Kinase Inhibitor Library | EMD | 655203 | CC1=CC(=CC(=CC1O)C)C=C2C(=O)C=CC2=O | InChI=1S/C14H12O3/c1-8-5-10(6-9(2)14(8)17)7-11-12(15)3-4-13(11)16/h3-7,17H,1-2H3 | 228.243280 000 | | 2-[(4-hydroxy-3,5-dimethylphenyl)methylene]cyclopent-4-ene-1,3-dione | 2.55985877 | 1.577623304 |
| 11 | ChemDiv Targeted Diversity Library | ChemDiv | D715-2437 | C1(=C2CCCC1)c3c(OC2=O)cc(O)c(O)c3 | InChI=1S/C13H12O4/c14-10-5-9-7-3-1-2-4-8(7)13(16)17-12(9)6-11(10)15/h5-6,14-15H,1-4H2 | 232.240000 000 | 5454495 | 2,3-dihydroxy-7,8,9,10-tetrahydro-6H-benzo[c]chromen-6-one | 1.6150824 | 1.195241733 |
| 11 | ChemDiv Targeted Diversity Library | ChemDiv | C200-8712 | c1(c(C)sc(c2ccc(cc2)CC)n1)c([nH]nc3C(O)=O)c3 | InChI=1S/C16H15N3O2S/c1-3-10-4-6-11(7-5-10)15-17-14(9(2)22-15)12-8-13(16(20)21)19-18-12/h4-8H,3H2,1-2H3,(H,18,19)(H,20,21) | 313.380000 000 | 50743186 | 3-[2-(4-ethylphenyl)-5-methyl-1,3-thiazol-4-yl]-1H-pyrazole-5-carboxylic acid | 1.38325383 | 1.104318353 |

FIG. 9 (continued)

| | | | | | | | | |
|---|---|---|---|---|---|---|---|---|
| 12 | ChemDiv Targeted Diversity Library | ChemDiv | D094-0034 | c1(nc(c2C(OCC)=O)C)n2c3c(cccc3)n1C | InChI=1S/C14H15NO2/c1-4-19-13(18)12-9(2)15-14-16(3)10-7-5-6-8-11(10)17(12)14/h5-8H,4H2,1-3H3 | 257.290000 000 | 3264092 | ethyl 2,4-dimethylimidazo[1,2-a]benzimidazole-1-carboxylate | 1.29970246 | 1.145793887 |
| 12 | ChemDiv Targeted Diversity Library | ChemDiv | D058-0287 | c12n(c3c(cccc3)n1c4cccc4)c(nn2)SCC(O)=O | InChI=1S/C16H12N4O2S/c21-14(22)10-23-16-18-17-15-19(11-6-2-1-3-7-11)12-8-4-5-9-13(12)20(15)16/h1-9H,10H2,(H,21,22) | 324.360000 000 | 2772582 | [(9-Phenyl-9H-[1,2,4]triazolo[4,3-a]benzimidazol-3-yl)thio]acetic acid | 1.70392262 | 1.249328318 |
| 12 | ChemDiv Targeted Diversity Library | ChemDiv | 6048-0117 | c1(NC(=O)c2cnccn2)sc(c(C)c1C(OCC)=O)C(N)=O | InChI=1S/C14H14N4O4S/c1-3-22-14(21)9-7(2)10(11(15)19)23-13(9)18-12(20)8-6-16-4-5-17-8/h4-6H,3H2,1-2H3,(H,15,19)(H,17,18,20) | 334.360000 000 | 5169463 | ethyl 5-carbamoyl-4-methyl-2-(pyrazine-2-carbonylamino)thiophene-3-carboxylate | 1.31308149 | 1.137989015 |
| 13 | ChemDiv Targeted Diversity Library | ChemDiv | D585-0116 | n(c1SCc2c(cccc2F)c([nH]cn3)c3c(O)n1 | InChI=1S/C12H8ClFN4OS/c13-7-2-1-3-8(14)6(7)4-20-12-17-10-9(11(19)18-12)15-5-16-10/h1-3,5H,4H2,(H2,15,16,17,18,19) | 310.740000 000 | 50754022 | 2-[(2-chloro-6-fluorobenzyl)thio]-9H-purin-6-ol | 1.42920254 | 1.128228364 |
| 13 | ChemDiv Targeted Diversity Library | ChemDiv | D071-0031 | n(c1SCc(cc2)ccc2F)c([nH]cn3)c3c(O)n1 | InChI=1S/C12H9FN4OS/c1-3-8-1-7(2-4-8)5-19-12-16-10-9(11(18)17-12)14-6-15-10/h1-4,6H,5H2,(H2,14,15,16,17,18) | 276.290000 000 | 2301965 | 2-[(4-fluorophenyl)methylsulfanyl]-3,7-dihydropurin-6-one | 1.43122924 | 1.153488372 |

FIG. 9 (continued)

| | | | | | | | |
|---|---|---|---|---|---|---|---|
| ![structure] | 14 | ChemDiv Targeted Diversity Library | ChemDiv | D148-0362 | c(sc(c12)nc(c(Br)c 1COC)C)(C3=O)c2 N=NN3c4ccccc4C( OC)=O | InChI=1S/C19H15BrN4O4S /c1-9-14(20)11(8-27-2)13-15-16(29-17(13)21-9)18(25)24(23-22-15)12-7-5-4-6-10(12)19(26)28-3/h4-7H,8H2,1-3H3 | 475.320000 000 | 23606314 | methyl 2-[8-bromo-9-(methoxymethyl)-7-methyl-4-oxopyrido[1,2]thieno[3,4-b]triazin-3-yl]benzoate | 1.995491911 | 1.41315301 |
| ![structure] | 14 | ChemDiv Targeted Diversity Library | ChemDiv | K784-4049 | c1(nc(C)c(c2O)C)n 2ncc1C(=O)NCc(c cc(c34)OCO3)c4 | InChI=1S/C16H13ClN4O4/c 1-8-13(17)16(23)21-14(20-8)10(6-19-21)15(22)18-5-9-2-3-11-12(4-9)25-7-24-11/h2-4,6,23H,5,7H2,1H3,(H,18,2 2) | 360.760000 000 | 3244191 | N-(1,3-benzodioxol-5-ylmethyl)-6-chloro-5-methyl-7-oxo-1H-pyrazolo[1,5-a]pyrimidine-3-carboxamide | 1.583986656 | 1.165313550 |
| ![structure] | 14 | ChemDiv Targeted Diversity Library | ChemDiv | C660-0966 | c12c(c(nn1c3ccc(c c3)Cl)C)cc(C(O)=O )s2 | InChI=1S/C13H9ClN2O2S/c 1-7-10-6-11(13(17)18)19-12(10)16(15-7)9-4-2-8(14)3-5-9/h2-6H,1H3,(H,17,18) | 292.750000 000 | 2314951 | 1-(4-Chlorophenyl)-3-methyl-1H-thieno[2,3-c]pyrazole-5-carboxylic acid | 1.2288049 | 1.073416752 |
| ![structure] | 14 | ChemDiv Targeted Diversity Library | ChemDiv | C301-9061 | c12c(n(c(Sc(nnc3N C(=O)c4ccccc4Br) s3)n1)C)N(C)c(=O)N2C)=O | InChI=1S/C17H14BrN7O3S 2/c1-23-10-11(24(2)17(28)25(3)13(10)2 7)19-15(23)30-16-22-21-14(29-16)20-12(26)8-4-5-7-9(8)18/h4-7H,1-3H3,(H,20,21,26) | 508.380000 000 | 50744020 | 2-bromo-N-(5-[[(1,3,7-trimethyl-2,6-dioxo-2,3,6,7-tetrahydro-1H-purin-8-yl)thio]-1,3,4-thiadiazol-2-yl]benzamide | 1.288104498 | 1.107031062 |
| ![structure] | 14 | ChemDiv6 | ChemDiv | E010-0092 | c1(c(CCc(cn2)c1fn H2)oc3C(=O)Nc4c (C)ccc(Cl)c4)c3C | InChI=1/C18H16ClN3O2/c1-9-3-5-12(19)7-13(9)21-18(23)17-10(2)15-14(24-17)6-4-11-8-20-22-16(11)15/h3,5,7-8H,4,6H2,1 2H3,(H,20,22)(H,21,23) | 341.791540 000 | 16016782 | N-(5-chloro-2-methylphenyl)-8-methyl-4,5-dihydro-1H-furo[2,3-g]indazole-7-carboxamide | 1.866962584 | 1.277945619 |

FIG. 9 (continued)

| | | | | | | | | |
|---|---|---|---|---|---|---|---|---|
| | 15 | ChemDiv Targeted Diversity Library | ChemDiv | C200-4692 | C12=C(SC(=S)N1CC)CN3C(c4c(ccc4)C(N3)=O)=N2)=O | InChI=1S/C14H10N4O2S2/c1-2-17-11-9(22-14(17)21)13(20)18-10(15-11)7-5-3-4-6-8(7)12(19)16-18/h3-6H,2H2,1H3,(H,16,19) | 330.390000000 | | 11-ethyl-10-thioxo-10,11-dihydro-6H-[1,3]thiazolo[4',5':4,5]pyrimido[2,1-a]phthalazine-5,8-dione | 1.360028669 | 1.068013388 |
| | 15 | ChemDiv Targeted Diversity Library | ChemDiv | C200-7327 | C1(=NNC2=S)N2c(ccc3)c3C(=O)N1CC(C)C | InChI=1S/C13H14N4OS/c1-8(2)7-16-11(18)9-5-3-4-6-10(9)17-12(16)14-15-13(17)19/h3-6,8H,7H2,1-2H3,(H,15,19) | 274.350000000 | 45106029 46507185 | 4-isobutyl-1-thioxo-2,4-dihydro[1,2,4]triazolo[4,3-a]quinazolin-5(1H)-one | 1.278013389 | 1.093396911 |
| | 15 | ChemDiv Targeted Diversity Library | ChemDiv | C200-7326 | C1(=NNC2=S)N2c(c3C(=O)N1CCC(C)C)cccc3 | InChI=1S/C14H16N4OS/c1-9(2)7-8-17-12(19)10-5-3-4-6-11(10)18-13(17)15-16-14(18)20/h3-6,9H,7-8H2,1-2H3,(H,15,19) | 288.370000000 | 2120341 | 1-mercapto-4-(3-methylbutyl)[1,2,4]triazolo[4,3-a]quinazolin-5(4H)-one | 1.870190002 | 1.371733967 |
| | 15 | ChemDiv Targeted Diversity Library | ChemDiv | C200-7262 | C1(=NNC2=S)N2c(c3C(=O)N1Cc4ccc(cc4)occ3 | InChI=1S/C17H10N4O2S2/c19-12-11-10(6-7-21-11)18-13(15-16-14(18)20)17(12)8-9-4-2-1-3-5-9/h1-7H,8H2,(H,16,20) | 314.390000000 | 46507169 | 4-benzyl-1-thioxo-2,4-dihydrothieno[2,3-e][1,2,4]triazolo[4,3-a]pyrimidin-5(1H)-one | 1.322361047 | 1.11001378 |
| | 15 | ChemDiv Targeted Diversity Library | ChemDiv | C200-7013 | C1(=NNC2=S)N2c(c3C(=O)N1Cc(cc4)ccc4CC)ccs3 | InChI=1S/C16H14N4OS2/c1-2-10-3-5-11(6-4-10)9-19-14(21)13-12(7-8-23-13)20-15(19)17-18-16(20)22/h3-8H,2,9H2,1H3,(H,18,22) | 342.440000000 | 46507134 | 4-(4-ethylbenzyl)-1-thioxo-2,4-dihydrothieno[2,3-e][1,2,4]triazolo[4,3-a]pyrimidin-5(1H)-one | 1.423175509 | 1.719499745 |

FIG. 9 (continued)

| | Source | ID | SMILES | InChI | MW | CID | Name | | |
|---|---|---|---|---|---|---|---|---|---|
| 15 | ChemDiv6 | E942-0326 | N1(CC(C)C)C(=C(N C(=O)NCc2ccccc2)c(c3C1=O)cccc3 | InChI=1/C21H23N3O2/c1-15(2)13-24-14-19(17-10-6-7-11-18(17)20(24)25)23-21(26)22-12-16-8-4-3-5-9-16/h3-11,14-15H,12-13H2,1-2H3,(H2,22,23,26) | 349.426220 000 | 16023510 | 1-benzyl-3-(2-(2-methylpropyl)-1-oxoisoquinolin-4-yl)urea | 1.57440737 | 1.099209833 |
| 15 | ChemDiv6 | E942-0186 | N1(CC(C)C)C(=C(N C(=O)NCc(cc2)ccc 2C)c(c3C1=O)cccc 3 | InChI=1/C22H25N3O2/c1-15(2)13-25-14-20(18-6-4-5-7-19(18)21(25)26)24-22(27)23-12-17-10-8-16(3)9-11-17/h4-11,14-15H,12-13H2,1-3H3,(H2,23,24,27) | 363.452800 000 | 16023480 | 1-[(4-methylphenyl)methyl]-3-[2-(2-methylpropyl)-1-oxoisoquinolin-4-yl]urea | 1.51783233 | 1.141848078 |
| 15 | ChemDiv Targeted Diversity Library | E580-0014 | N1(Cc2ccccc2)C(=O)C3=C(N=C1SCC(=O)N4CCC(CC4)C)CCS3 | InChI=1S/C21H25N3O2S2/c1-15-7-10-23(11-8-15)18(25)14-28-21-22-17-9-12-27-19(17)20(26)24(21)13-16-5-3-2-4-6-16/h2-6,15H,7-14H2,1H3 | 415.580000 000 | 20902182 | 3-benzyl-2-(4-methylpiperidin-1-yl)-2-oxoethyl)thio)-6,7-dihydrothieno[3,2-d]pyrimidin-4(3H)-one | 1.34185867 | 1.197993606 |
| 15 | ChemDiv Targeted Diversity Library | C696-0933 | N1(CC(=O)N(CC2)CC=C2c3ccccc3)C(=O)c4c(C(c(cc5)ccn5)=N1)cccc4 | InChI=1S/C27H24N4O2/c3 2-26(30-16-12-22(13-17-30)21-6-2-1-3-7-21)19-31-27(33)24-9-5-4-8-23(24)25(29-31)18-20-10-14-28-15-11-20/h1-12,14-15H,13,16-19H2 | 436.520000 000 | 20875875 | 2-[2-oxo-2-(4-phenyl-3,6-dihydropyridin-1(2H)-yl)ethyl]-4-(pyridin-4-yl)methyl)phthalazin-1(2H)-one | 1.27423487 | 1.093029527 |
| 16 | ChemDiv Targeted Diversity Library | D361-0309 | c12c(C(C(=O)N1)c3ccc(cc3)O)c(nn2c(ccc(n4c5)nn5)n4)C | InChI=1S/C18H15N7O2/c1-10-17-13(11-2-4-12(26)5-3-10)8-16(27)20-18(17)25(22-10)15-7-6-14-21-19-9-24(14)23-15/h2-7,9,13,26H,8H2,1H3,(H,20,27) | 361.370000 000 | 49654574 | 4-(4-hydroxyphenyl)-3-methyl-1-([1,2,4]triazolo[4,3-b]pyridazin-6-yl)-4,5-dihydro-2H-pyrazolo[3,4-b]pyridin-6-one | 1.24253076 | 1.117896895 |

FIG. 9 (continued)

| | | | | | | | | |
|---|---|---|---|---|---|---|---|---|
| 16 | ChemDiv Targeted Diversity Library | ChemDiv | J081-0512 | c12c(C(CCC(=O)N1)c3ccc(cc3)O)cnn2c(ccc4n5c(C)nn4)n5 | InChI=1S/C18H15N7O2/c1-10-21-22-15-6-7-16(25-13(8-17(27)20-18)11-2-4-24(10)15)25-18-14(9-19-12(26)5-3-11/h2-7,9,13,26H,8H2,1H3,(H,20,27) | 361.370000000 | 4-(4-hydroxyphenyl)-1-(3-methyl[1,2,4]triazolo[4,3-b]pyridazin-6-yl)-1,4,5,7-tetrahydro-6H-pyrazolo[3,4-b]pyridin-6-one | 1.21453067 | 1.049790423 |
| 16 | ChemDiv Targeted Diversity Library | ChemDiv | L384-0022 | S(=O)(=O)(c1ccc(cc1)Br)Nc(ccc(n2c3)c12-8-1-3-9(4-2-8)20(18,19)16-10-5-6-11-14-13-7-17(11)15-10/h1-7H,(H,15,16) | InChI=1S/C11H8BrN5O2S/ | 354.190000000 | 4-bromo-N-([1,2,4]triazolo[4,3-b]pyridazin-6-yl)benzenesulfonamide | 1.31844512 | 1.104573171 |
| 16 | ChemDiv | ChemDiv | C561-2511 | n1(ncn2)c2nc(C)c(CCC(=O)Nc(ccc3)cc c3C(OCC)=O)c1O | InChI=1S/C18H19N5O4/c1-3-27-17(26)12-4-6-13(7-5-12)22-15(24)9-8-14-11(2)21-18-19-10-20-23(18)H6(14)25H4-7,10,25H,3,8-9H2,1-2H3,(H,22,24) | 369.374550 | ethyl 4-{3-(5-methyl-7-oxo-1H-[1,2,4]triazolo[1,5-a]pyrimidin-6-yl)propanoylamino]benzoate | 1.308884 | 1.183130917 |
| 16 | ChemDiv | ChemDiv | 3268-0188 | c1(c(C)nn(c2ccccc2c1O)C(c(ccc(c(O CC)c3)O)c4c(C)nnc5cccccc5)c4O | InChI=1S/C29H28N4O4/c1-4-37-24-17-20(15-16-23(24)34)27(25-18(2)30-32(28(25)35)21-11-7-5-8-12-21)26-19(3)31-33(29(26)36)22-13-9-6-10-14-22/h5-17,27,34-36H,4H2,1-3H3 | 496.557010 | 4-[(3-ethoxy-4-hydroxyphenyl)-(5-methyl-3-oxo-2-phenyl-1H-pyrazol-4-yl)methyl]-5-methyl-2-phenyl-1H-pyrazol-3-one | 1.757708032 | 1.328598231 |
| 16 | ChemDiv6 | ChemDiv | D278-0486 | S(CC)(=O)c(cc(c1Nc2cc(C)nc(S C)n2)O)c1 | InChI=1S/C14H17N3O3S2/c1-4-22(19,20)10-5-6-12(18)11(8-10)16-13-7-9(2)15-14(17-13)21-3/h5-8,18H,4H2,1-3H3,(H,15,16,17) | 339.433070 | 4-ethylsulfonyl-2-[(6-methyl-2-methylsulfanylpyrimidin-4-yl)amino]phenol | 1.4337623 | 1.156050611 |

FIG. 9 (continued)

| | | | | | | | |
|---|---|---|---|---|---|---|---|
| 16 | ChemDiv Targeted Diversity Library | ChemDiv | D475-2526 | n1(nc(c(CCC(OC(=O)c1O)C)c2scc(c3ccc(cc3)C)n2 | InChI=1S/C18H19N3O3S/c1-11-4-6-13(7-5-11)15-10-25-18(19-15)21-17(23)14(12(2)20-21)8-9-16(22)24-3/h4-7,10,23H,8-9H2,1-3H3 | 357.430000 | 46269415 | methyl 3-[5-methyl-2-[4-(4-methylphenyl)-1,3-thiazol-2-yl]-3-oxo-1H-pyrazol-4-yl]propanoate | 1.638636518 | 1.291914463 |
| 16 | ChemDiv6 | ChemDiv | D205-0474 | n1(nc(n2)NC(=O)c3cccc3C)c2nc(c4cccc4)cc1O | InChI=1/C19H15N5O2/c1-12-7-5-6-10-14(12)17(26)21-16(25)24(19)23-18)13-8-3-2-4-9-13/h2-11,25H,1H3,(H,21,23,26) | 345.354700 | 16013914 | 2-methyl-N-(7-oxo-5-phenyl-1H-[1,2,4]triazolo[1,5-a]pyrimidin-2-yl)benzamide | 1.57703203 | 1.1898017 |
| 16 | ChemDiv6 | ChemDiv | D205-0478 | n1(nc(n2)NC(=O)c3cccc(C)c3)c2nc(c4cccc4)cc1O | InChI=1/C19H15N5O2/c1-12-6-5-9-14(10-12)17(26)21-18-22-19-20-15(11-16(25)24(19)23-18)13-7-3-2-4-8-13/h2-11,25H,1H3,(H,21,23,26) | 345.354700 | 6485801 | 3-methyl-N-(7-oxo-5-phenyl-1H-[1,2,4]triazolo[1,5-a]pyrimidin-2-yl)benzamide | 1.7991121 | 1.311653718 |
| 17 | ChemDiv Targeted Diversity Library | ChemDiv | T816-1418 | c12c(c(C)nc(c3cncn3)n1)CC(=O)N2CC4CCCO4 | InChI=1S/C16H17N5O2/c1-10-12-7-14(22)21(9-11-3-2-6-23-11)16(12)20-15(19-10)13-8-17-4-5-18-13/h4-5,8,11H,2-3,6-7,9H2,1H3 | 311.350000 | 531937198 | 4-methyl-2-(2-pyrazinyl)-7-(tetrahydro-2-furanylmethyl)-5,7-dihydro-6H-pyrrolo[2,3-d]pyrimidin-6-one | 1.527746886 | 1.052935943 |
| 17 | ChemDiv Targeted Diversity Library | ChemDiv | G417-0457 | N1(CC2CCCO2)C(=O)Nc3c1nc(c4ccc(c(OC)c4)O)nc3C(N)=O | InChI=1S/C18H19N5O5/c1-27-12-7-9(4-5-11(12)24)16-20-13(15(19)25)14-17(22-16)23(18(26)21-14)8-10-3-2-6-28-10/h4-5,7,10,24H,2-3,6,8H2,1H3,(H,2,19,25)(H,21,26) | 385.380000 | 507795582 | 2-(4-hydroxy-3-methoxyphenyl)-8-oxo-9-(tetrahydrofuran-2-ylmethyl)-8,9-dihydro-7H-purine-6-carboxamide | 1.68850092 | 1.224468364 |

FIG. 9 (continued)

| | | | | | | | | |
|---|---|---|---|---|---|---|---|---|
| | 17 | ChemDiv Targeted Diversity Library | ChemDiv | 4112-3222 | c1(c(c2c(s3)CCCC2) c3N=CN(CC(OCC) =O)C1=O | InChI=1S/C14H16N2O3S/c 1-2-19-11(17)7-16-8-15-13- 12(14(16)18)9-5-3-4-6- 10(9)20-13/h8H,2-7H2,1H3 | 292.360000 000 | | Ethyl (4-oxo-5,6,7,8-tetrahydro[1]benz othieno[2,3-d]pyrimidin-3(4H)-yl)acetate | 1.217711636 | 1.064713322 |
| | 17 | ChemDiv Targeted Diversity Library | ChemDiv | L921-0076 | S(=O)(=O)(Nc(oc1) ccc1S(N)(=O)=O)c 2c(C)sc(c3scc(C)n 3)c2 | InChI=1S/C15H15N3O4S4/ c1-9-8-23-15(17-9)13-7-14(10(2)24-13)26(21,22)18-11-3-5-12(6-4-11)25(16,19)20/h3-8,18H,1-2H3,(H2,16,19,20) | 429.560000 000 | 50835750 | 7-(3,4-dimethylphenyl)-N-[3-(2-furyl)propyl]pyraz olo[1,5-a]pyrimidine-3-carboxamide | 1.288555542 | 1.10824169 |
| | 17 | ChemDiv6 | ChemDiv | E512-0755 | c1(c(CCc(cn(CC(N CCCOC(C)C)=O)n 2)oc3C(=O)N4 CCCC4)c3C | InChI=1/C23H32N4O4/c1-15(2)30-12-6-9-24-19(28)14-27-13-17-7-8-18-20(21(17)25-27)16(3)22(31-18)23(29)26-10-4-5-11-26/h13,15H,4-12,14H2,1-3H3,(H,24,28) | 428.524570 000 | 16018742 | 2-[8-methyl-7-(pyrrolidine-1-carbonyl)-4,5-dihydrofuro[2,3-g]indazol-2-yl]-N-(3-propan-2-yloxypropyl)aceta mide | 1.67782721 | 1.45223601 |
| | 17 | ChemDiv6 | ChemDiv | E512-0748 | c1(c(CCc(cn(CC(N CCCOCC)=O)n2)c 12)oc3C(=O)N4CC CC4)c3C | InChI=1/C22H30N4O4/c1-3-29-12-6-9-23-18(27)14-26-13-16-7-8-17-19(20(16)24-26)15(2)21(30-17)22(28)25-10-4-5-11-25/h13H,3-12,14H2,1-2H3,(H,23,27) | 414.497990 000 | 16018740 | N-(3-ethoxypropyl)-2-[8-methyl-7-(pyrrolidine-1-carbonyl)-4,5-dihydrofuro[2,3-g]indazol-2-yl]acetamide | 1.87851923 | 1.454654367 |
| | 18 | ChemDiv Targeted Diversity Library | ChemDiv | E534-0239 | c1(CN(CC2)CCN2 C)csc(C)c1CC | InChI=1S/C13H22N2S/c1-4-13-11(2)16-10-12(13)9-15-7-5-14(3)6-8-15/h10H,4-9H2,1-3H3 | 238.400000 000 | 22554360 | 1-[(4-ethyl-5-methylthiophen-3-yl)methyl]-4-methylpiperazine | 1.84154973 | 1.436483298 |

| | | | | | | | | |
|---|---|---|---|---|---|---|---|---|
| 18 | ChemDiv Targeted Diversity Library | ChemDiv | E534-0255 | c1(CN(CC2)CCN2Cc(cccc(c34)OCO3)c4)ssc(C)c1CC | InChI=1S/C20H26N2O2S/c1-3-18-15(2)25-13-17(18)12-22-8-6-21(7-9-22)11-16-4-5-19-20(10-16)24-14-23-19/h4-5,10,13H,3,6-9,11-12,14H2,1-2H3 | 358.510000 | 22554371 | 1-(1,3-benzodioxol-5-ylmethyl)-4-[(4-ethyl-5-methylthiophen-3-yl)methyl]piperazine | 1.91818078 | 1.484401783 |
| 18 | ChemDiv6 | ChemDiv | E534-0231 | c1(CN(CC2)CCN2Cc3cccc(C)c3)ssc(C19-17(4)23-14-18(19)13-21-9-11-22(12-10-21)20-8-6-7-15(2)16(20)3/h6-8,14H,5,9-13H2,1-4H3)c1CC | InChI=1S/C20H28N2S/c1-5- | 328.514720 | 16019111 | 1-(2,3-dimethylphenyl)-4-[(4-ethyl-5-methylthiophen-3-yl)methyl]piperazine | 1.56310218 | 1.252289759 |
| 18 | LINCS4 Kinase Inhibitor Library | MedChem Express | HY-14268 | CC1=C(SC(=N1)C2=CC(=C(C=C2)OCC(C)C)C#N)C(=O)O | InChI=1S/C16H16N2O3S/c1-9(2)8-21-13-5-4-11(6-12(13)7-17)15-18-10(3)14(22-15)16(19)20/h4-6,9H,8H2,1-3H3,(H,19,20) | 316.374830 | | 2-[3-cyano-4-(2-methylpropoxy)phenyl]-4-methyl-1,3-thiazole-5-carboxylic acid | 1.91597891 | 1.377005961 |
| 19 | ChemDiv Targeted Diversity Library | ChemDiv | N004-0001 | c12cc(CCN=C1C)cc(cccc3)[nH]2 | InChI=1S/C12H12N2/c1-8-12-10(6-7-13-8)9-4-2-3-5-11(9)14-12/h2-5,14H,6-7H2,1H3 | 184.240000 | 5316718 | 1-Methyl-4,9-dihydro-3H-beta-carboline | 1.6739291 | 1.201994092 |
| 19 | ChemDiv6 | ChemDiv | C289-0470 | c1(CC(=O)Nc2cccccc2CC)c3c([nH]c1C)=O)cccc(Cl)c3 | InChI=1S/C19H17ClN2O3/c1-11-5-3-4-6-15(11)21-17(23)10-14-13-9-12(20)7-8-16(13)22-18(14)19(24)25/h3-9,22H,2,10H2,1H3,(H,21,23)(H,24,25) | 356.802870 | 15989964 | 5-chloro-3-[2-(2-ethylanilino)-2-oxoethyl]-1H-indole-2-carboxylic acid | 1.29836787 | 1.125527233 |

FIG. 9 (continued)

| | | | | | | | | |
|---|---|---|---|---|---|---|---|---|
| 20 | ChemDiv Targeted Diversity Library | ChemDiv | D433-1837 | n1(nc(n2)CNc(cc3)ccc3Br)c2NC(CCC4)=C4C1=O | InChI=1S/C15H14BrN5O/c1 6-9-4-6-10(7-5-9)17-8-13-19-15-18-12-3-1-2-11(12)14(22)21(15)20-13/h4-7,17H,1-3,8H2,(H,18,19,20) | 360.220000 | 50748901 | 2-[[(4-bromophenyl)ami no]methyl]-4,5,6,7-tetrahydro-8H-cyclopenta[d][1,2,4]triazolo[1,5-a]pyrimidin-8-one | 1.4605552 | 1.146158812 |
| 20 | ChemDiv Targeted Diversity Library | ChemDiv | D433-1829 | n1(nc(n2)CNc3ccc cc3F)c2NC(CCC4)=C4C1=O | InChI=1S/C15H14FN5O/c1 6-10-5-1-2-6-12(10)17-8-13-19-15-18-11-7-3-4-9(11)14(22)21(15)20-13/h1-2,5-6,17H,3-4,7-8H2,(H,18,19,20) | 299.310000 | 50748884 | 2-[[(2-fluorophenyl)amin o]methyl]-4,5,6,7-tetrahydro-8H-cyclopenta[d][1,2,4]triazolo[1,5-a]pyrimidin-8-one | 1.25933692 | 1.076529944 |
| 20 | ChemDiv Targeted Diversity Library | ChemDiv | D433-1833 | n1(nc(n2)CNc3c(C)ccc(Cl)c3)c2NC(CCC4)=C4C1=O | InChI=1S/C16H16ClN5O/c1-9-5-6-10(17)7-13(9)18-8-14-19-20-16-19-12-4-2-3-11(12)15(23)22(16)21-14/h5-7,18H,2-4,8H2,1H3,(H,19,20,21) | 329.790000 | 50748892 | 2-[[(5-chloro-2-methylphenyl)ami no]methyl]-4,5,6,7-tetrahydro-8H-cyclopenta[d][1,2,4]triazolo[1,5-a]pyrimidin-8-one | 1.28178557 | 1.013019795 |
| 20 | ChemDiv Targeted Diversity Library | ChemDiv | D433-1739 | n1(nc(n2)CNc(cc3)ccc3Cl)c2NC(CCC)=CC1=O | InChI=1S/C15H16ClN5O/c1-12-3-12-8-14(22)21-15(18-12)19-13(20-21)9-17-11-6-4-10(16)5-7-11/h4-8,17H,2-3,9H2,1H3,(H,18,19,20) | 317.780000 | 50748807 | 2-[[(4-chlorophenyl)ami no]methyl]-5-propyl[1,2,4]triazolo[1,5-a]pyrimidin-7(4H)-one | 1.37205902 | 1.096504054 |
| 20 | ChemDiv6 | ChemDiv | D043-0019 | n1(nc(n2)NCc3ccc(Br)c3)c2NC=C((OCC)=O)C1=O | InChI=1S/C15H14BrN5O3/c1 2-24-13(23)11-8-18-15-19-14(20-21(15)12(11)22)17-7-9-4-3-5-10(16)6-9/h3-6,8H,2,7H2,1H3,(H,2,17,18,19,20) | 392.207360 | 3910081 | ethyl 2-[(3-bromophenyl)met hylamino]-7-oxo-1H-[1,2,4]triazolo[1,5-a]pyrimidine-6-carboxylate | 1.5159893 | 1.212256338 |

| | | | | | | | |
|---|---|---|---|---|---|---|---|
| 20 | ChemDiv Targeted Diversity Library | ChemDiv | M071-0106 | c1(sc2c(ccc(c2)NS(=O)(=O)c3ccc(c(F)c3)F)n1)S(CC)(=O)=O | InChI=1S/C15H12F2N2O4S3/c1-2-25(20,21)15-18-13-6-3-9(7-14(13)24-15)19-26(22,23)10-4-5-11(16)12(17)8-10/h3-8,19H,2H2,1H3 | 418.460000 | 50839954 | 4-[2-(3-fluorophenoxy)ethyl]-1-(tetrahydrofuran-3-ylcarbonyl)piperidine | 1.22453004 | 1.079663468 |
| 20 | ChemDiv6 | ChemDiv | D413-0213 | c1(n2)n(C(C=C(c3cccc3)N1)c4ccc(cc4)F)nc2NS(=O)(=O)c5cccc(cc5)Cl | InChI=1/C23H17ClFN5O2S/c24-17-8-12-19(13-9-17)33(31,32)29-22-27-23-26-20(15-4-2-1-3-5-15)14-21(30(23)28-22)16-6-10-18(25)11-7-16/h1-14,21H,(H2,26,27,28,29) | 481.929780000 | 6053904 | 4-chloro-N-[7-(4-fluorophenyl)-5-phenyl-1,7-dihydro-[1,2,4]triazolo[1,5-a]pyrimidin-2-yl]benzenesulfonamide | 1.200330894 | 1.059073072 |
| 20 | ChemDiv | ChemDiv | 8525-0598 | n1(nc(n2)CC)c2NC(c3ccc(cc3)C)=CC1=O | InChI=1S/C14H14N4O/c1-3-12-16-14-15-11(8-13(19)18(14)17-12)10-6-4-9(2)5-7-10/h4-8H,3H2,1-2H3,(H,15,16,17) | 254.290000000 | 16457457 | 2-ethyl-5-(4-methylphenyl)[1,2,4]triazolo[1,5-a]pyrimidin-7(4H)-one | 1.364116256 | 1.129556665 |
| 20 | ChemDiv Targeted Diversity Library | ChemDiv | L912-0096 | n1c(c2occ(cc2)NC(C)=O)noc1C(CCCN3C(=O)Cc(c4)cc c4Br)C3 | InChI=1S/C23H23BrN4O3/c1-15(29)25-20-10-6-17(7-11-20)22-26-23(31-27-22)18-3-2-12-28(14-18)21(30)13-16-4-8-19(24)9-5-16/h4-11,18H,2-3,12-14H2,1H3,(H,25,29) | 483.370000000 | 50835553 | N-(4-ethoxyphenyl)-N'-(2-pyridin-3-yl-1H-indol-3-yl)urea | 1.46317635 | 1.24511523 |
| 20 | ChemDiv6 | ChemDiv | D413-0012 | c1(n2)n(C(C=C(c3cccc3)N1)c4ccc(cc4)Cl)nc2NS(=O)(=O)c5cccc(cc5)C | InChI=1S/C24H20ClN5O2S/c1-16-7-13-20(14-8-16)33(31,32)29-23-27-24-26-21(17-5-3-2-4-6-17)15-22(30(24)28-23)18-9-11-19(25)12-10-18/h2-15,22H,1H3,(H2,26,27,28,29) | 477.965900000 | 5909613 | N-[7-(4-chlorophenyl)-5-phenyl-1,7-dihydro-[1,2,4]triazolo[1,5-a]pyrimidin-2-yl]-4-methylbenzenesulfonamide | 1.220046271 | 1.119946092 |

| | | | | | | | | |
|---|---|---|---|---|---|---|---|---|
| 20 | ChemDiv6 | ChemDiv | E734-0033 | S(=O)(=O)(Nc1ccc(cc1C)Cl)c(c(C)cc(c23)NC(C(=O)N2)=O)c3 | InChI=1S/C16H14ClN3O4S/c1-8-5-10(17)3-4-11(8)20-25(23,24)14-7-13-12(6-9(14)2)18-15(21)16(22)19-13/h3-7,20H,1-2H3,(H,18,21)(H,19,22) | 379.818050000 | 16021586 | N-(4-chloro-2-methylphenyl)-7-methyl-2,3-dioxo-1,4-dihydroquinoxaline-6-sulfonamide | 1.29841118 | 1.124477362 |
| 20 | ChemDiv Targeted Diversity Library | ChemDiv | D538-0197 | c1(mnc(C)s1)N([H])C(=O)C(Oc(ccc(c2)F)c2C3=O)=C3 | InChI=1S/C13H8FN3O3S/c1-6-16-17-13(21-6)15-12(19)11-5-9(18)8-4-7(14)2-3-10(8)20-11/h2-5H,1H3,(H,15,17,19) | 305.290000000 | 29784338 | 6-fluoro-N-(5-methyl-1,3,4-thiadiazol-2-yl)-4-oxo-4H-chromene-2-carboxamide | 1.38129907 | 1.099928622 |
| 20 | ChemDiv Targeted Diversity Library | ChemDiv | C301-9211 | c1(NC(=O)c2ccc(c2)Cl)c(C)n(nc1nc(nn3)C)C | InChI=1S/C14H13ClN6O/c1-9-12(13(19-20(9)2)21-7-16-17-8-21)18-14(22)10-3-5-11(15)6-4-10/h3-8H,1-2H3,(H,18,22) | 316.750000000 | 46249614 | 4-chloro-N-[1,5-dimethyl-3-(4H-1,2,4-triazol-4-yl)-1H-pyrazol-4-yl]benzamide | 1.39745223 | 1.221656051 |
| 20 | ChemDiv Targeted Diversity Library | ChemDiv | D538-0059 | s1c(C(C)C)nnc1N([H])C(=O)C(O2)=CC(c(ccc(Br)c3)c23)=O | InChI=1S/C15H12BrN3O3S/c1-7(2)14-18-19-15(23-14)17-13(21)12-6-10(20)9-4-3-8(16)5-11(9)22-12/h3-7H,1-2H3,(H,17,19,21) | 394.250000000 | 4973680 | 7-bromo-4-oxo-N-(5-propan-2-yl-1,3,4-thiadiazol-2-yl)chromene-2-carboxamide | 1.25958072 | 1.11830685 |
| 20 | ChemDiv6 | ChemDiv | C200-5324 | C1(=CN=C(NC1=O)SCC(=O)Nc2ccc(cc2C(OC)=O)Cl)S(=O)(=O)c3ccc(cc3)Br | InChI=1S/C20H15BrClN3O6S2/c1-31-19(28)14-8-12(22)4-7-15(14)24-17(26)10-32-20-23-9-16(18(27)25-20)33(29,30)13-5-2-11(21)3-6-13/h2-9H,10H2,1H3,(H,24,26)(H,23,25,27) | 572.836590000 | 15988540 | methyl 2-[[2-[[5-(4-bromophenyl)sulfonyl-6-oxo-1H-pyrimidin-2-yl]sulfanyl]acetyl]amino]-5-chlorobenzoate | 1.36347693 | 1.127808835 |

| | | | | | | | | |
|---|---|---|---|---|---|---|---|---|
| 20 | ChemDiv Targeted Diversity Library | ChemDiv | D315-1886 | S(=O)(=O)(Nc(cc1)ccc1S(N)(=O)=O)cc(C)ccc2C3=NNC(=O)C((CCCC4)=C34)c2 | InChI=1S/C21H22N4O5S2/c1-13-6-7-14(20-17-4-2-3-5-18(17)21(26)24-23-20)12-19(13)32(29,30)25-15-8-10-16(11-9-15)31(22,27)28/h6-12,25H,2-5H2,1H3,(H,24,26)(H2,22,27,28) | 474.560000 | 236111909 | N-[4-(aminosulfonyl)phenyl]-2-methyl-5-(4-oxo-3,4,5,6,7,8-hexahydrophthalazin-1-yl)benzenesulfonamide | 1.49207514 | 1.211182859 |
| 20 | ChemDiv6 | ChemDiv | C999-0860 | c12c(c(c(CCC)(=O)Nc(ccc3)ccc3C(OC)=O)c(C)n1)C)c(n2C)C | InChI=1/C22H26N4O3/c1-6-29-22(28)16-7-9-17(10-8-16)24-19(27)12-11-18-13(2)20-15(4)25-26(5)21(20)23-14(18)3/h7-10H,6,11-12H2,1-5H3,(H,24,27) | 394.466830 000 | 16012630 | ethyl 4-[3-(1,3,4,6-tetramethylpyrazolo[3,4-b]pyridin-5-yl)propanoylamino]benzoate | 1.293725624 | 1.245009506 |
| 20 | ChemDiv Targeted Diversity Library | ChemDiv | F176-0470 | S(=O)(=O)(Nc(cc1)ccc1S(N)(=O)=O)cc(C)ccc2c(c3C)c(C)on3)c2 | InChI=1S/C18H19N3O5S2/c1-11-4-5-14(18-12(2)20-26-10-17(11)28(24,25)21-15-6-8-16(9-7-15)27(19,22)23/h4-10,21H,1-3H3,(H2,19,22,23) | 421.500000 000 | 53004461 | N-[4-(aminosulfonyl)phenyl]-5-(3,5-dimethylisoxazol-4-yl)-2-methylbenzenesulfonamide | 1.22674717 | 1.086073998 |
| 20 | ChemDiv6 | ChemDiv | D285-0076 | C(C#N)(C1=O)=C(c2cccc2)N=C(SC(=O)Nc(cc3)ccc3CC)N1 | InChI=1/C21H18N4O2S/c1-2-14-8-10-16(11-9-14)23-18(26)13-28-21-24-19(15-6-4-3-5-7-15)17(12-22)20(27)25-21/h3-11H,2,13H2,1H3,(H,23,26)(H,24,25,27) | 390.458220 000 | 16014959 | 2-[(5-cyano-4-oxo-6-phenyl-1H-pyrimidin-2-yl)sulfanyl]-N-(4-ethylphenyl)acetamide | 1.277730236 | 1.07396088 |
| 20 | ChemDiv Targeted Diversity Library | ChemDiv | C200-8556 | C1(=CNc2c(ccc(Cl)c2F)C1=O)S(=O)(=O)c3cccc(F)c3 | InChI=1S/C15H8ClF2NO3S/c16-11-5-4-10-14(13(11)18)19-7-12(15(10)20)23(21,22)9-3-1-2-8(17)6-9/h1-7H,(H,19,20) | 355.750000 000 | 465507327 | 7-chloro-8-fluoro-3-(3-fluorophenyl)sulfonyl-1H-quinolin-4-one | 1.23457684 | 1.047688036 |

FIG. 9 (continued)

| | | | | | | | |
|---|---|---|---|---|---|---|---|
| 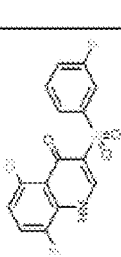 | 20 | ChemDiv Targeted Diversity Library | ChemDiv | C200-8554 | C1(=CNc(c2C1=O)c(F)ccc2Cl)S(=O)(=O)c3cccc(F)c3 | InChI=1S/C15H8ClF2NO3S/c16-10-4-5-11(18)14-13(10)15(20)12(7-19-14)23(21,22)9-3-1-2-8(17)6-9/h1-7H,(H,19,20) | 355.750000000 | 46507325 | 5-chloro-8-fluoro-3-(3-fluorophenyl)sulfonyl-1H-quinolin-4-one | 1.33255452 | 1.159916926 |
| 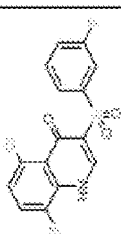 | 20 | ChemDiv Targeted Diversity Library | ChemDiv | G751-1265 | n1(C)c(SCC(=C2N c(c3C2=O)cc(cc3C)C)nnc1c4cccc(F)c4 | InChI=1S/C21H19FN4OS/c1-12-7-13(2)19-17(8-12)23-16(10-18(19)27)11-28-21-25-24-20(26(21)3)14-5-4-6-15(22)9-14/h4-10H,11H2,1-3H3,(H,23,27) | 394.470000000 | 22580194 | 2-[[5-(3-fluorophenyl)-4-methyl-1,2,4-triazol-3-yl]sulfanylmethyl]-5,7-dimethyl-1H-quinolin-4-one | 1.52183651 | 1.217525196 |
| 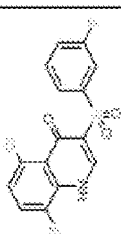 | 20 | ChemDiv6 | ChemDiv | C200-4570 | C1(=CN=C(NC1=O)SCC(=O)NCc(cc2)ccc2Cl)S(=O)(=O)c3ccc(cc3)Br | InChI=1/C19H15BrClN3O4 S2/c20-13-3-7-15(8-4-13)30(27,28)16-10-23-19(24-18(16)26)29-11-17(25)22-9-12-1-5-14(21)6-2-12/h1-8,10H,9,11H2,(H,22,25)(H,23,24,26) | 528.827100000 | 15988416 | 2-[[5-(4-bromophenyl)sulfonyl-6-oxo-1H-pyrimidin-2-yl]sulfanyl]-N-[(4-chlorophenyl)methyl]acetamide | 1.27838275 | 1.107601078 |
| 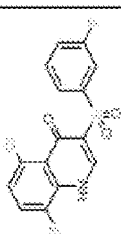 | 20 | ChemDiv Targeted Diversity Library | ChemDiv | D715-1040 | C1(=C2CCC1)c3c(OC2=O)cc(OCc(fnH)nn4)c(Cl)c3 | InChI=1S/C14H11ClN4O3/c15-10-4-9-7-2-1-3-8(7)14(20)22-11(9)5-12(10)21-6-13-16-18-19-17-13/h4-5H,1-3,6H2,(H,16,17,18,19) | 318.720000000 | 1956204 | 8-chloro-7-(1H-tetrazol-5-ylmethoxy)-2,3-dihydrocyclopenta[c]chromen-4(1H)-one | 1.50785284 | 1.185993976 |
| 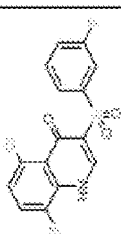 | 20 | ChemDiv Targeted Diversity Library | ChemDiv | D490-0913 | C(C#N)(C1=O)=C(c2ccc(cc2))N=C(SCC(=O)c(ccc(c34)OC(C(=O)N3)c4))N1 | InChI=1S/C22H15ClN4O4S/c1-11-20(29)25-16-8-13(4-7-18(16)31-11)17(28)10-32-22-26-19(15(9-24)21(30)27-22)12-2-5-14(23)6-3-12/h2-8,11H,10H2,1H3,(H,25,29)(H,26,27,30) | 466.910000000 | 20997705 | 4-(4-chlorophenyl)-2-{[2-(2-methyl-3-oxo-3,4-dihydro-2H-1,4-benzoxazin-6-yl)-2-oxoethyl]sulfanyl}-6-oxo-1,6-dihydro- | 1.859314 | 1.2562744 |

FIG. 9 (continued)

| | | | | | | | | |
|---|---|---|---|---|---|---|---|---|
|  | 20 | ChemDiv6 | ChemDiv | C248-0004 | c1(C(=O)N([H])C(N 2[H])=O)c2ncs3c(cc c(c3)N([H])C(C)=O) n1 | InChI=1S/C12H9N5O3/c1-5(18)13-6-2-3-7-8(4-6)15-10/000 9(14-7)11(19)17-12(20)16-10/h2-4H,1H3,(H,13,18)(H2,15,16,17,19,20) | 271.231560 | 5839674 | N-(2,4-dioxo-1H-benzo[g]pteridin-8-yl)acetamide | 1.64775216 | 1.318660686 |
|  | 21 | NIH Clinical Collection 1 - 2014 | Sigma Chemical Company | SAM001246 892 | CN(C)[C@H]1C2C C3C(=C(O)C@]2( O)C(=C(C(=O)NCN 4CCCCA)C1=O)O) C(=O)c5c(O)cccc5[ C@@]3(C)O | InChI=1S/C27H33N3O8/c1-26(37)13-7-6-8-16(31)17(13)21(32)18-14(26)11-15-20(29)(2)3)22(33)19(24(35)2 7(15,38)23(18)34)25(36)28-12-30-9-4-5-10-30/h6-8,14-15,20,31,34-35,37-38H,4-5,9-12H2,1- | 527.566210 000 | 6420073 | ROLITETRACYC LINE | 2.2021354 | 1.493690852 |
| 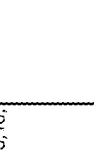 | 21 | Boston University Center for Molecular Discovery 2017 | | CMLD01047 0 | OC1=C2C(=O)C3= C(O)C=CC=C3O[C @@]22[C@@H]C 7(16)4-5-9-14(11,20-8)13(18)19-9/h1-3,9,15-16H,4-5H2/t9-,14+/m1/s1 C1)OC2=O | InChI=1S/C14H10O6/c15-6-2-1-3-8-10(6)12(17)11- | 274.225600 000 | | (1R,14S)-7,11-Dihydroxy-2,15-dioxatetracyclo[8.6.0.01,14.03,8]he xadeca-3,5,7,10-tetraene-9,16-dione | 1.30576631 | 1.128224583 |
| 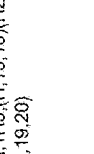 | 21 | Boston University Center for Molecular Discovery 2017 | | CMLD01096 6 | OC1=C2C[O[C@]{ C@H}(O)CCC3=O) (C(OC)=O)C3=C2 OC)=CC=C1 | InChI=1S/C19H16O7/c1-21-320.294040 14-12-8(17)4-3-5-10(12)23-000 16(15)20(22-2)11(19)7-6-9(18)13(14)16/h3-5,11,17,19H,6-7H2,1-2H3/t11-,16+/m1/s1 | | | Methyl (4R,4aR)-4,8-dihydroxy-9-methoxy-1-oxo-2,3,4,4a-tetrahydroxanthe ne-4a-carboxylate | 1.3268094 | 1.135820307 |
|  | 21 | ChemDiv Targeted Diversity Library | ChemDiv | L470-0090 | S(=O)(=O)(N1CCC C1)c2ccc(CNC(=O) C3(c4ccccc4)CC3) s2 | InChI=1S/C19H22N2O3S2/ c22-18(19(10-11-19)15-6-2-1-3-7-15)20-14-16-8-9-17(25-16)26(23,24)21-12-4-5-13-21/h1-3,6-9H,4-5,10-14H2,(H,20,22) | 390.530000 000 | 33158321 | Methyl 5-{[(cyclohexylamin o)carbonyl]amino }-3-propoxy-1-benzothiophene-2-carboxylate | 1.30703336 | 1.201232341 |

FIG. 9 (continued)

| | | | | | | | | |
|---|---|---|---|---|---|---|---|---|
| 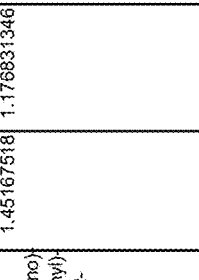 | 22 | ChemDiv6 | ChemDiv | E002-0798 | n12c(c(cn1)C#N)[nH]c(c3ccccc3F)c2NCACCCCC4 | InChI=1S/C18H18FN5/c19-15-9-5-4-8-14(15)16-18(22-13-6-2-1-3-7-13)24-17(23-16)12(10-20)11-21-24/h4-5,8-9,11,13,22-23H,1-3,6-7H2 | 323.367420000 | 16016698 | 3-(cyclohexylamino)-2-(2-fluorophenyl)-5H-imidazo[1,2-b]pyrazole-7-carbonitrile | 1.45167518 | 1.176831346 |
| 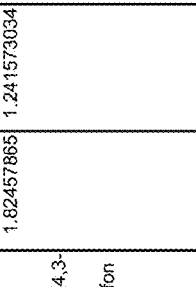 | 22 | ChemDiv Targeted Diversity Library | ChemDiv | L384-0099 | n12c(ccc(n1)NS(=O)c3ccc(cc3)Cl)nnc2c4ccccc4 | InChI=1S/C17H12ClN5O2S/c18-13-6-8-14(9-7-13)26(24,25)22-15-10-11-16-19-20-17(23(16)21-15)12-4-2-1-3-5-12/h1-11H,(H,21,22) | 385.830000000 | 50826285 | 4-chloro-N-(3-phenyl-[1,2,4]triazolo[4,3-b]pyridazin-6-yl)benzenesulfonamide | 1.82457865 | 1.241573034 |
| 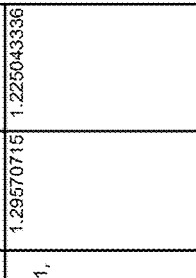 | 22 | ChemDiv6 | ChemDiv | C188-0366 | c1(NC(=O)c2ccc(cc2)Br)n[c3ccccc3]nc(cccc4)n14 | InChI=1S/C20H14BrN3O/c21-16-11-9-15(10-12-16)20(25)23-19-18(14-6-2-1-3-7-14)22-17-8-4-5-13-24(17)19/h1-13H,(H,23,25) | 392.248660000 | 979256 | 4-bromo-N-(2-phenylimidazo[1,2-a]pyridin-3-yl)benzamide | 1.29570715 | 1.225043336 |
| 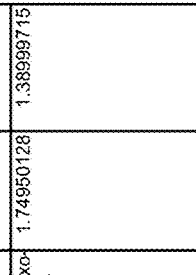 | 22 | ChemDiv Targeted Diversity Library | ChemDiv | D517-1064 | c12c(NC(=O)NC1=O)[nH]c(c3ccc(c4c3)cccc4)c2C5c6c(N(C)C5=O)cccc6 | InChI=1S/C25H18N4O3/c1-29-17-9-5-4-8-16(17)18(24(29)31)19-20-22(27-25(32)28-23(20)30)26-21(19)15-11-10-13-6-2-3-7-14(13)12-15/h2-12,18H,1H3,(H3,26,27,28,30,32) | 422.450000000 | 50751471 | 5-(1-methyl-2-oxo-2,3-dihydro-1H-indol-3-yl)-6-(2-naphthyl)-1H-pyrrolo[2,3-d]pyrimidine-2,4(3H,7H)-dione | 1.74950128 | 1.38999715 |
| 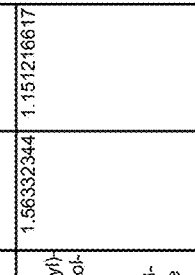 | 23 | ChemDiv Targeted Diversity Library | ChemDiv | 8249-3674 | N([N-])C(C1=C2O)=CC(N2CCc3[nH]cn3)=O)(C1=O)c4sc(c5n4)cccc5 | InChI=1S/C19H16N6O2S/c1-11-17-14(8-16(26)24(11)7-6-12-9-20-10-21-12)23-25(18(17)27)19-22-13-4-2-3-5-15(13)28-19/h2-5,8-10H,6-7H2,1H3,(H2,20,21,23,26)/p1 | 414.420000000 | 7342703 | 2-(1,3-benzothiazol-2-yl)-5-[2-(1H-imidazol-5-yl)ethyl]-4-methyl-3-oxopyrazolo[4,3-c]pyridin-6-olate | 1.56332344 | 1.151216617 |

FIG. 9 (continued)

| | | | | | | | | |
|---|---|---|---|---|---|---|---|---|
| 23 | NIH Clinical Collection 1 - 2014 | Sequoia Research Products Ltd. | SAM001246 782 | Cc1(nH]cnc1CN2C Cc3c(C2=O)c4cccc c4n3C.Cl- | InChI=1S/C17H18N4O.ClH/ c1-11-13(19-10-18-11)9-21- 8-7-15-16(17(21)22)12-5-3- 4-6-14(12)20(15)2;/h3- 6,10H,7-9H2,1- 2H3,(H,18,19);1H | 330.811960 000 | ALOSETRON HCl | 2.30791206 | 1.779778909 |
| 23 | ChemDiv Targeted Diversity Library | ChemDiv | 8249-3642 | N(NC(C1=C2C)=C C(N2Cc(cc3)ccc3C (O)=O)(C1=O)c 4sc(c5n4)cccc5 | InChI=1S/C22H16N4O4S/c 1-12-19-16(10- 18(27)25(12)11-13-6-8-14(9- 7-13)21(29)30)24- 26(20(19)28)22-23-15-4-2-3- 5-17(15)31-22/h2- 10,24H,11H2,1H3,(H,29,30) | 432.460000 000 | 4-[[2-(1,3-benzothiazol-2-yl)- 4-methyl-3,6-dioxo-1H-pyrazolo[4,3-c]pyridin-5-yl]methyl]benzoic acid | 1.399839065 | 1.053029435 |
| 23 | SYNthesis med chem Kinase Inhibitor 2 | SYNthesis | SYN-1027 | c1cc(cc(c1)NC(=O) N2CCCC2)Nc3ncc( c(n3)NCCc4c(nH]c n4)Br | InChI=1S/C20H23BrN8O/c2 1-17-12-24-19(28-18(17)23- 7-6-16-11-22-13-25-16)26- 14-4-3-5-15(10-14)27- 20(30)29-8-1-2-9-29/h3- 5,10-13H,1-2,6- 9H2,(H,22,25)(H,27,30)(H2, 23,24,26,28) | 471.353610 | N-[3-[[5-bromo-4-[2-(1H-imidazol-5-yl)ethylamino]pyrimidin-2-yl]amino]phenyl]pyrrolidine-1-carboxamide | 1.34082445 | 1.122511879 |
| 23 | ChemDiv Targeted Diversity Library | ChemDiv | M384-0056 | c(C1)(c2c(n3CC)c c([H])c3CCN1C( C(C4)CC4)=O | InChI=1S/C18H22N2O/c1-2-20-16-9-4-3-8-14(16)15-12-19(11-10-17(15)20)18(21)13-6-5-7-13/h3-4,8-9,13H,2,5-7,10-12H2,1H3 | 282.390000 000 | 50844153 | cyclobutyl-(5-ethyl-3,4-dihydro-1H-pyrido[4,3-b]indol-2-yl)methanone | 1.93004307 | 1.187172623 |
| 24 | ChemDiv6 | ChemDiv | E715-0518 | c12c(ncnc1N3CCC (CC3)C(NCCc(cc4) ccc4S(N)(=O)=O) O)n5c(CCCCC5)n2 | InChI=1/C24H31N7O3S/c2 5-35(33,34)19-7-5-17(6-8-19)9-12-26-24(32)18-10-14-30(15-11-18)22-21-23(28-16-27-22)31-13-3-1-2-4-20(31)29-21/h5-8,16,18H,1-4,9-15H2,(H,26,32)(H2,25,33,3 4) | 497.613030 000 | 16021547 | N-[2-(4-sulfamoyl)phenyl) ethyl]-1-(7,8,9,10-tetrahydro-6H-purino[9,8-a]azepin-4-yl)piperidine-4-carboxamide | 1.44533426 | 1.182799443 |

| | | | | | | | | |
|---|---|---|---|---|---|---|---|---|
| 24 | ChemDiv Targeted Diversity Library | ChemDiv | D341-0231 | c1(c2c(s3)CCCC2)c3ncnc1N4CCC(CC4)C(N)=O | InChI=1S/C16H20N4OS/c1 7-14(21)10-5-7-20(8-6-10)15-13-11-3-1-2-4-12(11)22-16(13)19-9-18-15/h9-10H,1-8H2,(H2,17,21) | 316.430000 000 | 2403385 | 1-(5,6,7,8-tetrahydro[1]benz othieno[2,3-d]pyrimidin-4-yl)piperidine-4-carboxamide | 2.29386923 | 1.647589923 |
| 24 | ChemDiv Targeted Diversity Library | ChemDiv | E565-0007 | c12n(c(c3c(N4CCC(CC4)C(N)=O)n1)c cs3)nnc2S(c5ccccc 5)(=O)=O | InChI=1S/C19H18N6O3S2/c20-16(26)12-6-9-24(10-7-25)30(27,28)13-4-2-1-3-5-13/h1-5,8,11-12H,6-7,9-10H2,(H2,20,26) | 442.520000 000 | 20901114 | 1-(3-(phenylsulfonyl)th ieno[1,2,3]triazolo[1,5-a]pyrimidin-5-yl)piperidine-4-carboxamide | 1.65089683 | 1.272661611 |
| 24 | ChemDiv Targeted Diversity Library | ChemDiv | L928-0447 | c12c(ncnc1N(CCC C3C(=O)NCc(cc4)c cn4)C3)c5c(cccc5)o2 | InChI=1S/C22H21N5O2/c2 8-22(24-12-15-7-9-23-10-8-15)16-4-3-11-27(13-16)21-20-19(25-14-26-21)17-5-1-2-6-18(17)29-20/h1-5,10,14,16H,3-4,11-13H2,(H,24,28) | 387.440000 000 | 50835328 | 1-([1]benzofuro[3,2-d]pyrimidin-4-yl)-N-(pyridin-4-ylmethyl)piperidin e-3-carboxamide | 1.23942371 | 1.096267191 |
| 24 | ChemDiv Targeted Diversity Library | ChemDiv | L928-0445 | c12c(ncnc1N(CCC C3C(=O)NCc4ccccn4)C3)c5c(cccc5)o2 | InChI=1S/C22H21N5O2/c2 8-22(24-12-16-7-3-4-10-23-16)15-6-5-11-27(13-15)21-20-19(25-14-26-21)17-8-1-2-9-18(17)29-20/h1-4,7-10,14-15H,5-6,11-13H2,(H,24,28) | 387.440000 000 | 50835300 | 1-([1]benzofuro[3,2-d]pyrimidin-4-yl)-N-(pyridin-2-ylmethyl)piperidin e-3-carboxamide | 1.21786815 | 1.077017868 |
| 24 | ChemDiv6 | ChemDiv | C768-0260 | c1(onc(c2c1N(CCC )CCC3C(N)=O)ccc( CC)c2)C(=O)c4ccc (c(C)c4)C | InChI=1/C26H29N3O2/c1-18-6-8-23-21(14-18)24(29-29)26(27)31)22(15-28-23)25(30)20-7-5-16(2)17(3)13-20/h5-8,13-15,19H,4,9-12H2,1-3H3,(H2,27,31) | 415.527350 000 | 16010865 | 1-(3-(3,4-dimethylbenzoyl)-6-ethylquinolin-4-yl)piperidine-4-carboxamide | 1.84370105 | 1.312262251 |

FIG. 9 (continued)

| | | | | | | | |
|---|---|---|---|---|---|---|---|
| 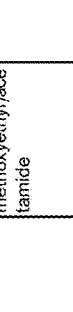 | 24 | ChemDiv6 | ChemDiv | C618-0374 | c(SCC(NCCCC)=O)(c1c2CCCC1)c(ccc(c3)Cl)c3n2 | InChI=1/C18H21ClN2O2S/c1-23-9-8-20-17(22)11-24-18-13-4-2-3-5-15(13)21-16-10-12(19)6-7-14(16)18/h6-7,10H,2-5,8-9,11H2,1H3,(H,20,22) | 364.889530 | 16009146 | 2-[(6-chloro-1,2,3,4-tetrahydroacridin-9-yl)sulfanyl]-N-(2-methoxyethyl)acetamide | 1.21110414 | 1.098494354 |
| 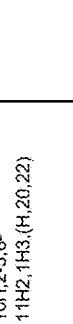 | 24 | ChemDiv Targeted Diversity Library | ChemDiv | C509-2036 | c1(SCC(NCCC)=O)c2c(CCCC2)nc(cc(Cl)c3)c13 | InChI=1S/C18H21ClN2OS/c1-2-9-20-17(22)11-23-18-13-5-3-4-6-15(13)21-16-8-7-12(19)10-14(16)18/h7-8,10H,2-6,9,11H2,1H3,(H,20,22) | 348.900000 | 16007539 | 2-[(7-chloro-1,2,3,4-tetrahydroacridin-9-yl)sulfanyl]-N-propylacetamide | 1.25283461 | 1.104652678 |
|  | 24 | ChemDiv Targeted Diversity Library | ChemDiv | K844-0672 | C1(C(NCNCCO)=O)=C()c2c(N3C1=O)c(ccc2)CCC3 | InChI=1S/C17H21N3O4/c2 1-10-8-18-6-7-19-16(23)13-15(22)12-5-1-3-11-4-2-9-20(14(11)12)17(13)24/h1,3,5,18,21-22H,2,4,6-10H2,(H,19,23) | 367.830000 000 | 54686429 | 1-Hydroxy-3-oxo-6,7-dihydro-3H,5H-pyrido[3,2,1-ij]quinoline-2-carboxylic acid [2-(2-hydroxy-ethylamino)-ethyl]-amide | 1.55604804 | 1.198741779 |
|  | 24 | ChemDiv Targeted Diversity Library | ChemDiv | C696-0397 | c1(c2c(ccoc2)(c(nn1)Cc(cc3)ccn3)N4CCC(CC4)Cc5cccc5 | InChI=1S/C26H26N4/c1-2-6-20(7,3-1)18-22-12-16-30(17-000 13-22)26-24-9-5-4-8-23(24)25(28-29-26)19-21-10-14-27-15-11-21/h1-11,14,15,22H,12-13,16-19H2 | 394.520000 | 20875732 | 1-(4-benzylpiperidin-1-yl)-4-(pyridin-4-ylmethyl)phthalazine | 1.591 96509 | 1.262225645 |
|  | 25 | ChemDiv Targeted Diversity Library | ChemDiv | N039-0019 | c12c(ccc(O)c1OC)c(OC)c(c3n2)cco3 | InChI=1S/C13H11NO4/c1-16-11-7-3-4-9(15)12(17-2)10(7)14-13-8(11)5-6-18-13/h3-6,15H,1-2H3 | 245.240000 000 | 165368 | 4,8-dimethoxy-9H-furo[2,3-b]quinolin-7-one | 1.53708668 | 1.196859441 |

| | | | | | | | | |
|---|---|---|---|---|---|---|---|---|
| | 25 | ChemDiv Targeted Diversity Library | ChemDiv | N038-0009 | n1c2c(cccc2OC)c(c(cco3)c13)OC | InChI=1S/C13H11NO3/c1-15-10-5-3-4-8-11(10)14-13-9(6-7-17-13)12(8)16-2/h3-7H,1-2H3 | 229.240000000 | 107936 | 4,8-dimethoxyfuro[2,3-b]quinoline | 1.47791839 | 1.17536157 |
| | 25 | ChemDiv Targeted Diversity Library | ChemDiv | N039-0059 | c(cco1)(c(OC)c2c(n3)cccc2)c13 | InChI=1S/C12H9NO2/c1-14-11-8-4-2-3-5-10(8)13-12-9(11)6-7-15-12/h2-7H,1H3 | 199.210000000 | 68085 | 4-Methoxyfuro[2,3-b]quinoline | 1.64513779 | 1.243899478 |
| | 25 | ChemDiv Targeted Diversity Library | ChemDiv | N036-0105 | [nH]1c2c(c(cccc(OC)c3)cc13)cccc2C | InChI=1S/C13H12N2O/c1-8-13-11(5-6-14-8)10-4-3-9(16-2)7-12(10)15-13/h3-7,15H,1-2H3 | 212.250000000 | 5280953 | 7-Methoxy-1-methyl-9H-pyrido[3,4-b]indole | 1.34171685 | 1.100011808 |
| | 25 | ChemDiv Targeted Diversity Library | ChemDiv | N042-0031 | c12c(ccnc1Cc(ccc(c3OC)OC)c3)cc(c(OC)c2)OC | InChI=1S/C20H21NO4/c1-22-17-6-5-13(10-18(17)23-2)9-16-15-12-20(25-4)19(24-3)11-14(15)7-8-21-16/h5-8,10-12H,9H2,1-4H3 | 339.390000000 | 4680 | Papaverine | 1.36232283 | 1.166093298 |
| | 25 | ChemDiv Targeted Diversity Library | ChemDiv | C202-1892 | c12c(n[nH]c1c3ccc(cc3)OC)nc(c4ccc(c(Oc4)O)cc2C(O)=O | InChI=1S/C20H15N3O5/c1-28-12-5-2-10(3-6-12)18-17-13(20(26)27)9-14(21-19(17)23-22-18)11-4-7-15(24)16(25)8-11/h2-9,24-25H,1H3,(H,26,27)(H,21,22,23) | 377.360000000 | 54724325 | 4-(3,4-dihydroxyphenyl)-3-(4-methoxyphenyl)-1H-pyrazolo[3,4-b]pyridine-6-carboxylic acid | 1.63260666 | 1.2171199412 |

FIG. 9 (continued)

| | | | | | | | |
|---|---|---|---|---|---|---|---|
| 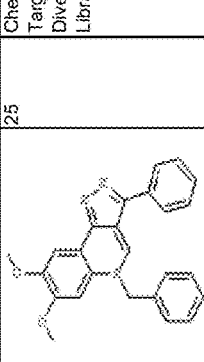 | 25 | ChemDiv Targeted Diversity Library | ChemDiv | C645-0005 | c(c(c1ccccc1)nn2)(cn(Cc3cccccc3)c4c5cc(c(OC)c4)OC)c25 | InChI=1S/C25H21N3O2/c1-29-22-13-19-21(14-23(22)30-2)28(15-17-9-5-3-6-10-17)16-20-24(26-27-25(19)20)18-11-7-4-8-12-18/h3-14,16H,15H2,1-2H3 | 395.470000000 | 2136872 | 5-benzyl-7,8-dimethoxy-3-phenyl-5H-pyrazolo[4,3-c]quinoline | 1.23456904 | 1.13540569 |
| 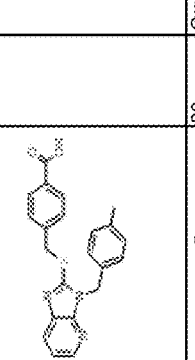 | 25 | ChemDiv6 | ChemDiv | C797-1227 | n1(Cc(ccc2)ccc2)c3c(nc1SCc(cc4)ccc4C(O)=O)cccn3 | InChI=1S/C22H19N3O2S/c1-15-4-6-16(7-5-15)13-25-20-19(3-2-12-23-20)24-22(25)28-14-17-8-10-18(11-9-17)21(26)27/h2-12H,13-14H2,1H3,(H,26,27) | 389.470160000 | 16011318 | 4-{[3-({(4-methylphenyl)methyl]imidazo[4,5-b]pyridin-2-yl}sulfanyl)methyl]benzoic acid | 1.23822987 | 1.118869084 |
| 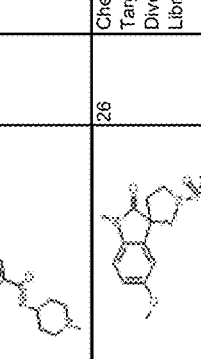 | 26 | Gray Kinase Inhibitor-Focused Library | Nathanael Gray Lab | XMD11-85c | O=C1N(C)c(c2N(C3CCCCC3)CC1)on c(Nc4c(OC)cc(C(=O)NC5CCCN(C)CC5)cc4)n2 | InChI=1S/C28H39N7O3/c1-33-14-11-20(12-15-33)30-27(37)19-9-10-22(24(17-19)38-3)31-28-29-18-23-26(32-28)35(16-13-25(36)34(23)2)21-7-5-4-6-8-21/h9-10,17-18,20-21H,4-8,11-16H2,1-3H3,(H,30,37)(H,29,31,32) | 521.654350000 | 250015463 | 4-[(9-cyclohexyl-5-methyl-6-oxo-7,8-dihydropyrimido[4,5-b][1,4]diazepin-2-yl)amino]-3-methoxy-N-(1-methylpiperidin-4-yl)benzamide | 1.2723174 | 1.099059642 |
| 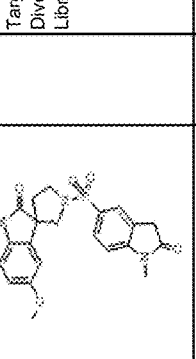 | 26 | ChemDiv Targeted Diversity Library | ChemDiv | P681-0433 | C1(CCN2S(=O)(=O)c(cc3)cc(c34)CC(N4C)=O)(C2)c(cc(OC)cc5)c5N(C)C1=O | InChI=1S/C22H23N3O5S/c1-23-18-7-5-16(10-14(18)11-20(23)26)31(28,29)25-9-8-22(13-25)17-12-15(30-3)4-6-19(17)24(2)21(22)27/h4-7,10,12H,8-9,11,13H2,1-3H3 | 441.510000000 | 53177290 | 5-methoxy-1-methyl-1'-[(1-methyl-2-oxo-2,3-dihydro-1H-indol-5-yl)sulfonyl]spiro[indole-3,3'-pyrrolidin]-2(1H)-one | 1.37374498 | 1.145958835 |
| 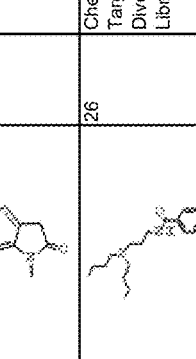 | 26 | ChemDiv Targeted Diversity Library | ChemDiv | C797-0939 | c12n(c(c3s1)ccc(c3)C(NCCCN(CCCC)CCCC)=O)cc(c4cc c(cc4)OC)n2 | InChI=1S/C28H36N4O2S/c1-4-6-16-31(17-7-5-2)18-8-15-29-27(33)22-11-14-25-26(19-22)35-28-30-24(20-32(25)28)21-9-12-23(34-3)13-10-21/h9-14,19-20H,4-8,15-18H2,1-3H3,(H,29,33) | 582.730000000 | 20887178 | N-[3-(dibutylamino)propyl]-2-(4-methoxyphenyl)imidazo[2,1-b][1,3]benzothiazole-7-carboxamide | 1.53099328 | 1.162932537 |

FIG. 9 (continued)

| | | | | | | | | |
|---|---|---|---|---|---|---|---|---|
| 26 | ChemDiv Targeted Diversity Library | ChemDiv | P237-0063 | c12c(CCCN1Cc)cc(C(=O)NC3CCCCC3)s2 | InChI=1S/C15H22N2OS/c1-17-9-5-6-11-10-13(19-15(11)17)14(18)16-12-7-3-2-4-8-12/h10,12H,2-9H2,1H3,(H,16,18) | 278.420000 | 53014818 | N-2-cyclohexyl-7-methyl-4,5,6,7-tetrahydrothieno[2,3-b]pyridine-2-carboxamide | 1.31449237 | 1.124698634 |
| 26 | ChemDiv | ChemDiv | E524-1589 | N1(Cc(cc2)ccc2C(NCCN(C)C)=O)c3c(ccn3)n4c(ccc4)C1=O | InChI=1/C22H23N5O2/c1-25(2)14-12-24-21(28)17-9-7-20(8-10-17)15-27-20-18(5-3-11-23-20)26-13-4-6-19(26)22(27)29/h3-11,13H,12,14-15H2,1-2H3,(H,24,28) | 389.450320 | 16018989 | N-[2-(dimethylamino)ethyl]-4-[(6-oxopyrrolo[2,3-e]pyrrolo[1,2-a]pyrazin-5(6H)-yl)methyl]benzamide | 1.20581006 | 1.103351955 |
| 26 | ChemDiv Targeted Diversity Library | ChemDiv | F154-0585 | c1(SCc(cc2)ccc2Cl)nc(c(c3)n1Cc(cc4)ccc4C(NCCCN5CCCC5)=O)ccn3 | InChI=1S/C27H28ClN5OS/c28-3-9-5-21(6-10-23)19-35-16-25(24)33(27)18-20-3-7-22(8-4-20)26(34)30-13-16-32-14-1-2-15-32/h3-12,17H,1-2,13-16,18-19H2,(H,30,34) | 506.070000 | 50764032 | 4-{[2-[(4-chlorobenzyl)thio]-3H-imidazo[4,5-c]pyridin-3-yl]methyl}-N-(2-pyrrolidin-1-ylethyl)benzamide | 1.31041919 | 1.106463354 |
| 26 | ChemDiv | ChemDiv | E235-0211 | c12n(c(c3s1)ccc(c3)C(NCCCN4CCCCC4)=O)cc(c5ccc(cc5)C)n2 | InChI=1/C26H30N4OS/c1-19-7-9-20(10-8-19)22-18-30-23-12-11-21(17-24(23)32-26(30)28-22)25(31)27-13-6-16-29-14-4-2-3-5-15-29/h7-12,17-18H,2-6,13-16H2,1H3,(H,27,31) | 446.607590 | 16018333 | N-[3-(azepan-1-yl)propyl]-2-(4-methylphenyl)imidazo[2,1-b][1,3]benzothiazole-6-carboxamide | 1.26208378 | 1.108055854 |
| 26 | ChemDiv | ChemDiv | 5233-2329 | S(=O)(=O)(NCCC1CCO1)c(c(C)ccc2c3o4c(cccc4)c(nn3)Nc(cc5)ccc5OCC(N)=O)c2 | InChI=1/C28H29N5O5S/c1-18-8-9-19(15-25(18)39)35,36)30-16-22-5-4-14-37-22)27-23-6-2-3-7-24(23)28(33-32-27)31-20-10-12-21(13-11-20)38-17-26(29)34/h2-3,6-13,15,22,30H,4-5,14,16-17H2,1H3,(H2,29,34)(H,31, | 547.625350 | 39221619 | 2-[4-[[4-methyl-3-(oxolan-2-ylmethylsulfamoyl)phenyl]phthalazin-1-yl]amino]phenoxy]acetamide | 1.48679569 | 1.225855658 |

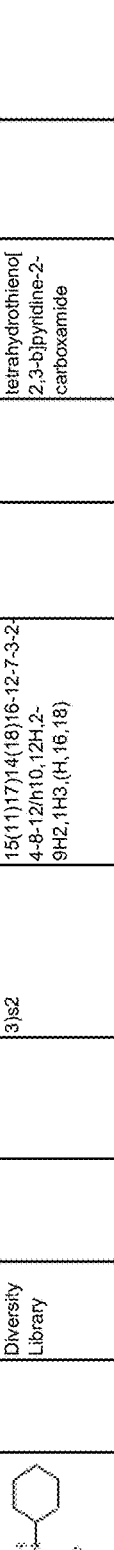
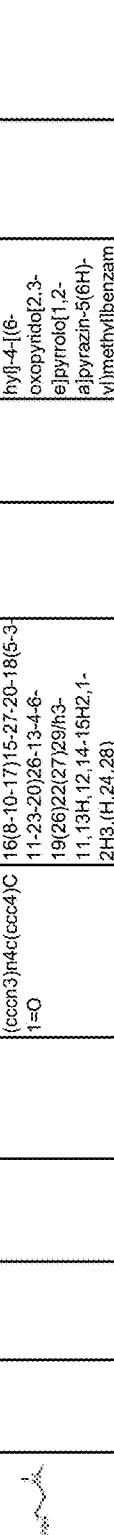
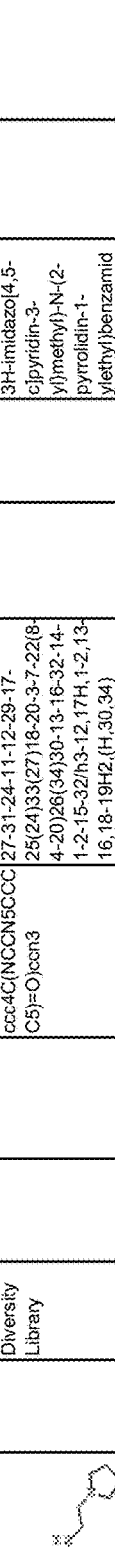
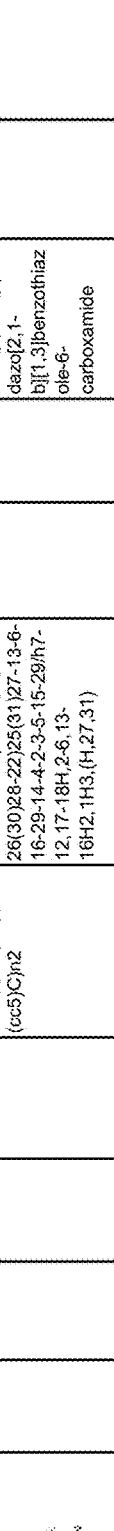
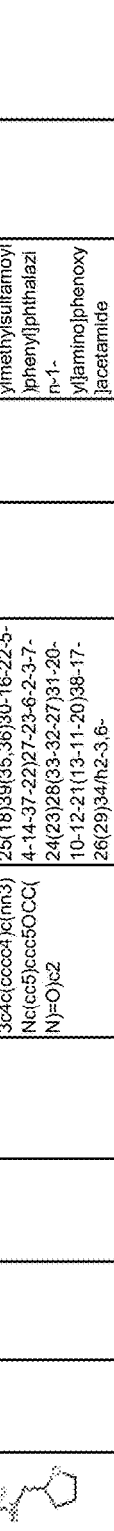

FIG. 9 (continued)

| | | | | | | | |
|---|---|---|---|---|---|---|---|
| 27 | ChemDiv Targeted Diversity Library | ChemDiv | C200-8619 | c1(NC(CS(=O)(=O)c2ccc(cc2C)C)=CC3=O)n3ncc1C(OC)=O | InChI=1S/C17H17N3O5S/c1-10-4-5-14(11(2)6-3=O)n3ncc1C(OC)=O)10)26(23,24)9-12-7-15(21)20-16(19-12)13(8-18-20)17(22)25-3/h4-8,19H,9H2,1-3H3 | 375.410000 | 45499584 | Methyl 5-{[(2,4-dimethylphenyl)sulfonyl][methyl}-7-oxo-4,7-dihydropyrazolo[1,5-a]pyrimidine-3-carboxylate | 1.289590006 | 1.089040277 |
| 27 | ChemDiv Targeted Diversity Library | ChemDiv | D298-0053 | n1(nc(n2)Ncc3ccccc3C)c2NC(CC)=CC1=O | InChI=1S/C15H17N5O/c1-3-12-8-13(21)20-15(17-12)18-14(19-20)16-9-11-7-5-4-6-10(11)2/h4-8H,3,9H2,1-2H3,(H2,16,17,18,19) | 283.340000 | 53003168 | 5-ethyl-2-{[(2-methylbenzyl)amino][1,2,4]triazolo[1,5-a]pyrimidin-7(4H)-one | 1.254936663 | 1.116416151 |
| 27 | ChemDiv6 | ChemDiv | D103-1980 | c1(nnc(SC)s1)N([H])C(=O)C(O2)=CC(c3c2cc(C)c(c3C)C)=O | InChI=1/C15H13N3O3S2/c1-7-4-9-10(19)6-12(21-11(9)5-8(7)2)13(20)16-14-17-18-15(22-3)23-14/h4-6H,1-3H3,(H,16,17,20) | 347.412020 | 4970779 | 6,7-dimethyl-N-[5-(methylsulfanyl)-1,3,4-thiadiazol-2-yl]-4-oxo-4H-chromene-2-carboxamide | 1.44356563 | 1.147178281 |
| 27 | ChemDiv6 | ChemDiv | E233-0714 | c1(c(CCc(cn(CC)n2)c12)oc3C(=O)Nc(cccc4(OCC)=O)c4)c3C | InChI=1/C22H23N3O4/c1-4-25-12-15-9-10-17-18(19(15)24-25)13(3)20(29-17)21(26)23-16-8-6-7-14(11-16)22(27)28-5-2/h6-8,11-12H,4,5,9-10H2,1-3H3,(H,23,26) | 393.435710 | 16018166 | ethyl 3-{[(2-ethyl-8-methyl-4,5-dihydrofuro[2,3-g]indazole-7-carbonyl)amino]b enzoate | 1.65744705 | 1.189908575 |
| 27 | ChemDiv6 | ChemDiv | C188-0367 | c1(NC(=O)c2ccc(c(C)c2)Cc)c(c3cccccc3)nc(cccc4)n14 | InChI=1/C22H19N3O/c1-15-11-12-18(14-16(15)2)22(26)24-21-20(17-8-4-3-5-9-17)23-19-10-6-7-13-25(19)21/h3-14H,1-2H3,(H,24,26) | 341.405760 | 4433436 | 3,4-dimethyl-N-(2-phenylimidazo[1,2-a]pyridin-3-yl)benzamide | 1.31117553 | 1.206317473 |

FIG. 9 (continued)

| | | | | | | | | |
|---|---|---|---|---|---|---|---|---|
| | 27 | ChemDiv6 | ChemDiv | D103-1833 | c1(c(ccc(C)c1C)C(=O)C=C2C(=O)N([H])c3nnc(CC(C)C)s3)O2 | InChI=1/C18H19N3O3S/c1-9(2)7-15-20-21-18(25-15)19-17(23)14-8-13(22)12-6-5-10(3)11(4)16(12)24-14/h5-6,8-9H,7H2,1-4H3,(H,19,21,23) | 357.426750 000 | 4974247 | 7,8-dimethyl-N-[5-(2-methylpropyl)-1,3,4-thiadiazol-2-yl]-4-oxochromene-2-carboxamide | 1.3016129 | 1.150201613 |
| | 27 | ChemDiv6 | ChemDiv | G751-0678 | c12c(ccc(C)c1C)C=C(CSc3nnc[nH]3)N2)=O | InChI=1/C14H14N4OS/c1-8-3-4-11-12(19)5-10(17-13(11)9(8)2)6-20-14-15-7-16-18-14/h3-5,7H,6H2,1-2H3,(H,17,19),(H,15,16,18) | 286.352150 000 | 16030304 | 7,8-dimethyl-2-(1H-1,2,4-triazol-5-ylsulfanylmethyl)-1H-quinolin-4-one | 1.883463322 | 1.318801754 |
| | 27 | ChemDiv6 | ChemDiv | D103-1943 | c1(nnc(CCC)s1)N([H])C(=O)C(O2)=CC(c3c2cc(C)c(C)c)=O | InChI=1/C17H17N3O3S/c1-4-5-15-19-20-17(24-15)18-16(22)14-8-12(21)11-6-9(2)10(3)7-13(11)23-14/h6-8H,4-5H2,1-3H3,(H,18,20,22) | 343.400170 000 | 4871195 | 6,7-dimethyl-4-oxo-N-(5-propyl-1,3,4-thiadiazol-2-yl)-4H-chromene-2-carboxamide | 1.98350127 | 1.397298195 |
| | 27 | ChemDiv6 | ChemDiv | E512-0834 | c1(c(CCc(cn(CC(=O)NCc2ccccc2C)n3)c13)oc4C(=O)N5CCCC5)c4C | InChI=1/C25H28N4O3/c1-16-7-3-4-8-18(16)13-26-21(30)15-29-14-19-9-10-20-22(23(19)27-29)17(2)24(32-20)25(31)28-11-5-6-12-28/h3-4,7-8,14H,5-6,9,13,15H2,1-2H3,(H,26,30) | 432.514810 000 | 16018792 | N-[(2-methylphenyl)methyl]-2-[8-methyl-7-(pyrrolidine-1-carbonyl)-4,5-dihydrofuro[2,3-g]indazol-2-yl]acetamide | 1.815696941 | 1.301888979 |
| | 27 | ChemDiv6 | ChemDiv | E854-6540 | c12c(C(=NN(CCC(=O)NCc3ccccc3)C)C1=O)C)c(n(c4cc(cc4)C)n2)C | InChI=1/C26H29N5O2/c1-17-11-13-22(14-12-17)31-20(4)24-19(3)28-30(26(33)25(24)29-31)15-7-10-23(32)27-16-21-9-6-5-8-18(21)2/h5-6,8-9,11-14H,7,10,15-16H2,1-4H3,(H,27,32) | 443.540750 000 | 16022702 | 4-[3,4-dimethyl-2-(4-methylphenyl)-7-oxopyrazolo[3,4-d]pyridazin-6-yl]-N-[(2-methylphenyl)methyl]butanamide | 1.20592997 | 1.090973487 |

| | | | | | | | | |
|---|---|---|---|---|---|---|---|---|
| 27 | ChemDiv6 | ChemDiv | C188-0385 | c1(NC(=O)c2ccc(c2)C)c(c3ccccc3)nc(cccc4)n14 | InChI=1/C21H17N3O/c1-15-10-12-17(13-11-15)21(25)23-20-19(16-7-3-2-4-8-16)22-18-9-5-6-14-24(18)20/h2-14H,1H3,(H,23,25) | 327.379180 000 | 4454082 | 4-methyl-N-(2-phenylimidazo[1,2-a]pyridin-3-yl)benzamide | 1.48192268 | 1.308777429 |
| 27 | ChemDiv Targeted Diversity Library | ChemDiv | D538-0120 | s1c(C(C)C)nnc1N([H])C(=O)C(O2)=CC(c3c2cc(C)c(c3)C)=O | InChI=1S/C17H17N3O3S/c1-8(2)16-19-20-17(24-16)18-15(22)14-7-12(21)11-5-9(3)10(4)6-13(11)23-14/h5-8H,1-4H3,(H,18,20,22) | 343.410000 000 | 4973222 | 6,7-dimethyl-4-oxo-N-(5-propan-2-yl-1,3,4-thiadiazol-2-yl)chromene-2-carboxamide | 1.37731284 | 1.133788785 |
| 27 | ChemDiv6 | ChemDiv | D103-1942 | c1(nnc(CC)s1)N([H])C(=O)C(O2)=CC(c3c2cc(C)c(c3)C)=O | InChI=1/C16H15N3O3S/c1-4-14-18-19-16(23-14)17-15(21)13-7-11(20)10-5-8(2)9(3)6-12(10)22-13/h5-7H,4H2,1-3H3,(H,17,19,21) | 329.373590 000 | 4974983 | N-(5-ethyl-1,3,4-thiadiazol-2-yl)-6,7-dimethyl-4-oxo-4H-chromene-2-carboxamide | 2.18949635 | 1.528053595 |
| 27 | ChemDiv6 | ChemDiv | D103-2012 | c1(nnc(SCC)s1)NC(=O)C(O2)=CC(c3c2cc(C)c(c3)C)=O | InChI=1/C16H15N3O3S2/c1-4-23-16-19-18-15(24-16)17-14(21)13-7-11(20)10-5-8(2)9(3)6-12(10)22-13/h5-7H,4H2,1-3H3,(H,17,18,21) | 361.438590 000 | 4898244 | N-(5-ethylsulfanyl-1,3,4-thiadiazol-2-yl)-6,7-dimethyl-4-oxochromene-2-carboxamide | 1.85816145 | 1.437102114 |
| 27 | ChemDiv6 | ChemDiv | E512-0723 | c1(c(c(CCc(cn(cCC(N CCOC)=O)n2)c12)oc3C(=O)N4CCCC4)c3C | InChI=1/C20H26N4O4/c1-13-17-15(28-19(13)20(26)23-8-3-4-9-23)6-5-14-11-24(22-18(14)17)12-16(25)21-7-10-27-2/h11H,3-10,12H2,1-2H3,(H,21,25) | 386.444830 000 | 16018736 | N-(2-methoxyethyl)-2-[8-methyl-7-(pyrrolidine-1-carbonyl)-4,5-dihydrofuro[2,3-g]indazol-2-yl]acetamide | 1.77693868 | 1.37364743 |

| Structure | # | Library | Source | ID | SMILES | InChI | MW | CID | Name | Val1 | Val2 |
|---|---|---|---|---|---|---|---|---|---|---|---|
| (structure) | 28 | NIH Clinical Collection 2 - 2013 | BioFocus | SAM002554896 | OC(=O)c1cc(ccc1O)c2ccc(F)cc2F | InChI=1S/C13H8F2O3/c14-8-2-3-9(11(15)6-8)7-1-4-12(16)10(5-7)13(17)18/h1-6,16H,(H,17,18) | 250.197620000 | 3059 | Diflunisal | 2.492223852 | 1.736408348 |
| (structure) | 28 | Biomol 4 - FDA Approved Drug Library | BIOMOL | DL-326 | c1(C(=O)o)cc(N)cc1O | InChI=1S/C7H7NO3/c8-4-1-2-6(9)5(3-4)7(10)11/h1-3,9H,8H2,(H,10,11) | 153.135380000 | 4075 | 5-aminosalicylic acid | 2.91123622 | 1.775395304 |
| (structure) | 28 | NIH Clinical Collection 1 - 2014 | Sequoia Research Products Ltd. | SAM001246804 | OC(=O)CCNC(=O)c1ccc(N=Nc2ccc(O)c(c2)C(=O)O)cc1 | InChI=1S/C17H15N3O6/c21-13(14)17(25)26)20-19-11-3-1-10(2-4-11)16(24)18-8-7-15(22)23/h1-6,9,21H,7-8H2,(H,18,24)(H,22,23)(H,25,26) | 357.317490000 | 6335412 | BALSALAZIDE | 1.597654821 | 1.239892513 |
| (structure) | 28 | ChemDiv Targeted Diversity Library | ChemDiv | D401-0759 | c1(Nc(ccc2)c(nc1c(O)=O)n(cc3)c(nc1c4cc(Br)ccc4O)cn3 | InChI=1S/C19H13BrN4O3/c20-12-3-6-15(25)14(9-12)17-18(24-8-7-21-10-16(24)23-17)22-13-4-1-11(2-5-13)19(26)27/h1-10,22,25H,(H,26,27) | 425.240000000 | 53003285 | 4-{[2-(5-bromo-2-hydroxyphenyl)imidazo[1,2-a]pyrazin-3-yl]amino}benzoic acid | 1.419604651 | 1.105620155 |
| (structure) | 28 | ChemDiv Targeted Diversity Library | ChemDiv | D401-0791 | c1(Nc(cccc2C(O)=O)c2)n(cc3)c(nc1c4cc(Br)ccc4O)cn3 | InChI=1S/C19H13BrN4O3/c20-12-4-5-15(25)14(9-12)17-18(24-7-6-21-10-16(24)23-17)22-13-3-1-2-11(8-13)19(26)27/h1-10,22,25H,(H,26,27) | 425.240000000 | 53003288 | 3-{[2-(5-bromo-2-hydroxyphenyl)imidazo[1,2-a]pyrazin-3-yl]amino}benzoic acid | 1.446161714 | 1.134116745 |

FIG. 9 (continued)

| | | | | | | | | |
|---|---|---|---|---|---|---|---|---|
| 28 | ChemDiv6 | ChemDiv | C908-0116 | c1(C(C)=O)sc(c1 NC(=O)c2cccc(F)c 2)c3ccccc3 | InChI=1/C18H12FNO3S/c1 9-13-8-4-7-12(9-13)17(21)20-14-10-15(24-16(14)18(22)23)11-5-2-1-3-6-11/h1-10H,(H,20,21)(H,22,23) | 341.356180000 | 16012569 | 3-[(3-fluorobenzoyl)amino]-5-phenylthiophene-2-carboxylic acid | 1.36488411 | 1.202641461 |
| 28 | NIH Clinical Collection 1 - 2014 | Sequoia Research Products Ltd. | SAM001246530 | OC(=O)c1cc(N=Nc2ccc(cc2)S(=O)(=O)Nc3occcn3)ccc1O | InChI=1S/C18H14N4O5S/c23-16-9-6-13(11-7-14(8-5-12)28(26,27)22-17-3-1-2-10-19-17/h1-11,23H,(H,19,22)(H,24,25) | 398.392560000 | 5353980 | SULFASALAZINE | 1.491021460 | 1.179920709 |
| 28 | ChemDiv6 Targeted Diversity Library | ChemDiv | C660-1021 | c1(c(cc(s1)C(=O)=O)c2c3ccc(cc3)Cl)c1n(n2)C | InChI=1S/C13H9ClN2O2S/c1-16-12-9(6-10(19-12)13(17)18)11(15-16)7-2-4-8(14)5-3-7/h2-6H,1H3,(H,17,18) | 292.750000000 | 44121471 | 3-(4-chlorophenyl)-1-methylthieno[2,3-c]pyrazole-5-carboxylic acid | 2.05483309 | 1.231934576 |
| 28 | ChemDiv6 | ChemDiv | E455-0215 | c12c(n[nH]c1c3ccc(cc3)OC)nc(c4cc(Br)ccc4OC)cc2C(O)=O | InChI=1/C21H16BrN3O4/c1-28-13-6-11(4-7-13)19-18-15(21(26)27)10-16(23-20(18)25-24-19)14-9-12(22)5-8-17(14)29-2/h3-10H,1-2H3,(H,26,27)(H,23,24,25) | 454.273430000 | 16018594 | 6-(5-bromo-2-methoxyphenyl)-3-(4-methoxyphenyl)-2H-pyrazolo[3,4-b]pyridine-4-carboxylic acid | 1.30949683 | 1.11162738 |
| 28 | ChemDiv Targeted Diversity Library | ChemDiv | C202-1858 | c12c(n[nH]c1c3ccc(cc3)C)nc(c4ccc(c(O)c4)O)cc2C(O)=O | InChI=1S/C20H15N3O4/c1-10-2-4-11(5-3-10)18-17-13(20(26)27)9-14(21-19(17)23-22-18)12-6-7-15(24)16(25)8-12/h2-9,24-25H,1H3,(H,26,27)(H,21,22,23) | 361.360000000 | 54724324 | 4-(3,4-dihydroxyphenyl)-3-(4-methylphenyl)-1H-pyrazolo[3,4-b]pyridine-6-carboxylic acid | 1.73600404 | 1.302919247 |

FIG. 9 (continued)

| | | | | | | | | |
|---|---|---|---|---|---|---|---|---|
| 28 | ChemDiv6 | ChemDiv | 8008-9116 | c1([nH]c(c2n1)cccc2-16-7-5-12/10-2)C(/C#N)=C\c(cc c3c(ccc(c4C(O)=O)c4)o3 | InChI=1/C21H12ClN3O3/c2 -16-7-5-12/10-15(16)21(26)27)19-8-6-14(28-19)9-13(11-23)20-24-17-3-1-2-4-18(17)25-20/h1-10H,(H,24,25)(H,26,27)/b13-9+ | 389.791280 000 | 5289916 | 5-[5-[((E)-2-(1H-benzimidazol-2-yl)-2-cyanoethenyl]fura n-2-yl]-2-chlorobenzoic acid | 1.63786531 | 1.236047307 |
| 28 | NIH Clinical Collection 2 - 2013 | BioFocus | SAM002554 902 | OCCOCCN1CCN( CC1)C(c2ccccc2)c 3ccc(Cl)cc3.OC(=O)c1cc2ccccc2c(C c3c(O)c(cc4ccccc3 4)C(=O)[O-])c1O | InChI=1S/C23H16O6.C21H 27ClN2O2/c24-20-16(14-7-3-1-5-12(14)9-18(20)22(26)27)11-17-15-8-4-2-6-13(15)10-19(21(17)25)23(28)29.22-20-8-6-19(7-9-20)21(18-4-2-1-3-5-18)24-12-10-23(11-13-24)14-16-26-17-15-25/ | 762.265880 000 | 49842934 | Vistarsi Pamoate | 2.85196416 | 1.783184011 |
| 28 | ChemDiv6 | ChemDiv | 4789-4085 | c1(Nc(cccc2C(O)=O)c2)ncnc(ccc(Br)c 3)c13 | InChI=1/C15H10BrN3O2/c1 6-10-4-5-13-12(7-10)14(18-8-17-13)19-11-3-1-2-9(6-11)15(20)21/h1-8H,(H,20,21)(H,17,18,19) | 344.162790 000 | 693193 | 3-[(6-bromoquinazolin-4-yl)amino]benzoic acid | 1.23626212 | 1.114212949 |
| 28 | EMD Kinase Inhibitor 1 | EMD Biosciences | 218710 | c1(Br)c(Br)c(\C=C\ C(=O)O)cc(Br)c1Br | InChI=1/C9H4Br4O2/c10-5-3-4(1-2-6(14)15)7(11)9(13)8(5)12/h 1-3H,(H,14,15)/b2-1+ | 463.742850 000 | 16760346 | Casein Kinase II Inhibitor III, TBCA | 1.54280279 | 1.157387445 |
| 28 | ChemDiv6 | ChemDiv | C202-1714 | c12c(n[nH]c1c3ccc cc3)nc(c4ccc(c(OC C)c4)O)cc2C(O)=O | InChI=1/C21H17N3O4/c1-2-28-17-10-13(8-9-16(17)25)15-11-14(21(26)27)18-19(23-24-20(18)22-15)12-6-4-3-5-7-12/h3-11,25H,2H2,1H3,(H,26,27)(H,22,23,24) | 375.377370 000 | 15988333 | (6Z)-6-(3-ethoxy-4-oxocyclohexa-2,5-dien-1-ylidene)-3-phenyl-1,2-dihydropyrazolo[3,4-b]pyridine-4-carboxylic acid | 1.27218692 | 1.12441074 |

FIG. 9 (continued)

| | | | | | | | |
|---|---|---|---|---|---|---|---|
| 28 | ChemDiv Targeted Diversity Library | ChemDiv | D356-2542 | S1(=O)(=O)c2c(cc cc2)c(c3N1CC(N)= O)cc(cc3)F | InChI=1S/C14H11FN2O3S/ c15-9-5-6-12-11(7-9)10-3-1-2-4-13(10)21(19,20)17(12)8-14(16)18/h1-7H,8H2,(H2,16,18) | 306.320000 | 17744417 | 2-(9-fluoro-5,5-dioxido-6H-dibenzo[c,e][1,2]t hiazin-6-yl)acetamide | 1.24866951 | 1.099121873 |
| 28 | ChemDiv Targeted Diversity Library | ChemDiv | D475-2646 | n1(nc(c(CCC(OC)= O)c1O)C)c2scc(c3 ccc(cc3)Cl)n2 | InChI=1S/C17H16ClN3O3S /c1-10-13(7-8-15(22)24-2)16(23)21(20-10)17-19-14(9-25-17)11-3-5-12(18)6-4-11/h3-6,9,23H,7-8H2,1-2H3 | 377.850000 | 46269440 | methyl 3-[2-[4-(4-chlorophenyl)-1,3-thiazol-2-yl]-5-methyl-3-oxo-1H-pyrazol-4-yl]propanoate | 1.294418635 | 1.114586037 |
| 28 | ChemDiv Targeted Diversity Library | ChemDiv | D475-2586 | n1(nc(c(CCC(OC)= O)c1O)C)c2scc(c3 ccc(cc3)F)n2 | InChI=1S/C17H16FN3O3S/ c1-10-13(7-8-15(22)24-2)16(23)21(20-10)17-19-14(9-25-17)11-3-5-12(18)6-4-11/h3-6,9,23H,7-8H2,1-2H3 | 361.400000 | 46269430 | methyl 3-[2-[4-(4-fluorophenyl)-1,3-thiazol-2-yl]-5-methyl-3-oxo-1H-pyrazol-4-yl]propanoate | 1.21477552 | 1.097920858 |
| 28 | ChemDiv Targeted Diversity Library | ChemDiv | C390-0187 | c12c(c(n(nH)1)c3cc ccc3)C(N(c(cc4A)cc c4C(O)=O)C2=O)c 5cccc(O)c5 | InChI=1S/C24H17N3O4/c2 8-18-8-4-7-16(13-18)22-19-20(14-5-2-1-3-6-14)25-26-21(19)23(29)27(22)17-11-9-15(10-12-17)24(30)H,(H,25,26)(H,30,3 1) | 411.420000 | 19589042 | 4-[4-(3-hydroxyphenyl)-6-oxo-3-phenyl-1,4-dihydropyrrolo[3,4-c]pyrazol-5-yl]benzoic acid | 1.28274428 | 1.067873303 |
| 28 | Microsource 1 - US Drug Collection | Microsourc e | 1503278 | c(c(NCCNCCO)ccc 1NCCNCCO)C2=Op1Oc3c2c(O)cc c3O)=O.Cl.Cl | InChI=1S/C22H28N4O6.2Cl H/c27-11-9-23-5-7-25-13-1-2-14(26-8-6-24-10-12-28)18-17(13)21(31)19-15(29)3-4-16(30)20(19)22(18)32;;/h1-4,23-30H,5-12H2;2*1H | 517.402790 | 45114134 | Mitoxanthrone hydrochloride | 1.29408673 | 1.242575558 |

FIG. 9 (continued)

| | | | | | | | | |
|---|---|---|---|---|---|---|---|---|
| 28 | ChemDiv Targeted Diversity Library | ChemDiv | D715-2716 | C1(CC(OCC)=O)=CC(=O)Oc(cc(O)cc2O)c12 | InChI=1S/C13H12O6/c1-2-18-11(16)3-7-4-12(17)19-10-6-8(14)5-9(15)13(7)10/h4-6,14-15H,2-3H2,1H3 | 264.240000 | 337748683 | Ethyl (5,7-dihydroxy-2-oxo-2H-chromen-4-yl)acetate | 1.95727937 | 1.314446318 |
| 28 | ChemDiv6 | ChemDiv | E455-0302 | c12c(n[nH]c1c3ccccc3)nc(cc(cc4)ccc4C(F)(F)F)cc2C(=O)O | InChI=1S/C20H12F3N3O2/c2-1-20(22,23)13-8-6-11(7-9-13)15-10-14(19(27)28)16-17(25-26-18(16)24-15)12-4-2-1-3-5-12/h1-10H,(H,27,28)(H,24,25,26) | 383.323380 | 16018596 | 3-phenyl-6-[4-(trifluoromethyl)phenyl]-2H-pyrazolo[3,4-b]pyridine-4-carboxylic acid | 1.3497728 | 1.17810041 |
| 28 | ChemDiv Targeted Diversity Library | ChemDiv | C790-0709 | c1(ccc(C)cc2C)c2nc(C)cc1C(O)=O | InChI=1S/C13H13NO2/c1-7-4-8(2)12-10(5-7)11(13(15)16)6-9(3)14-12/h4-6H,1-3H3,(H,15,16) | 215.250000 | 865218 | 2,6,8-trimethylquinoline-4-carboxylic acid | 1.25199746 | 1.061382372 |
| 29 | SYNthesis med chem Kinase Inhibitor 2 | SYNthesis | SYN-1051 | c1ccc2c(c1)Sc3ccc(c3S2)c4cc(=O)cc(o4)N5CCOCC5 | InChI=1S/C21H17NO3S2/c23-14-12-16(25-20(13-14)22-8-10-24-11-9-22)15-4-3-7-19-21(15)27-18-6-2-1-5-17(18)26-19/h1-7,12-13H,8-11H2 | 395.494570 | | 2-morpholin-4-yl-6-thianthren-1-ylpyran-4-one | 1.47116622 | 1.323663586 |
| 29 | ChemDiv Targeted Diversity Library | ChemDiv | D430-2380 | c(N(CC1)CCN1C(=O)Nc(ccc(c23)OCCO2)c3)(c4)nc(nc4N(CC5)CCO5)C | InChI=1S/C22H28N6O4/c1-16-23-20(15-21(24-16)27-8-10-30-11-9-27)26-4-6-28(7-5-26)22(29)25-17-2-3-18-19(14-17)32-13-12-31-18/h2-3,14-15H,4-13H2,1H3,(H,25,29) | 440.510000 | 50748159 | N-(2,3-dihydro-1,4-benzodioxin-6-yl)-4-(2-methyl-6-morpholin-4-ylpyrimidin-4-yl)piperazine-1-carboxamide | 1.2574196 | 1.064448032 |

FIG. 9 (continued)

| Structure | | Source | ID | SMILES | InChI | MW | CID | Name | | | |
|---|---|---|---|---|---|---|---|---|---|---|---|
| | 30 | ChemDiv Targeted Diversity Library | ChemDiv Z601-7873 | n1c(N)c2c(nc1N3CCCC3)cccc2 | InChI=1S/C12H14N4/c13-11-9-5-1-2-6-10(9)14-12(15-11)16-7-3-4-8-16/h1-2,5-6H,3-4,7-8H2,(H2,13,14,15) | 214.270000 | 10703843 | 2-(1-pyrrolidinyl)-4-quinazolinamine | | 1.5049285 | 1.175343607 |
| | 30 | NIH Clinical Collection 2 - 2013 | BioFocus SAM002264609 | OCCN(CCO)c1nc(N2CCCCC2)c3nc(nc(N4CCCCC4)c3n1)N(CCO)CCO | InChI=1S/C24H40N8O4/c3 3-15-11-31(12-16-34)23-26-20-19(21(27-23)29-7-3-1-4-8-29)25-24(32(13-17-35)14-18-36)28-22(20)30-9-5-2-6-10-30/h33-36H,1-18H2 | 504.625590 000 | 3108 | Dipyridamole | | 1.21167349 | 1.097571679 |
| | 30 | ChemDiv Targeted Diversity Library | ChemDiv C200-9494 | c12c(ncnc1N(CCCC3C(=O)C3)c4c(0-16(21)10-4-3-7-19(8-ccc4)o2 | InChI=1S/C16H15N3O3/c2 10)15-14-13(17-9-18-15)11-5-1-2-6-12(11)22-14/h1-2,5-6,9-10H,3-4,7-8H2,(H,20,21) | 297.320000 000 | 50743347 | 1-[1]benzofuro[3,2-d]pyrimidin-4-ylpiperidine-3-carboxylic acid | | 1.28661675 | 1.040126345 |
| | 30 | Microsource 1 - US Drug Collection | Microsource 1504218 | c(N)(c1c2occc1)c3c(n2)cccc3.c4(O)c(CCCCC)ccc(O)c4 | InChI=1S/C13H10N2.C12H 18O2/c14-13-9-5-1-3-7-10(12)13;1-2-3-4-5-6-10-7-8-11(13)9-12(10)14/m1-8H,(H2,14,15);7-9,13-14H,2-6H2,1H3 | 388.502010 000 | 24144 | Acrisorcin | | 1.94386405 | 1.312856944 |
| | 30 | ChemDiv6 | ChemDiv E677-2575 | c1(N(CCCN(C)C)c(=O)c2cccco2)sc(c3n1)c(OC)ccc3OC | InChI=1/C19H23N3O4S/c1-21(2)10-6-11-22(18(23)15-7-000 5-12-26-15)19-20-16-13(24-3)8-9-14(25-4)17(16)27-19/h5,7-9,12H,6,10-11H2,1-4H3 | 389.468610 000 | 7512923 | N-(4,7-dimethoxy-1,3-benzothiazol-2-yl)-N-[3-(dimethylamino)propyl]furan-2-carboxamide | | 1.20049228 | 1.118035355 |

FIG. 9 (continued)

| | | | | | | | |
|---|---|---|---|---|---|---|---|
| 30 | ChemDiv Targeted Diversity Library | ChemDiv | L921-0024 | S(=O)(=O)(Nc(cc1C)c2c(n1)cccc2)c3cc(C)sc(c4scc(C)n4)c3 | InChI=1S/C19H17N3O2S3/c1-11-8-16(14-6-4-5-7-15(14)20-11)22-27(23,24)18-9-17(26-13(18)3)19-21-12(2)10-25-19/h4-10H,1-3H3,(H,20,22) | 415.560000000 | 50835848 | 2-methyl-N-(2-methylquinolin-4-yl)-5-(4-methyl-1,3-thiazol-2-yl)thiophene-3-sulfonamide | 1.219709591 | 1.072720781 |
| 30 | ChemDiv Targeted Diversity Library | ChemDiv | L150-1101 | c12cc(C(N(C(C(=O)N1C)=O)nc(SCCC(O)=O)n2Cc3ccccc3 | InChI=1S/C17H18N4O4S/c1-19-14-13(15(24)20(2)17(19)25)18-16(26-9-8-12(22)23)21(14)10-11-6-4-3-5-7-11/h3-7H,8-10H2,1-2H3,(H,22,23) | 374.420000000 | 45032938 | 3-(9-benzyl-1,3-dimethyl-2,6-dioxopurin-8-yl)sulfanyl)propanoic acid | 1.30571155 | 1.121764142 |
| 31 | ChemDiv6 | ChemDiv | C499-0394 | N1(CN(C2CCCCC2)CS3)C3=C(C(c(o4c26-17,9-17,15(8-10-17)18-11-11-000 cc(cc4)OC)CC1=O)C#N | InChI=1/C21H25N3O2S/c1-000 20(25)24-13-23(16-5-3-2-4-6-16)14-27-21(24)19(18)12-22/h7-10,16,18H,2-6,11,13-14H2,1H3 | 383.507090 | 4971465 | 3-cyclohexyl-8-(4-methoxyphenyl)-6-oxo-3,4,7,8-tetrahydro-2H,6H-pyrido[2,1-b][1,3,5]thiadiazine-9-carbonitrile | 1.61257709 | 1.32261652 |
| 31 | ChemDiv6 | ChemDiv | C499-0610 | N1(CN(C2CCCCC2)CS3)C3=C(C(c(c4)ccc4C(C)C)CC1=O)C#N | InChI=1/C23H29N3OS/c1-16(2)17-8-10-18(11-9-17)20-12-22(27)26-14-25(19-6-4-3-5-7-19)15-28-23(26)21(20)13-24/h8-11,16,19-20H,3-7,12,14-15H2,1-2H3 | 395.560850000 | 16020361 | 3-cyclohexyl-6-oxo-8-(4-propan-2-ylphenyl)-2,4,7,8-tetrahydropyrido[2,1-b][1,3,5]thiadiazine-9-carbonitrile | 1.228256678 | 1.071724398 |
| 31 | ChemDiv6 | ChemDiv | C499-0853 | N1(CN(C2CCCCC2)CS3)C3=C(C(c(cc4)Br)CC1=O)C#N | InChI=1/C20H22BrN3OS/c2-000 1-15-8-6-14(7-9-15)17-10-19(25)24-12-23(16-4-2-1-3-5-16)13-26-20(24)18(17)11-22/h6-9,16-17H,1-5,10,12-13H2 | 432.377170 | 16020366 | 8-(4-bromophenyl)-3-cyclohexyl-6-oxo-3,4,7,8-tetrahydro-2H,6H-pyrido[2,1-b][1,3,5]thiadiazine-9-carbonitrile | 1.32554745 | 1.090024331 |

FIG. 9 (continued)

| | | | | | | | | |
|---|---|---|---|---|---|---|---|---|
| | 31 | ChemDiv6 | ChemDiv | D222-0073 | C1(CN(CC2)CCN2C(=O)c3ccc(c(OC)c3)OC)=CC(=O)Oc(ccc(OCC)c4)c14 | InChI=1/C25H28N2O6/c1-4-32-19-6-8-21-20(15-19)18(14-24(28)33-21)16-26-9-11-27(12-10-26)25(29)17-5-7-22(30-2)23(13-17)31-3/h5-8,13-15H,4,9-12,16H2,1-3H3 | 452.499610000 | 16014154 | 4-[[4-(3,4-dimethoxybenzoyl)piperazin-1-yl]methyl]-6-ethoxychromen-2-one | 1.39504579 | 1.152617985 |
| | 31 | ChemDiv Targeted Diversity Library | ChemDiv | D715-2605 | C1(=O)Oc2c(C3=C1CCC3)ccc(c2)OC(C)C(O)=O | InChI=1S/C15H14O5/c1-8(14(16)17)19-9-5-6-11-10-3-2-4-12(10)15(18)20-13(11)7-9/h5-8H,2-4H2,1H3,(H,16,17) | 274.280000000 | 2771984 | 2-[(4-Oxo-1,2,3,4-tetrahydrocyclopenta[c]chromen-7-yl)oxy]propanoic acid | 1.65251839 | 1.19524618 |
| | 31 | ChemDiv6 | ChemDiv | D129-0130 | C1(C)=C(CC(O)=O)C(=O)Oc(cc(c2c3occ2c4ccc(cc4)OC)C)c13 | InChI=1/C22H18O6/c1-11-8-17-20(12(2)15(9-18(23)24)22(25)28-17)21-19(11)16(10-27-21)13-4-6-14(26-3)7-5-13/h4-8,10H,9H2,1-3H3,(H,23,24) | 378.374720000 | 4913713 | [3-(4-methoxyphenyl)-4,9-dimethyl-7-oxo-7H-furo[2,3-f]chromen-8-yl]acetic acid | 1.77414819 | 1.302866414 |

FIG. 9 (continued)

| Chemical Structure | Cluster | Cluster Size | Library | Vendor | Vendor Reagent ID | SMILES | InChi | PubChem_CID | Chemical_Name | Fold_Change 100µM compound | Fold_Change 33µM compound |
|---|---|---|---|---|---|---|---|---|---|---|---|
| 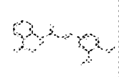 | 5 | 73 | NIH Clinical Collection 1 - 2014 | Sequoia Research Products Ltd. | SAM001246737 | COc1ccc(/C=C/C(=O)Nc2ccccc2C(=O)O)cc1O | InChI=1S/C18H17NO5/c1-23-15-8-7-12(11-16(15)24-2)6-10-17(20)19-14-6-4-3-5-13(14)18(21)22/h3-11H,1-2H3,(H,19,20)(H,21,22)/b10-8+ | 5282230 | TRANILAST | 1.402726433 | 1.132858823 |
| 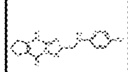 | 20 | 26 | ChemDiv Targeted Diversity Library | ChemDiv | D433-1837 | n1(nc(n2)CNc(cc3)ccc3Br)c2NC(CCC4)=C4C1=O | InChI=1S/C15H14BrN5O/c16-9-4-6-10(7-5-9)17-8-13-19-15-18-12-3-1-2-11(12)14(22)21(15)20-13/h4-7,17H,1-3,8H2,(H,18,19,20) | 50748901 | 2-{[(4-bromophenyl)amino]methyl}-4,5,6,7-tetrahydro-8H-cyclopenta[d][1,2,4]triazolo[1,5-a]pyrimidin-8-one | 1.460555197 | 1.146158812 |
| 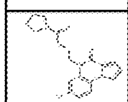 | 1 | 24 | ChemDiv Targeted Diversity Library | ChemDiv | E228-3001 | n1(c(ccc(c2)Br)c2N(C3=O)CCC2)N(C3=O)N4CCCC4)c3ccc1 | InChI=1S/C19H20BrN3O2/c20-14-7-8-15-17(13-14)23(19(25))16-5-3-11-22(15)16)12-4-6-18(24)21-9-1-2-10-21/h3,5,7-8,11,13H,1-2,4,6,9-10,12H2 | 46272920 | 7-bromo-5-(4-oxo-4-pyrrolidin-1-ylbutyl)pyrrolo[1,2-a]quinoxalin-4-one | 1.393691589 | 1.230490654 |
| 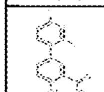 | 28 | 23 | NIH Clinical Collection 2 - 2013 | BioFocus | SAM002554896 | OC(=O)c1cc(cc10)c2cc(F)cc2F | InChI=1S/C13H8F2O3/c14-8-2-3-9(11(15)6-8)7-1-4-12(16)10(5-7)13(17)18/h1-6,16H,(H,17,18) | 3059 | Difunisal | 2.492223847 | 1.736408348 |
| 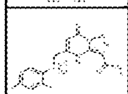 | 27 | 15 | ChemDiv Targeted Diversity Library | ChemDiv | C200-8619 | c1(NC(CS(=O)(=O)c2ccc(cc2C)C)=CC3=O)n3ncc1C(OC)=O | InChI=1S/C17H17N3O5S/c1-10-4-5-14(11(2)6-10)26(23,24)9-12-7-15(21)20-16(19-12)13(8-18-20)17(22)25-3/h4-8,19H,8H2,1-3H3 | 45499564 | Methyl 5-{[(2,4-dimethylphenyl)sulfonyl]methyl}-7-oxo-4,7-dihydropyrazolo[1,5-a]pyrimidine-3-carboxylate | 1.269590056 | 1.089040277 |
| 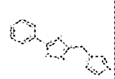 | 4 | 14 | ChemDiv Targeted Diversity Library | ChemDiv | T742-0069 | n1(c2ccccc2)onc1Cn(ccn3)c3 | InChI=1S/C12H10N4O/c1-2-4-10(5-3-1)12-15-17-12)8-16-7-6-13-9-16/h1-7,9H,8H2 | 53015251 | 3-(1H-imidazol-1-ylmethyl)-5-phenyl-1,2,4-oxadiazole | 1.983981136 | 1.431920781 |

FIG. 10

| Vendor | Vendor_Reagent_ID | PubChem_CID | SMILES | Chemical_Name |
|---|---|---|---|---|
| BioFocus | SAM002554896 | 3059 | OC(=O)c1cc(ccc1O)c2ccc(F)cc2F | Diflunisal |
| BIOMOL | DL-326 | 4075 | c1(C(=O)O)cc(N)ccc1O | 5-aminosalicylic acid |
| ChemDiv | 8008-9116 | 5289916 | c1([nH]c(c2n1)cccc2)\C(\C#N)=C\c(ccc3c(ccc(c4C(O)=O)Cl)c4)o3 | 5-[5-[(E)-2-(1H-benzimidazol-2-yl)-2-cyanoethenyl]furan-2-yl]-2-chlorobenzoic acid; 5-{5-[(E)-2-(1H-benzimidazol-2-yl)-2-cyanoethenyl]furan-2-yl}-2-chlorobenzoic acid |
| EMD Biosciences | 218710 | 16760346 | c1(Br)c(Br)c(\C=C\C(=O)O)cc(Br)c1Br | Casein Kinase II Inhibitor III, TBCA or (E)-3-(2,3,4,5-Tetrabromophenyl)acrylic acid |
| ChemDiv | C798-1439 | 46261177 | c1(C2=O)n(c3c(cc(cc3)C)N2Cc(cc4)ccc4Cl)nc(C(O)=O)n1 | 5-(4-chlorobenzyl)-7-methyl-4-oxo-4,5-dihydro[1,2,4]triazolo[1,5-a]quinoxaline-2-carboxylic acid |
| ChemDiv | L384-0099 | 50826285 | n12c(ccc(n1)NS(=O)(=O)c3ccc(cc3)Cl)nnc2c4ccccc4 | 4-chloro-N-(3-phenyl-[1,2,4]triazolo[4,3-b]pyridazin-6-yl)benzenesulfonamide |
| ChemDiv | F232-0763 | 53004596 | C(C1c2ccc(cc2)Cl)(S(c3ccccc3)(=O)=O)=C(O)C(N1Cc(ccc(c45)OCO4)c5)=O | 3-(benzenesulfonyl)-1-(1,3-benzodioxol-5-ylmethyl)-2-(4-chlorophenyl)-4-hydroxy-2H-pyrrol-5-one |
| ChemDiv | E010-0092 | 16016782 | c1(c(CCc(cn2)c1[nH]2)oc3C(=O)Nc4c(C)ccc(Cl)c4)c3C | N-(5-chloro-2-methylphenyl)-8-methyl-4,5-dihydro-1H-furo[2,3-g]indazole-7-carboxamide |
| ChemDiv | T742-0014 | 53015246 | n1c(c2ccc(cc2)F)onc1Cn(ccn3)c3 | 5-(4-fluorophenyl)-3-(imidazol-1-ylmethyl)-1,2,4-oxadiazole |
| Microsource | 1300037 | 11963579 | [Fe-2](C#N)(C#N)(C#N)(C#N)(C#N)N=O.[Na+].[Na+] | disodium;iron(4+);nitroxyl anion;pentacyanide (aka nitroprusside) |

FIG. 11

| | | | | |
|---|---|---|---|---|
| Microsource | 1500844 | 16717690 | [Co+]1(C[C@H]([C@@H](O)[C@H]2C2n3cnc4c3ncnc4N)O)O2)(N(C(C(C5(C)CC(N)=O)CCC(N)=O)=C6C)C57C)([N](C78)=C9C(C8CC(N)=O)(C)CCC(=O)NCC(OP(=O)([O-]))O[C@H]([C@@H](CO)O%10)[C@@H](O)C%10N(c(cc(C)c(C)c%11)c%11%12 | (3R,4S,5R)-2-(6-aminopurin-9-yl)-5-methanidyloxolane-3,4-diol;cobalt(3+);[(2R,3S,4R)-5-(5,6-dimethylbenzimidazol-1-yl)-4-hydroxy-2-(hydroxymethyl)oxolan-3-yl] 1-[3-[(5Z,10Z,15Z)-2,13,18-tris(2-amino-2-oxoethyl)-7,12,17-tris(3-amino-3-oxopropyl)-3,5,8,8,13,15,18,19-octamethyl-2,7,12,17-tetrahydro-1H-corrin-24-id-3-yl]propanoylamino]propan-2-yl phosphate |
| ChemDiv | E534-0239 | 22554360 | c1(CN(CC2)CCN2C)csc(C)c1CC | 1-[(4-ethyl-5-methylthiophen-3-yl)methyl]-4-methylpiperazine |
| ChemDiv | E534-0255 | 22554371 | c1(CN(CC2)CCN2Cc(ccc(c34)OCO3)c4)csc(C)c1CC | 1-(1,3-benzodioxol-5-ylmethyl)-4-[(4-ethyl-5-methylthiophen-3-yl)methyl]piperazine |
| ChemDiv | E534-0231 | 16019111 | c1(CN(CC2)CCN2c3cccc(C)c3C)csc(C)c1CC | 1-(2,3-dimethylphenyl)-4-[(4-ethyl-5-methylthiophen-3-yl)methyl]piperazine |
| MedChem Express | HY-14268 | 134018 | CC1=C(SC(=N1)C2=CC(=C(C=C2)OCC(C)C)C#N)C(=O)O | 2-[3-cyano-4-(2-methylpropoxy)phenyl]-4-methyl-1,3-thiazole-5-carboxylic acid |
| ChemDiv | L150-0829 | 50820754 | c1(cn(c(ccc2S(=O)(=O)N(C)C)c1c2)C)C(=O)n(ccn3)c3 | 3-(imidazole-1-carbonyl)-N,N,1-trimethylindole-5-sulfonamide |
| ChemDiv | E734-0048 | 16021588 | S(=O)(=O)(Nc(cccc1C(OCC)=O)c1)c(c(C)cc(c23)NC(=O)N2)=O)c3 | ethyl 3-[(7-methyl-2,3-dioxo-1,4-dihydroquinoxalin-6-yl)sulfonylamino]benzoate |
| ChemDiv | E233-0714 | 16018166 | c1(c(cCCc(cn(CC)n2)c12)oc3C(=O)Nc(cccc4C(OCC)=O)c4)c3C | ethyl 3-[(2-ethyl-8-methyl-4,5-dihydrofuro[2,3-g]indazole-7-carbonyl)amino]benzoate |
| ChemDiv | 3388-1008 | 737912 | C1(Nc(ccc(c2C)C)c2)=CC(=O)NC(=O)N1 | 6-(3,4-Dimethyl-phenylamino)-1H-pyrimidine-2,4-dione |
| ChemDiv | D103-1622 | 16013427 | S(=O)(=O)(c1ccc(cc1)N([H])C(=O)C(Oc(cc(C)cc2C)c2C3=O)=C3)Nc4onc(C)c4C | N-[4-[(3,4-dimethyl-1,2-oxazol-5-yl)sulfamoyl]phenyl]-5,7-dimethyl-4-oxochromene-2-carboxamide |
| ChemDiv | C102-0340 | 2154009 | N1C(=O)C=NN=C1Nc(ccc(c2Cl)C)c2 | 3-[(3-chloro-4-methylphenyl)amino]-1,2,4-triazin-5-ol |

FIG. 11 (continued)

| | | | | |
|---|---|---|---|---|
| ChemDiv | 8011-6852 | 1043578 | c1(c2c(ccc(c2)OC(F)(F)F)ncc1C(OCC)=O)Nc3ccccc3C(O)=O | 2-[[3-ethoxycarbonyl-6-(trifluoromethoxy)quinolin-4-yl]amino]benzoic acid |
| ChemDiv | C248-0004 | 5839674 | c1(C(=O)N([H])C(N2[H])=O)c2nc3c(ccc(c3)N([H])C(C)=O)n1 | N-(2,4-dioxo-1H-benzo[g]pteridin-8-yl)acetamide |
| ChemDiv | D043-0019 | 3910081 | n1(nc(n2)NCc3cccc(Br)c3)c2NC=C(C(OCC)=O)C1=O | ethyl 2-[[(3-bromophenyl)methylamino]-7-oxo-1H-[1,2,4]triazolo[1,5-a]pyrimidine-6-carboxylate |
| ChemDiv | D103-1942 | 4974983 | c1(nnc(CC)s1)N([H])C(=O)C(O2)=CC(c3c2cc(C)c(c3)C)=O | N-(5-ethyl-1,3,4-thiadiazol-2-yl)-6,7-dimethyl-4-oxo-4H-chromene-2-carboxamide |
| ChemDiv | D103-2012 | 4898244 | c1(nnc(SCC)s1)NC(=O)C(O2)=CC(c3c2cc(C)c(c3)C)=O | N-(5-ethylsulfanyl-1,3,4-thiadiazol-2-yl)-6,7-dimethyl-4-oxochromene-2-carboxamide |
| ChemDiv | D103-1943 | 4871195 | c1(nnc(CCC)s1)N([H])C(=O)C(O2)=CC(c3c2cc(C)c(c3)C)=O | 6,7-dimethyl-4-oxo-N-(5-propyl-1,3,4-thiazol-2-yl)-4H-chromene-2-carboxamide |
| SYNthesis | SYN-1028 | 10430360 | c1cc(cc(c1)OCCN2CCCCC2)c3c4cc(ccc4[nH]n3)c5nc[nH]n5.Cl | 3-[3-(2-piperidin-1-ylethoxy)phenyl]-5-(1H-1,2,4-triazol-5-yl)-1H-indazole |
| ChemDiv | C797-0939 | 20887178 | c12n(c(c3s1)ccc(c3)C(NCCCN(CCCC)CCCC)=O)cc(c4ccc(cc4)OC)n2 | N-[3-(dibutylamino)propyl]-2-(4-methoxyphenyl)imidazo[2,1-b][1,3]benzothiazole-6-carboxamide |
| ChemDiv | 4109-2013 | 1417297 | S(=O)(=O)(N(C)C)c1c(C)ccc(c1)c2c3c(cccc3)c(nn2)Nc(cc4)cc4OCC(N)=O | 2-[4-({4-[3-(dimethylsulfamoyl)-4-methylphenyl]phthalazin-1-yl}amino)phenoxy]acetamide |
| Microsource | 1500132 | 454937 | [C@@H]1(O)[C@@H](O)[C@H](O)[C@H](OC1S[Au])CO | Aurothioglucose |
| ChemDiv | 8249-3674 | 7342703 | N([N-]C(C1=C2C)=CC(N2CCc3c[nH]cn3)=O)(C1=O)c4sc(c5n4)cccc5 | 2-(1,3-benzothiazol-2-yl)-5-[2-(1H-imidazol-5-yl)ethyl]-4-methyl-3-oxopyrazolo[4,3-c]pyridin-6-olate |

FIG. 11 (continued)

| | | | | |
|---|---|---|---|---|
| Sequoia Research Products Ltd. | SAM001246782 | 60758 | Cc1[nH]cnc1CN2CCc3c(C2=O)c4ccccc4n3C.Cl- | ALOSETRON HCl |
| ChemDiv | M384-0056 | 50844153 | c(C1)(c2c(n3CC)ccc([H])c2)c3CCN1C(C(C4)CC4)=O | cyclobutyl-(5-ethyl-3,4-dihydro-1H-pyrido[4,3-b]indol-2-yl)methanone |
| ChemDiv | F083-0377 | 50761579 | N1(c2c(cc(OCO3)c3c2)C(N4)=O)C4=C(SC1=S)C(N([H])[H])=O | 5-oxo-1-thioxo-4,5-dihydro[1,3]dioxolo[4,5-g][1,3]thiazolo[3,4-a]quinazoline-3-carboxamide |
| ChemDiv | D103-1154 | 4898047 | c1(nnc(C)s1)N([H])C(=O)C2=CC(c3c(cc(C)cc3)O2)=O | 7-methyl-N-(5-methyl-1,3,4-thiadiazol-2-yl)-4-oxo-4H-chromene-2-carboxamide |
| ChemDiv | D517-1064 | 50751471 | c12c(NC(=O)NC1=O)[nH]c(c3ccc(c4c3)cccc4)c2C5c6c(N(C)C5=O)cccc6 | 5-(1-methyl-2-oxo-2,3-dihydro-1H-indol-3-yl)-6-(2-naphthyl)-1H-pyrrolo[2,3-d]pyrimidine-2,4(3H,7H)-dione |
| ChemDiv | D341-0243 | 17011310 | c1(ncnc2N([H])Cc(cc3)ccn3)c2c4c(CCCC4)s1 | N-(pyridin-4-ylmethyl)-5,6,7,8-tetrahydro[1]benzothieno[2,3-d]pyrimidin-4-amine |
| ChemDiv | D341-0231 | 2403385 | c1(c2c(s3)CCCC2)c3ncnc1N4CCC(CC4)C(N)=O | 1-(5,6,7,8-tetrahydro[1]benzothieno[2,3-d]pyrimidin-4-yl)piperidine-4-carboxamide |
| ChemDiv | 2425-4322 | 1011051 | c1(NC(=O)c2ccccc2C(O)=O)sc(c3c1C(OC)=O)CCCC3 | 2-[[3-methoxycarbonyl-4,5,6,7-tetrahydro-1-benzothiophen-2-yl]carbamoyl]benzoic acid |
| ChemDiv | D058-0287 | 2772582 | c12n(c3c(cccc3)n1c4ccccc4)c(nn2)SCC(O)=O | [(9-Phenyl-9H-[1,2,4]triazolo[4,3-a]benzimidazol-3-yl)thio]acetic acid |
| ChemDiv | L150-1097 | 45032956 | c12c(C(N(C)C(=O)N1C)=O)nc(SCC(O)=O)n2Cc3ccccc3 | 2-(9-benzyl-1,3-dimethyl-2,6-dioxopurin-8-yl)sulfanylacetic acid |
| ChemDiv | D475-2526 | 46269415 | n1(nc(c(CCC(OC)=O)c1O)C)c2scc(c3ccc(cc3)C)n2 | methyl 3-[5-methyl-2-[4-(4-methylphenyl)-1,3-thiazol-2-yl]-3-oxo-1H-pyrazol-4-yl]propanoate |
| ChemDiv | D205-0478 | 6485801 | n1(nc(n2)NC(=O)c3cccc(C)c3)c2nc(c4ccccc4)cc1O | 3-methyl-N-(7-oxo-5-phenyl-1H-[1,2,4]triazolo[1,5-a]pyrimidin-2-yl)benzamide |
| ChemDiv | D420-4983 | 50748653 | c1(noc(CCC(=O)Nc2sccn2)n1)c3cc(ccc(c4)C)c4nc3O | 3-[3-(2-hydroxy-7-methylquinolin-3-yl)-1,2,4-oxadiazol-5-yl]-N-1,3-thiazol-2-ylpropanamide |
| ChemDiv | D136-0028 | 7454989 | c12c(ccc(c(c3)nc(c4c3C(O)=O)cccc4)c1)noc2c5ccc(cc5)C | 2-[3-(4-methylphenyl)-2,1-benzoxazol-5-yl]quinoline-4-carboxylic acid |
| ChemDiv | D205-0474 | 16013914 | n1(nc(n2)NC(=O)c3ccccc3C)c2nc(c4ccccc4)cc1O | 2-methyl-N-(7-oxo-5-phenyl-1H-[1,2,4]triazolo[1,5-a]pyrimidin-2-yl)benzamide |

FIG. 11 (continued)

| | | | | |
|---|---|---|---|---|
| ChemDiv | D205-0477 | 1877725 | n1(nc(n2)NC(=O)c3ccccc3OC)c2nc(c4ccccc4)cc1O | N-(7-hydroxy-5-phenyl[1,2,4]triazolo[1,5-a]pyrimidin-2-yl)-2-methoxybenzamide |
| ChemDiv | D205-0472 | 6485799 | n1(nc(n2)NC(=O)c3cccc(OC)c3)c2nc(c4ccccc4)cc1O | 3-methoxy-N-(7-oxo-5-phenyl-1H-[1,2,4]triazolo[1,5-a]pyrimidin-2-yl)benzamide |
| ChemDiv | D205-0473 | 16013912 | n1(nc(n2)NC(=O)c(cc3OC)cc(c3OC)OC)c2nc(c4ccccc4)cc1O | 3,4,5-trimethoxy-N-(7-oxo-5-phenyl-1H-[1,2,4]triazolo[1,5-a]pyrimidin-2-yl)benzamide |
| ChemDiv | 3681-3709 | 15991111 | C(/C#N)(=C/c(ccc1c(cc2)ccc2C(O)=O)o1)\C(=O)Nc3ccccc3C(O)=O | 2-[[(E)-3-[5-(4-carboxyphenyl)furan-2-yl]-2-cyanoprop-2-enoyl]amino]benzoic acid |
| ChemDiv | E512-0834 | 16018792 | c1(c(CCc(cn(CC(=O)NCc2cccc2C)n3)c13)oc4C(=O)N5CCCC5)c4C | N-[(2-methylphenyl)methyl]-2-[8-methyl-7-(pyrrolidine-1-carbonyl)-4,5-dihydrofuro[2,3-g]indazol-2-yl]acetamide |
| ChemDiv | D129-0130 | 4913713 | C1(C)=C(CC(O)=O)C(=O)Oc(cc(c2c3occ2c4ccc(cc4)OC)C)c13 | [3-(4-methoxyphenyl)-4,9-dimethyl-7-oxo-7H-furo[2,3-f]chromen-8-yl]acetic acid |
| ChemDiv | E512-0723 | 16018736 | c1(c(CCc(cn(CC(NCCOC)=O)n2)c12)oc3C(=O)N4CCCC4)c3C | N-(2-methoxyethyl)-2-[8-methyl-7-(pyrrolidine-1-carbonyl)-4,5-dihydrofuro[2,3-g]indazol-2-yl]acetamide |
| ChemDiv | E512-0832 | 16018772 | c1(c(CCc(cn(CC(=O)NCc2cccc2Br)n3)c13)oc4C(=O)N5CCCC5)c4C | N-[(2-bromophenyl)methyl]-2-[8-methyl-7-(pyrrolidine-1-carbonyl)-4,5-dihydrofuro[2,3-g]indazol-2-yl]acetamide |
| ChemDiv | D148-0362 | 23606314 | c(sc(c12)nc(c(Br)c1COC)C)(C3=O)c2N=NN3c4ccccc4C(OC)=O | methyl 2-[8-bromo-9-(methoxymethyl)-7-methyl-4-oxopyrido[1,2]thieno[3,4-b]triazin-3-yl]benzoate |
| ChemDiv | C200-7014 | 46507135 | C1(=NNC2=S)N2c(c3C(=O)N1CCCC)ccs3 | 4-butyl-1-thioxo-2,4-dihydrothieno[2,3-e][1,2,4]triazolo[4,3-a]pyrimidin-5(1H)-one |
| ChemDiv | C200-7326 | 2120341 | C1(=NNC2=S)N2c(c3C(=O)N1CCC(C)C)cccc3 | 4-(3-methylbutyl)-1-sulfanylidene-2H-[1,2,4]triazolo[4,3-a]quinazolin-5-one |
| ChemDiv | C200-9508 | 50743396 | C1(N(CCCC2C(O)=O)C2)=Nc(ccs3)c3C(=O)N1c4ccc(cc4)C | 1-[3-(4-methylphenyl)-4-oxo-3,4-dihydrothieno[3,2-d]pyrimidin-2-yl]piperidine-3-carboxylic acid |

FIG. 11 (continued)

| Source | ID | Number | SMILES | Name |
|---|---|---|---|---|
| ChemDiv | Z250-2455 | 49668129 | c12c(scc1c3ccccc3)C(NC(N(CCCC4C(O)=O)C4)=N2)=O | 1-(4-oxo-7-phenyl-3,4-dihydrothieno[3,2-d]pyrimidin-2-yl)piperidine-3-carboxylic acid |
| ChemDiv | E512-0748 | 16018740 | c1(c(CCc(cn(CC(NCCCOCC)=O)n2)c12)oc3C(=O)N4CCCC4)c3C | N-(3-ethoxypropyl)-2-[8-methyl-7-(pyrrolidine-1-carbonyl)-4,5-dihydrofuro[2,3-g]indazol-2-yl]acetamide |
| ChemDiv | E512-0755 | 16018742 | c1(c(CCc(cn(CC(NCCCOC(C)C)=O)n2)c12)oc3C(=O)N4CCCC4)c3C | 2-[8-methyl-7-(pyrrolidine-1-carbonyl)-4,5-dihydrofuro[2,3-g]indazol-2-yl]-N-(3-propan-2-yloxypropyl)acetamide |
| ChemDiv | C367-0001 | 3264670 | C1(N(C=CC=C1C(O)=O)C2=O)=Nc3c2c4c(CCCC4)s3 | 12-oxo-1,2,3,4-tetrahydro-12H-[1]benzothieno[2,3-d]pyrido[1,2-a]pyrimidine-7-carboxylic acid |
| ChemDiv | G417-0457 | 50795582 | N1(CC2CCCO2)C(=O)Nc3c1nc(c4ccc(c(OC)c4)O)nc3C(N)=O | 2-(4-hydroxy-3-methoxyphenyl)-8-oxo-9-(tetrahydrofuran-2-ylmethyl)-8,9-dihydro-7H-purine-6-carboxamide |
| ChemDiv | C768-0260 | 16010865 | c1(cnc(c2c1N(CC3)CCC3C(N)=O)ccc(CC)c2)C(=O)c4ccc(c(C)c4)C | 1-[3-(3,4-dimethylbenzoyl)-6-ethylquinolin-4-yl]piperidine-4-carboxamide |
| ChemDiv | C066-4801 | 15987617 | N1(CC(C)C)C=C(NC(=O)NCc2ccc(cc2OC)OC)c(c3C1=O)cccc3 | 1-[(2,4-dimethoxyphenyl)methyl]-3-[2-(2-methylpropyl)-1-oxoisoquinolin-4-yl]urea |
| ChemDiv | E942-0210 | 16023484 | N1(CC(C)C)C=C(NC(=O)NCc2ccc(OC)c2)c(c3C1=O)cccc3 | 1-[(3-methoxyphenyl)methyl]-3-[2-(2-methylpropyl)-1-oxoisoquinolin-4-yl]urea |
| ChemDiv | E942-0326 | 16023510 | N1(CC(C)C)C=C(NC(=O)NCc2ccccc2)c(c3C1=O)cccc3 | 1-benzyl-3-[2-(2-methylpropyl)-1-oxoisoquinolin-4-yl]urea |
| ChemDiv | L220-0095 | 53010058 | N1(CCc(ccc(CNS(C)(=O)=O)c2)c12)C(=O)c3ccc(cc3)OC | N-[[1-(4-methoxybenzoyl)-2,3-dihydroindol-6-yl]methyl]methanesulfonamide |
| Microsource | 1505333 | 5282230 | c1(ccccc1NC(=O)\C=C\c(ccc(c2OC)OC)c2)C(O)=O | Tranilast |
| ChemDiv | F723-0459 | 50783959 | c(N(C)CCCC)(c1)nc(c2c1C(O)=O)ccc(c2)NC(=O)c3ccccc3OC | 2-[butyl(methyl)amino]-6-[(2-methoxybenzoyl)amino]quinoline-4-carboxylic acid |

FIG. 11 (continued)

| ChemDiv | K844-0672 | 54686429 | C1(C(NCCNCCO)=O)=C(O)c2c(N3C1=O)c(ccc2)CCC3 | 1-Hydroxy-3-oxo-6,7-dihydro-3H,5H-pyrido[3,2,1-ij]quinoline-2-carboxylic acid [2-(2-hydroxy-ethylamino)-ethyl]-amide |

FIG. 11 (continued)

a 3' RACE strategy
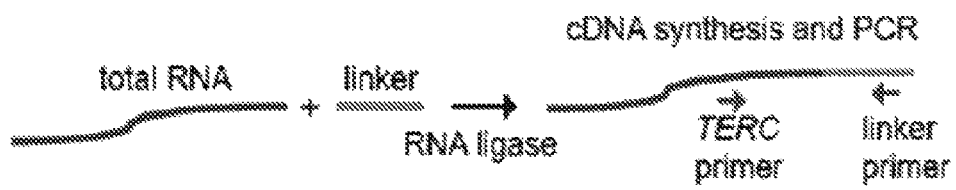
b 3' RACE *TERC* PCR amplicons
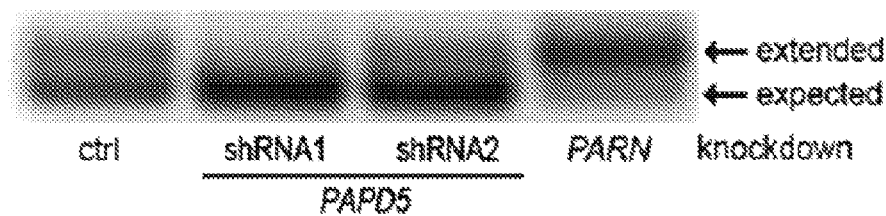
c 3' RACE of TERC in 293 cells with drug treatment
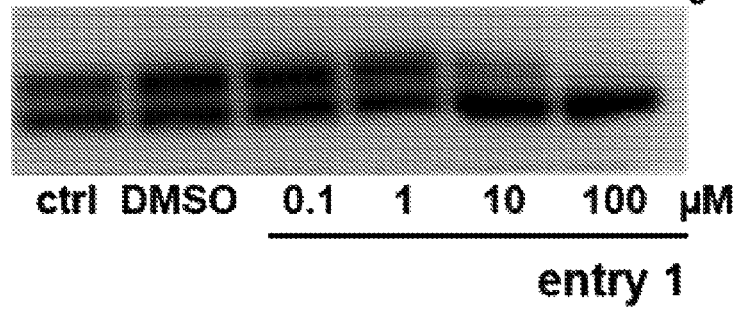
FIG. 19

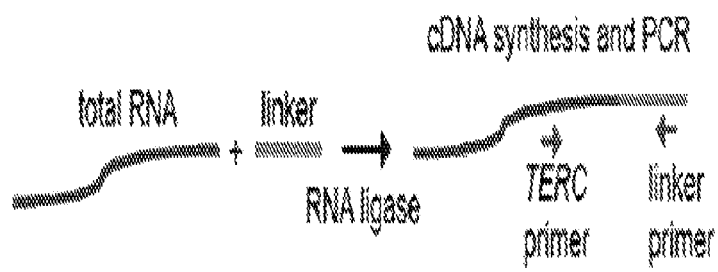
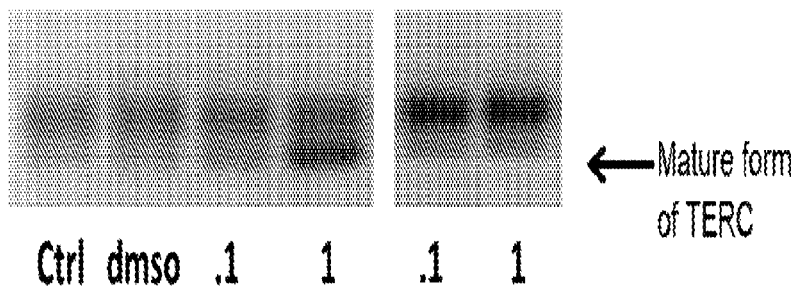
FIG. 24

SEQUENCE LISTING

<160> NUMBER OF SEQ ID NOS: 4

<210> SEQ ID NO 1
<211> LENGTH: 631
<212> TYPE: PRT
<213> ORGANISM: Artificial
<220> FEATURE:
<223> OTHER INFORMATION: synthetic polypeptide

<400> SEQUENCE: 1

Met Tyr Arg Ser Gly Glu Arg Leu Leu Gly Ser His Ala Leu Pro Ala
1               5                   10                  15

Glu Gln Arg Asp Phe Leu Pro Leu Glu Thr Thr Asn Asn Asn Asn
            20                  25                  30

His His Gln Pro Gly Ala Trp Ala Arg Ala Gly Ser Ser Ala Ser
    35                  40                  45

Ser Pro Pro Ser Ala Ser Ser Ser Pro His Pro Ser Ala Ala Val Pro
    50                  55                  60

Ala Ala Asp Pro Ala Asp Ser Ala Ser Gly Ser Ser Asn Lys Arg Lys
65                  70                  75                  80

Arg Asp Asn Lys Ala Ser Thr Tyr Gly Leu Asn Tyr Ser Leu Leu Gln
                85                  90                  95

Pro Ser Gly Gly Arg Ala Ala Gly Gly Arg Ala Asp Gly Gly Gly
            100                 105                 110

Val Val Tyr Ser Gly Thr Pro Trp Lys Arg Arg Asn Tyr Asn Gln Gly
        115                 120                 125

Val Val Gly Leu His Glu Glu Ile Ser Asp Phe Tyr Glu Tyr Met Ser
    130                 135                 140

Pro Arg Pro Glu Glu Glu Lys Met Arg Met Glu Val Val Asn Arg Ile
145                 150                 155                 160

Glu Ser Val Ile Lys Glu Leu Trp Pro Ser Ala Asp Val Gln Ile Phe
                165                 170                 175

Gly Ser Phe Lys Thr Gly Leu Tyr Leu Pro Thr Ser Asp Ile Asp Leu
            180                 185                 190

Val Val Phe Gly Lys Trp Glu Asn Leu Pro Leu Trp Thr Leu Glu Glu
        195                 200                 205

Ala Leu Arg Lys His Lys Val Ala Asp Glu Asp Ser Val Lys Val Leu
    210                 215                 220

Asp Lys Ala Thr Val Pro Ile Ile Lys Leu Thr Asp Ser Phe Thr Glu
225                 230                 235                 240

Val Lys Val Asp Ile Ser Phe Asn Val Gln Asn Gly Val Arg Ala Ala
                245                 250                 255

Asp Leu Ile Lys Asp Phe Thr Lys Lys Tyr Pro Val Leu Pro Tyr Leu
            260                 265                 270

Val Leu Val Leu Lys Gln Phe Leu Leu Gln Arg Asp Leu Asn Glu Val
        275                 280                 285

Phe Thr Gly Gly Ile Gly Ser Tyr Ser Leu Phe Leu Met Ala Val Ser
    290                 295                 300

Phe Leu Gln Leu His Pro Arg Glu Asp Ala Cys Ile Pro Asn Thr Asn
305                 310                 315                 320

Tyr Gly Val Leu Leu Ile Glu Phe Phe Glu Leu Tyr Gly Arg His Phe
                325                 330                 335

Asn Tyr Leu Lys Thr Gly Ile Arg Ile Lys Asp Gly Gly Ser Tyr Val
            340                 345                 350

Ala Lys Asp Glu Val Gln Lys Asn Met Leu Asp Gly Tyr Arg Pro Ser

```
                355                 360                 365
Met Leu Tyr Ile Glu Asp Pro Leu Gln Pro Gly Asn Asp Val Gly Arg
    370                 375                 380

Ser Ser Tyr Gly Ala Met Gln Val Lys Gln Ala Phe Asp Tyr Ala Tyr
385                 390                 395                 400

Val Val Leu Ser His Ala Val Ser Pro Ile Ala Lys Tyr Tyr Pro Asn
                405                 410                 415

Asn Glu Thr Glu Ser Ile Leu Gly Arg Ile Ile Arg Val Thr Asp Glu
            420                 425                 430

Val Ala Thr Tyr Arg Asp Trp Ile Ser Lys Gln Trp Gly Leu Lys Asn
        435                 440                 445

Arg Pro Glu Pro Ser Cys Asn Gly Asn Gly Val Thr Leu Ile Val Asp
    450                 455                 460

Thr Gln Gln Leu Asp Lys Cys Asn Asn Asn Leu Ser Glu Glu Asn Glu
465                 470                 475                 480

Ala Leu Gly Lys Cys Arg Ser Lys Thr Ser Glu Ser Leu Ser Lys His
                485                 490                 495

Ser Ser Asn Ser Ser Ser Gly Pro Val Ser Ser Ser Ala Thr Gln
            500                 505                 510

Ser Ser Ser Ser Asp Val Asp Ser Asp Ala Thr Pro Cys Lys Thr Pro
        515                 520                 525

Lys Gln Leu Leu Cys Arg Pro Ser Thr Gly Asn Arg Val Gly Ser Gln
    530                 535                 540

Asp Val Ser Leu Glu Ser Ser Gln Ala Val Gly Lys Met Gln Ser Thr
545                 550                 555                 560

Gln Thr Thr Asn Thr Ser Asn Ser Thr Asn Lys Ser Gln His Gly Ser
                565                 570                 575

Ala Arg Leu Phe Arg Ser Ser Lys Gly Phe Gln Gly Thr Thr Gln
            580                 585                 590

Thr Ser His Gly Ser Leu Met Thr Asn Lys Gln His Gln Gly Lys Ser
        595                 600                 605

Asn Asn Gln Tyr Tyr His Gly Lys Lys Arg Lys His Lys Arg Asp Ala
    610                 615                 620

Pro Leu Ser Asp Leu Cys Arg
625                 630

<210> SEQ ID NO 2
<211> LENGTH: 20
<212> TYPE: RNA
<213> ORGANISM: Artificial
<220> FEATURE:
<223> OTHER INFORMATION: synthetic oligonucleotide

<400> SEQUENCE: 2
ccucuuguug cugcugcccg                                                  20

<210> SEQ ID NO 3
<211> LENGTH: 20
<212> TYPE: RNA
<213> ORGANISM: Artificial
<220> FEATURE:
<223> OTHER INFORMATION: synthetic oligonucleotide

<400> SEQUENCE: 3
cggagcgaua caugccggcc                                                  20

<210> SEQ ID NO 4
```

```
<211> LENGTH: 20
<212> TYPE: RNA
<213> ORGANISM: Artificial
<220> FEATURE:
<223> OTHER INFORMATION: synthetic oligonucleotide

<400> SEQUENCE: 4
ccucuuguug cugcugcccg                                              20
```

PAPD5 INHIBITORS AND METHODS OF USE THEREOF

CLAIM OF PRIORITY

This application is a 371 U.S. National Phase Application of PCT/US2018/057514, filed on Oct. 25, 2018, which claims priority to U.S. Patent Application Ser. No. 62/577,107, filed on Oct. 25, 2017; U.S. Patent Application Ser. No. 62/608,327, filed on Dec. 20, 2017; U.S. Patent Application Ser. No. 62/614,158, filed on Jan. 5, 2018; and U.S. Patent Application Ser. No. 62/727,380, filed on Sep. 5, 2018, the entire contents of which are hereby incorporated by reference.

STATEMENT AS TO FEDERALLY SPONSORED RESEARCH

This invention was made with government support under Grant No. DK107716, awarded by the National Institutes of Health. The government has certain rights in the invention.

TECHNICAL FIELD

The present disclosure relates to compounds that inhibit PAP Associated Domain Containing 5 (PAPD5), and to methods of using these compounds to treat conditions mediated by PAPD5 such as telomere diseases, developmental and aging-related degenerative disorders, and other diseases.

BACKGROUND

A telomere is a region of repetitive nucleotide sequences at each end of a chromosome, which protects the end of the chromosome from deterioration or from fusion with neighboring chromosomes. The length of a telomere is a key determinant of cellular self-renewal capacity. The telomerase ribonucleoprotein maintains telomere length in tissue stem cells, and its function is critical for human health and longevity.

Short telomeres, due to genetic or acquired insults, cause a loss of cellular self-renewal and result in life-threatening diseases, for which there are few if any effective medical therapies. In these diseases involving short telomeres, e.g., aplastic anemia, pulmonary fibrosis, hepatic cirrhosis, bone marrow failure, etc., there is an unmet clinical need for new therapies.

SUMMARY

Poly(A) ribonuclease (PARN) mutations can result in the accumulation of 3' oligo-adenylated forms of nascent Telomerase RNA Component (TERC) RNA transcripts, which are targeted for destruction, thus causing telomerase deficiency and telomere diseases. Disruption of the non-canonical poly(A) polymerase PAP Associated Domain Containing 5 (PAPD5; also known as Topoisomerase-related function protein 4-2 (TRF4-2)) may restore TERC levels, telomerase activity, and telomere elongation in PARN-mutant patient cells. This disclosure relates, at least in part, to PAPD5 inhibitors and methods of using such inhibitors.

In one general aspect, the present disclosure provides a method selected from:
(a) treating a disorder associated with telomere or telomerase dysfunction in a subject;
(b) treating a disorder associated with aging in a subject;
(c) treating a pre-leukemic or pre-cancerous condition in subject;
(d) treating or preventing HBV infection in a subject;
(e) treating or preventing a neurodevelopmental disorder in a subject;
(f) treating an acquired or genetic disease or condition associated with alterations in RNA in a subject;
(g) decreasing PAPD5 activity in a subject;
(h) inhibiting of HBsAg production or secretion in a subject;
(i) inhibiting HBV DNA production in a subject
(j) decreasing PAPD5 activity in a cell;
(k) inhibiting of HBsAg production or secretion in a cell;
(l) inhibiting HBV DNA production in a cell;
(m) modulating non-coding RNAs in a cell; and
(n) modulating ex vivo expansion of a stem cell,
the method comprising contacting the cell with an effective amount of, or administering to a subject in need thereof a therapeutically effective amount of, a compound of Formula (II-II):

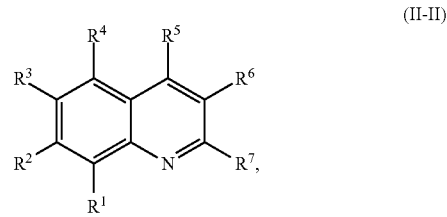

or a pharmaceutically acceptable salt thereof, wherein:
$R^1$, $R^2$, $R^3$, $R^4$, $R^5$, $R^6$, and $R^7$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, thioxo and oxo; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$;
$R^{a1}$, $R^{c1}$, and $R^{d1}$ are each independently selected from H, $C_{1-6}$ alkyl, $C_{2-6}$ alkenyl, $C_{2-6}$ alkynyl, $C_{1-4}$ haloalkyl, $Cy^3$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $S(O)R^{b3}$, $S(O)NR^{c3}R^{d3}$, $S(O)_2R^{b3}$, $S(O)_2NR^{c3}R^{d3}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^3$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$;
each $R^{b1}$ is independently selected from $C_{1-6}$ alkyl, $C_{2-6}$ alkenyl, $C_{2-6}$ alkynyl, $C_{1-4}$ haloalkyl, and $Cy^3$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^3$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$;

$R^{a3}$, $R^{c3}$, and $R^{d3}$ are each independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, $C(O)R^{b4}$, $C(O)NR^{c4}R^{d4}$, $C(O)OR^{a4}$, $NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are each optionally substituted with 1, 2, 3, 4, or 5 substituents independently selected from oxo, $C_{1-6}$ alkyl, $C_{1-4}$ haloalkyl, $C_{1-4}$ hydroxyalkyl, $C_{1-6}$ cyanoalkyl, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^{b3}$ is independently selected from $C_{1-6}$ alkyl, $C_{2-6}$ alkenyl, $C_{2-6}$ alkynyl, $C_{1-4}$ haloalkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are each optionally substituted with 1, 2, 3, 4, or 5 substituents independently selected from $C_{1-6}$ alkyl, $C_{1-4}$ haloalkyl, $C_{1-4}$ hydroxyalkyl, $C_{1-6}$ cyanoalkyl, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

any two $R^1$ and $R^2$ together with the carbon atoms to which they are attached form a ring selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy5}$; or any two $R^2$ and $R^3$ together with the carbon atoms to which they are attached form a ring selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy5}$; or any two $R^4$ and $R^3$ together with the carbon atoms to which they are attached form a ring selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy5}$; or any two $R^4$ and $R^5$ together with the carbon atoms to which they are attached form a ring selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy5}$; or any two $R^6$ and $R^5$ together with the carbon atoms to which they are attached form a ring selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy5}$; or any two $R^6$ and $R^7$ together with the carbon atoms to which they are attached form a ring selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy5}$;

each $Cy^1$ is independently selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy1}$;

each $Cy^3$ is independently selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy3}$;

$R^{Cy1}$, $R^{Cy3}$, and $R^{Cy5}$ are each independently selected from halo, $C_{1-4}$ alkyl, $C_{1-4}$ haloalkyl, $C_{2-6}$ alkenyl, $C_{2-6}$ alkynyl, $Cy^4$, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-4}$ alkyl, $C_{2-6}$ alkenyl, and $C_{2-6}$ alkynyl are each optionally substituted by 1, 2, 3, 4, or 5 substituents independently selected from $Cy^4$, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $Cy^4$ is independently selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy4}$;

each $R^{Cy4}$ is independently selected from halo, $C_{1-4}$ alkyl, $C_{1-4}$ haloalkyl, $C_{2-6}$ alkenyl, $C_{2-6}$ alkynyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene, $C_{3-7}$ cycloalkyl-$C_{1-4}$ alkylene, (5-6 membered heteroaryl)-$C_{1-4}$ alkylene, and (4-7 membered heterocycloalkyl)-$C_{1-4}$ alkylene, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2$ NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$, wherein said C$_{1-4}$ alkyl, C$_{1-4}$ haloalkyl, C$_{2-6}$ alkenyl, C$_{2-6}$ alkynyl, C$_{6-10}$ aryl, C$_{3-7}$ cycloalkyl, 5-6 membered heteroaryl, 4-7 membered heterocycloalkyl, C$_{6-10}$ aryl-C$_{1-4}$ alkylene, C$_{3-7}$ cycloalkyl-C$_{1-4}$ alkylene, (5-6 membered heteroaryl)-C$_{1-4}$ alkylene, and (4-7 membered heterocycloalkyl)-C$_{1-4}$ alkylene are each optionally substituted by 1, 2, 3, 4, or 5 substituents independently selected from halo, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{c4}$)NR$^{c4}$R$^{d4}$, NR$^{c4}$C(=NR$^{c4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$;

R$^{a4}$, R$^{c4}$, and R$^{d4}$ are each independently selected from H, C$_{1-6}$ alkyl, C$_{1-4}$ haloalkyl, C$_{1-4}$ hydroxyalkyl, C$_{1-4}$ cyanoalkyl, C$_{2-6}$ alkenyl, C$_{2-6}$ alkynyl, C$_{6-10}$ aryl, C$_{3-10}$ cycloalkyl, 5-10 membered heteroaryl, 4-12 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, (4-12 membered heterocycloalkyl)-C$_{1-4}$ alkylene and R$^g$, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-12 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, and (4-12 membered heterocycloalkyl)-C$_{1-4}$ alkylene are each optionally substituted with 1, 2, 3, 4, or 5 substituents independently selected from R$^g$;

each R$^{b4}$ is independently selected from C$_{1-6}$ alkyl, C$_{1-4}$ haloalkyl, C$_{1-4}$ hydroxyalkyl, C$_{1-4}$ cyanoalkyl, C$_{2-6}$ alkenyl, C$_{2-6}$ alkynyl, C$_{6-10}$ aryl, C$_{3-10}$ cycloalkyl, 5-10 membered heteroaryl, 4-12 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, (4-12 membered heterocycloalkyl)-C$_{1-4}$ alkylene and R$^g$, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-12 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, and (4-12 membered heterocycloalkyl)-C$_{1-4}$ alkylene is optionally substituted with 1, 2, 3, 4, or 5 substituents independently selected from R$^g$;

or any R$^{c1}$ and R$^{d1}$ together with the N atom to which they are attached form a 4-, 5-, 6-, or 7-membered heterocycloalkyl group optionally substituted with 1, 2, or 3 substituents independently selected from R$^g$;

or any R$^{c3}$ and R$^{d3}$ together with the N atom to which they are attached form a 4-, 5-, 6-, or 7-membered heterocycloalkyl group optionally substituted with 1, 2, or 3 substituents independently selected from R$^g$;

or any R$^{c4}$ and R$^{d4}$ together with the N atom to which they are attached form a 4-, 5-, 6-, or 7-membered heterocycloalkyl group optionally substituted with 1, 2, or 3 substituents independently selected from R$^g$;

each R$^{e1}$, R$^{e3}$, and R$^{e4}$ is independently selected from H, C$_{1-4}$ alkyl, C$_{1-4}$ alkoxy, OH, and CN; and each R$^g$ is independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkylene, HO—C$_{1-3}$ alkylene, C$_{6-10}$ aryl, C$_{6-10}$ aryloxy, C$_{3-10}$ cycloalkyl, 5-10 membered heteroaryl, 4-12 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, (4-12 membered heterocycloalkyl)-C$_{1-4}$ alkylene, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl) carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl) aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

In some embodiments, R$^1$, R$^2$, R$^3$, R$^4$, R$^5$, R$^6$, and R$^7$ are each independently selected from H, C$_{1-6}$ alkyl, Cy$^1$, halo, CN, OR$^{a1}$, SR$^{a1}$, C(O)R$^{b1}$, C(O)NR$^{c1}$R$^{d1}$, C(O)OR$^{a1}$, C(O)R$^{b1}$, NR$^{c1}$R$^{d1}$, NR$^{c1}$C(O)R$^{b1}$, NR$^{c1}$C(O)NR$^{c1}$R$^{d1}$, NR$^{c1}$S(O)$_2$R$^{b1}$, S(O)$_2$R$^{b1}$, S(O)$_2$NR$^{c1}$R$^{d1}$, and oxo; wherein said C$_{1-6}$ alkyl is optionally substituted with 1, 2, or 3 substituents independently selected from Cy$^1$, SR$^{a1}$, C(O)NR$^{c1}$R$^{d1}$, C(O)OR$^{a1}$, NR$^{c1}$R$^{d1}$, NR$^{c1}$S(O)$_2$R$^{b1}$, and S(O)$_2$R$^{b1}$.

In some embodiments, R$^{a1}$, R$^{c1}$, and R$^{d1}$ are each independently selected from H, C$_{1-6}$ alkyl, C$_{1-4}$ haloalkyl, Cy$^3$, C(O)R$^{b3}$, wherein said C$_{1-6}$ alkyl is optionally substituted with 1, 2, or 3 substituents independently selected from Cy$^3$, OR$^{a3}$, C(O)R$^{b3}$, C(O)NR$^{c3}$R$^{d3}$, C(O)OR$^{a3}$, and NR$^{c3}$R$^{d3}$.

In some embodiments, each R$^{b1}$ is independently selected from C$_{1-6}$ alkyl and Cy$^3$, wherein said C$_{1-6}$ alkyl is optionally substituted with SR$^{a3}$.

In some embodiments, R$^{a3}$, R$^{c3}$, and R$^{d3}$ are each independently selected from H, C$_{1-6}$ alkyl, C$_{1-4}$ haloalkyl, C$_{6-10}$ aryl, C$_{3-10}$ cycloalkyl, 5-10 membered heteroaryl, 4-12 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, and (4-12 membered heterocycloalkyl)-C$_{1-4}$ alkylene; wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-12 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, and (4-12 membered heterocycloalkyl)-C$_{1-4}$ alkylene are each optionally substituted with 1, 2, or 3 substituents independently selected from oxo, C$_{1-6}$ alkyl, halo, CN, NO$_2$, OR$^{a4}$, C(O)R$^{b4}$, C(O)NR$^{c4}$R$^{d4}$, C(O)OR$^{a4}$, NR$^{c4}$R$^{d4}$, NR$^{c4}$C(O)R$^{b4}$, NR$^{c4}$S(O)$_2$R$^{b4}$, S(O)$_2$R$^{b4}$, and S(O)$_2$NR$^{c4}$R$^{d4}$.

In some embodiments, each R$^{b3}$ is selected from C$_{1-6}$ alkyl, C$_{6-10}$ aryl, C$_{3-10}$ cycloalkyl, 5-10 membered heteroaryl, 4-12 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, and (4-12 membered heterocycloalkyl)-C$_{1-4}$ alkylene, wherein said C$_{1-6}$ alkyl, C$_{6-10}$ aryl, C$_{3-10}$ cycloalkyl, 5-10 membered heteroaryl, 4-12 membered heterocycloalkyl, C$_{6-10}$ aryl-C$_{1-4}$ alkylene, C$_{3-10}$ cycloalkyl-C$_{1-4}$ alkylene, (5-10 membered heteroaryl)-C$_{1-4}$ alkylene, and (4-12 membered heterocycloalkyl)-C$_{1-4}$ alkylene are optionally substituted with 1, 2, or 3 substituents independently selected from oxo, C$_{1-6}$ alkyl, C$_{1-4}$ haloalkyl, C$_{1-4}$ hydroxyalkyl, C$_{1-6}$ cyanoalkyl, halo, CN, NO$_2$, OR$^{a4}$, C(O)R$^{b4}$, C(O)NR$^{c4}$R$^{d4}$, C(O)OR$^{a4}$, NR$^{c4}$R$^{d4}$, NR$^{c4}$C(O)R$^{b4}$, NR$^{c4}$S(O)$_2$R$^{b4}$, S(O)$_2$R$^{b4}$, and S(O)$_2$NR$^{c4}$R$^{d4}$.

In some embodiments, each R$^{Cy1}$ is independently selected from halo, C$_{1-4}$ alkyl, C$_{1-4}$ haloalkyl, Cy$^4$, OR$^{a4}$, C(O)R$^{b4}$, C(O)NR$^{c4}$R$^{d4}$, C(O)OR$^{a4}$, NR$^{c4}$R$^{d4}$, and S(O)$_2$NR$^{c4}$R$^{d4}$, wherein said C$_{1-4}$ alkyl is optionally substituted by 1, 2, or 3 substituents independently selected from Cy$^4$, C(O)NR$^{c4}$R$^{d4}$, and NR$^{c4}$S(O)$_2$R$^{b4}$.

In some embodiments, each R$^{Cy3}$ is independently selected from halo, C$_{1-4}$ alkyl, Cy$^4$, OR$^{a4}$, C(O)R$^{b4}$, C(O)NR$^{c4}$R$^{d4}$, and C(O)OR$^{a4}$.

In some embodiments, each $R^{Cy5}$ is independently selected from halo, $C_{1-4}$ alkyl, $Cy^4$, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $S(O)_2R^{b4}$, and $S(O)_2NR^{c4}R^{d4}$, wherein said $C_{1-4}$ alkyl is optionally substituted by 1, 2, or 3 substituents independently selected from $Cy^4$, $OR^{a4}$, $C(O)NR^{c4}R^{d4}$, $C(O)OR^{a4}$, and $NR^{c4}R^{d4}$.

In some embodiments, each $R^{Cy4}$ is independently selected from halo, $C_{1-4}$ alkyl, $C_{1-4}$ haloalkyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, and (4-7 membered heterocycloalkyl)-$C_{1-4}$ alkylene-, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl, $C_{1-4}$ haloalkyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, and (4-7 membered heterocycloalkyl)-$C_{1-4}$ alkylene- are each optionally substituted by 1, 2 or 3 substituents independently selected from halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$.

In some embodiments, $R^{a4}$, $R^{c4}$, and $R^{d4}$ are each independently selected from H, $C_{1-6}$ alkyl, $C_{6-10}$ aryl, 5-10 membered heteroaryl, 4-12 membered heterocycloalkyl, $C_{6-10}$ aryl-$C_{1-4}$ alkylene, (5-10 membered heteroaryl)-$C_{1-4}$ alkylene, (4-12 membered heterocycloalkyl)-$C_{1-4}$ alkylene, wherein said $C_{1-6}$ alkyl, $C_{6-10}$ aryl, 5-10 membered heteroaryl, 4-12 membered heterocycloalkyl, $C_{6-10}$ aryl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, or 3 substituents independently selected from $R^g$.

In some embodiments, each $R^{b4}$ is independently selected from $C_{1-6}$ alkyl, $C_{6-10}$ aryl, $C_{3-10}$ cycloalkyl, 5-10 membered heteroaryl, 4-12 membered heterocycloalkyl, wherein said $C_{1-6}$ alkyl, $C_{6-10}$ aryl, $C_{3-10}$ cycloalkyl, 5-10 membered heteroaryl, and 4-12 membered heterocycloalkyl are each optionally substituted with 1, 2, or 3 substituents independently selected from $R^g$.

In some embodiments:
$R^1$, $R^2$, $R^3$, $R^4$, $R^5$, $R^6$, and $R^7$ are each independently selected from H, $C_{1-6}$ alkyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, $S(O)_2NR^{c1}R^{d1}$, and oxo; wherein said $C_{1-6}$ alkyl is optionally substituted with 1, 2, or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$ and $S(O)_2NR^{c1}R^{d1}$;

$R^{a1}$, $R^{c1}$, and $R^{d1}$ are each independently selected from H, $C_{1-6}$ alkyl, $C_{1-4}$ haloalkyl, $Cy^3$, $C(O)R^{b3}$, $C(O)NR^{c3}R^{d3}$, $C(O)OR^{a3}$, $S(O)_2R^{b3}$, $S(O)_2NR^{c3}R^{d3}$; wherein said $C_{1-6}$ alkyl is optionally substituted with 1, 2, or 3 substituents independently selected from $Cy^3$, halo, CN, $NO_2$, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$ and $S(O)_2NR^{c3}R^{d3}$;

each $R^{b1}$ is independently selected from $C_{1-6}$ alkyl and $Cy^3$, wherein said $C_{1-6}$ alkyl is optionally substituted with $SR^{a3}$;

wherein $R^{a3}$, $R^{c3}$, and $R^{d3}$ are each independently selected from H, $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are each optionally substituted with 1, 2, or 3 substituents independently selected from oxo, $C_{1-6}$ alkyl, halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}S(O)_2R^{b4}$, $S(O)_2R^{b4}$, and $S(O)_2NR^{c4}R^{d4}$;

each $R^{b3}$ is selected from $C_{1-6}$ alkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene, wherein said $C_{1-6}$ alkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are optionally substituted with 1, 2, or 3 substituents independently selected from oxo, $C_{1-6}$ alkyl, $C_{1-4}$ haloalkyl, $C_{1-4}$ hydroxyalkyl, $C_{1-6}$ cyanoalkyl, halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}S(O)_2R^{b4}$, $S(O)_2R^{b4}$, and $S(O)_2NR^{c4}R^{d4}$;

each $Cy^1$ is independently selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy1}$;

each $Cy^3$ is independently selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy3}$;

each $R^{Cy1}$ is independently selected from halo, $C_{1-4}$ alkyl, $C_{1-4}$ haloalkyl, $Cy^4$, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl is optionally substituted by 1, 2, or 3 substituents independently selected from $Cy^4$, halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$;

each $R^{Cy3}$ is independently selected from halo, $C_{1-4}$ alkyl, $C_{1-4}$ haloalkyl, $Cy^4$, $OR^{a4}$, $C(O)R^{b4}$, $C(O)NR^{c4}R^{d4}$, and $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl is optionally substituted by 1, 2, or 3 substituents independently selected from $Cy^4$, halo, CN, $NO_2$, $OR^{a4}$, $C(O)R^{b4}$, $C(O)NR^{c4}R^{d4}$, $C(O)OR^{a4}$, NR$^{c4}$R$^{d4}$, NR$^{c4}$C(O)R$^{b4}$, NR$^{c4}$C(O)OR$^{d4}$, NR$^{c4}$C(O)NR$^{c4}$R$^{d4}$, NR$^{c4}$S(O)$_2$R$^{b4}$, NR$^{c4}$S(O)$_2$NR$^{c4}$R$^{d4}$, S(O)$_2$R$^{b4}$, and S(O)$_2$NR$^{c4}$R$^{d4}$;

each R$^{Cy5}$ is independently selected from halo, C$_{1-4}$ alkyl, C$_{1-4}$ haloalkyl, Cy$^4$, CN, NO$_2$, OR$^{a4}$, SR$^{a4}$, C(O)R$^{b4}$, C(O)NR$^{c4}$R$^{d4}$, C(O)OR$^{a4}$, NR$^{c4}$R$^{d4}$, NR$^{c4}$C(O)R$^{b4}$, S(O)$_2$R$^{b4}$, and S(O)$_2$NR$^{c4}$R$^{d4}$, wherein said C$_{1-4}$ alkyl is optionally substituted by 1, 2, or 3 substituents independently selected from Cy$^4$, halo, CN, NO$_2$, OR$^{a4}$, C(O)R$^{b4}$, C(O)NR$^{c4}$R$^{d4}$, C(O)OR$^{d4}$, NR$^{c4}$R$^{d4}$, NR$^{c4}$S(O)$_2$R$^{b4}$, S(O)$_2$R$^{b4}$, and S(O)$_2$NR$^{c4}$R$^{d4}$;

each Cy$^4$ is independently selected from C$_{6-10}$ aryl, C$_{3-10}$ cycloalkyl, 5-10 membered heteroaryl, and 4-12 membered heterocycloalkyl, each of which is optionally substituted with 1, 2, or 3 substituents independently selected from R$^{Cy4}$;

R$^{a4}$, R$^{c4}$, and R$^{d4}$ are each independently selected from H, C$_{1-6}$ alkyl, C$_{6-10}$ aryl, 5-10 membered heteroaryl, 4-12 membered heterocycloalkyl, C$_{6-10}$ aryl-C$_{1-4}$ alkylene, (5-10 membered heteroaryl)-C$_{1-4}$ alkylene, (4-12 membered heterocycloalkyl)-C$_{1-4}$ alkylene, wherein said C$_{1-6}$ alkyl, C$_{6-10}$ aryl, 5-10 membered heteroaryl, 4-12 membered heterocycloalkyl, C$_{6-10}$ aryl-C$_{1-4}$ alkylene, (5-10 membered heteroaryl)-C$_{1-4}$ alkylene, and (4-12 membered heterocycloalkyl)-C$_{1-4}$ alkylene is optionally substituted with 1, 2, or 3 substituents independently selected from R$^g$; and each R$^{b4}$ is independently selected from C$_{1-6}$ alkyl, C$_{6-10}$ aryl, C$_{3-10}$ cycloalkyl, 5-10 membered heteroaryl, 4-12 membered heterocycloalkyl, wherein said C$_{1-6}$ alkyl, C$_{6-10}$ aryl, C$_{3-10}$ cycloalkyl, 5-10 membered heteroaryl, and 4-12 membered heterocycloalkyl are each optionally substituted with 1, 2, or 3 substituents independently selected from R$^g$.

In some embodiments:

R$^1$, R$^2$, R$^3$, R$^4$, R$^5$, R$^6$, and R$^7$ are each independently selected from H, C$_{1-6}$ alkyl, Cy$^1$, halo, CN, OR$^{a1}$, SR$^{a1}$, C(O)R$^{b1}$, C(O)NR$^{c1}$R$^{d1}$, C(O)OR$^{a1}$, C(O)R$^{b1}$, NR$^{c1}$R$^{d1}$, NR$^{c1}$C(O)R$^{b1}$, NR$^{c1}$C(O)NR$^{c1}$R$^{d1}$, NR$^{c1}$S(O)$_2$R$^{b1}$, S(O)$_2$R$^{b1}$, S(O)$_2$NR$^{c1}$R$^{d1}$, and oxo; wherein said C$_{1-6}$ alkyl is optionally substituted with 1, 2, or 3 substituents independently selected from Cy$^1$, SR$^{a1}$, C(O)NR$^{c1}$R$^{d1}$, C(O)OR$^{a1}$, NR$^{c1}$R$^{d1}$, NR$^{c1}$S(O)$_2$R$^{b1}$, and S(O)$_2$R$^{b1}$;

R$^{a1}$, R$^{c1}$, and R$^{d1}$ are each independently selected from H, C$_{1-6}$ alkyl, C$_{1-4}$ haloalkyl, Cy$^3$, C(O)R$^{b3}$, wherein said C$_{1-6}$ alkyl is optionally substituted with 1, 2, or 3 substituents independently selected from Cy$^3$, OR$^{a3}$, C(O)R$^{b3}$, C(O)NR$^{c3}$R$^{d3}$, C(O)OR$^{a3}$, and NR$^{c3}$R$^{d3}$;

each R$^{Cy1}$ is independently selected from halo, C$_{1-4}$ alkyl, C$_{1-4}$ haloalkyl, Cy$^4$, OR$^{a4}$, C(O)R$^{b4}$, C(O)NR$^{c4}$R$^{d4}$, C(O)OR$^{a4}$, NR$^{c4}$R$^{d4}$, and S(O)$_2$NR$^{c4}$R$^{d4}$, wherein said C$_{1-4}$ alkyl is optionally substituted by 1, 2, or 3 substituents independently selected from Cy$^4$, C(O)NR$^{c4}$R$^{d4}$, and NR$^{c4}$S(O)$_2$R$^{b4}$;

each R$^{Cy3}$ is independently selected from halo, C$_{1-4}$ alkyl, Cy$^4$, OR$^{a4}$, C(O)R$^{b4}$, C(O)NR$^{c4}$R$^{d4}$, and C(O)OR$^{a4}$; and each R$^{Cy5}$ is independently selected from halo, C$_{1-4}$ alkyl, Cy$^4$, OR$^{a4}$, SR$^{a4}$, C(O)R$^{b4}$, C(O)NR$^{c4}$R$^{d4}$, C(O)OR$^{a4}$, NR$^{c4}$R$^{d4}$, NR$^{c4}$C(O)R$^{b4}$, S(O)$_2$R$^{b4}$, and S(O)$_2$NR$^{c4}$R$^{d4}$, wherein said C$_{1-4}$ alkyl is optionally substituted by 1, 2, or 3 substituents independently selected from Cy$^4$, OR$^{a4}$, C(O)NR$^{c4}$R$^{d4}$, C(O)OR$^{a4}$, and NR$^{c4}$R$^{d4}$.

In some embodiments, the compound of Formula (II-II) has Formula (II-IIa):

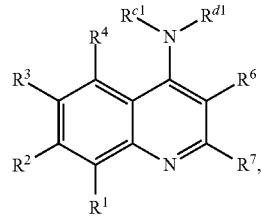

or a pharmaceutically acceptable salt thereof.

In some embodiments, the compound of Formula (II-IIa) has Formula (II-IIb):

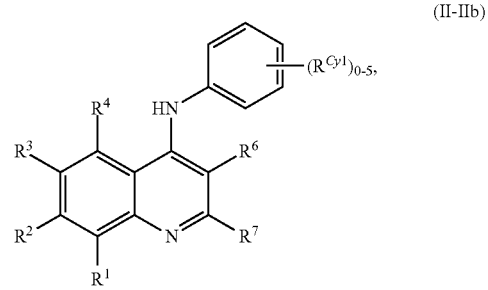

(II-IIb)

or a pharmaceutically acceptable salt thereof.

In some embodiments, each R$^{Cy1}$ is independently selected from C$_{1-6}$ alkyl, C(O)OR$^{a4}$, OR$^{a4}$, C(O)R$^{b4}$, and halo.

In some embodiments, the compound of Formula (II-II) has Formula (II-IIc):

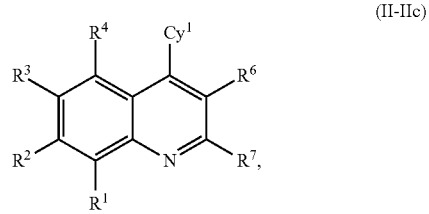

(II-IIc)

or a pharmaceutically acceptable salt thereof.

In some embodiments, the compound of Formula (II-II) has Formula (II-IId):

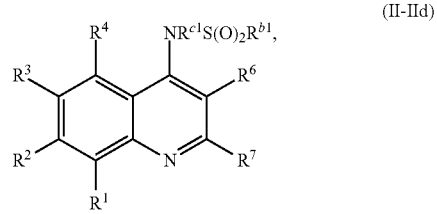

(II-IId)

or a pharmaceutically acceptable salt thereof.

In some embodiments, the compound of Formula (II-II) has Formula (II-IIe):

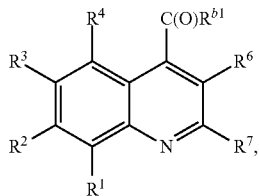
(II-IIe)

or a pharmaceutically acceptable salt thereof.

In some embodiments, $R^1$, $R^2$, $R^3$, $R^4$, $R^6$, and $R^7$ are each independently selected from H, halo $Cy^1$, $C_{1-6}$ alkyl, $OR^{a1}$, $SR^{a1}$, $C(O)OR^{a1}$, $C(O)NR^{c1}R^{d1}$, $NR^{c1}C(O)R^{b1}$, $NR^{c1}R^{d1}$, $S(O)_2R^{b1}$ and $C(O)R^{b1}$.

In some embodiments, $R^1$, $R^2$, $R^3$, $R^4$, $R^6$, and $R^7$ are each independently selected from H, $C_{1-6}$ alkyl, $OR^{a1}$, $C(O)OR^{a1}$, $C(O)R^{b1}$, $NR^{c1}R^{d1}$, and $NR^{c1}C(O)R^{b1}$.

In some embodiments, the compound of Formula (II-II) is selected from any one of the following compounds, or a pharmaceutically acceptable salt thereof:

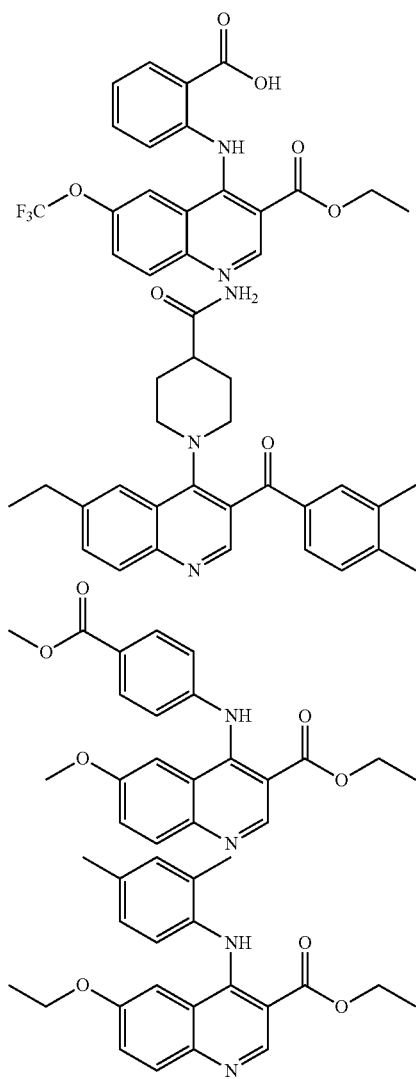

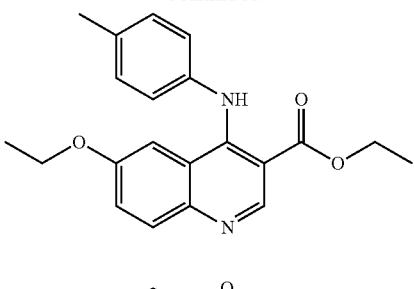

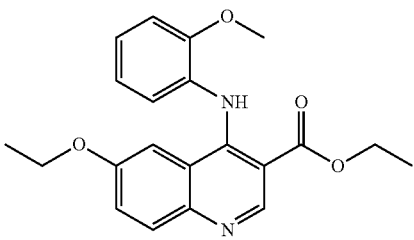

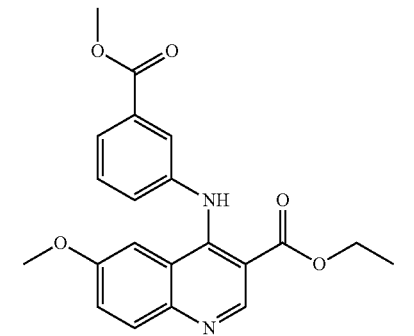

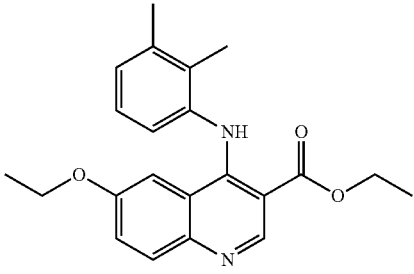

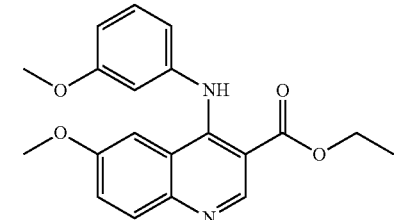

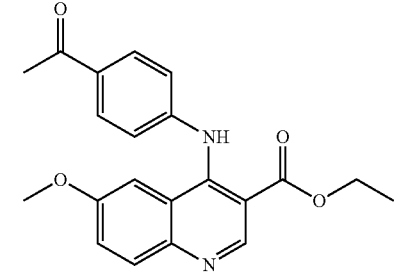

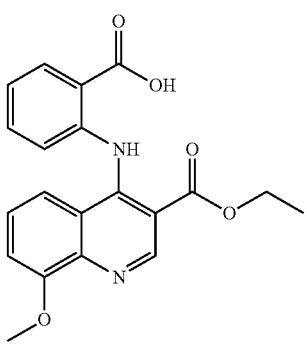
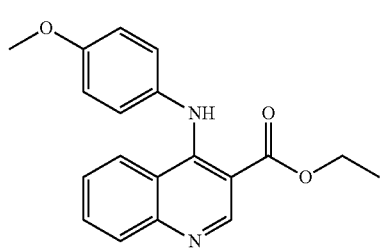
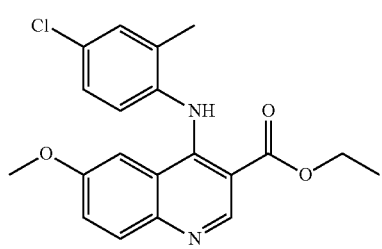
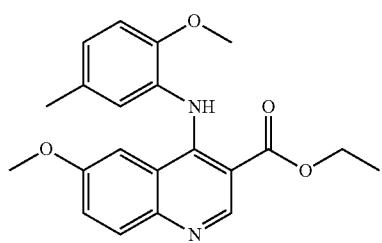
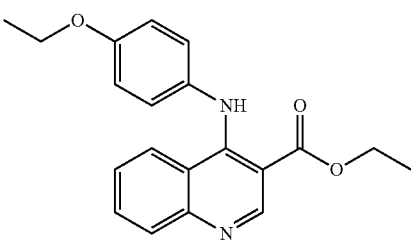
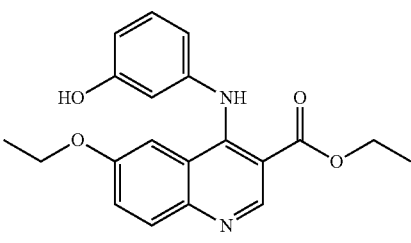
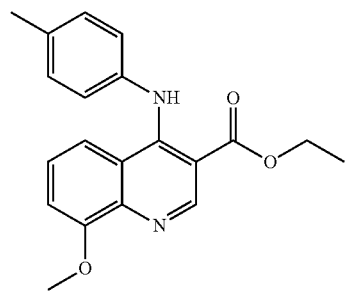
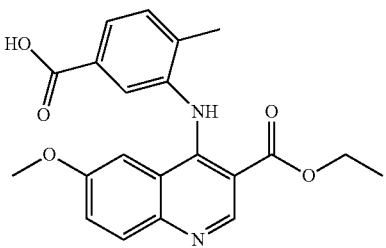
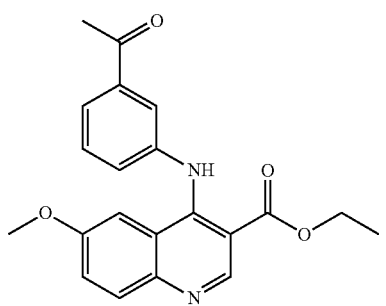
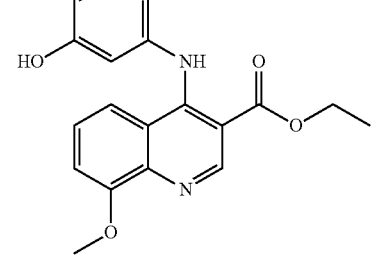
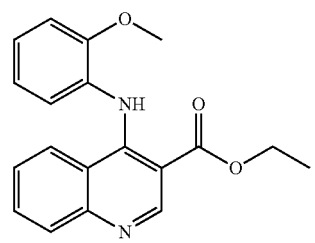

-continued

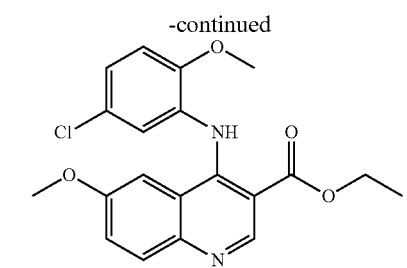

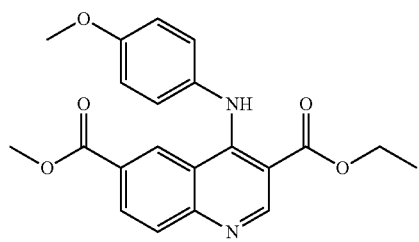

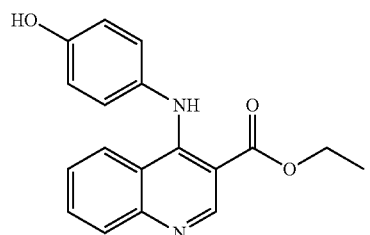

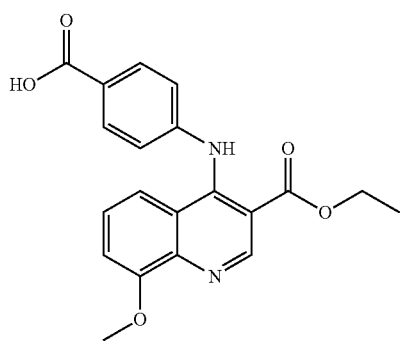

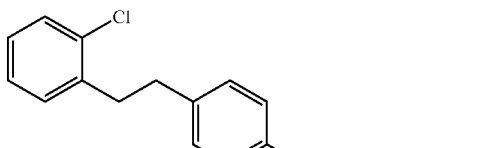

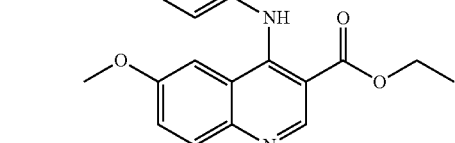

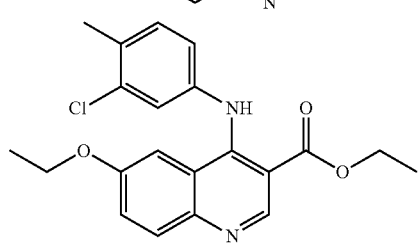

-continued

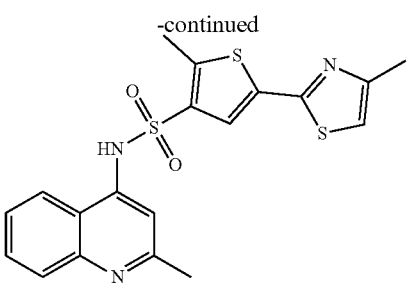

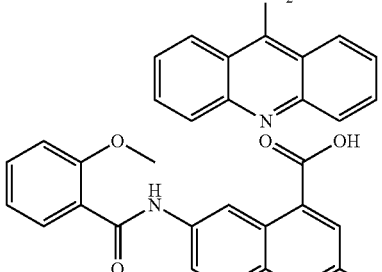

In another general aspect, the present disclosure provides a method selected from:
(a) treating a disorder associated with telomere or telomerase dysfunction in a subject;
(b) treating a disorder associated with aging in a subject;
(c) treating a pre-leukemic or pre-cancerous condition in a subject;
(d) treating or preventing HBV infection in a subject;
(e) treating or preventing a neurodevelopmental disorder in a subject;
(f) treating an acquired or genetic disease or condition associated with alterations in RNA in a subject;
(g) decreasing PAPD5 activity in a subject;
(h) inhibiting of HBsAg production or secretion in a subject;
(i) inhibiting HBV DNA production in a subject
(j) decreasing PAPD5 activity in a cell;
(k) inhibiting of HBsAg production or secretion in a cell;
(l) inhibiting HBV DNA production in a cell;
(m) modulating non-coding RNAs in a cell; and
(n) modulating ex vivo expansion of a stem cell,
the method comprising contacting the cell with an effective amount of, or administering to a subject in need thereof a therapeutically effective amount of, a compound of Formula (A):

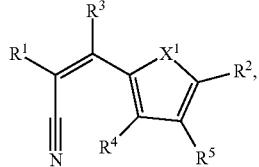

(A)

or a pharmaceutically acceptable salt thereof, wherein:
$X^1$ is selected from O, S, S(O), S(O)$_2$, C(=O), N(R$^N$), C$_{1-6}$ alkylene, C$_{2-6}$ alkenylene, and C$_{2-6}$ alkynylene, wherein said C$_{1-6}$ alkylene, C$_{2-6}$ alkenylene, and C$_{2-6}$ alkynylene are each optionally substituted with 1, 2, 3, 4, or 5 substituents independently selected from R$^1$;

$R^1$ is selected from H, $C_{1-6}$ alkyl, $C_{2-6}$ alkenyl, $C_{2-6}$ alkynyl, $C_{1-4}$ haloalkyl, $Cy^1$, CN, $NO_2$, $OR^{a1}$, $SR^{a1}$, $C(O)R^{b1}$, $C(O)NR^{c1}R^{d1}$, $C(O)OR^{a1}$, $S(O)_2R^{b1}$, $S(O)_2NR^{c1}R^{d1}$, wherein said $C_{1-6}$ alkyl, $C_{2-6}$ alkenyl and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$;

$R^2$, $R^3$, $R^4$ and $R^5$ are each independently selected from H, $C_{1-6}$ alkyl, $C_{2-6}$ alkenyl, $C_{2-6}$ alkynyl, $C_{1-6}$ haloalkyl, $Cy^2$, halo, CN, $NO_2$, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^2$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$ and $S(O)_2NR^{c2}R^{d2}$;

$R^N$ is selected from H, $C_{1-6}$ alkyl, $C_{2-6}$ alkenyl, $C_{2-6}$ alkynyl, $C_{1-6}$ haloalkyl, $Cy^3$, $C(O)R^{b3}$, $C(O)NR^{c3}R^{d3}$, $C(O)OR^{a3}$, $C(=NR^{e3})NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, and $C_{2-6}$ alkynyl of $R^3$ are each optionally substituted with 1, 2, 3, 4, or 5 substituents independently selected from $Cy^3$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$;

each $Cy^1$, $Cy^2$, and $Cy^3$ are independently selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy}$;

each $R^{Cy}$ is independently selected from halo, $C_{1-4}$ alkyl, $C_{1-4}$ haloalkyl, $C_{2-6}$ alkenyl, $C_{2-6}$ alkynyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, and (4-7 membered heterocycloalkyl)-$C_{1-4}$ alkylene-, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-4}$ alkyl, $C_{2-6}$ alkenyl, $C_{2-6}$ alkynyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, and (4-7 membered heterocycloalkyl)-$C_{1-4}$ alkylene- are each optionally substituted by 1, 2, 3, 4, or 5 substituents independently selected from $C_{1-6}$ alkyl, $C_{1-4}$ haloalkyl, $C_{1-6}$ cyanoalkyl, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{c4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^{a1}$, $R^{b1}$, $R^{a2}$, $R^{b2}$, $R^{a3}$, $R^{b3}$, $R^{a4}$, and $R^{b4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are optionally substituted with 1, 2, 3, 4, or 5 substituents independently selected from $R^g$;

each $R^{c1}$, $R^{d1}$, $R^{c2}$, $R^{d2}$, $R^{e3}$, $R^{d3}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, $C(O)R^{b5}$, $C(O)NR^{c5}R^{d5}$, $C(O)OR^{a5}$, $NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, 3, 4, or 5 substituents independently selected from $R^g$;

each $R^{a5}$, $R^{b5}$, $R^{c5}$, and $R^{d5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene and $R^g$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, 3, 4, or 5 substituents independently selected from $R^g$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $R^g$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $R^g$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $R^g$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $R^g$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $R^g$;

each $R^{e1}$, $R^{e2}$, $R^{e3}$, and $R^{e4}$ is independently selected from H, $C_{1-4}$ alkyl, $C_{1-4}$ alkoxy, OH, and CN; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $X^1$ is selected from O, S and N($R^N$).

In some embodiments, $R^1$ is selected from H, $C_{1-6}$ alkyl, $C_{1-4}$ haloalkyl, $Cy^1$, CN, $NO_2$, OH, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl is optionally substituted with 1, 2, or 3 substituents independently selected from halo, CN, $NO_2$, OH, $C(O)NH_2$, C(O)OH, and $NH_2$.

In some embodiments, $R^2$ is selected from H, $C_{1-6}$ alkyl, $C_{1-4}$ haloalkyl, $Cy^2$, $OR^{a2}$, $C(O)R^{b2}$, $NR^{c2}R^{d2}$, $S(O)_2R^{b2}$, and $S(O)_2NR^{c2}R^{d2}$; wherein said $C_{1-6}$ alkyl is optionally substituted with 1, 2, or 3 substituents independently selected from $Cy^2$, halo, CN, $NO_2$, and OH.

In some embodiments, $R^3$, $R^4$ and $R^5$ are each independently selected from H, $C_{1-6}$ alkyl, $C_{1-6}$ haloalkyl.

In some embodiments, $R^N$ is selected from H, $C_{1-6}$ alkyl, and $C_{1-6}$ haloalkyl.

In some embodiments, $Cy^1$ is 5-10 membered heteroaryl, which is optionally substituted with 1, 2, or 3 independently selected $R^{Cy}$.

In some embodiments, $Cy^2$ is $C_{6-10}$ aryl, which is optionally substituted with 1, 2, or 3 independently selected $R^{Cy}$.

In some embodiments, $Cy^3$ is selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy}$.

In some embodiments, each $R^{Cy}$ is independently selected from halo and $C(O)OR^{a4}$.

In some embodiments, each $R^{a1}$, $R^{b1}$, $R^{a2}$, $R^{b2}$, $R^{a3}$, $R^{b3}$, $R^{a4}$, and $R^{b4}$ is independently selected from H, $C_{1-6}$ alkyl and $C_{6-10}$ aryl, wherein said $C_{1-6}$ alkyl is optionally substituted with 1, 2, or 3 substituents independently selected from $R^g$.

In some embodiments, each $R^{c1}$, $R^{d1}$, $R^{c2}$, $R^{d2}$, $R^{c3}$, $R^{d3}$, $R^{c4}$, and $R^{d4}$ is independently selected from H, $C_{1-6}$ alkyl and $C_{6-10}$ aryl, wherein said $C_{1-6}$ alkyl is optionally substituted with 1, 2, or 3 substituents independently selected from $R^g$.

In some embodiments:

$X^1$ is selected from O, S, $S(O)_2$, $N(R^N)$, $C_{1-6}$ alkylene, and $C_{2-6}$ alkenylene, wherein said $C_{1-6}$ alkylene and $C_{2-6}$ alkenylene are each optionally substituted with 1, 2, or 3 substituents independently selected from $R^1$;

$R^1$ is selected from H, $C_{1-6}$ alkyl, $C_{1-4}$ haloalkyl, $Cy^1$, CN, $NO_2$, $OR^{a1}$, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl is optionally substituted with 1, 2, or 3 substituents independently selected from $Cy^1$, halo, CN, $NO_2$, OH, $C(O)NH_2$, C(O)OH, $NH_2$, and $S(O)_2NH_2$;

$R^2$ is selected from H, $C_{1-6}$ alkyl, $C_{1-4}$ haloalkyl, $Cy^2$, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein said $C_{1-6}$ alkyl is optionally substituted with 1, 2, or 3 substituents independently selected from $Cy^2$, halo, CN, $NO_2$, OH, $C(O)NH_2$, C(O)OH, $NH_2$, and $S(O)_2NH_2$;

$R^3$, $R^4$ and $R^5$ are each independently selected from H, $C_{1-6}$ alkyl, $C_{1-6}$ haloalkyl, $Cy^2$, halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2N^{c2}R^{d2}$, $S(O)_2R^{b2}$, and $S(O)_2NR^{c2}R^{d2}$; wherein said $C_{1-6}$ alkyl is optionally substituted with 1, 2, or 3 substituents independently selected from $Cy^2$, halo, CN, $NO_2$, $OR^{a2}$, $SR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$ and $S(O)_2NR^{c2}R^{d2}$;

$R^N$ is selected from H, $C_{1-6}$ alkyl, $C_{1-6}$ haloalkyl, $Cy^3$, $C(O)R^{b3}$, $C(O)NR^{c3}R^{d3}$, $C(O)OR^{a3}$, $S(O)_2R^{b3}$, and $S(O)_2NR^{c3}R^{d3}$; wherein said $C_{1-6}$ alkyl is optionally substituted with 1, 2, or 3 substituents independently selected from $Cy^3$, halo, CN, $NO_2$, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $S(O)_2R^{b3}$ and $S(O)_2NR^{c3}R^{d3}$;

$Cy^1$ is selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy}$;

$Cy^2$ is selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy}$;

$Cy^3$ is selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy}$;

each $R^{Cy}$ is independently selected from halo, $C_{1-4}$ alkyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl is optionally substituted by 1, 2, or 3 substituents independently selected from halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$;

each $R^{a1}$, $R^{b1}$, $R^{a2}$, $R^{b2}$, $R^{a3}$, $R^{b3}$, $R^{a4}$, and $R^{b4}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl are optionally substituted with 1, 2, or 3 substituents independently selected from $R^g$; and each $R^{c1}$, $R^{d1}$, $R^{c2}$, $R^{d2}$, $R^{c3}$, $R^{d3}$, $R^{c4}$, and $R^{d4}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, wherein said $C_{1-6}$ alkyl, $C_{6-10}$ aryl, $C_{3-10}$ cycloalkyl, 5-10 membered heteroaryl, and 4-12 membered heterocycloalkyl is optionally substituted with 1, 2, or 3 substituents independently selected from $R^g$.

In some embodiments:

$X^1$ is selected from O, S, $C_{1-6}$ alkylene, and $C_{2-6}$ alkenylene, wherein said $C_{1-6}$ alkylene and $C_{2-6}$ alkenylene are each optionally substituted with 1, 2, or 3 substituents independently selected from $R^1$;

$R^1$ is selected from H, $C_{1-6}$ alkyl, $C_{1-4}$ haloalkyl, $Cy^1$, CN, $NO_2$, OH, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl is optionally substituted with 1, 2, or 3 substituents independently selected from halo, CN, $NO_2$, OH, $C(O)NH_2$, $C(O)OH$, and $NH_2$;

$R^2$ is selected from H, $C_{1-6}$ alkyl, $C_{1-4}$ haloalkyl, $Cy^2$, $OR^{a2}$, $C(O)R^{b2}$, $NR^{c2}R^{d2}$, $S(O)_2R^{b2}$, and $S(O)_2N^{c2}R^{d2}$; wherein said $C_{1-6}$ alkyl is optionally substituted with 1, 2, or 3 substituents independently selected from $Cy^2$, halo, CN, $NO_2$, and OH;

$R^3$, $R^4$ and $R^5$ are each independently selected from H, $C_{1-6}$ alkyl, $C_{1-6}$ haloalkyl, $Cy^2$, halo, CN, $NO_2$, $C(O)R^{b2}$, $C(O)NR^{c2}R^{d2}$, $C(O)OR^{a2}$, $S(O)_2R^{b2}$, and $S(O)_2NR^{c2}R^{d2}$; wherein said $C_{1-6}$ alkyl is optionally substituted with 1, 2, or 3 substituents independently selected from $Cy^2$, halo, CN, $NO_2$, $C(O)R^{b2}$, $C(O)NR^{c2}R^{d2}$, $C(O)OR^{a2}$, $S(O)_2R^{b2}$ and $S(O)_2NR^{c2}R^{d2}$; $Cy^1$ is 5-10 membered heteroaryl, which is optionally substituted with 1, 2, or 3 independently selected $R^{Cy}$;

$Cy^2$ is $C_{6-10}$ aryl, which is optionally substituted with 1, 2, or 3 independently selected $R^{Cy}$;

$R^{Cy}$ is independently selected from halo, $C_{1-4}$ alkyl, $C_{1-4}$ haloalkyl, CN, $NO_2$, $OR^{a4}$, $C(O)NR^{c4}R^{d4}$, $C(O)OR^{a4}$, $NR^{c4}R^{d4}$, $S(O)_2R^{b4}$, and $S(O)_2NR^{c4}R^{d4}$, wherein said $C_{1-4}$ alkyl is optionally substituted by 1, 2, or 3 substituents independently selected from halo, CN, $NO_2$, OH, $C(O)NH_2$, $C(O)OH$, $NH_2$, and $S(O)_2NH_2$;

each $R^{a1}$, $R^{b1}$, $R^{a2}$, $R^{b2}$, $R^{a3}$, $R^{b3}$, $R^{a4}$, and $R^{b4}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl are optionally substituted with 1, 2, or 3 substituents independently selected from $R^g$; and each $R^{c1}$, $R^{d1}$, $R^{c2}$, $R^{d2}$, $R^{e3}$, $R^{d3}$, $R^{c4}$, and $R^{d4}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, wherein said $C_{1-6}$ alkyl, $C_{6-10}$ aryl, $C_{3-10}$ cycloalkyl, 5-10 membered heteroaryl, and 4-12 membered heterocycloalkyl is optionally substituted with 1, 2, or 3 substituents independently selected from $R^g$.

In some embodiments:

$X^1$ is selected from O, S, methylene, and ethenylene, wherein said methylene and ethenylene are each optionally substituted with 1 or 2 independently selected $R^1$;

each $R^1$ is independently selected from $C(O)NR^{c1}R^{d1}$ and $Cy^1$;

$R^2$ is $Cy^2$;

$R^3$, $R^4$ and $R^5$ are each independently selected from H, $C_{1-6}$ alkyl, $C_{1-6}$ haloalkyl;

$Cy^1$ is 5-10 membered heteroaryl, which is optionally substituted with 1, 2, or 3 independently selected $R^{Cy}$;

$Cy^2$ is $C_{6-10}$ aryl, which is optionally substituted with 1, 2, or 3 independently selected $R^{Cy}$;

each $R^{Cy}$ is independently selected from halo and $C(O)OR^{a4}$;

each $R^{a1}$, $R^{b1}$, $R^{a2}$, $R^{b2}$, $R^{a3}$, $R^{b3}$, $R^{a4}$, and $R^{b4}$ is independently selected from H, $C_{1-6}$ alkyl and $C_{6-10}$ aryl, wherein said $C_{1-6}$ alkyl is optionally substituted with 1, 2, or 3 substituents independently selected from $R^g$; and each $R^{c1}$, $R^{d1}$, $R^{c2}$, $R^{d2}$, $R^{c3}$, $R^{d3}$, $R^{c4}$, is independently selected from H, $C_{1-6}$ alkyl and $C_{6-10}$ aryl, wherein said $C_{1-6}$ alkyl is optionally substituted with 1, 2, or 3 substituents independently selected from $R^g$.

In some embodiments, the compound of Formula (A) is selected from any of the following compounds, or a pharmaceutically acceptable salt thereof:

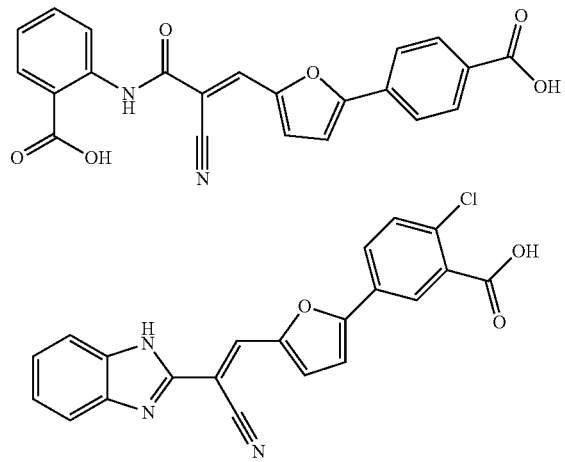

In yet another general aspect, the present disclosure provides a method selected from:
(a) treating a disorder associated with telomere or telomerase dysfunction in a subject;
(b) treating a disorder associated with aging in a subject;
(c) treating a pre-leukemic or pre-cancerous condition in a subject;
(d) treating or preventing HBV infection in a subject;
(e) treating or preventing a neurodevelopmental disorder in a subject;
(f) treating an acquired or genetic disease or condition associated with alterations in RNA in a subject;
(g) decreasing PAPD5 activity in a subject;
(h) inhibiting of HBsAg production or secretion in a subject;
(i) inhibiting HBV DNA production in a subject
(j) decreasing PAPD5 activity in a cell;
(k) inhibiting of HBsAg production or secretion in a cell;
(l) inhibiting HBV DNA production in a cell;
(m) modulating non-coding RNAs in a cell; and
(n) modulating ex vivo expansion of a stem cell,
the method comprising contacting the cell with an effective amount of, or administering to a subject in need thereof a therapeutically effective amount of, a compound of Formula (I-IIc):

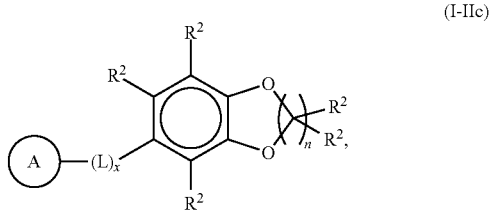

(I-IIc)

or a pharmaceutically acceptable salt thereof, wherein:

ring A is selected from $C_{3-10}$ cycloalkyl, 6-10 membered aryl, 5-12 membered heteroaryl, and 4-12 membered heterocycloalkyl, each of which is optionally substituted by 1-10 independently selected R' groups;

each L is independently selected from O, S, C(=O), S(=O), S(=O)$_2$, N(R$^3$), $C_{1-6}$ alkylene, $C_{2-6}$ alkenylene, $C_{2-6}$ alkynylene, $C_{3-10}$ cycloalkylene, $C_{6-10}$ arylene, 5-14 membered heteroarylene, and 4-12 membered heterocycloalkylene, wherein said $C_{1-6}$ alkylene, $C_{2-6}$ alkenylene, $C_{2-6}$ alkynylene, $C_{3-10}$ cycloalkylene, $C_{6-10}$ arylene, 5-14 membered heteroarylene, and 4-12 membered heterocycloalkylene are each optionally substituted with 1, 2, 3, 4, or 5 substituents independently selected from $R^4$;

x is an integer from 0 to 10, wherein when x is 0 then L is a bond;

each $R^1$ is independently selected from H, $C_{1-6}$ alkyl, $C_{2-6}$ alkenyl, $C_{2-6}$ alkynyl, $C_{1-4}$ haloalkyl, Cy$^1$, halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$ NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, S(O)$_2$NR$^{c1}$R$^{d1}$, thioxo and oxo; wherein said $C_{1-6}$ alkyl, $C_{2-6}$ alkenyl, and $C_{2-6}$ alkynyl substituents of $R^1$ are each optionally substituted with 1, 2, 3, 4, or 5 substituents independently selected from Cy$^1$, halo, CN, NO$_2$, OR$^{a1}$, SR$^{a1}$, C(O)R$^{b1}$, C(O) NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O) NR$^{c1}$R$^{d1}$, NR$^{c1}$S(O)R$^{b1}$, NR$^{c1}$S(O)$_2$R$^{b1}$, NR$^{c1}$S(O)$_2$ NR$^{c1}$R$^{d1}$, S(O)R$^{b1}$, S(O)NR$^{c1}$R$^{d1}$, S(O)$_2$R$^{b1}$ and S(O)$_2$ NR$^{c1}$R$^{d1}$;

each $R^2$ is independently selected from H, $C_{1-6}$ alkyl, $C_{2-6}$ alkenyl, $C_{2-6}$ alkynyl, $C_{1-6}$ haloalkyl, Cy$^2$, halo, CN, NO$_2$, OR$^{a2}$, C(O)R$^{b2}$, C(O)NR$^{c2}$R$^{d2}$, C(O)OR$^{a2}$, OC(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$, thioxo and oxo; wherein said $C_{1-6}$ alkyl, $C_{2-6}$ alkenyl, and $C_{2-6}$ alkynyl substituents of $R^1$ are each optionally substituted with 1, 2, 3, 4, or 5 substituents independently selected from Cy$^2$, halo, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$) NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$ R$^{b2}$ and S(O)$_2$NR$^{c2}$R$^{d2}$;

or $R^1$ together with the atom of ring A to which it is attached, $R^2$ together with the carbon atom to which it is attached, and moiety (L)$_x$ together form a ring selected from: $C_{3-10}$ cycloalkyl, 6-10 membered aryl, 5-10 membered heteroaryl, and 4-12 membered heterocycloalkyl group, each of which is optionally substituted with 1, 2, 3, 4, or 5 substituents independently selected from $R^4$;

each $R^3$ is independently selected from H, $C_{1-6}$ alkyl, $C_{2-6}$ alkenyl, $C_{2-6}$ alkynyl, $C_{1-6}$ haloalkyl, Cy$^3$, C(O)R$^{b3}$, C(O)NR$^{c3}$R$^{d3}$, C(O)OR$^{a3}$, C(=NR$^{e3}$)NR$^{c3}$R$^{d3}$, S(O) R$^{b3}$, S(O)NR$^{c3}$R$^{d3}$, S(O)$_2$R$^{b3}$, and S(O)$_2$NR$^{c3}$R$^{d3}$; wherein said $C_{1-6}$ alkyl, $C_{2-6}$ alkenyl, and $C_{2-6}$ alkynyl of $R^3$ are each optionally substituted with 1, 2, 3, 4, or 5 substituents independently selected from Cy$^3$, halo, CN, NO$_2$, OR$^{a3}$, SR$^{a3}$, C(O)R$^{b3}$, C(O)NR$^{c3}$R$^{d3}$, C(O) OR$^{a3}$, OC(O)R$^{b3}$, OC(O)NR$^{c3}$R$^{d3}$, C(=NR$^{e3}$) NR$^{c3}$R$^{d3}$, NR$^{c3}$C(=NR$^{e3}$)NR$^{c3}$R$^{d3}$, NR$^{c3}$R$^{d3}$, NR$^{c3}$C (O)R$^{b3}$, NR$^{c3}$C(O)OR$^{a3}$, NR$^{c3}$C(O)NR$^{c3}$R$^{d3}$, NR$^{c3}$S (O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$ and S(O)$_2$NR$^{c3}$R$^{d3}$;

each $R^4$ is independently selected from $C_{1-6}$ alkyl, $C_{1-6}$ haloalkyl, $C_{2-6}$ alkenyl, $C_{2-6}$ alkynyl, Cy$^3$, halo, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O) NR$^{c3}$R$^{d3}$, S(O)$_2$R$^{b3}$, and S(O)$_2$NR$^{c3}$R$^{d3}$; wherein said $C_{1-6}$ alkyl, $C_{2-6}$ alkenyl, and $C_{2-6}$ alkynyl of $R^4$ are each optionally substituted with 1, 2, 3, 4, or 5 substituents independently selected from Cy$^3$, halo, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$ NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O) NR$^{c3}$R$^{d3}$, S(O)$_2$R$^{b3}$ and S(O)$_2$NR$^{c3}$R$^{d3}$;

each Cy$^1$, Cy$^2$, and Cy$^3$ are independently selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from R$^{Cy}$;

each R$^{Cy}$ is independently selected from halo, $C_{1-4}$ alkyl, $C_{1-4}$ haloalkyl, $C_{2-6}$ alkenyl, $C_{2-6}$ alkynyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, and (4-7 membered heterocycloalkyl)-$C_{1-4}$ alkylene-, CN, NO$_2$, OR$^{a4}$, SR$^{a4}$, C(O)R$^{b4}$, C(O) NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O) NR$^{c4}$R$^{d4}$, NR$^{c4}$S(O)R$^{b4}$, NR$^{c4}$S(O)$_2$R$^{b4}$, NR$^{c4}$S(O)$_2$ NR$^{c4}$R$^{d4}$, S(O)R$^{b4}$, S(O)NR$^{c4}$R$^{d4}$, S(O)$_2$R$^{b4}$, and S(O)$_2$ NR$^{c4}$R$^{d4}$, wherein said $C_{1-4}$ alkyl, $C_{2-6}$ alkenyl, $C_{2-6}$ alkynyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, and (4-7 membered heterocycloalkyl)-$C_{1-4}$ alkylene- are each optionally substituted by 1, 2, 3, 4, or 5 substituents independently selected from $C_{1-6}$ alkyl, $C_{1-4}$ haloalkyl, $C_{1-6}$ cyanoalkyl, halo, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O) NR$^{c4}$R$^{d4}$, C(=NR$^{e4}$)NR$^{c4}$R$^{d4}$, NR$^{c4}$C(=NR$^{e4}$) NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, and S(O)$_2$NR$^{c4}$R$^{d4}$;

each R$^{a1}$, R$^{b1}$, R$^{a2}$, R$^{b2}$, R$^{a3}$, R$^{b3}$, R$^{a4}$, and R$^{b4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are optionally substituted with 1, 2, 3, 4, or 5 substituents independently selected from $R^g$;

each $R^{c1}$, $R^{d1}$, $R^{c2}$, $R^{d2}$, $R^{e3}$, $R^{d3}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, C(O)$R^{b5}$, C(O)NR$^{c5}$R$^{d5}$, C(O)OR$^{a5}$, NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, 3, 4, or 5 substituents independently selected from $R^g$;

each $R^{a5}$, $R^{b5}$, RCS, and $R^{d5}$ is in dependently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene and $R^g$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, 3, 4, or 5 substituents independently selected from $R^g$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $R^g$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $R^g$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $R^g$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $R^g$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $R^g$;

each $R^{e1}$, $R^{e2}$, $R^{e3}$, and $R^{e4}$ is independently selected from H, $C_{1-4}$ alkyl, $C_{1-4}$ alkoxy, OH, and CN;

each $R^g$ is independently selected from OH, NO$_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is an integer from 0 to 4.

In some embodiments, n is 1 or 2.

In some embodiments, ring A is selected from 5-12 membered heteroaryl and 4-12 membered heterocycloalkyl, each of which is optionally substituted by 1, 2, 3, 4, or 5 independently selected $R^1$ groups.

In some embodiments, ring A is a moiety selected from (A-1) to (A-7):

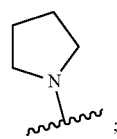

(A-1)

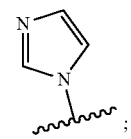

(A-2)

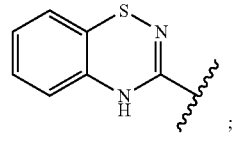

(A-3)

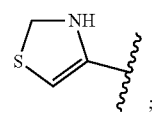

(A-4)

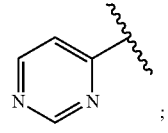

(A-5)

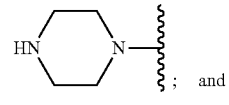

(A-6); and

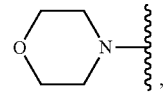

(A-7), wherein each of the moieties (A-1) to (A-7) is optionally substituted with 1, 2, 3, 4, or 5 substituents independently selected from $R^1$.

In some embodiments, each L is independently selected from C(=O), N($R^3$), $C_{1-6}$ alkylene, 4-10 membered heterocycloalkylene, and 5-14 membered heteroarylene, wherein said $C_{1-6}$ alkylene, 4-10 membered heterocycloalkylene, and 5-14 membered heteroarylene are each optionally substituted with 1, 2, or 3 substituents independently selected from $R^4$.

In some embodiments, $R^3$ is selected from H, $C_{1-6}$ alkyl, and $C_{1-6}$ haloalkyl.

In some embodiments, the moiety $(L)_x$ is selected from:

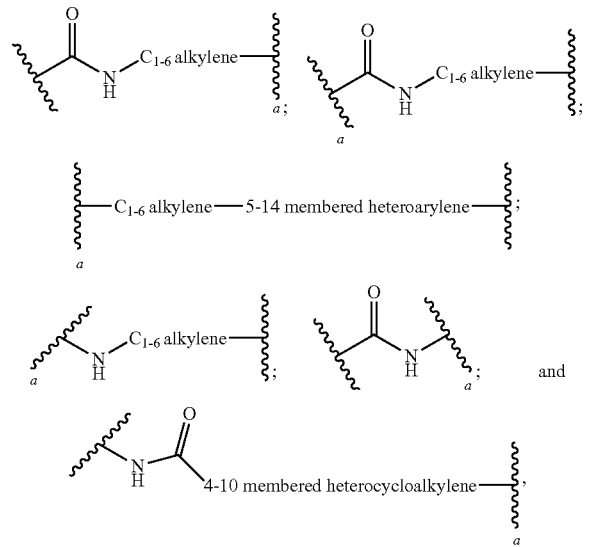

wherein said $C_{1-6}$ alkylene, 5-14 membered heteroarylene, and 4-10 membered heterocycloalkylene are each optionally substituted with 1, 2, or 3 substituents independently selected from $R^4$; and wherein a denotes a point of attachment of $(L)_x$ to ring A.

In some embodiments, $R^4$ is selected from $C_{1-6}$ alkyl, $C_{1-6}$ haloalkyl, halo, CN, $NO_2$, OH, $NH_2$, wherein said $C_{1-6}$ alkyl of $R^4$ is optionally substituted with 1, 2, or 3 substituents independently selected from halo, CN, $NO_2$, OH, and $NH_2$.

In some embodiments, $R^1$ is selected from $C_{1-6}$ alkyl, $C_{1-4}$ haloalkyl, $Cy^1$, halo, CN, $NO_2$, OH, C(O)$NR^{c1}R^{d1}$, C(O)$OR^{a1}$, $NH_2$, S(O)$_2R^{b1}$, thioxo and oxo; wherein said $C_{1-6}$ alkyl of $R^1$ is optionally substituted with 1, 2, or 3 substituents independently selected from halo, CN, $NO_2$, OH, C(O)$NH_2$, C(O)OH, and $NH_2$.

In some embodiments, $R^2$ is selected from H, $C_{1-6}$ alkyl, $C_{1-4}$ haloalkyl, $Cy^2$, halo, CN, $NO_2$, OH, C(O)$R^{b2}$, C(O)$OR^{a2}$, $NH_2$, S(O)$_2R^{b2}$, thioxo and oxo; wherein said $C_{1-6}$ alkyl of $R^2$ is optionally substituted with 1, 2, or 3 substituents independently selected from halo, CN, $NO_2$, OH, C(O)$NH_2$, C(O)OH, and $NH_2$.

In some embodiments, $Cy^1$, $Cy^2$, and $Cy^3$ are each independently selected from $C_{6-10}$ aryl and 4-12 membered heterocycloalkyl, each of which is optionally substituted with 1, 2, or 3 substituents independently selected from $R^{Cy}$.

In some embodiments, $R^{Cy}$ is selected from halo, $C_{1-4}$ alkyl, $C_{1-4}$ haloalkyl, CN, $NO_2$, OH, C(O)$NH_2$, C(O)OH, $NH_2$, and S(O)$_2NH_2$, wherein said $C_{1-4}$ alkyl is optionally substituted by 1, 2, or 3 substituents independently selected from halo, CN, $NO_2$, OH, C(O)$NH_2$, C(O)OH, $NH_2$, and S(O)$_2NH_2$.

In some embodiments, each $R^{a1}$, $R^{b1}$, $R^{a2}$, $R^{b2}$, $R^{a3}$, $R^{b3}$, $R^{a4}$, and $R^{b4}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl are optionally substituted with 1, 2, or 3 substituents independently selected from $R^g$.

In some embodiments, each $R^{c1}$, $R^{d1}$, $R^{c2}$, $R^{d2}$, $R^{e3}$, $R^{d3}$, $R^{c4}$, and $R^{d4}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, wherein said $C_{1-6}$ alkyl, $C_{6-10}$ aryl, $C_{3-10}$ cycloalkyl, 5-10 membered heteroaryl, and 4-12 membered heterocycloalkyl is optionally substituted with 1, 2, or 3 substituents independently selected from $R^g$.

In some embodiments, each $R^{a5}$, $R^{b5}$, $R^{c5}$, and $R^{d5}$ is independently selected from H, $C_{1-6}$ alkyl, $C_{1-4}$ haloalkyl, and $C_{2-6}$ alkenyl.

In some embodiments:
ring A is selected from 6-10 membered aryl, 5-12 membered heteroaryl, and 4-12 membered heterocycloalkyl, each of which is optionally substituted by 1, 2, 3, 4, or 5 independently selected $R^1$ groups;
each L is independently selected from O, C(=O), S(=O)$_2$, N($R^3$), $C_{1-6}$ alkylene, $C_{3-10}$ cycloalkylene, $C_{6-10}$ arylene, 5-14 membered heteroarylene, and 4-10 membered heterocycloalkylene, wherein said $C_{1-6}$ alkylene, $C_{3-10}$ cycloalkylene, $C_{6-10}$ arylene, 5-14 membered heteroarylene, and 4-10 membered heterocycloalkylene are each optionally substituted with 1, 2, or 3 substituents independently selected from $R^4$;
x is 1, 2, or 3;
$R^3$ is selected from H, $C_{1-6}$ alkyl, $C_{1-6}$ haloalkyl, $Cy^3$, C(O)$R^{b3}$, C(O)$NR^{c3}R^{d3}$, C(O)$OR^{a3}$, S(O)$_2R^{b3}$, and S(O)$_2NR^{c3}R^{d3}$; wherein said $C_{1-6}$ alkyl of $R^3$ is optionally substituted with 1, 2, or 3 substituents independently selected from $Cy^3$, halo, CN, $NO_2$, $OR^{a3}$, C(O)$R^{b3}$, C(O)$NR^{c3}R^{d3}$, C(O)$OR^{a3}$, $NR^{c3}R^{d3}$, $NR^{c3}$C(O)$R^{b3}$, $NR^{c3}$C(O)$OR^{a3}$, $NR^{c3}$C(O)$NR^{c3}R^{d3}$, $NR^{c3}$S(O)$_2R^{b3}$, S(O)$_2R^{b3}$ and S(O)$_2NR^{c3}R^{d3}$;
$R^4$ is selected from $C_{1-6}$ alkyl, $C_{1-6}$ haloalkyl, $Cy^3$, halo, CN, $NO_2$, $OR^{a3}$, C(O)$R^{b3}$, C(O)$NR^{c3}R^{d3}$, C(O)$OR^{a3}$, $NR^{c3}R^{d3}$, S(O)$_2R^{b3}$, and S(O)$_2NR^{c3}R^{d3}$; wherein said $C_{1-6}$ alkyl of $R^4$ is optionally substituted with 1, 2, or 3 substituents independently selected from $Cy^3$, halo, CN, $NO_2$, $OR^{a3}$, C(O)$R^{b3}$, C(O)$NR^{c3}R^{d3}$, C(O)$OR^{a3}$, $NR^{c3}R^{d3}$, S(O)$_2R^{b3}$ and S(O)$_2NR^{c3}R^{d3}$;
$R^1$ is selected from $C_{1-6}$ alkyl, $C_{1-4}$ haloalkyl, $Cy^1$, halo, CN, $NO_2$, $OR^{a1}$, C(O)$R^{b1}$, C(O)$NR^{c1}R^{d1}$, C(O)$OR^{a1}$, $NR^{c1}R^{d1}$, S(O)$_2R^{b1}$, S(O)$_2NR^{c1}R^{d1}$, thioxo and oxo; wherein said $C_{1-6}$ alkyl of $R^1$ is optionally substituted with 1, 2, or 3 substituents independently selected from $Cy^1$, halo, CN, $NO_2$, OH, C(O)$NH_2$, C(O)OH, $NH_2$, and S(O)$_2NH_2$;
$R^2$ is selected from $C_{1-6}$ alkyl, $C_{1-4}$ haloalkyl, $Cy^2$, halo, CN, $NO_2$, $OR^{a2}$, C(O)$R^{b2}$, C(O)$NR^{c2}R^{d2}$, C(O)$OR^{a2}$, $NR^{c2}R^{d2}$, S(O)$_2R^{b2}$, S(O)$_2NR^{c2}R^{d2}$, thioxo and oxo; wherein said $C_{1-6}$ alkyl of $R^2$ is optionally substituted with 1, 2, or 3 substituents independently selected from $Cy^2$, halo, CN, $NO_2$, OH, C(O)$NH_2$, C(O)OH, $NH_2$, and S(O)$_2NH_2$;
or $R^1$ together with the atom of ring A to which it is attached, $R^2$ together with the atom of ring B to which it is attached, and moiety $(L)_x$ together form a 4-12 membered heterocycloalkyl ring, which is optionally substituted with 1, 2, or 3 substituents independently selected from $R^4$;

$Cy^1$, $Cy^2$, and $Cy^3$ are each independently selected from $C_{6-10}$ aryl and 4-12 membered heterocycloalkyl, each of which is optionally substituted with 1, 2, or 3 substituents independently selected from $R^{Cy}$;

$R^{Cy}$ is selected from halo, $C_{1-4}$ alkyl, $C_{1-4}$ haloalkyl, CN, $NO_2$, OH, $C(O)NH_2$, $C(O)OH$, $NH_2$, and $S(O)_2NH_2$, wherein said $C_{1-4}$ alkyl is optionally substituted by 1, 2, or 3 substituents independently selected from halo, CN, $NO_2$, OH, $C(O)NH_2$, $C(O)OH$, $NH_2$, and $S(O)_2NH_2$;

each $R^{a1}$, $R^{b1}$, $R^{a2}$, $R^{b2}$, $R^{a3}$, and $R^{b3}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, and 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl are each optionally substituted with 1, 2, or 3 substituents independently selected from $R^g$; and each $R^{c1}$, $R^{d1}$, $R^{c2}$, $R^{d2}$, $R^{c3}$ and $R^{d3}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, and 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl are each optionally substituted with 1, 2, or 3 substituents independently selected from $R^g$.

In some embodiments:

ring A is selected from 5-12 membered heteroaryl and 4-12 membered heterocycloalkyl, each of which is optionally substituted by 1, 2, 3, 4, or 5 independently selected $R^1$ groups;

each L is independently selected from C(=O), $N(R^3)$, $C_{1-6}$ alkylene, 4-10 membered heterocycloalkylene, and 5-14 membered heteroarylene, wherein said $C_{1-6}$ alkylene, 4-10 membered heterocycloalkylene, and 5-14 membered heteroarylene are each optionally substituted with 1, 2, or 3 substituents independently selected from $R^4$;

$R^3$ is selected from H, $C_{1-6}$ alkyl, and $C_{1-6}$ haloalkyl;

$R^4$ is selected from $C_{1-6}$ alkyl, $C_{1-6}$ haloalkyl, halo, CN, $NO_2$, OH, and $NH_2$, wherein said $C_{1-6}$ alkyl of $R^4$ is optionally substituted with 1, 2, or 3 substituents independently selected from halo, CN, $NO_2$, OH, and $NH_2$;

$R^1$ is selected from $C_{1-6}$ alkyl, $C_{1-4}$ haloalkyl, $Cy^1$, halo, CN, $NO_2$, OH, $C(O)NR^{c1}R^{d1}$, $C(O)OR^{a1}$, $NH_2$, $S(O)_2R^{b1}$, thioxo and oxo; wherein said $C_{1-6}$ alkyl of $R^1$ is optionally substituted with 1, 2, or 3 substituents independently selected from halo, CN, $NO_2$, OH, $C(O)NH_2$, $C(O)OH$, and $NH_2$; and $R^2$ is selected from $C_{1-6}$ alkyl, $C_{1-4}$ haloalkyl, $Cy^2$, halo, CN, $NO_2$, OH, $C(O)R^{b2}$, $C(O)OR^{a2}$, $NH_2$, $S(O)_2R^{b2}$, thioxo and oxo; wherein said $C_{1-6}$ alkyl of $R^2$ is optionally substituted with 1, 2, or 3 substituents independently selected from halo, CN, $NO_2$, OH, $C(O)NH_2$, $C(O)OH$, and $NH_2$.

In some embodiments:

ring A is a moiety of formula:

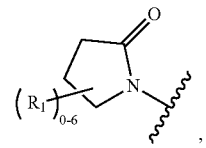

the moiety $(L)_x$ is selected from:

—$C_{1-6}$ alkylene-;

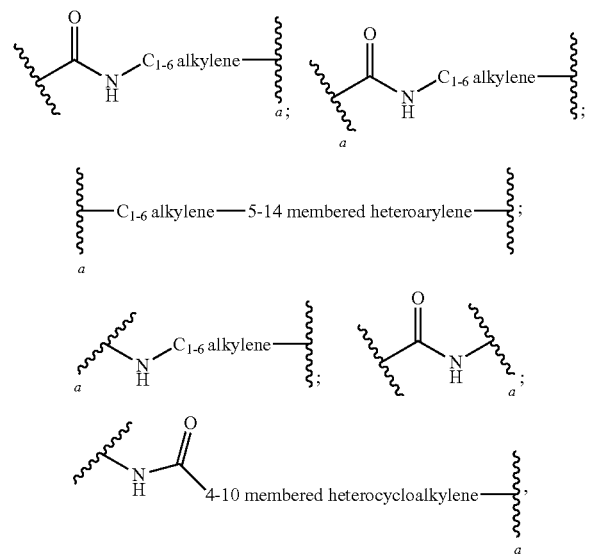

wherein said $C_{1-6}$ alkylene, 5-14 membered heteroarylene, and 4-10 membered heterocycloalkylene of $(L)_x$ are each optionally substituted with 1, 2, or 3 substituents independently selected from $R^4$; and wherein a denotes a point of attachment of $(L)_x$ to ring A.

In some embodiments, $R^1$ together with the atom of ring A to which it is attached, $R^2$ together with the carbon atom to which it is attached, and moiety $(L)_x$ together form a 4-12 membered heterocycloalkyl ring, which is optionally substituted with 1, 2, or 3 substituents independently selected from $R^4$.

In some embodiments, the compound of Formula (I-IIc) has Formula (I-VIa):

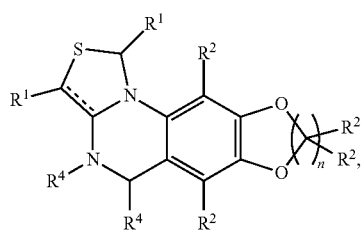

or a pharmaceutically acceptable salt thereof.

In some embodiments, the compound of Formula (I-IIc) has Formula

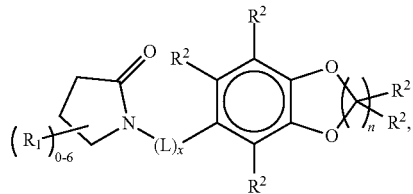
(I-Vc)

or a pharmaceutically acceptable salt thereof.

In some embodiments, the compound of Formula (I-IIc) is selected from any one of the following compounds, or a pharmaceutically acceptable salt thereof:

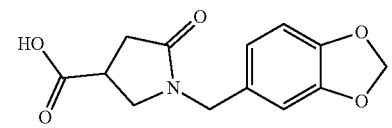

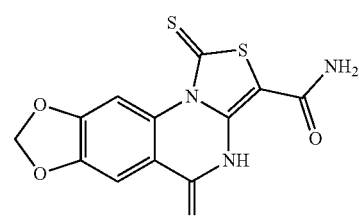

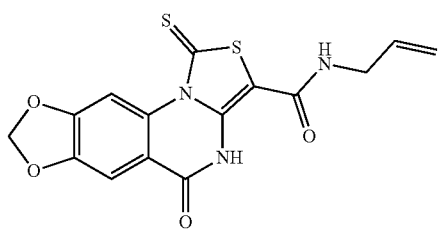

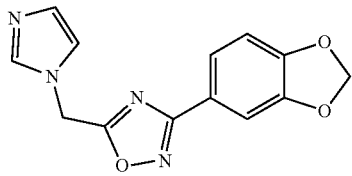

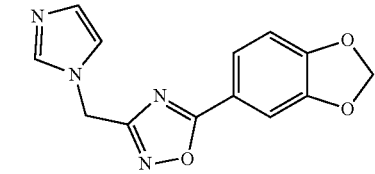

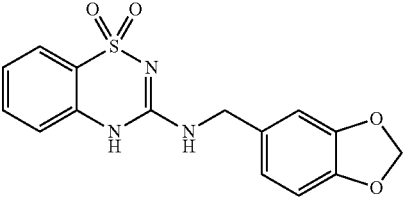

-continued

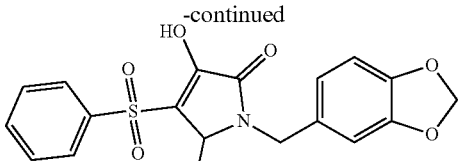

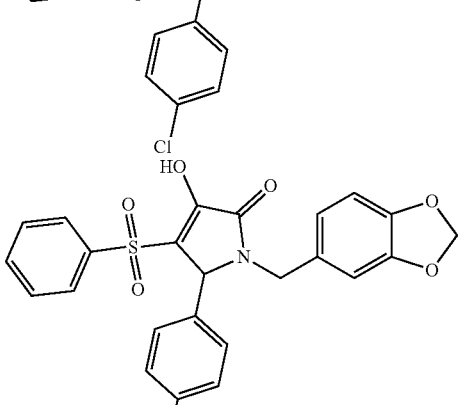

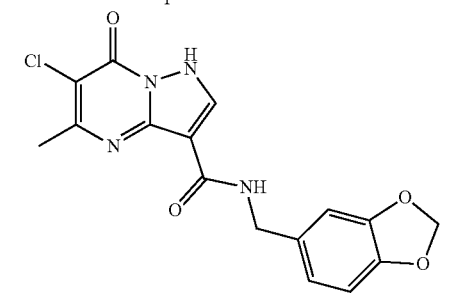

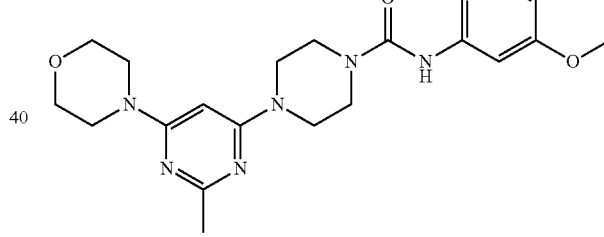

Certain implementations of the above general aspects are described below.

In some embodiments, the disorder associated with telomere or telomerase dysfunction is dyskeratosis congenita, aplastic anemia, pulmonary fibrosis, myelodysplastic syndrome, idiopathic pulmonary fibrosis, hematological disorder, or hepatic fibrosis.

In some embodiments, the disorder associated with aging is macular degeneration, diabetes mellitus, osteoarthritis, rheumatoid arthritis, sarcopenia, cardiovascular disease, hypertension, atherosclerosis, coronary artery disease, ischemia/reperfusion injury, cancer, premature death, age-related decline in cognitive function, cardiopulmonary function, muscle strength, vision, or hearing.

In some embodiments, the RNA comprises ncRNA.

In some embodiments, the ncRNA is selected from snRNA, scaRNA, snoRNA, IRNA, and miRNA.

In some embodiments, the RNA disrupted by disruption of PARN or TOE1 deadenylases.

In some embodiments, the acquired or genetic disease or condition associated with alterations in RNA comprises a neurodevelopmental disorder.

In some embodiments, the neurodevelopmental disorder is pontocerebellar hypoplasia.

In yet another general aspect, the present application provides a method of screening an agent for modulating the level or activity of PAPD5, the method comprising:
a) incubating PAPD5, an oligonucleotide, ATP, and a test agent in a solution for a sufficient period of time;
b) adding a luciferase to the solution;
c) detecting the level of luminescence;
d) comparing the level of luminescence to a reference level; and
e) determining the test agent is an agent that can modulate the level or activity of PAPD5.

In some embodiments, the reference level is the level of luminescence in a solution that has not been treated with a test agent.

In some embodiments, the test agent increases the level or activity of PAPD5.

In some embodiments, the test agent decreases the level or activity of PAPD5.

In some embodiments, the test agent is a nucleic acid, a vector comprising a nucleic acid, a small molecule, an antibody, an antibody fragment, an aminoglycoside, or a nucleoside analogue.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DESCRIPTION OF DRAWINGS

FIG. 10 shows 6 clusters of compounds that can inhibit PAPD5 activity.

FIG. 11 shows 72 compounds that have the best PAPD5 inhibition rates.

FIG. 19 shows restoration of TERC 3' end processing by (2-[[3-ethoxycarbonyl-6-(trifluoromethoxy) quinolin-4-yl]amino]benzoic acid) (Table 5, Entry 1) in human PARN-deficient cells.

FIG. 24 shows that compound of table 5 (entry 1) restores telomerase RNA (TERC) end processing whereas the compound of table 3 (entry 5) does not.

DETAILED DESCRIPTION

Figure 1:
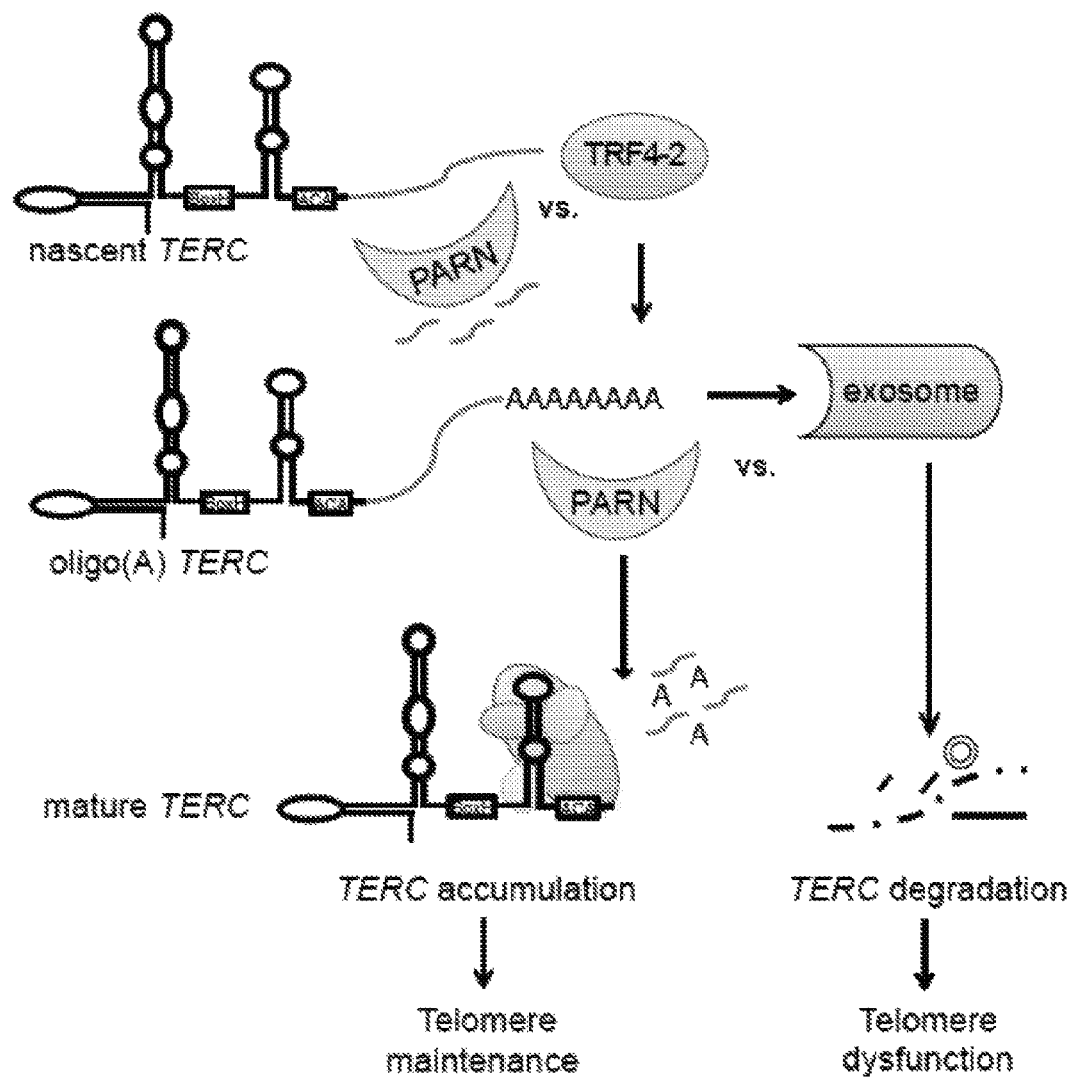
FIG. 1 is a schematic diagram showing an exemplary model for TERC 3' end maturation by PARN.

A telomere is a region of repetitive nucleotide sequences at each end of a chromosome. For vertebrates, the sequence of nucleotides in telomeres is TTAGGG. In humans, this sequence of TTAGGG is repeated approximately hundreds to thousands of times. Telomerase is a ribonucleoprotein that adds the telomere repeat sequence to the 3' end of telomeres. Cells with impaired telomerase function often have limited capacity for self-renewal, i.e., an abnormal state or condition characterized by an inability of cells (e.g., stem cells) to divide sufficiently. This deficiency in cells can, for example, lead to various diseases and disorders.

Telomerase RNA component (TERC) serves at least two functions: (1) it encodes the template sequence used by telomerase reverse transcriptase (TERT) for the addition of hexanucleotide repeats to telomeres, and (2) it is the scaffold that nucleates multiple proteins that target telomerase to the Cajal body, where telomeres are extended.

The disclosure provides compounds and methods to modulate TERC levels, e.g., by using compounds that target TERC, or compounds that modulate the level or activity of PAP Associated Domain Containing 5 (PAPD5) and/or Poly (A) specific ribonuclease (PARN), both of which are involved in the 3'-end maturation of TERC.

Also provided are methods of diagnosing patients and methods of treating patients having various telomere diseases. Various implementations of these compounds and methods are described herein.

Definitions

As used herein, the term "about" means "approximately" (e.g., plus or minus approximately 10% of the indicated value).

The term "telomere disease," "telomere syndrome," "disorder associated with telomere dysfunction," or "disorder associated with telomerase dysfunction" refers to a disorder associated with abnormal telomeres or abnormal telomerase function. They include, but are not limited to, dyskeratosis congenita (DC), Revesz syndrome, Hoyeraal-Hreidarrson syndrome, Coats plus syndrome, and some forms of inherited aplastic anemia, myelodysplastic syndrome, aplastic anemia, pulmonary fibrosis, interstitial lung disease, emphysema, bone marrow failure, hematological disorder, hepatic disease (e.g., hepatic fibrosis, chronic liver disease, non-alcoholic steatohepatitis, and hepatic cirrhosis), among others. Telomere diseases also include those affecting the blood and immune systems, lungs, liver, skin, mucosal surfaces, bones, cardiovascular system, endocrine system, and/or gastrointestinal system, as cells with the impaired self-renewal capacity can affect the normal function of organs or systems. Some of these disorders include aplastic anemia, pulmonary fibrosis, hepatic cirrhosis, osteoporosis and osteonecrosis, vascular malformations, diabetes, primary immunodeficiency, and inflammatory bowel disease. This group of diseases is often associated with a cellular state marked with decreased self-renewal capacity that can be attributed to an alteration in telomere length. Telomere disease also includes tissue failure and organ failure. The tissue failure that relates to telomere disease can have various causes, e.g., infection, inflammation, environmental (radiation, chemical, physical insults) causes, medications and chemotherapy, among others. These various causes can all contribute to telomere deficiency.

The term "telomere deficiency" as used herein refers to a cellular state in the body, including stem cells, induced pluripotent cells and fibroblasts, and is often marked by a perturbation in expression or activity of an enzyme that is involved in regulating telomere size. As used herein, the term "telomerase dysfunction" refers to abnormal levels or function of telomerase in a cell or patient. For example, telomerase dysfunction can include telomerase deficiency, such as where telomerase levels are lower than normal due to excess or unwanted telomerase degradation, and telomerase over-activity, such as where telomerase levels are higher than normal due to deficient telomerase degradation.

The terms "subject" and "patient" are used interchangeably throughout the specification and describe an animal, human or non-human. Veterinary and non-veterinary applications are contemplated by the present invention. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

As used herein, the term "compound" as used herein is meant to include all stereoisomers, geometric isomers, tautomers, and isotopes of the structures named or depicted. Compounds herein identified by name or structure as one particular tautomeric form are intended to include other tautomeric forms unless otherwise specified.

The terms "pharmaceutical" and "pharmaceutically acceptable" are employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "preventing" or "prevention" of a disease, condition or disorder refers to decreasing the risk of occurrence of the disease, condition or disorder in a subject or group of subjects (e.g., a subject or group of subjects predisposed to or susceptible to the disease, condition or disorder). In some embodiments, preventing a disease, condition or disorder refers to decreasing the possibility of acquiring the disease, condition or disorder and/or its associated symptoms. In some embodiments, preventing a disease, condition or disorder refers to completely or almost completely stopping the disease, condition or disorder from occurring.

The terms "inhibition", "inhibiting", "inhibit," or "inhibitor" refer to the ability of a compound to reduce, slow, halt, and/or prevent activity of a particular biological process in a cell relative to vehicle. In some embodiments, "inhibit", "block", "suppress" or "prevent" means that the activity being inhibited, blocked, suppressed, or prevented is reduced by at least 5%, 10%, 15%, 20%, 25%, 30%, 35%, 40%, 45%, 50%, 55%, 60%, 65%, 70%, 75%, 80%, 85%, 90%, 95%, or 100% as compared to the activity of a control (e.g., activity in the absence of the inhibitor).

An "effective amount" refers to an amount sufficient to elicit the desired biological response, i.e., treating cancer. As will be appreciated by those of ordinary skill in this art, the effective amount of the compounds described herein can vary depending on such factors as the desired biological endpoint, the pharmacokinetics of the compound, the condition being treated, the mode of administration, and the age and health of the subject, and the guidance of the treating physician. An effective amount includes that amount necessary to slow, reduce, inhibit, ameliorate or reverse one or more symptoms associated with cancer. For example, in the treatment of cancer, such terms can refer to a reduction in the size of the tumor.

The term "Cn-m alkyl" includes straight-chain alkyl groups (e.g., methyl, ethyl, propyl, butyl, pentyl, hexyl, heptyl, octyl, nonyl, decyl, etc.) and branched-chain alkyl groups (e.g., isopropyl, tert-butyl, isobutyl, etc.). In certain embodiments, a straight chain or branched chain alkyl has twelve or fewer carbon atoms in its backbone (e.g., $C_{1-12}$ for straight chain; $C_{3-12}$ for branched chain). For example, the term $C_{1-12}$ includes alkyl groups containing 1 to 12 carbon atoms.

As used herein, the term "Cn-m alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, "Cn-m alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms. The term "$C_{n-m}$ alkenylene" refers to a divalent alkenyl linking group.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms. The term "$C_{n-m}$ alkynylene" refers to a divalent alkynyl linking group.

As used herein, the term "$C_{n-m}$ alkoxy", employed alone or in combination with other terms, refers to a group of formula-O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl) amino and N-isopropylamino), N-butylamino (e.g., N-(n-butyl)amino and N-(tert-butyl)amino), and the like.

As used herein, the term "di($C_{n-m}$-alkyl)amino" refers to a group of formula-N(alkyl)$_2$, wherein the two alkyl groups each have, independently, n to m carbon atoms. In some embodiments, each alkyl group independently has 1 to 6, 1 to 4, or 1 to 3 carbon atoms.

As used herein, the term "$C_{n-m}$ alkoxycarbonyl" refers to a group of formula —C(O)O— alkyl, wherein the alkyl group has n to m carbon atoms. In some embodiments, the alkyl group has 1 to 6, 1 to 4, or 1 to 3 carbon atoms. Examples of alkoxycarbonyl groups include, but are not limited to, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms. Examples of alkylcarbonyl groups include, but are not limited to, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkylthio" refers to a group of formula-S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O) 2-alkyl, wherein the alkyl group has n to m carbon atoms. In some embodiments, the alkyl group has 1 to 6, 1 to 4, or 1 to 3 carbon atoms.

As used herein, the term "carbamyl" to a group of formula —C(O) $NH_2$.

As used herein, the term "di($C_{n-m}$-alkyl) carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, the term "oxo" refers to an oxygen atom as a divalent substituent, forming a carbonyl group when attached to a carbon (e.g., C=O), or attached to a heteroatom forming a sulfoxide or sulfone group.

As used herein, the term "thioxo" refers to a sulfur atom as a divalent substituent, forming, e.g., a group of formula C=S when attached to a carbon atom, or forming a thiosulfoxide or thiosulfone group, when attached to a heteroatom.

As used herein, the term "thio" refers to a group of formula SH.

As used herein, the term "cyano" refers to a group of formula CN.

As used herein, the term "amino" refers to a group of formula —$NH_2$.

As used herein, the term "carboxy" or "carboxyl" refers to a —C(O)OH group.

As used herein, "halo" or "halogen" refers to F, Cl, Br, or I. In some embodiments, halo is F, Cl, or Br. In some embodiments, halo is F or Cl.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

The term "n-membered" where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the non-aromatic cyclic hydrocarbon, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, 10, 11, or 12 ring-forming atoms. In some embodiments, the cycloalkyl is a 3-12 membered monocyclic or bicyclic cycloalkyl. In some embodiments, the cycloalkyl is a $C_{3-7}$ monocyclic cycloalkyl. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cyclooctyl, cyclooctenyl, and the like. In some embodiments, cycloalkyl is cyclopropyl, cyclobutyl, cyclopentyl, cyclohexyl, cyclooctyl, or cyclooctenyl. In some embodiments, the cycloalkyl is a cyclooctenyl ring fused with 1 or 2 benzene rings. In some embodiments, the cycloalkyl is a 3-8 membered or 3-7 membered monocyclic cycloalkyl group (e.g., $C_{3-8}$ or $C_{3-7}$ cycloalkyl). In some embodiments, the cycloalkyl is a 8-12-membered bicyclic cycloalkyl. In some embodiments, the cycloalkyl is a 8-16-membered bicyclic or tricyclic cycloalkyl (e.g., $C_{8-16}$ cycloalkyl). The term "cycloalkylene" refers to a divalent cycloalkyl linking group.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 membered monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered heteroaryls are pyridyl, pyrazinyl, pyrimidinyl, triazinyl and pyridazinyl. The term "heteroarylene" refers to a divalent heteroaryl linking group.

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl and the like. In some embodiments, aryl groups have from 6 to about 20 carbon atoms, from 6 to about 15 carbon atoms, or from 6 to about 10 carbon atoms. In some embodiments, the aryl group is phenyl. The term "arylene" refers to a divalent aryl linking group.

As used herein, "heterocycloalkyl" or "aliphatic heterocycle" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido groups (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the non-aromatic heterocycle, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members. In some embodiments, the heterocycloalkyl is a 8-12-membered heterocycloalkyl (e.g., bicyclic heterocycloalkyl). In some embodiments, the heterocycloalkyl is a 8-16-membered heterocycloalkyl (e.g., bicyclic or tricyclic heterocycloalkyl). In some embodiments, the 8-12 membered bicyclic heterocycloalkyl is a 8-12 membered fused heterocycloalkylaryl group or a 8-12 membered fused heterocycloalkylheteroaryl group. In some embodiments, the heterocycloalkyl is a 9-12 membered bicyclic heterocycloalkyl. In some embodiments, the 9-10 membered bicyclic heterocycloalkyl is a 9-10 membered fused heterocycloalkylaryl group or a 9-10 membered fused heterocycloalkylheteroaryl group. The term "heterocycloalkylene" refers to a divalent heterocycloalkyl linking group.

The term "aromatic" refers to a carbocycle or heterocycle having one or more polyunsaturated rings having aromatic character (i.e., having (4n+2) delocalized π (pi) electrons where n is an integer).

The term "aliphatic" refers to organic compounds (I-Including polymers) in which carbon atoms and heteroatoms form open chains and which do not contain polyunsaturated rings having aromatic character. Aliphatic compounds may be linear or cyclic, saturated or unsaturated, straight chain or branched.

Therapeutic Compounds

Figure 9:
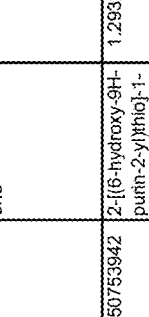
FIG. 9 shows 308 compounds that can inhibit PAPD5 activity.

The present disclosure provides PAPD5 inhibitors and the derivatives thereof. Exemplary PAPD5 inhibitors are shown in FIGS. 9-11. These PAPD5 inhibitors and their derivatives can be used in various methods as described herein (e.g., treating a disorder associated with telomerase dysfunction, or treating a disorder associated with aging).

FIG. 9 includes 308 compounds that can inhibit PAPD5. FIG. 9 lists the chemical structure for each compound. It also lists various other identifiers for the compound, e.g., Vendor Reagent ID, SMILES (simplified molecular-input line-entry system), InChi (I-IUPAC International Chemical Identifier), and PubChem_CID (PubChem Compound Identifier or CID). These identifiers can also be used to determine the chemical structure for the compound.

In FIG. 9, the compounds are organized by the structure similarity. Compounds with similar chemical structures are placed in the same cluster. These 308 compounds are placed in a total of 31 clusters. Among these clusters, there are 73 compounds in Cluster 5. In fact, member molecules in Cluster 5 provide the highest inhibition rate in the screening assay. Five other clusters also have a large number of compounds. These clusters (I-Including Cluster 5) are shown in FIG. 10.

Among these 308 compounds, 72 compounds have higher inhibition rates. These compounds are shown in FIG. 11. Particularly, 1-(1,3-benzodioxol-5-ylmethyl)-5-oxopyrrolidine-3-carboxylic acid (PubChem Compound Identifier (or PubChem_CID; CID): 2742111) has a fold change of 3.9 at 100 μM concentration, and N-allyl-5-oxo-1-thioxo-4,5-dihydro[1,3]dioxolo[4,5-g][1,3]thiazolo[3,4-a]quinazoline-3-carboxamide (CID: 50761931) has a fold change of 3.1 at 100 μM concentration in the assay. Included within the present disclosure are each of the compounds described in FIGS. 9, 10, and 11, and compositions (e.g., pharmaceutical compositions) comprising such compounds. Skilled practitioners will appreciate that derivatives of such compounds and compositions comprising them are also within the present invention.

In a general aspect, the present disclosure provides compound of Formula (I-I):

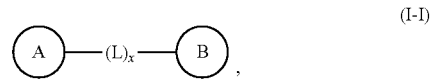

(I-I)

or a pharmaceutically acceptable salt thereof.

In some embodiments:
ring A is selected from C$_{3-10}$ cycloalkyl, 6-10 membered aryl, 5-12 membered heteroaryl, and 4-12 membered heterocycloalkyl, each of which is optionally substituted by 1-10 independently selected R$^1$ groups;

ring B is selected from C$_{3-10}$ cycloalkyl, 6-10 membered aryl, 5-12 membered heteroaryl, and 4-12 membered heterocycloalkyl, each of which is optionally substituted by 1-10 independently selected R$^2$ groups;

each L is independently selected from O, S, C(=O), S(=O), S(=O)$_2$, N(R$^3$), C$_{1-6}$ alkylene, C$_{2-6}$ alkenylene, C$_{2-6}$ alkynylene, C$_{3-10}$ cycloalkylene, C$_{6-10}$ arylene, 5-14 membered heteroarylene, and 4-12 membered heterocycloalkylene, wherein said C$_{1-6}$ alkylene, C$_{2-6}$ alkenylene, C$_{2-6}$ alkynylene, C$_{3-10}$ cycloalkylene, C$_{6-10}$ arylene, 5-14 membered heteroarylene, and 4-12 membered heterocycloalkylene are each optionally substituted with 1, 2, 3, 4, or 5 substituents independently selected from R$^4$;

x is an integer from 0 to 10, wherein when x is 0 then L is a bond between ring A and ring B;

each $R^1$ is independently selected from $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, thioxo and oxo; wherein said $C_{1-6}$ alkyl, $C_{2-6}$ alkenyl, and $C_{2-6}$ alkynyl substituents of $R^1$ are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{c1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$;

each $R^2$ is independently selected from H, $C_{1-6}$ alkyl, $C_{2-6}$ alkenyl, $C_{2-6}$ alkynyl, $C_{1-6}$ haloalkyl, $Cy^2$, halo, CN, $NO_2$, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})N^{c2}R^{d2}$, $NR^{c2}C(=NR^{e2})N^{c2}R^{d2}$, $N^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, thioxo and oxo; wherein said $C_{1-6}$ alkyl, $C_{2-6}$ alkenyl, and $C_{2-6}$ alkynyl substituents of $R^1$ are each optionally substituted with 1, 2, 3, 4, or 5 substituents independently selected from $Cy^2$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$ and $S(O)_2NR^{c2}R^{d2}$;

or $R^1$ together with the atom of ring A to which it is attached, $R^2$ together with the atom of ring B to which it is attached, and moiety $(L)_x$ together form a ring selected from: $C_{3-10}$ cycloalkyl, 6-10 membered aryl, 5-10 membered heteroaryl, and 4-12 membered heterocycloalkyl group, each of which is optionally substituted with 1, 2, 3, 4, or 5 substituents independently selected from $R^4$;

each $R^3$ is independently selected from H, $C_{1-6}$ alkyl, $C_{2-6}$ alkenyl, $C_{2-6}$ alkynyl, $C_{1-6}$ haloalkyl, $Cy^3$, $C(O)R^{b3}$, $C(O)NR^{c3}R^{d3}$, $C(O)OR^{a3}$, $C(=NR^{e3})NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, and $C_{2-6}$ alkynyl of $R^3$ are each optionally substituted with 1, 2, 3, 4, or 5 substituents independently selected from $Cy^3$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$;

each $R^4$ is independently selected from $C_{1-6}$ alkyl, $C_{1-6}$ haloalkyl, $C_{2-6}$ alkenyl, $C_{2-6}$ alkynyl, $Cy^3$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$; wherein said $C_{1-6}$ alkyl, $C_{2-6}$ alkenyl, and $C_{2-6}$ alkynyl of $R^4$ are each optionally substituted with 1, 2, 3, 4, or 5 substituents independently selected from $Cy^3$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$ $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$;

each $Cy^1$, $Cy^2$, and $Cy^3$ are independently selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy}$;

each $R^{Cy}$ is independently selected from halo, $C_{1-4}$ alkyl, $C_{1-4}$ haloalkyl, $C_{2-6}$ alkenyl, $C_{2-6}$ alkynyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, and (4-7 membered heterocycloalkyl)-$C_{1-4}$ alkylene-, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-4}$ alkyl, $C_{2-6}$ alkenyl, $C_{2-6}$ alkynyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, and (4-7 membered heterocycloalkyl)-$C_{1-4}$ alkylene- are each optionally substituted by 1, 2, 3, 4, or 5 substituents independently selected from $C_{1-6}$ alkyl, $C_{1-4}$ haloalkyl, $C_{1-6}$ cyanoalkyl, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^{a1}$, $R^{b1}$, $R^{a2}$, $R^{b2}$, $R^{a3}$, $R^{b3}$, $R^{a4}$, and $R^{b4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are optionally substituted with 1, 2, 3, 4, or 5 substituents independently selected from $R^g$;

each $R^{c1}$, $R^{d1}$, $R^{c2}$, $R^{d2}$, $R^{c3}$, $R^{d3}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, $C(O)R^{b5}$, $C(O)NR^{c5}R^{d5}$, $C(O)OR^{a5}$, $NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, 3, 4, or 5 substituents independently selected from $R^g$;

each $R^{a5}$, $R^{b5}$, $R^{c5}$, and $R^{d5}$ is in dependently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene and $R^g$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, 3, 4, or 5 substituents independently selected from $R^g$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $R^g$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $R^g$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $R^g$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $R^g$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $R^g$;

each $R^{e1}$, $R^{e2}$, $R^{e3}$, and $R^{e4}$ is independently selected from H, $C_{1-4}$ alkyl, $C_{1-4}$ alkoxy, OH, and CN;

each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, ring A is a $C_{3-10}$ cycloalkyl (e.g., cyclopropyl, cyclobutyl, cyclopentyl, or cyclohexyl), which is optionally substituted with 1-10 independently selected $R^1$ groups (e.g., 1, 2, 3, 4, or 5 independently selected $R^1$ groups).

In some embodiments, ring A is 6-10 membered aryl (e.g., phenyl or naphthyl), which is optionally substituted with 1-10 independently selected $R^1$ groups (e.g., 1, 2, 3, 4, or 5 independently selected $R^1$ groups).

In some embodiments, ring A is 5-12 membered heteroaryl, which is optionally substituted with 1-10 independently selected $R^1$ groups (e.g., 1, 2, 3, 4, or 5 independently selected $R^1$ groups). In some aspects of these embodiments, ring A is a five-membered heteroaryl ring. Suitable examples of such rings include thienyl, furanyl, pyrrolyl, imidazolyl, thiazolyl, oxazolyl, isoxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. In other aspects of these embodiments, ring A is six-membered heteroaryl ring. Suitable examples of such rings include pyridyl, pyrazinyl, pyrimidinyl, triazinyl and pyridazinyl. In yet other aspects of these embodiments, ring A is a fused 9-11-membered heteroaryl ring. Suitable examples of such rings include quinolinyl, isoquinolinyl, indolyl or isoindolyl, benzazepinyl, thienothiophenyl, purinyl, pyrazolopyrimidinyl, pyrazolopyridinyl, imidazolopyrimidinyl, imidazolopyridinyl, benzothiadiazinyl, and thienodihydropyridinyl. In some embodiments, each of the aforementioned heteroaryl rings is optionally substituted with 1-5 (e.g., 1, 2, or 3) independently selected $R^1$ groups.

In some embodiments, ring A is 4-12 membered heterocycloalkyl, which is optionally substituted with 1-10 (e.g., 1, 2, 3, 4, or 5) independently selected $R^1$ groups. In some aspects of these embodiments, ring A is a 4-membered heterocycloalkyl ring. Suitable examples of such rings include azetidinyl, diazetidinyl, oxetanyl, dioxetanyl, thietanyl, and dithietanyl. In other aspects of these embodiments, ring A is a 5-membered heterocycloalkyl ring. Suitable examples of such rings include tetrahydrofuranyl, tetrahydrothiophenyl, pyrrolidinyl, dihydroimidazolyl, imidazolidinyl, pyrazolidinyl, oxazolidinyl, oxazolidinyl, isoxazolidinyl, dihydrothiazol, thiazolidinyl, isothiazolidinyl, dioxolanyl, and dithiolanyl. In yet other aspects of these embodiments, ring A is a 6-membered heterocycloalkyl ring. Suitable examples of such rings include piperidinyl, tetrahydropyranyl, thienyl, piperazinyl, morpholinyl, thiomorpholinyl, dioxanyl, dithianyl, and dihydrothiadiazinyl. In yet other aspects of these embodiments, ring A is a 9-10-membered benzo- or heteroaryl-fused heterocycloalkyl ring. Suitable examples of such rings include benzodioxolyl, dihydrobenzodiozinyl, isochromanyl, tetrahydroisoquinolinyl, tetrahydroquinazolinyl, dihydrobenzofuranyl, dihydrobenzothienyl, indolinyl, isoindolinyl, tetrahydropyrrolopyridinyl, tetrahydrofuropyridinyl, and benzothiadiazinyl. In some embodiments, each of the aforementioned heterocycloalkyl rings of ring A is optionally substituted with 1-5 (e.g., 1, 2, or 3) independently selected $R^1$ groups.

In some embodiments, ring A is selected from $C_{3-10}$ cycloalkyl, 6-10 membered aryl, 5-12 membered heteroaryl, or 4-12 membered heterocycloalkyl, each of which is optionally substituted by 1, 2, 3, 4, or 5 independently selected $R^1$ groups.

In some embodiments, ring A is selected from 6-10 membered aryl, 5-12 membered heteroaryl, or 4-12 membered heterocycloalkyl, each of which is optionally substituted by 1, 2, 3, 4, or 5 independently selected $R^1$ groups.

In some embodiments, ring A is selected from 5-12 membered heteroaryl and 4-12 membered heterocycloalkyl, each of which is optionally substituted by 1, 2, 3, 4, or 5 independently selected $R^1$ groups.

In some embodiments, ring A is a moiety of formula (A-9):

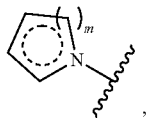
(A-9)

wherein ◯ represents that the ring is saturated, partially unsaturated, or aromatic; m is an integer from 0 to 5, the and moiety of formula (A-9) is optionally substituted with 1-10 independently selected $R^1$ groups (e.g., 1, 2, 3, 4, 5, 6, 7, 8, 9, or 10 independently selected $R^1$ groups).

In some embodiments, m is an integer from 1 to 4 (e.g., 1, 2, 3, or 4).

In some embodiments, the moiety of formula (A-9) has formula (A-8)

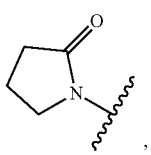
(A-8)

wherein the moiety of formula (A-8) is optionally substituted with 1-6 (1, 2, 3, 4, 5 or 6) independently selected $R^1$ groups.

In some embodiments, ring A is a moiety selected from (A-1) to (A-7):

(A-1)

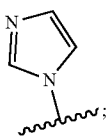
(A-2)

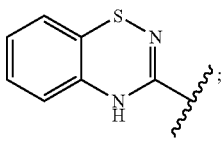
(A-3)

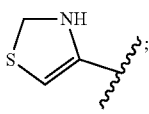
(A-4)

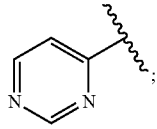
(A-5)

-continued

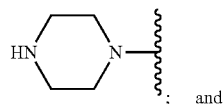
(A-6)

and

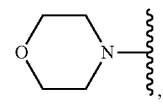
(A-7)

wherein each of the moieties (A-1) to (A-7) is optionally substituted with 1-8 (e.g., 1, 2, 3, 4, or 5) substituents independently selected from $R^1$.

In some embodiments, ring B is selected from $C_{3-10}$ cycloalkyl (e.g., cyclopropyl, cyclobutyl, cyclopentyl, or cyclohexyl), 6-10 membered aryl (e.g., phenyl or naphthyl), 5-12 membered heteroaryl (e.g., thienyl, furanyl, pyrrolyl, imidazolyl, thiazolyl, oxazolyl, isoxazolyl, pyrazolyl, pyridyl, pyrazinyl, pyrimidinyl, triazinyl, or pyridazinyl), and 4-12 membered heterocycloalkyl, each of which is optionally substituted by 1-10 (e.g., 1, 2, 3, 4, or 5) independently selected $R^2$ groups.

In some embodiments, ring B is 4-12 membered heterocycloalkyl, which is optionally substituted by 1-10 (e.g., 1, 2, or 3) independently selected $R^2$ groups. Suitable examples of heterocycloalkyl groups of ring B include: pyrrolidinyl, isoxazolidinyl, tetrahydropyranyl, oxetanyl, azetidinyl, morpholinyl, thiomorpholinyl, piperazinyl, dioxolanyl, tetrahydrofuranyl, dioxanyl, tetrahydrothienyl, piperidinyl, pyrrolidinyl, isothiazolidinyl, pyrazolidinyl, oxazolidinyl, thiazolidinyl, imidazolidinyl, and azepanyl. In some embodiments, ring B is a 9-11-membered benzo- or heteroaryl-fused heterocycloalkyl ring. Suitable examples of such rings include benzodioxolyl, tetrahydrobenzoazepinyl, tetrahydrobenzodiazepinyl, dihydrobenzodiozinyl, isochromanyl, tetrahydroisoquinolinyl, tetrahydroquinazolinyl, dihydrobenzofuranyl, dihydrobenzothienyl, indolinyl, isoindolinyl, tetrahydropyrrolopyridinyl, tetrahydrofuropyridinyl, dihydrothienopyridinyl and benzothiadiazinyl. In some embodiments, each of the aforementioned heterocycloalkyl rings of ring B is optionally substituted with 1-5 (e.g., 1, 2, or 3) independently selected $R^2$ groups.

In some embodiments, ring B is 5-12 membered heteroaryl, optionally substituted by 1, 2, 3, 4, or 5 independently selected $R^2$ groups.

In some embodiments, ring B is 6-10 membered aryl, optionally substituted by 1, 2, 3, 4, or 5 independently selected $R^2$ groups.

In some embodiments, ring B is selected from 6-10 membered aryl, 5-12 membered heteroaryl, and 4-12 membered heterocycloalkyl, each of which is optionally substituted by 1, 2, 3, 4, or 5 independently selected $R^2$ groups.

In some embodiments, ring B is selected from 6-10 membered aryl and 5-12 membered heteroaryl, each of which is optionally substituted by 1, 2, 3, 4, or 5 independently selected $R^2$ groups.

In some embodiments, ring B is selected from 5-12 membered heteroaryl and 4-12 membered heterocycloalkyl, each of which is optionally substituted by 1, 2, 3, 4, or 5 independently selected $R^2$ groups.

In some embodiments, ring B is a moiety of formula (B-6):

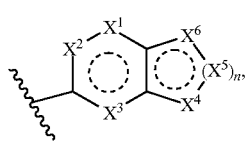

(B-6)

wherein ◯ represents that the ring is saturated, partially unsaturated, or aromatic; n is an integer from 0 to 4 (wherein when n is 0, $X^5$ is a bond between $X^4$ and $X^6$), and $X^1$, $X^2$, $X^3$, $X^4$, $X^5$, and $X^6$ are each independently selected from $C(R^2)_{1-2}$, O, S, and $N(R^2)_{0-1}$.

In some embodiments, the moiety of formula (B-6) has formula (B-5):

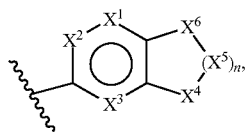

(B-5)

wherein ⃝ represents that the ring is aromatic.

In some embodiments, n is an integer from 1 to 4 (e.g., 1, 2, 3, or 4).

In some embodiments, $X^1$, $X^2$, $X^3$, and $X^5$ are each independently selected from $C(R^2)_{1-2}$ and $N(R^2)_{0-1}$. In some embodiments, $X^4$ and $X^6$ are each independently selected from O and S.

In some embodiments, the ring containing $X^1$, $X^2$, and $X^3$ is not aromatic, and (1) $X^1$ is $C(R^2)_2$, $X^2$ is $N(R^2)$, and $X^3$ is N; or (2) $X^1$ is $C(R^2)_2$, $X^2$ is $N(R^2)$, and $X^3$ is $N(R^2)$; or (3) $X^1$ is $C(R^2)_2$, $X^2$ is $C(R^2)_2$, and $X^3$ is $C(R^2)_2$; or (4) $X^1$ is $C(R^2)$, $X^2$ is N. and $X^3$ is $C(R^2)_2$; or (5) $X^1$ is $C(R^2)$, $X^2$ is $C(R^2)$, and $X^3$ is $N(R^2)$.

In some embodiments, the ring containing $X^1$, $X^2$, and $X^3$ is aromatic, and (1) $X^1$ is $C(R^2)$, $X^2$ is N. and $X^3$ is N; or (2) $X^1$ is $C(R^2)$, $X^2$ is $C(R^2)$, and $X^3$ is N; or (3) $X^1$ is $C(R^2)$, $X^2$ is N, and $X^3$ is $C(R^2)$; or (4) $X^1$ is N, $X^2$ is $C(R^2)$, and $X^3$ is $C(R^2)$; or (5) $X^1$ is $C(R^2)$, $X^2$ is $C(R^2)$, and $X^3$ is $C(R^2)$.

In some embodiments, n is 1, the ring containing $X^4$, $X^5$, and $X^6$ is aromatic, and (1) $X^4$ is O, $X^6$ is $C(R^2)$, and $X^5$ is $C(R^2)$; or (2) $X^4$ is S, $X^6$ is $C(R^2)$, and $X^5$ is $C(R^2)$; or (3) $X^4$ is S, $X^6$ is N, and $X^5$ is $C(R^2)$; or (4) $X^4$ is O, $X^6$ is N, and $X^5$ is $C(R^2)$; or (5) $X^4$ is $C(R^2)$, $X^6$ is N, and $X^5$ is N.

In some embodiments, n is 2, the ring containing $X^4$, $X^5$, and $X^6$ is aromatic, and (1) $X^4$ is O, $X^6$ is $C(R^2)$, and each $X^5$ is $C(R^2)$; or (2) $X^4$ is S, $X^6$ is $C(R^2)$, and each $X^5$ is $C(R^2)$; or (3) $X^4$ is S, $X^6$ is N, and each $X^5$ is $C(R^2)$; or (4) $X^4$ is O, $X^6$ is N, and each $X^5$ is $C(R^2)$; or (5) $X^4$ is $C(R^2)$, $X^6$ is $C(R^2)$, and each $X^5$ is N.

In some embodiments, n is 1, the ring containing $X^4$, $X^5$, and $X^6$ is not aromatic, and (1) $X^4$ is O, $X^6$ is $C(R^2)$, and $X^5$ is $C(R^2)$; or (2) $X^4$ is S, $X^6$ is $C(R^2)_2$, and $X^5$ is $C(R^2)_2$; or (3) $X^4$ is O, $X^6$ is O, and $X^5$ is $C(R^2)_2$; or (4) $X^4$ is O, $X^6$ is $N(R^2)$, and $X^5$ is $C(R^2)_2$; or (5) $X^4$ is O, $X^6$ is S and $X^5$ is $C(R^2)_2$.

In some embodiments, n is 2, the ring containing $X^4$, $X^5$, and $X^6$ is not aromatic, and (1) $X^4$ is O, $X^6$ is $C(R^2)$, and each $X^3$ is $C(R^2)$; or (2) $X^4$ is S, $X^6$ is $C(R^2)_2$, and each $X^5$ is $C(R^2)_2$; or (3) $X^4$ is O, $X^6$ is O, and each $X^5$ is $C(R^2)_2$; or (4) $X^4$ is O, $X^6$ is $N(R^2)$, and each $X^5$ is $C(R^2)_2$; or (5) $X^4$ is O, $X^6$ is S and each $X^5$ is $C(R^2)_2$.

In some embodiments, ring B is a moiety of any one of formulae (B-4a)-(B-4e):

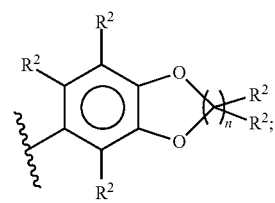

(B-4a)

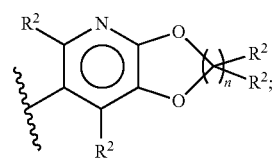

(B-4b)

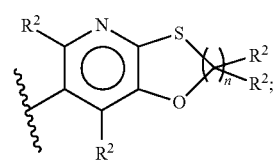

(B-4c)

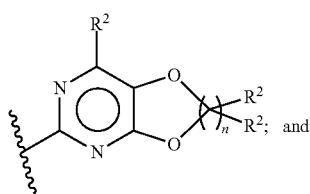

(B-4d)

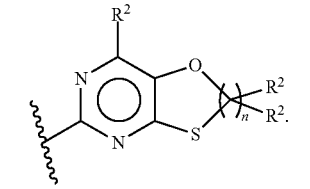

(B-4e)

In some embodiments, ring B is a moiety selected from (B-1) to (B-3):

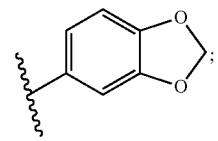

(B-1)

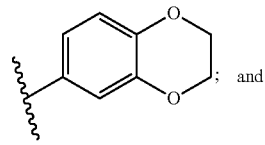

(B-2)

; and

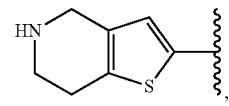

(B-3)

, wherein each of the moieties (B-1) to (B-3) is optionally substituted with 1, 2, 3, 4, 5, 6, or 7 substituents independently selected from R².

In some embodiments, ring A is selected from C$_{3-10}$ cycloalkyl, 6-10 membered aryl, 5-12 membered heteroaryl, or 4-12 membered heterocycloalkyl, each of which is optionally substituted by 1, 2, 3, 4, or 5 independently selected R¹ groups; and ring B is selected from C$_{3-10}$ cycloalkyl, 6-10 membered aryl, 5-12 membered heteroaryl, and 4-12 membered heterocycloalkyl, each of which is optionally substituted by 1-10 (e.g., 1, 2, 3, 4, or 5) independently selected R² groups.

In some embodiments, ring A is selected from 6-10 membered aryl, 5-12 membered heteroaryl, and 4-12 membered heterocycloalkyl, each of which is optionally substituted by 1, 2, 3, 4, or 5 independently selected R¹ groups; and ring B is selected from 6-10 membered aryl, 5-12 membered heteroaryl, and 4-12 membered heterocycloalkyl, each of which is optionally substituted by 1, 2, 3, 4, or 5 independently selected R² groups.

In some embodiments, ring A is selected from 5-12 membered heteroaryl and 4-12 membered heterocycloalkyl, each of which is optionally substituted by 1, 2, 3, 4, or 5 independently selected R¹ groups; and ring B is selected from 5-12 membered heteroaryl and 4-12 membered heterocycloalkyl, each of which is optionally substituted by 1, 2, 3, 4, or 5 independently selected R² groups.

In some embodiments, ring A is a 4-membered heterocycloalkyl ring optionally substituted with 1-5 independently selected R¹ groups; and ring B is 4-12 membered heterocycloalkyl (e.g., 9-11-membered benzo- or heteroaryl-fused heterocycloalkyl) optionally substituted with 1-5 independently selected R² groups.

In some embodiments, ring A is a 5-membered heterocycloalkyl ring optionally substituted with 1-5 independently selected R¹ groups; and ring B is 4-12 membered heterocycloalkyl (e.g., 9-11-membered benzo- or heteroaryl-fused heterocycloalkyl) optionally substituted with 1-5 independently selected R² groups.

In some embodiments, ring A is 6-membered heterocycloalkyl ring optionally substituted with 1-5 independently selected R¹ groups; and ring B is 4-12 membered heterocycloalkyl (e.g., 9-11-membered benzo- or heteroaryl-fused heterocycloalkyl) optionally substituted with 1-5 independently selected R² groups.

In some embodiments, ring A is 9-10-membered benzo- or heteroaryl-fused heterocycloalkyl ring optionally substituted with 1-5 independently selected R¹ groups; and ring B is 4-12 membered heterocycloalkyl (e.g., 9-11-membered benzo- or heteroaryl-fused heterocycloalkyl) optionally substituted with 1-5 independently selected R² groups.

In some embodiments, ring A is any one of moieties (A-1)-(A-7) and ring B is a moiety (B-4a). In some embodiments, ring A is a moiety of formula (A-8), and ring B is any one of moieties of formula (B1)-(B-3). In some embodiments, ring A is any one of moieties (A-1)-(A-7) and ring B is any one of moieties of formula (B1)-(B-3). In some embodiments, ring A is any one of moieties (A-1)-(A-7) and ring B is any one of moieties of formula (B-4a)-(B-4e).

In some embodiments, the compound of Formula (I-I) has Formula (I-IIa):

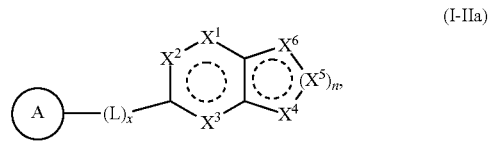

(I-IIa)

or a pharmaceutically acceptable salt thereof, wherein ◯, ring A, L, x, n, and X¹-X⁶ are as described herein.

In some embodiments, the compound of Formula (I-I) has Formula (I-IIb):

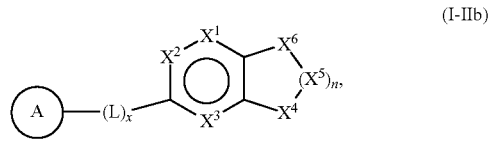

(I-IIb)

or a pharmaceutically acceptable salt thereof, wherein ⋯, ring A, L, x, n, and X¹-X⁶ are as described herein.

In some embodiments, the compound of Formula (I-I) has Formula (I-IIc):

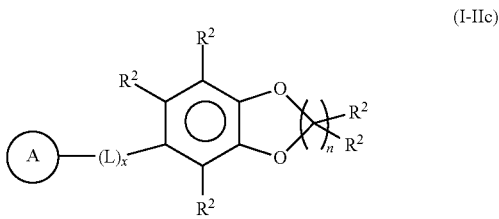

(I-IIc)

or a pharmaceutically acceptable salt thereof, wherein ⋯, ring A, L, x, n, and R² are as described herein.

In some embodiments, the compound of Formula (I-I) has Formula (I-IIIa):

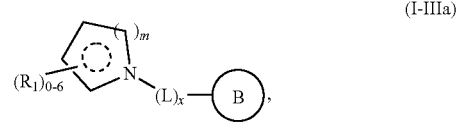

(I-IIIa)

or a pharmaceutically acceptable salt thereof, wherein ◯, ring B, L, x, m, and R¹ are as described herein.

In some embodiments, the compound of Formula (I-I) has Formula (I-IIIb):

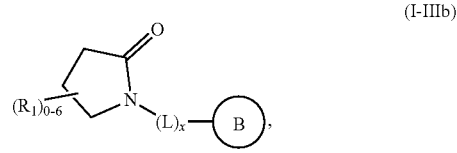

(I-IIIb)

or a pharmaceutically acceptable salt thereof, wherein ring B, L, x, and R¹ are as described herein.

In some embodiments, the compound of Formula (I-I) has Formula (I-IVa):

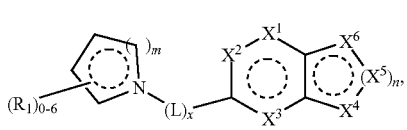

(I-IVa)

or a pharmaceutically acceptable salt thereof, wherein ◯, L, x, n, m, $R^1$, and $X^1$-$X^6$ are as described herein.

In some embodiments, the compound of Formula (I-I) has Formula (I-IVb):

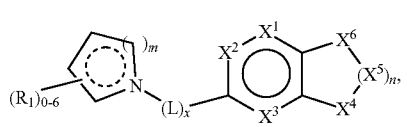

(I-IVb)

or a pharmaceutically acceptable salt thereof, wherein ◌, ◯, L, x, n, m, $R^1$, and $X^1$-$X^6$ are as described herein.

In some embodiments, the compound of Formula (I-I) has Formula (I-IVc):

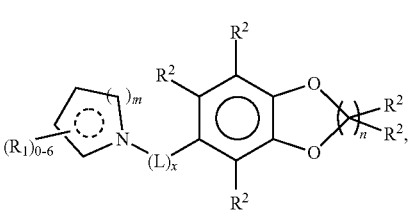

(I-IVc)

or a pharmaceutically acceptable salt thereof, wherein ◌, ◯, L, x, n, m, $R^1$, and $R^2$ are as described herein.

In some embodiments, the compound of Formula (I-I) has Formula (I-Va):

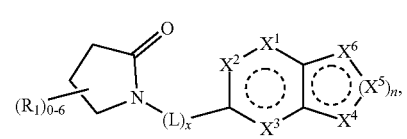

(I-Va)

or a pharmaceutically acceptable salt thereof, wherein ◯, L, x, n, $R^1$, and $X^1$-$X^6$ are as described herein.

In some embodiments, the compound of Formula (I-I) has Formula (I-Vb):

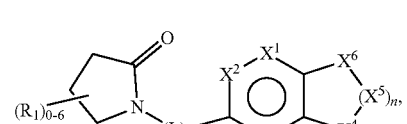

(I-Vb)

or a pharmaceutically acceptable salt thereof, wherein ◌, L, x, n, $R^1$, and $X^1$-$X^6$ are as described herein.

In some embodiments, the compound of Formula (I-I) has Formula (I-Vc):

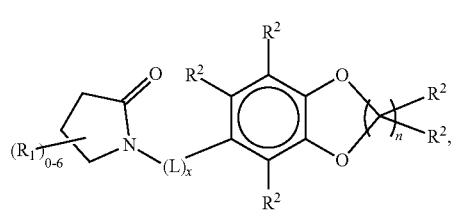

(I-Vc)

or a pharmaceutically acceptable salt thereof, wherein ◌, L, x, n, $R^1$, and $R^2$ are as described herein.

In some embodiments, x is 1. In other embodiments, x is 2. In yet other embodiments, x is 3. In yet further embodiments, x is 4.

In some embodiments, each L is independently selected from O, C(=O), S(=O)$_2$, N($R^3$), $C_{1-6}$ alkylene, $C_{3-10}$ cycloalkylene, $C_{6-10}$ arylene, 5-14 membered heteroarylene, and 4-10 membered heterocycloalkylene, wherein said $C_{1-6}$ alkylene, $C_{3-10}$ cycloalkylene, $C_{6-10}$ arylene, 5-14 membered heteroarylene, and 4-10 membered heterocycloalkylene are each optionally substituted with 1-10 (e.g., 1, 2, or 3) substituents independently selected from $R^4$.

In some embodiments, each L is independently selected from O, C(=O), N($R^3$), $C_{1-6}$ alkylene, 4-10 membered heterocycloalkylene, and 5-14 membered heteroarylene, wherein said $C_{1-6}$ alkylene, 4-10 membered heterocycloalkylene, and 5-14 membered heteroarylene are each optionally substituted with 1-10 (e.g., 1, 2, or 3) substituents independently selected from $R^4$.

In some embodiments, each L is independently selected from C(=O), N($R^3$), $C_{1-6}$ alkylene, 4-10 membered heterocycloalkylene, and 5-14 membered heteroarylene, wherein said $C_{1-6}$ alkylene, 4-10 membered heterocycloalkylene, and 5-14 membered heteroarylene are each optionally substituted with 1-10 (e.g., 1, 2, or 3) substituents independently selected from $R^4$.

In some embodiments, x is 4, 5, 6, 7, 8, 9, or 10, and each L is independently selected from O, $C_{1-6}$ alkylene, wherein said $C_{1-6}$ alkylene is optionally substituted with 1, 2, or 3 substituents independently selected from $R^4$.

In some embodiments, x is 4, and each L is independently selected from C(=O), N($R^3$), and $C_{1-6}$ alkylene, wherein said $C_{1-6}$ alkylene is optionally substituted with 1, 2, or 3 substituents independently selected from $R^4$.

In some embodiments, x is 4, and each L is independently selected from O, C(=O), N($R^3$), and $C_{1-6}$ alkylene, wherein said $C_{1-6}$ alkylene is optionally substituted with 1, 2, or 3 substituents independently selected from $R^4$.

In some embodiments, x is 4, and each L is independently selected from O, C(=O), N($R^3$), and 5-14 membered heteroarylene, wherein said 5-14 membered heteroarylene is optionally substituted with 1, 2, or 3 substituents independently selected from $R^4$.

In some embodiments, x is 3, and each L is independently selected from C(=O), N($R^3$), and $C_{1-6}$ alkylene, wherein said $C_{1-6}$ alkylene is optionally substituted with 1, 2, or 3 substituents independently selected from $R^4$.

In some embodiments, x is 3, and each L is independently selected from C(=O), N($R^3$), and 4-10 membered heterocycloalkylene, wherein said 4-10 membered heterocycloalkylene is optionally substituted with 1, 2, or 3 substituents independently selected from $R^4$.

In some embodiments, x is 3, and each L is independently selected from S(=O)$_2$, N($R^3$), $C_{1-6}$ alkylene, wherein said $C_{1-6}$ alkylene is optionally substituted with 1, 2, or 3 substituents independently selected from $R^4$.

In some embodiments, x is 3, and each L is independently selected from O, C(=O), $C_{1-6}$ alkylene, wherein said $C_{1-6}$ alkylene is optionally substituted with 1, 2, or 3 substituents independently selected from $R^4$.

In some embodiments, x is 3, and each L is independently selected from O, C(=O), $C_{3-10}$ cycloalkylene, wherein said $C_{3-10}$ cycloalkylene is optionally substituted with 1, 2, or 3 substituents independently selected from $R^4$.

In some embodiments, x is 3, and each L is independently selected from S(=O)$_2$, N(R$^3$), $C_{3-10}$ cycloalkylene, wherein said $C_{3-10}$ cycloalkylene is optionally substituted with 1, 2, or 3 substituents independently selected from $R^4$.

In some embodiments, x is 3, and each L is independently selected from C(=O), N(R$^3$), $C_{6-10}$ arylene, wherein said $C_{6-10}$ arylene is optionally substituted with 1, 2, or 3 substituents independently selected from $R^4$.

In some embodiments, x is 3, and each L is independently selected from O, N(R$^3$), $C_{1-6}$ alkylene, wherein said $C_{1-6}$ alkylene is optionally substituted with 1, 2, or 3 substituents independently selected from $R^4$.

In some embodiments, x is 3, and each L is independently selected from O, $C_{1-6}$ alkylene, wherein said $C_{1-6}$ alkylene is optionally substituted with 1, 2, or 3 substituents independently selected from $R^4$.

In some embodiments, x is 3, and each L is independently selected from $C_{1-6}$ alkylene, 5-14 membered heteroarylene and 4-12 membered heterocycloalkylene, each of which is optionally substituted with 1, 2, or 3 substituents independently selected from $R^4$.

In some embodiments, x is 2, and each L is independently selected from O, $C_{1-6}$ alkylene, wherein said $C_{1-6}$ alkylene is optionally substituted with 1, 2, or 3 substituents independently selected from $R^4$.

In some embodiments, x is 2, and each L is independently selected from N(R$^3$), $C_{1-6}$ alkylene, wherein said $C_{1-6}$ alkylene is optionally substituted with 1, 2, or 3 substituents independently selected from $R^4$.

In some embodiments, x is 2, and each L is independently selected from C(=O), N(R$^3$), $C_{1-6}$ alkylene, and 5-14 membered heteroarylene, wherein said $C_{1-6}$ alkylene and 5-14 membered heteroarylene are each optionally substituted with 1, 2, or 3 substituents independently selected from $R^4$.

In some embodiments, x is 2, and each L is independently selected from C(=O) and N(R$^3$).

In some embodiments, x is 2, and each L is independently selected from $C_{1-6}$ alkylene and 5-14 membered heteroarylene, each of which is optionally substituted with 1, 2, or 3 substituents independently selected from $R^4$.

In some embodiments, x is 2, and each L is independently selected from $C_{1-6}$ alkylene and 4-12 membered heterocycloalkylene, each of which is optionally substituted with 1, 2, or 3 substituents independently selected from $R^4$.

In some embodiments, x is 2, and each L is independently selected from 5-14 membered heteroarylene and 4-12 membered heterocycloalkylene, each of which is optionally substituted with 1, 2, or 3 substituents independently selected from $R^4$.

In some embodiments, x is 1, and L is 5-14 membered heteroarylene, which is optionally substituted with 1, 2, or 3 substituents independently selected from $R^4$.

In some embodiments, x is 1, and L is $C_{1-6}$ alkylene, which is optionally substituted with 1, 2, or 3 substituents independently selected from $R^4$.

In some embodiments, x is 1, and L is O or S.

In some embodiments, x is 1, and 4-12 membered heterocycloalkylene, which is optionally substituted with 1, 2, or 3 substituents independently selected from $R^4$.

In some embodiments, $R^3$ is selected from H, $C_{1-6}$ alkyl, $C_{2-6}$ alkenyl, $C_{2-6}$ alkynyl, $C_{1-6}$ haloalkyl, $Cy^3$, $C(O)R^{b3}$, $C(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, and $C_{2-6}$ alkynyl of $R^3$ are each optionally substituted with 1, 2, 3, 4, or 5 substituents independently selected from $Cy^3$, halo, CN, NO$_2$, OR$^{a3}$, C(O)R$^{b3}$, C(O)NR$^{c3}$R$^{d3}$, C(O)OR$^{a3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)$_2$R$^{b3}$, NR$^{c3}$S(O)$_2$NR$^{c3}$R$^{d3}$, S(O)$_2$R$^{b3}$ and S(O)$_2$NR$^{c3}$R$^{d3}$.

In some embodiments, $R^3$ is selected from H, $C_{1-6}$ alkyl, $C_{2-6}$ alkenyl, $C_{1-6}$ haloalkyl, $Cy^3$, C(O)R$^{b3}$, C(O)NR$^{c3}$R$^{d3}$, S(O)$_2$R$^{b3}$, and S(O)$_2$NR$^{c3}$R$^{d3}$; wherein said $C_{1-6}$ alkyl, $C_{2-6}$ alkenyl, and $C_{2-6}$ alkynyl of $R^3$ are each optionally substituted with 1, 2, 3, 4, or 5 substituents independently selected from $Cy^3$, halo, CN, NO$_2$, OR$^{a3}$, C(O)R$^{b3}$, C(O)NR$^{c3}$R$^{d3}$, C(O)OR$^{a3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)$_2$R$^{b3}$, NR$^{c3}$S(O)$_2$NR$^{c3}$R$^{d3}$, S(O)$_2$R$^{b3}$ and S(O)$_2$NR$^{c3}$R$^{d3}$.

In some embodiments, $R^3$ is selected from H, $C_{1-6}$ alkyl, $C_{1-6}$ haloalkyl, $Cy^3$, C(O)R$^{b3}$, C(O)NR$^{c3}$R$^{d3}$, C(O)OR$^{a3}$, S(O)$_2$R$^{b3}$, and S(O)$_2$NR$^{c3}$R$^{d3}$; wherein said $C_{1-6}$ alkyl of $R^3$ is optionally substituted with 1, 2, or 3 substituents independently selected from $Cy^3$, halo, CN, NO$_2$, OR$^{a3}$, C(O)R$^{b3}$, C(O)NR$^{c3}$R$^{d3}$, C(O)OR$^{a3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)$_2$R$^{b3}$, S(O)$_2$R$^{b3}$ and S(O)$_2$NR$^{c3}$R$^{d3}$.

In some embodiments, $R^3$ is selected from H, $C_{1-6}$ alkyl, $C_{1-6}$ haloalkyl, C(O)R$^{b3}$, and S(O)$_2$R$^{b3}$, wherein said $C_{1-6}$ alkyl of $R^3$ is optionally substituted with 1, 2, or 3 substituents independently selected from $Cy^3$, halo, $C_{1-3}$ alkoxy, CN, NO$_2$, OH, C(O)R$^{b3}$, C(O)NR$^{c3}$R$^{d3}$, C(O)OR$^{a3}$, NR$^{c3}$R$^{d3}$, S(O)$_2$R$^{b3}$ and S(O)$_2$NR$^{c3}$R$^{d3}$.

In some embodiments, $R^3$ is selected from H, $C_{1-6}$ alkyl, $C_{1-6}$ haloalkyl, wherein said $C_{1-6}$ alkyl of $R^3$ is optionally substituted with 1, 2, or 3 substituents independently selected from $Cy^3$, $C_{1-3}$ alkoxy, CN, NO$_2$, OH, C(O)NH$_2$, C(O)OH, NH$_2$, and S(O)$_2$NH$_2$.

In some embodiments, $R^3$ is selected from H, $C_{1-6}$ alkyl, and $C_{1-6}$ haloalkyl. In some embodiments, $R^3$ is selected from H and $C_{1-6}$ alkyl. In some embodiments, $R^3$ is H. In some embodiments, $R^3$ is $C_{1-3}$ alkyl. In some embodiments, $R^3$ is $Cy^3$. In some embodiments, $R^3$ is $C_{1-6}$ alkyl substituted with $Cy^3$.

In some embodiments, the moiety (L)$_x$ is:

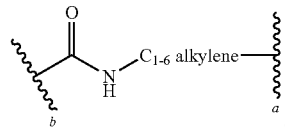

wherein a denotes a point of attachment of (L)$_x$ to ring A, and b denotes a point of attachment of (L)$_x$ to ring B, and wherein said $C_{1-6}$ alkylene is optionally substituted with 1, 2, or 3 substituents independently selected from $R^4$.

In some embodiments, the moiety $(L)_x$ is:

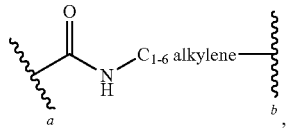

wherein a denotes a point of attachment of $(L)_x$ to ring A, and b denotes a point of attachment of $(L)_x$ to ring B, and wherein said $C_{1-6}$ alkylene is optionally substituted with 1, 2, or 3 substituents independently selected from $R^4$.

In some embodiments, the moiety $(L)_x$ is:

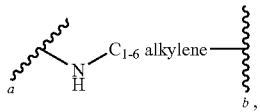

wherein a denotes a point of attachment of $(L)_x$ to ring A, and b denotes a point of attachment of $(L)_x$ to ring B, and wherein said $C_{1-6}$ alkylene is optionally substituted with 1, 2, or 3 substituents independently selected from $R^4$.

In some embodiments, the moiety $(L)_x$ is:

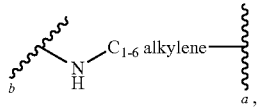

wherein a denotes a point of attachment of $(L)_x$ to ring A, and b denotes a point of attachment of $(L)_x$ to ring B, and wherein said $C_{1-6}$ alkylene is optionally substituted with 1, 2, or 3 substituents independently selected from $R^4$.

In some embodiments, the moiety $(L)_x$ is:

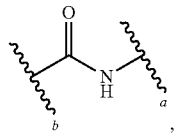

wherein a denotes a point of attachment of $(L)_x$ to ring A, and b denotes a point of attachment of $(L)_x$ to ring B.

In some embodiments, the moiety $(L)_x$ is:

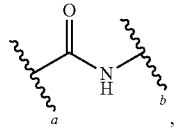

wherein a denotes a point of attachment of $(L)_x$ to ring A, and b denotes a point of attachment of $(L)_x$ to ring B.

In some embodiments, the moiety $(L)_x$ is:

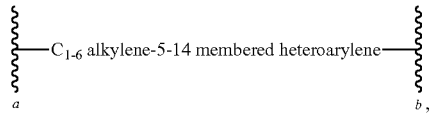

wherein a denotes a point of attachment of $(L)_x$ to ring A, and b denotes a point of attachment of $(L)_x$ to ring B, and wherein said $C_{1-6}$ alkylene and 5-14 membered heteroarylene are each optionally substituted with 1, 2, or 3 substituents independently selected from $R^4$.

In some embodiments, the moiety $(L)_x$ is:

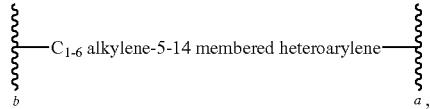

wherein a denotes a point of attachment of $(L)_x$ to ring A, and b denotes a point of attachment of $(L)_x$ to ring B, and wherein said $C_{1-6}$ alkylene and 5-14 membered heteroarylene are each optionally substituted with 1, 2, or 3 substituents independently selected from $R^4$.

In some embodiments, the moiety $(L)_x$ is:

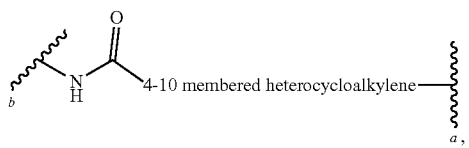

wherein a denotes a point of attachment of $(L)_x$ to ring A, and b denotes a point of attachment of $(L)_x$ to ring B, and wherein said 4-10 membered heterocycloalkylene is optionally substituted with 1, 2, or 3 substituents independently selected from $R^4$.

In some embodiments, the moiety $(L)_x$ is:

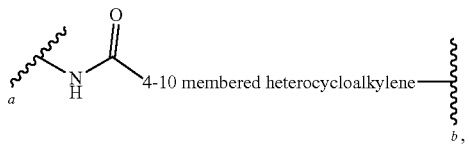

wherein a denotes a point of attachment of $(L)_x$ to ring A, and b denotes a point of attachment of $(L)_x$ to ring B, and wherein said 4-10 membered heterocycloalkylene is optionally substituted with 1, 2, or 3 substituents independently selected from $R^4$.

Certain implementations of $C_{1-6}$ alkylene, $C_{3-10}$ cycloalkylene, $C_{6-10}$ arylene, 5-14 membered heteroarylene, and 4-12 membered heterocycloalkylene of L contain one or more of the following features.

In some embodiments, $C_{1-6}$ alkylene is selected from methylene, ethan-1,1-diyl, ethan-1,2-diyl, propan-1,1-diyl, propan-1,3-diyl, propan-1,2-diyl, butan-1,4-diyl, butan-1,3-diyl, butan-1,2-diyl, and 2-methyl-propan-1,3-diyl, each of which is optionally substituted with 1, 2, or 3 substituents independently selected from $R^4$.

In some embodiments, $C_{1-6}$ alkylene is methylene. In some embodiments, $C_{1-6}$ alkylene is ethan-1,2-diyl. In some embodiments, $C_{1-6}$ alkylene is ethan-1,1-diyl. In some embodiments, $C_{1-6}$ alkylene is propan-1,3-diyl. In any of these embodiments, the $C_{1-6}$ alkylene group is optionally substituted with 1, 2, or 3 substituents independently selected from $R^4$.

In some embodiments, $C_{3-10}$ cycloalkylene is selected from cyclopropylene, cyclobutylene, cyclopentylene, and cyclohexylene, each of which is optionally substituted with 1, 2, or 3 substituents independently selected from $R^4$.

In some embodiments, $C_{6-10}$ arylene is selected from phenylene and naphthylene, each of which is optionally substituted with 1, 2, or 3 substituents independently selected from $R^4$.

In some embodiments, heteroarylene is selected from oxodiazold-diyl, pyridin-diyl, triazole-diyl, oxadiazol-diyl, thiadiazol-diyl, pyrazol-diyl, pyrrol-diyl, pyrazin-diyl, pyrimidin-diyl, triazin-diyl and pyridazin-diyl, each of which is optionally substituted with 1, 2, or 3 substituents independently selected from $R^4$.

In some embodiments, 4-10 membered heterocycloalkylene is selected from pyrrolidine-diyl, 1,3-isoxazolidin-diyl, pyran-diyl, tetrahydropuran-diyl, oxetan-diyl, azetidin-diyl, morpholin-diyl, thiomorpholin-diyl, piperazin-diyl, tetrahydrofuran-diyl, tetrahydrothien-diyl, piperidin-diyl, pyrrolidin-diyl, isoxazolidin-diyl, isothiazolidin-diyl, pyrazolidin-diyl, oxazolidin-diyl, thiazolidin-diyl, imidazolidin-diyl, azepan-diyl, and benzazapen-diyl, each of which is optionally substituted with 1, 2, or 3 substituents independently selected from $R^4$.

In some embodiments, $R^4$ is selected from $C_{1-6}$ alkyl, $C_{1-6}$ haloalkyl, $C_{2-6}$ alkenyl, $C_{2-6}$ alkynyl, $Cy^3$, halo, CN, $NO_2$, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$; wherein said $C_{1-6}$ alkyl, $C_{2-6}$ alkenyl, and $C_{2-6}$ alkynyl of $R^4$ are each optionally substituted with 1, 2, 3, 4, or 5 substituents independently selected from $Cy^3$, halo, CN, $NO_2$, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$ and $S(O)_2NR^{c3}R^{d3}$.

In some embodiments, $R^4$ is selected from $C_{1-6}$ alkyl, $C_{1-6}$ haloalkyl, $Cy^3$, halo, CN, $NO_2$, $OR^{a3}$, $C(O)R^{b3}$, $C(O)NR^{c3}R^{d3}$, $C(O)OR^{a3}$, $NR^{c3}R^{d3}$, $S(O)_2R^{b3}$, and $S(O)_2NR^{c3}R^{d3}$; wherein said $C_{1-6}$ alkyl of $R^4$ is optionally substituted with 1, 2, or 3 substituents independently selected from $Cy^3$, halo, CN, $NO_2$, $OR^{a3}$, $C(O)R^{b3}$, $C(O)NR^{c3}R^{d3}$, $C(O)OR^{a3}$, $NR^{c3}R^{d3}$, $S(O)_2R^{b3}$ and $S(O)_2NR^{c3}R^{d3}$.

In some embodiments, $R^4$ is selected from $C_{1-6}$ alkyl, $C_{1-6}$ haloalkyl, $C_{2-6}$ alkenyl, $Cy^3$, halo, CN, $NO_2$, $OR^{a3}$, $NR^{c3}R^{d3}$, wherein said $C_{1-6}$ alkyl, and $C_{2-6}$ alkenyl of $R^4$ are each optionally substituted with 1, 2, 3, 4, or 5 substituents independently selected from $Cy^3$, halo, CN, $NO_2$, $OR^{a3}$, and $NR^{c3}R^{d3}$.

In some embodiments, $R^4$ is selected from $C_{1-6}$ alkyl, $C_{1-6}$ haloalkyl, $Cy^3$, halo, CN, $NO_2$, OH, $C(O)NH_2$, $C(O)OH$, and $NH_2$, wherein said $C_{1-6}$ alkyl of $R^4$ is optionally substituted with 1, 2, or 3 substituents independently selected from $Cy^3$, halo, CN, $NO_2$, OH, $C(O)NH_2$, $C(O)OH$, and $NH_2$.

In some embodiments, $R^4$ is selected from $C_{1-6}$ alkyl, $C_{1-6}$ haloalkyl, halo, CN, $NO_2$, OH, and $NH_2$, wherein said $C_{1-6}$ alkyl of $R^4$ is optionally substituted with 1, 2, or 3 substituents independently selected from halo, CN, $NO_2$, OH, and $NH_2$.

In some embodiments, $R^1$ is H. In some embodiments, $R^1$ is selected from $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}Rd'$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, thioxo and oxo; wherein said $C_{1-6}$ alkyl, $C_{2-6}$ alkenyl, and $C_{2-6}$ alkynyl substituents of $R^1$ are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{c1})NR^{c1}R^{d1}$, $NR^{c1}C(=NR^{c1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$.

In some embodiments, $R^1$ is selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, $S(O)_2NR^{c1}R^{d1}$, thioxo and oxo; wherein said $C_{1-6}$ alkyl, $C_{2-6}$ alkenyl, and $C_{2-6}$ alkynyl substituents of $R^1$ are each optionally substituted with 1, 2, 3, 4, or 5 substituents independently selected from $Cy^1$, halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$ and $S(O)_2NR^{c1}R^{d1}$.

In some embodiments, $R^1$ is selected from H, $C_{1-6}$ alkyl, $C_{2-6}$ alkenyl, $C_{1-4}$ haloalkyl, $Cy^1$, halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, $S(O)_2NR^{c1}R^{d1}$, thioxo and oxo; wherein said $C_{1-6}$ alkyl and $C_{2-6}$ alkenyl substituents of $R^1$ are each optionally substituted with 1, 2, or 3 substituents independently selected from $Cy^1$, halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$ and $S(O)_2NR^{c1}R^{d1}$.

In some embodiments, $R^1$ is selected from H, $C_{1-6}$ alkyl, $C_{1-4}$ haloalkyl, $Cy^1$, halo, CN, $NO_2$, $OR^{a1}$, $C(O)R^{b1}$, $C(O)NR^{c1}R^{d1}$, $C(O)OR^{a1}$, $NR^{c1}R^{d1}$, $S(O)_2R^{b1}$, $S(O)_2NR^{c1}R^{d1}$, thioxo and oxo; wherein said $C_{1-6}$ alkyl of $R^1$ is optionally substituted with 1, 2, or 3 substituents independently selected from $Cy^1$, halo, CN, $NO_2$, OH, $C(O)NH_2$, $C(O)OH$, $NH_2$, and $S(O)_2NH_2$.

In some embodiments, $R^1$ is selected from H, $C_{1-6}$ alkyl, $C_{1-4}$ haloalkyl, $Cy^1$, halo, CN, $NO_2$, OH, $C(O)NR^{c1}R^{d1}$, $C(O)OR^{a1}$, $NH_2$, $S(O)_2R^{b1}$, thioxo and oxo; wherein said $C_{1-6}$ alkyl of $R^1$ is optionally substituted with 1, 2, or 3 substituents independently selected from halo, CN, $NO_2$, OH, $C(O)NH_2$, $C(O)OH$, and $NH_2$.

In some embodiments, $R^2$ is H. In some embodiments, $R^2$ is selected from $C_{1-6}$ alkyl, $C_{2-6}$ alkenyl, $C_{2-6}$ alkynyl, $C_{1-6}$ haloalkyl, $Cy^2$, halo, CN, $NO_2$, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2N^{c2}R^{d2}$, $S(O)R^{b2}$, $S(O)NR^{c2}R^{d2}$, $S(O)_2R^{b2}$, and $S(O)_2NR^{c2}R^{d2}$, thioxo and oxo; wherein said $C_{1-6}$ alkyl, $C_{2-6}$ alkenyl, and $C_{2-6}$ alkynyl substituents of $R^1$ are each optionally substituted with 1, 2, 3, 4, or 5 substituents independently selected from $Cy^2$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $N^{c2}R^{d2}$, $NR^{c1}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$ and $S(O)_2NR^{c2}R^{d2}$.

each $R^2$ is independently selected from H, $C_{1-6}$ alkyl, $C_{2-6}$ alkenyl, $C_{2-6}$ alkynyl, $C_{1-6}$ haloalkyl, $Cy^2$, halo, CN, NO₂, OR^{a2}, C(O)R^{b2}, C(O)NR^{c2}R^{d2}, C(O)OR^{a2}, NR^{c2}R^{d2}, NR^{c2}C(O)R^{b2}, NR^{c2}C(O)OR^{a2}, NR^{c2}C(O)NR^{c2}R^{d2}, NR^{c2}S(O)₂R^{b2}, NR^{c2}S(O)₂NR^{c2}R^{d2}, S(O)₂R^{b2}, and S(O)₂NR^{c2}R^{d2}, thioxo and oxo; wherein said C_{1-6} alkyl, C_{2-6} alkenyl, and C_{2-6} alkynyl substituents of R¹ are each optionally substituted with 1, 2, 3, 4, or 5 substituents independently selected from Cy², halo, CN, NO₂, OR^{a2}, C(O)R^{b2}, C(O)NR^{c2}R^{d2}, C(O)OR^{a2}, NR^{c2}R^{d2}, NR^{c2}C(O)R^{b2}, NR^{c2}C(O)OR^{a2}, NR^{c2}C(O)NR^{c2}R^{d2}, NR^{c2}S(O)₂R^{b2}, NR^{c2}S(O)₂NR^{c2}R^{d2}, S(O)₂R^{b2} and S(O)₂NR^{c2}R^{d2}.

each R₂ is independently selected from H, C_{1-6} alkyl, C_{2-6} alkenyl, C_{2-6} alkynyl, C_{1-6} haloalkyl, Cy², halo, CN, NO₂, OR^{a2}, C(O)R^{b2}, C(O)NR^{c2}R^{d2}, C(O)OR^{a2}, NR^{c2}R^{d2}, NR^{c2}C(O)R^{b2}, NR^{c2}C(O)OR^{a2}, NR^{c2}C(O)NR^{c2}R^{d2}, NR^{c2}S(O)₂R^{b2}, NR^{c2}S(O)₂N^{c2}R^{d2}, S(O)₂R^{b2}, and S(O)₂NR^{c2}R^{d2}, thioxo and oxo; wherein said C_{1-6} alkyl, C_{2-6} alkenyl, and C_{2-6} alkynyl substituents of R¹ are each optionally substituted with 1, 2, 3, 4, or 5 substituents independently selected from Cy², halo, CN, NO₂, OR^{a2}, C(O)R^{b2}, C(O)NR^{c2}R^{d2}, C(O)OR^{a2}, NR^{c2}R^{d2}, NR^{c2}C(O)R^{b2}, NR^{c2}C(O)OR^{a2}, NR^{c1}C(O)NR^{c2}R^{d2}, NR^{c2}S(O)₂R^{b2}, NR^{c2}S(O)₂NR^{c2}R^{d2}, S(O)₂R^{b2} and S(O)₂NR^{c2}R^{d2}.

each R₂ is independently selected from H, C_{1-6} alkyl, C_{2-6} alkenyl, C_{1-6} haloalkyl, Cy², halo, CN, NO₂, OR^{a2}, C(O)R^{b2}, C(O)NR^{c2}R^{d2}, C(O)OR^{a2}, NR^{c2}R^{d2}, NR^{c2}C(O)R^{b2}, NR^{c2}S(O)₂R^{b2}, S(O))₂R^{b2}, and S(O)₂NR^{c2}R^{d2}, thioxo and oxo; wherein said C_{1-6} alkyl, C_{2-6} alkenyl, and C_{2-6} alkynyl substituents of R' are each optionally substituted with 1, 2, 3, 4, or 5 substituents independently selected from Cy², halo, CN, NO₂, OR^{a2}, C(O)R^{b2}, C(O)NR^{c2}R^{d2}, C(O)OR^{a2}, NR^{c2}R^{d2}, NR^{c2}C(O)R^{b2}, NR^{c2}S(O)₂R^{b2}, S(O)₂R^{b2} and S(O)₂NR^{c2}R^{d2}.

each R₂ is independently selected from H, C_{1-6} alkyl, C_{1-6} haloalkyl, Cy², halo, CN, NO₂, OR^{a2}, C(O)R^{b2}, C(O)NR^{c2}R^{d2}, C(O)OR^{a2}, NR^{c2}R^{d2}, S(O)₂R^{b2}, and S(O)₂NR^{c2}R^{d2}, thioxo and oxo; wherein said C_{1-6} alkyl, C_{2-6} alkenyl, and C_{2-6} alkynyl substituents of R¹ are each optionally substituted with 1, 2, 3, 4, or 5 substituents independently selected from Cy², halo, CN, NO₂, OR^{a2}, C(O)R^{b2}, C(O)NR^{c2}R^{d2}, C(O)OR^{a2}, NR^{c2}R^{d2}, S(O)₂R^{b2} and S(O)₂NR^{c2}R^{d2}.

In some embodiments, R² is selected from H, C_{1-6} alkyl, C_{1-4} haloalkyl, Cy², halo, CN, NO₂, OR^{a2}, C(O)R^{b2}, C(O)NR^{c2}R^{d2}, C(O)OR^{a2}, NR^{c2}R^{d2}, S(O)₂R^{b2}, S(O)₂NR^{c2}R^{d2}, thioxo and oxo; wherein said C_{1-6} alkyl of R² is optionally substituted with 1, 2, or 3 substituents independently selected from Cy², halo, CN, NO₂, OH, C(O)NH₂, C(O)OH, NH₂, and S(O)₂NH₂.

In some embodiments, R² is selected from H, C_{1-6} alkyl, C_{1-4} haloalkyl, Cy², halo, CN, NO₂, OH, C(O)R^{b2}, C(O)OR^{a2}, NH₂, S(O)₂R^{b2}, thioxo and oxo; wherein said C_{1-6} alkyl of R² is optionally substituted with 1, 2, or 3 substituents independently selected from halo, CN, NO₂, OH, C(O)NH₂, C(O)OH, and NH₂.

In some embodiments, R¹ together with the atom of ring A to which it is attached, R² together with the atom of ring B to which it is attached, and moiety (L)_x together form a ring selected from: C_{3-10} cycloalkyl, 6-10 membered aryl, 5-10 membered heteroaryl, and 4-12 membered heterocycloalkyl group, each of which is optionally substituted with 1, 2, 3, 4, or 5 substituents independently selected from R⁴.

In some embodiments, when R¹ together with the atom of ring A to which it is attached, R² together with the atom of ring B to which it is attached, and moiety (L)_x together form a ring, the compound of Formula (I-I) has Formula (I-VI):

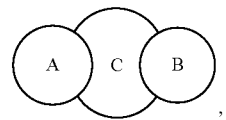

(I-VI)

or a pharmaceutically acceptable salt thereof, wherein rings A and B are as described herein, and ring C is selected from: C_{3-10} cycloalkyl, 6-10 membered aryl, 5-10 membered heteroaryl, and 4-12 membered heterocycloalkyl group, each of which is optionally substituted with 1, 2, 3, 4, or 5 substituents independently selected from R⁴.

In some embodiments, ring C is C_{3-10} cycloalkyl, optionally substituted with 1, 2, 3, 4, or 5 substituents independently selected from R⁴.

In some embodiments, ring C is 6-10 membered aryl, optionally substituted with 1, 2, 3, 4, or 5 substituents independently selected from R⁴.

In some embodiments, ring C is 5-10 membered heteroaryl, optionally substituted with 1, 2, 3, 4, or 5 substituents independently selected from R⁴.

In some embodiments, ring C is 4-12 membered heterocycloalkyl, optionally substituted with 1, 2, 3, 4, or 5 substituents independently selected from R⁴.

In some embodiments, the compound of Formula (I-VI) has Formula (I-VIa):

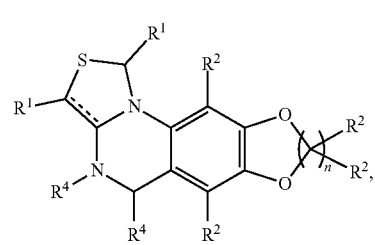

(I-VIa)

or a pharmaceutically acceptable salt thereof,
wherein ⚌ is a single bond or a double bond.

In some embodiments, the compound of Formula (I) is selected from any one of the following compounds, or a pharmaceutically acceptable salt the 'reof:

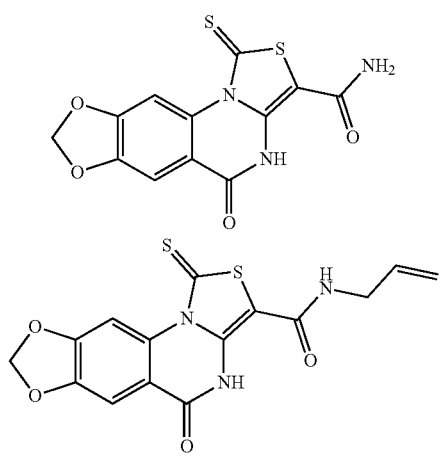

In some embodiments, $Cy^1$ is selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy}$. In some aspects of these embodiments, $Cy^1$ is $C_{6-10}$ aryl. In other aspects of these embodiments, $Cy^1$ is $C_{3-10}$ cycloalkyl. In yet other aspects of these embodiments, $Cy^1$ is 5-10 membered heteroaryl. In yet other aspects of these embodiments, $Cy^1$ is 4-12 membered heterocycloalkyl. In yet other aspects of these embodiments, $Cy^1$ is selected from $C_{6-10}$ aryl, 5-10 membered heteroaryl, and 4-12 membered heterocycloalkyl.

In some embodiments, $Cy^2$ is selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy}$. In some aspects of these embodiments, $Cy^2$ is $C_{6-10}$ aryl. In other aspects of these embodiments, $Cy^2$ is $C_{3-10}$ cycloalkyl. In yet other aspects of these embodiments, $Cy^2$ is 5-10 membered heteroaryl. In yet other aspects of these embodiments, $Cy^2$ is 4-12 membered heterocycloalkyl. In yet other aspects of these embodiments, $Cy^2$ is selected from $C_{6-10}$ aryl, 5-10 membered heteroaryl, and 4-12 membered heterocycloalkyl.

In some embodiments, $Cy^3$ is selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy}$. In some aspects of these embodiments, $Cy^3$ is $C_{6-10}$ aryl. In other aspects of these embodiments, $Cy^3$ is $C_{3-10}$ cycloalkyl. In yet other aspects of these embodiments, $Cy^3$ is 5-10 membered heteroaryl. In yet other aspects of these embodiments, $Cy^3$ is 4-12 membered heterocycloalkyl. In yet other aspects of these embodiments, $Cy^3$ is selected from $C_{6-10}$ aryl, 5-10 membered heteroaryl, and 4-12 membered heterocycloalkyl.

In some embodiments, $Cy^1$, $Cy^2$, and $Cy^3$ are each independently selected from $C_{6-10}$ aryl and 4-12 membered heterocycloalkyl, each of which is optionally substituted with 1, 2, or 3 substituents independently selected from $R^{Cy}$.

In some embodiments, $R^{Cy}$ is selected from halo, $C_{1-4}$ alkyl, $C_{1-4}$ haloalkyl, $C_{2-6}$ alkenyl, $C_{2-6}$ alkynyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, (4-7 membered heterocycloalkyl)-$C_{1-4}$ alkylene-, CN, NO$_2$, OR$^{a4}$, C(O)R$^{b4}$, C(O)NR$^{c4}$R$^{d4}$, C(O)OR$^{a4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)$_2$R$^{b4}$, NR$^{c4}$S(O)$_2$NR$^{c4}$R$^{d4}$, S(O)$_2$R$^{b4}$, and S(O)$_2$NR$^{c4}$R$^{d4}$, wherein said $C_{1-4}$ alkyl, $C_{2-6}$ alkenyl, $C_{2-6}$ alkynyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, and (4-7 membered heterocycloalkyl)-$C_{1-4}$ alkylene- are each optionally substituted by 1, 2, 3, 4, or 5 substituents independently selected from $C_{1-6}$ alkyl, $C_{1-4}$ haloalkyl, $C_{1-6}$ cyanoalkyl, halo, CN, NO$_2$, OR$^{a4}$, C(O)R$^{b4}$, C(O)NR$^{c4}$R$^{d4}$, C(O)OR$^{a4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)$_2$R$^{b4}$, NR$^{c4}$S(O)$_2$NR$^{c4}$R$^{d4}$, S(O)$_2$R$^{b4}$, and S(O)$_2$NR$^{c4}$R$^{d4}$.

In some embodiments, $R^{Cy}$ is selected from halo, $C_{1-4}$ alkyl, $C_{1-4}$ haloalkyl, $C_{2-6}$ alkenyl, $C_{6-10}$ aryl, $C_{3-7}$ cycloalkyl, 5-6 membered heteroaryl, 4-7 membered heterocycloalkyl, CN, NO$_2$, OR$^{a4}$, C(O)R$^{b4}$, C(O)NR$^{c4}$R$^{d4}$, C(O)OR$^{a4}$, NR$^{c4}$R$^{d4}$, NR$^{c4}$C(O)R$^{b4}$, NR$^{c4}$C(O)OR$^{a4}$, NR$^{c4}$C(O) NR$^{c4}$R$^{d4}$, NR$^{c4}$S(O)$_2$R$^{b4}$, NR$^{c4}$S(O)$_2$NR$^{c4}$R$^{d4}$, S(O)$_2$R$^{b4}$, and S(O)$_2$NR$^{c4}$R$^{d4}$, wherein said $C_{1-4}$ alkyl, $C_{2-6}$ alkenyl, $C_{6-10}$ aryl, $C_{3-7}$ cycloalkyl, 5-6 membered heteroaryl, 4-7 membered heterocycloalkyl are each optionally substituted by 1, 2, 3, 4, or 5 substituents independently selected from $C_{1-6}$ alkyl, $C_{1-4}$ haloalkyl, halo, CN, NO$_2$, OR$^{a4}$, C(O)R$^{b4}$, C(O)NR$^{c4}$R$^{d4}$, C(O)OR$^{a4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)$_2$R$^{b4}$, NR$^{c4}$S(O)$_2$NR$^{c4}$R$^{d4}$, S(O)$_2$R$^{b4}$, and S(O)$_2$NR$^{c4}$R$^{d4}$.

In some embodiments, $R^{Cy}$ is selected from $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, and (4-7 membered heterocycloalkyl)-$C_{1-4}$ alkylene, each of which is optionally substituted with 1, 2, 3, 4, or 5 substituents independently selected from $C_{1-3}$ alkyl, $C_{1-3}$ haloalkyl, $C_{1-3}$ alkoxy, $C_{1-3}$ haloalkoxy, halo, CN, NO$_2$, OH, C(O)NH$_2$, C(O)OH, NH$_2$, and S(O)$_2$NH$_2$.

In some embodiments, $R^{Cy}$ is selected from $C_{6-10}$ aryl, $C_{3-7}$ cycloalkyl, 5-6 membered heteroaryl, and 4-7 membered heterocycloalkyl, each of which is optionally substituted with 1, 2, 3, 4, or 5 substituents independently selected from $C_{1-3}$ alkyl, $C_{1-3}$ haloalkyl, $C_{1-3}$ alkoxy, $C_{1-3}$ haloalkoxy, halo, CN, NO$_2$, OH, C(O)NH$_2$, C(O)OH, NH$_2$, and S(O)$_2$NH$_2$.

In some embodiments, $R^{Cy}$ is $C_{1-6}$ alkyl, optionally substituted with 1, 2, or 3 substituents independently selected from halo, CN, NO$_2$, OR$^{a4}$, C(O)R$^{b4}$, C(O)NR$^{c4}$R$^{d4}$, C(O)OR$^{a4}$, NR$^{c4}$R$^{d4}$, NR$^{c4}$C(O)R$^{b4}$, NR$^{c4}$C(O)OR$^{a4}$, NR$^{c4}$C(O) NR$^{c4}$R$^{d4}$, NR$^{c4}$S(O)$_2$R$^{b4}$, NR$^{c4}$S(O)$_2$NR$^{c4}$R$^{d4}$, S(O)$_2$R$^{b4}$, and S(O)$_2$NR$^{c4}$R$^{d4}$.

In some embodiments, $R^{Cy}$ is $C_{1-6}$ alkyl, optionally substituted with 1, 2, or 3 substituents independently selected from $C_{1-3}$ alkoxy, $C_{1-3}$ haloalkoxy, halo, CN, NO$_2$, OH, C(O)NH$_2$, C(O)OH, NH$_2$, and S(O)$_2$NH$_2$.

In some embodiments, $R^{Cy}$ is selected from halo, $C_{1-4}$ alkyl, $C_{1-4}$ haloalkyl, and $C_{2-6}$ alkenyl. In some embodiments, $R^{Cy}$ is $C_{1-4}$ alkyl. In some embodiments, $R^{Cy}$ is $C_{1-4}$ haloalkyl. In some embodiments, $R^{Cy}$ is halo (e.g., $C_1$, Br, F, or I).

In some embodiments, each $R^{a1}$ is H. In some embodiments, $R^{a1}$ is $C_{1-3}$ alkyl. In some embodiments, each $R^{a2}$ is H. In some embodiments, $R^{a2}$ is $C_{1-3}$ alkyl. In some embodiments, each $R^{a3}$ is H. In some embodiments, $R^{a3}$ is $C_{1-3}$ alkyl. In some embodiments, each $R^{a4}$ is H. In some embodiments, $R^{a4}$ is $C_{1-3}$ alkyl.

In some embodiments, each $R^{b1}$ is $C_{1-3}$ alkyl or $C_{6-10}$ aryl, each of which is optionally substituted with 1, 2, or 3 substituents independently selected from $R^g$. In some embodiments, each $R^{b2}$ is $C_{1-3}$ alkyl or $C_{6-10}$ aryl, each of which is optionally substituted with 1, 2, or 3 substituents independently selected from $R^g$. In some embodiments, each $R^{b3}$ is $C_{1-3}$ alkyl or $C_{6-10}$ aryl, each of which is optionally substituted with 1, 2, or 3 substituents independently selected from $R^g$. In some embodiments, each $R^{b4}$ is $C_{1-3}$ alkyl or $C_{6-10}$ aryl, each of which is optionally substituted with 1, 2, or 3 substituents independently selected from $R^g$.

In some embodiments, each $R^{a1}$, $R^{b1}$, $R^{a2}$, $R^{b2}$, $R^{a3}$, $R^{b3}$, $R^{a4}$, and $R^{b4}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, and 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl are each optionally substituted with 1, 2, or 3 substituents independently selected from $R^g$.

In some embodiments, each $R^{a1}$, $R^{b1}$, $R^{a2}$, $R^{b2}$, $R^{a3}$, $R^{b3}$, $R^{a4}$, and $R^{b4}$ is independently selected from $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene, wherein said $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are each optionally substituted with 1, 2, 3, 4, or 5 substituents independently selected from $R^g$.

In some embodiments, each $R^{c1}$, $R^{d1}$, $R^{c2}$, $R^{d2}$, $R^{c3}$, $R^{d3}$, $R^{c4}$, and $R^{d4}$ is independently selected from H, $C_{1-6}$ alkyl, and $C_{1-4}$ haloalkyl, wherein the $C_{1-6}$ alkyl is optionally substituted with 1, 2, or 3 substituents independently selected from $R^g$.

In some embodiments, each $R^{c1}$, $R^{d1}$, $R^{c2}$, $R^{d2}$, $R^{c3}$, $R^{d3}$, $R^{c4}$, and $R^{d4}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, and 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl is optionally substituted with 1, 2, or 3 substituents independently selected from $R^g$.

In some embodiments, each $R^{c1}$, $R^{d1}$, $R^{c2}$, $R^{d2}$, $R^{e3}$, $R^{d3}$, $R^{c4}$, and $R^{d4}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, $C(O)R^{b5}$, $C(O)NR^{c5}R^{d5}$, $C(O)OR^{a5}$, $S(O)_2R^{b5}$, and $S(O)_2NR^{c5}R^{d5}$; wherein said $C_{1-6}$ alkyl, $C_{6-10}$ aryl, $C_{3-10}$ cycloalkyl, 5-10 membered heteroaryl, 4-12 membered heterocycloalkyl are each optionally substituted with 1, 2, or 3 substituents independently selected from $R^g$.

In some embodiments, each $R^{c1}$, $R^{d1}$, $R^{c2}$, $R^{d2}$, $R^{c3}$, $R^{d3}$, $R^{c4}$, and $R^{d4}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, $C(O)R^{b5}$, $C(O)NR^{c5}R^{d5}$, $C(O)OR^{a5}$, $S(O)_2R^{b5}$, and $S(O)_2NR^{c5}R^{d5}$; wherein said $C_{1-6}$ alkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, 3, 4, or 5 substituents independently selected from $R^g$.

In some embodiments, each $R^{a5}$, $R^{b5}$, $R^{c5}$, and $R^{d5}$ is independently selected from H, $C_{1-6}$ alkyl, $C_{1-4}$ haloalkyl, and $C_{2-6}$ alkenyl, wherein said $C_{1-6}$ alkyl is optionally substituted with 1, 2, or 3 substituents independently selected from $R^g$.

In some embodiments, each $R^{a5}$, $R^{b5}$, $R^{c5}$, and $R^{d5}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^g$.

In Some Embodiments of Formula (I-I):
  ring A is selected from 6-10 membered aryl, 5-12 membered heteroaryl, and 4-12 membered heterocycloalkyl, each of which is optionally substituted by 1, 2, 3, 4, or 5 independently selected $R^1$ groups;
  ring B is selected from 6-10 membered aryl, 5-12 membered heteroaryl, and 4-12 membered heterocycloalkyl, each of which is optionally substituted by 1, 2, 3, 4, or 5 independently selected $R^1$ groups;
  each L is independently selected from O, C(=O), S(=O)$_2$, N($R^3$), $C_{1-6}$ alkylene, $C_{3-10}$ cycloalkylene, $C_{6-10}$ arylene, 5-14 membered heteroarylene, and 4-10 membered heterocycloalkylene, wherein said $C_{1-6}$ alkylene, $C_{3-10}$ cycloalkylene, $C_{6-10}$ arylene, 5-14 membered heteroarylene, and 4-10 membered heterocycloalkylene are each optionally substituted with 1, 2, or 3 substituents independently selected from $R^4$;
  x is 1, 2, or 3;
  $R^3$ is selected from H, $C_{1-6}$ alkyl, $C_{1-6}$ haloalkyl, $Cy^3$, $C(O)R^{b3}$, $C(O)NR^{c3}R^{d3}$, $C(O)OR^{a3}$, $S(O)_2R^{b3}$, and $S(O)_2NR^{c3}R^{d3}$; wherein said $C_{1-6}$ alkyl of $R^3$ is optionally substituted with 1, 2, or 3 substituents independently selected from $Cy^3$, halo, CN, NO$_2$, OR$^{a3}$, C(O)R$^{b3}$, C(O)NR$^{c3}R^{d3}$, C(O)OR$^{a3}$, NR$^{c3}R^{d3}$, NR$^{c3}$C(O)R$^{b3}$, NR$^{c3}$C(O)OR$^{a3}$, NR$^{c3}$C(O)NR$^{c3}R^{d3}$, NR$^{c3}$S(O)$_2$R$^{b3}$, S(O)$_2$R$^{b3}$ and S(O)$_2$NR$^{c3}R^{d3}$;
  $R^4$ is selected from $C_{1-6}$ alkyl, $C_{1-6}$ haloalkyl, $Cy^3$, halo, CN, NO$_2$, OR$^{a3}$, C(O)R$^{b3}$, C(O)NR$^{c3}R^{d3}$, C(O)OR$^{a3}$, NR$^{c3}R^{d3}$, S(O)$_2$R$^{b3}$, and S(O)$_2$NR$^{c3}R^{d3}$; wherein said $C_{1-6}$ alkyl of $R^4$ is optionally substituted with 1, 2, or 3 substituents independently selected from $Cy^3$, halo, CN, NO$_2$, OR$^{a3}$, C(O)R$^{b3}$, C(O)NR$^{c3}R^{d3}$, C(O)OR$^{a3}$, NR$^{c3}R^{d3}$, S(O)$_2$R$^{b3}$ and S(O)$_2$NR$^{c3}R^{d3}$;
  $R^1$ is selected from $C_{1-6}$ alkyl, $C_{1-4}$ haloalkyl, $Cy^1$, halo, CN, NO$_2$, OR$^{a1}$, C(O)R$^{b1}$, C(O)NR$^{c1}R^{d1}$, C(O)OR$^{a1}$, NR$^{c1}R^{d1}$, S(O)$_2$R$^{b1}$, S(O)$_2$NR$^{c1}R^{d1}$, thioxo and oxo; wherein said $C_{1-6}$ alkyl of $R^1$ is optionally substituted with 1, 2, or 3 substituents independently selected from $Cy^1$, halo, CN, NO$_2$, OH, C(O)NH$_2$, C(O)OH, NH$_2$, and S(O)$_2$NH$_2$;
  $R^2$ is selected from $C_{1-6}$ alkyl, $C_{1-4}$ haloalkyl, $Cy^2$, halo, CN, NO$_2$, OR$^{a2}$, C(O)R$^{b2}$, C(O)NR$^{c2}R^{d2}$, C(O)OR$^{a2}$, NR$^{c2}R^{d2}$, S(O)$_2$R$^{b2}$, S(O)$_2$NR$^{c2}R^{d2}$, thioxo and oxo; wherein said $C_{1-6}$ alkyl of $R^2$ is optionally substituted with 1, 2, or 3 substituents independently selected from $Cy^2$, halo, CN, NO$_2$, OH, C(O)NH$_2$, C(O)OH, NH$_2$, and S(O)$_2$NH$_2$;
  or $R^1$ together with the atom of ring A to which it is attached, $R^2$ together with the atom of ring B to which it is attached, and moiety (L)$_x$ together form a 4-12 membered heterocycloalkyl ring, which is optionally substituted with 1, 2, or 3 substituents independently selected from $R^4$;
  $Cy^1$, $Cy^2$, and $Cy^3$ are each independently selected from $C_{6-10}$ aryl and 4-12 membered heterocycloalkyl, each of which is optionally substituted with 1, 2, or 3 substituents independently selected from $R^{Cy}$;
  $R^{Cy}$ is selected from halo, $C_{1-4}$ alkyl, $C_{1-4}$ haloalkyl, CN, NO$_2$, OH, C(O)NH$_2$, C(O)OH, NH$_2$, and S(O)$_2$NH$_2$, wherein said $C_{1-4}$ alkyl is optionally substituted by 1, 2, or 3 substituents independently selected from halo, CN, NO$_2$, OH, C(O)NH$_2$, C(O)OH, NH$_2$, and S(O)$_2$NH$_2$;
  each $R^{a1}$, $R^{b1}$, $R^{a2}$, $R^{b2}$, $R^{a3}$, and $R^{b3}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, and 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl are each optionally substituted with 1, 2, or 3 substituents independently selected from $R^g$; and
  each $R^{c1}$, $R^{d1}$, $R^{c2}$, $R^{d2}$, $R^{c3}$ and $R^{d3}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, and 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl are each optionally substituted with 1, 2, or 3 substituents independently selected from $R^g$.

In some aspects of these embodiments:
- ring A is selected from 5-12 membered heteroaryl and 4-12 membered heterocycloalkyl, each of which is optionally substituted by 1, 2, 3, 4, or 5 independently selected $R^1$ groups;
- ring B is a 4-12 membered heterocycloalkyl, which is optionally substituted by 1, 2, 3, 4, or 5 independently selected $R^2$ groups;
- each L is independently selected from C(=O), N($R^3$), $C_{1-6}$ alkylene, 4-10 membered heterocycloalkylene, and 5-14 membered heteroarylene, wherein said $C_{1-6}$ alkylene, 4-10 membered heterocycloalkylene, and 5-14 membered heteroarylene are each optionally substituted with 1, 2, or 3 substituents independently selected from $R^4$;
- $R^3$ is selected from H, $C_{1-6}$ alkyl, and $C_{1-6}$ haloalkyl;
- $R^4$ is selected from $C_{1-6}$ alkyl, $C_{1-6}$ haloalkyl, halo, CN, $NO_2$, OH, and $NH_2$, wherein said $C_{1-6}$ alkyl of $R^4$ is optionally substituted with 1, 2, or 3 substituents independently selected from halo, CN, $NO_2$, OH, and $NH_2$;
- $R^1$ is selected from $C_{1-6}$ alkyl, $C_{1-4}$ haloalkyl, $Cy^1$, halo, CN, $NO_2$, OH, C(O)N$R^{c1}R^{d1}$, C(O)O$R^{a1}$, $NH_2$, $S(O)_2R^{b1}$, thioxo and oxo; wherein said $C_{1-6}$ alkyl of $R^1$ is optionally substituted with 1, 2, or 3 substituents independently selected from halo, CN, $NO_2$, OH, C(O)$NH_2$, C(O)OH, and $NH_2$; and
- $R^2$ is selected from $C_{1-6}$ alkyl, $C_{1-4}$ haloalkyl, $Cy^2$, halo, CN, $NO_2$, OH, C(O)$R^{b2}$, C(O)O$R^{a2}$, $NH_2$, $S(O)_2R^{b2}$, thioxo and oxo; wherein said $C_{1-6}$ alkyl of $R^2$ is optionally substituted with 1, 2, or 3 substituents independently selected from halo, CN, $NO_2$, OH, C(O)$NH_2$, C(O)OH, and $NH_2$.

In some embodiments of Formulae (I-I), (I-IIa), (I-IIb), or (I-IIc):
- ring A is selected from 5-12 membered heteroaryl and 4-12 membered heterocycloalkyl, each of which is optionally substituted by 1-6 independently selected $R^1$ groups;
- each L is independently selected from C(=O), N($R^3$), $C_{1-6}$ alkylene, 4-10 membered heterocycloalkylene, and 5-14 membered heteroarylene, wherein said $C_{1-6}$ alkylene, 4-10 membered heterocycloalkylene, and 5-14 membered heteroarylene are each optionally substituted with 1, 2, or 3 substituents independently selected from $R^4$;
- x is 1, 2, or 3;
- $R^3$ is selected from H, $C_{1-6}$ alkyl, $C_{1-6}$ haloalkyl, $Cy^3$, C(O)$R^{b3}$, C(O)N$R^{c3}R^{d3}$, C(O)O$R^{a3}$, $S(O)_2R^{b3}$, and $S(O)_2NR^{c3}R^{d3}$; wherein said $C_{1-6}$ alkyl of $R^3$ is optionally substituted with 1, 2, or 3 substituents independently selected from $Cy^3$, halo, CN, $NO_2$, O$R^{a3}$, C(O)$R^{b3}$, C(O)N$R^{c3}R^{d3}$, C(O)O$R^{a3}$, N$R^{c3}R^{d3}$, N$R^{c3}$C(O)$R^{b3}$, N$R^{c3}$C(O)O$R^{a3}$, N$R^{c3}$C(O)N$R^{c3}R^{d3}$, N$R^{c3}$S(O)$_2R^{b3}$, $S(O)_2R^{b3}$ and $S(O)_2NR^{c3}R^{d3}$;
- $R^4$ is selected from $C_{1-6}$ alkyl, $C_{1-6}$ haloalkyl, $Cy^3$, halo, CN, $NO_2$, O$R^{a3}$, C(O)$R^{b3}$, C(O)N$R^{c3}R^{d3}$, C(O)O$R^{a3}$, N$R^{c3}R^{d3}$, $S(O)_2R^{b3}$, and $S(O)_2NR^{c3}R^{d3}$; wherein said $C_{1-6}$ alkyl of $R^4$ is optionally substituted with 1, 2, or 3 substituents independently selected from $Cy^3$, halo, CN, $NO_2$, O$R^{a3}$, C(O)$R^{b3}$, C(O)N$R^{c3}R^{d3}$, C(O)O$R^{a3}$, N$R^{c3}R^{d3}$, $S(O)_2R^{b3}$ and $S(O)_2NR^{c3}R^{d3}$;
- $R^1$ is selected from $C_{1-6}$ alkyl, $C_{1-4}$ haloalkyl, $Cy^1$, halo, CN, $NO_2$, O$R^{a1}$, C(O)$R^{b1}$, C(O)N$R^{c1}R^{d1}$, C(O)O$R^{a1}$, N$R^{c1}R^{d1}$, $S(O)_2R^{b1}$, $S(O)_2NR^{c1}R^{d1}$, thioxo and oxo; wherein said $C_{1-6}$ alkyl of $R^1$ is optionally substituted with 1, 2, or 3 substituents independently selected from $Cy^1$, halo, CN, $NO_2$, OH, C(O)$NH_2$, C(O)OH, $NH_2$, and $S(O)_2NH_2$;
- $R^2$ is selected from H, $C_{1-6}$ alkyl, $C_{1-4}$ haloalkyl, $Cy^2$, halo, CN, $NO_2$, O$R^{a2}$, C(O)$R^{b2}$, C(O)N$R^{c2}R^{d2}$, C(O)O$R^{a2}$, N$R^{c2}R^{d2}$, $S(O)_2R^{b2}$, $S(O)_2NR^{c2}R^{d2}$, thioxo and oxo; wherein said $C_{1-6}$ alkyl of $R^2$ is optionally substituted with 1, 2, or 3 substituents independently selected from $Cy^2$, halo, CN, $NO_2$, OH, C(O)$NH_2$, C(O)OH, $NH_2$, and $S(O)_2NH_2$;
- or $R^1$ together with the atom of ring A to which it is attached, $R^2$ together with the atom of ring B to which it is attached, and moiety $(L)_x$ together form a 4-12 membered heterocycloalkyl ring, which is optionally substituted with 1, 2, or 3 substituents independently selected from $R^4$;
- $Cy^1$, $Cy^2$, and $Cy^3$ are each independently selected from $C_{6-10}$ aryl and 4-12 membered heterocycloalkyl, each of which is optionally substituted with 1, 2, or 3 substituents independently selected from $R^{Cy}$;
- $R^{Cy}$ is selected from halo, $C_{1-4}$ alkyl, $C_{1-4}$ haloalkyl, CN, $NO_2$, OH, C(O)$NH_2$, C(O)OH, $NH_2$, and $S(O)_2NH_2$, wherein said $C_{1-4}$ alkyl is optionally substituted by 1, 2, or 3 substituents independently selected from halo, CN, $NO_2$, OH, C(O)$NH_2$, C(O)OH, $NH_2$, and $S(O)_2NH_2$;
- each $R^{a1}$, $R^{b1}$, $R^{a2}$, $R^{b2}$, $R^{a3}$, and $R^{b3}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl are optionally substituted with 1, 2, or 3 substituents independently selected from $R^g$; and
- each $R^{c1}$, $R^{d1}$, $R^{c2}$, $R^{d2}$, $R^{c3}$ and $R^{d3}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl are each optionally substituted with 1, 2, or 3 substituents independently selected from $R^g$.

In some aspects of these embodiments,
ring A is a moiety of formula:

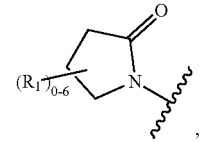

the moiety $(L)_x$ is selected from:

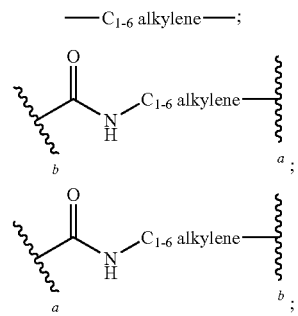

-continued

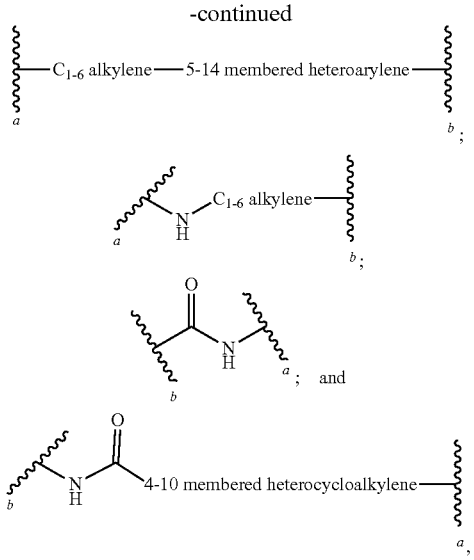

wherein said $C_{1-6}$ alkylene, 5-14 membered heteroarylene, and 4-10 membered heterocycloalkylene of $(L)_x$ are each optionally substituted with 1, 2, or 3 substituents independently selected from $R^4$;
wherein a denotes a point of attachment of $(L)_x$ to ring A, and b denotes a point of attachment of $(L)_x$ to ring B; and wherein:

$R^4$ is selected from $C_{1-6}$ alkyl, $C_{1-6}$ haloalkyl, halo, CN, $NO_2$, OH, and $NH_2$, wherein said $C_{1-6}$ alkyl of $R^4$ is optionally substituted with 1, 2, or 3 substituents independently selected from halo, CN, $NO_2$, OH, and $NH_2$;

$R^1$ is selected from $C_{1-6}$ alkyl, $C_{1-4}$ haloalkyl, $Cy^1$, halo, CN, $NO_2$, OH, $C(O)NR^{c1}R^{d1}$, $C(O)OR^{a1}$, $NH_2$, $S(O)_2R^{b1}$, thioxo and oxo; wherein said $C_{1-6}$ alkyl of $R^1$ is optionally substituted with 1, 2, or 3 substituents independently selected from halo, CN, $NO_2$, OH, $C(O)NH_2$, $C(O)OH$, and $NH_2$; and $R^2$ is selected from H, $C_{1-6}$ alkyl, $C_{1-4}$ haloalkyl, $Cy^2$, halo, CN, $NO_2$, OH, $C(O)R^{b2}$, $C(O)OR^{a2}$, $NH_2$, $S(O)_2R^{b2}$, thioxo and oxo; wherein said $C_{1-6}$ alkyl of $R^2$ is optionally substituted with 1, 2, or 3 substituents independently selected from halo, CN, $NO_2$, OH, $C(O)NH_2$, $C(O)OH$, and $NH_2$.

In some embodiments of Formulae (I-I), (I-IIIa), or (I-IIIb):
ring B is a 4-12 membered heterocycloalkyl, each of which is optionally substituted by 1-10 independently selected $R^1$ groups.
each L is independently selected from $C(=O)$, $N(R^3)$, $C_{1-6}$ alkylene, 4-10 membered heterocycloalkylene, and 5-14 membered heteroarylene, wherein said $C_{1-6}$ alkylene, 4-10 membered heterocycloalkylene, and 5-14 membered heteroarylene are each optionally substituted with 1, 2, or 3 substituents independently selected from $R^4$;
x is 1, 2, or 3;
$R^3$ is selected from H, $C_{1-6}$ alkyl, $C_{1-6}$ haloalkyl, $Cy^3$, $C(O)R^{b3}$, $C(O)NR^{c3}R^{d3}$, $C(O)OR^{a3}$, $S(O)_2R^{b3}$, and $S(O)_2NR^{c3}R^{d3}$; wherein said $C_{1-6}$ alkyl of $R^3$ is optionally substituted with 1, 2, or 3 substituents independently selected from $Cy^3$, halo, CN, $NO_2$, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $S(O)_2R^{b3}$ and $S(O)_2NR^{c3}R^{d3}$;

$R^4$ is selected from $C_{1-6}$ alkyl, $C_{1-6}$ haloalkyl, $Cy^3$, halo, CN, $NO_2$, $OR^{a3}$, $C(O)R^{b3}$, $C(O)NR^{c3}R^{d3}$, $C(O)OR^{a3}$, $NR^{c3}R^{d3}$, $S(O)_2R^{b3}$, and $S(O)_2NR^{c3}R^{d3}$; wherein said $C_{1-6}$ alkyl of $R^4$ is optionally substituted with 1, 2, or 3 substituents independently selected from $Cy^3$, halo, CN, $NO_2$, $OR^{a3}$, $C(O)R^{b3}$, $C(O)NR^{c3}R^{d3}$, $C(O)OR^{a3}$, $NR^{c3}R^{d3}$, $S(O)_2R^{b3}$ and $S(O)_2NR^{c3}R^{d3}$;

$R^1$ is selected from $C_{1-6}$ alkyl, $C_{1-4}$ haloalkyl, $Cy^1$, halo, CN, $NO_2$, $OR^{a1}$, $C(O)R^{b1}$, $C(O)NR^{c1}R^{d1}$, $C(O)OR^{a1}$, $NR^{c1}R^{d1}$, $S(O)_2R^{b1}$, $S(O)_2NR^{c1}R^{d1}$, thioxo and oxo; wherein said $C_{1-6}$ alkyl of $R^1$ is optionally substituted with 1, 2, or 3 substituents independently selected from $Cy^1$, halo, CN, $NO_2$, OH, $C(O)NH_2$, $C(O)OH$, $NH_2$, and $S(O)_2NH_2$;

$R^2$ is selected from $C_{1-6}$ alkyl, $C_{1-4}$ haloalkyl, $Cy^2$, halo, CN, $NO_2$, $OR^{a2}$, $C(O)R^{b2}$, $C(O)NR^{c2}R^{d2}$, $C(O)OR^{a2}$, $NR^{c2}R^{d2}$, $S(O)_2R^{b2}$, $S(O)_2NR^{c2}R^{d2}$, thioxo and oxo; wherein said $C_{1-6}$ alkyl of $R^2$ is optionally substituted with 1, 2, or 3 substituents independently selected from $Cy^2$, halo, CN, $NO_2$, OH, $C(O)NH_2$, $C(O)OH$, $NH_2$, and $S(O)_2NH_2$;

or $R^1$ together with the atom of ring A to which it is attached, $R^2$ together with the atom of ring B to which it is attached, and moiety $(L)_x$ together form a 4-12 membered heterocycloalkyl ring, which is optionally substituted with 1, 2, or 3 substituents independently selected from $R^4$;

$Cy^1$, $Cy^2$, and $Cy^3$ are each independently selected from $C_{6-10}$ aryl and 4-12 membered heterocycloalkyl, each of which is optionally substituted with 1, 2, or 3 substituents independently selected from $R^{Cy}$;

$R^{Cy}$ is selected from halo, $C_{1-4}$ alkyl, $C_{1-4}$ haloalkyl, CN, $NO_2$, OH, $C(O)NH_2$, $C(O)OH$, $NH_2$, and $S(O)_2NH_2$, wherein said $C_{1-4}$ alkyl is optionally substituted by 1, 2, or 3 substituents independently selected from halo, CN, $NO_2$, OH, $C(O)NH_2$, $C(O)OH$, $NH_2$, and $S(O)_2NH_2$;

each $R^{a1}$, $R^{b1}$, $R^{a2}$, $R^{b2}$, $R^{a3}$, and $R^{b3}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, and 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl are each optionally substituted with 1, 2, or 3 substituents independently selected from $R^g$; and each $R^{c1}$, $R^{d1}$, $R^{c2}$, $R^{d2}$, $R^{c3}$ and $R^{d3}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl are each optionally substituted with 1, 2, or 3 substituents independently selected from $R^g$.

In some aspects of these embodiments:
ring B is a moiety of formula:

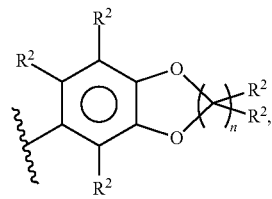

n is 1 or 2;

the moiety $(L)_x$ is selected from:

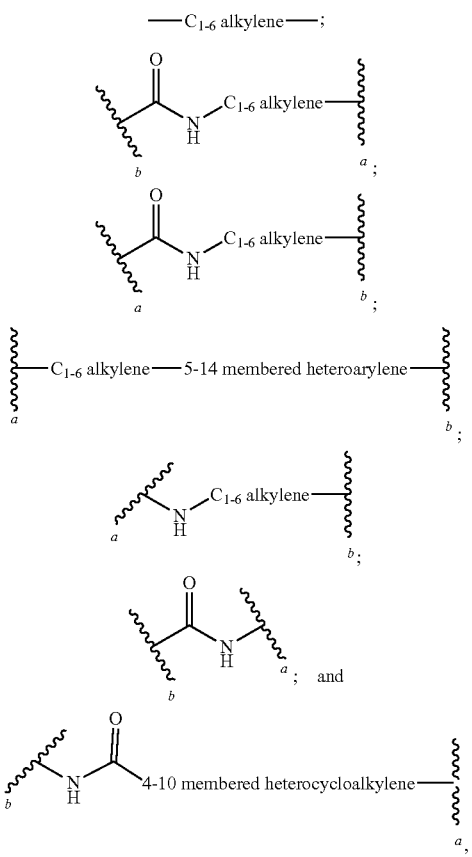

wherein said $C_{1-6}$ alkylene, 5-14 membered heteroarylene, and 4-10 membered heterocycloalkylene of $(L)_x$ are each optionally substituted with 1, 2, or 3 substituents independently selected from $R^4$;

wherein a denotes a point of attachment of (L), to ring A, and b denotes a point of attachment of $(L)_x$ to ring B; and wherein:

$R^4$ is selected from $C_{1-6}$ alkyl, $C_{1-6}$ haloalkyl, halo, CN, $NO_2$, OH, and $NH_2$, wherein said $C_{1-6}$ alkyl of $R^4$ is optionally substituted with 1, 2, or 3 substituents independently selected from halo, CN, $NO_2$, OH, and $NH_2$;

$R^1$ is selected from $C_{1-6}$ alkyl, $C_{1-4}$ haloalkyl, $Cy^1$, halo, CN, $NO_2$, OH, $C(O)NR^{c1}R^{d1}$, $C(O)OR^{a1}$, $NH_2$, $S(O)_2 R^{b1}$, thioxo and oxo; wherein said $C_{1-6}$ alkyl of $R^1$ is optionally substituted with 1, 2, or 3 substituents independently selected from halo, CN, $NO_2$, OH, C(O)$NH_2$, C(O)OH, and $NH_2$; and $R^2$ is selected from $C_{1-6}$ alkyl, $C_{1-4}$ haloalkyl, $Cy^2$, halo, CN, $NO_2$, OH, $C(O)R^{b2}$, $C(O)OR^{a2}$, $NH_2$, $S(O)_2R^{b2}$, thioxo and oxo; wherein said $C_{1-6}$ alkyl of $R^2$ is optionally substituted with 1, 2, or 3 substituents independently selected from halo, CN, $NO_2$, OH, C(O)$NH_2$, C(O)OH, and $NH_2$.

In some embodiments of Formulae (I-I), (I-IVa)-(I-IVc), or (I-Va)-(I-Vc):

x is 1, 2, 3, or 4;
each L is independently selected from C(=O), $N(R^3)$, $C_{1-6}$ alkylene, 4-10 membered heterocycloalkylene, and 5-14 membered heteroarylene, wherein said $C_{1-6}$ alkylene, 4-10 membered heterocycloalkylene, and 5-14 membered heteroarylene are each optionally substituted with 1-10 (e.g., 1, 2, or 3) substituents independently selected from $R^4$.

m (if present) is 1 or 2;
n is 1 or 2;
$X^1$, $X^2$, $X^3$, and $X^5$ (if present) are each independently selected from $C(R^2)_{1-2}$ and $N(R^2)_{0-1}$;
$X^4$ and $X^6$ (if present) are each independently selected from O and S;
$R^3$ is selected from H, $C_{1-6}$ alkyl, and $C_{1-6}$ haloalkyl;
$R^4$ is selected from $C_{1-6}$ alkyl, $C_{1-6}$ haloalkyl, $C_{2-6}$ alkenyl, $Cy^3$, halo, CN, $NO_2$, $OR^{a3}$, $NR^{c3}R^{d3}$, wherein said $C_{1-6}$ alkyl, and $C_{2-6}$ alkenyl of $R^4$ are each optionally substituted with 1, 2, 3, 4, or 5 substituents independently selected from $Cy^3$, halo, CN, $NO_2$, $OR^{a3}$, and $NR^{c3}R^{d3}$.

each $R^1$ is selected from H, $C_{1-6}$ alkyl, $C_{2-6}$ alkenyl, $C_{1-4}$ haloalkyl, $Cy^1$, halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, $S(O)_2NR^{c1}R^{d1}$, thioxo and oxo; wherein said $C_{1-6}$ alkyl and $C_{2-6}$ alkenyl substituents of $R^1$ are each optionally substituted with 1, 2, or 3 substituents independently selected from $Cy^1$, halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$ and $S(O)_2NR^{c1}R^{d1}$;

each $R_2$ is independently selected from H, $C_{1-6}$ alkyl, $C_{1-6}$ haloalkyl, $Cy^2$, halo, CN, $NO_2$, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$, thioxo and oxo; wherein said $C_{1-6}$ alkyl, $C_{2-6}$ alkenyl, and $C_{2-6}$ alkynyl substituents of $R^1$ are each optionally substituted with 1, 2, 3, 4, or 5 substituents independently selected from $Cy^2$, halo, CN, $NO_2$, $OR^{a2}$, $C(O)R^{b2}$, $C(O)NR^{c2}R^{d2}$, $C(O)OR^{a2}$, $NR^{c2}R^{d2}$, $S(O)_2R^{b2}$ and $S(O)_2NR^{c2}R^{d2}$;

each $Cy^1$ and $Cy^2$ is independently selected from $C_{6-10}$ aryl, 5-10 membered heteroaryl, and 4-12 membered heterocycloalkyl, each of which is optionally substituted with 1, 2, or 3 substituents independently selected from $R^{Cy}$.

each $R^{Cy}$ is independently selected from halo, $C_{1-4}$ alkyl, $C_{1-4}$ haloalkyl, $C_{2-6}$ alkenyl, $C_{6-10}$ aryl, $C_{3-7}$ cycloalkyl, 5-6 membered heteroaryl, 4-7 membered heterocycloalkyl, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl, $C_{2-6}$ alkenyl, $C_{6-10}$ aryl, $C_{3-7}$ cycloalkyl, 5-6 membered heteroaryl, 4-7 membered heterocycloalkyl are each optionally substituted by 1, 2, 3, 4, or 5 substituents independently selected from $C_{1-6}$ alkyl, $C_{1-4}$ haloalkyl, halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$;

each $R^{a1}$, $R^{b1}$, $R^{a2}$, $R^{b2}$, $R^{a3}$, $R^{b3}$, $R^{a4}$, and $R^{b4}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, and 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl are optionally substituted with 1, 2, or 3 substituents independently selected from $R^g$;

each $R^{c1}$, $R^{d1}$, $R^{c2}$, $R^{d2}$, $R^{c3}$, $R^{d3}$, $R^{c4}$, and $R^{d4}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, $C(O)R^{b5}$, C(O)

$NR^{c5}R^{d5}$, $C(O)OR^{a5}$, $S(O)_2R^{b5}$, and $S(O)_2NR^{c5}R^{d5}$; wherein said $C_{1-6}$ alkyl, $C_{6-10}$ aryl, $C_{3-10}$ cycloalkyl, 5-10 membered heteroaryl, and 4-12 membered heterocycloalkyl are each optionally substituted with 1, 2, or 3 substituents independently selected from $R^g$; and each $R^{a5}$, $R^{b5}$, $R^{c5}$, and $R^{d5}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^g$.

In some embodiments, the compound described herein is selected from any one of the compounds listed in Table 3. In some embodiments, the compound described herein is not any one of the compounds listed in Table 3.

In a general aspect, the present disclosure provides compound of Formula (II-I):

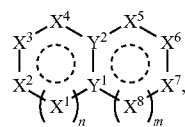

(II-I)

or a pharmaceutically acceptable salt thereof, wherein:

◯ represents that the ring is saturated, partially unsaturated, or aromatic;

$Y^1$ and $Y^2$ are each independently selected from C, N and $CR^1$;

$X^1$ is selected from N, $NR^{N1}$, O, S, $CR^1$, and $C(R^1)_2$;
$X^2$ is selected from N, $NR^{N2}$, O, S, $CR^2$, and $C(R^2)_2$;
$X^3$ is selected from N, $NR^{N3}$, O, S, $CR^3$, and $C(R^3)_2$;
$X^4$ is selected from N, $NR^{N4}$, O, S, $CR^4$, and $C(R^4)_2$;
$X^5$ is selected from N, $NR^{N5}$, O, S, $CR^5$, and $C(R^5)_2$;
$X^6$ is selected from N, $NR^{N6}$, O, S, $CR^6$, and $C(R^6)_2$;
$X^7$ is selected from N, $NR^{N7}$, O, S, $CR^7$, and $C(R^7)_2$;
$X^8$ is selected from N, $NR^{N8}$, O, S, $CR^8$, and $C(R^8)_2$;

$R^1$, $R^2$, $R^3$, $R^4$, $R^5$, $R^6$, $R^7$, and $R^8$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, thioxo and oxo; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$;

$R^{N1}$, $R^{N2}$, $R^{N3}$, $R^{N4}$, $R^{N5}$, $R^{N6}$, $R^{N7}$, and $R^{N8}$ are each independently selected from H, $C_{1-6}$ alkyl, $C_{2-6}$ alkenyl, $C_{2-6}$ alkynyl, $C_{1-6}$ haloalkyl, $Cy^2$, $C(O)R^{b2}$, $C(O)NR^{c2}R^{d2}$, $C(O)OR^{a2}$, $C(=NR^{e2})NR^{c2}R^{d2}$, $S(O)R^{b2}$, $S(O)NR^{c2}R^{d2}$, $S(O)_2R^{b2}$, and $S(O)_2NR^{c2}R^{d2}$, wherein said $C_{1-6}$ alkyl, $C_{2-6}$ alkenyl, and $C_{2-6}$ alkynyl are each optionally substituted with 1, 2, 3, 4, or 5 substituents independently selected from $Cy^2$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$ and $S(O)_2NR^{c2}R^{d2}$; or any two $R^1$ together with the carbon atom to which they are attached form a ring selected from $C_{3-10}$ cycloalkyl and 4-12 membered heterocycloalkyl, each of which is optionally substituted with 1, 2, 3, 4, or 5 substituents independently selected from $R^{Cy5}$; or any two $R^2$ together with the carbon atom to which they are attached form a ring selected from $C_{3-10}$ cycloalkyl and 4-12 membered heterocycloalkyl, each of which is optionally substituted with 1, 2, 3, 4, or 5 substituents independently selected from $R^{Cy5}$; or any two $R^3$ together with the carbon atom to which they are attached form a ring selected from $C_{3-10}$ cycloalkyl and 4-12 membered heterocycloalkyl, each of which is optionally substituted with 1, 2, 3, 4, or 5 substituents independently selected from $R^{Cy5}$; or any two $R^4$ together with the carbon atom to which they are attached form a ring selected from $C_{3-10}$ cycloalkyl and 4-12 membered heterocycloalkyl, each of which is optionally substituted with 1, 2, 3, 4, or 5 substituents independently selected from $R^{Cy5}$; or any two $R^5$ together with the carbon atom to which they are attached form a ring selected from $C_{3-10}$ cycloalkyl and 4-12 membered heterocycloalkyl, each of which is optionally substituted with 1, 2, 3, 4, or 5 substituents independently selected from $R^{Cy5}$; or any two $R^6$ together with the carbon atom to which they are attached form a ring selected from $C_{3-10}$ cycloalkyl and 4-12 membered heterocycloalkyl, each of which is optionally substituted with 1, 2, 3, 4, or 5 substituents independently selected from $R^{Cy5}$; or any two $R^7$ together with the carbon atom to which they are attached form a ring selected from $C_{3-10}$ cycloalkyl and 4-12 membered heterocycloalkyl, each of which is optionally substituted with 1, 2, 3, 4, or 5 substituents independently selected from $R^{Cy5}$; or any two $R^8$ together with the carbon atom to which they are attached form a ring selected from $C_{3-10}$ cycloalkyl and 4-12 membered heterocycloalkyl, each of which is optionally substituted with 1, 2, 3, 4, or 5 substituents independently selected from $R^{Cy5}$; or any two $R^1$ and $R^2$ together with the carbon atoms to which they are attached form a ring selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy5}$; or any two $R^1$ and $R^{N2}$ together with the carbon atom to which $R^1$ is attached and N to which $R^{N2}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N1}$ and $R^2$ together with the carbon atom to which $R^2$ is attached and N to which $R^{N1}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N1}$ and $R^{N2}$ together with the N atoms to which they are attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^1$ and $R^4$ together with the carbon atoms to which they are attached form a ring selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy5}$; or any two $R^1$ and $R^{N4}$ together with the carbon atom to which $R^1$ is attached and N to which $R^{N4}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N1}$ and $R^4$ together with the carbon atom to which $R^4$ is attached and N to which $R^{N1}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N1}$ and $R^{N4}$ together with the N atoms to which they are attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^1$ and $R^8$ together with the carbon atoms to which they are attached form a ring selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy5}$; or any two $R^1$ and $R^{N8}$ together with the carbon atom to which $R^1$ is attached and N to which $R^{N8}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N1}$ and $R^8$ together with the carbon atom to which $R^g$ is attached and N to which $R^{N1}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N1}$ and $R^{N8}$ together with the N atoms to which they are attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^2$ and $R^3$ together with the carbon atoms to which they are attached form a ring selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy5}$; or any two $R^2$ and $R^{N3}$ together with the carbon atom to which $R^2$ is attached and N to which $R^{N3}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N2}$ and $R^3$ together with the carbon atom to which $R^3$ is attached and N to which $R^{N2}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N2}$ and $R^{N3}$ together with the N atoms to which they are attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^4$ and $R^3$ together with the carbon atoms to which they are attached form a ring selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy5}$; or any two $R^4$ and $R^{N3}$ together with the carbon atom to which $R^4$ is attached and N to which $R^{N3}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N4}$ and $R^3$ together with the carbon atom to which $R^3$ is attached and N to which $R^{N4}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N4}$ and $R^{N3}$ together with the N atoms to which they are attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^4$ and $R^5$ together with the carbon atoms to which they are attached form a ring selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy5}$; or any two $R^4$ and $R^{N5}$ together with the carbon atom to which $R^4$ is attached and N to which $R^{N5}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N4}$ and $R^5$ together with the carbon atom to which $R^5$ is attached and N to which $R^{N4}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N4}$ and RNS together with the N atoms to which they are attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^6$ and $R^5$ together with the carbon atoms to which they are attached form a ring selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy5}$; or any two $R^6$ and $R^{N5}$ together with the carbon atom to which $R^6$ is attached and N to which RNS is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N6}$ and $R^5$ together with the carbon atom to which $R^5$ is attached and N to which $R^{N6}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N6}$ and $R^{N5}$ together with the N atoms to which they are attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^6$ and $R^7$ together with the carbon atoms to which they are attached form a ring selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy5}$; or any two $R^6$ and $R^{N7}$ together with the carbon atom to which $R^6$ is attached and N to which $R^{N7}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N6}$ and $R^7$ together with the carbon atom to which $R^7$ is attached and N to which $R^{N6}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N6}$ and $R^{N7}$ together with the N atoms to which they are attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^8$ and $R^7$ together with the carbon atoms to which they are attached form a ring selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy5}$; or any two $R^8$ and $R^{N7}$ together with the carbon atom to which $R^g$ is attached and N to which $R^{N7}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N8}$ and $R^7$ together with the carbon atom to which $R^7$ is attached and N to which $R^{N8}$ is attached form a ring selected from 5-10 membered heteroaryl and 4-12 membered heterocycloalkyl, each of which is optionally substituted with 1, 2, 3, 4, or 5 substituents independently selected from $R^{Cy5}$; or any two $R^{N8}$ and $R^{N7}$ together with the N atoms to which they are attached form a ring selected from 5-10 membered heteroaryl and 4-12 membered heterocycloalkyl, each of which is optionally substituted with 1, 2, 3, 4, or 5 substituents independently selected from $R^{Cy5}$;

$R^{a1}$, $R^{a2}$, $R^{c1}$, $R^{c2}$, $R^{d1}$, and $R^{d2}$ are each independently selected from H, $C_{1-6}$ alkyl, $C_{2-6}$ alkenyl, $C_{2-6}$ alkynyl, $C_{1-4}$ haloalkyl, $Cy^3$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $S(O)R^{b3}$, $S(O)NR^{c3}R^{d3}$, $S(O)_2R^{b3}$, $S(O)_2 NR^{c3}R^{d3}$, wherein said $C_{1-6}$ alkyl, $C_{2-6}$ alkenyl, and $C_{2-6}$ alkynyl are each optionally substituted with 1, 2, 3, 4, or 5 substituents independently selected from $Cy^3$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$.

$R^{b1}$ and $R^{b2}$ are each independently selected from $C_{1-6}$ alkyl, $C_{2-6}$ alkenyl, $C_{2-6}$ alkynyl, $C_{1-4}$ haloalkyl, and $Cy^3$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^3$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$;

$R^{a3}$, $R^{c3}$, and $R^{d3}$ are each independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, $C(O)R^{b4}$, $C(O)NR^{c4}R^{d4}$, $C(O)OR^{a4}$, $NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are each optionally substituted with 1, 2, 3, 4, or 5 substituents independently selected from oxo, $C_{1-6}$ alkyl, $C_{1-4}$ haloalkyl, $C_{1-4}$ hydroxyalkyl, $C_{1-6}$ cyanoalkyl, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2 NR^{c4}R^{d4}$;

$R^{b3}$ is selected from $C_{1-6}$ alkyl, $C_{2-6}$ alkenyl, $C_{2-6}$ alkynyl, $C_{1-4}$ haloalkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are each optionally substituted with 1, 2, 3, 4, or 5 substituents independently selected from $C_{1-6}$ alkyl, $C_{1-4}$ haloalkyl, $C_{1-4}$ hydroxyalkyl, $C_{1-6}$ cyanoalkyl, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $Cy^1$ is independently selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy1}$;

each $Cy^2$ is independently selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy2}$, each $Cy^3$ is independently selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy3}$;

$R^{Cy1}$, $R^{Cy2}$, $R^{Cy3}$, and $R^{Cy5}$ are each independently selected from halo, $C_{1-4}$ alkyl, $C_{1-4}$ haloalkyl, $C_{2-6}$ alkenyl, $C_{2-6}$ alkynyl, $Cy^4$, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-4}$ alkyl, $C_{2-6}$ alkenyl, and $C_{2-6}$ alkynyl are each optionally substituted by 1, 2, 3, 4, or 5 substituents independently selected from $Cy^4$, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $Cy^4$ is independently selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy4}$;

each $R^{Cy4}$ is independently selected from halo, $C_{1-4}$ alkyl, $C_{1-4}$ haloalkyl, $C_{2-6}$ alkenyl, $C_{2-6}$ alkynyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene, $C_{3-7}$ cycloalkyl-$C_{1-4}$ alkylene, (5-6 membered heteroaryl)-$C_{1-4}$ alkylene, and (4-7 membered heterocycloalkyl)-$C_{1-4}$ alkylene, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{d4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-4}$ alkyl, $C_{1-4}$ haloalkyl, $C_{2-6}$ alkenyl, $C_{2-6}$ alkynyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene, $C_{3-7}$ cycloalkyl-$C_{1-4}$ alkylene, (5-6 membered heteroaryl)-$C_{1-4}$ alkylene, and (4-7 membered heterocycloalkyl)-$C_{1-4}$ alkylene are each optionally substituted by 1, 2, 3, 4, or 5 substituents independently selected from halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

$R^{a4}$, $R^{c4}$, and $R^{d4}$ are each independently selected from H, $C_{1-6}$ alkyl, $C_{1-4}$ haloalkyl, $C_{1-4}$ hydroxyalkyl, $C_{1-4}$ cyanoalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene and $R^g$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are each optionally substituted with 1, 2, 3, 4, or 5 substituents independently selected from $R^g$;

each $R^{b4}$ is independently selected from $C_{1-6}$ alkyl, $C_{1-4}$ haloalkyl, $C_{1-4}$ hydroxyalkyl, $C_{1-4}$ cyanoalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene and $R^g$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, 3, 4, or 5 substituents independently selected from $R^g$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $R^g$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $R^g$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $R^g$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $R^g$;

each $R^{e1}$, $R^{e2}$, $R^{e3}$, and $R^{e4}$ is independently selected from H, $C_{1-4}$ alkyl, $C_{1-4}$ alkoxy, OH, and CN;

each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

n is an integer from 0 to 3, wherein when n is 0 then $X^1$ is a bond between $Y^1$ and $X^2$; and m is an integer from 0 to 3, wherein when m is 0 then $X^8$ is a bond between $Y^1$ and $X^7$.

In some embodiments, $Y^1$ is C. In some embodiments, $Y^1$ is N.

In some embodiments, $Y^2$ is C. In some embodiments, $Y^2$ is N.

In some embodiments, $X^1$ is N. In some embodiments, $X^1$ is $NR^{N1}$. In some embodiments, $X^1$ is $CR^1$. In some embodiments, $X^1$ is $C(R^1)_2$.

In some embodiments, $X^2$ is N. In some embodiments, $X^2$ is $NR^{N2}$. In some embodiments, $X^2$ is O. In some embodiments, $X^2$ is S. In some embodiments, $X^2$ is $CR^2$. In some embodiments, $X^2$ is and $C(R^2)_2$.

In some embodiments, $X^3$ is N. In some embodiments, $X^3$ is $NR^{N3}$. In some embodiments, $X^3$ is O. In some embodiments, $X^3$ is S. In some embodiments, $X^3$ is $CR^3$. In some embodiments, $X^3$ is and $C(R^3)_2$.

In some embodiments, $X^4$ is N. In some embodiments, $X^4$ is $NR^{N4}$. In some embodiments, $X^4$ is S. In some embodiments, $X^4$ is $CR^4$. In some embodiments, $X^4$ is and $C(R^4)_2$.

In some embodiments, $X^5$ is N. In some embodiments, $X^5$ is $NR^{N5}$. In some embodiments, $X^5$ is O. In some embodiments, $X^5$ is S. In some embodiments, $X^5$ is $CR^5$. In some embodiments, $X^5$ is and $C(R^5)_2$.

In some embodiments, $X^6$ is N. In some embodiments, $X^6$ is $NR^{N6}$. In some embodiments, $X^6$ is $CR^6$. In some embodiments, $X^6$ is and $C(R^6)_2$.

In some embodiments, $X^7$ is N. In some embodiments, $X^7$ is $NR^{N7}$. In some embodiments, $X^7$ is S. In some embodiments, $X^7$ is $CR^7$. In some embodiments, $X^7$ is and $C(R^7)_2$.

In some embodiments, $X^8$ is N. In some embodiments, $X^8$ is $NR^{N8}$. In some embodiments, $X^8$ is O. In some embodiments, $X^8$ is S. In some embodiments, $X^8$ is $CR^8$. In some embodiments, $X^8$ is and $C(R^8)_2$.

In some embodiments, not more than two of $X^1$, $X^2$, $X^3$, $X^4$, $X^5$, $X^6$, $X^7$, and $X^8$ is N. In some embodiments, not more than four of $X^1$, $X^2$, $X^3$, $X^4$, $X^5$, $X^6$, $X^7$, and $X^8$ is N. In some embodiments, not more than one of $X^1$, $X^2$, $X^3$, $X^4$, $X^5$, $X^6$, $X^7$, and $X^8$ is O. In some embodiments, not more than two of $X^1$, $X^2$, $X^3$, $X^4$, $X^5$, $X^6$, $X^7$, and $X^8$ is S. In some embodiments, at least one of $X^1$, $X^2$, $X^3$, $X^4$, $X^5$, $X^6$, $X^7$, and $X^8$ contains N. That is, at least one of $X^1$, $X^2$, $X^3$, $X^4$, $X^5$, $X^6$, $X^7$, and $X^8$ is N or N bonded to an $R^N$ group (e.g., $R^{N1}$, $R^{N2}$, $R^{N3}$, $R^{N4}$, $R^{N5}$, $R^{N6}$, $R^{N7}$, or $R^{N8}$). In some embodiments, at least one of $X^1$, $X^2$, $X^3$, $X^4$, $X^5$, $X^6$, $X^7$, and $X^8$ is O. In some embodiments, at least one of $X^1$, $X^2$, $X^3$, $X^4$, $X^5$, $X^6$, $X^7$, and $X^8$ is S. In some embodiments, at least four of $X^1$, $X^2$, $X^3$, $X^4$, $X^5$, $X^6$, $X^7$, and $X^8$ contain C, wherein C is bonded to an R-group (e.g., at least one of $R^1$, $R^2$, $R^3$, $R^4$, $R^5$, $R^6$, $R^7$, or $R^8$).

In some embodiments, both of the rings ◯ are aromatic. In some embodiments, both of the rings ◯ are fully saturated. In some embodiments, both of the rings ◯ are partially unsaturated. In some embodiments, one of the rings ◯ is aromatic and the other ring is fully saturated. In some embodiments, one of the rings ◯ is aromatic, and the other ring is partially unsaturated. In some embodiments, one of the rings ◯ is partially unsaturated and the other ring is fully saturated.

In some embodiments, n is 0. In some embodiments, n is 1. In some embodiments, n is 2. In some embodiments, n is 3. In some embodiments, m is 0.

In some embodiments, m is 1. In some embodiments, m is 2. In some embodiments, m is 3.

In some embodiments, n is 0 and m is 1. In some embodiments, n is 1 and m is 0. In some embodiments, n is 0 and m is 0. In some embodiments, n is 1 and m is 1.

In some embodiments, $R^1$, $R^2$, $R^3$, $R^4$, $R^5$, $R^6$, $R^7$, and $R^8$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, thioxo and oxo; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$.

In some embodiments, $R^1$, $R^2$, $R^3$, $R^4$, $R^5$, $R^6$, $R^7$, and $R^8$ are each independently selected from H, $C_{1-6}$ alkyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NRCS(O)_2R^{b1}$, $NR^{c1}S(O)_2NR^{c1}R^{d1}$, $S(O)_2R^{b1}$, $S(O)_2NR^{c1}R^{d1}$, and oxo; wherein said $C_{1-6}$ alkyl is optionally substituted with 1, 2, or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$ and $S(O)_2NR^{c1}R^{d1}$.

In some embodiments, $R^1$, $R^2$, $R^3$, $R^4$, $R^5$, $R^6$, $R^7$, and $R^8$ are each independently selected from H, $C_{1-6}$ alkyl, $Cy^1$, halo, CN, $OR^{a1}$, $SR^{a1}$, $C(O)R^{b1}$, $C(O)NR^{c1}R^{d1}$, $C(O)OR^{a1}$, $C(O)R^{b1}$, $NR^{c1}R^{d1}$, $NR^{c1}C(O)R^{b1}$, $NR^{c1}C(O)NR^{c1}R^{d1}$, $NR^{c1}S(O)_2R^{b1}$, $S(O)_2R^{b1}$, $S(O)_2NR^{c1}R^{d1}$, and oxo; wherein said $C_{1-6}$ alkyl is optionally substituted with 1, 2, or 3 substituents independently selected from $Cy^1$, $SR^{a1}$, $C(O)NR^{c1}R^{d1}$, $C(O)OR^{a1}$, $NR^{c1}R^{d1}$, $NR^{c1}S(O)_2R^{b1}$, and $S(O)_2R^{b1}$.

In some embodiments, at least one of $R^1$, $R^2$, $R^3$, $R^4$, $R^5$, $R^6$, $R^7$, and $R^8$ is trifluoromethoxy. In some embodiments, at least one of $R^1$, $R^2$, $R^3$, $R^4$, $R^5$, $R^6$, $R^7$, and $R^8$ is trifluoromethyl.

In some embodiments, $R^1$ is $C_{1-6}$ alkyl, optionally substituted with 1, 2, or 3 substituents independently selected from $Cy^1$, $SR^{a1}$, $C(O)NR^{c1}R^{d1}$, $C(O)OR^{a1}$, $NR^{c1}R^{d1}$, $NR^{c1}S(O)_2R^{b1}$, and $S(O)_2R^{b1}$. In some embodiments, $R^1$ is H. In some embodiments, $R^1$ is $Cy^1$. In some embodiments, $R^1$ is halo. In some embodiments, $R^1$ is CN. In some embodiments, $R^1$ is $OR^{a1}$. In some embodiments, $R^1$ is $SR^{a1}$. In some embodiments, $R^1$ is $C(O)R^{b1}$. In some embodiments, $R^1$ is $C(O)NR^{c1}R^{d1}$. In some embodiments, $R^1$ is $C(O)OR^{a1}$. In some embodiments, $R^1$ is $C(O)R^{b1}$. In some embodiments, $R^1$ is $NR^{c1}R^{d1}$. In some embodiments, $R^1$ is $NR^{c1}C(O)R^{b1}$. In some embodiments, $R^1$ is $NR^{c1}C(O)NR^{c1}R^{d1}$. In some embodiments, $R^1$ is $NR^{c1}S(O)_2R^{b1}$. In some embodiments, $R^1$ is $S(O)_2R^{b1}$. In some embodiments, $R^1$ is $S(O)_2NR^{c1}R^{d1}$. In some embodiments, $R^1$ is oxo. In some embodiments, $R^1$ is trifluoromethoxy.

In some embodiments, $R^2$ is $C_{1-6}$ alkyl, optionally substituted with 1, 2, or 3 substituents independently selected from $Cy^1$, $SR^{a1}$, $C(O)NR^{c1}R^{d1}$, $C(O)OR^{a1}$, $NR^{c1}R^{d1}$, $NR^{c1}S(O)_2R^{b1}$, and $S(O)_2R^{b1}$. In some embodiments, $R^2$ is H. In some embodiments, $R^2$ is $Cy^1$. In some embodiments, $R^2$ is halo. In some embodiments, $R^2$ is CN. In some embodiments, $R^2$ is $OR^{a1}$. In some embodiments, $R^2$ is $SR^{a1}$. In some embodiments, $R^2$ is $C(O)R^{b1}$. In some embodiments, $R^2$ is $C(O)NR^{c1}R^{d1}$. In some embodiments, $R^2$ is $C(O)OR^{a1}$. In some embodiments, $R^2$ is $C(O)R^{b1}$. In some embodiments, $R^2$ is $NR^{c1}R^{d1}$. In some embodiments, $R^2$ is $NR^{c1}C(O)R^{b1}$. In some embodiments, $R^2$ is $NR^{c1}C(O)$ $NR^{c1}R^{d1}$. In some embodiments, $R^2$ is $NR^{c1}S(O)_2R^{b1}$. In some embodiments, $R^2$ is $S(O)_2R^{b1}$. In some embodiments, $R^2$ is $S(O)_2NR^{c1}R^{d1}$. In some embodiments, $R^2$ is oxo. In some embodiments, $R^2$ is trifluoromethoxy.

In some embodiments, $R^3$ is $C_{1-6}$ alkyl, optionally substituted with 1, 2, or 3 substituents independently selected from $Cy^1$, $SR^{a1}$, $C(O)NR^{c1}R^{d1}$, $C(O)OR^{a1}$, $NR^{c1}R^{d1}$, $NR^{c1}S(O)_2R^{b1}$, and $S(O)_2R^{b1}$. In some embodiments, $R^3$ is H. In some embodiments, $R^3$ is $Cy^1$. In some embodiments, $R^3$ is halo. In some embodiments, $R^3$ is CN. In some embodiments, $R^3$ is $OR^{a1}$. In some embodiments, $R^3$ is $SR^{a1}$. In some embodiments, $R^3$ is $C(O)R^{b1}$. In some embodiments, $R^3$ is $C(O)NR^{c1}R^{d1}$. In some embodiments, $R^3$ is $C(O)OR^{a1}$. In some embodiments, $R^3$ is $C(O)R^{b1}$. In some embodiments, $R^3$ is $NR^{c1}R^{d1}$. In some embodiments, $R^3$ is $NR^{c1}C(O)R^{b1}$. In some embodiments, $R^3$ is $NR^{c1}C(O)NR^{c1}R^{d1}$. In some embodiments, $R^3$ is $NR^{c1}S(O)_2R^{b1}$. In some embodiments, $R^3$ is $S(O)_2R^{b1}$. In some embodiments, $R^3$ is $S(O)_2NR^{c1}R^{d1}$. In some embodiments, $R^3$ is oxo. In some embodiments, $R^3$ is trifluoromethoxy.

In some embodiments, $R^4$ is $C_{1-6}$ alkyl, optionally substituted with 1, 2, or 3 substituents independently selected from $Cy^1$, $SR^{a1}$, $C(O)NR^{c1}R^{d1}$, $C(O)OR^{a1}$, $NR^{c1}R^{d1}$, $NR^{c1}S(O)_2R^{b1}$, and $S(O)_2R^{b1}$. In some embodiments, $R^4$ is H. In some embodiments, $R^4$ is $Cy^1$. In some embodiments, $R^4$ is halo. In some embodiments, $R^4$ is CN. In some embodiments, $R^4$ is $OR^{a1}$. In some embodiments, $R^4$ is $SR^{a1}$. In some embodiments, $R^4$ is $C(O)R^{b1}$. In some embodiments, $R^4$ is $C(O)NR^{c1}R^{d1}$. In some embodiments, $R^4$ is $C(O)OR^{a1}$. In some embodiments, $R^4$ is $C(O)R^{b1}$. In some embodiments, $R^4$ is $NR^{c1}R^{d1}$. In some embodiments, $R^4$ is $NR^{c1}C(O)R^{b1}$. In some embodiments, $R^4$ is $NR^{c1}C(O)NR^{c1}R^{d1}$. In some embodiments, $R^4$ is $NR^{c1}S(O)_2R^{b1}$. In some embodiments, $R^4$ is $S(O)_2R^{b1}$. In some embodiments, $R^4$ is $S(O)_2NR^{c1}R^{d1}$. In some embodiments, $R^4$ is oxo. In some embodiments, $R^4$ is trifluoromethoxy.

In some embodiments, $R^5$ is $C_{1-6}$ alkyl, optionally substituted with 1, 2, or 3 substituents independently selected from $Cy^1$, $SR^{a1}$, $C(O)NR^{c1}R^{d1}$, $C(O)OR^{a1}$, $NR^{c1}R^{d1}$, $NRC'S(O)_2R^{b1}$, and $S(O)_2R^{b1}$. In some embodiments, $R^5$ is H. In some embodiments, $R^5$ is $Cy^1$. In some embodiments, $R^5$ is halo. In some embodiments, $R^5$ is CN. In some embodiments, $R^5$ is $OR^{a1}$. In some embodiments, $R^5$ is $SR^{a1}$. In some embodiments, $R^5$ is $C(O)R^{b1}$. In some embodiments, $R^5$ is $C(O)NR^{c1}R^{d1}$. In some embodiments, $R^5$ is $C(O)OR^{a1}$. In some embodiments, $R^5$ is $C(O)R^{b1}$. In some embodiments, $R^5$ is $NR^{c1}R^{d1}$. In some embodiments, $R^5$ is $NR^{c1}C(O))R^{b1}$. In some embodiments, $R^5$ is $NR^{c1}C(O)NR^{c1}R^{d1}$. In some embodiments, $R^5$ is $NR^{c1}S(O)_2R^{b1}$. In some embodiments, $R^5$ is $S(O)_2R^{b1}$. In some embodiments, $R^5$ is $S(O)_2NR^{c1}R^{d1}$. In some embodiments, $R^5$ is oxo. In some embodiments, $R^5$ is trifluoromethoxy.

In some embodiments, $R^6$ is $C_{1-6}$ alkyl, optionally substituted with 1, 2, or 3 substituents independently selected from $Cy^1$, $SR^{a1}$, $C(O)NR^{c1}R^{d1}$, $C(O)OR^{a1}$, $NR^{c1}R^{d1}$, $NR^{c1}S(O)_2R^{b1}$, and $S(O)_2R^{b1}$. In some embodiments, $R^6$ is H. In some embodiments, $R^6$ is $Cy^1$. In some embodiments, $R^6$ is halo. In some embodiments, $R^6$ is CN. In some embodiments, $R^6$ is $OR^{a1}$. In some embodiments, $R^6$ is $SR^{a1}$. In some embodiments, $R^6$ is $C(O)R^{b1}$. In some embodiments, $R^6$ is $C(O)NR^{c1}R^{d1}$. In some embodiments, $R^6$ is $C(O)OR^{a1}$. In some embodiments, $R^6$ is $C(O)R^{b1}$. In some embodiments, $R^6$ is $NR^{c1}R^{d1}$. In some embodiments, $R^6$ is $NR^{c1}C(O)R^{b1}$. In some embodiments, $R^6$ is $NR^{c1}C(O)NR^{c1}R^{d1}$. In some embodiments, $R^6$ is $NR^{c1}S(O)_2R^{b1}$. In some embodiments, $R^6$ is $S(O)_2R^{b1}$. In some embodiments, $R^6$ is $S(O)_2NR^{c1}R^{d1}$. In some embodiments, $R^6$ is oxo. In some embodiments, $R^6$ is trifluoromethoxy.

In some embodiments, $R^7$ is $C_{1-6}$ alkyl, optionally substituted with 1, 2, or 3 substituents independently selected from $Cy^1$, $SR^{a1}$, $C(O)NR^{c1}R^{d1}$, $C(O)OR^{a1}$, $NR^{c1}R^{d1}$, $NR^{c1}S(O)_2R^{b1}$, and $S(O)_2R^{b1}$. In some embodiments, $R^7$ is H. In some embodiments, $R^7$ is $Cy^1$. In some embodiments, $R^7$ is halo. In some embodiments, $R^7$ is CN. In some embodiments, $R^7$ is $OR^{a1}$. In some embodiments, $R^7$ is $SR^{a1}$. In some embodiments, $R^7$ is $C(O)R^{b1}$. In some embodiments, $R^7$ is $C(O)NR^{c1}R^{d1}$. In some embodiments, $R^7$ is $C(O)OR^{a1}$. In some embodiments, $R^7$ is $C(O)R^{b1}$. In some embodiments, $R^7$ is $NR^{c1}R^{d1}$. In some embodiments, $R^7$ is $NR^{c1}C(O)R^{b1}$. In some embodiments, $R^7$ is $NR^{c1}C(O)NR^{c1}R^{d1}$. In some embodiments, $R^7$ is $NR^{c1}S(O)_2R^{b1}$. In some embodiments, $R^7$ is $S(O)_2R^{b1}$. In some embodiments, $R^7$ is $S(O)_2NR^{c1}R^{d1}$. In some embodiments, $R^7$ is oxo. In some embodiments, $R^7$ is trifluoromethoxy.

In some embodiments, $R^8$ is $C_{1-6}$ alkyl, optionally substituted with 1, 2, or 3 substituents independently selected from $Cy^1$, $SR^{a1}$, $C(O)NR^{c1}R^{d1}$, $C(O)OR^{a1}$, $NR^{c1}R^{d1}$, $NR^{c1}S(O)_2R^{b1}$, and $S(O)_2R^{b1}$. In some embodiments, $R^g$ is H. In some embodiments, $R^g$ is $Cy^1$. In some embodiments, $R^g$ is halo. In some embodiments, $R^8$ is CN. In some embodiments, $R^g$ is $OR^{a1}$. In some embodiments, $R^g$ is $SR^{a1}$. In some embodiments, $R^g$ is $C(O)R^{b1}$. In some embodiments, $R^8$ is $C(O)NR^{c1}R^{d1}$. In some embodiments, $R^8$ is $C(O)OR^{a1}$. In some embodiments, $R^8$ is $C(O)R^{b1}$. In some embodiments, $R^g$ is $NR^{c1}R^{d1}$. In some embodiments, $R^g$ is $NR^{c1}C(O)R^{b1}$. In some embodiments, $R^g$ is $NR^{c1}C(O)NR^{c1}R^{d1}$. In some embodiments, $R^g$ is $NR^{c1}S(O)_2R^{b1}$. In some embodiments, $R^g$ is $S(O)_2R^{b1}$. In some embodiments, $R^g$ is $S(O)_2NR^{c1}R^{d1}$. In some embodiments, $R^g$ is oxo. In some embodiments, $R^8$ is trifluoromethoxy.

In some embodiments, $R^{N1}$, $R^{N2}$, $R^{N3}$, $R^{N4}$, $R^{N5}$, $R^{N6}$, $R^{N7}$, and $R^{N8}$ are each independently selected from H, $C_{1-6}$ alkyl, $C_{2-6}$ alkenyl, $C_{2-6}$ alkynyl, $C_{1-6}$ haloalkyl, $Cy^2$, $C(O)R^{b2}$, $C(O)NR^{c2}R^{d2}$, $C(O)OR^{a2}$, $C(=NR^{e2})NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^2$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})N^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$ and $S(O)_2NR^{c2}R^{d2}$.

In some embodiments, $R^{N1}$, $R^{N2}$, $R^{N3}$, $R^{N4}$, $R^{N5}$, $R^{N6}$, $R^{N7}$, and $R^{N8}$ are each independently selected from H, $C_{1-6}$ alkyl, $C_{1-6}$ haloalkyl, $Cy^2$, $C(O)R^{b2}$, $C(O)NR^{c2}R^{d2}$, $C(O)OR^{a2}$, $S(O)_2R^{b2}$, and $S(O)_2NR^{c2}R^{d2}$; wherein said $C_{1-6}$ alkyl is optionally substituted with 1, 2, or 3 substituents independently selected from $Cy^2$, halo, CN, $NO_2$, $OR^{a2}$, $SR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2N^{c2}R^{d2}$, $S(O)_2R^{b2}$ and $S(O)_2NR^{c2}R^{d2}$.

In some embodiments, $R^{N1}$, $R^{N2}$, $R^{N3}$, $R^{N4}$, $R^{N5}$, $R^{N6}$, $R^{N7}$, and $R^{N8}$ are each independently selected from H, $C_{1-6}$ alkyl, $Cy^2$, and $C(O)R^{b2}$; wherein said $C_{1-6}$ alkyl is optionally substituted with 1, 2, or 3 substituents independently selected from $Cy^2$, $C(O)NR^{c2}R^{d2}$, and $C(O)OR^{a2}$.

In some embodiments, $R^{N1}$ is H. In some embodiments, $R^{N1}$ is $C_{1-6}$ alkyl, optionally substituted with 1, 2, or 3 substituents independently selected from $Cy^2$, $C(O)NR^{c2}R^{d2}$, and $C(O)OR^{a2}$. In some embodiments, $R^{N1}$ is $Cy^2$. In some embodiments, $R^{N1}$ is $C(O)R^{b2}$.

In some embodiments, $R^{N2}$ is H. In some embodiments, $R^{N2}$ is $C_{1-6}$ alkyl, optionally substituted with 1, 2, or 3 substituents independently selected from $Cy^2$, $C(O)NR^{c2}R^{d2}$, and $C(O)OR^{a2}$. In some embodiments, $R^{N2}$ is $Cy^2$. In some embodiments, $R^{N2}$ is $C(O)R^{b2}$.

In some embodiments, $R^{N3}$ is H. In some embodiments, $R^{N3}$ is $C_{1-6}$ alkyl, optionally substituted with 1, 2, or 3 substituents independently selected from $Cy^2$, $C(O)NR^{c2}R^{d2}$, and $C(O)OR^{a2}$. In some embodiments, $R^{N3}$ is $Cy^2$. In some embodiments, $R^{N3}$ is $C(O)R^{b2}$.

In some embodiments, $R^{N4}$ is H. In some embodiments, $R^{N4}$ is $C_{1-6}$ alkyl, optionally substituted with 1, 2, or 3 substituents independently selected from $Cy^2$, $C(O)NR^{c2}R^{d2}$, and $C(O)OR^{a2}$. In some embodiments, $R^{N4}$ is $Cy^2$. In some embodiments, $R^{N4}$ is $C(O)R^{b2}$.

In some embodiments, $R^{N5}$ is H. In some embodiments, $R^{N5}$ is $C_{1-6}$ alkyl, optionally substituted with 1, 2, or 3 substituents independently selected from $Cy^2$, $C(O)NR^{c2}R^{d2}$, and $C(O)OR^{a2}$. In some embodiments, $R^{N5}$ is $Cy^2$. In some embodiments, $R^{N5}$ is $C(O)R^{b2}$.

In some embodiments, $R^{N6}$ is H. In some embodiments, $R^{N6}$ is $C_{1-6}$ alkyl, optionally substituted with 1, 2, or 3 substituents independently selected from $Cy^2$, $C(O)NR^{c2}R^{d2}$, and $C(O)OR^{a2}$. In some embodiments, $R^{N6}$ is $Cy^2$. In some embodiments, $R^{N6}$ is $C(O)R^{b2}$.

In some embodiments, $R^{N7}$ is H. In some embodiments, $R^{N7}$ is $C_1$-7 alkyl, optionally substituted with 1, 2, or 3 substituents independently selected from $Cy^2$, $C(O)NR^{c2}R^{d2}$, and $C(O)OR^{a2}$. In some embodiments, $R^{N7}$ is $Cy^2$. In some embodiments, $R^{N7}$ is $C(O)R^{b2}$.

In some embodiments, $R^{N8}$ is H. In some embodiments, $R^{N8}$ is $C_1$-8 alkyl, optionally substituted with 1, 2, or 3 substituents independently selected from $Cy^2$, $C(O)NR^{c2}R^{d2}$, and $C(O)OR^{a2}$. In some embodiments, $R^{N8}$ is $Cy^2$. In some embodiments, $R^{N8}$ is $C(O)R^{b2}$.

In some embodiments, $R^{a1}$, $R^{a2}$, $R^{c1}$, $R^{c2}$, $R^{d1}$, and $R^{d2}$ are each independently selected from H, $C_{1-6}$ alkyl, $C_{2-6}$ alkenyl, $C_{2-6}$ alkynyl, $C_{1-4}$ haloalkyl, $Cy^3$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $S(O)R^{b3}$, $S(O)NR^{c3}R^{d3}$, $S(O)_2R^{b3}$, $S(O)_2NR^{c3}R^{d3}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^3$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$.

In some embodiments, $R^{a1}$, $R^{a2}$, $R^{c1}$, $R^{c2}$, $R^{d1}$, and $R^{d2}$ are each independently selected from H, $C_{1-6}$ alkyl, $C_{1-4}$ haloalkyl, $Cy^3$, $C(O)R^{b3}$, $C(O)NR^{c3}R^{d3}$, $C(O)OR^{a3}$, $S(O)_2R^{b3}$, $S(O)_2NR^{c3}R^{d3}$; wherein said $C_{1-6}$ alkyl is optionally substituted with 1, 2, or 3 substituents independently selected from $Cy^3$, halo, CN, $NO_2$, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$ and $S(O)_2NR^{c3}R^{d3}$.

In some embodiments, $R^{a1}$, $R^{a2}$, $R^{c1}$, $R^{c2}$, $R^{d1}$, and $R^{d2}$ are each independently selected from H, $C_{1-6}$ alkyl, $C_{1-4}$ haloalkyl, $Cy^3$, $C(O)R^{b3}$, wherein said $C_{1-6}$ alkyl is optionally substituted with 1, 2, or 3 substituents independently selected from $Cy^3$, $OR^{a3}$, $C(O)R^{b3}$, $C(O)NR^{c3}R^{d3}$, $C(O)OR^{a3}$, and $NR^{c3}R^{d3}$.

In some embodiments, $R^{a1}$ is H. In some embodiments, $R^{a1}$ is $C_{1-6}$ alkyl, optionally substituted with 1, 2, or 3 substituents independently selected from $Cy^3$, $OR^{a3}$, $C(O)R^{b3}$, $C(O)NR^{c3}R^{d3}$, $C(O)OR^{a3}$, and $NR^{c3}R^{d3}$. In some embodiments, $R^{a1}$ is $C_{1-4}$ haloalkyl. In some embodiments, $R^{a1}$ is $Cy^3$. In some embodiments, $R^{a1}$ is $C(O)R^{b3}$. In some embodiments, $R^{a1}$ is trifluoromethyl.

In some embodiments, $R^{a2}$ is H. In some embodiments, $R^{a2}$ is $C_{1-6}$ alkyl, optionally substituted with 1, 2, or 3 substituents independently selected from $Cy^3$, $OR^{a3}$, $C(O)R^{b3}$, $C(O)NR^{c3}R^{d3}$, $C(O)OR^{a3}$, and $NR^{c3}R^{d3}$. In some embodiments, $R^{a2}$ is $C_{1-4}$ haloalkyl. In some embodiments, $R^{a2}$ is $Cy^3$. In some embodiments, $R^{a2}$ is $C(O)R^{b3}$. In some embodiments, $R^{a2}$ is trifluoromethyl.

In some embodiments, $R^{c1}$ is H. In some embodiments, $R^{c1}$ is $C_{1-6}$ alkyl, optionally substituted with 1, 2, or 3 substituents independently selected from $Cy^3$, $OR^{a3}$, $C(O)R^{b3}$, $C(O)NR^{c3}R^{d3}$, $C(O)OR^{a3}$, and $NR^{c3}R^{d3}$. In some embodiments, $R^{c1}$ is $C_{1-4}$ haloalkyl. In some embodiments, $R^{c1}$ is $Cy^3$. In some embodiments, $R^{c1}$ is $C(O)R^{b3}$.

In some embodiments, $R^{c2}$ is H. In some embodiments, $R^{c2}$ is $C2_{-6}$ alkyl, optionally substituted with 1, 2, or 3 substituents independently selected from $Cy^3$, $OR^{a3}$, $C(O)R^{b3}$, $C(O)NR^{c3}R^{d3}$, $C(O)OR^{a3}$, and $NR^{c3}R^{d3}$. In some embodiments, $R^{c2}$ is $C2_{-4}$ haloalkyl. In some embodiments, $R^{c2}$ is $Cy^3$. In some embodiments, $R^{c2}$ is $C(O)R^{b3}$.

In some embodiments, $R^{d1}$ is H. In some embodiments, $R^{d1}$ is $D1_{-6}$ alkyl, optionally substituted with 1, 2, or 3 substituents independently selected from $Cy^3$, $OR^{a3}$, $C(O)R^{b3}$, $C(O)NR^{c3}R^{d3}$, $C(O)OR^{a3}$, and $NR^{c3}R^{d3}$. In some embodiments, $R^{d1}$ is $D1_{-4}$ haloalkyl. In some embodiments, $R^{d1}$ is $Cy^3$. In some embodiments, $R^{d1}$ is $C(O)R^{b3}$.

In some embodiments, $R^{d2}$ is H. In some embodiments, $R^{d2}$ is $D2_{-6}$ alkyl, optionally substituted with 1, 2, or 3 substituents independently selected from $Cy^3$, $OR^{a3}$, $C(O)R^{b3}$, $C(O)NR^{c3}R^{d3}$, $C(O)OR^{a3}$, and $NR^{c3}R^{d3}$. In some embodiments, $R^{d2}$ is $D2_{-4}$ haloalkyl. In some embodiments, $R^{d2}$ is $Cy^3$. In some embodiments, $R^{d2}$ is $C(O)R^{b3}$.

In some embodiments, $R^{b1}$ and $R^{b2}$ are each independently selected from $C_{1-6}$ alkyl and $Cy^3$; wherein said $C_{1-6}$ alkyl is optionally substituted with 1, 2, or 3 substituents independently selected from $Cy^3$, halo, CN, $NO_2$, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$ and $S(O)_2NR^{c3}R^{d3}$.

In some embodiments, $R^{b1}$ and $R^{b2}$ are each independently selected from $C_{1-6}$ alkyl and $Cy^3$, wherein said $C_{1-6}$ alkyl is optionally substituted with $SR^{a3}$.

In some embodiments, $R^{b1}$ is $C_{1-6}$ alkyl is optionally substituted with $SR^{a3}$.

In some embodiments, $R^{b2}$ is $C_{1-6}$ alkyl is optionally substituted with $SR^{a3}$.

In some embodiments, $R^{b1}$ is $Cy^3$.
In some embodiments, $R^{b2}$ is $Cy^3$.

In some embodiments, $R^{a3}$, $R^{c3}$, and $R^{d3}$ are each independently selected from H, $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are each optionally substituted with 1, 2, or 3 substituents independently selected from oxo, $C_{1-6}$ alkyl, $C_{1-4}$ haloalkyl, $C_{1-4}$ hydroxyalkyl, $C_{1-6}$ cyanoalkyl, halo, CN, $NO_2$, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$.

In some embodiments, $R^{a3}$, $R^{c3}$, and $R^{d3}$ are each independently selected from H, $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are each optionally substituted with 1, 2, or 3 substituents independently selected from oxo, $C_{1-6}$ alkyl, halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}S(O)_2R^{b4}$, $S(O)_2R^{b4}$, and $S(O)_2NR^{c4}R^{d4}$.

In some embodiments, $R^{a3}$, $R^{c3}$, and $R^{d3}$ are each independently selected from H, $C_{1-6}$ alkyl, 5-10 membered heteroaryl, and (5-10 membered heteroaryl)-$C_{1-4}$ alkylene; wherein said $C_{1-6}$ alkyl, 5-10 membered heteroaryl and (5-10 membered heteroaryl)-$C_{1-4}$ alkylene are each optionally substituted with 1, 2, or 3 substituents independently selected from oxo, $C_{1-6}$ alkyl, $OR^{a4}$, and $NR^{c4}R^{d4}$.

In some embodiments, $R^{a3}$ is H. In some embodiments, $R^{a3}$ is $C_{1-6}$ alkyl, which is optionally substituted with 1, 2, or 3 substituents independently selected from oxo, $C_{1-6}$ alkyl, $OR^{a4}$, and $NR^{c4}R^{d4}$. In some embodiments, $R^{a3}$ is 5-10 membered heteroaryl, which is optionally substituted with 1, 2, or 3 substituents independently selected from oxo, $C_{1-6}$ alkyl, $OR^{a4}$, and $NR^{c4}R^{d4}$. In some embodiments, $R^{a3}$ is (5-10 membered heteroaryl)-$C_{1-4}$ alkylene, which is optionally substituted with 1, 2, or 3 substituents independently selected from oxo, $C_{1-6}$ alkyl, $OR^{a4}$, and $NR^{c4}R^{d4}$. In some embodiments, $R^{a3}$ is trifluoromethyl.

In some embodiments, $R^{c3}$ is H. In some embodiments, $R^{c3}$ is $C_{1-6}$ alkyl, which is optionally substituted with 1, 2, or 3 substituents independently selected from oxo, $C_{1-6}$ alkyl, $OR^{a4}$, and $NR^{c4}R^{d4}$. In some embodiments, $R^{c3}$ is 5-10 membered heteroaryl, which is optionally substituted with 1, 2, or 3 substituents independently selected from oxo, $C_{1-6}$ alkyl, $OR^{a4}$, and $NR^{c4}R^{d4}$. In some embodiments, $R^{c3}$ is (5-10 membered heteroaryl)-$C_{1-4}$ alkylene, which is optionally substituted with 1, 2, or 3 substituents independently selected from oxo, $C_{1-6}$ alkyl, $OR^{a4}$, and $NR^{c4}R^{d4}$.

In some embodiments, $R^{d3}$ is H. In some embodiments, $R^{d3}$ is $C_{1-6}$ alkyl, which is optionally substituted with 1, 2, or 3 substituents independently selected from oxo, $C_{1-6}$ alkyl, $OR^{a4}$, and $NR^{c4}R^{d4}$. In some embodiments, $R^{d3}$ is 5-10 membered heteroaryl, which is optionally substituted with 1, 2, or 3 substituents independently selected from oxo, $C_{1-6}$ alkyl, $OR^{a4}$, and $NR^{c4}R^{d4}$. In some embodiments, $R^{d3}$ is (5-10 membered heteroaryl)-$C_{1-4}$ alkylene, which is optionally substituted with 1, 2, or 3 substituents independently selected from oxo, $C_{1-6}$ alkyl, $OR^{a4}$, and $NR^{c4}R^{d4}$.

In some embodiments, each $R^{b3}$ is selected from $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene, wherein said $C_{1-6}$ alkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are optionally substituted with 1, 2, or 3 substituents independently selected from oxo, $C_{1-6}$ alkyl, $C_{1-4}$ haloalkyl, $C_{1-4}$ hydroxyalkyl, $C_{1-6}$ cyanoalkyl, halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}S(O)_2R^{b4}$, $S(O)_2R^{b4}$, and $S(O)_2NR^{c4}R^{d4}$.

In some embodiments, each $R^{b3}$ is selected from $C_{1-6}$ alkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene, wherein said $C_{1-6}$ alkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are optionally substituted with 1, 2, or 3 substituents independently selected from oxo, $C_{1-6}$ alkyl, $C_{1-4}$ haloalkyl, $C_{1-4}$ hydroxyalkyl, $C_{1-6}$ cyanoalkyl, halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}S(O)_2R^{b4}$, $S(O)_2R^{b4}$, and $S(O)_2NR^{c4}R^{d4}$.

In some embodiments, $R^{b3}$ is selected from 5-10 membered heteroaryl, 4-12 membered heterocycloalkyl, each of which is optionally substituted with 1, 2, or 3 substituents independently selected from oxo, $C_{1-6}$ alkyl, and $OR^{a4}$.

In some embodiments, $Cy^1$ is independently selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy1}$.

In some embodiments, $Cy^1$ is $C_{6-10}$ aryl, optionally substituted with 1, 2, or 3 substituents independently selected from $R^{Cy1}$.

In some embodiments, $Cy^1$ is $C_{3-10}$ cycloalkyl, optionally substituted with 1, 2, or 3 substituents independently selected from $R^{Cy1}$.

In some embodiments, $Cy^1$ is 5-10 membered heteroaryl, optionally substituted with 1, 2, or 3 substituents independently selected from $R^{Cy1}$.

In some embodiments, $Cy^1$ is 4-12 membered heterocycloalkyl, optionally substituted with 1, 2, or 3 substituents independently selected from $R^{Cy1}$.

In some embodiments, $Cy^1$ is independently selected from piperidinyl, pyrrolidinyl, morpholinyl, cyclohexyl, cyclopropyl, phenyl, naphthyl, oxadiazolyl, piperazinyl, pyridinyl, triazolyl, pyridinyl, pyrazinyl, pyranyl, and indolinyl, each of which is optionally substituted with 1, 2, or 3 substituents independently selected from $R^{Cy1}$.

In some embodiments, $Cy^2$ is independently selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy2}$.

In some embodiments, $Cy^2$ is $C_{6-10}$ aryl, optionally substituted with 1, 2, or 3 substituents independently selected from $R^{Cy2}$.

In some embodiments, $Cy^2$ is $C_{3-10}$ cycloalkyl, optionally substituted with 1, 2, or 3 substituents independently selected from $R^{Cy2}$.

In some embodiments, $Cy^2$ is 5-10 membered heteroaryl, optionally substituted with 1, 2, or 3 substituents independently selected from $R^{Cy2}$.

In some embodiments, $Cy^2$ is 4-12 membered heterocycloalkyl, optionally substituted with 1, 2, or 3 substituents independently selected from $R^{Cy2}$.

In some embodiments, $Cy^2$ is independently selected from phenyl, cyclohexyl, benzothiazolyl, and tetrahydrofuranyl, each of which is optionally substituted with 1, 2, or 3 substituents independently selected from $R^{Cy2}$.

In some embodiments, $Cy^3$ is independently selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy3}$.

In some embodiments, $Cy^3$ is $C_{6-10}$ aryl, optionally substituted with 1, 2, or 3 substituents independently selected from $R^{Cy3}$.

In some embodiments, $Cy^3$ is $C_{3-10}$ cycloalkyl, optionally substituted with 1, 2, or 3 substituents independently selected from $R^{Cy3}$.

In some embodiments, $Cy^3$ is 5-10 membered heteroaryl, optionally substituted with 1, 2, or 3 substituents independently selected from $R^{Cy3}$.

In some embodiments, $Cy^3$ is 4-12 membered heterocycloalkyl, optionally substituted with 1, 2, or 3 substituents independently selected from $R^{Cy3}$.

In some embodiments, $Cy^3$ is independently selected from phenyl, thiophenyl, pyridinyl, pyrimidinyl, thiadiazolyl, triazolyl, imidazolyl, cyclobutyl, cyclohexyl, oxazolyl, thiadiazolyl, piperazinyl, tetrazolyl, furanyl, pyrrolidinyl, and benzofuranyl, each of which is optionally substituted with 1, 2, or 3 substituents independently selected from $R^{Cy3}$.

In some embodiments, $R^{Cy1}$ is independently selected from halo, $C_{1-4}$ alkyl, $C_{1-4}$ haloalkyl, $C_{2-6}$ alkenyl, $C_{2-6}$ alkynyl, $Cy^4$, CN, $NO_2$, $OR^{a4}$, $SR^{a4}$, $C(O)R^{b4}$, $C(O)NR^{c4}R^{d4}$, $C(O)OR^{d4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-4}$ alkyl, $C_{2-6}$ alkenyl, and $C_{2-6}$ alkynyl are each optionally substituted by 1, 2, 3, 4, or 5 substituents independently selected from $Cy^4$, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$.

In some embodiments, $R^{Cy1}$ is independently selected from halo, $C_{1-4}$ alkyl, $C_{1-4}$ haloalkyl, $Cy^4$, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{d4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl is optionally substituted by 1, 2, or 3 substituents independently selected from $Cy^4$, halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$.

In some embodiments, $R^{Cy1}$ is independently selected from halo, $C_{1-4}$ alkyl, $C_{1-4}$ haloalkyl, $Cy^4$, $OR^{a4}$, $C(O)R^{b4}$, $C(O)NR^{c4}R^{d4}$, $C(O)OR^{a4}$, $NR^{c4}R^{d4}$, and $S(O)_2NR^{c4}R^{d4}$, wherein said $C_{1-4}$ alkyl is optionally substituted by 1, 2, or 3 substituents independently selected from $Cy^4$, $C(O)NR^{c4}R^{d4}$, and $NR^{c4}S(O)_2R^{b4}$.

In some embodiments, $R^{Cy1}$ is selected from $C_{1-6}$ alkyl, $C(O)OR^{a1}$, $OR^{a1}$, $C(O)R^{b1}$, and halo.

In some embodiments, $R^{Cy1}$ is halo. In some embodiments, $R^{Cy1}$ is $C_{1-4}$ alkyl optionally substituted by 1, 2, or 3 substituents independently selected from $Cy^4$, $C(O)NR^{c4}R^{d4}$, and $NR^{c4}S(O)_2R^{b4}$. In some embodiments, $R^{Cy1}$ is $C_{1-4}$ alkyl. In some embodiments, $R^{Cy1}$ is $C_{1-4}$ haloalkyl. In some embodiments, $R^{Cy1}$ is $Cy^4$. In some embodiments, $R^{Cy1}$ is $OR^{a4}$. In some embodiments, $R^{Cy1}$ is $C(O)R^{b4}$. In some embodiments, $R^{Cy1}$ is $C(O)NR^{c4}R^{d4}$. In some embodiments, $R^{Cy1}$ is $C(O)OR^{a4}$. In some embodiments, $R^{Cy1}$ is $NR^{c4}R^{d4}$. In some embodiments, $R^{Cy1}$ is $S(O)_2NR^{c4}R^{d4}$.

In some embodiments, each $R^{Cy2}$ is independently selected from halo, $C_{1-4}$ alkyl, $C_{1-4}$ haloalkyl, $Cy^4$, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl is optionally substituted by 1, 2, or 3 substituents independently selected from $Cy^4$, halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$.

In some embodiments, each $R^{Cy2}$ is independently selected from halo, $C_{1-4}$ alkyl, $C_{1-4}$ haloalkyl, CN, $NO_2$, $C(O)NR^{c4}R^{d4}$, $C(O)OR^{a4}$, $NR^{c4}R^{d4}$, $NR^{c4}C(O)R^{b4}$, $S(O)_2R^{b4}$, and $S(O)_2NR^{c4}R^{d4}$, wherein said $C_{1-4}$ alkyl is optionally substituted by 1, 2, or 3 substituents independently selected from halo, CN, $NO_2$, $C(O)NR^{c4}R^{d4}$, $C(O)OR^{a4}$, $NR^{c4}R^{d4}$, $NR^{c4}C(O)R^{b4}$, $S(O)_2R^{b4}$, and $S(O)_2NR^{c4}R^{d4}$.

In some embodiments, $R^{Cy2}$ is independently selected from halo, $C_{1-4}$ alkyl, $C(O)NR^{c4}R^{d4}$, and $C(O)OR^{a4}$.

In some embodiments, $R^{Cy2}$ is halo. In some embodiments, $R^{Cy2}$ is $C_{1-4}$ alkyl. In some embodiments, $R^{Cy2}$ is $C(O)NR^{c4}R^{d4}$. In some embodiments, $C(O)OR^{a4}$.

In some embodiments, each $R^{Cy3}$ is independently selected from halo, $C_{1-4}$ alkyl, $C_{1-4}$ haloalkyl, $Cy^4$, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl is optionally substituted by 1, 2, or 3 substituents independently selected from $Cy^4$, halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$.

In some embodiments, each $R^{Cy3}$ is independently selected from halo, $C_{1-4}$ alkyl, $C_{1-4}$ haloalkyl, $Cy^4$, $OR^{a4}$, $C(O)R^{b4}$, $C(O)NR^{c4}R^{d4}$, and $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl is optionally substituted by 1, 2, or 3 substituents independently selected from $Cy^4$, halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $S(O)_2R^{b4}$, and $S(O)_2NR^{c4}R^{d4}$.

In some embodiments, each $R^{Cy3}$ is independently selected from halo, $C_{1-4}$ alkyl, $Cy^4$, $OR^{a4}$, $C(O)R^{b4}$, $C(O)NR^{c4}R^{d4}$, and $C(O)OR^{a4}$. In some embodiments, $R^{Cy3}$ is halo. In some embodiments, $R^{Cy3}$ is $C_{1-4}$ alkyl. In some embodiments, $R^{Cy3}$ is $Cy^4$. In some embodiments, $R^{Cy3}$ is $OR^{a4}$. In some embodiments, $R^{Cy3}$ is $C(O)R^{b4}$. In some embodiments, $R^{Cy3}$ is $C(O)NR^{c4}R^{d4}$. In some embodiments, $R^{Cy3}$ is $C(O)OR^{a4}$.

In some embodiments, each $R^{Cy5}$ is independently selected from halo, $C_{1-4}$ alkyl, $C_{1-4}$ haloalkyl, $Cy^4$, CN, $NO_2$, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl is optionally substituted by 1, 2, or 3 substituents independently selected from $Cy^4$, halo, CN, $NO_2$, $OR^{a4}$, $SR^{a4}$, $C(O)R^{b4}$, $C(O)NR^{c4}R^{d4}$, $C(O)$ $OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$.

In some embodiments, each $R^{Cy5}$ is independently selected from halo, $C_{1-4}$ alkyl, $C_{1-4}$ haloalkyl, $Cy^4$, CN, $NO_2$, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $S(O)_2R^{b4}$, and $S(O)_2NR^{c4}R^{d4}$, wherein said $C_{1-4}$ alkyl is optionally substituted by 1, 2, or 3 substituents independently selected from $Cy^4$, halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}S(O)_2R^{b4}$, $S(O)_2R^{b4}$, and $S(O)_2NR^{c4}R^{d4}$.

In some embodiments, each $R^{Cy5}$ is independently selected from halo, $C_{1-4}$ alkyl, $Cy^4$, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $S(O)_2R^{b4}$, and $S(O)_2NR^{c4}R^{d4}$, wherein said $C_{1-4}$ alkyl is optionally substituted by 1, 2, or 3 substituents independently selected from $Cy^4$, $OR^{a4}$, $C(O)NR^{c4}R^{d4}$, $C(O)OR^{a4}$, and $NR^{c4}R^{d4}$.

In some embodiments, $R^{Cy5}$ is halo. In some embodiments, $R^{Cy5}$ is $C_{1-4}$ alkyl is optionally substituted by 1, 2, or 3 substituents independently selected from $Cy^4$, $OR^{a4}$, $C(O)NR^{c4}R^{d4}$, $C(O)OR^{a4}$, and $NR^{c4}R^{d4}$. In some embodiments, $R^{Cy5}$ is $Cy^4$. In some embodiments, $R^{Cy5}$ is $OR^{a4}$. In some embodiments, $R^{Cy5}$ is $SR^{a4}$. In some embodiments, $R^{Cy5}$ is $C(O)R^{b4}$. In some embodiments, $R^{Cy5}$ is $C(O)NR^{c4}R^{d4}$. In some embodiments, $R^{Cy5}$ is $C(O)OR^{a4}$. In some embodiments, $R^{Cy5}$ is $NR^{c4}R^{d4}$. In some embodiments, $R^{Cy5}$ is $NR^{c4}C(O)R^{b4}$. In some embodiments, $R^{Cy5}$ is $S(O)_2R^{b4}$. In some embodiments, $R^{Cy5}$ is $S(O)_2NR^{c4}R^{d4}$.

In some embodiments, each $Cy^4$ is independently selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy4}$.

In some embodiments, $Cy^4$ is $C_{6-10}$ aryl, optionally substituted with 1, 2, or 3 substituents independently selected from $R^{Cy4}$.

In some embodiments, $Cy^4$ is $C_{3-10}$ cycloalkyl, optionally substituted with 1, 2, or 3 substituents independently selected from $R^{Cy4}$.

In some embodiments, $Cy^4$ is 5-10 membered heteroaryl, optionally substituted with 1, 2, or 3 substituents independently selected from $R^{Cy4}$.

In some embodiments, $Cy^4$ is 4-12 membered heterocycloalkyl, optionally substituted with 1, 2, or 3 substituents independently selected from $R^{Cy4}$.

In some embodiments, $Cy^4$ is selected from the group consisting of phenyl, pyridinyl, morpholinyl, thiazolyl, and cyclohexyl.

In some embodiments, each $R^{Cy4}$ is independently selected from halo, $C_{1-4}$ alkyl, $C_{1-4}$ haloalkyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, and (4-7 membered heterocycloalkyl)-$C_{1-4}$ alkylene-, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl, $C_{1-4}$ haloalkyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, and (4-7 membered heterocycloalkyl)-$C_{1-4}$ alkylene- are each optionally substituted by 1, 2, or 3 substituents independently selected from halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$.

In some embodiments, $R^{Cy4}$ is $C_{1-4}$ alkyl. In some embodiments, $R^{Cy4}$ is halo.

In some embodiments, $R^{a4}$, $R^{c4}$, and $R^{d4}$ are each independently selected from H, $C_{1-6}$ alkyl, $C_{1-4}$ haloalkyl, $C_{1-4}$ hydroxyalkyl, $C_{1-4}$ cyanoalkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, wherein said $C_{1-6}$ alkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, or 3 substituents independently selected from $R^g$.

In some embodiments, $R^{a4}$, $R^{c4}$, and $R^{d4}$ are each independently selected from H, $C_{1-6}$ alkyl, $C_{6-10}$ aryl, 5-10 membered heteroaryl, 4-12 membered heterocycloalkyl, $C_{6-10}$ aryl-$C_{1-4}$ alkylene, (5-10 membered heteroaryl)-$C_{1-4}$ alkylene, (4-12 membered heterocycloalkyl)-$C_{1-4}$ alkylene, wherein said $C_{1-6}$ alkyl, $C_{6-10}$ aryl, 5-10 membered heteroaryl, 4-12 membered heterocycloalkyl, $C_{6-10}$ aryl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, or 3 substituents independently selected from $R^g$.

In some embodiments, $R^{a4}$, $R^{c4}$, and $R^{d4}$ are each independently selected from H, $C_{1-6}$ alkyl, $C_{6-10}$ aryl, 5-10 membered heteroaryl, 4-12 membered heterocycloalkyl, $C_{6-10}$ aryl-$C_{1-4}$ alkylene, (4-12 membered heterocycloalkyl)-$C_{1-4}$ alkylene, wherein said $C_{1-6}$ alkyl, $C_{6-10}$ aryl, 5-10 membered heteroaryl, 4-12 membered heterocycloalkyl, $C_{6-10}$ aryl-$C_{1-4}$ alkylene, and (4-12 membered heterocycloalkyl)-$C_{1-4}$ alkylene are each optionally substituted with 1, 2, or 3 substituents independently selected from $R^g$.

In some embodiments, $R^{a4}$ is $C_{1-6}$ alkyl. In some embodiments, $R^{a4}$ is $C_{6-10}$ aryl. In some embodiments, $R^{a4}$ is 5-10 membered heteroaryl. In some embodiments, $R^{a4}$ is 4-12 membered heterocycloalkyl. In some embodiments, $R^{a4}$ is $C_{6-10}$ aryl-$C_{1-4}$ alkylene. In some embodiments, $R^{a4}$ is (4-12 membered heterocycloalkyl)-$C_{1-4}$ alkylene. In some embodiments, $R^{a4}$ is trifluoromethyl.

In some embodiments, $R^{c4}$ is $C_{1-6}$ alkyl. In some embodiments, $R^{c4}$ is $C_{6-10}$ aryl. In some embodiments, $R^{c4}$ is 5-10 membered heteroaryl. In some embodiments, $R^{c4}$ is 4-12 membered heterocycloalkyl. In some embodiments, $R^{c4}$ is $C_{6-10}$ aryl-$C_{1-4}$ alkylene. In some embodiments, $R^{c4}$ is (4-12 membered heterocycloalkyl)-$C_{1-4}$ alkylene.

In some embodiments, $R^{d4}$ is $C_{1-6}$ alkyl. In some embodiments, $R^{d4}$ is $C_{6-10}$ aryl. In some embodiments, $R^{d4}$ is 5-10 membered heteroaryl. In some embodiments, $R^{d4}$ is 4-12 membered heterocycloalkyl. In some embodiments, $R^{d4}$ is $C_{6-10}$ aryl-$C_{1-4}$ alkylene. In some embodiments, $R^{d4}$ is (4-12 membered heterocycloalkyl)-$C_{1-4}$ alkylene.

In some embodiments, each $R^{b4}$ is independently selected from $C_{1-6}$ alkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, wherein said $C_{1-6}$ alkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, or 3 substituents independently selected from $R^g$.

In some embodiments, each $R^{b4}$ is independently selected from $C_{1-6}$ alkyl, $C_{6-10}$ aryl, $C_{3-10}$ cycloalkyl, 5-10 membered heteroaryl, 4-12 membered heterocycloalkyl, wherein said $C_{1-6}$ alkyl, $C_{6-10}$ aryl, $C_{3-10}$ cycloalkyl, 5-10 membered heteroaryl, and 4-12 membered heterocycloalkyl are each optionally substituted with 1, 2, or 3 substituents independently selected from $R^g$.

In some embodiments, $R^{b4}$ is $C_{1-6}$ alkyl, optionally substituted with 1, 2, or 3 substituents independently selected from $R^g$.

In some embodiments, $R^{b4}$ is $C_{6-10}$ aryl, optionally substituted with 1, 2, or 3 substituents independently selected from $R^g$.

In some embodiments, $R^{b4}$ is $C_{3-10}$ cycloalkyl, optionally substituted with 1, 2, or 3 substituents independently selected from $R^g$.

In some embodiments, $R^{b4}$ is 5-10 membered heteroaryl, optionally substituted with 1, 2, or 3 substituents independently selected from $R^g$.

In some embodiments, $R^{b4}$ is 4-12 membered heterocycloalkyl, optionally substituted with 1, 2, or 3 substituents independently selected from $R^g$.

In Some Embodiments of Formula (II-I):

$Y^1$ and $Y^2$ are each independently selected from C and N;

$X^1$ is selected from N, $NR^{N1}$, $CR^1$, and $C(R^1)_2$;

$X^2$ is selected from N, $NR^{N2}$, O, S, $CR^2$, and $C(R^2)_2$;

$X^3$ is selected from N, $NR^{N3}$, O, S, $CR^3$, and $C(R^3)_2$;

$X^4$ is selected from N, $NR^{N4}$, S, $CR^4$, and $C(R^4)_2$;

$X^5$ is selected from N, $NR^{N5}$, O, S, $CR^5$, and $C(R^5)_2$;

$X^6$ is selected from N, $NR^{N6}$, $CR^6$, and $C(R^6)_2$;

$X^7$ is selected from N, $NR^{N7}$, S, $CR^7$, and $C(R^7)_2$;

$X^8$ is selected from N, $NR^{N8}$, O, S, $CR^8$, and $C(R^8)_2$;

$R^1$, $R^2$, $R^3$, $R^4$, $R^5$, $R^6$, $R^7$, and $R^8$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, thioxo and oxo; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$;

$R^{N1}$, $R^{N2}$, $R^{N3}$, $R^{N4}$, $R^{N5}$, $R^{N6}$, $R^{N7}$, and $R^{N8}$ are each independently selected from H, $C_{1-6}$ alkyl, $C_{2-6}$ alkenyl, $C_{2-6}$ alkynyl, $C_{1-6}$ haloalkyl, $Cy^2$, $C(O)R^{b2}$, $C(O)NR^{c2}R^{d2}$, $C(O)OR^{a2}$, $C(=NR^{e2})NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^2$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}R^{d2}$, $NR^{c2}C(=NR^{e2})NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$ and $S(O)_2NR^{c2}R^{d2}$;

$R^{a1}$, $R^{a2}$, $R^{c1}$, $R^{c2}$, $R^{d1}$, and $R^{d2}$ are each independently selected from H, $C_{1-6}$ alkyl, $C_{2-6}$ alkenyl, $C_{2-6}$ alkynyl, $C_{1-4}$ haloalkyl, $Cy^3$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $S(O)R^{b3}$, $S(O)NR^{c3}R^{d3}$, $S(O)_2R^{b3}$, $S(O)_2NR^{c3}R^{d3}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^3$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{c3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$;

$R^{b1}$ and $R^{b2}$ are each independently selected from $C_{1-6}$ alkyl and $Cy^3$; wherein said $C_{1-6}$ alkyl is optionally substituted with 1, 2, or 3 substituents independently selected from $Cy^3$, halo, CN, $NO_2$, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$ and $S(O)_2NR^{c3}R^{d3}$;

$R^{a3}$, $R^{c3}$, and $R^{d3}$ are each independently selected from H, $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are each optionally substituted with 1, 2, or 3 substituents independently selected from oxo, $C_{1-6}$ alkyl, $C_{1-4}$ haloalkyl, $C_{1-4}$ hydroxyalkyl, $C_{1-6}$ cyanoalkyl, halo, CN, $NO_2$, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$;

each $R^{b3}$ is selected from $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene, wherein said $C_{1-6}$ alkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are optionally substituted with 1, 2, or 3 substituents independently selected from oxo, $C_{1-6}$ alkyl, $C_{1-4}$ haloalkyl, $C_{1-4}$ hydroxyalkyl, $C_{1-6}$ cyanoalkyl, halo, CN, $NO_2$, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$;

$Cy^1$ is independently selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy1}$;

each $Cy^2$ is independently selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy2}$;

$Cy^3$ is independently selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy3}$;

each $R^{Cy1}$ is independently selected from halo, $C_{1-4}$ alkyl, $C_{1-4}$ haloalkyl, $C_{2-6}$ alkenyl, $C_{2-6}$ alkynyl, $Cy^4$, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-4}$ alkyl, $C_{2-6}$ alkenyl, and $C_{2-6}$ alkynyl are each optionally substituted by 1, 2, 3, 4, or 5 substituents independently selected from $Cy^4$, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$ $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^{Cy2}$ is independently selected from halo, $C_{1-4}$ alkyl, $C_{1-4}$ haloalkyl, $Cy^4$, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl is optionally substituted by 1, 2, or 3 substituents independently selected from $Cy^4$, halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$;

each $R^{Cy3}$ is independently selected from halo, $C_{1-4}$ alkyl, $C_{1-4}$ haloalkyl, $Cy^4$, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl is optionally substituted by 1, 2, or 3 substituents independently selected from $Cy^4$, halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$.

each $R^{Cy5}$ is independently selected from halo, $C_{1-4}$ alkyl, $C_{1-4}$ haloalkyl, $Cy^4$, CN, $NO_2$, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl is optionally substituted by 1, 2, or 3 substituents independently selected from $Cy^4$, halo, CN, $NO_2$, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$;

$Cy^4$ is independently selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy4}$;

each $R^{Cy4}$ is independently selected from halo, $C_{1-4}$ alkyl, $C_{1-4}$ haloalkyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, and (4-7 membered heterocycloalkyl)-$C_{1-4}$ alkylene-, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl, $C_{1-4}$ haloalkyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, and (4-7 membered heterocycloalkyl)-$C_{1-4}$ alkylene- are each optionally substituted by 1, 2, or 3 substituents independently selected from halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, $R^{a4}$, $R^{c4}$, and $R^{d4}$ are each independently selected from H, $C_{1-6}$ alkyl, $C_{1-4}$ haloalkyl, $C_{1-4}$ hydroxyalkyl, $C_{1-4}$ cyanoalkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, wherein said $C_{1-6}$ alkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, or 3 substituents independently selected from $R^g$; and each $R^{b4}$ is independently selected from $C_{1-6}$ alkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, wherein said $C_{1-6}$ alkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, or 3 substituents independently selected from $R^g$.

In Some Aspects of these Embodiments of Formula (II-I): $R^1$, $R^2$, $R^3$, $R^4$, $R^5$, $R^6$, $R^7$, and $R^8$ are each independently selected from H, $C_{1-6}$ alkyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, $S(O)_2NR^{c1}R^{d1}$, and oxo; wherein said $C_{1-6}$ alkyl is optionally substituted with 1, 2, or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$ and $S(O)_2NR^{c1}R^{d1}$;

$R^{N1}$, $R^{N2}$, $R^{N3}$, $R^{N4}$, $R^{N5}$, $R^{N6}$, $R^{N7}$, and $R^{N8}$ are each independently selected from H, $C_{1-6}$ alkyl, $C_{1-6}$ haloalkyl, $Cy^2$, $C(O)R^{b2}$, $C(O)NR^{c2}R^{d2}$, $C(O)OR^{a2}$, $S(O)_2R^{b2}$, and $S(O)_2NR^{c2}R^{d2}$, wherein said $C_{1-6}$ alkyl is optionally substituted with 1, 2, or 3 substituents independently selected from $Cy^2$, halo, CN, $NO_2$, $OR^{a2}$, $SR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$ and $S(O)_2NR^{c2}R^{d2}$;

$R^{a1}$, $R^{a2}$, $R^{c1}$, $R^{c2}$, $R^{d1}$, and $R^{d2}$ are each independently selected from H, $C_{1-6}$ alkyl, $C_{1-4}$ haloalkyl, $Cy^3$, $C(O)$ $R^{b3}$, C(O)$NR^{c3}R^{d3}$, C(O)$OR^{a3}$, S(O)$_2R^{b3}$, S(O)$_2$$NR^{c3}R^{d3}$; wherein said $C_{1-6}$ alkyl is optionally substituted with 1, 2, or 3 substituents independently selected from $Cy^3$, halo, CN, NO$_2$, $OR^{a3}$, $SR^{a3}$, C(O)$R^{b3}$, C(O)$NR^{c3}R^{d3}$, C(O)$OR^{a3}$, $NR^{c3}R^{d3}$, $NR^{c3}$C(O)$R^{b3}$, $NR^{c3}$C(O)$OR^{a3}$, $NR^{c3}$C(O)$NR^{c3}R^{d3}$, $NR^{c3}$S(O)$_2R^{b3}$, $NR^{c3}$S(O)$_2NR^{c3}R^{d3}$, S(O)$_2R^{b3}$ and S(O)$_2NR^{c3}R^{d3}$;

$R^{b1}$ and $R^{b2}$ are each independently selected from $C_{1-6}$ alkyl and $Cy^3$, wherein said $C_{1-6}$ alkyl is optionally substituted with $SR^{a3}$;

wherein $R^{a3}$, $R^{c3}$, and $R^{d3}$ are each independently selected from H, $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are each optionally substituted with 1, 2, or 3 substituents independently selected from oxo, $C_{1-6}$ alkyl, halo, CN, NO$_2$, $OR^{a4}$, C(O)$R^{b4}$, C(O)$NR^{c4}R^{d4}$, C(O)$OR^{a4}$, $NR^{c4}R^{d4}$, $NR^{c4}$C(O)$R^{b4}$, $NR^{c4}$S(O)$_2R^{b4}$, S(O)$_2R^{b4}$, and S(O)$_2NR^{c4}R^{d4}$;

each $R^{b3}$ is selected from $C_{1-6}$ alkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene, wherein said $C_{1-6}$ alkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are optionally substituted with 1, 2, or 3 substituents independently selected from oxo, $C_{1-6}$ alkyl, $C_{1-4}$ haloalkyl, $C_{1-4}$ hydroxyalkyl, $C_{1-6}$ cyanoalkyl, halo, CN, NO$_2$, $OR^{a4}$, C(O)$R^{b4}$, C(O)$NR^{c4}R^{d4}$, C(O)$OR^{a4}$, $NR^{c4}R^{d4}$, $NR^{c4}$C(O)$R^{b4}$, $NR^{c4}$S(O)$_2R^{b4}$, S(O)$_2R^{b4}$, and S(O)$_2NR^{c4}R^{d4}$;

each $R^{Cy1}$ is independently selected from halo, $C_{1-4}$ alkyl, $C_{1-4}$ haloalkyl, $Cy^4$, CN, NO$_2$, $OR^{a4}$, C(O)$R^{b4}$, C(O)$NR^{c4}R^{d4}$, C(O)$OR^{a4}$, $NR^{c4}R^{d4}$, $NR^{c4}$C(O)$R^{b4}$, $NR^{c4}$C(O)$OR^{a4}$, $NR^{c4}$C(O)$NR^{c4}R^{d4}$, $NR^{c4}$S(O)$_2R^{b4}$, $NR^{c4}$S(O)$_2NR^{c4}R^{d4}$, S(O)$_2R^{b4}$, and S(O)$_2NR^{c4}R^{d4}$, wherein said $C_{1-4}$ alkyl is optionally substituted by 1, 2, or 3 substituents independently selected from $Cy^4$, halo, CN, NO$_2$, $OR^{a4}$, C(O)$R^{b4}$, C(O)$NR^{c4}R^{d4}$, C(O)$OR^{a4}$, $NR^{c4}R^{d4}$, $NR^{c1}$C(O)$R^{b4}$, $NR^{c4}$C(O)$OR^{a4}$, $NR^{c4}$C(O)$NR^{c4}R^{d4}$, $NR^{c4}$S(O)$_2R^{b4}$, $NR^{c4}$S(O)$_2NR^{c4}R^{d4}$, S(O)$_2R^{b4}$, and S(O)$_2NR^{c4}R^{d4}$;

each $R^{Cy2}$ is independently selected from halo, $C_{1-4}$ alkyl, $C_{1-4}$ haloalkyl, CN, NO$_2$, C(O)$NR^{c4}R^{d4}$, C(O)$OR^{a4}$, $NR^{c4}R^{d4}$, $NR^{c4}$C(O)$R^{b4}$, S(O)$_2R^{b4}$, and S(O)$_2NR^{c4}R^{d4}$, wherein said $C_{1-4}$ alkyl is optionally substituted by 1, 2, or 3 substituents independently selected from halo, CN, NO$_2$, C(O)$NR^{c4}R^{d4}$, C(O)$OR^{a4}$, $NR^{c4}R^{d4}$, $NR^{c4}$C(O)$R^{b4}$, S(O)$_2R^{b4}$, and S(O)$_2NR^{c4}R^{d4}$;

each $R^{Cy3}$ is independently selected from halo, $C_{1-4}$ alkyl, $C_{1-4}$ haloalkyl, $Cy^4$, $OR^{a4}$, C(O)$R^{b4}$, C(O)$NR^{c4}R^{d4}$, and C(O)$OR^{a4}$, $NR^{c4}R^{d4}$, $NR^{c4}$C(O)$R^{b4}$, $NR^{c4}$C(O)$OR^{a4}$, $NR^{c4}$C(O)$NR^{c4}R^{d4}$, $NR^{c4}$S(O)$_2R^{b4}$, $NR^{c4}$S(O)$_2NR^{c4}R^{d4}$, S(O)$_2R^{b4}$, and S(O)$_2NR^{c4}R^{d4}$, wherein said $C_{1-4}$ alkyl is optionally substituted by 1, 2, or 3 substituents independently selected from $Cy^4$, halo, CN, NO$_2$, $OR^{a4}$, C(O)$R^{b4}$, C(O)$NR^{c4}R^{d4}$, C(O)$OR^{a4}$, $NR^{c4}R^{d4}$, $NR^{c4}$C(O)$R^{b4}$, $NR^{c4}$C(O)$OR^{a4}$, $NR^{c4}$C(O)$NR^{c4}R^{d4}$, S(O)$_2R^{b4}$, and S(O)$_2NR^{c4}R^{d4}$;

each $R^{Cy5}$ is independently selected from halo, $C_{1-4}$ alkyl, $C_{1-4}$ haloalkyl, $Cy^4$, CN, NO$_2$, $OR^{a4}$, $SR^{a4}$, C(O)$R^{b4}$, C(O)$NR^{c4}R^{d4}$, C(O)$OR^{a4}$, $NR^{c4}R^{d4}$, $NR^{c4}$C(O)$R^{b4}$, S(O)$_2R^{b4}$, and S(O)$_2NR^{c4}R^{d4}$, wherein said $C_{1-4}$ alkyl is optionally substituted by 1, 2, or 3 substituents independently selected from $Cy^4$, halo, CN, NO$_2$, $OR^{a4}$, C(O)$R^{b4}$, C(O)$NR^{c4}R^{d4}$, C(O)$OR^{a4}$, $NR^{c4}R^{d4}$, $NR^{c4}$S(O)$_2R^{b4}$, S(O)$_2R^{b4}$, and S(O)$_2NR^{c4}R^{d4}$;

$R^{a4}$, $R^{c4}$, and $R^{d4}$ are each independently selected from H, $C_{1-6}$ alkyl, $C_{6-10}$ aryl, 5-10 membered heteroaryl, 4-12 membered heterocycloalkyl, $C_{6-10}$ aryl-$C_{1-4}$ alkylene, (5-10 membered heteroaryl)-$C_{1-4}$ alkylene, (4-12 membered heterocycloalkyl)-$C_{1-4}$ alkylene, wherein said $C_{1-6}$ alkyl, $C_{6-10}$ aryl, 5-10 membered heteroaryl, 4-12 membered heterocycloalkyl, $C_{6-10}$ aryl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, or 3 substituents independently selected from $R^g$; and each $R^{b4}$ is independently selected from $C_{1-6}$ alkyl, $C_{6-10}$ aryl, $C_{3-10}$ cycloalkyl, 5-10 membered heteroaryl, 4-12 membered heterocycloalkyl, wherein said $C_{1-6}$ alkyl, $C_{6-10}$ aryl, $C_{3-10}$ cycloalkyl, 5-10 membered heteroaryl, and 4-12 membered heterocycloalkyl are each optionally substituted with 1, 2, or 3 substituents independently selected from $R^g$.

In Other Aspects of these Embodiments:

$R^1$, $R^2$, $R^3$, $R^4$, $R^5$, $R^6$, $R^7$, and $R^8$ are each independently selected from H, $C_{1-6}$ alkyl, $Cy^1$, halo, CN, $OR^{a1}$, $SR^{a1}$, C(O)$R^{b1}$, C(O)$NR^{c1}R^{d1}$, C(O)$OR^{a1}$, C(O)$R^{b1}$, $NR^{c1}R^{d1}$, $NR^{c1}$C(O)$R^{b1}$, $NR^{c1}$C(O)$NR^{c1}R^{d1}$, $NR^{c1}$S(O)$_2R^{b1}$, S(O)$_2R^{b1}$, S(O)$_2NR^{c1}R^{d1}$, and oxo; wherein said $C_{1-6}$ alkyl is optionally substituted with 1, 2, or 3 substituents independently selected from $Cy^1$, $SR^{a1}$, C(O)$NR^{c1}R^{d1}$, C(O)$OR^{a1}$, $NR^{c1}R^{d1}$, $NR^{c1}$S(O)$_2R^{b1}$, and S(O)$_2R^{b1}$;

$R^{N1}$, $R^{N2}$, $R^{N3}$, $R^{N4}$, $R^{N5}$, $R^{N6}$, $R^{N7}$, and $R^{N8}$ are each independently selected from H, $C_{1-6}$ alkyl, $Cy^2$, and C(O)$R^{b2}$; wherein said $C_{1-6}$ alkyl is optionally substituted with 1, 2, or 3 substituents independently selected from $Cy^2$, C(O)$NR^{c2}R^{d2}$, and C(O)$OR^{a2}$;

$R^{a1}$, $R^{a2}$, $R^{c1}$, $R^{c2}$, $R^{d1}$, and $R^{d2}$ are each independently selected from H, $C_{1-6}$ alkyl, $C_{1-4}$ haloalkyl, $Cy^3$, C(O)$R^{b3}$, wherein said $C_{1-6}$ alkyl is optionally substituted with 1, 2, or 3 substituents independently selected from $Cy^3$, $OR^{a3}$, C(O)$R^{b3}$, C(O)$NR^{c3}R^{d3}$, C(O)$OR^{a3}$, and $NR^{c3}R^{d3}$;

each $R^{Cy1}$ is independently selected from halo, $C_{1-4}$ alkyl, $C_{1-4}$ haloalkyl, $Cy^4$, $OR^{a4}$, C(O)$R^{b4}$, C(O)$NR^{c4}R^{d4}$, C(O)$OR^{a4}$, $NR^{c4}R^{d4}$, and S(O)$_2NR^{c4}R^{d4}$, wherein said $C_{1-4}$ alkyl is optionally substituted by 1, 2, or 3 substituents independently selected from $Cy^4$, C(O)$NR^{c4}R^{d4}$, and $NR^{c4}$S(O)$_2R^{b4}$;

each $R^{Cy2}$ is independently selected from halo, $C_{1-4}$ alkyl, C(O)$NR^{c4}R^{d4}$, and C(O)$OR^{a4}$;

each $R^{Cy3}$ is independently selected from halo, $C_{1-4}$ alkyl, $Cy^4$, $OR^{a4}$, C(O)$R^{b4}$, C(O)$NR^{c4}R^{d4}$, and C(O)$OR^{a4}$; and each $R^{Cy5}$ is independently selected from halo, $C_{1-4}$ alkyl, $Cy^4$, $OR^{a4}$, $SR^{a4}$, C(O)$R^{b4}$, C(O)$NR^{c4}R^{d4}$, C(O)$OR^{a4}$, $NR^{c4}R^{d4}$, $NR^{c4}$C(O)$R^{b4}$, S(O)$_2R^{b4}$, and S(O)$_2$ NR$^{c4}$R$^{d4}$, wherein said C$_{1-4}$ alkyl is optionally substituted by 1, 2, or 3 substituents independently selected from Cy$^4$, OR$^{a4}$, C(O)NR$^{c4}$R$^{d4}$, C(O)OR$^{a4}$, and NR$^{c4}$R$^{d4}$.

In some embodiments, the compound of Formula (II-I) is selected from any one of the compounds listed in Table 5. In some embodiments, the compound of Formula (II-I) is not any one of the compounds listed in Table 5.

In some embodiments, the compound of Formula (II-I) has Formula (II-Ia):

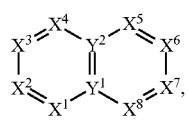

(II-Ia)

or pharmaceutically acceptable salt thereof, wherein:

X$^1$, X$^2$, X$^3$, X$^4$, X$^5$, X$^6$, X$^7$, and X$^8$ are each independently N or CR (i.e., R$^1$, R$^2$, R$^3$, R$^4$, R$^5$, R$^6$, R$^7$, or R$^8$). In some aspects of these embodiments, not more than four of X$^1$, X$^2$, X$^3$, X$^4$, X$^5$, X$^6$, X$^7$, and X$^8$ are N. In other aspects of these embodiments, not more than two of X$^1$, X$^2$, X$^3$, X$^4$, X$^5$, X$^6$, X$^7$, and X$^8$ are N. In yet other aspects of these embodiments, not more than three of X$^1$, X$^2$, X$^3$, X$^4$, X$^5$, X$^6$, X$^7$, and X$^8$ are N. In yet other aspects of these embodiments, not more than two of X$^1$, X$^2$, X$^3$, X$^4$, X$^5$, X$^6$, X$^7$, and X$^8$ are N. In yet other aspects of these embodiments, two of X$^1$, X$^2$, X$^3$, X$^4$, X$^5$, X$^6$, X$^7$, and X$^8$ are N. In yet other aspects of these embodiments, one of X$^1$, X$^2$, X$^3$, X$^4$, X$^5$, X$^6$, X$^7$, and X$^8$ is N. In yet other aspects of these embodiments, three of X$^1$, X$^2$, X$^3$, X$^4$, X$^5$, X$^6$, X$^7$, and X$^8$ are N. In yet other aspects of these embodiments, four of X$^1$, X$^2$, X$^3$, X$^4$, X$^5$, X$^6$, X$^7$, and X$^8$ are N.

In some embodiments, the compound of Formula (II-I) has Formula (II-Ib):

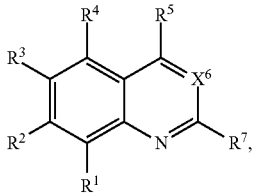

(II-Ib)

or pharmaceutically acceptable salt thereof, wherein:

X$^6$ is N or CR$^6$, and at least one of R$^1$, R$^2$, R$^3$, R$^4$, R$^5$, and R$^7$ is NR$^{c1}$R$^{d1}$. In some aspects of these embodiments, R$^5$ is NR$^{c1}$R$^{d1}$. In other aspects of these embodiments, R$^7$ is NR$^{c1}$R$^{d1}$. In some aspects of these embodiments, at least one of R$^1$, R$^2$, R$^3$, R$^4$, R$^5$, R$^6$ and R$^7$ is trifluoromethoxy.

In some embodiments, he compound of Formula (II-I) has Formula (II-II):

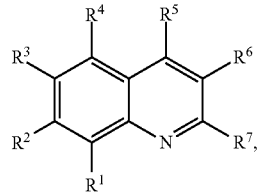

(II-II)

or a pharmaceutically acceptable salt thereof, wherein R$^1$, R$^2$, R$^3$, R$^4$, R$^5$, R$^6$, and R$^7$ are as described herein. In some aspects of these embodiments, at least one of R$^1$, R$^2$, R$^3$, R$^4$, R$^5$, R$^6$ and R$^7$ is trifluoromethoxy.

In some embodiments, he compound of Formula (II-II) has Formula (II-IIa):

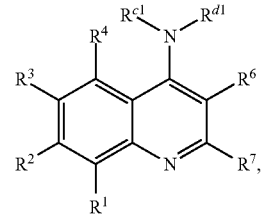

(II-IIa)

or a pharmaceutically acceptable salt thereof, wherein R$^1$, R$^2$, R$^3$, R$^4$, R$^6$, R$^7$, R$^{c1}$ and R$^{d1}$ are as described herein. In some aspects of these embodiments, at least one of R$^1$, R$^2$, R$^3$, R$^4$, R$^6$ and R$^7$ is trifluoromethoxy.

In some embodiments, the compound of Formula (II-IIa) has formula (II-IIb):

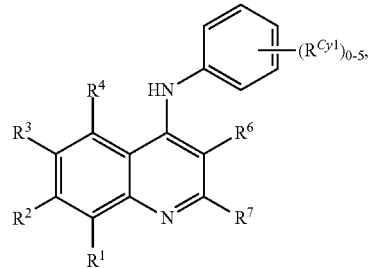

(II-IIb)

or a pharmaceutically acceptable salt thereof, wherein R$^1$, R$^2$, R$^3$, R$^4$, R$^6$, R$^7$, and R$^{Cy1}$ are as described herein.

In some embodiments of Formula (II-IIb):

each R$^{Cy1}$ is independently selected from C$_{1-6}$ alkyl, C(O)OR$^{a1}$, OR$^{a1}$, C(O)R$^{b1}$, and halo; and R$^1$, R$^2$, R$^3$, R$^4$, R$^6$, and R$^7$ are each independently selected from H, halo Cy$^1$, C$_{1-6}$ alkyl, OR$^{a1}$, SR$^{a1}$, C(O)OR$^{a1}$, C(O)NR$^{c1}$R$^{d1}$, NR$^{c1}$C(O)R$^{b1}$, NR$^{c1}$R$^{d1}$, S(O)$_2$R$^{b1}$ and C(O)R$^{b1}$.

In some aspects of these embodiments, R$^1$, R$^2$, R$^3$, R$^4$, R$^6$, and R$^7$ are each independently selected from H, C$_{1-6}$ alkyl, OR$^{a1}$, C(O)OR$^{a1}$, and C(O)R$^{b1}$. In other aspects of these embodiments, at least one of R$^1$, R$^2$, R$^3$, R$^4$, R$^6$ and R$^7$ is trifluoromethoxy.

In some embodiments, the compound of Formula (II-II) is any one of compounds 1-31 listed in Table 5. In some embodiments, the compound of Formula (II-II) is not any one of compounds 1-31 listed in Table 5.

In some embodiments, the compound of Formula (II-II) is any one of compounds 83-96 listed in Table 5. In some embodiments, the compound of Formula (II-II) is not any one of compounds 83-96 listed in Table 5.

In some embodiments, the compound of Formula (II-IIa) has formula (II-IIc):

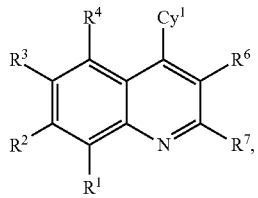

(II-IIc)

or a pharmaceutically acceptable salt thereof, wherein $R^1$, $R^2$, $R^3$, $R^4$, $R^6$, $R^7$, and $Cy^1$ are as described herein. In some aspects of these embodiments, at least one of $R^1$, $R^2$, $R^3$, $R^4$, $R^6$ and $R^7$ is trifluoromethoxy.

In some embodiments of Formula (II-IIc), $Cy^1$ in Formula (II-IIc) is 4-12 membered heterocycloalkyl, which is optionally substituted with 1, 2, or 3 independently selected $R^{Cy1}$. In some aspects of these embodiments, $Cy^1$ is a 6-membered heterocycloalkyl of formula:

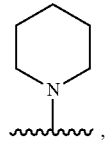

which is optionally substituted with 1, 2, or 3 independently selected $R^{Cy1}$. In some aspects of these embodiments, at least one $R^{Cy1}$ is $C(O)NR^{c4}R^{d4}$.

In some embodiments, the compound of Formula (II-IIa) has formula (II-IId):

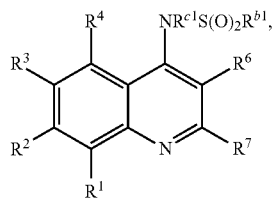

(II-IId)

or a pharmaceutically acceptable salt thereof, wherein $R^1$, $R^2$, $R^3$, $R^4$, $R^6$, $R^7$, $R^{c1}$ and $R^{b1}$ are as described herein. In some aspects of these embodiments, at least one of $R^1$, $R^2$, $R^3$, $R^4$, $R^6$ and $R^7$ is trifluoromethoxy.

In some embodiments, the compound of Formula (II-IIa) has formula (II-IIe):

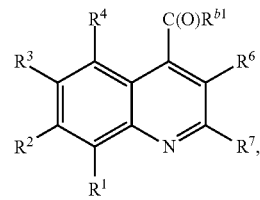

(II-IIe)

or a pharmaceutically acceptable salt thereof, wherein $R^1$, $R^2$, $R^3$, $R^4$, $R^6$, $R^7$, and $R^{b1}$ are as described herein. In some aspects of these embodiments, at least one of $R^1$, $R^2$, $R^3$, $R^4$, $R^6$ and $R^7$ is trifluoromethoxy.

In some embodiments, the compound of Formula (II-II) has any one of Formulae:

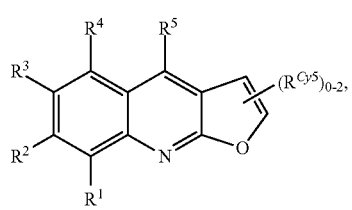

(II-IIf)

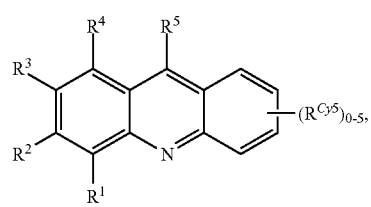

(II-IIg)

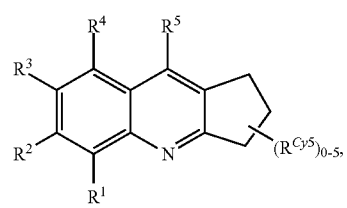

(II-IIh)

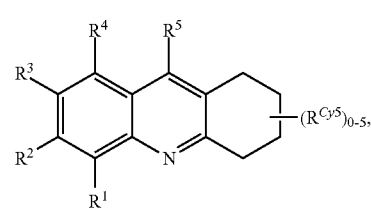

(II-IIi)

or a pharmaceutically acceptable salt thereof, wherein $R^1$, $R^2$, $R^3$, $R^4$, $R^5$, and $R^{Cy5}$ are as described herein.

In some embodiments, the compound of Formula (II-I) has Formula (II-III):\

(II-III)

or a pharmaceutically acceptable salt thereof, wherein R¹, R², R³, R⁴, and R⁷ are as described herein.

In some embodiments, a compound of Formula (II-III) is selected from any one of compounds 32-33 listed in Table 5. In some embodiments, a compound of Formula (II-III) is not any one of compounds 32-33 listed in Table 5.

In some embodiments, the compound of Formula (II-I) has formula:

or a pharmaceutically acceptable salt thereof, wherein R², R⁴, R⁶, and R⁸ are as described herein.

In some embodiments, the compound of Formula (II-I) has formula:

or a pharmaceutically acceptable salt thereof, wherein R², R³, R⁵, and R⁷ are as described herein.

In some embodiments, the compound of Formula (II-I) has formula:

or a pharmaceutically acceptable salt thereof, wherein R⁵, R⁷, and $R^{Cy5}$ are as described herein.

In some embodiments, the compound of Formula (II-I) has formula:

or a pharmaceutically acceptable salt thereof, wherein R², R³, R⁷, and $R^{N6}$ are as described herein.

In some embodiments, the compound of Formula (II-I) has formula:

or a pharmaceutically acceptable salt thereof, wherein R², R⁴, R⁵, and R⁶ are as described herein.

In some embodiments, the compound of Formula (II-I) has formula:

or a pharmaceutically acceptable salt thereof, wherein $R^{N2}$, R³, R⁶, and R⁷ are as described herein.

In some embodiments, the compound of Formula (II-I) has formula:

or a pharmaceutically acceptable salt thereof, wherein R², R⁴, and $R^{Cy5}$ are as described herein.

In some embodiments, the compound of Formula (II-I) has formula:

or a pharmaceutically acceptable salt thereof, wherein R², R³, R⁵, and $R^{Cy5}$ are as described herein.

In some embodiments, the compound of Formula (II-I) has formula:

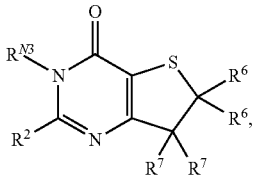

or a pharmaceutically acceptable salt thereof, wherein $R^2$, $R^{N3}$, $R^6$, and $R^7$ are as described herein.

In some embodiments, the compound of Formula (II-I) has formula:

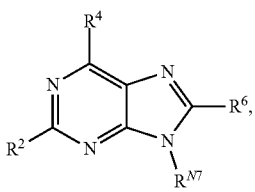

or a pharmaceutically acceptable salt thereof, wherein $R^2$, $R^4$, $R^6$, and $R^{N7}$ are as described herein.

In some embodiments, the compound of Formula (II-I) has formula:

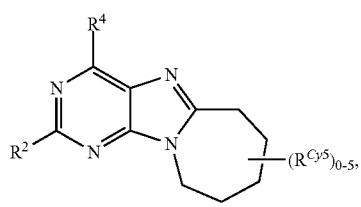

or a pharmaceutically acceptable salt thereof, wherein $R^2$, $R^4$, and $R^{Cy5}$ are as described herein.

In some embodiments, the compound of Formula (II-I) has formula:

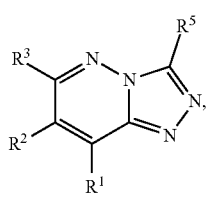

or a pharmaceutically acceptable salt thereof, wherein $R^1$, $R^2$, $R^3$, and $R^5$ are as described herein.

In some embodiments, the compound of Formula (II-I) has formula:

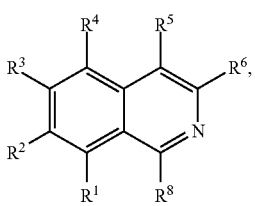

or a pharmaceutically acceptable salt thereof, wherein $R^1$, $R^2$, $R^3$, $R^4$, $R^5$, $R^6$, and $R^8$ are as described herein.

In some embodiments, the compound of Formula (II-I) has formula:

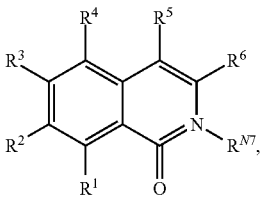

or a pharmaceutically acceptable salt thereof, wherein $R^1$, $R^2$, $R^3$, $R^4$, $R^5$, $R^6$, and $R^{N7}$ are as described herein.

In some embodiments, the compound of Formula (II-I) has formula:

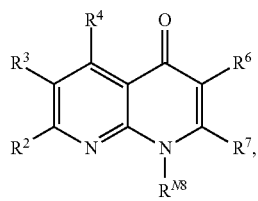

or a pharmaceutically acceptable salt thereof, wherein $R^2$, $R^3$, $R^4$, $R^6$, $R^7$, and $R^{N8}$ are as described herein.

In some embodiments, the compound of Formula (II-I) has formula:

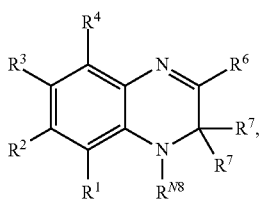

or a pharmaceutically acceptable salt thereof, wherein $R^1$, $R^2$, $R^3$, $R^4$, $R^6$, $R^7$, and $R^{N8}$ are as described herein.

In some embodiments, the compound of Formula (II-I) has formula:

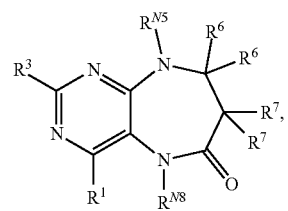

or a pharmaceutically acceptable salt thereof, wherein $R^1$, $R^3$, $R^4$, $R^{N5}$, $R^6$, $R^7$, and $R^{N8}$ are as described herein.

In some embodiments, the compound of Formula (II-I) has formula:

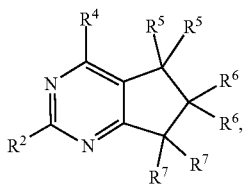

or a pharmaceutically acceptable salt thereof, wherein $R^2$, $R^4$, $R^6$, $R^7$, and $R^5$ are as described herein.

In some embodiments, the compound of Formula (II-I) has formula:

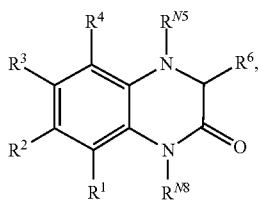

or a pharmaceutically acceptable salt thereof, wherein $R^1$, $R^2$, $R^3$, $R^4$, $R^6$, $R^{N5}$, and $R^{N8}$ are as described herein.

In some embodiments, the compound of Formula (II-I) has formula:

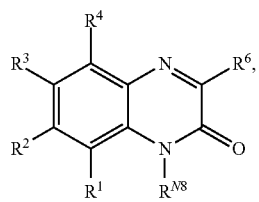

or a pharmaceutically acceptable salt thereof, wherein $R^1$, $R^2$, $R^3$, $R^4$, $R^6$, and $R^{N8}$ are as described herein.

In some embodiments, the compound of Formula (II-I) has formula:

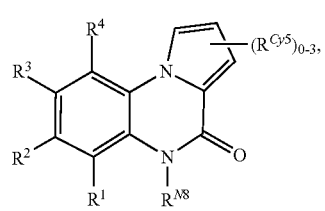

or a pharmaceutically acceptable salt thereof, wherein $R^1$, $R^2$, $R^3$, $R^4$, $R^{N5}$, and $R^{Cy5}$ are as described herein.

In some embodiments, the compound of Formula (II-I) has formula:

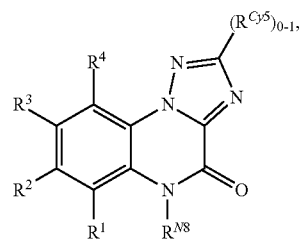

or a pharmaceutically acceptable salt thereof, wherein $R^1$, $R^2$, $R^3$, $R^4$, $R^{N5}$, and $R^{Cy5}$ are as described herein. In some embodiments, the compound of Formula (II-I) has formula:

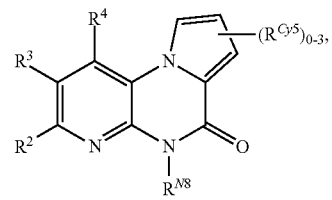

or a pharmaceutically acceptable salt thereof, wherein $R^2$, $R^3$, $R^4$, $R^{N5}$, and $R^{Cy5}$ are as described herein.

In some embodiments, the compound of Formula (II-I) has formula:

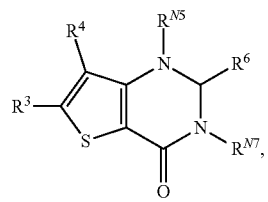

or a pharmaceutically acceptable salt thereof, wherein $R^3$, $R^4$, $R^6$, $R^{N7}$, and $R^{N5}$ are as described herein.

In some embodiments, the compound of Formula (II-I) has formula:

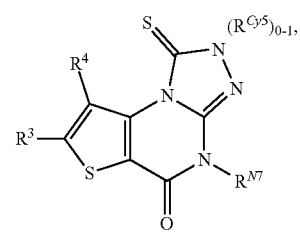

or a pharmaceutically acceptable salt thereof, wherein $R^3$, $R^4$, $R^{N7}$, and $R^{Cy5}$ are as described herein.

In some embodiments, the compound of Formula (II-I) has formula:

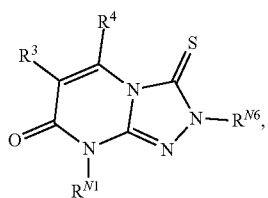

or a pharmaceutically acceptable salt thereof, wherein $R^{N1}$, $R^3$, $R^4$, and $R^{N6}$ are as described herein.

In some embodiments, the compound of Formula (II-I) has formula:

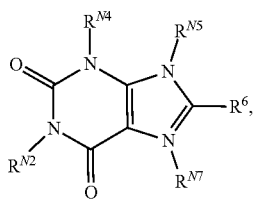

or a pharmaceutically acceptable salt thereof, wherein $R^{N2}$, $R^{N4}$, $R^{N5}$, $R^6$, and $R^{N7}$ are as described herein.

In some embodiments, the compound of Formula (II-I) has formula:

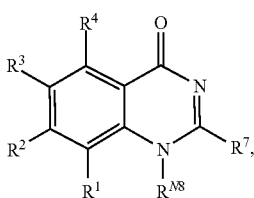

or a pharmaceutically acceptable salt thereof, wherein $R^1$, $R^2$, $R^3$, $R^4$, $R^7$, and $R^{N8}$ are as described herein.

In some embodiments, the compound of Formula (II-I) has formula:

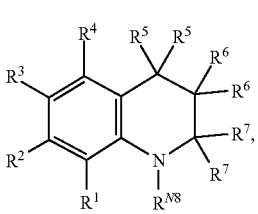

or a pharmaceutically acceptable salt thereof, wherein $R^1$, $R^2$, $R^3$, $R^4$, $R^5$, $R^6$, $R^7$, and $R^{N8}$ are as described herein.

In some embodiments, the compound of Formula (II-I) has formula:

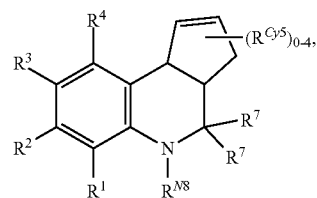

or a pharmaceutically acceptable salt thereof, wherein $R^1$, $R^2$, $R^3$, $R^4$, $R^{N8}$, $R^7$, and $R^{Cy5}$ are as described herein.

In some embodiments, the compound of Formula (II-I) has formula:

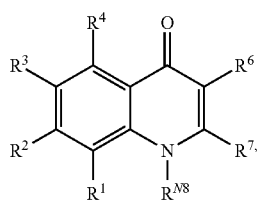

or a pharmaceutically acceptable salt thereof, wherein $R^1$, $R^2$, $R^3$, $R^4$, $R^6$, $R^7$, and $R^{N8}$ are as described herein.

In some embodiments, the compound of Formula (II-I) has formula:

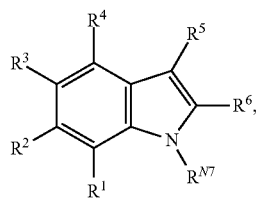

or a pharmaceutically acceptable salt thereof, wherein $R^1$, $R^2$, $R^3$, $R^4$, $R^6$, $R^{N7}$, and $R^5$ are as described herein.

In some embodiments, the compound of Formula (II-I) has formula:

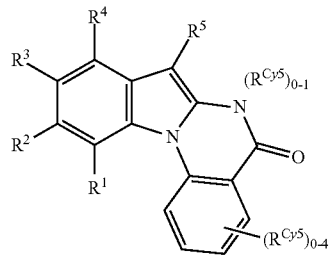

or a pharmaceutically acceptable salt thereof, wherein $R^1$, $R^2$, $R^3$, $R^4$, $R^5$, and $R^{Cy5}$ are as described herein.

In some embodiments, the compound of Formula (II-I) has formula:

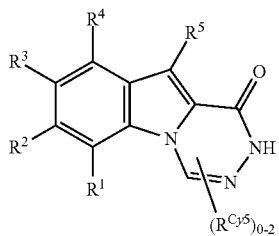

or a pharmaceutically acceptable salt thereof, wherein $R^1$, $R^2$, $R^3$, $R^4$, $R^5$, and $R^{Cy5}$ are as described herein.

In some embodiments, the compound of Formula (II-I) has formula:

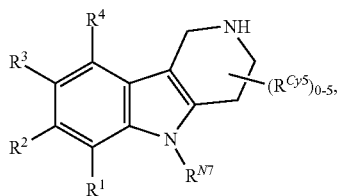

or a pharmaceutically acceptable salt thereof, wherein $R^1$, $R^2$, $R^3$, $R^4$, $R^{N7}$, and $R^{Cy5}$ are as described herein.

In some embodiments, the compound of Formula (II-I) has formula:

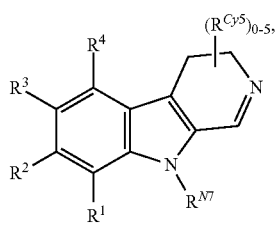

or a pharmaceutically acceptable salt thereof, wherein $R^1$, $R^2$, $R^3$, $R^4$, $R^{N7}$, and $R^{Cy5}$ are as described herein.

In some embodiments, the compound of Formula (II-I) has formula:

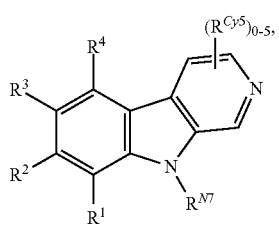

or a pharmaceutically acceptable salt thereof, wherein $R^1$, $R^2$, $R^3$, $R^4$, $R^{N7}$, and $R^{Cy5}$ are as described herein.

In some embodiments, the compound of Formula (II-I) has formula:

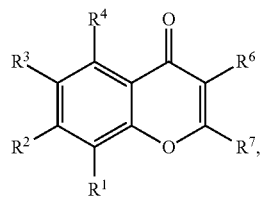

or a pharmaceutically acceptable salt thereof, wherein $R^1$, $R^2$, $R^3$, $R^4$, $R^6$, and $R^7$ are as described herein.

In some embodiments, the compound of Formula (II-I) has formula:

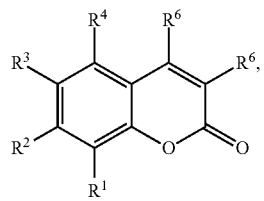

or a pharmaceutically acceptable salt thereof, wherein $R^1$, $R^2$, $R^3$, $R^4$, $R^6$, and $R^5$ are as described herein.

In some embodiments, the compound of Formula (II-I) has formula:

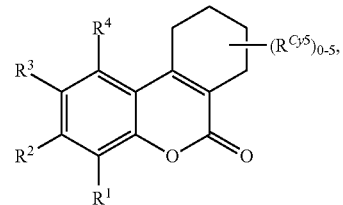

or a pharmaceutically acceptable salt thereof, wherein $R^1$, $R^2$, $R^3$, $R^4$, and $R^{Cy5}$ are as described herein.

In some embodiments, the compound of Formula (II-I) has formula:

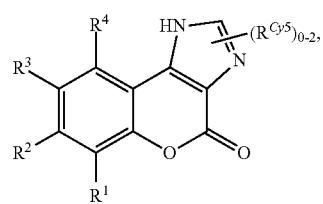

or a pharmaceutically acceptable salt thereof, wherein $R^1$, $R^2$, $R^3$, $R^4$, and $R^{Cy5}$ are as described herein.

In some embodiments, the compound of Formula (II-I) has formula:

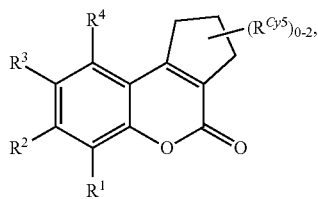

or a pharmaceutically acceptable salt thereof, wherein $R^1$, $R^2$, $R^3$, $R^4$, and $R^{Cy5}$ are as described herein.

In some embodiments, the compound of Formula (II-I) has formula:

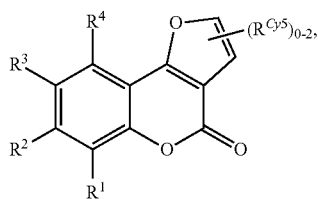

or a pharmaceutically acceptable salt thereof, wherein $R^1$, $R^2$, $R^3$, $R^4$, and $R^{Cy5}$ are as described herein.

In some embodiments, the compound of Formula (II-I) has formula:

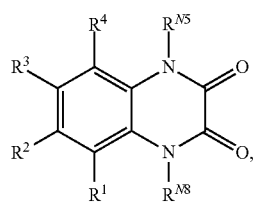

or a pharmaceutically acceptable salt thereof, wherein $R^1$, $R^2$, $R^3$, $R^4$, $R^{N5}$, and $R^{N8}$ are as described herein.

In some embodiments, the compound of Formula (II-I) has formula:

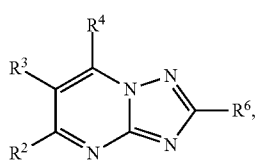

or a pharmaceutically acceptable salt thereof, wherein $R^2$, $R^3$, $R^4$, and $R^6$ are as described herein.

In some embodiments, the compound of Formula (II-I) has formula:

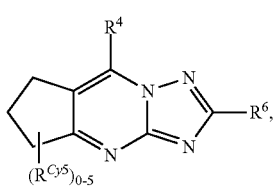

or a pharmaceutically acceptable salt thereof, wherein $R^4$, $R^6$, and $R^{Cy5}$ are as described herein.

In some embodiments, the compound of Formula (II-I) has formula:

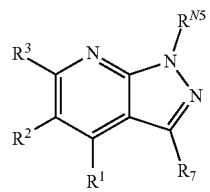

or a pharmaceutically acceptable salt thereof, wherein $R^1$, $R^2$, $R^3$, $R^{N5}$, and $R^7$ are as described herein.

In some embodiments, the compound of Formula (II-I) has formula:

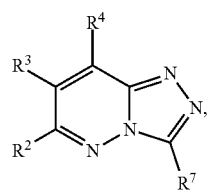

or a pharmaceutically acceptable salt thereof, wherein $R^2$, $R^3$, $R^4$, and $R^7$ are as described herein.

In some embodiments, the compound of Formula (II-I) has formula:

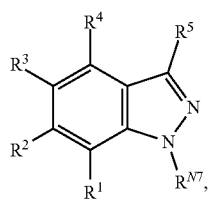

or a pharmaceutically acceptable salt thereof, wherein $R^1$, $R^2$, $R^3$, $R^4$, $R^5$, and $R^{N7}$ are as described herein.

In some embodiments, the compound of Formula (II-I) has formula:

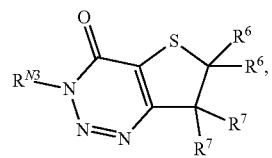

or a pharmaceutically acceptable salt thereof, wherein $R^{N3}$, $R^6$, and $R^7$ are as described herein.

In some embodiments, the compound of Formula (II-I) has formula:

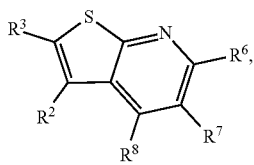

or a pharmaceutically acceptable salt thereof, wherein $R^2$, $R^3$, $R^6$, $R^7$, and $R^8$ are as described herein.

In some embodiments, the compound of Formula (II-I) has formula:

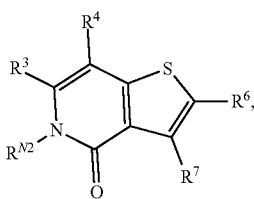

or a pharmaceutically acceptable salt thereof, wherein $R^{N2}$, $R^3$, $R^4$, $R^6$, and $R^7$ are as described herein.

In some embodiments, the compound of Formula (II-I) has formula:

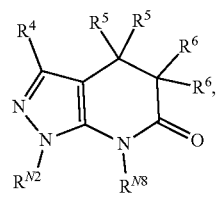

or a pharmaceutically acceptable salt thereof, wherein $R^{N2}$, $R^4$, $R^6$, $R^5$, and $R^{N8}$ are as described herein.

In some embodiments, the compound of Formula (II-I) has formula:

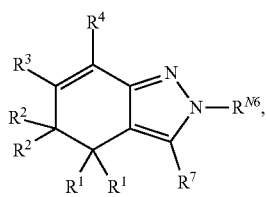

or a pharmaceutically acceptable salt thereof, wherein $R^1$, $R^2$, $R^3$, $R^4$, $R^{N6}$, and $R^7$ are as described herein.

In some embodiments, the compound of Formula (II-I) has formula:

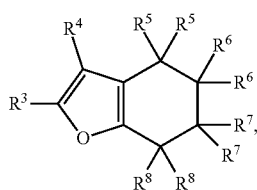

or a pharmaceutically acceptable salt thereof, wherein $R^3$, $R^4$, $R^5$, $R^6$, $R^7$, and $R^8$ are as described herein.

In some embodiments, the compound of Formula (II-I) has formula:

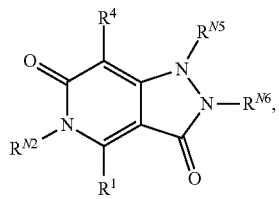

or a pharmaceutically acceptable salt thereof, wherein $R^1$, $R^{N2}$, $R^4$, $R^{N5}$, and $R^{N6}$ are as described herein.

In some embodiments, the compound of Formula (II-I) has formula:

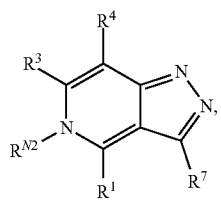

or a pharmaceutically acceptable salt thereof, wherein $R^1$, $R^{N2}$, $R^3$, $R^4$, and $R^7$ are as described herein.

In some embodiments, the compound of Formula (II-I) has formula:

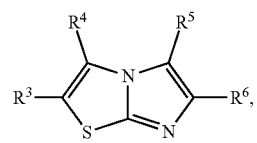

or a pharmaceutically acceptable salt thereof, wherein $R^3$, $R^4$, $R^6$, and $R^5$ are as described herein.

In some embodiments, the compound of Formula (II-I) has formula:

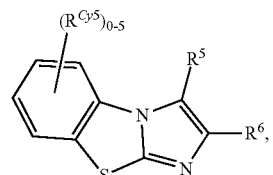

or a pharmaceutically acceptable salt thereof, wherein $R^5$, $R^6$, and $R^{Cy5}$ are as described herein.

In some embodiments, the compound of Formula (II-I) has formula:

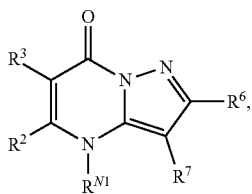

or a pharmaceutically acceptable salt thereof, wherein $R^{N1}$, $R^2$, $R^3$, $R^6$, and $R^7$ are as described herein.

In some embodiments, the compound of Formula (II-I) has formula:

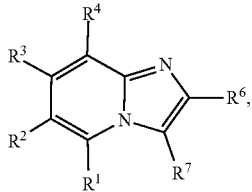

or a pharmaceutically acceptable salt thereof, wherein $R^1$, $R^2$, $R^3$, $R^4$, $R^6$, and $R^7$ are as described herein.

In some embodiments, the compound of Formula (II-I) has formula:

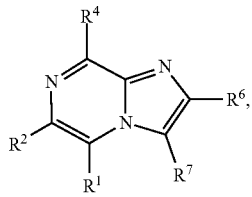

or a pharmaceutically acceptable salt thereof, wherein $R^1$, $R^2$, $R^4$, $R^6$, and $R^7$ are as described herein.

In some embodiments, the compound of Formula (II-I) has formula:

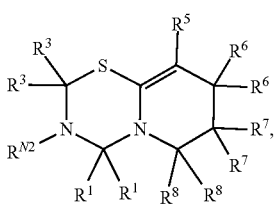

or a pharmaceutically acceptable salt thereof, wherein $R^1$, $R^{N2}$, $R^3$, $R^3$, $R^6$, $R^7$, and $R^8$ are as described herein.

In some embodiments, the compound of Formula (II-I) has formula:

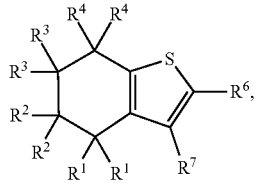

or a pharmaceutically acceptable salt thereof, wherein $R^1$, $R^2$, $R^3$, $R^4$, $R^6$, and $R^7$ are as described herein.

In some embodiments, the compound of Formula (II-I) has formula:

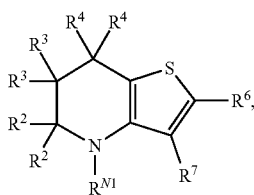

or a pharmaceutically acceptable salt thereof, wherein $R^{N1}$, $R^2$, $R^3$, $R^4$, $R^6$, and $R^7$ are as described herein.

In some embodiments, the compound of Formula (II-I) has formula:

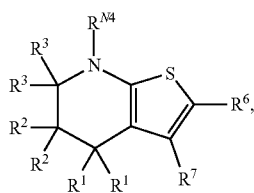

or a pharmaceutically acceptable salt thereof, wherein $R^1$, $R^2$, $R^3$, $R^{N4}$, $R^6$, and $R^7$ are as described herein.

In some embodiments, the compound of Formula (II-I) has formula:

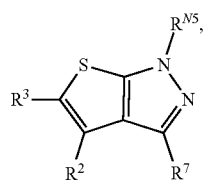

or a pharmaceutically acceptable salt thereof, wherein $R^2$, $R^3$, $R^{N5}$, and $R^7$ are as described herein.

In some embodiments, the compound of Formula (II-I) has formula:

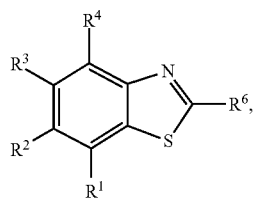

or a pharmaceutically acceptable salt thereof, wherein $R^1$, $R^2$, $R^3$, $R^4$, and $R^6$ are as described herein.

In some embodiments, the compound of Formula (II-I) has formula:

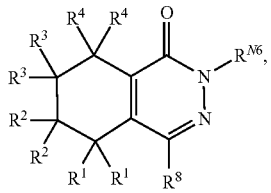

or a pharmaceutically acceptable salt thereof, wherein $R^1$, $R^2$, $R^3$, $R^4$, $R^{N6}$, and $R^8$ are as described herein.

In some embodiments, the compound of Formula (II-I) has formula:

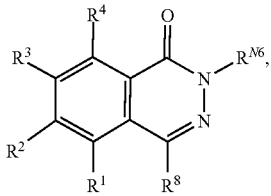

or a pharmaceutically acceptable salt thereof, wherein $R^1$, $R^2$, $R^3$, $R^4$, $R^{N6}$, and $R^8$ are as described herein.

In some embodiments, the compound of Formula (II-I) has formula:

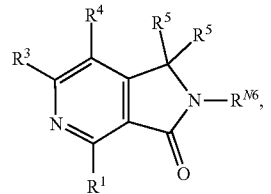

or a pharmaceutically acceptable salt thereof, wherein $R^1$, $R^3$, $R^4$, $R^5$, and $R^{N6}$ are as described herein.

In some embodiments, the compound of Formula (II-I) has formula:

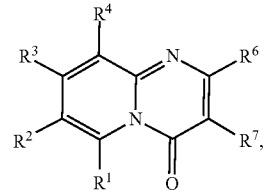

or a pharmaceutically acceptable salt thereof, wherein $R^1$, $R^2$, $R^3$, $R^4$, $R^6$, and $R^7$ are as described herein.

In some embodiments, the compound of Formula (II-I) has formula:

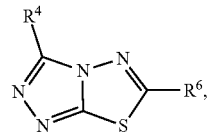

or a pharmaceutically acceptable salt thereof, wherein $R^4$ and $R^6$ are as described herein.

In some embodiments, the compound of Formula (II-I) has formula:

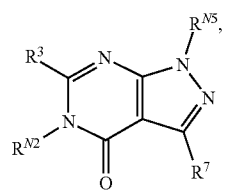

or a pharmaceutically acceptable salt thereof, wherein $R^{N2}$, $R^3$, $R^{N5}$, and $R^7$ are as described herein.

In some embodiments, the compound of Formula (II-I) has formula:

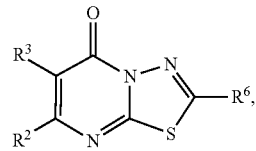

or a pharmaceutically acceptable salt thereof, wherein $R^2$, $R^3$, and $R^6$ are as described herein.

In some embodiments, the compound of Formula (II-I) has formula:

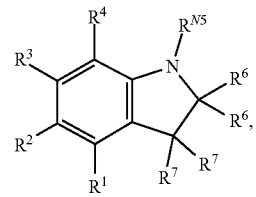

or a pharmaceutically acceptable salt thereof, wherein $R^1$, $R^2$, $R^3$, $R^4$, $R^{N5}$, $R^6$, and $R^7$ are as described herein.

In some embodiments, the compound of Formula (II-I) has formula:

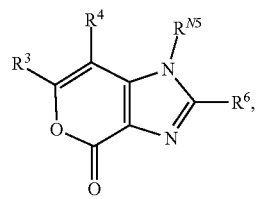

or a pharmaceutically acceptable salt thereof, wherein $R^3$, $R^4$, $R^{N5}$, and $R^6$ are as described herein.

In some embodiments, the compound of Formula (II-I) has formula:

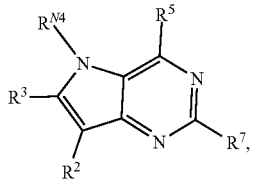

or a pharmaceutically acceptable salt thereof, wherein $R^2$, $R^3$, $R^{N4}$, $R^5$, and $R^7$ are as described herein.

In some embodiments, the compound of Formula (II-I) has formula:

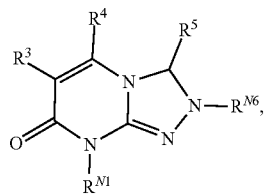

or a pharmaceutically acceptable salt thereof, wherein $R^{N1}$, $R^3$, $R^4$, $R^5$, and $R^{N6}$ are as described herein.

In some embodiments, the compound of Formula (II-I) has formula:

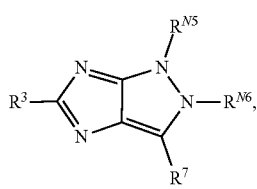

or a pharmaceutically acceptable salt thereof, wherein $R^3$, $R^{N5}$, $R^{N6}$, and $R^7$ are as described herein.

In some embodiments, the compound of Formula (II-I) has formula:

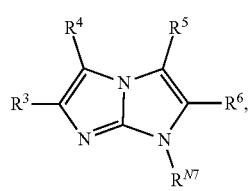

or a pharmaceutically acceptable salt thereof, wherein $R^3$, $R^4$, $R^5$, $R^6$, and $R^{N7}$ are as described herein.

In some embodiments, the compound of Formula (II-I) has formula:

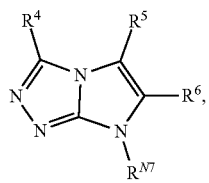

or a pharmaceutically acceptable salt thereof, wherein $R^4$, $R^5$, $R^6$, and $R^{N7}$ are as described herein.

In some embodiments, the compound of Formula (II-I) has formula:

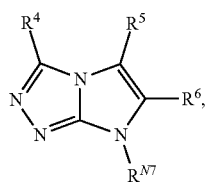

or a pharmaceutically acceptable salt thereof, wherein $R^4$, $R^5$, $R^6$, and $R^{N7}$ are as described herein.

In some embodiments, the compound of Formula (II-I) has formula:

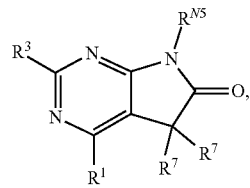

or a pharmaceutically acceptable salt thereof, wherein $R^1$, $R^3$, $R^{N5}$, and $R^7$ are as described herein.

In some embodiments, the compound of Formula (II-I) has formula:

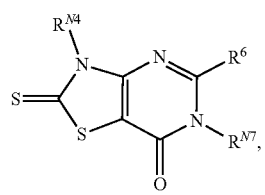

or a pharmaceutically acceptable salt thereof, wherein $R^{N4}$, $R^6$, and $R^{N7}$ are as described herein.

In some embodiments, the compound of Formula (II-I) has formula:

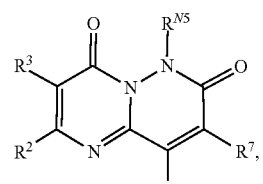

In some embodiments, the compound of Formula (II-I) has formula:

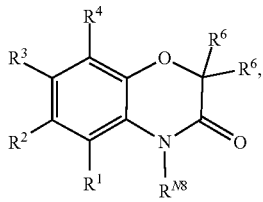

or a pharmaceutically acceptable salt thereof, wherein $R^1$, $R^2$, $R^3$, $R^4$, $R^6$, and $R^{N8}$ are as described herein.

In some embodiments, the compound of Formula (II-I) has formula:

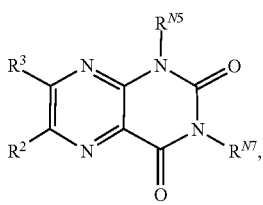

or a pharmaceutically acceptable salt thereof, wherein $R^2$, $R^3$, $R^{N5}$, and $R^{N7}$ are as described herein.

In some embodiments, the compound of Formula (II-I) has formula:

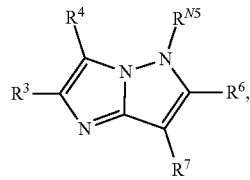

or a pharmaceutically acceptable salt thereof, wherein $R^3$, $R^4$, $R^{N5}$, $R^6$, $R^7$, and $R^{Cy5}$ are as described herein.

In some embodiments, the compound of Formula (II-I) has formula:

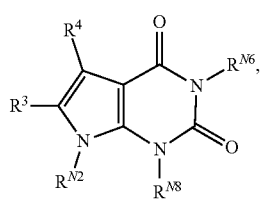

or a pharmaceutically acceptable salt thereof, wherein $R^{N2}$, $R^3$, $R^4$, $R^{N6}$, and $R^{N8}$ are as described herein.

In some embodiments, the compound of Formula (II-I) has formula:

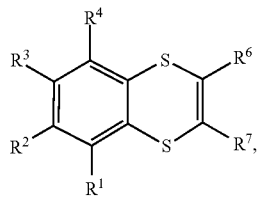

or a pharmaceutically acceptable salt thereof, wherein $R^1$, $R^2$, $R^3$, $R^4$, $R^6$, and $R^7$ are as described herein.

In some embodiments, the compound of Formula (II-I) has formula:

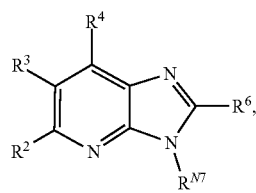

or a pharmaceutically acceptable salt thereof, wherein $R^2$, $R^3$, $R^4$, $R^6$, and $R^{N7}$ are as described herein.

In some embodiments, the compound of Formula (II-I) has formula:

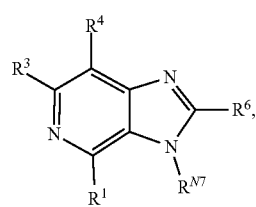

or a pharmaceutically acceptable salt thereof, wherein $R^1$, $R^3$, $R^4$, $R^6$, and $R^{N7}$ are as described herein.

In some embodiments, the compound of Formula (II-I) has formula:

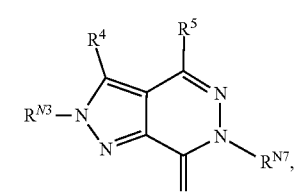

or a pharmaceutically acceptable salt thereof, wherein $R^{N3}$, $R^4$, $R^5$, and $R^{N7}$ are as described herein.

In some embodiments, the compound of Formula (II-I) has formula:

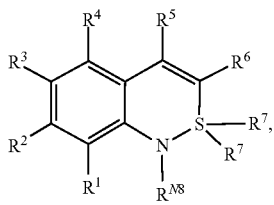

or a pharmaceutically acceptable salt thereof, wherein $R^1$, $R^2$, $R^3$, $R^4$, $R^6$, $R^7$, and $R^{N8}$ are as described herein.

In some embodiments, the compound of Formula (II-I) has formula:

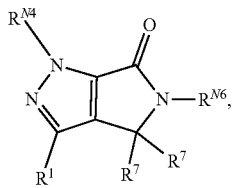

or a pharmaceutically acceptable salt thereof, wherein $R^1$, $R^{N4}$, $R^{N6}$, and $R^7$ are as described herein.

In some embodiments, the compound of Formula (II-I) is any one of compounds 34-243 listed in Table 5. In some embodiments, the compound of Formula (II-I) is not any one of compounds 34-243 listed in Table 5.

In a general aspect, the disclosure provides a compound of Formula (A):

(A)

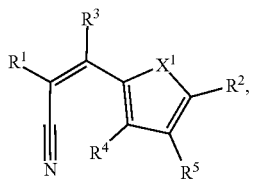

or a pharmaceutically acceptable salt thereof, wherein:
$X^1$ is selected from O, S, S(O), S(O)$_2$, C(=O), N(R$^N$), $C_{1-6}$ alkylene, $C_{2-6}$ alkenylene, and $C_{2-6}$ alkynylene, wherein said $C_{1-6}$ alkylene, $C_{2-6}$ alkenylene, and $C_{2-6}$ alkynylene are each optionally substituted with 1, 2, 3, 4, or 5 substituents independently selected from $R^1$;
$R^1$ is selected from H, $C_{1-6}$ alkyl, $C_{2-6}$ alkenyl, $C_{2-6}$ alkynyl, $C_{1-4}$ haloalkyl, Cy$^1$, CN, NO$_2$, OR$^{a1}$, SR$^{a1}$, C(O)R$^{b1}$, C(O)NR$^{c1}$R$^{d1}$, C(O)OR$^{a1}$, S(O)$_2$R$^{b1}$, S(O)$_2$NR$^{c1}$R$^{d1}$, wherein said $C_{1-6}$ alkyl, $C_{2-6}$ alkenyl and $C_{2-6}$ alkynyl are each optionally substituted with 1, 2, 3, 4, or 5 substituents independently selected from Cy$^1$, halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$ and S(O)$_2$NR$^{c1}$R$^{d1}$;
$R^2$, $R^3$, $R^4$ and $R^5$ are each independently selected from H, $C_{1-6}$ alkyl, $C_{2-6}$ alkenyl, $C_{2-6}$ alkynyl, $C_{1-6}$ haloalkyl, Cy$^2$, halo, CN, NO$_2$, OR$^{a2}$, C(O)R$^{b2}$, C(O)N$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)N$^{c2}$R$^{d2}$, NR$^{c2}$S(O)R$^{b2}$, NR$^{c2}$S(O)$_2$R$^{b2}$, NR$^{c2}$S(O)$_2$N$^{c2}$R$^{d2}$, S(O)R$^{b2}$, S(O)N$^{c2}$R$^{d2}$, S(O)$_2$R$^{b2}$, and S(O)$_2$NR$^{c2}$R$^{d2}$; wherein said $C_{1-6}$ alkyl, $C_{2-6}$ alkenyl, and $C_{2-6}$ alkynyl are each optionally substituted with 1, 2, 3, 4, or 5 substituents independently selected from Cy$^2$, halo, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$N$^{c2}$R$^{d2}$, S(O)R$^{b2}$, S(O)NR$^{c2}$R$^{d2}$, S(O)$_2$R$^{b2}$ and S(O)$_2$NR$^{c2}$R$^{d2}$;

$R^N$ is selected from H, $C_{1-6}$ alkyl, $C_{2-6}$ alkenyl, $C_{2-6}$ alkynyl, $C_{1-6}$ haloalkyl, Cy$^3$, C(O)R$^{b3}$, C(O)NR$^{c3}$R$^{d3}$, C(O)OR$^{a3}$, C(=NR$^{e3}$)NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$; wherein said $C_{1-6}$ alkyl, $C_{2-6}$ alkenyl, and $C_{2-6}$ alkynyl of $R^3$ are each optionally substituted with 1, 2, 3, 4, or 5 substituents independently selected from Cy$^3$, halo, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O) NR$^{c3}$R$^{d3}$, S(O)$_2$R$^{b3}$ and S(O)$_2$NR$^{c3}$R$^{d3}$;

each Cy$^1$, Cy$^2$, and Cy$^3$ are independently selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from R$^{Cy}$;

each R$^{Cy}$ is independently selected from halo, $C_{1-4}$ alkyl, $C_{1-4}$ haloalkyl, $C_{2-6}$ alkenyl, $C_{2-6}$ alkynyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, and (4-7 membered heterocycloalkyl)-$C_{1-4}$ alkylene-, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O) NR$^{c4}$R$^{d4}$, NR$^{c4}$S(O)R$^{b4}$, NR$^{c4}$S(O)$_2$R$^{b4}$, NR$^{c4}$S(O)$_2$ NR$^{c4}$R$^{d4}$, S(O)R$^{b4}$, S(O)NR$^{c4}$R$^{d4}$, S(O)$_2$R$^{b4}$, and S(O)$_2$ NR$^{c4}$R$^{d4}$, wherein said $C_{1-4}$ alkyl, $C_{2-6}$ alkenyl, $C_{2-6}$ alkynyl, $C_{6-10}$ aryl, $C_{3-7}$ cycloalkyl, 5-6 membered heteroaryl, 4-7 membered heterocycloalkyl, $C_{6-10}$ aryl-$C_{1-4}$ alkylene-, $C_{3-7}$ cycloalkyl-$C_{1-4}$ alkylene-, (5-6 membered heteroaryl)-$C_{1-4}$ alkylene-, and (4-7 membered heterocycloalkyl)-$C_{1-4}$ alkylene- are each optionally substituted by 1, 2, 3, 4, or 5 substituents independently selected from $C_{1-6}$ alkyl, $C_{1-4}$ haloalkyl, $C_{1-6}$ cyanoalkyl, halo, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O) NR$^{c4}$R$^{d4}$, C(=NR$^{e4}$)NR$^{c4}$R$^{d4}$, NR$^{c4}$C(=NR$^{e4}$) NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$ R$^{b4}$, and S(O)$_2$NR$^{c4}$R$^{d4}$, each R$^{a1}$, R$^{b1}$, R$^{a2}$, R$^{b2}$, R$^{a3}$, R$^{b3}$, R$^{a4}$, and R$^{b4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are optionally substituted with 1, 2, 3, 4, or 5 substituents independently selected from $R^g$;

each $R^{c1}$, $R^{d1}$, $R^{c2}$, $R^{d2}$, $R^{e3}$, $R^{d3}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, C(O)$R^{b5}$, C(O)NR$^{c5}$R$^{d5}$, C(O)OR$^{a5}$, NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, 3, 4, or 5 substituents independently selected from $R^g$;

each $R^{a5}$, $R^{b5}$, $R^{c5}$, and $R^{d5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene and $R^g$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, 3, 4, or 5 substituents independently selected from $R^g$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $R^g$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $R^g$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $R^g$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $R^g$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $R^g$;

each $R^{e1}$, $R^{e2}$, $R^{e3}$, and $R^{e4}$ is independently selected from H, $C_{1-4}$ alkyl, $C_{1-4}$ alkoxy, OH, and CN; and each $R^g$ is independently selected from OH, NO$_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $X^1$ is selected from O, S, S(O)$_2$, N(R$^N$), $C_{1-6}$ alkylene, and $C_{2-6}$ alkenylene, wherein said $C_{1-6}$ alkylene and $C_{2-6}$ alkenylene are each optionally substituted with 1, 2, or 3 substituents independently selected from $R^1$.

In some embodiments, $X^1$ is selected from O, S and N(R$^N$). In some embodiments, $X^1$ is O. In some embodiments, $X^1$ is S. In some embodiments, $X^1$ is N(R$^N$). In some embodiments, $X^1$ is $C_{1-6}$ alkylene optionally substituted with 1, 2, or 3 independently selected $R^1$. In some embodiments, $X^1$ is methylene, optionally substituted with $R^1$. In some embodiments, $X^1$ is $C_{2-6}$ alkenylene, which is optionally substituted with 1, 2, or 3 independently selected $R^1$. In some embodiments, $X^1$ is ethenylene, which is optionally substituted with 1 or 2 independently selected $R^1$.

In some embodiments, $R^1$ is selected from H, $C_{1-6}$ alkyl, $C_{1-4}$ haloalkyl, Cy$^1$, CN, NO$_2$, OR$^{a1}$, C(O)R$^{b1}$, C(O)NR$^{c1}$R$^{d1}$, C(O)OR$^{a1}$, S(O)$_2$R$^{b1}$, and S(O)$_2$NR$^{c1}$R$^{d1}$, wherein said $C_{1-6}$ alkyl is optionally substituted with 1, 2, or 3 substituents independently selected from Cy$^1$, halo, CN, NO$_2$, OH, C(O)NH$_2$, C(O)OH, NH$_2$, and S(O)$_2$NH$_2$.

In some embodiments, $R^1$ is selected from H, $C_{1-6}$ alkyl, $C_{1-4}$ haloalkyl, Cy$^1$, CN, NO$_2$, OH, C(O)R$^{b1}$, C(O)NR$^{c1}$R$^{d1}$, C(O)OR$^{a1}$, S(O)$_2$R$^{b1}$, and S(O)$_2$NR$^{c1}$R$^{d1}$, wherein said $C_{1-6}$ alkyl is optionally substituted with 1, 2, or 3 substituents independently selected from halo, CN, NO$_2$, OH, C(O)NH$_2$, C(O)OH, and NH$_2$.

In some embodiments, $R^1$ is C(O)NR$^{c1}$R$^{d1}$. In some embodiments, $R^1$ is Cy$^1$.

In some embodiments, $R^2$ is selected from H, $C_{1-6}$ alkyl, $C_{1-4}$ haloalkyl, Cy$^2$, OR$^{a2}$, C(O)R$^{b2}$, C(O)NR$^{c2}$R$^{d2}$, C(O)OR$^{a2}$, NR$^{c2}$R$^{d2}$, S(O)$_2$R$^{b2}$, and S(O)$_2$NR$^{c2}$R$^{d2}$, wherein said $C_{1-6}$ alkyl is optionally substituted with 1, 2, or 3 substituents independently selected from Cy$^2$, halo, CN, NO$_2$, OH, C(O)NH$_2$, C(O)OH, NH$_2$, and S(O)$_2$NH$_2$.

In some embodiments, $R^2$ is selected from H, $C_{1-6}$ alkyl, $C_{1-4}$ haloalkyl, Cy$^2$, OR$^{a2}$, C(O)R$^{b2}$, NR$^{c2}$R$^{d2}$, S(O)$_2$R$^{b2}$, and S(O)$_2$NR$^{c2}$R$^{d2}$; wherein said $C_{1-6}$ alkyl is optionally substituted with 1, 2, or 3 substituents independently selected from Cy$^2$, halo, CN, NO$_2$, and OH.

In some embodiments, $R^2$ is Cy$^2$. In some embodiments, $R^3$, $R^4$ and $R^5$ are each independently selected from H, $C_{1-6}$ alkyl, $C_{1-6}$ haloalkyl, Cy$^2$, halo, CN, NO$_2$, OR$^{a2}$, C(O)R$^{b2}$, C(O)NR$^{c2}$R$^{d2}$, C(O)OR$^{a2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)$_2$R$^{b2}$, NR$^{c2}$S(O)$_2$NR$^{c2}$R$^{d2}$, S(O)$_2$R$^{b2}$, and S(O)$_2$NR$^{c2}$R$^{d2}$; wherein said $C_{1-6}$ alkyl is optionally substituted with 1, 2, or 3 substituents independently selected from Cy$^2$, halo, CN, NO$_2$, OR$^{a2}$, SR$^{a2}$, C(O)R$^{b2}$, C(O)NR$^{c2}$R$^{d2}$, C(O)OR$^{a2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)$_2$R$^{b2}$, NR$^{c2}$S(O)$_2$NR$^{c2}$R$^{d2}$, S(O)$_2$R$^{b2}$ and S(O)$_2$NR$^{c2}$R$^{d2}$.

In some embodiments, $R^3$, $R^4$ and $R^5$ are each independently selected from H, $C_{1-6}$ alkyl, $C_{1-6}$ haloalkyl, Cy$^2$, halo, CN, NO$_2$, C(O)R$^{b2}$, C(O)NR$^{c2}$R$^{d2}$, C(O)OR$^{a2}$, S(O)$_2$R$^{b2}$, and S(O)$_2$NR$^{c2}$R$^{d2}$; wherein said $C_{1-6}$ alkyl is optionally substituted with 1, 2, or 3 substituents independently selected from Cy$^2$, halo, CN, NO$_2$, C(O)R$^{b2}$, C(O)NR$^{c2}$R$^{d2}$, C(O)OR$^{a2}$, S(O)$_2$R$^{b2}$ and S(O)$_2$NR$^{c2}$R$^{d2}$.

In some embodiments, $R^3$, $R^4$ and $R^5$ are each independently selected from H, $C_{1-6}$ alkyl, $C_{1-6}$ haloalkyl. In some embodiments, $R^3$, $R^4$ and $R^5$ are each H.

In some embodiments, $R^N$ is selected from H, $C_{1-6}$ alkyl, $C_{1-6}$ haloalkyl, $Cy^3$, $C(O)R^{b3}$, $C(O)NR^{c3}R^{d3}$, $C(O)OR^{a3}$, $S(O)_2R^{b3}$, and $S(O)_2NR^{c3}R^{d3}$; wherein said $C_{1-6}$ alkyl is optionally substituted with 1, 2, or 3 substituents independently selected from $Cy^3$, halo, CN, $NO_2$, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $S(O)_2R^{b3}$ and $S(O)_2NR^{c3}R^{d3}$.

In some embodiments, $R^N$ is selected from H, $C_{1-6}$ alkyl, and $C_{1-6}$ haloalkyl.

In some embodiments, $Cy^1$ is selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy}$.

In some embodiments, $Cy^1$ is 5-10 membered heteroaryl, which is optionally substituted with 1, 2, or 3 independently selected $R^{Cy}$.

In some embodiments, $Cy^2$ is selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy}$.

In some embodiments, $Cy^2$ is $C_{6-10}$ aryl, which is optionally substituted with 1, 2, or 3 independently selected $R^{Cy}$.

In some embodiments, $Cy^3$ is selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy}$.

In some embodiments, each $R^{Cy}$ is independently selected from halo, $C_{1-4}$ alkyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl is optionally substituted by 1, 2, or 3 substituents independently selected from halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O))_2R^{b4}$, and $S(O)_2NR^{c4}R^{d4}$.

In some embodiments, each $R^{Cy}$ is independently selected from halo, $C_{1-4}$ alkyl, $C_{1-4}$ haloalkyl, CN, $NO_2$, $OR^{a4}$, $C(O)NR^{c4}R^{d4}$, $C(O)OR^{a4}$, $NR^{c4}R^{d4}$, $S(O)_2R^{b4}$, and $S(O)_2NR^{c4}R^{d4}$, wherein said $C_{1-4}$ alkyl is optionally substituted by 1, 2, or 3 substituents independently selected from halo, CN, $NO_2$, OH, $C(O)NH_2$, $C(O)OH$, $NH_2$, and $S(O)_2NH_2$.

In some embodiments, each $R^{Cy}$ is independently selected from halo and $C(O)OR^{a4}$.

In some embodiments, each $R^{a1}$, $R^{b1}$, $R^{a2}$, $R^{b2}$, $R^{a3}$, $R^{b3}$, $R^{a4}$, and $R^{b4}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl are optionally substituted with 1, 2, or 3 substituents independently selected from $R^g$.

In some embodiments, each $R^{a1}$, $R^{b1}$, $R^{a2}$, $R^{b2}$, $R^{a3}$, $R^{b3}$, $R^{a4}$, and $R^{b4}$ is independently selected from H, $C_{1-6}$ alkyl and $C_{6-10}$ aryl, wherein said $C_{1-6}$ alkyl is optionally substituted with 1, 2, or 3 substituents independently selected from $R^g$.

In some embodiments, each $R^{c1}$, $R^{d1}$, $R^{c2}$, $R^{d2}$, $R^{c3}$, $R^{d3}$, $R^{c4}$, and $R^{d4}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, wherein said $C_{1-6}$ alkyl, $C_{6-10}$ aryl, $C_{3-10}$ cycloalkyl, 5-10 membered heteroaryl, and 4-12 membered heterocycloalkyl is optionally substituted with 1, 2, or 3 substituents independently selected from $R^g$.

In some embodiments, each $R^{c1}$, $R^{d1}$, $R^{c2}$, $R^{d2}$, $R^{c3}$, $R^{d3}$, $R^{c4}$, and $R^{d4}$ is independently selected from H, $C_{1-6}$ alkyl and $C_{6-10}$ aryl, wherein said $C_{1-6}$ alkyl is optionally substituted with 1, 2, or 3 substituents independently selected from $R^g$.

In some embodiments, $R^{c1}$ is H and $R^{d1}$ is $C_{6-10}$ aryl, which is optionally substituted with 1, 2, or 3 substituents independently selected from $R^g$.

In Some Embodiments of a Compound of Formula (A):
$X^1$ is selected from O, S, $S(O)_2$, $N(R^N)$, $C_{1-6}$ alkylene, and $C_{2-6}$ alkenylene, wherein said $C_{1-6}$ alkylene and $C_{2-6}$ alkenylene are each optionally substituted with 1, 2, or 3 substituents independently selected from $R^1$;

$R^1$ is selected from H, $C_{1-6}$ alkyl, $C_{1-4}$ haloalkyl, $Cy^1$, CN, $NO_2$, $OR^{a1}$, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl is optionally substituted with 1, 2, or 3 substituents independently selected from $Cy^1$, halo, CN, $NO_2$, OH, $C(O)NH_2$, $C(O)OH$, $NH_2$, and $S(O)_2NH_2$;

$R^2$ is selected from H, $C_{1-6}$ alkyl, $C_{1-4}$ haloalkyl, $Cy^2$, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein said $C_{1-6}$ alkyl is optionally substituted with 1, 2, or 3 substituents independently selected from $Cy^2$, halo, CN, $NO_2$, OH, $C(O)NH_2$, $C(O)OH$, $NH_2$, and $S(O)_2NH_2$;

$R^3$, $R^4$ and $R^5$ are each independently selected from H, $C_{1-6}$ alkyl, $C_{1-6}$ haloalkyl, $Cy^2$, halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl is optionally substituted with 1, 2, or 3 substituents independently selected from $Cy^2$, halo, CN, $NO_2$, $OR^{a2}$, $SR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}C(O)N^{c2}R^{d2}$, $NR^{c2}S(O)_2R^{b2}$, $NR^{c2}S(O)_2N^{c2}R^{d2}$, $S(O)_2R^{b2}$ and $S(O)_2NR^{c2}R^{d2}$;

$R^N$ is selected from H, $C_{1-6}$ alkyl, $C_{1-6}$ haloalkyl, $Cy^3$, $C(O)R^{b3}$, $C(O)NR^{c3}R^{d3}$, $C(O)OR^{a3}$, $S(O)_2R^{b3}$, and $S(O)_2NR^{c3}R^{d3}$; wherein said $C_{1-6}$ alkyl is optionally substituted with 1, 2, or 3 substituents independently selected from $Cy^3$, halo, CN, $NO_2$, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $S(O)_2R^{b3}$ and $S(O)_2NR^{c3}R^{d3}$;

$Cy^1$ is selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy}$;

$Cy^2$ is selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy}$;

$Cy^3$ is selected from $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^{Cy}$;

each $R^{Cy}$ is independently selected from halo, $C_{1-4}$ alkyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$, wherein said $C_{1-4}$ alkyl is optionally substituted by 1, 2, or 3 substituents independently selected from halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{d4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$;

each $R^{a1}$, $R^{b1}$, $R^{a2}$, $R^{b2}$, $R^{a3}$, $R^{b3}$, $R^{a4}$, and $R^{b4}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl are optionally substituted with 1, 2, or 3 substituents independently selected from $R^g$; and each $R^{c1}$, $R^{d1}$, $R^{c2}$, $R^{d2}$, $R^{c3}$, $R^{d3}$, $R^{c4}$, and $R^{d4}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, wherein said $C_{1-6}$ alkyl, $C_{6-10}$ aryl, $C_{3-10}$ cycloalkyl, 5-10 membered heteroaryl, and 4-12 membered heterocycloalkyl is optionally substituted with 1, 2, or 3 substituents independently selected from $R^g$.

In Some Embodiments of a Compound of Formula (A):

$X^1$ is selected from O, S, $C_{1-6}$ alkylene, and $C_{2-6}$ alkenylene, wherein said $C_{1-6}$ alkylene and $C_{2-6}$ alkenylene are each optionally substituted with 1, 2, or 3 substituents independently selected from $R^1$;

$R^1$ is selected from H, $C_{1-6}$ alkyl, $C_{1-4}$ haloalkyl, $Cy^1$, CN, $NO_2$, OH, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl is optionally substituted with 1, 2, or 3 substituents independently selected from halo, CN, $NO_2$, OH, $C(O)NH_2$, $C(O)OH$, and $NH_2$;

$R^2$ is selected from H, $C_{1-6}$ alkyl, $C_{1-4}$ haloalkyl, $Cy^2$, $OR^{a2}$, $C(O)R^{b2}$, $NR^{c2}R^{d2}$, $S(O)_2R^{b2}$, and $S(O)_2NR^{c2}R^{d2}$; wherein said $C_{1-6}$ alkyl is optionally substituted with 1, 2, or 3 substituents independently selected from $Cy^2$, halo, CN, $NO_2$, and OH;

$R^3$, $R^4$ and $R^5$ are each independently selected from H, $C_{1-6}$ alkyl, $C_{1-6}$ haloalkyl, $Cy^2$, halo, CN, $NO_2$, $C(O)R^{b2}$, $C(O)NR^{c2}R^{d2}$, $C(O)OR^{a2}$, $S(O)_2R^{b2}$, and $S(O)_2NR^{c2}R^{d2}$; wherein said $C_{1-6}$ alkyl is optionally substituted with 1, 2, or 3 substituents independently selected from $Cy^2$, halo, CN, $NO_2$, $C(O)R^{b2}$, $C(O)NR^{c2}R^{d2}$, $C(O)OR^{a2}$, $S(O)_2R^{b2}$ and $S(O)_2NR^{c2}R^{d2}$;

$Cy^1$ is 5-10 membered heteroaryl, which is optionally substituted with 1, 2, or 3 independently selected $R^{Cy}$;

$Cy^2$ is $C_{6-10}$ aryl, which is optionally substituted with 1, 2, or 3 independently selected $R^{Cy}$;

$R^{Cy}$ is independently selected from halo, $C_{1-4}$ alkyl, $C_{1-4}$ haloalkyl, CN, $NO_2$, $OR^{a4}$, $C(O)NR^{c4}R^{d4}$, $C(O)OR^{d4}$, $NR^{c4}R^{d4}$, $S(O)_2R^{b4}$, and $S(O)_2NR^{c4}R^{d4}$, wherein said $C_{1-4}$ alkyl is optionally substituted by 1, 2, or 3 substituents independently selected from halo, CN, $NO_2$, OH, $C(O)NH_2$, $C(O)OH$, $NH_2$, and $S(O)_2NH_2$;

each $R^{a1}$, $R^{b1}$, $R^{a2}$, $R^{b2}$, $R^{a3}$, $R^{b3}$, $R^{a4}$, and $R^{b4}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, 4-12 membered heterocycloalkyl, wherein said $C_{1-6}$ alkyl, $C_{2-6}$ alkenyl, $C_{6-10}$ aryl, $C_{3-10}$ cycloalkyl, 5-10 membered heteroaryl, and 4-12 membered heterocycloalkyl are optionally substituted with 1, 2, or 3 substituents independently selected from $R^g$; and each $R^{c1}$, $R^{d1}$, $R^{c2}$, $R^{d2}$, $R^{c3}$, $R^{d3}$, $R^{c4}$, and $R^{d4}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, wherein said $C_{1-6}$ alkyl, $C_{6-10}$ aryl, $C_{3-10}$ cycloalkyl, 5-10 membered heteroaryl, and 4-12 membered heterocycloalkyl is optionally substituted with 1, 2, or 3 substituents independently selected from $R^g$.

In Some Embodiments of a Compound of Formula (A):

$X^1$ is selected from O, S, methylene, and ethenylene, wherein said methylene and ethenylene are each optionally substituted with 1 or 2 independently selected $R^1$;

each $R^1$ is independently selected from $C(O)NR^{c1}R^{d1}$ and $Cy^1$;

$R^2$ is $Cy^2$;

$R^3$, $R^4$ and $R^5$ are each independently selected from H, $C_{1-6}$ alkyl, $C_{1-6}$ haloalkyl;

$Cy^1$ is 5-10 membered heteroaryl, which is optionally substituted with 1, 2, or 3 independently selected $R^{Cy}$;

$Cy^2$ is $C_{6-10}$ aryl, which is optionally substituted with 1, 2, or 3 independently selected $R^{Cy}$;

each $R^{Cy}$ is independently selected from halo and $C(O)OR^{a4}$;

each $R^{a1}$, $R^{b1}$, $R^{a2}$, $R^{b2}$, $R^{a3}$, $R^{b3}$, $R^{a4}$, and $R^{b4}$ is independently selected from H, $C_{1-6}$ alkyl and $C_{6-10}$ aryl, wherein said $C_{1-6}$ alkyl is optionally substituted with 1, 2, or 3 substituents independently selected from $R^g$; and each $R^{c1}$, $R^{d1}$, $R^{c2}$, $R^{d2}$, $R^{c3}$, $R^{d3}$, $R^{c4}$, is independently selected from H, $C_{1-6}$ alkyl and $C_{6-10}$ aryl, wherein said $C_{1-6}$ alkyl is optionally substituted with 1, 2, or 3 substituents independently selected from $R^g$.

In some embodiments, a compound of Formula (A) is selected from any one of compounds 244-245 listed in Table 5. In some embodiments, a compound of Formula (A) is not any one of compounds 244-245 listed in Table 5.

In some embodiments, of a compound of Formula (II-I) or a compound of Formula (A), each 5-10 membered heteroaryl is independently selected from thienyl, furanyl, pyrrolyl, imidazolyl, thiazolyl, oxazolyl, isoxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl, pyridyl, pyrazinyl, pyrimidinyl, triazinyl, pyridazinyl, quinolinyl, isoquinolinyl, indolyl or isoindolyl, benzazepinyl, thienothiophenyl, purinyl, pyrazolopyrimidinyl, pyrazolopyridinyl, imidazolopyrimidinyl, imidazolopyridinyl, benzothiadiazinyl, and thienodihydropyridinyl, and benzimidazol-2-yl. In some embodiments, the 5-10 membered heteroaryl is benzimidazol-2-yl.

In some embodiments, of a compound of Formula (II-I) or a compound of Formula (A), each aryl is independently selected from phenyl and naphthyl.

In some embodiments, of a compound of Formula (II-I) or a compound of Formula (A), any 4-12 membered heterocycloalkyl is independently selected from pyrrolidinyl, isoxazolidinyl, tetrahydropyranyl, oxetanyl, azetidinyl, morpholinyl, thiomorpholinyl, piperazinyl, dioxolanyl, tetrahydrofuranyl, dioxanyl, tetrahydrothienyl, piperidinyl, pyrrolidinyl, isothiazolidinyl, pyrazolidinyl, oxazolidinyl, thiazolidinyl, imidazolidinyl, azepanyl, benzodioxolyl, tetrahydrobenzoazepinyl, tetrahydrobenzodiazepinyl, dihydrobenzodiozinyl, isochromanyl, tetrahydroisoquinolinyl, tetrahydroquinazolinyl, dihydrobenzofuranyl, dihydrobenzothienyl, indolinyl, isoindolinyl, tetrahydropyrrolopyridinyl, tetrahydrofuropyridinyl, dihydrothienopyridinyl and benzothiadiazinyl.

In some embodiments, of a compound of Formula (II-I) or a compound of Formula (A), any $C_{3-10}$ cycloalkyl is independently selected from cyclopropyl, cyclobutyl, cyclopentyl, cyclohexyl, and cycloheptyl.

As used herein, the term "pharmaceutically acceptable salt" refers to a salt that is formed between an acid and a basic group of the compound, such as an amino functional group, or between a base and an acidic group of the compound, such as a carboxyl functional group. In some embodiments, the compound is a pharmaceutically acceptable acid addition salt. In some embodiments, acids commonly employed to form pharmaceutically acceptable salts of the therapeutic compounds described herein include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the therapeutic compounds described herein include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Methods of Making

Compounds of any one of Formulae disclosed herein, including salts thereof, can be prepared using known organic synthesis techniques and can be synthesized according to any of numerous possible synthetic routes. For example, the compounds described herein can be prepared using methods and procedures similar to those described in Donnelly, A. et al, The Design, Synthesis, and Evaluation of Coumarin Ring Derivatives of the Novobiocin Scaffold that Exhibit Antiproliferative Activity, *Journal of Organic Chemistry* 2008, 73, 8901-8920, which is incorporated herein by reference in its entirety. A person skilled in the art knows how to select and implement appropriate synthetic protocols, and appreciates that a broad repertoire of synthetic organic reactions is available to be potentially employed in synthesizing compounds provided herein.

Suitable synthetic methods of starting materials, intermediates and products can be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, $4^{th}$ Ed., Wiley & Sons, Inc., New York (2006).

CRISPR/Cas9 (CRISPR-Associated 9)

Genome engineering and genetic modulation by the control of individual gene expression can be used in therapeutics as well. CRISPR (clustered regularly interspaced short palindromic repeats) is a family of DNA sequences found within the genomes of prokaryotic organisms such as bacteria and archaea. CRISPR/Cas RNA-guided genome targeting and gene regulation in mammalian cells (e.g., using modified bacterial CRISPR/Cas components) can be used to inhibit the expression and/or activity of genes (e.g., PAPD5).

In some embodiments, a catalytically silent Cas-9 mutant (a null nuclease) can be tethered to specified gene promoter regions and has the effect of reducing expression of those genes. In some embodiments, the Cas-9 mutant is linked to a transcription factor.

In some embodiments, the CRISPR/Cas9 genome targeting can create biallelic null mutations, thus inhibit the expression and the activity of a gene (e.g., PAPD5). Thus, in some embodiments, the PAPD5 inhibitor can be a vector that encode guide RNAs (gRNAs) that target PAPD5 for CRISPR/Cas9, wherein CRISPR/Cas9 creates null mutations in PAPD5, thereby decreasing the level and activity of PAPD5. In some embodiments, the PAPD5 inhibitor includes the CRISPR/Cas9 system and the guide RNAs. In some embodiments, the guide RNA can have the following sequences:

CCUCUUGUUGCUGCUGCCCG; (SEQ ID NO: 2)

CGGAGCGAUACAUGCCGGCC; (SEQ ID NO: 3)
or

CCUCUUGUUGCUGCUGCCCG. (SEQ ID NO: 4)

The CRISPR/Cas9 targeting can be used in the various methods as described herein, for example, modulating telomerase RNA component, screening, diagnosing, treating or preventing a disease or condition selected from: a disorder associated with telomere or telomerase dysfunction, a disorder associated with aging, a pre-leukemic or pre-cancerous condition, a viral infection (e.g., an HBV infection), a neurodevelopmental disorder, and an acquired or genetic disease or condition associated with alterations in RNA, etc.

Methods of Use

Modulation of Telomerase RNA Component (TERC)

Telomerase has been a therapeutic target of great interest for over two decades, based on its activity in numerous cancers. The telomerase RNA component (TERC) contains a box H/ACA domain at its 3' end, a motif that is functionally separable from the template domain and dispensable for telomerase activity in vitro. In vivo, the H/ACA motif is bound by a heterotrimer of dyskerin, NOP10, and NHP2 which stabilize TERC, and also by TCAB1, which is responsible for localizing the telomerase complex to Cajal bodies (I-Venteicher, A. S. et al. A human telomerase holoenzyme protein required for Cajal body localization and telomere synthesis. Science 323, 644-8 (2009)). Disruption of any of these interactions can also compromise telomere maintenance and cause telomere disease (Mitchell, J. R., Wood, E. & Collins, K. A telomerase component is defective in the human disease dyskeratosis congenita. Nature 402, 551-5 (1999); Vulliamy, T. et al. Mutations in the telomerase component NHP2 cause the premature ageing syndrome dyskeratosis congenita. Proceedings of the National Academy of Sciences of the United States of America 105, 8073-8 (2008); Walne, A. J. et al. Genetic heterogeneity in autosomal recessive dyskeratosis congenita with one subtype due to mutations in the telomerase-associated protein NOP10. Human molecular genetics 16, 1619-29 (2007)). The H/ACA motif serve as guides for pseudouridylation of other RNAs by dyskerin (Kiss, T., Fayet-Lebaron, E. & Jady, B. E. Box H/ACA small ribonucleoproteins. Molecular cell 37, 597-606 (2010)).

Increasing telomerase activity can be beneficial in several degenerative and age-related disorders. Conversely, inhibiting telomerase activity would be of significant utility for the treatment of cancer and disorders in which hyper-proliferative cells depend on telomerase for self-renewal.

Modulation of Poly(A) Specific Ribonuclease (PARN)

PARN is known as a 3'-5' exoribonuclease responsible for degradation of the poly(A) tails of eukaryotic mRNAs, which is a rate-limiting step in mRNA turnover (Korner, C. G. & Wahle, E. Poly(A) tail shortening by a mammalian poly(A)-specific 3'-exoribonuclease. The Journal of biological chemistry 272, 10448-56 (1997)). PARN is stimulated by presence of a m7G-cap, and requires a minimal substrate of adenosine di- or tri-nucleotides—in other words, oligo (A) rather than strictly poly(A). PARN is a widely-expressed cap-dependent, poly(A) deadenylase with a canonical role in regulating global mRNA levels during development, and additional, more specialized functions including end-trimming of the Dicer-independent microRNA (miR)-451 and deadenylation of small nucleolar (sno)RNAs. PARN loss-of-function mutations are implicated in idiopathic pulmonary fibrosis and dyskeratosis congenita. The disclosure provides methods and agents that modulate the level or activity of human PARN. The nucleotide sequence of human PARN is NM_002582 and the amino acid sequence of PARN is O95453 (Table 1). Variants of the nucleotide sequence and the amino acid sequence are also shown in Table 1.

TABLE 1

Accession numbers for genes, RNA and proteins

| Gene | Ensembl Gene ID | Nucleotide sequence(s) and variants therein (RefSeq unless otherwise indicated) | Protein ID(s) and variants therein (Uniprot unless otherwise indicated) |
|---|---|---|---|
| TERC | ENSG00000270141 | NR_001566 | N/A |
| PARN | ENSG00000140694 | NM_002582 | O95453 |
| | | NM_001242992 | |
| | | NM_001134477 | |
| TRF4-2 a.k.a. PAPD5 | ENSG00000121274 | NM_001040284 | Q8NDF8 |
| | | NM_001040285 | H3BQM0 |
| | | FR872509.1 (GenBank) | CCB84642.1 (GenBank) |

PAP Associated Domain Containing 5 (PAPD5)

PAPD5, also known as Topoisomerase-Related Function Protein 4-2 (TRF4-2), also known as TUT3, also known as GLD4, also known as TENT4B, is one of the seven members of the family of noncanonical poly(A) polymerases in human cells. PAPD5 has been shown to act as a polyadenylase on abnormal pre-ribosomal RNAs in vivo in a manner analogous to degradation-mediating polyadenylation by the non-canonical poly(A) polymerase Trf4p in yeast. PAPD5 is also involved in the uridylation-dependent degradation of histone mRNAs.

Both PARN and PAPD5 are involved in the 3'-end maturation of the telomerase RNA component (TERC). Patient cells, fibroblast cells as well as converted fibroblasts (I-IPS cells) in which PARN is disrupted show decreased levels of TERC which can be restored by decreasing levels or activities of PAPD5. Deep sequencing of TERC RNA 3' termini or ends, reveals that PARN and PAPD5 are critically important for processing of post-transcriptionally acquired oligo (A) tails that target nuclear RNAs for degradation. Diminished TERC levels and the increased oligo (A) forms of TERC are normalized by restoring PARN or inhibiting PAPD5. The disclosure reveals PARN and PAPD5 as important players in the regulation and biogenesis of TERC (FIG. 1). FIG. 1 shows 3' ends of nascent TERC RNA are subject to PAPD5-mediated oligo-adenylation, which targets transcripts for degradation by the exosome. PARN counteracts the degradation pathway by removing oligo (A) tails and/or trimming genomically-encoded bases (green) of nascent TERC to yield a mature 3' end. Mature TERC is protected from further oligo-adenylation and exonucleolytic processing, possibly by the dyskerin/NOP10/NHP2/GAR1 complex, and assembles into the telomerase holoenzyme to maintain telomeres. PARN deficiency tips the balance in favor of degradation, leading to reduced TERC levels and telomere dysfunction. Thus, the disclosure also provides compounds and methods that modulate the level or activity of human PAPD5. The nucleotide sequence of human PAPD5 used is FR872509.1, and the amino acid sequence is CCB84642.1 (Table 1). Variants of the nucleotide sequence and the amino acid sequence are also shown in Table 1. The amino acid sequence of PAPD5 used is shown below:

```
PAPD5 (TRF4-2)(CCB84642.1)
                                        (SEQ ID NO: 1)
MYRSGERLLG  SHALPAEQRD  FLPLETTNNN  NNHHQPGAWA

RRAGSSASSP  PSASSSPHPS  AAVPAADPAD  SASGSSNKRK

RDNKASTYGL  NYSLLQPSGG  RAAGGGRADG  GGVVYSGTPW

KRRNYNQGVV  GLHEEISDFY  EYMSPRPEEE  KMRMEVVNRI

ESVIKELWPS  ADVQIFGSFK  TGLYLPTSDI  DLVVFGKWEN

LPLWTLEEAL  RKHKVADEDS  VKVLDKATVP  IIKLTDSFTE

VKVDISFNVQ  NGVRAADLIK  DFTKKYPVLP  YLVLVLKQFL

LQRDLNEVFT  GGIGSYSLFL  MAVSFLQLHP  REDACIPNTN

YGVLLIEFFE  LYGRHFNYLK  TGIRIKDGGS  YVAKDEVQKN

MLDGYRPSML  YIEDPLQPGN  DVGRSSYGAM  QVKQAFDYAY

VVLSHAVSPI  AKYYPNNETE  SILGRIIRVT  DEVATYRDWI

SKQWGLKNRP  EPSCNGNGVT  LIVDTQQLDK  CNNNLSEENE

ALGKCRSKTS  ESLSKHSSNS  SSGPVSSSSA  TQSSSSDVDS

DATPCKTPKQ  LLCRPSTGNR  VGSQDVSLES  SQAVGKMQST

QTTNTSNSTN  KSQHGSARLF  RSSSKGFQGT  TQTSHGSLMT

NKQHQGKSNN  QYYHGKKRKH  KRDAPLSDLC  R
```

Figure 2:
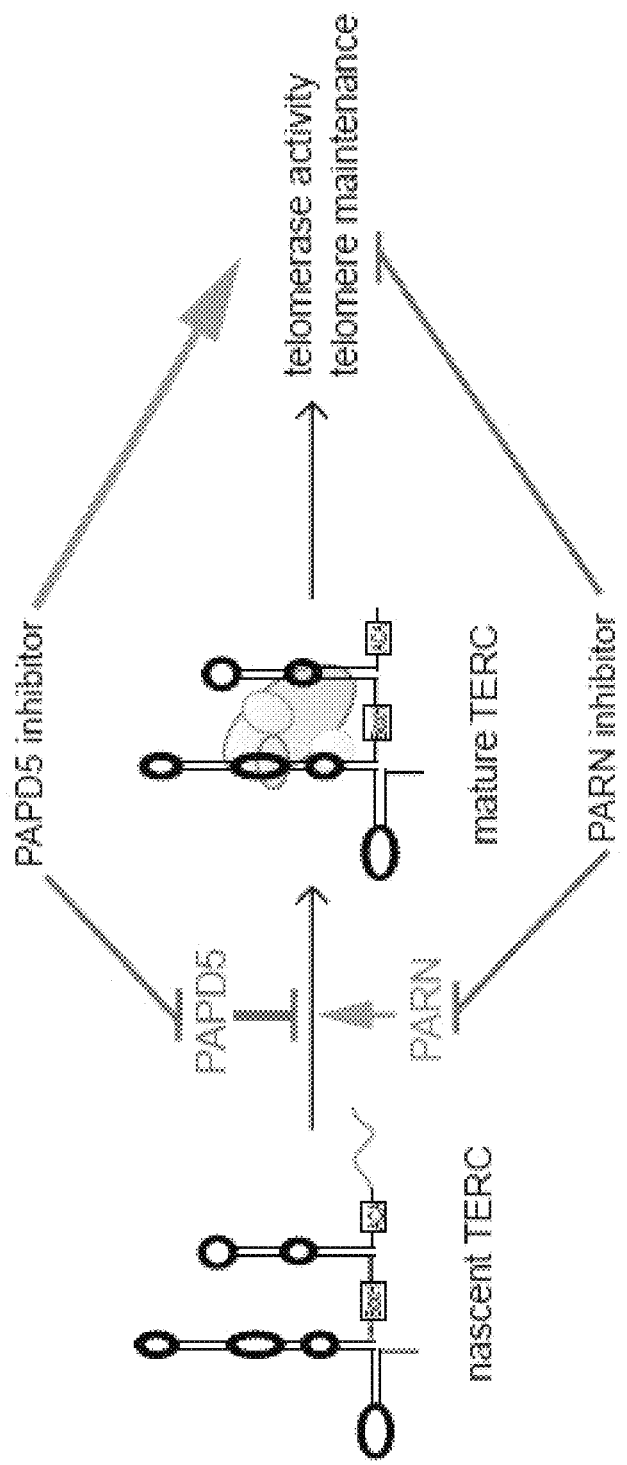
FIG. 2 is a schematic diagram showing an exemplary model of reciprocal regulation of TERC maturation by PARN and PAPD5.

FIG. 2 is a diagram demonstrating the reciprocal regulation of TERC levels by PAPD5 and PARN, and the potential for therapeutic manipulation of telomerase in degenerative or malignant disorders. As shown in FIG. 2, a PAPD5 inhibitor can inhibit PAPD5-mediated oligo-adenylation, which targets nascent TERC RNA for degradation by the exosome, thus increases the level or activity of TERC. In contrast, as PARN counteracts the degradation pathway by removing oligo (A) tails and/or trimming genomically-encoded bases of nascent TERC to yield a mature 3' end, PARN inhibitor will decrease the level or activity of TERC. In addition, increasing the level or activity of PARN can increase the level or activity of TERC, and increasing the level or activity of PAPD5 can decrease the level or activity of TERC.

In one aspect, the present disclosure provides compounds and associated methods of modulating TERC levels in cells. The cells can be, e.g., primary human cells, stem cells, induced pluripotent cells, fibroblasts, etc. In some embodiments, the cells are within a subject (e.g., a human subject). Therefore, the present disclosure provides methods modulating TERC levels in cells in vivo. In some embodiments, the cells can be isolated from a sample obtained from the subject, e.g., the cells can be derived from any part of the body including, but not limited to, skin, blood, and bone marrow. The cells can also be cultured in vitro using routine methods with commercially available cell reagents (e.g., cell culture media). In some embodiments, the cells are obtained from a subject, having a telomere disease, being at risk of developing a telomere disease, or being suspected of having a telomere disease. In some embodiments, the subject has no overt symptoms.

The level or activity of TERC can be determined by various means, e.g., by determining the size of telomere in the cell, by determining the stability of TERC, by determining the amount of RNA, by measuring the activity of telomerase function, and/or by measuring oligo-adenylated (oligo (A)) forms of TERC. TERC stability can be assessed, e.g., by measuring the TERC decay rates. Oligo-adenylated (oligo (A)) forms of TERC can be measured, e.g., using rapid amplification of cDNA ends (RACE) coupled with targeted deep sequencing (e.g., at the TERC 3' end) to detect oligo-adenylated (oligo (A)) forms of TERC. The size of a telomere can be measured, e.g., using Flow-fluorescent in-situ hybridization (Flow-FISH) technique.

In some embodiments, the modulation of endogenous TERC is performed. Such methods can include, e.g., altering telomerase activity, e.g., increasing or decreasing telomerase activity. The methods can involve reducing RNA expression in cells, e.g., non-coding RNA in TERC. Telomerase activity can be, e.g., regulated by modulating TERC levels by contacting cells with test compounds known to modulate protein synthesis. The methods may involve targeting post-processing activity of the endogenous TERC locus. These methods involve manipulating TERC including identifying subjects with genetic mutation (e.g., mutation in PARN), isolating cells (e.g., fibroblast), and treating cells with agents that modulate TERC levels.

The present disclosure shows that TERC levels are modulated at the post-transcriptional level. Thus, in one aspect, methods of modulating the level or activity of TERC involve modulating the level or activity of PARN and PAPD5.

In some embodiments, the methods involve an agent that modulates the level or activity of PARN, thereby altering the level or activity of TERC. In some cases, the agent increases the level or activity of PARN. Alternatively, the agent decreases the level or activity of PARN. In some embodiments, the methods involve an agent that modulates the level or activity of PAPD5, thereby altering the level or activity of TERC. In some embodiments, the agent increases the level or activity of PAPD5. Alternatively, the agent decreases the level or activity of PAPD5 (e.g., PAPD5 inhibitors). In some embodiments, the agent is any one of compounds described herein.

Accordingly, the present application provides compounds that modulate TERC levels and are thus useful in treating a broad array of telomere diseases or disorders associated with telomerase dysfunction, e.g., dyskeratosis congenita, aplastic anemia, pulmonary fibrosis, idiopathic pulmonary fibrosis, hematological disorder, hepatic disease (e.g., chronic liver disease), and cancer, e.g., hematological cancer and hepatocarcinoma, etc.

In some embodiments, in order to successfully treat a telomere disease, a therapeutic agent has to selectively inhibit PAPD5, while not inhibiting PARN or other polynucleotide polymerases. A PAPD5 inhibitor that is not selective and concurrently inhibits other polymerases, may not be useful in treating telomere diseases; that is, the fact that a compound is a PAPD5 inhibitor (e.g., non-selective inhibitor) is not indicative of its usefulness in prevention and treatment of telomere diseases. The selectivity to PAPD5 as opposed to other polymerases is required for potency. In some embodiments, the compounds of the present application are selective and specific inhibitors of PAPD5 and do not inhibit PARN or other polymerases.

In some embodiments, it was surprisingly discovered that in order to successfully treat a telomere disease, a therapeutic agent has to be a selective inhibitor of PAPD5. In other words, a successful therapeutic agent has to inhibit PAPD5 while not substantially inhibiting PARN and/or other polynucleotide polymerases. In some embodiments, a PAPD5 inhibitor that is not selective to PAPD5 and concurrently inhibits other polymerases, may not be useful in treating telomere diseases; that is, the fact that a compound is a PAPD5 inhibitor (e.g., non-selective inhibitor) is not indicative of its usefulness in prevention and treatment of telomere diseases. The selectivity to PAPD5 as opposed to other polymerases is required for potency. In some embodiments, the compounds of the present application are selective and specific inhibitors of PAPD5 and do not substantially inhibit PARN or other polymerases.

Telomere Diseases

Telomere diseases or disorders associated with telomerase dysfunction are typically associated with changes in the size of telomere. Many proteins and RNA components are involved in the telomere regulatory pathway, including TERC, PARN and PAPD5 (also known as TRF4-2). FIGS. 1 and 2 show how these proteins or RNA components work in the regulatory pathway and how they are related to telomere diseases.

Among these telomere diseases is dyskeratosis congenita (DC), which is a rare, progressive bone marrow failure syndrome characterized by the triad of reticulated skin hyperpigmentation, nail dystrophy, and oral leukoplakia. Early mortality is often associated with bone marrow failure, infections, fatal pulmonary complications, or malignancy. Short-term treatment options for bone marrow failure in patients include anabolic steroids (e.g., oxymetholone), granulocyte macrophage colony-stimulating factor, granulocyte colony-stimulating factor, and erythropoietin. Other treatments include hematopoietic stem cell transplantation (SCT).

Idiopathic pulmonary fibrosis is a chronic and ultimately fatal disease characterized by a progressive decline in lung function. In some appropriate cases, the following agents are used to treat idiopathic pulmonary fibrosis: nintedanib, a tyrosine kinase inhibitor that targets multiple tyrosine kinases, including vascular endothelial growth factor, fibroblast growth factor, and PDGF receptors; and pirfenidone. Other treatments include lung transplantation. In some cases, lung transplantation for idiopathic pulmonary fibrosis (I-IPF) has been shown to confer a survival benefit over medical therapy.

Generally, a method of treating a telomere disease includes administering a therapeutically effective amount of a compound described herein, to a subject who is in need of, or who has been determined to be in need of, such treatment.

Cancer

The present disclosure also provides compounds, compositions, and methods for treating pre-leukemic conditions, pre-cancerous conditions, dysplasia and/or cancers. Pre-leukemic conditions include, e.g., Myelodysplastic syndrome, and smoldering leukemia. Dysplasia refers to an abnormality of development or an epithelial anomaly of growth and differentiation, including e.g., hip dysplasia, fibrous dysplasia, and renal dysplasia, Myelodysplastic syndromes, and dysplasia of blood-forming cells.

A precancerous condition or premalignant condition is a state of disordered morphology of cells that is associated with an increased risk of cancer. If left untreated, these conditions may lead to cancer. Such conditions are can be dysplasia or benign neoplasia.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells.

Many cancer cells have abnormal telomeres. Thus, treatments described herein (e.g., PAPD5 inhibitors) can also be used to treat cancers. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

In some embodiments, the methods described herein are used for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. Cancers treatable using the methods described herein are cancers that have increased levels of TERC, an increased expression of genes such as TERC and/or TERT, or increased activity of a telomerase relative to normal tissues or to other cancers of the same tissues.

In some embodiments, the tumor cells isolated from subjects diagnosed with cancer can be used to screen test for compounds that alter TERC levels. In some embodiments, the tumor cells can be used to screen test compounds that alter the expressive or activity of PARN or PAPD5. The cancer cells used in the methods can be, e.g., cancer stem cells. Such methods can be used to screen a library of test compounds, e.g., compounds that alter or change expression of protein or RNA of telomere-associated genes (e.g., TERC, PARN, PAPD5/PAPD5).

In some embodiments, agents that decrease the level or activity of TERC (e.g., PANR inhibitors) are used to treat cancer. In some embodiments, these agents are used in combination with other cancer treatments, e.g., chemotherapies, surgery, or radiotherapy.

Aging

Telomeres shorten over the human life span. In large population based studies, short or shortening telomeres are associated with numerous diseases. Thus, telomeres have an important role in the aging process, and can contribute to various diseases. The role of telomeres as a contributory and interactive factor in aging, disease risks, and protection is described, e.g., in Blackburn, Elizabeth H., Elissa S. Epel, and Jue Lin. "Human telomere biology: A contributory and interactive factor in aging, disease risks, and protection," Science 350.6265 (2015): 1193-1198, which is incorporated by reference in its entirety.

Telomere attrition is also a major driver of the senescence associated response. In proliferating human cells, progressive telomere erosion ultimately exposes an uncapped free double-stranded chromosome end, triggering a permanent DNA damage response (DDR). The permanent DNA damage response has a profound impact on cell functions. For example, the damage sensor ataxia telangiectasia mutated (ATM) is recruited to uncapped telomeres, leading to the stabilization of tumor suppressor protein 53 (p53) and upregulation of the p53 transcriptional target p21. In turn, p21 prevents cyclin-dependent kinase 2 (CDK2)-mediated inactivation of RB, subsequently preventing entry into the S phase of the cell cycle. Cellular senescence contributes to various age-related diseases, e.g., glaucoma, cataracts, diabetic pancreas, type 2 diabetes mellitus, atherosclerosis, osteoarthritis, inflammation, atherosclerosis, diabetic fat, cancer, pulmonary fibrosis, and liver fibrosis, etc. The permanent DNA damage response and age-related diseases are described, e.g., in Childs, Bennett G., et al. "Cellular senescence in aging and age-related disease: from mechanisms to therapy." Nature medicine 21.12 (2015): 1424, which is incorporated herein by reference in its entirety.

As used herein, the term "aging" refers to degeneration of organs and tissues over time, in part due to inadequate replicative capacity in stem cells that regenerate tissues over time. Aging may be due to natural disease processes that occur over time, or those that are driven by cell intrinsic or extrinsic pressures that accelerate cellular replication and repair. Such pressures include natural chemical, mechanical, and radiation exposure; biological agents such as bacteria, viruses, fungus, and toxins; autoimmunity, medications, chemotherapy, therapeutic radiation, cellular therapy. As the telomere is an important factor in aging and disease development, the methods described herein can be used for treating, mitigating, or minimizing the risk of, a disorder associated with aging (and/or one or more symptoms of a disorder associated with aging) in a subject. The methods include the step of identifying a subject as having, or being at risk of a disorder associated with aging; and administering a pharmaceutical composition to the subject. In some embodiments, the pharmaceutical composition includes an agent that alters the level or activity of TERC, e.g., increase the level or activity of TERC.

As used herein, the term "disorders associated with aging" or "age-related diseases" refers to disorders that are associated with the ageing process. Exemplary disorders include, e.g., macular degeneration, diabetes mellitus (e.g., type 2 diabetes), osteoarthritis, rheumatoid arthritis, sarcopenia, cardiovascular diseases such as hypertension, atherosclerosis, coronary artery disease, ischemia/reperfusion injury, cancer, premature death, as well as age-related decline in cognitive function, cardiopulmonary function, muscle strength, vision, and hearing.

The disorder associated with aging can also be a degenerative disorder, e.g., a neurodegenerative disorder. Degenerative disorders that can be treated or diagnosed using the methods described herein include those of various organ systems, such as those affecting brain, heart, lung, liver, muscles, bones, blood, gastrointestinal and genito-urinary tracts. In some embodiments, degenerative disorders are those that have shortened telomeres, decreased levels of TERC, and/or decreased levels of telomerase relative to normal tissues. In some embodiments, the degenerative disorder is a neurodegenerative disorder. Exemplary neurodegenerative disorders include Motor Neuron Disease, Creutzfeldt-Jakob disease, Machado-Joseph disease, Spinocerebellar ataxia, Multiple sclerosis (MS), Parkinson's disease, Alzheimer's disease, Huntington's disease, hearing and balance impairments, ataxias, epilepsy, mood disorders such as schizophrenia, bipolar disorder, and depression, dementia, Pick's Disease, stroke, CNS hypoxia, cerebral senility, and neural injury such as head trauma. Recent studies have shown the association between shorter telomeres and Alzheimer's disease. The relationship between telomere length shortening and Alzheimer's disease is described, e.g., in Zhan, Yiqiang, et al. "Telomere length shortening and Alzheimer disease—a Mendelian Randomization Study," JAMA neurology 72.10 (2015): 1202-1203, which is incorporated by reference in its entirety. In some embodiments, the neurodegenerative disorder is dementia, e.g., Alzheimer's disease.

It has also been determined that there an inverse association between leucocyte telomere length and risk of coronary heart disease. This relationship is described, e.g., in Haycock, Philip C., et al. "Leucocyte telomere length and risk of cardiovascular disease: systematic review and meta-analysis." (2014): g4227; and Codd, Veryan, et al. "Identification of seven loci affecting mean telomere length and their association with disease." Nature genetics 45.4 (2013): 422-427; each of which is incorporated by reference in its entirety. Thus, there is strong evidence for a causal role of telomere-length variation in cardiovascular disease (CVD), or coronary artery disease (CAD). In some embodiments, the disorder is a cardiovascular disease (CVD), and/or coronary artery disease (CAD), and the present disclosure provides methods of treating, mitigating, or minimizing the risk of, these disorders. In some cases, the disorder is an atherosclerotic cardiovascular disease.

Furthermore, a meta-analysis of 5759 cases and 6518 controls indicated that shortened telomere length was significantly associated with type 2 diabetes mellitus risk. The relationship between telomere length and type 2 diabetes mellitus is described, e.g., in Zhao, Jinzhao, et al. "Association between telomere length and type 2 diabetes mellitus: a meta-analysis." PLOS One 8.11 (2013): e79993, which is incorporated by reference in its entirety. In some embodiments, the disorder is a metabolic disorder, e.g., type 2 diabetes mellitus.

In some embodiments, aged cells can be used to screen test compounds that alter the expressive or activity of PARN or PAPD5. The aged cells used in the methods can be, e.g., those with genetic lesions in telomere biology genes, those isolated from elderly subjects, or those that undergo numerous rounds of replication in the lab. Such methods can be used to screen a library of test compounds, e.g., compounds that alter or change expression of protein or RNA of telomere-associated genes (e.g., TERC, PARN, PAPD5/PAPD5). Exemplary methods of screening and screening techniques are described herein.

In some embodiments, agents that increase the level or activity of TERC (e.g., PAPD5/PAPD5 inhibitors) are used to treat age-related degenerative disorders due to natural causes or environmental causes. In some embodiments, these agents are used in combination with other treatments.

Viral Infections

The hepatitis B virus (HBV) is an enveloped, partially double-stranded D A virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, A., P. Gripon & S. Urban. Hepatology, 46. (2007). 1759-68) and via the specific binding of HBV surface antigens (HBsAg) to the hepatocyte sodium-taurocholate cotransporting polypeptide (NTCP) receptor (Yan, H. et al. J Virol, 87, (2013), 7977-91). Once the virion has entered the cell, the viral cores and the encapsidated RC DNA are transported by host factors, via a nuclear localization signal, into the nucleus through the Impβ/Impα nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzcr. J Viral Hepat, 1 7, (2010), 527-36). Inhibition of HBV gene expression or HBV RNA synthesis leads to the inhibit ion of HBV viral replication and antigens production (Mao, R. et al. PLOS Pathog, 9, (2013), e1003494; Mao, R. et al. J Virol, 85, (2011), 1048-57). For instance, IFN-a was shown to inhibit HBV replication and viral HBsAg production by decreasing the transcription of pgRNA and subgenomic RNA from the HBV covalently closed circular DNA (cccDNA) minichromosome. (Belloni, L. et al. J Clin Invest, 122, (2012), 529-37; Mao, R. et al. J Virol, 85, (2011), 1048-57). All HBV viral mRNAs are capped and polyadenylated and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. Semin Liver Dis, (2005), 25 Suppl 1, 9-1 9). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prangc. Virol J, (2007), 4, 45).

The control of viral infection needs a tight surveillance of the host innate immune system which could respond within minutes to hours after infect ion to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

The secretion of antiviral cytokines in response to HBV infection by the hepatocytes and/or the intra-hepatic immune cells plays a central role in the viral clearance of infected liver.

However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion o to progressive functional impairment (Kondo et al. Journal of Immunology (1993), 150, 4659 4671; Kondo et al. Journal of Medical Virology (2004), 74, 425 433; Fisicaro et al. Gastroenterology, (2010), 138, 682-93). Moreover HBsAg has been reported to suppress the function of immune cells such as monocytes, dendritic cells (DCs) and natural killer (NK) cells by direct interaction (Op den Brouw et al. Immunology, (2009b), 1 26, 280-9; Woltman et al. PLOS One, (201 1), 6, e15324; Shi et al. J Viral Hepat. (2012). 19, c26-33; Kondo et al. ISRN Gastroenterology, (2013), Article ID 935295).

HBsAg quantification is a significant bio marker for prognosis and treatment response in chronic hepatitis B. However the achievement of HBsAg loss and seroconversion is rarely observed in chronically infected patients but remains the ultimate goal of therapy. Current therapy such as Nucleos (t) ide analogues are molecules that inhibit HBV DA synthesis but are not directed at reducing HBsAg level. Nucleos (t) ide analogs, even with prolonged therapy, have demonstrated rates of HBsAg clearance comparable to those observed naturally (between-1%-2%) (Janssen et al. Lancet, (2005), 365, 123-9; Marcellin et al. N. Engl. J Med., (2004), 351, 1206-17; Buster et al. Hepatology, (2007), 46, 388-94). Therefore, targeting HBsAg together with HBV DNA levels in CHB patients may significantly improve CHB patient immune reactivation and remission (Wieland, S. F. & F. V. Chisari. J Virol, (2005), 79, 9369-80; Kumar et al. J Virol, (2011), 85, 987-95; Woltman et al. PLOS One, (2011), 6, e15324; Op den Brouw et al. Immunology, (2009b), 126, 280-9).

The compounds of the present disclosure are inhibitors of virion production and inhibitors of production and secretion of surface proteins HBsAg and HBeAg. The compounds reduce effective HBV RNA production at the transcriptional or post-transcriptional levels, such as the result of accelerated viral RNA degradation in the cell. In the alternative, the compounds of the present disclosure inhibit initiation of viral transcription. In sum, the compounds reduce overall levels of HBV RNA, especially HBsAg mRNA, and viral surface proteins. HBsAg may suppress immune reactions against virus or virus infected cells, and high level of HBsAg is thought to be responsible for T cell exhaustion and depletion. Disappearance of HBsAg followed by the emergence of anti-HBsAg antibodies results in a sustained virological response to HBV, which is regarded as a sign of a functional cure.

In some embodiments, the compounds may modulate any of the molecular mechanisms described, for example, in Zhou et al., Antiviral Research 149 (2018) 191-201, which is incorporated herein by reference in its entirety. In some embodiments, the compounds may modulate any of the physiological or molecular mechanisms described, for example, in Mueller et al., Journal of Hepatology 68 (2018) 412-420, which is incorporated herein by reference in its entirety. For example, the compounds of the present disclosure induce HBV RNA degradation (degradation of HBV pgRNA and HBsAg mRNA occurs in the hepatocyte nucleus and requires de novo synthesis of host proteins).

In some embodiments, the compounds of the present disclosure are useful in inhibiting of HBsAg production or secretion, in inhibiting HBV DNA production, and/or in treating or preventing hepatitis B virus (HBV) infection (acute, fulminant, or chronic) in a subject. In some embodiments, the subject is in need of such treatment or prevention (e.g., prior to the administration of the compound of the present disclosure, the subject is diagnosed as having HBV infection by a treating physician).

ADDITIONAL USES

In some embodiments, the compound of the present disclosure modulates RNAs whose transcription, post-transcriptional processing, stability, steady state levels or function are altered due to acquired or genetic defects in one or more of any cellular pathways. In some embodiments, these include non-coding RNAs (ncRNAs) that are members of the small nucleolar RNA (snoRNA), small Cajal body RNA (scaRNA), small nuclear RNA (snRNA), ribosomal RNA (rRNA), Y RNA, transfer RNA (tRNA), microRNA (miRNA), PIWI-interacting RNA (piRNA) or long non-coding RNA (lncRNA) families. The compounds may also by useful for modulating non-coding RNAs in a cell (e.g. scaRNA13, scaRNA8), and concomitantly for preventing and treating the associated disease and conditions. In some embodiments, these also include those ncRNAs affected by any of the molecular mechanisms described, for example, in Lardelli et al, Nature Genetics, 49 (3), 2017, 457-464; and in Son et al., 2018, Cell Reports 23, 888-898, including those affected by disruption of PARN or TOE1 deadenylases. As such, the compounds are useful in treating or preventing genetic and other disorders, including neurodevelopmental disorders such as pontocerebellar hypoplasia. Neurodevelopmental disorders are a group of disorders in which the development of the central nervous system is disturbed. This can include developmental brain dysfunction, which can manifest as neuropsychiatric problems or impaired motor function, learning, language or non-verbal communication. In some embodiments, a neurodevelopmental disorder is selected from attention deficit hyperactivity disorder (ADHD), reading disorder (dyslexia), writing disorder (disgraphia), calculation disorder (dyscalculia), expression disorder (ability for oral expression is substantially below the appropriate level for a child's mental age), comprehension disorder (ability for comprehension is markedly below the appropriate level for a child's mental age), mixed receptive-expressive language disorder, speech disorder (dislalia) (inability to use the sounds of speech that are developmentally appropriate), stuttering (disruption of normal fluency and temporal structure of speech), and autism spectrum disorders (persistent difficulties in social communication). In some embodiments, the present disclosure provides a method of treating an acquired or genetic disease or condition associated with alterations in RNA, the method comprising administering to the subject in need thereof a therapeutically effective amount of any one of the compounds described herein, or a pharmaceutically acceptable salt thereof, or a pharmaceutically acceptable composition comprising same. In some embodiments, the RNA comprises ncRNA (e.g., snRNA, scaRNA, snoRNA, rRNA, and miRNA). In some embodiments, the RNA is disrupted by disruption of PARN or TOEI deadenylase. In some embodiments, the acquired or genetic disease or condition associated with alterations in RNA comprises a neurodevelopmental disorder such as pontocerebellar hypoplasia.

Because the compounds are PAPD5 inhibitors, and because these affect TERC, telomerase, telomere maintenance and stem cell self-renewal, the compounds are useful in modulating ex vivo expansion of stem cells, and also useful for allograft exhaustion, in hematopoietic or other tissues. For example, PAPD5 inhibitors may be useful for the ex vivo expansion of hematopoietic stem cells as described in Fares, et al, 2015, Science 345, 1590-1512, and Boitano, et al, 2010 329, 1345-1348, both of which are incorporated by reference herein in their entireties.

Methods of Screening

Included herein are methods for screening test compounds, e.g., polypeptides, nucleic acids, fusion proteins, polynucleotides, inorganic or organic large or small molecule test compounds, to identify agents useful in the treatment of telomere diseases e.g., diseases associated with altered levels of TERC, activity and/or telomerase function. Also included are methods for screening test compounds, e.g., polypeptides, nucleic acids, fusion proteins, polynucleotides, inorganic or organic large or small molecule test compounds, to identify agents that modulate the level or activity of TERC, PARN, and/or PAPD5.

The small molecules can be, e.g., natural products or members of a combinatorial chemistry library. A set of diverse molecules can be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods as described herein can include a variety of types of test compounds. A given library can comprise a set of structurally related or unrelated test compounds. In some embodiments, the test compounds are nucleic acids (e.g., shRNA). In some embodiments, the test compounds are nucleic acids (e.g., isolated cDNA). In some embodiments, the test compounds are small molecules. In some embodiments, the test compounds are vectors comprising nucleic acids that can encode fusion proteins (e.g., CRSPR-based fusion proteins). In some embodiments, the fusion proteins can encode modified PAPD5. In some embodiments, the fusion proteins can encode an active domain of PARN protein. In some embodiments, the test compounds can be peptides or peptidomimetic molecules e.g., molecules that bind PAPD5. In some embodiments, the test compounds are viral encoded nucleic acids e.g., PARN cDNA.

Cell-Based Screening Methods

Generally, the methods of screening involve isolating a cell, e.g., human or an animal cell, contacting the cell with a test compound, e.g., small molecules and/or nucleic acids, comparing levels or activity of TERC, PARN, and/or PAPD5 to a reference level.

The term "reference" level is an art-known term and typically refers to a baseline value. Skilled practitioners will appreciate that baseline values can be established by standard methods and generally are determined in the absence of a test compound, treatment step, or disease. Often the reference level from a patient derived cell is compared to a reference level from a human or other eukaryotic cell that is recognized by a skilled artisan as a control level or a baseline level for the cell. For example, it is art recognized that normal cultured fibroblast cell with known characteristic levels of housekeeping genes, e.g., beta actin. All such levels are generally detectable, but can also be low or undetectable.

In the presently described methods, reference levels can include baseline RNA or protein levels that generally known to occur in a cell, in a "naïve" state, e.g., in absence of an administrative or a treatment step or disease. In some embodiments, a reference level is determined at baseline in a patient who is identified with a telomere disease. In some embodiments, the reference level is determined by way of determining amount of mature TERC species, before a compound is administered into a cell, e.g., a patient-derived iPS cell. In some embodiments, the reference level is the baseline RNA or protein level in a cell derived from a subject without telomere diseases.

The cells can be treated with commercially available reagents by standard methods, wherein the cells will be further manipulated with test compounds that modulate TERC in the cells. The desired effect is not limiting to any condition but in some embodiments can be to alter TERC levels. In some embodiment the desired effect can be to alter telomere size in the cell. In some embodiment the desired effect can restore or alter telomerase activity in the cell. In some embodiments, the desired effect can include alteration (I-Increase or decrease) TERC species but not all RNA species in a cell.

In some embodiments, a test compound is applied to a cell, e.g., an isolated fibroblast cell, e.g., a normal fibroblast cell or a diseased fibroblast cell, and one or more effects of the test compound is evaluated, e.g., using a quantitative RT-PCR assay or, a polyacrylamide gel based telomerase activity assay (TRAP) in the presence of reducing agents including dithiothreitol (DTT) or mercaptoethanol, which detects change or modulation of telomerase activity by rendering fragments of telomeres that can be separated on a polyacrylamide gel.

A candidate compound that has been selected from the screening methods can be further validated and purified to test in animal models by further screening (I-In vivo screening methods).

A test compound can also be used to screen a library to develop a "probe" compound that may be further used in a counter-screen, e.g., sequencing probes. Such test compounds are not necessarily structurally or functionally similar but when contacted with a cell have an effect that is rendered in a robust manner, e.g., TERC levels are altered or desirable levels at any treatment time-point or upon repetition. By using a first screen and a counter-screen, the method disclosed will select a therapeutic compound that can be administered to treat one or more cellular defect of a said disorder (e.g., telomere size, TERC decay rate, TERC expression or telomerase maturation in the aspect of telomere disease), and can be considered a candidate therapeutic agent. Candidate therapeutic agents, once screened in an animal model and clinical setting, are therapeutic agents. Candidate compounds, candidate therapeutic agents, and therapeutic agents can be optionally optimized and/or derivatized, and formulated with physiologically acceptable excipients to form pharmaceutical compositions.

The candidate compound (e.g., test compounds that decrease PAPD5 and restore steady-state levels of TERC and optionally, that also do not reduce cell proliferation or viability, and so not affect non-specific targets, and optionally that also have activity in an in vivo model) can be selected and systematically altered, e.g., using rational design, to optimize binding affinity, avidity, specificity, or other parameter for use in therapy. A variety of techniques useful for determining the structures of candidate compounds can be used, e.g., NMR, mass spectrometry, gas chromatography equipped with electron capture detectors, fluorescence and absorption spectroscopy.

The disclosure also provides methods for screening modulators of TERC, PARN and/or PAPD5. In some embodiments, methods of screening include contacting a cell with a test compound, e.g., a nucleic acid or a small molecule; determining the level or activity of TERC, PARN or PAPD5 in the cell; comparing the level or activity of TERC, PARN or PAPD5 in the cells to a reference level. If the level or activity of TERC, PARN or PAPD5 in the cells is significantly different from the reference level, the test compound will be selected as a candidate compound.

As used herein, the term "significant" or "significantly" refers to statistical significance (or a statistically significant result) is attained when a p-value is less than the significance level (denoted a, alpha). The p-value is the probability of obtaining at least as extreme results given that the null hypothesis is true whereas the significance level a is the probability of rejecting the null hypothesis given that it is true. In some embodiments, the significance level is 0.05, 0.01, 0.005, 0.001, 0.0001, or 0.00001, etc. In some embodiments, "significantly altered" or "significantly different" refers to the difference between the two groups have attained the statistical significance.

In some embodiments, the methods of screening involve determining whether the test compound can achieve a desired effect. In some embodiments, the "desired effect" is determined by the quality, density or source of cells (e.g., human or animal), and herein are provided in the various examples of cells that are contacted with a test compound, to elicit a desired effect.

These cells can be obtained from various sources, e.g., from a patient diagnosed with cancer, from a control subject, or from a cell line. In some embodiments, the cells are iPSC cells. In some embodiments, the iPSC cells are obtained from a subject who has telomere disease. In some embodiments, the cells are PARN deficient cells. The test compounds will be selected as a candidate compound if the test compound restores the level or activity of PARN to a normal level (the level or activity of PARN in a cell without PAN deficiency). In some embodiments, the test compound restores the level or activity or TERC to a normal level (the level or activity of PARN in a cell without PAN deficiency). In some embodiments, these cells are tumor cells or cancer cells.

The presence and/or level of a nucleic acid can be evaluated using methods known in the art, e.g., using polymerase chain reaction (PCR), reverse transcriptase polymerase chain reaction (RT-PCR), quantitative or semi-quantitative real-time RT-PCR, digital PCR i.e. BEAMing ((Beads, Emulsion, Amplification, Magnetics) Diehl (2006) Nat Methods 3:551-559); RNAse protection assay; Northern blot; various types of nucleic acid sequencing (Sanger, pyrosequencing, NextGeneration Sequencing); fluorescent in-situ hybridization (FISH); or gene array/chips) (Lehninger Biochemistry (Worth Publishers, Inc., current addition; Sambrook, et al, Molecular Cloning: A Laboratory Manual (3. Sup.rd Edition, 2001); Bernard (2002) Clin Chem 48 (8): 1178-1185; Miranda (2010) Kidney International 78:191-199; Bianchi (2011) EMBO Mol Med 3:495-503; Taylor (2013) Front. Genet. 4:142; Yang (2014) PLOS One 9 (11): e110641); Nordstrom (2000) Biotechnol. Appl. Biochem. 31 (2): 107-112; Ahmadian (2000) Anal Biochem 280:103-110. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; Mac-Beath and Schreiber, Science 2000, 289 (5485): 1760-1763; Simpson, Proteins and Proteomics: A Laboratory Manual, Cold Spring Harbor Laboratory Press; 2002; Hardiman, Microarrays Methods and Applications: Nuts & Bolts, DNA Press, 2003), can be used to detect the presence and/or level of PARN, TERC or PAPD5 Measurement of the level of a biomarker can be direct or indirect. For example, the abundance levels of TERC can be directly quantitated. For example, the RNA levels of PSRN or PAPD5 can be directly quantitated using quantitative PCR. Alternatively, the amount of a protein or RNA can be determined indirectly by measuring abundance levels of cDNA, amplified RNAs or DNAs, or by measuring quantities or activities of other RNAs associated with the protein or protein-associated molecules (e.g., sno RNAs that interact with TERC RNA) that are indicative of the expression level of the protein or RNA. In some embodiments, a technique suitable for the detection of alterations in the structure or sequence of nucleic acids, such as the presence of deletions, amplifications, or substitutions, can be used for the detection of biomarkers of this invention.

Luminescence-Based Screening Methods and High-Throughput Screening

Figure 3A:
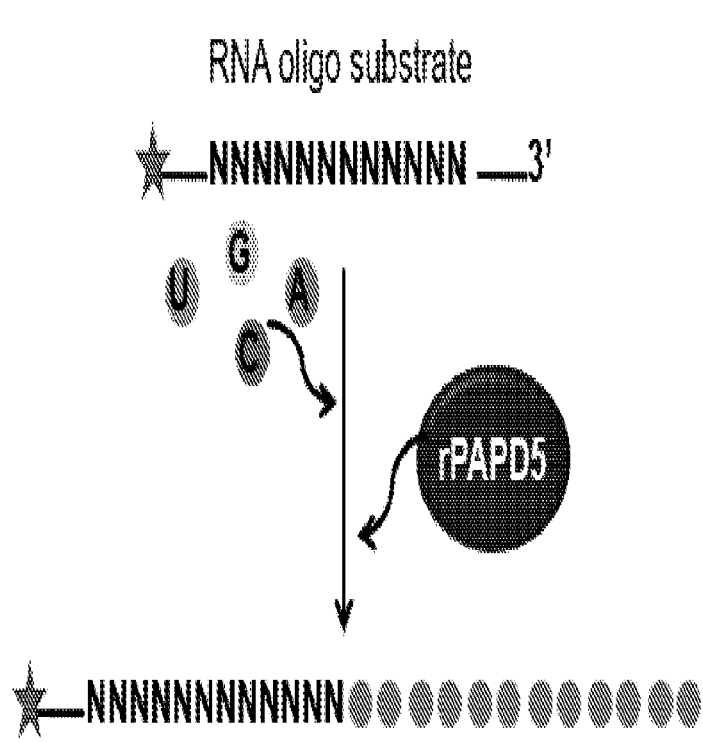
FIG. 3A is a schematic diagram showing PAPD5 can polyadenylate RNA oligonucleotides in vitro.
Figure 3B:
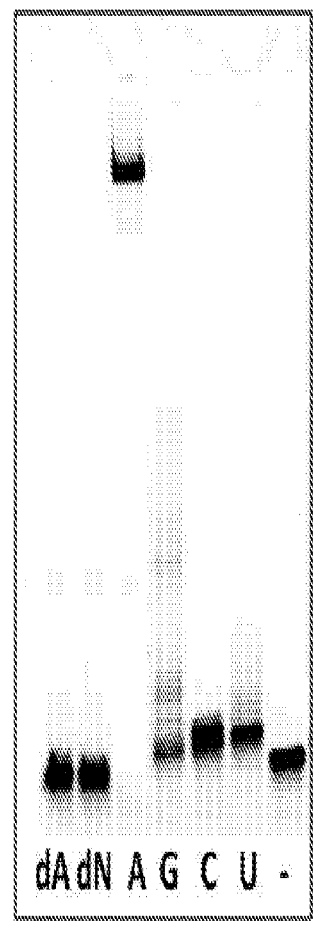
FIG. 3B shows PAPD5 has a strong preference for ATP when PAPD5 polyadenylates RNA oligonucleotides.
Figure 4A:
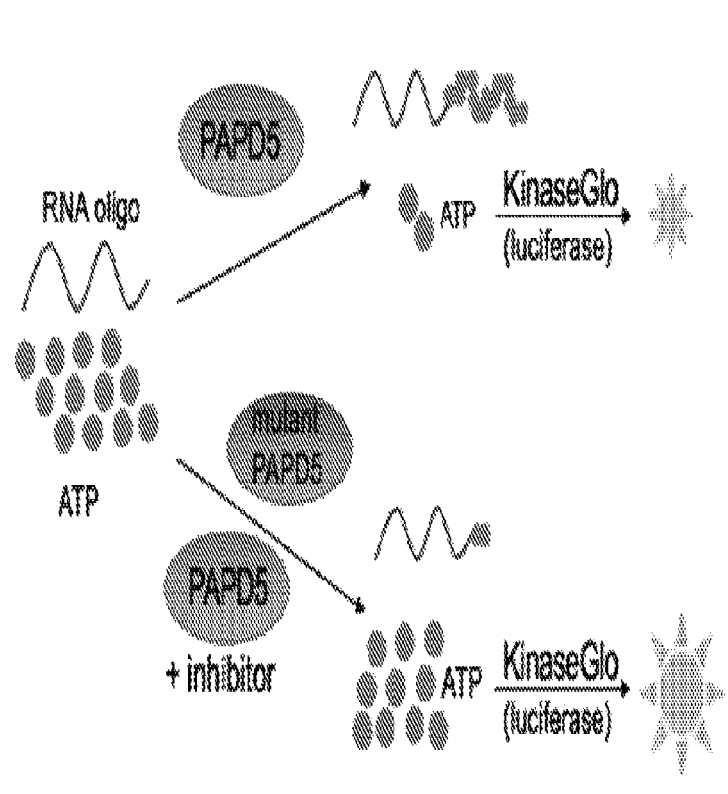
FIG. 4A is a schematic diagram showing an assay for determining that a compound is a PAPD5 inhibitor.
Figure 4B:
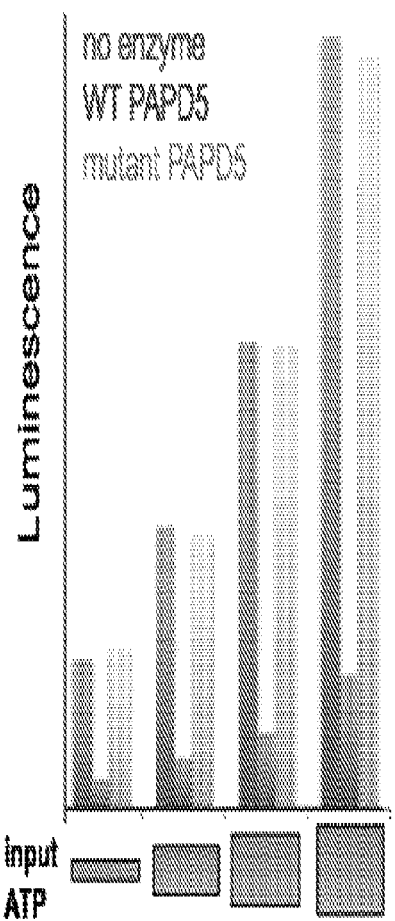
FIG. 4B is a graph showing luminescence signal generated in a high throughput screening setting for reactions performed using no enzyme, wildtype PAPD5, and mutant PAPD5 at different input ATP concentrations.

PAPD5 can polyadenylate an RNA oligonucleotide in vitro. When PAPD5 polyadenylates RNA oligonucleotides, tens to hundreds of ATP molecules are consumed for each RNA substrate molecule (FIGS. 3A-3B). The present disclosure exploits ATP consumption in the process of poly-adenylation of an RNA substrate using recombinant PAPD5 and provides functional screening assays for PAPD5 inhibitors (FIG. 4A). After PAPD5 polyadenylates RNA oligonucleotides for a period of time, luciferase reagents can be added to the solution. Luminescence will inversely correlate with PAPD5 activity, because with higher levels of PAPD5 activity, more ATP is consumed. Thus, inhibitors of PAPD5 can be detected by decreased consumption of ATP, and thus an increased luminescence signal. As shown in FIG. 4A, an input pool of ATP is depleted by wild-type PAPD5 during poly-adenylation of a substrate RNA oligonucleotide. When luciferase is subsequently added, the luminescence of the reaction is low due to a paucity of ATP remaining in the reaction. In the presence of mutant PAPD5 (FIG. 4B), or in the presence of an effective PAPD5 inhibitor, the ATP pool remaining after the reaction will be higher, giving a high luminescence signal upon addition of luciferase.

In some embodiments, the screening assay can be used in a high-throughput setting, measuring luminescence after enzymatic reactions in multiple wells (e.g., in 384-well plates). For example, the screening can involves dispensing a reaction solution containing oligo-ribonucleotide substrate, recombinant PAPD5, and ATP in a high throughput setting using robotic liquid handling instruments, followed by addition of chemical libraries by pin transfer. In some embodiments, the reactions can be performed in duplicate at a fixed concentration of each chemical compound. The reaction can be allowed to proceed for a sufficient period of time (e.g., about 30 minutes, about 1 hour, or about 2 hours), followed by addition of a luciferase reagent and measurement of luminescence. Appropriate controls such as mutant PAPD5 and competitor oligonucleotide chain terminators can be included. Compounds that yield high light output are selected.

Candidate inhibitors can be further assayed at a range of concentrations in PAPD5 functional assays, which entail extension of fluorescently- or radioactively-labelled RNA oligos in the presence of PAPD5 with and without inhibitors, followed by polyacrylamide gel electrophoresis. The specificity of putative inhibitors can also be tested in similar assays using related enzymes, such as the terminal uridylyl transferase ZCCHC11.

The effect of candidate PAPD5 inhibitors can also be further determined in cell-based assays as described herein. The effect of candidate compounds on TERC RNA levels and processing, telomerase activity, and telomere length over various periods of exposure can be determined in PARN-mutant patient iPSCs. Furthermore, cell viability and population doubling can be monitored. RNA-Seq can be performed to assess changes in the global transcriptome, which can provide a measure of off-target effects.

Diagnosing a Subject in Need of Treatment

The present specification provides methods of diagnosing a subject in need of treatment (e.g., as having any one of telomere diseases described herein). As an example, if the level or activity of TERC, PARN, and/or PAPD5 in a subject is comparable to the level or activity of TERC, PARN, and/or PAPD5 in a subject having the telomere disease and, optionally, the subject has one or more symptoms associated with telomere disease (e.g., aplastic anemia, pulmonary fibrosis, hepatic cirrhosis), then the subject can be diagnosed as having or being at risk of developing a telomere disease.

In some embodiments, if the level or activity of TERC, PARN, and/or PAPD5 in a subject is comparable to the level or activity of TERC, PARN, and/or PAPD5 in a control subject who does not have a telomere disease, then the subject can be diagnosed as not having telomere disease or not being at risk of developing a telomere disease.

In some embodiments, the subject is determined to have or being at risk of developing a telomere disease if there is a mutation at PARN. The mutation can be a deletion containing part of PARN gene or the entire PARN gene. The mutation can also be a mutation at position 7 and/or 87 of PARN, e.g., the amino acid residue at position 7 is not asparagine, and/or the amino acid residue at position 87 of PARN is not serine. For example, the mutation can be a missense variant c.19A>C, resulting in a substitution of a highly conserved amino acid p.Asn7His. In some cases, the mutation is a missense mutation c.260C>T, encoding the substitution of a highly conserved amino acid, p.Ser87Leu.

In some embodiments, a subject has no overt signs or symptoms of a telomere disease, but the level or activity of TERC, PARN or PAPD5 may be associated with the presence of a telomeres disease, then the subject has an increased risk of developing telomere disease. In some embodiments, once it has been determined that a person has telomere disease, or has an increased risk of developing telomere disease, then a treatment, e.g., with a small molecule (e.g., a PAPD5 inhibitor) or a nucleic acid encoded by a construct, as known in the art or as described herein, can be administered.

Suitable reference values can be determined using methods known in the art, e.g., using standard clinical trial methodology and statistical analysis. The reference values can have any relevant form. In some cases, the reference comprises a predetermined value for a meaningful level of PAPD5 protein, e.g., a control reference level that represents a normal level of PAPD5 protein, e.g., a level in an unaffected subject or a subject who is not at risk of developing a disease described herein, and/or a disease reference that represents a level of the proteins associated with conditions associated with telomere disease, e.g., a level in a subject having telomere disease (e.g., pulmonary fibrosis, hepatic cirrhosis or aplastic anemia). In another embodiment, the reference comprises a predetermined value for a meaningful level of PARN protein, e.g., a control reference level that represents a normal level of PARN protein, e.g., a level in an unaffected subject or a subject who is not at risk of developing a disease described herein, and/or a disease reference that represents a level of the proteins associated with conditions associated with telomere disease, e.g., a level in a subject having telomere disease (e.g., pulmonary fibrosis, hepatic cirrhosis or aplastic anemia).

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level is a level or occurrence in the same subject, e.g., at a different time point, e.g., an earlier time point.

Subjects associated with predetermined values are typically referred to as reference subjects. For example, in some embodiments, a control reference subject does not have a disorder described herein. In some embodiments, it may be desirable that the control subject is deficient in PARN gene (e.g., Dyskeratosis Congenita), and in other embodiments, it may be desirable that a control subject has cancer. In some cases, it may be desirable that the control subject has high telomerase activity, and in other cases it may be desirable that a control subject does not have substantial telomerase activity.

In some embodiments, the level of TERC or PARN in a subject being less than or equal to a reference level of TERC or PARN is indicative of a clinical status (e.g., indicative of a disorder as described herein, e.g., telomere disease). In some embodiments, the activity of TERC or PARN in a subject being greater than or equal to the reference activity level of TERC or PARN is indicative of the absence of disease.

The predetermined value can depend upon the particular population of subjects (e.g., human subjects or animal models) selected. For example, an apparently healthy population will have a different 'normal' range of levels of TERC than will a population of subjects which have, are likely to have, or are at greater risk to have, a disorder described herein. Accordingly, the predetermined values selected may take into account the category (e.g., sex, age, health, risk, presence of other diseases) in which a subject (e.g., human subject) falls. Appropriate ranges and categories can be selected with no more than routine experimentation by those of ordinary skill in the art. In characterizing likelihood, or risk, numerous predetermined values can be established.

In some embodiments, the methods described in this disclosure involves identifying a subject as having, being at risk of developing, or suspected of having a disorder associated with telomerase dysfunction. The methods include determining the level or activity of TERC, PARN, or PAPD5 in a cell from the subject; comparing the level or activity of TERC, PARN, or PAPD5 to the reference level or reference activity of TERC, PARN, or PAPD5; and identifying the subject as having, being at risk of developing, or suspected of having a disorder associated with telomerase dysfunction if the level or activity of TERC, PARN, or PAPD5 is significantly different from the reference level or activity of TERC, PARN, or PAPD5. In some embodiments, the reference level or activity of TERC, PARN, or PAPD5 are determined by cells obtained from subjects without disorders associated with telomerase dysfunction.

The level or activity of TERC, PARN, or PAPD5 can be determined in various types of cells from a subject. The methods can include obtaining cells from a subject, and transforming these cells to induced pluripotent stem cells (I-IPS) cells, and these iPS cells can be used to determine the level or activity of TERC, PARN, or PAPD5. These cells can be, e.g., primary human cells or tumor cells. Pluripotent stem cells (I-IPS) cells can be generated from somatic cells by methods known in the art (e.g., somatic cells may be genetically reprogrammed to an embryonic stem cell-like state by being forced to express genes and factors important for maintaining the defining properties of embryonic stem cells). In some embodiments, the methods of diagnosing a subject include analyzing blood sample of the subject, or a sample of hair, urine, saliva, or feces of the subject (e.g., a subject may be diagnosed without any cell culture surgically obtained from the subject).

The subject may be one having a mutation at PARN, e.g., a deletion containing part of PARN gene or the entire PARN gene. For example, the mutation may be one wherein the amino acid residue at position 7 of PARN is not asparagine or serine. For example, the subject can have a missense variant c.19A>C, resulting in a substitution of a highly conserved amino acid p.Asn7His. The subject can have a missense mutation c.260C>T, encoding the substitution of a highly conserved amino acid, p.Ser87Leu.

Induced Pluripotent Stem Cells

Induced pluripotent stem cells (I-IPSC or iPS), are somatic cells (e.g., derived from patient skin or other cell) that have been genetically reprogrammed to an embryonic stem cell-like state by being forced to express genes and factors important for maintaining the defining properties of embryonic stem cells. These cells can be generated by methods known in the art.

It is known that mouse iPSCs demonstrate important characteristics of pluripotent stem cells, including expressing stem cell markers, forming tumors containing cells from all three germ layers, and being able to contribute to many different tissues, when injected into mouse embryos at a very early stage in development.

Human iPSCs also express stem cell markers and are capable of generating cells characteristic of all three germ layers. iPSCs can be generated from human fibroblasts and are already useful tools for drug development and modeling of diseases. Viruses are currently used to introduce the reprogramming factors into adult cells (e.g., lentiviral vectors disclosed herein), and this process can be carefully controlled and tested in cultured, isolated cells first to then treat cells (e.g., by contacting with a test compound) to express altered markers, e.g., iPSCs from tumor cells can be manipulated to differentiate or iPSCs from cardiomyocytes can be manipulated to de-differentiate.

The iPSC manipulation strategy can be applied to any cells obtained from a subject to test whether the compound can alter the level or activity of TERC, PARN, or PAPD5. The cells are contacted with test compounds (e.g., small molecules). In some embodiments, these iPSC cells can be used for screening compounds that modulate TERC. In some embodiments, the iPSC cells can be converted from patient skin fibroblasts.

Pharmaceutical Compositions and Formulations

The methods described herein include the use of pharmaceutical compositions comprising an agent that modulates the level or activity of TERC, PARN, or PAPD5 (e.g., PAPD5 inhibitors). As used herein, an agent can be any number of agents, e.g., a small molecule, a nucleic acid, a polypeptide peptide, or a fragment thereof. In some embodiments, the agent can modulate the level or activity of PARN or PAPD5, e.g., a compound that can alter the level of a protein, e.g., PARN or PAPD5 protein (e.g., PAPD5 inhibitors). Exemplary of the pharmaceutical compositions are compositions that include at least one of the PAPD5 inhibitors or their derivatives described herein, e.g., those described in FIGS. 9, 10, and 11.

The present application also provides pharmaceutical compositions comprising an effective amount of any one of the compounds disclosed herein, or a pharmaceutically acceptable salt thereof, and a pharmaceutically acceptable carrier. The pharmaceutical composition can also comprise at least one of any one of the additional therapeutic agents described herein. In certain embodiments, the application also provides pharmaceutical compositions and dosage forms comprising any one the additional therapeutic agents described herein (e.g., in a kit). The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that can be used in the pharmaceutical compositions of the present application include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms can contain any one of the compounds and therapeutic agents described herein in the range of 0.005% to 100% with the balance made up from the suitable pharmaceutically acceptable excipients. The contemplated compositions can contain 0.001%-100% of any one of the compounds and therapeutic agents provided herein, in one embodiment 0.1-95%, in another embodiment 75-85%, in a further embodiment 20-80%, wherein the balance can be made up of any pharmaceutically acceptable excipient described herein, or any combination of these excipients.

Routes of Administration and Dosage Forms

The pharmaceutical compositions of the present application include those suitable for any acceptable route of administration. Acceptable routes of administration include, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intramenigeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Compositions and formulations described herein can conveniently be presented in a unit dosage form, e.g., tablets, capsules (e.g., hard or soft gelatin capsules), sustained release capsules, and in liposomes, and can be prepared by any methods well known in the art of pharmacy. See, for example, Remington: The Science and Practice of Pharmacy, Lippincott Williams & Wilkins, Baltimore, MD (20th ed. 2000). Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, any one of the compounds and therapeutic agents disclosed herein are administered orally. Compositions of the present application suitable for oral administration can be presented as discrete units such as capsules, sachets, granules or tablets each containing a predetermined amount (e.g., effective amount) of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which can beneficially increase the rate of compound absorption. In the case of tablets for oral use, carriers that are commonly used include lactose, sucrose, glucose, mannitol, and silicic acid and starches. Other acceptable excipients can include: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents can be added. Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions or infusion solutions which can contain antioxidants, buffers, bacteriostats and solutes which render the formulation isotonic with the blood of the intended recipient; and aqueous and non-aqueous sterile suspensions which can include suspending agents and thickening agents. The formulations can be presented in unit-dose or multi-dose containers, for example, sealed ampules and vials, and can be stored in a freeze dried (lyophilized) condition requiring only the addition of the sterile liquid carrier, for example water for injections, saline (e.g., 0.9% saline solution) or 5% dextrose solution, immediately prior to use. Extemporaneous injection solutions and suspensions can be prepared from sterile powders, granules and tablets. The injection solutions can be in the form, for example, of a sterile injectable aqueous or oleaginous suspension. This suspension can be formulated according to techniques known in the art using suitable dispersing or wetting agents and suspending agents. The sterile injectable preparation can also be a sterile injectable solution or suspension in a non-toxic parenterally-acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant.

The pharmaceutical compositions of the present application can be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include cocoa butter, beeswax, and polyethylene glycols.

The pharmaceutical compositions of the present application can be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J Pharm Pharmacol,* 56:3-17, 2004 and Ilium, L., *Eur J Pharm Sci* 11:1-18, 2000.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of the pharmaceutical compositions of the present application is especially useful when the desired treatment involves areas or organs readily accessible by topical application. In some embodiments, the topical composition comprises a combination of any one of the compounds and therapeutic agents disclosed herein, and one or more additional ingredients, carriers, excipients, or diluents including absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

The compounds and therapeutic agents of the present application can be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polydimethylsiloxane, polycaprolactone, polyethylene glycol, polylactic acid, ethylene vinyl acetate, and mixtures thereof. The coatings can optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present application provides an implantable drug release device impregnated with or containing a compound or a therapeutic agent, or a composition comprising a compound of the present application or a therapeutic agent, such that said compound or therapeutic agent is released from said device and is therapeutically active.

Dosages and Regimens

In the pharmaceutical compositions of the present application, a therapeutic compound is present in an effective amount (e.g., a therapeutically effective amount).

Effective doses can vary, depending on the diseases treated, the severity of the disease, the route of administration, the sex, age and general health condition of the subject, excipient usage, the possibility of co-usage with other therapeutic treatments such as use of other agents and the judgment of the treating physician.

In some embodiments, an effective amount of a therapeutic compound can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; or from about 0.1 mg/kg to about 0.5 mg/kg).

In some embodiments, an effective amount of a therapeutic compound is about 0.1 mg/kg, about 0.5 mg/kg, about 1 mg/kg, about 2 mg/kg, or about 5 mg/kg.

The foregoing dosages can be administered on a daily basis (e.g., as a single dose or as two or more divided doses, e.g., once daily, twice daily, thrice daily) or non-daily basis (e.g., every other day, every two days, every three days, once weekly, twice weekly, once every two weeks, once a month). The compounds and compositions described herein can be administered to the subject in any order. A first therapeutic agent, such as a compound of any one of the Formulae disclosed herein, can be administered prior to or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before or after), or concomitantly with the administration of a second therapeutic agent, such as an anti-cancer therapy described herein, to a subject in need of treatment. Thus, the compound of any one of the Formulae disclosed herein, or a composition containing the compound, can be administered separately, sequentially or simultaneously with the second therapeutic agent, such as a chemotherapeutic agent described herein. When the compound of any one of the Formulae disclosed herein, or a pharmaceutically acceptable salt thereof, and a second or third therapeutic agent are administered to the subject simultaneously, the therapeutic agents can be administered in a single dosage form (e.g., tablet, capsule, or a solution for injection or infusion).

Combination Therapies

In some embodiments, the compounds described here may be administered to a subject in any combination with treatments for telomere diseases that are known in the art. The combination treatment may be administered to the subject either consecutively or concomitantly with the compound of any one of the Formulae disclosed herein. When combination treatment comprises an alternative therapeutic agent, the therapeutic agent may be administered to the subject in any one of the pharmaceutical compositions described herein.

In some embodiments, the compounds of the present disclosure may be used in combination with a therapeutic agent that is useful in treating a telomere disease (e.g., a therapeutic agent that modulates the level or activity of TERC). In some embodiments, the agent useful in treating a telomere disease is a nucleic acid comprising a nucleotide sequence that encodes PARN. The agent can also be an anti-PARN antibody or anti-PARN antibody fragment. In some embodiments, the agent is an antisense molecule or a small interfering nucleic acid which is specific for a nucleic acid encoding PARN. In some embodiments, the agent is a nucleic acid comprising a nucleotide sequence that encodes PAPD5. The agent can also be an anti-PAPD5 antibody or anti-PAPD5 antibody fragment. In some embodiments, the agent is an antisense molecule or a small interfering nucleic acid which is specific for a nucleic acid encoding PAPD5. The antisense molecule described herein can be an oligonucleotide. In some cases, the agent binds to PARN or PAPD5.

In some embodiments, the therapeutic agent that is useful in treating a telomere disease is selected from adenosine analogues, aminoglycosides, and purine nucleotides, etc. In some cases, the aminoglycoside can be a member of the neomycin and kanamycin families. The aminoglycoside can be, for example, kanamycin B sulfate, pramycin sulfate, spectinomycin dihydrochloride pentahydrate, ribostamycin sulfate, sisomicin sulfate, amikacin disulfide, dihydrostreptomycin sesquisulfate, hygromycin B, netilmicin sulfate, paromomycin sulfate, kasugamycin, neomycin, gentamicin, tobramycin sulfate, streptomycin sulfate, or neomycin B, or derivatives thereof.

In some embodiments, the therapeutic agent that is useful in treating a telomere disease a nucleoside analogue, e.g., an adenosine analogue, 8-chloroadenosine (8-Cl-Ado) and 8-aminoadenosine (8-amino-Ado), or the triphosphate derivative thereof, synthetic nucleoside analogue bearing a fluoroglucopyranosyl sugar moiety, benzoyl-modified cytosine or adenine, adenosine- and cytosine-based glucopyranosyl nucleoside analogue, or glucopyranosyl analogue bearing uracil, 5-fluorouracil or thymine, etc.

Adenosine analogues, aminoglycosides, and purine nucleotides are known in the art, and they are described, e.g., in Kim, Kyumin, et al. "Exosome Cofactors Connect Transcription Termination to RNA Processing by Guiding Terminated Transcripts to the Appropriate Exonuclease within the Nuclear Exosome." Journal of Biological Chemistry (2016): jbc-M116; Chen, Lisa S., et al. "Chain termination and inhibition of mammalian poly (A) polymerase by modified ATP analogues." Biochemical pharmacology 79.5 (2010): 669-677; Ren, Yan-Guo, et al. "Inhibition of Klenow DNA polymerase and poly (A)-specific ribonuclease by aminoglycosides." Rna 8.11 (2002): 1393-1400; Thuresson, Ann-Charlotte, Leif A. Kirsebom, and Anders Virtanen. "Inhibition of poly (A) polymerase by aminoglycosides." Biochimie 89.10 (2007): 1221-1227; AA Balatsos, N., et al. "Modulation of poly (A)-specific ribonuclease (PARN): current knowledge and perspectives." Current medicinal chemistry 19.28 (2012): 4838-4849; Balatsos, Nikolaos AA, Dimitrios Anastasakis, and Constantinos Stathopoulos. "Inhibition of human poly (A)-specific ribonuclease (PARN) by purine nucleotides: kinetic analysis." Journal of enzyme inhibition and medicinal chemistry 24.2 (2009): 516-523; Balatsos, Nikolaos A A, et al. "Competitive inhibition of human poly (A)-specific ribonuclease (PARN) by synthetic fluoro-pyranosyl nucleosides." Biochemistry 48.26 (2009): 6044-6051; and Balatsos, Nikolaos, et al. "Kinetic and in silico analysis of the slow-binding inhibition of human poly (A)-specific ribonuclease (PARN) by novel nucleoside analogues." Biochimie 94.1 (2012): 214-221; each of which is incorporated herein by reference in its entirety. Numerous therapeutic agents that can modulate the level or activity of PARN and/or PAPD5 are described, e.g., in WO 2017/066796, which is incorporated herein by reference in its entirety.

In some embodiments, the compounds of the present disclosure are used in combination with an anti-cancer therapy. In some embodiments, the anti-cancer therapy is selected from the group consisting of surgery, radiation therapy, chemotherapy, gene therapy, DNA therapy, viral therapy, RNA therapy, adjuvant therapy, and immunotherapy. In some embodiments, the anti-cancer therapy is selected from the group consisting of a platinum agent, mitomycin C, a poly (ADP-ribose) polymerase (PARP) inhibitor, a radioisotope, a vinca alkaloid, an antitumor alkylating agent, a monoclonal antibody and an antimetabolite. In some embodiments, the anti-cancer therapy is an ataxia telangiectasia mutated (ATM) kinase inhibitor. Suitable examples of platinum agents include cisplatin, carboplatin, oxaliplatin, satraplatin, picoplatin, nedaplatin, triplatin, and lipoplatin. Suitable examples of cytotoxic radioisotopes include $^{67}$Cu, $^{67}$Ga, $^{90}$Y, $^{131}$I, $^{177}$Lu, $^{186}$Re, $^{188}$Re, α-Particle emitter, $^{211}$At, $^{213}$Bi, $^{225}$Ac, Auger-electron emitter, $^{125}$I, $^{212}$Pb, and $^{111}$In. Suitable examples of antitumor alkylating agents include nitrogen mustards, cyclophosphamide, mechlorethamine or mustine (HN2), uramustine or uracil mustard, melphalan, chlorambucil, ifosfamide, bendamustine, nitrosoureas, carmustine, lomustine, streptozocin, alkyl sulfonates, busulfan, thiotepa, procarbazine, altretamine, triazenes, dacarbazine, mitozolomide, and temozolomide. Suitable examples of anti-cancer monoclonal antibodies include to necitumumab, dinutuximab, nivolumab, blinatumomab, pembrolizumab, ramucirumab, obinutuzumab, adotrastuzumab emtansine, pertuzumab, brentuximab, ipilimumab, ofatumumab, catumaxomab, bevacizumab, cetuximab, tositumomab-I$^{131}$, ibritumomab tiuxetan, alemtuzumab, gemtuzumab ozogamicin, trastuzumab, and rituximab. Suitable examples of vinca alkaloids include vinblastine, vincristine, vindesine, vinorelbine, desoxyvincaminol, vincaminol, vinburnine, vincamajine, vineridine, vinburnine, and vinpocetine. Suitable examples of antimetabolites include fluorouracil, cladribine, capecitabine, mercaptopurine, pemetrexed, fludarabine, gemcitabine, hydroxyurea, methotrexate, nelarbine, clofarabine, cytarabine, decitabine, pralatrexate, floxuridine, and thioguanine.

Kits

The present disclosure also includes pharmaceutical kits useful, for example, in the treatment of disorders, diseases and conditions referred to herein, which include one or more containers containing a pharmaceutical composition comprising a therapeutically effective amount of a compound of the present disclosure. Such kits can further include, if desired, one or more of various conventional pharmaceutical kit components, such as, for example, containers with one or more pharmaceutically acceptable carriers, additional containers, etc. Instructions, either as inserts or as labels, indicating quantities of the components to be administered, guidelines for administration, and/or guidelines for mixing the components, can also be included in the kit. The kit can optionally include directions to perform a test to determine that a subject is in need of treatment with a compound of Formula (I-I) as described herein, and/or any of the reagents and device(s) to perform such tests. The kit can also optionally include an additional therapeutic agent (e.g., a nucleic acid comprising a nucleotide sequence that encodes PARN or PAPD5).

EXAMPLES

The disclosure further describes the following examples, which do not limit the scope of the invention.

Example 1. Compound Screening

Recombinant PAPD5 as well as catalytically inactive mutant PAPD5 (D189A, D191A) were purified for in vitro assays and high-throughput screening (HTS).

Figure 7:
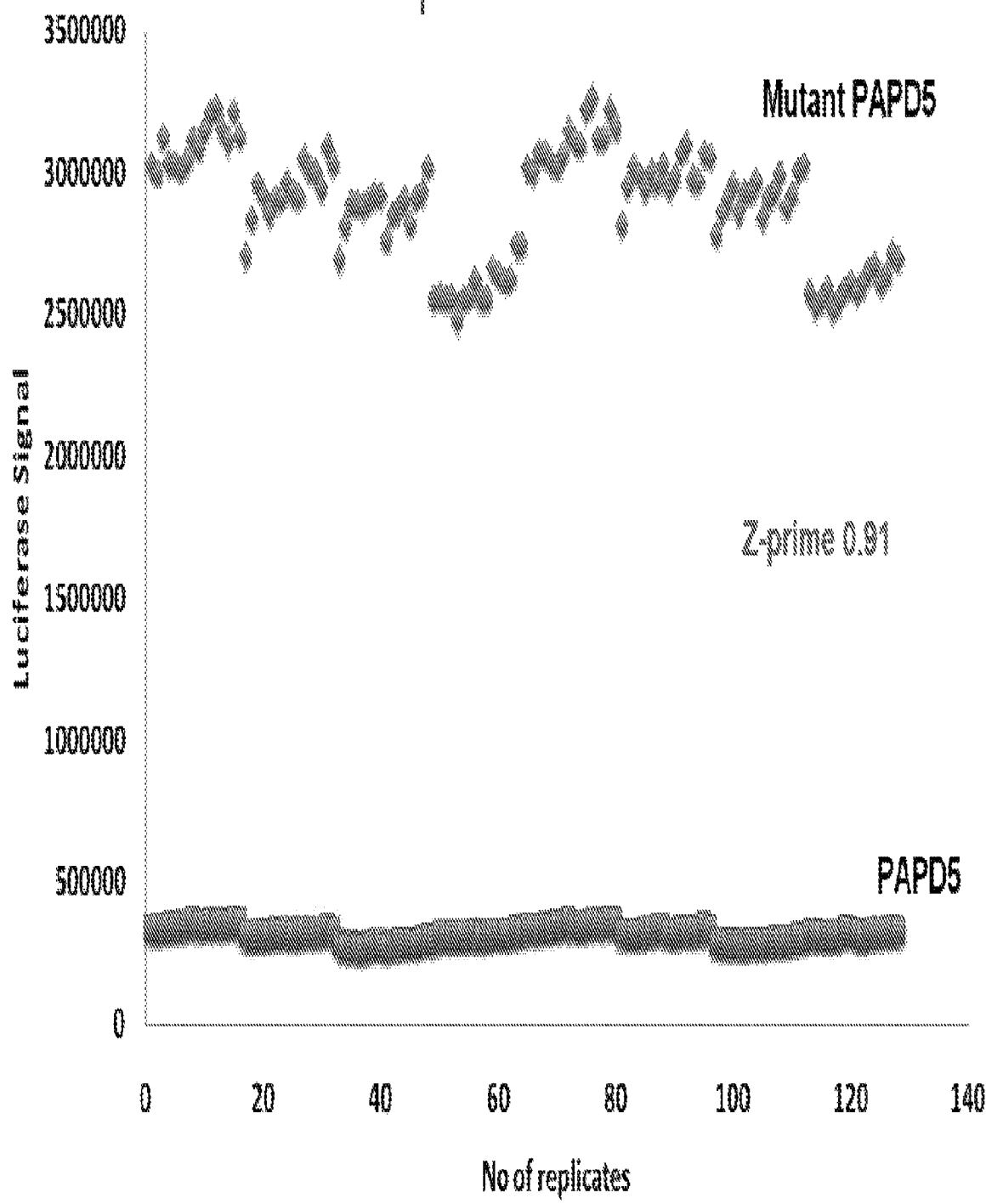
FIG. 7 is a graph showing Z-score for high-throughput screening for PAPD5 inhibitors.

Optimal conditions for an in vitro RNA polyadenylation assay using recombinant PAPD5, ATP and an oligonucleotide substrate were identified. The HTS assay involved ATP utilization by PAPD5, which reads out as a decreased luminescence signal produced by luciferase (KinaseGlo, Promega, Madison, WI). The Z-primefactor of 0.9 indicated a very robust screen (FIG. 7).

0.25 ul of PAPD5 in a buffer composition at a concentration of 50 nM was added to each well of a Corning 384-well microtitre plate (Product #3820; non-binding surface; Corning Incorporated, Corning, NY) using a Thermo MultiDrop Combi (Thermo Fisher Scientific, Waltham, MA). For positive control (typically wells A24: P24), 0.5 ul of mutant PAPD5 was added at a concentration of 50 nM.

100 nl of compound dissolved in DMSO was transferred to each well of the assay plate via pin transfer. For negative control wells, DMSO alone was added. Plates were gently vortexed for 5 seconds, then incubated for 2 hours at room temperature.

Figures 6A, 6B:
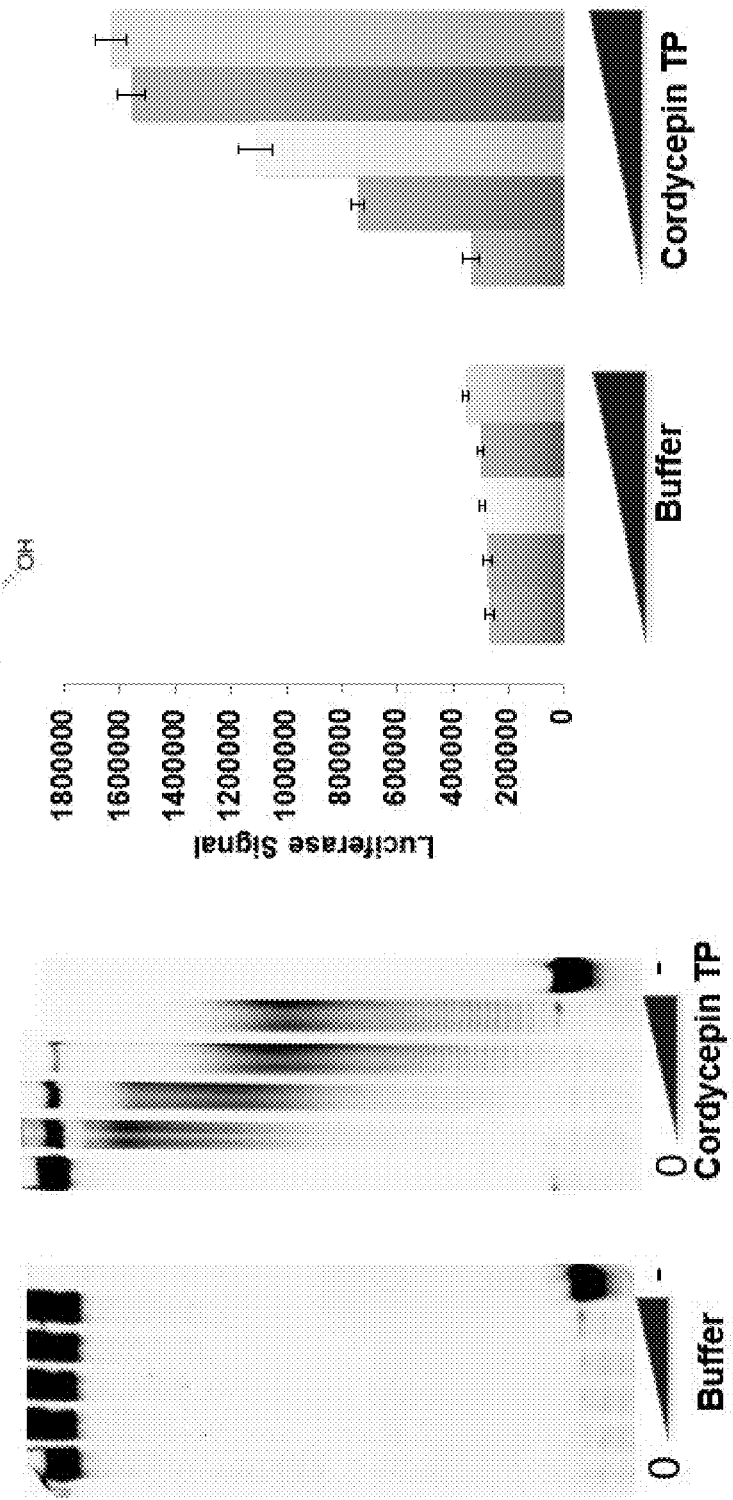
FIG. 6A shows screen validation results using chain terminator cordycepin triphosphate.
FIG. 6B is a graph showing luciferase signal for buffer and cordycepin triphosphate (cordycepin TP) at different concentrations.

After 2 hours, 5 ul of luciferase (Promega KinaseGlo, Madison, WI) was added using a MultiDrop Combi (Thermo Fisher Scientific, Waltham, MA). The mixture was gently vortexed for 5 seconds and incubated for 10 minutes at room temperature. Plates were spun for 1 minute prior to luminescent measurements. Luminescent measurements were quantitated using a PerkinElmer EnVision™ plate reader. The screening method was also validated using chain terminator cordycepin triphosphate (FIGS. 6A-6B).

~100,000 compounds from various libraries at the ICCB-Longwood were screened in this manner in duplicate. A Z-score was calculated for those luminescence that were significantly higher than the control wells (higher luminescence was obtained with inhibitors).

The fold-change for 100 μM compound and 33 μM compound were calculated. The fold change was the ratio of luminescence from a sample with inhibitor compared to that with DMSO. Thus, a higher number indicates higher inhibition.

308 compound that can inhibit PAPD5 were identified. These compounds were organized by the structure similarity. Compounds with similar chemical structures were placed in the same cluster. These 308 compounds were shown in FIG. 9. The cluster number for each compound is also shown in FIG. 9. Among these clusters, there are 73 compounds in Cluster 5, and member molecules of cluster 5 provide the highest inhibition rate in the screening assay. Five other clusters also have a large number of compounds. These clusters (I-Including Cluster 5) are shown in FIG. 10.

Among these 308 compounds, 72 compounds have better inhibition rates. These compounds are shown in FIG. 11. Particularly, 1-(1,3-benzodioxol-5-ylmethyl)-5-oxopyrrolidine-3-carboxylic acid (PubChem Compound Identifier (or PubChem_CID; CID): 2742111) had a fold change of 3.9 at 100 μM concentration, and N-allyl-5-oxo-1-thioxo-4,5-dihydro[1,3]dioxolo[4,5-g][1,3]thiazolo[3,4-a]quinazoline-3-carboxamide (CID: 50761931) had a fold change of 3.1 at 100 μM concentration in the assay.

Example 2. Dose-Response Validation of Hits Using the Initial Screening Platform Hits are selected and assayed using the original luminescence-based assay in a 384-well format in duplicate using concentrations ranging over a 4-log range (10 nM to 100 μM). A specificity screen is performed simultaneously using recombinant canonical yeast poly(A) polymerase (Thermo Fisher, Waltham, MA). The candidate small molecules that can inhibit PAPD5 specifically (I-Vs. yeast poly(A) polymerase) and at lower doses (≤1 µM) are prioritized. Lead compound classes are identified based on chemical structures.

Figure 5:
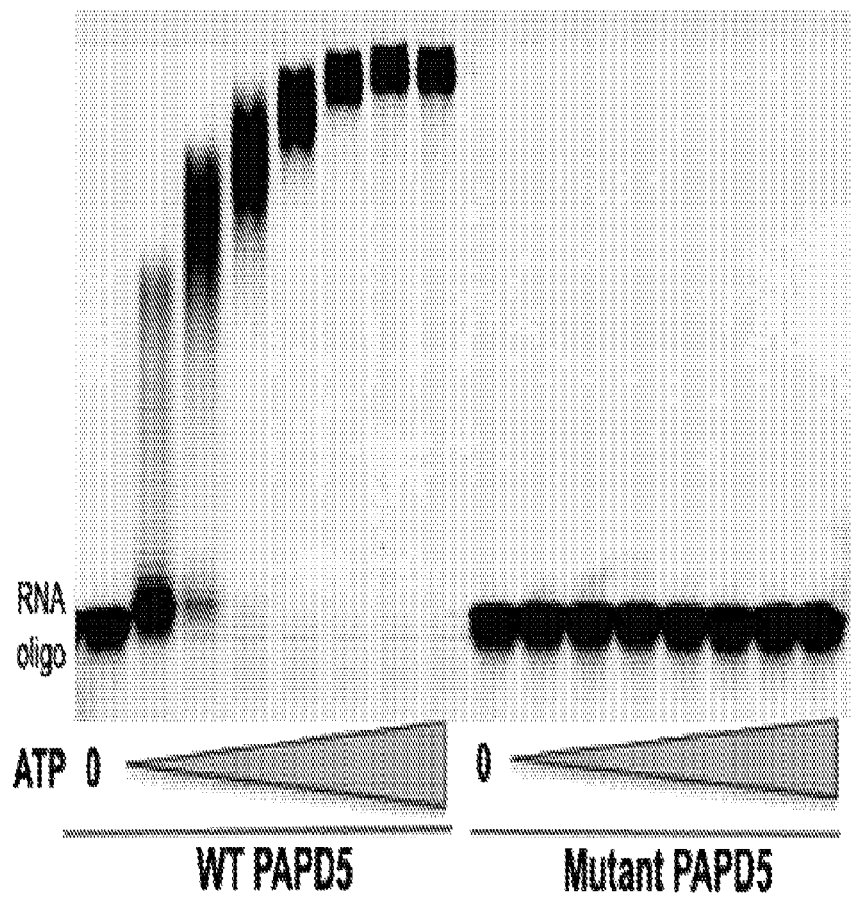
FIG. 5 shows the results of PAPD5 oligonucleotide adenylation assay with wildtype PAPD5, and mutant PAPD5.
Figure 8:
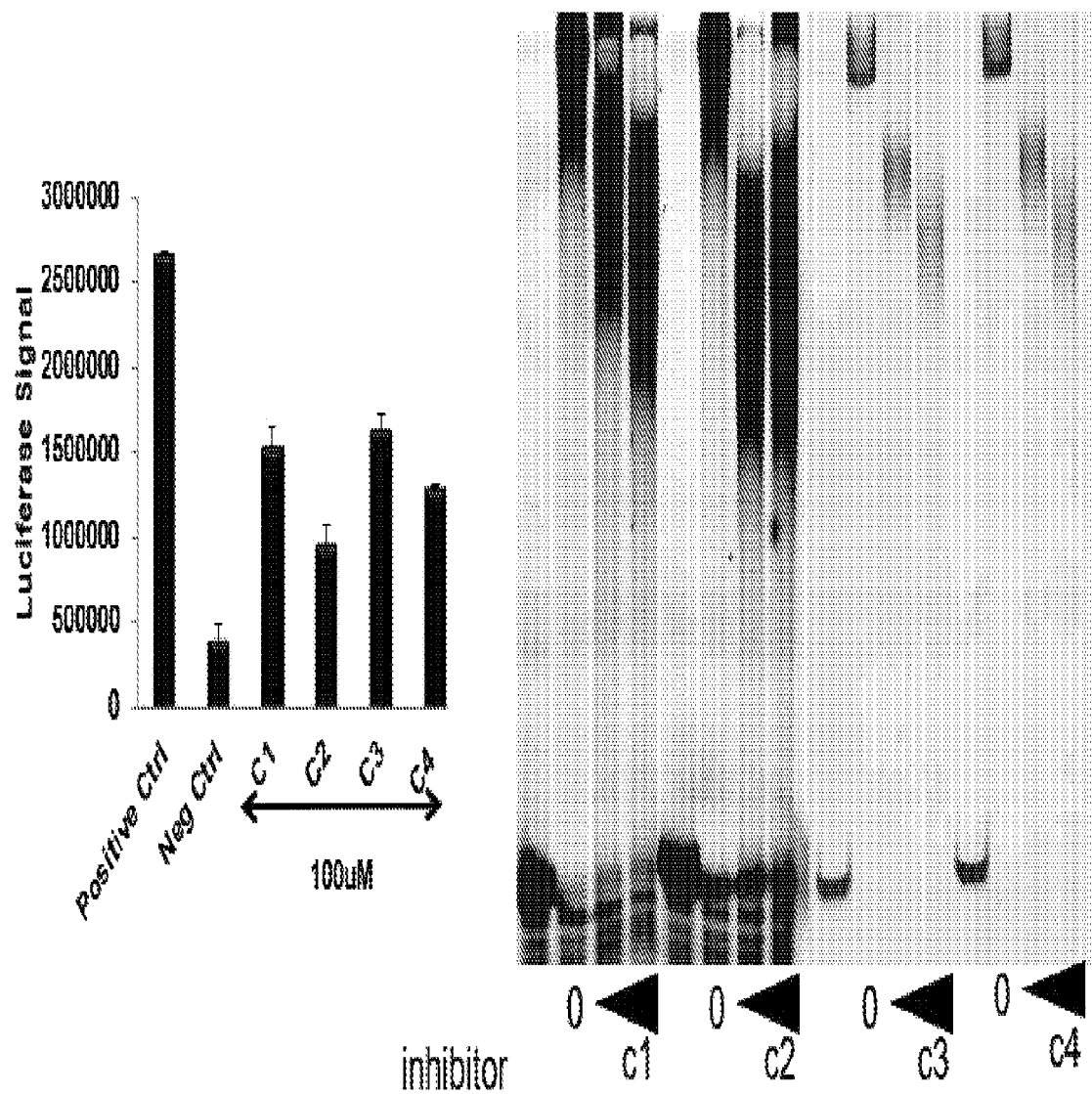
FIG. 8 shows hit validation results using oligo-extension assay.

Example 3. Validation, Dose-Response, and IC50 Determination of Lead Compounds Using Oligonucleotide Extension Assays Candidate inhibitors are assayed at a range of concentrations in functional assays entailing extension of fluorescently-labelled RNA oligonucleotide substrates in the presence of PAPD5, followed by gel electrophoresis. FIG. 5 shows that mutant PAPD5 cannot polyadenylate RNA oligonucleotides. In FIG. 5, a 20-mer 5'-fluorescently labelled RNA oligonucleotide was incubated with recombinant WT or mutant PAPD5 for 1 hour in the presence of varying concentrations of ATP, and products were visualized by polyacrylamide gel electrophoresis. It is expected that wild-type (WT) PAPD5 with PAPD5 inhibitors can have similar results. In fact, 4 compounds were selected to test the validation assay. The results were shown in FIG. 8, and were consistent with the expected results.

Furthermore, using varying substrates, substrate concentrations and reaction times along with appropriate controls, the $IC_{50}$ of each molecule with PAPD5 inhibitory function can be determined in this assay.

Example 4. Specificity—Canonical and Non-Canonical Poly-Nucleotide-Polymerases

The specificity of the selected compounds for PAPD5 can be determined by testing their capacity to inhibit other canonical and non-canonical poly-nucleotide polymerases (ncPAPs). Canonical poly(A) polymerases include PAP, PAP-alpha and PAP-gamma from humans and various species. These are purified. Another poly-nucleotide polymerase is poly(U) polymerases from various species. These are purified. The following recombinant ncPAPs: PAPD1, PAPD2, PAPD3, PAPD4, PAPD6, and PAPD7 are also purified. These recombinant ncPAPs are the 6 ncPAPs other than PAPD5 in humans known to use ATP or other nucleotide triphosphates as a substrate (Schmidt, M. J. & Norbury, C. J. Polyadenylation and beyond: emerging roles for non-canonical poly(A) polymerases. Wiley Interdiscip Rev RNA 1, 142-51 (2010)).

His-tagged constructs encoding codon-optimized versions of these polymerases for expression in *E. Coli* are generated. The activity of each canonical or ncPAP is characterized using oligonucleotide-based extension assays. The candidate small molecules are tested for their capacity to inhibit canonical or ncPAP activity at various concentrations, in comparison to PAPD5. Molecules that inhibit PAPD5 specifically are selected for further evaluation based on in vitro PAPD5 inhibitory function, $IC_{50}$, and specificity.

Example 5. Effects of PAPD5 Inhibitors on TERC Levels and Telomere Biology

PARN-mutant patient iPSCs are used to determine the effect of candidate compounds on (1) TERC RNA processing and (2) telomere length at various concentrations and after various periods of exposure.

iPSCs are exposed to either DMSO (control) or the candidate small molecules at three concentrations each (e.g. 10 nM, 100 nM, 1 µM). Patient iPSCs are cultured in the presence of inhibitors, and total RNA are isolated from a fraction of these cells at day 7 post-exposure. 3' RNA-ligation mediated rapid amplification of cDNA ends (3' RACE) of the TERC RNA transcript are performed to determine whether TERC RNA processing is restored to the mature form found in WT cells. Cells exposed to compounds that show restored TERC RNA 3' processing are continued to be cultured in the presence of these compounds. DNA is collected serially and analyzed for telomere length changes in the culture after 3-4 weeks. This time point is sufficient to observe telomere elongation using genetic inhibitors of PAPD5 in patient iPSCs.

Example 6. Cytotoxicity and Cell Growth

Cell population doubling and cell viability are tracked and documented for iPSC cultures treated with candidate molecules. For compounds causing increased cell death and/or slower growth, flow cytometry based cell cycle analyses and apoptosis assays are performed to determine the reasons of cytotoxicity.

Example 7. Transcriptional Analysis

RNA-Seq is performed in iPSCs treated with selected compounds. Comparison is made to normal control cells as well as patient iPSCs with and without PAPD5 disruption by RNA interference and CRISPR/Cas9.

Example 8-Inhibition of Recombinant PAPD5

The assay is described in Example 1. The assay results for tested compounds are shown in Table 2.

TABLE 2

Fold-change for tested compounds

| Entry No. | Fold-change determined at compound concentration | | | | |
|---|---|---|---|---|---|
| | 100 µM | 33 µM | 10 µM | 3.3 µM | 1 µM |
| 1 | 1.495296753 | 1.041881299 | n/a | n/a | n/a |
| 2 | 1.715710723 | 1.305289408 | n/a | n/a | n/a |
| 3 | 1.601784652 | 1.213920286 | n/a | n/a | n/a |
| 4 | 1.261110322 | 1.123810876 | n/a | n/a | n/a |
| 5 | 3.906301012 | 3.574600065 | 2.297529655 | 1.429208837 | 1.272608554 |
| 6 | 1.689486893 | 1.189347462 | n/a | n/a | n/a |
| 7 | 1.493129981 | 1.131079967 | n/a | n/a | n/a |
| 8 | 1.881468531 | 1.273776224 | n/a | n/a | n/a |
| 9 | 3.116755793 | 1.814282531 | 1.288101604 | n/a | n/a |
| 10 | 1.583986562 | 1.16531355 | n/a | n/a | n/a |
| 11 | 1.257419595 | 1.064448032 | n/a | n/a | n/a |

The compound names and structures for assay Entries 1-11 referenced in Table 2 are provided in Table 3.

TABLE 3

Chemical names and structures of tested compounds

| Entry No. | Structure | Chemical name |
|---|---|---|
| 1 | 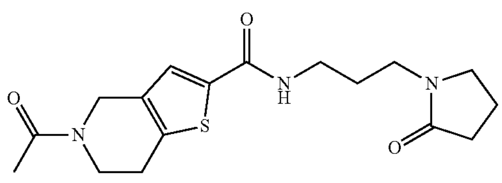 [SMILES: CC(=O)N1CCc2sc(C(=O)NCCCN3CCCC3=O)cc2C1] | 5-acetyl-N-[3-(2-oxopyrrolidin-1-yl)propyl]-6,7-dihydro-4H-thieno[3,2-c]pyridine-2-carboxamide |
| 2 | 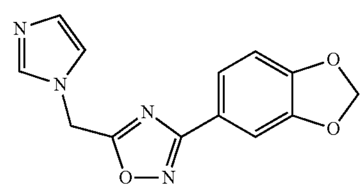 [SMILES: c1cn(Cc2nc(-c3ccc4c(c3)OCO4)no2)cn1] | 3-(1,3-benzodioxol-5-yl)-5-(I-Imidazol-1-ylmethyl)-1,2,4-oxadiazole |
| 3 | 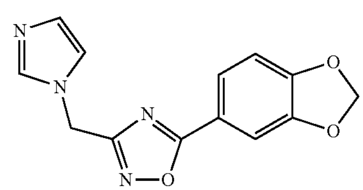 [SMILES: c1cn(Cc2noc(-c3ccc4c(c3)OCO4)n2)cn1] | 5-(1,3-benzodioxol-5-yl)-3-(1H-imidazol-1-ylmethyl)-1,2,4-oxadiazole |
| 4 | 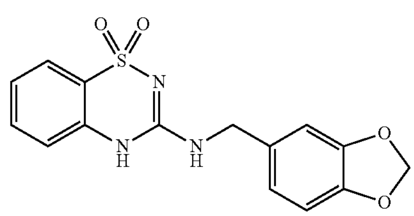 [SMILES: O=S1(=O)N=C(NCc2ccc3c(c2)OCO3)Nc2ccccc21] | 3-((benzo[d][1,3]dioxol-5-ylmethyl)amino)-4H-benzo[e][1,2,4]thiadiazine 1,1-dioxide |
| 5 | 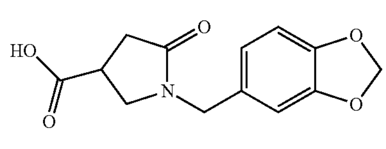 [SMILES: O=C(O)C1CC(=O)N(Cc2ccc3c(c2)OCO3)C1] | 1-(1,3-benzodioxol-5-ylmethyl)-5-oxopyrrolidine-3-carboxylic acid |
| 6 | 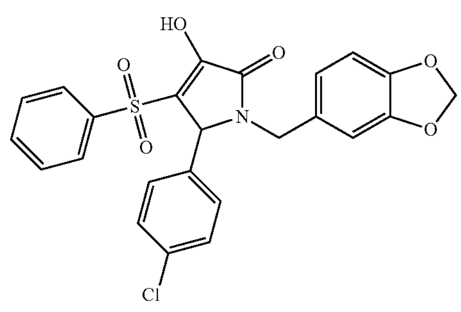 | 1-(1,3-benzodioxol-5-ylmethyl)-5-(4-chlorophenyl)-3-hydroxy-4-(phenylsulfonyl)-1,5-dihydro-2H-pyrrol-2-one |

TABLE 3-continued

Chemical names and structures of tested compounds

| Entry No. | Structure | Chemical name |
|---|---|---|
| 7 | 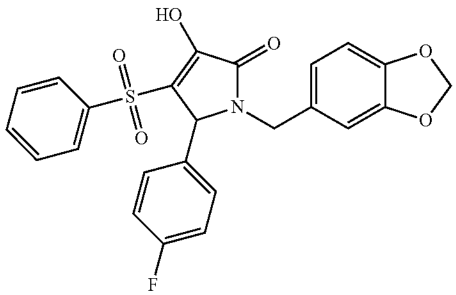 [SMILES: O=C1C(O)=C(S(=O)(=O)c2ccccc2)C(c2ccc(F)cc2)N1Cc1ccc2c(c1)OCO2] | 1-(1,3-benzodioxol-5-ylmethyl)-5-(4-fluorophenyl)-3-hydroxy-4-(phenylsulfonyl)-1,5-dihydro-2H-pyrrol-2-one |
| 8 | 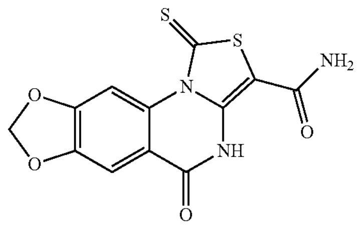 [SMILES: NC(=O)c1sc(=S)n2c1[nH]c(=O)c1cc3c(cc12)OCO3] | 5-oxo-1-thioxo-4,5-dihydro[1,3]dioxolo[4,5-g][1,3]thiazolo[3,4-a]quinazoline-3-carboxamide |
| 9 | 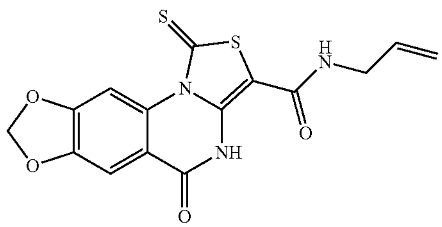 [SMILES: C=CCNC(=O)c1sc(=S)n2c1[nH]c(=O)c1cc3c(cc12)OCO3] | N-allyl-5-oxo-1-thioxo-4,5-dihydro[1,3]dioxolo[4,5-g][1,3]thiazolo[3,4-a]quinazoline-3-carboxamide |
| 10 | 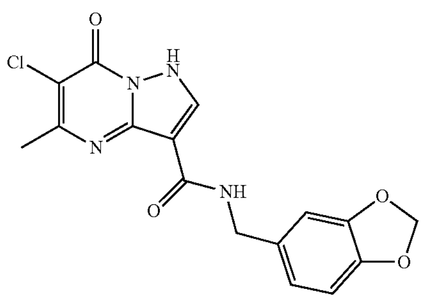 [SMILES: Cc1nc2c(C(=O)NCc3ccc4c(c3)OCO4)c[nH]n2c(=O)c1Cl] | N-(1,3-benzodioxol-5-ylmethyl)-6-chloro-5-methyl-7-oxo-1H-pyrazolo[1,5-a]pyrimidine-3-carboxamide |
| 11 | 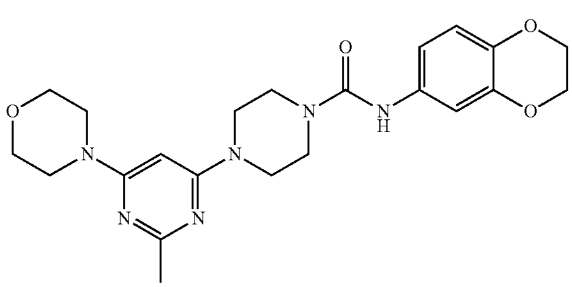 [SMILES: Cc1nc(N2CCOCC2)cc(N2CCN(C(=O)Nc3ccc4c(c3)OCCO4)CC2)n1] | N-(2,3-dihydro-1,4-benzodioxin-6-yl)-4-(2-methyl-6-morpholin-4-ylpyrimidin-4-yl)piperazine-1-carboxamide |

Example 9

Figure 12:
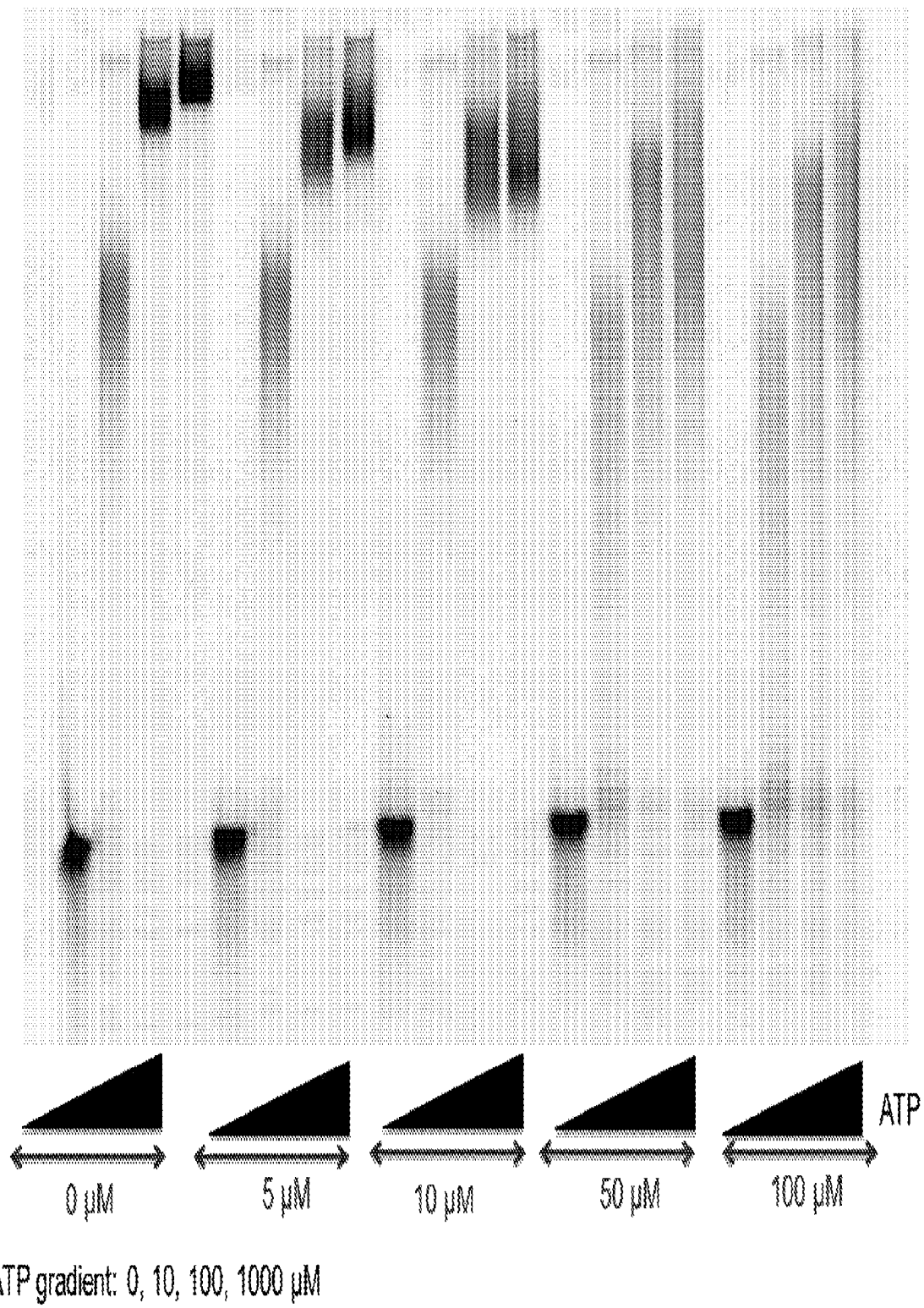
FIG. 12 shows the results of dose response of 5-oxo-1-thioxo-4,5-dihydro[1,3]dioxolo[4,5-g][1,3]thiazolo[3,4-a]quinazoline-3-carboxamide (Table 3, Entry 8)) vs ATP in the PAPD5 oligonucleotide extension assay.
Figure 13:
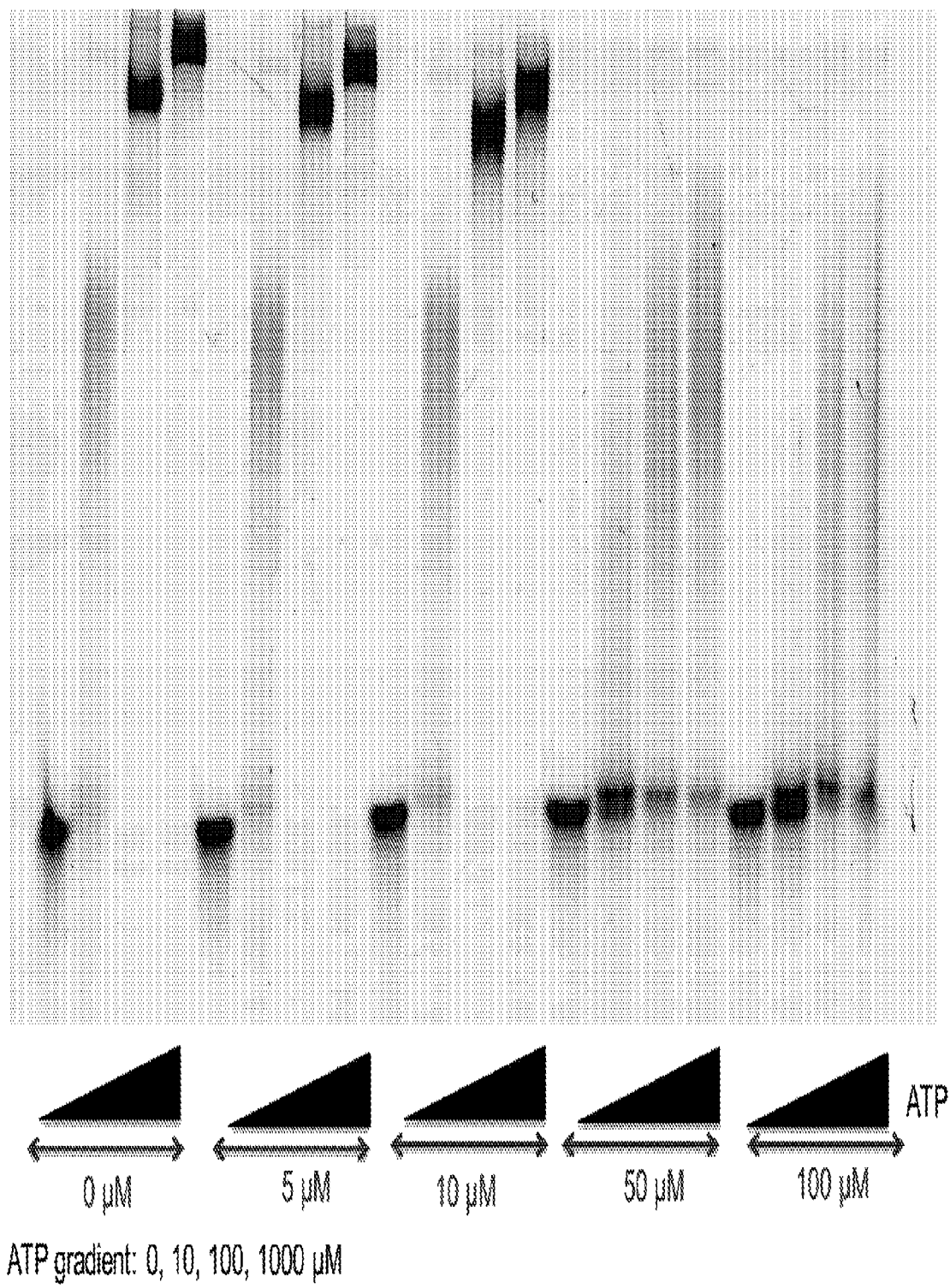
FIG. 13 shows the results of dose response of 1-(1,3-benzodioxol-5-ylmethyl)-5-oxopyrrolidine-3-carboxylic acid (Table 3, Entry 5)) vs ATP in the PAPD5 oligonucleotide extension assay.

FIGS. 12 and 13 show images of gels demonstrating results of dose response of compound corresponding to entry 8 in table 3 (FIG. 12) and compound corresponding to entry 5 in table 3 vs ATP in the PAPD5 oligonucleotide extension assay. Each compound tested in the assay was tested at 0 µM, 5 µM, 10 µM, 50 µM, and 100 µM. At each concentration, each compound was tested at 0 µM, 10 µM, 100 µM, and 1000 µM concentration of ATP. The assay shows that both compounds are active at less than 10 UM concentration.

Example 10—Inhibition of Recombinant PAPD5

Assay is described in Example 1. The assay results for tested compounds are shown in Table 4.

TABLE 4

Fold-change for tested compounds

| Entry No. | Fold-change determined at compound concentration | | | | |
|---|---|---|---|---|---|
| | 100 μM | 33 μM | 10 μM | 3.3 μM | 1 μM |
| 1 | 1.522690924 | 1.18952419 | | | |
| 2 | 1.843701052 | 1.312262251 | | | |
| 3 | n/a | | | | |
| 4 | n/a | | | | |
| 5 | n/a | | | | |
| 6 | n/a | | | | |
| 7 | n/a | | | | |
| 8 | n/a | | | | |
| 9 | n/a | | | | |
| 10 | n/a | | | | |
| 11 | n/a | | | | |
| 13 | n/a | | | | |
| 14 | n/a | | | | |
| 15 | n/a | | | | |
| 16 | n/a | | | | |
| 17 | n/a | | | | |
| 18 | n/a | | | | |
| 19 | n/a | | | | |
| 20 | n/a | | | | |
| 21 | n/a | | | | |
| 22 | n/a | | | | |
| 23 | n/a | | | | |
| 24 | n/a | | | | |
| 25 | n/a | | | | |
| 26 | n/a | | | | |
| 24 | n/a | | | | |
| 28 | n/a | | | | |
| 29 | 1.219709593 | 1.072720781 | | | |
| 30 | 1.943864048 | 1.312856944 | | | |
| 31 | 1.894758395 | 1.304122304 | | | |
| 32 | 1.236262122 | 1.114212949 | | | |
| 33 | 1.504928502 | 1.175343607 | | | |
| 34 | 1.211673493 | 1.097571679 | | | |
| 35 | 1.286616752 | 1.040126345 | | | |
| 36 | 1.239423707 | 1.096267191 | | | |
| 37 | 1.217868145 | 1.077017868 | | | |
| 38 | 1.631160365 | 1.207040417 | | | |
| 39 | 1.526574803 | 1.18996063 | | | |
| 40 | 2.955919395 | 1.588581024 | | | |
| 41 | 2.279095422 | 1.620932157 | 1.249034749 | | |
| 42 | 2.528399717 | 1.905373556 | 1.382394532 | | |
| 43 | 2.29386923 | 1.647589923 | 1.291539246 | | |
| 44 | 1.650896834 | 1.272661611 | | | |
| 45 | 1.935764117 | 1.428853495 | | | |
| 46 | 1.328151261 | 1.079096639 | | | |
| 47 | 1.392796333 | 1.09535036 | | | |
| 48 | 1.445334262 | 1.182799443 | | | |
| 49 | 1.318445122 | 1.104573171 | | | |
| 50 | 2.082561846 | 1.336469874 | | | |
| 51 | 1.824578652 | 1.241573034 | | | |
| 52 | 1.275356303 | 1.132696831 | | | |
| 53 | 1.807123656 | 1.307526882 | | | |
| 54 | 1.561583145 | 1.324308359 | | | |
| 55 | 1.591965088 | 1.262225645 | | | |
| 56 | 1.486795691 | 1.225855658 | | | |
| 57a | 1.574407375 | 1.099209833 | | | |
| 57 | 1.51783233 | 1.141848078 | | | |
| 58 | 1.363967243 | 1.075523203 | | | |
| 59 | 1.690454028 | 1.11335195 | | | |
| 60a | 1.507473967 | 1.163755459 | | | |
| 60 | 1.620737327 | 1.088133641 | | | |
| 61 | 1.23531485 | 1.069666353 | | | |
| 62 | 1.410158014 | 1.297629797 | | | |
| 63 | 1.416836884 | 1.112780858 | | | |
| 64 | 1.272317403 | 1.099059642 | | | |
| 65 | 1.393692 | 1.230491 | | | |
| 66 | 1.229492 | 1.083442 | | | |
| 67 | 1.238349 | 1.122059 | | | |
| 68 | 1.388672 | 1.161978 | | | |
| 69 | 1.223429 | 1.115978 | | | |
| 70 | 1.20581 | 1.103352 | | | |
| 71 | 1.531089 | 1.172583 | | | |
| 72 | 1.255614 | 1.099424 | | | |
| 73 | 1.278014 | 1.093397 | | | |
| 74 | 1.87019 | 1.371734 | | | |
| 75 | 1.32361 | 1.110014 | | | |
| 76 | 1.423175 | 1.7195 | | | |
| 77 | 1.418801 | 1.142234 | | | |
| 78 | 1.259997 | 1.049756 | | | |
| 79 | 1.446868 | 1.163891 | | | |
| 80 | 1.550488 | 1.163854 | | | |
| 81 | 1.288105 | 1.107031 | | | |
| 82 | 1.305712 | 1.121764 | | | |
| 83 | 1.203291 | 1.041499 | | | |
| 84 | 1.567991 | 1.120331 | | | |
| 85 | 1.251997 | 1.061382 | | | |
| 86 | 1.23295 | 1.08482 | | | |
| 87 | 1.253103 | 1.096552 | | | |
| 88 | 1.27552 | 1.082066 | | | |
| 89 | 1.211104 | 1.098494 | | | |
| 90 | 1.252835 | 1.104653 | | | |
| 91 | 1.537087 | 1.196859 | | | |
| 92 | 1.477918 | 1.175362 | | | |
| 93 | 1.645138 | 1.243899 | | | |
| 94 | 1.925951 | 1.294013 | | | |
| 95 | 1.228249 | 1.156257 | | | |
| 96 | 1.229548 | 1.184066 | | | |
| 97 | 1.402791 | 1.17051 | | | |
| 98 | 2.764505 | 1.96967 | | | |
| 99 | 1.909932 | 1.232621 | | | |
| 100 | 2.29703 | 1.315084 | | | |
| 101 | 2.042252 | 1.264574 | | | |
| 102 | 1.267969 | 1.066411 | | | |
| 103 | 1.217624 | 1.039556 | | | |
| 104 | 1.234577 | 1.047688 | | | |
| 105 | 1.332555 | 1.159917 | | | |
| 106 | 1.521837 | 1.217525 | | | |
| 107 | 1.883463 | 1.318802 | | | |
| 108 | 1.547289 | 1.255738 | | | |
| 109 | 1.231293 | 1.07645 | | | |
| 110 | 1.298368 | 1.125527 | | | |
| 111 | 2.307912 | 1.779779 | | | |
| 112 | 1.930043 | 1.187173 | | | |
| 113 | 1.673929 | 1.201994 | | | |
| 114 | 1.341717 | 1.100012 | | | |
| 115 | 1.777372 | 1.315824 | | | |
| 116 | 2.138417 | 1.459342 | | | |
| 117 | 1.443523 | 1.176866 | | | |
| 118 | 1.615082 | 1.195242 | | | |
| 119 | 1.366256 | 1.318889 | | | |
| 120 | 1.381299 | 1.099929 | | | |
| 121 | 1.259581 | 1.118307 | | | |
| 122 | 1.377313 | 1.133789 | | | |
| 123 | 2.189496 | 1.528054 | 1.21091 | | |
| 124 | 1.858161 | 1.437102 | 1.241024 | | |
| 125 | 1.443566 | 1.147178 | | | |
| 126 | 1.301613 | 1.150202 | | | |
| 127 | 1.983501 | 1.397298 | | | |
| 128 | 1.957279 | 1.314446 | | | |
| 129 | 1.395046 | 1.152618 | | | |
| 130 | 1.212181 | 1.085586 | | | |
| 131 | 1.652518 | 1.195246 | | | |
| 132 | 1.774148 | 1.302866 | | | |
| 133 | 1.507853 | 1.185994 | | | |
| 134 | 1.298411 | 1.124477 | | | |
| 135 | 1.346526 | 1.190606 | | | |
| 136 | 1.303069 | 1.081546 | | | |
| 137 | 1.300907 | 1.119893 | | | |
| 138 | 1.316949 | 1.160827 | | | |
| 139 | 1.548912 | 1.272161 | | | |

TABLE 4-continued

Fold-change for tested compounds

Fold-change determined at compound concentration

| Entry No. | 100 μM | 33 μM | 10 μM | 3.3 μM | 1 μM |
|---|---|---|---|---|---|
| 140 | 1.91047 | 1.329161 | | | |
| 141 | 1.882132 | 1.30805 | | | |
| 142 | 1.558737 | 1.211429 | | | |
| 143 | 1.254937 | 1.116416 | | | |
| 144 | 1.464973 | 1.210803 | | | |
| 145 | 1.218103 | 1.100247 | | | |
| 146 | 1.216839 | 1.070162 | | | |
| 147 | 1.242531 | 1.117897 | | | |
| 148 | 1.214531 | 1.04979 | | | |
| 149 | 1.308884 | 1.183131 | | | |
| 150 | 1.577032 | 1.189802 | | | |
| 151 | 1.799112 | 1.311654 | | | |
| 152 | 1.460555 | 1.146159 | | | |
| 153 | 1.259337 | 1.07653 | | | |
| 154 | 1.281786 | 1.01302 | | | |
| 155 | 1.372059 | 1.096504 | | | |
| 156 | 1.515989 | 1.212256 | | | |
| 157 | 1.203309 | 1.059073 | | | |
| 158 | 1.364163 | 1.129557 | | | |
| 159 | 1.220463 | 1.119946 | | | |
| 160 | 1.239287 | 1.075427 | | | |
| 161 | 1.429203 | 1.128228 | | | |
| 162 | 1.431229 | 1.153488 | | | |
| 163 | 1.286753 | 1.109221 | | | |
| 164 | 1.293282 | 1.125969 | | | |
| 165 | 1.688501 | 1.224468 | | | |
| 166 | 1.320731 | 1.12799 | | | |
| 167 | 1.995492 | 1.413153 | | | |
| 168 | 1.677827 | 1.452236 | | | |
| 169 | 1.878519 | 1.454654 | | | |
| 170 | 1.815969 | 1.301889 | | | |
| 171 | 1.776939 | 1.373647 | | | |
| 172 | 1.61646 | 1.295965 | | | |
| 173 | 1.657447 | 1.189909 | | | |
| 174 | 1.869626 | 1.277946 | | | |
| 175 | 1.352438 | 1.094462 | | | |
| 176 | 1.563323 | 1.151217 | | | |
| 177 | 1.39984 | 1.053029 | | | |
| 178 | 1.632607 | 1.217199 | | | |
| 179 | 1.309497 | 1.111627 | | | |
| 180 | 1.736004 | 1.302919 | | | |
| 181 | 1.272187 | 1.124411 | | | |
| 182 | 1.349773 | 1.1781 | | | |
| 183 | 1.346496 | 1.151985 | | | |
| 184 | 1.293726 | 1.24501 | | | |
| 185 | 1.234589 | 1.135406 | | | |
| 186 | 1.530993 | 1.162933 | | | |
| 187 | 1.262084 | 1.108056 | | | |
| 188 | 1.28959 | 1.08904 | | | |
| 189 | 1.311176 | 1.206317 | | | |
| 190 | 1.481923 | 1.308777 | 1.213584 | | |
| 191 | 1.295707 | 1.225043 | | | |
| 192 | 1.418605 | 1.10562 | | | |
| 193 | 1.446162 | 1.134117 | | | |
| 194 | 1.612577 | 1.322617 | | | |
| 195 | 1.228257 | 1.071724 | | | |
| 196 | 1.325547 | 1.090024 | | | |
| 197 | 1.41232 | 1.14185 | | | |
| 198 | 1.264242 | 1.084213 | | | |
| 199 | 1.606936 | 1.199122 | | | |
| 200 | 1.414209 | 1.037992 | | | |
| 201 | 1.286229 | 1.143955 | | | |
| 202 | 1.360859 | 1.163914 | | | |
| 203 | 1.310419 | 1.106483 | | | |
| 204 | 1.228805 | 1.073417 | | | |
| 205 | 2.054833 | 1.231935 | | | |
| 206 | 1.22453 | 1.079663 | | | |
| 207 | 1.200492 | 1.118035 | | | |
| 208 | 1.492075 | 1.211183 | | | |
| 209 | 1.274235 | 1.09303 | | | |
| 210 | 1.310585 | 1.136488 | | | |
| 211 | 1.217116 | 1.064713 | | | |
| 212 | 1.798522 | 1.076527 | | | |
| 213 | 1.579276 | 1.198753 | | | |
| 214 | 1.212599 | 1.117578 | | | |
| 215 | 2.037364 | 1.073502 | | | |
| 216 | 1.238568 | 1.102924 | | | |
| 217 | 1.244542 | 1.113685 | | | |
| 218 | 1.304177 | 1.096194 | | | |
| 219 | 1.338519 | 1.08614 | | | |
| 220 | 1.277267 | 1.06809 | | | |
| 221 | 1.585382 | 1.084375 | | | |
| 222 | 1.204604 | 1.049757 | | | |
| 223 | 1.253921 | 1.207404 | | | |
| 224 | 1.369571 | 1.192929 | | | |
| 225 | 1.219098 | 1.17317 | | | |
| 226 | 1.227947 | 1.094988 | | | |
| 227 | 1.425419 | 1.096581 | | | |
| 228 | 1.299702 | 1.145794 | | | |
| 229 | 1.703923 | 1.249328 | | | |
| 230 | 1.527469 | 1.052936 | | | |
| 231 | 1.360029 | 1.068013 | | | |
| 232 | 1.341859 | 1.197994 | | | |
| 233 | 1.859314 | 1.256274 | | | |
| 234 | 1.647752 | 1.318661 | | | |
| 235 | 1.451675 | 1.176831 | | | |
| 236 | 1.749501 | 1.389997 | 1.272442 | | |
| 237 | 1.362323 | 1.166093 | | | |
| 238 | 1.23823 | 1.118869 | | | |
| 239 | 1.314492 | 1.124699 | | | |
| 240 | 1.20593 | 1.090973 | | | |
| 241 | 1.24867 | 1.099122 | | | |
| 242 | 1.282744 | 1.067873 | | | |
| 243 | 1.471166 | 1.323664 | | | |
| 244 | 2.571710898 | 1.736683606 | 1.320440429 | | |
| 245 | 1.637865311 | 1.236047307 | | | |

The compound names and structures for assay Entries 1-245 referenced in Table 4 are provided in Table 5.

TABLE 5

Chemical names and structures of tested compounds

| Entry No. | Structure | Chemical name |
|---|---|---|
| 1 | 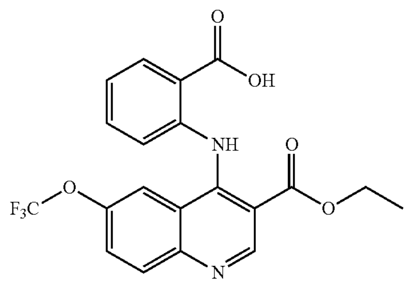 [SMILES: CCOC(=O)c1cnc2ccc(OC(F)(F)F)cc2c1Nc1ccccc1C(=O)O] | 2-[[3-ethoxycarbonyl-6-(trifluoromethoxy)quinolin-4-yl]amino]benzoic acid |
| 2 | 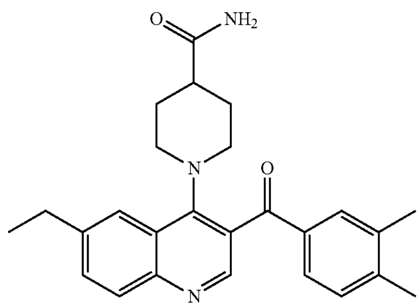 [SMILES: CCc1ccc2ncc(C(=O)c3ccc(C)c(C)c3)c(N3CCC(C(N)=O)CC3)c2c1] | 1-[3-(3,4-dimethylbenzoyl)-6-ethylquinolin-4-yl]piperidine-4-carboxamide |
| 3 | 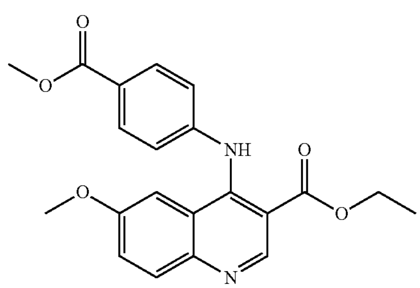 [SMILES: CCOC(=O)c1cnc2ccc(OC)cc2c1Nc1ccc(C(=O)OC)cc1] | ethyl 6-methoxy-4-{[4-(methoxycarbonyl)phenyl]amino}-3-quinolinecarboxylate |
| 4 | 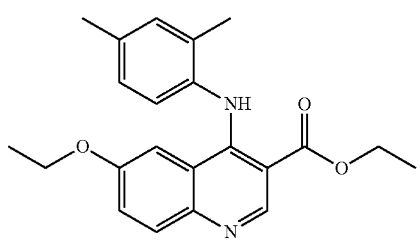 [SMILES: CCOC(=O)c1cnc2ccc(OCC)cc2c1Nc1ccc(C)cc1C] | ethyl 4-[(2,4-dimethylphenyl)amino]-6-ethoxy-3-quinolinecarboxylate |
| 5 | 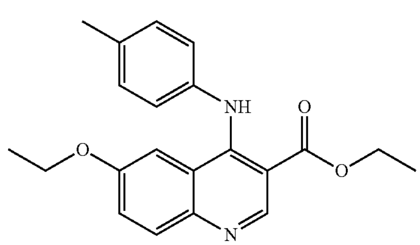 [SMILES: CCOC(=O)c1cnc2ccc(OCC)cc2c1Nc1ccc(C)cc1] | ethyl 6-ethoxy-4-[(4-methylphenyl)amino]-3-quinolinecarboxylate |

TABLE 5-continued

Chemical names and structures of tested compounds

| Entry No. | Structure | Chemical name |
|---|---|---|
| 6 | 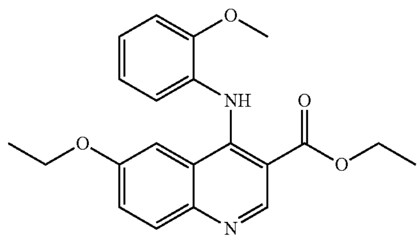 [SMILES: CCOC(=O)c1cnc2ccc(OCC)cc2c1Nc1ccccc1OC] | ethyl 6-ethoxy-4-[(2-methoxyphenyl)amino]-3-quinolinecarboxylate |
| 7 | 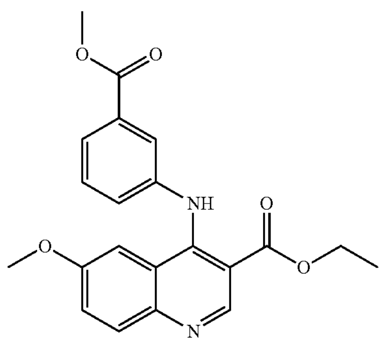 [SMILES: CCOC(=O)c1cnc2ccc(OC)cc2c1Nc1cccc(C(=O)OC)c1] | ethyl 6-methoxy-4-{[3-(methoxycarbonyl)phenyl]amino}-3-quinolinecarboxylate |
| 8 | 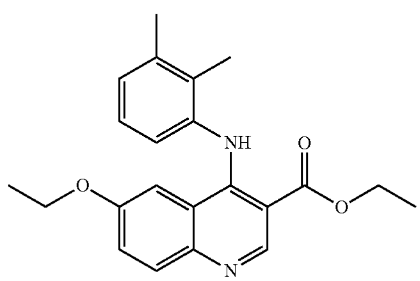 [SMILES: CCOC(=O)c1cnc2ccc(OCC)cc2c1Nc1cccc(C)c1C] | ethyl 4-[(2,3-dimethylphenyl)amino]-6-ethoxy-3-quinolinecarboxylate |
| 9 | 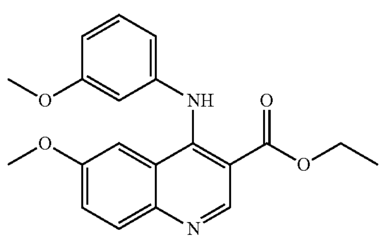 [SMILES: CCOC(=O)c1cnc2ccc(OC)cc2c1Nc1cccc(OC)c1] | ethyl 6-methoxy-4-[(3-methoxyphenyl)amino]-3-quinolinecarboxylate |
| 10 | 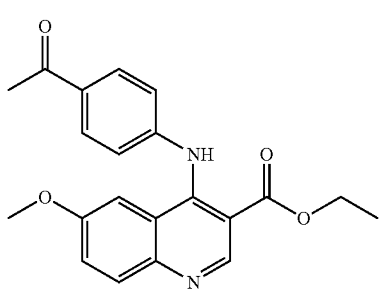 [SMILES: CCOC(=O)c1cnc2ccc(OC)cc2c1Nc1ccc(C(C)=O)cc1] | ethyl 4-[(4-acetylphenyl)amino]-6-methoxy-3-quinolinecarboxylate |

TABLE 5-continued

Chemical names and structures of tested compounds

| Entry No. | Structure | Chemical name |
|---|---|---|
| 11 | 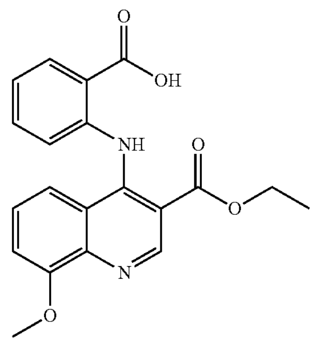 [SMILES: CCOC(=O)c1cnc2c(OC)cccc2c1Nc1ccccc1C(=O)O] | 2-{[3-(ethoxycarbonyl)-8-methoxyquinolin-4-yl]amino}benzoic acid |
| 12 | 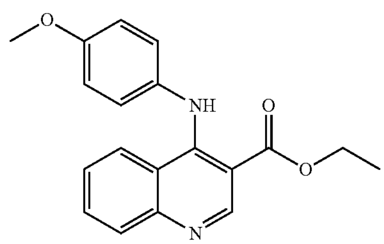 [SMILES: CCOC(=O)c1cnc2ccccc2c1Nc1ccc(OC)cc1] | ethyl 4-[(4-methoxyphenyl)amino]-3-quinolinecarboxylate |
| 13 | 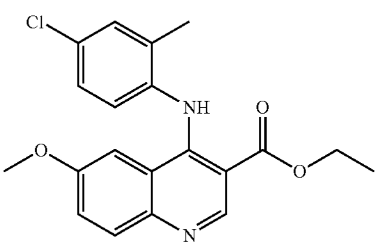 [SMILES: CCOC(=O)c1cnc2ccc(OC)cc2c1Nc1ccc(Cl)cc1C] | ethyl 4-[(4-chloro-2-methylphenyl)amino]-6-methoxy-3-quinolinecarboxylate |
| 14 | 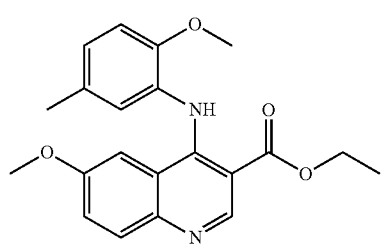 [SMILES: CCOC(=O)c1cnc2ccc(OC)cc2c1Nc1cc(C)ccc1OC] | ethyl 6-methoxy-4-[(2-methoxy-5-methylphenyl)amino]-3-quinolinecarboxylate |
| 15 | 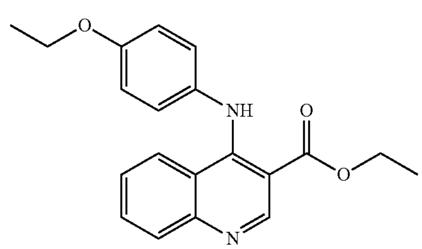 [SMILES: CCOC(=O)c1cnc2ccccc2c1Nc1ccc(OCC)cc1] | ethyl 4-[(4-ethoxyphenyl)amino]-3-quinolinecarboxylate |

TABLE 5-continued

Chemical names and structures of tested compounds

| Entry No. | Structure | Chemical name |
|---|---|---|
| 16 | 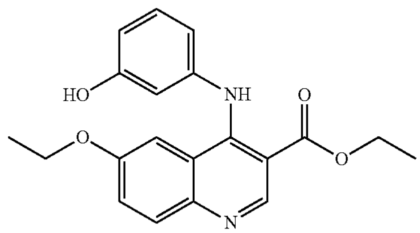 [SMILES: CCOC(=O)c1cnc2ccc(OCC)cc2c1Nc1cccc(O)c1] | ethyl 6-ethoxy-4-[(3-hydroxyphenyl)amino]-3-quinolinecarboxylate |
| 17 | 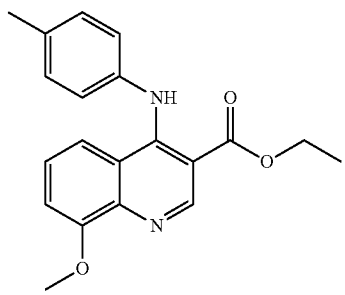 [SMILES: CCOC(=O)c1cnc2c(OC)cccc2c1Nc1ccc(C)cc1] | ethyl 8-methoxy-4-[(4-methylphenyl)amino]-3-quinolinecarboxylate |
| 18 | 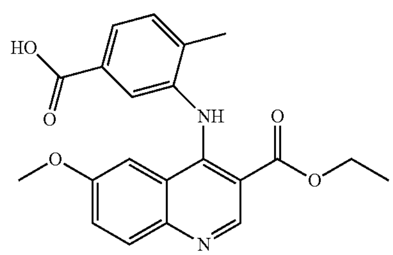 [SMILES: CCOC(=O)c1cnc2ccc(OC)cc2c1Nc1cc(C(=O)O)ccc1C] | 3-{[3-(ethoxycarbonyl)-6-methoxy-4-quinolinyl]amino}-4-methylbenzoic acid |
| 19 | 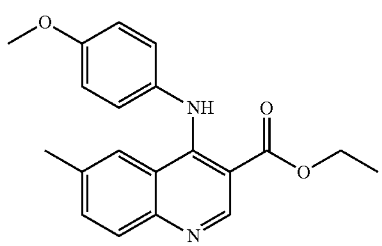 [SMILES: CCOC(=O)c1cnc2ccc(C)cc2c1Nc1ccc(OC)cc1] | ethyl 4-[(4-methoxyphenyl)amino]-6-methyl-3-quinolinecarboxylate |
| 20 | 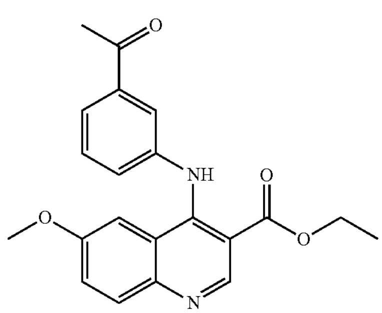 [SMILES: CCOC(=O)c1cnc2ccc(OC)cc2c1Nc1cccc(C(C)=O)c1] | ethyl 4-[(3-acetylphenyl)amino]-6-methoxy-3-quinolinecarboxylate |

TABLE 5-continued

Chemical names and structures of tested compounds

| Entry No. | Structure | Chemical name |
|---|---|---|
| 21 | 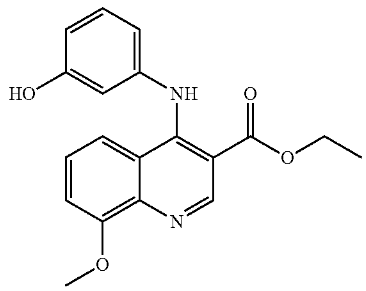 [SMILES: CCOC(=O)c1cnc2c(OC)cccc2c1Nc1cccc(O)c1] | ethyl 4-[(3-hydroxyphenyl)amino]-8-methoxy-3-quinolinecarboxylate |
| 22 | 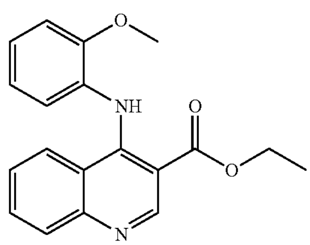 [SMILES: CCOC(=O)c1cnc2ccccc2c1Nc1ccccc1OC] | ethyl 4-[(2-methoxyphenyl)amino]-3-quinolinecarboxylate |
| 23 | 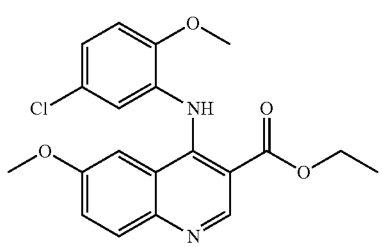 [SMILES: CCOC(=O)c1cnc2ccc(OC)cc2c1Nc1cc(Cl)ccc1OC] | ethyl 4-[(5-chloro-2-methoxyphenyl)amino]-6-methoxy-3-quinolinecarboxylate |
| 24 | 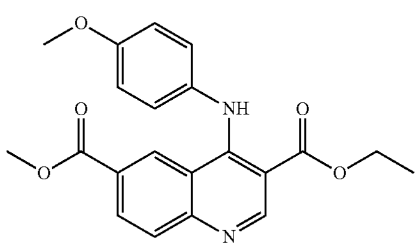 [SMILES: CCOC(=O)c1cnc2ccc(C(=O)OC)cc2c1Nc1ccc(OC)cc1] | 3-ethyl 6-methyl 4-[(4-methoxyphenyl)amino]-3,6-quinolinedicarboxylate |
| 25 | 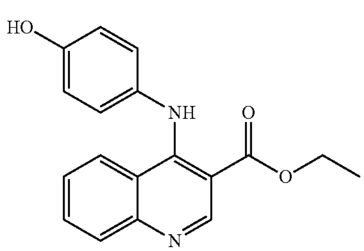 [SMILES: CCOC(=O)c1cnc2ccccc2c1Nc1ccc(O)cc1] | ethyl 4-[(4-hydroxyphenyl)amino]-3-quinolinecarboxylate |

TABLE 5-continued

Chemical names and structures of tested compounds

| Entry No. | Structure | Chemical name |
|---|---|---|
| 26 | 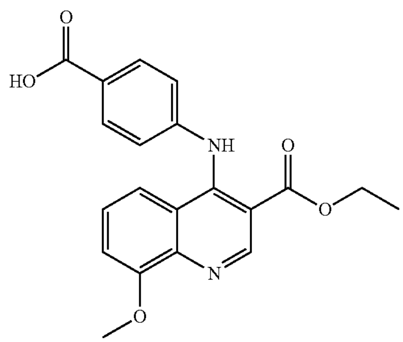 [SMILES: CCOC(=O)c1cnc2c(OC)cccc2c1Nc1ccc(C(=O)O)cc1] | 4-{[3-(ethoxycarbonyl)-8-methoxy-4-quinolinyl]amino}benzoic acid |
| 27 | 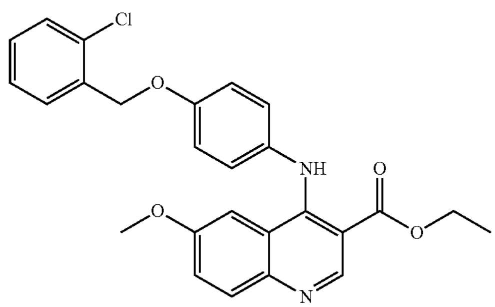 [SMILES: CCOC(=O)c1cnc2ccc(OC)cc2c1Nc1ccc(OCc2ccccc2Cl)cc1] | ethyl 4-({4-[(2-chlorobenzyl)oxy]phenyl}amino)-6-methoxy-3-quinolinecarboxylate |
| 28 | 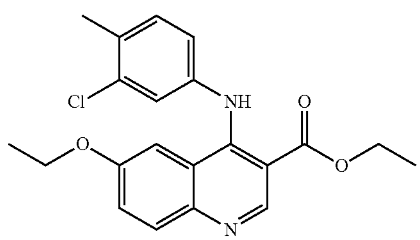 [SMILES: CCOC(=O)c1cnc2ccc(OCC)cc2c1Nc1ccc(C)c(Cl)c1] | ethyl 4-[(3-chloro-4-methylphenyl)amino]-6-ethoxy-3-quinolinecarboxylate |
| 29 | 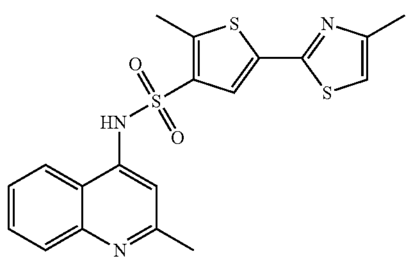 [SMILES: Cc1csc(-c2cc(S(=O)(=O)Nc3cc(C)nc4ccccc34)c(C)s2)n1] | 2-methyl-N-(2-methylquinolin-4-yl)-5-(4-methyl-1,3-thiazol-2-yl)thiophene-3-sulfonamide |
| 30 | 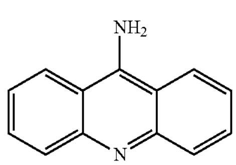 [SMILES: Nc1c2ccccc2nc2ccccc12] | acridin-9-amine |
| 31 | 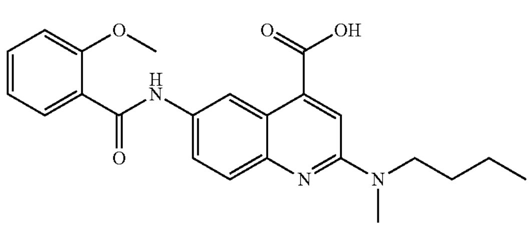 [SMILES: CCCCN(C)c1cc(C(=O)O)c2cc(NC(=O)c3ccccc3OC)ccc2n1] | 2-[butyl(methyl)amino]-6-[(2-methoxybenzoyl)amino]quinoline-4-carboxylic acid |

TABLE 5-continued

Chemical names and structures of tested compounds

| Entry No. | Structure | Chemical name |
|---|---|---|
| 32 | 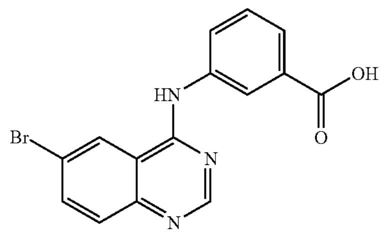 [SMILES: O=C(O)c1cccc(Nc2ncnc3ccc(Br)cc23)c1] | 3-[(6-bromoquinazolin-4-yl)amino]benzoic acid |
| 33 | 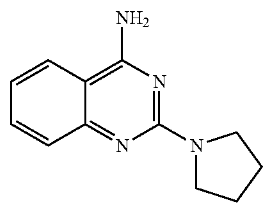 [SMILES: Nc1nc(N2CCCC2)nc2ccccc12] | 2-(1-pyrrolidinyl)-4-quinazolinamine |
| 34 | 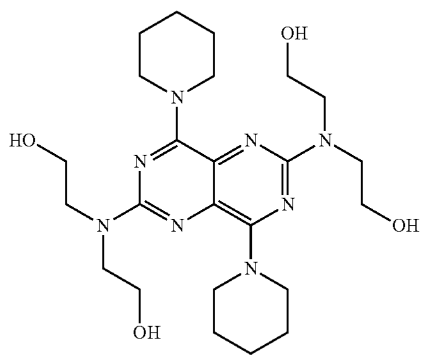 [SMILES: OCCN(CCO)c1nc(N2CCCCC2)c2nc(N(CCO)CCO)nc(N3CCCCC3)c2n1] | 2,2',2'',2'''-((4,8-Di(piperidin-1-yl)pyrimido[5,4-d]pyrimidine-2,6-diyl)bis(azanetriyl))tetraethanol |
| 35 | 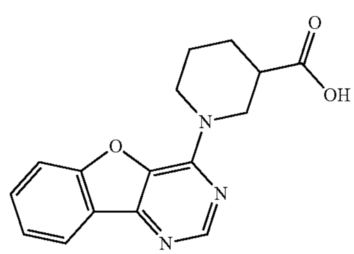 [SMILES: O=C(O)C1CCCN(c2ncnc3c2oc2ccccc23)C1] | 1-[1]benzofuro[3,2-d]pyrimidin-4-ylpiperidine-3-carboxylic acid |
| 36 | 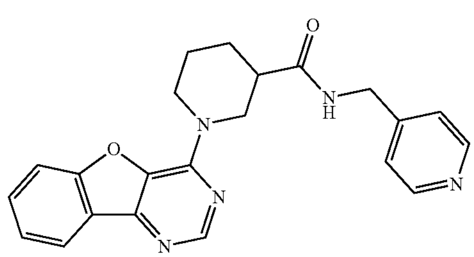 [SMILES: O=C(NCc1ccncc1)C1CCCN(c2ncnc3c2oc2ccccc23)C1] | 1-([1]benzofuro[3,2-d]pyrimidin-4-yl)-N-(pyridin-4-ylmethyl)piperidine-3-carboxamide |

TABLE 5-continued

Chemical names and structures of tested compounds

| Entry No. | Structure | Chemical name |
|---|---|---|
| 37 | 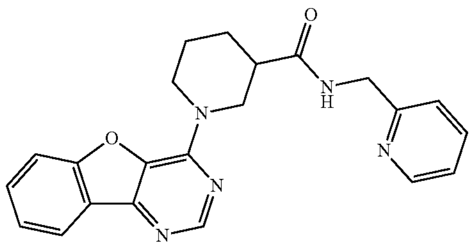 | 1-([1]benzofuro[3,2-d]pyrimidin-4-yl)-N-(pyridin-2-ylmethyl)piperidine-3-carboxamide |
| 38 | 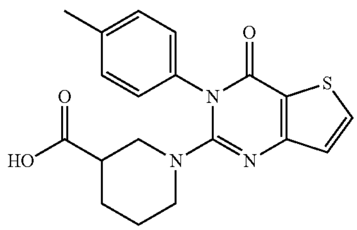 [SMILES: Cc1ccc(-n2c(N3CCCC(C(=O)O)C3)nc3ccsc3c2=O)cc1] | 1-[3-(4-methylphenyl)-4-oxo-3,4-dihydrothieno[3,2-d]pyrimidin-2-yl]piperidine-3-carboxylic acid |
| 39 | 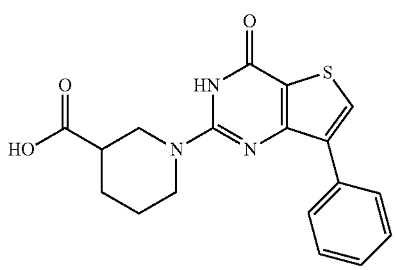 [SMILES: O=C(O)C1CCCN(c2nc3c(-c4ccccc4)csc3c(=O)[nH]2)C1] | 1-(4-oxo-7-phenyl-3,4-dihydrothieno[3,2-d]pyrimidin-2-yl)piperidine-3-carboxylic acid |
| 40 | 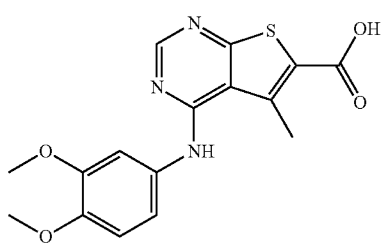 [SMILES: COc1ccc(Nc2ncnc3sc(C(=O)O)c(C)c23)cc1OC] | 4-(3,4-dimethoxyanilino)-5-methylthieno[2,3-d]pyrimidine-6-carboxylic acid |
| 41 | 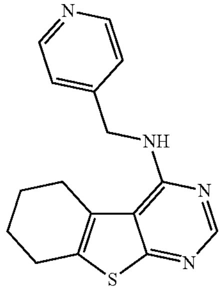 [SMILES: c1cc(CNc2ncnc3sc4c(c23)CCCC4)ccn1] | N-(pyridin-4-ylmethyl)-5,6,7,8-tetrahydro[1]benzothieno[2,3-d]pyrimidin-4-amine |

TABLE 5-continued

Chemical names and structures of tested compounds

| Entry No. | Structure | Chemical name |
|---|---|---|
| 42 | 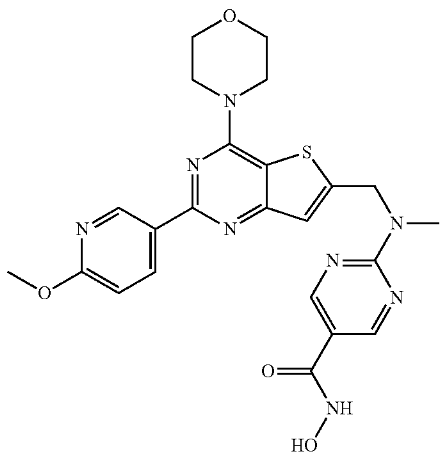 | N-hydroxy-2-[[2-(6-methoxypyridin-3-yl)-4-morpholin-4-ylthieno[3,2-d]pyrimidin-6-yl]methyl-methylamino]pyrimidine-5-carboxamide |
| 43 | 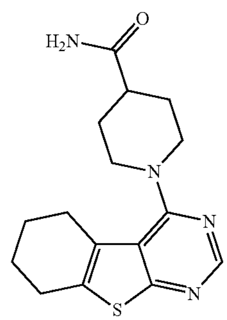 [SMILES: NC(=O)C1CCN(c2ncnc3sc4c(c23)CCCC4)CC1] | 1-(5,6,7,8-tetrahydro[1]benzothieno[2,3-d]pyrimidin-4-yl)piperidine-4-carboxamide |
| 44 | 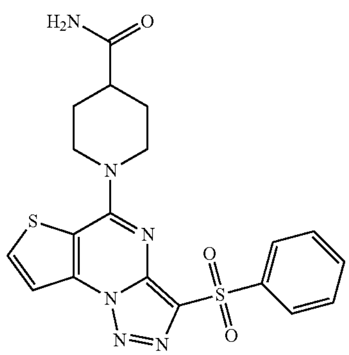 [SMILES: NC(=O)C1CCN(c2nc3c(S(=O)(=O)c4ccccc4)nnn3c3ccsc23)CC1] | 1-(3-(phenylsulfonyl)thieno[2,3-e][1,2,3]triazol[1,5-a]pyrimidin-5-yl)piperidine-4-carboxamide |
| 45 | 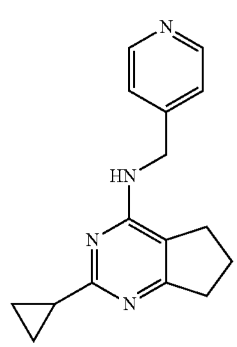 [SMILES: c1cc(CNc2nc(C3CC3)nc3c2CCC3)ccn1] | N-(2-cyclopropyl-6,7-dihydro-5H-cyclopenta[d]pyrimidin-4-yl)-N-(4-pyridylmethyl)amine |

TABLE 5-continued

Chemical names and structures of tested compounds

| Entry No. | Structure | Chemical name |
|---|---|---|
| 46 | 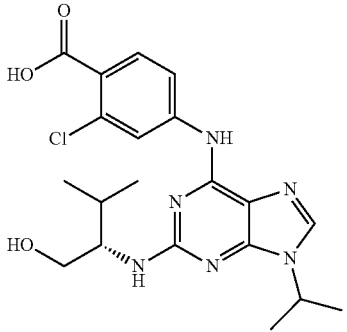 [SMILES: CC(C)[C@@H](CO)Nc1nc(Nc2ccc(C(=O)O)c(Cl)c2)c2ncn(C(C)C)c2n1] | 2-chloro-4-[[2-[[(2R)-1-hydroxy-3-methylbutan-2-yl]amino]-9-propan-2-ylpurin-6-yl]amino]benzoic acid |
| 47 | 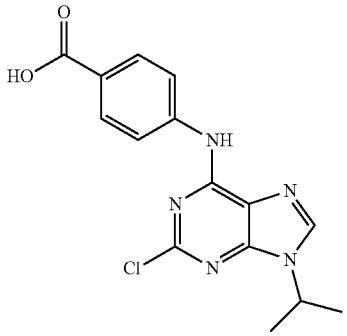 [SMILES: CC(C)n1cnc2c(Nc3ccc(C(=O)O)cc3)nc(Cl)nc21] | 4-[(2-chloro-9-propan-2-ylpurin-6-yl)amino]benzoic acid |
| 48 | 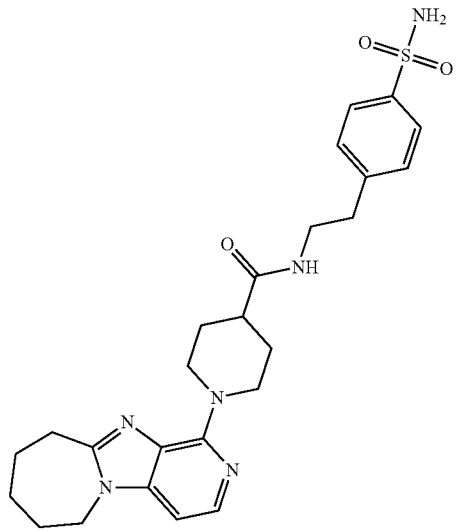 [SMILES: NS(=O)(=O)c1ccc(CCNC(=O)C2CCN(c3nccc4c3nc3n4CCCCC3)CC2)cc1] | N-[2-(4-sulfamoylphenyl)ethyl]-1-(7,8,9,10-tetrahydro-6H-purino[9,8-a]azepin-4-yl)piperidine-4-carboxamide |
| 49 | 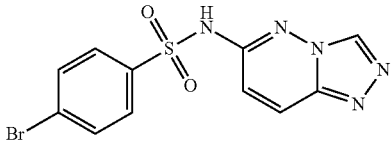 [SMILES: O=S(=O)(Nc1ccc2nncn2n1)c1ccc(Br)cc1] | 4-bromo-N-([1,2,4]triazolo[4,3-b]pyridazin-6-yl)benzenesulfonamide |
| 50 | 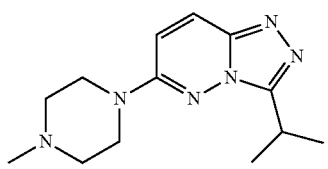 [SMILES: CC(C)c1nnc2ccc(N3CCN(C)CC3)nn12] | 3-isopropyl-6-(4-methylpiperazino)[1,2,4]triazolo[4,3-b]pyridazine |

TABLE 5-continued

Chemical names and structures of tested compounds

| Entry No. | Structure | Chemical name |
|---|---|---|
| 51 | 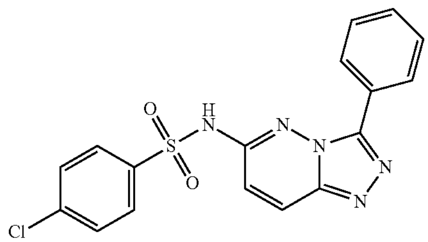 [SMILES: O=S(=O)(Nc1ccc2nnc(-c3ccccc3)n2n1)c1ccc(Cl)cc1] | 4-chloro-N-(3-phenyl-[1,2,4]triazolo[4,3-b]pyridazin-6-yl)benzenesulfonamide |
| 52 | 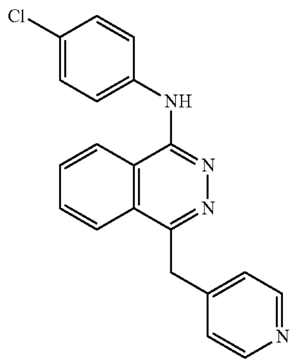 [SMILES: Clc1ccc(Nc2nnc(Cc3ccncc3)c3ccccc23)cc1] | N-(4-chlorophenyl)-4-(pyridin-4-ylmethyl)phthalazin-1-amine |
| 53 | 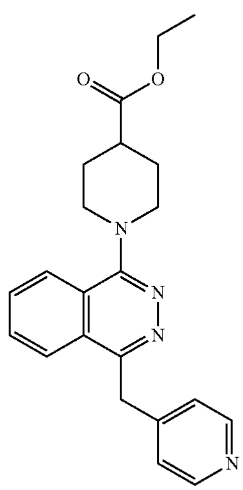 [SMILES: CCOC(=O)C1CCN(c2nnc(Cc3ccncc3)c3ccccc23)CC1] | Ethyl 1-[4-(pyridin-4-ylmethyl)phthalazin-1-yl]piperidine-4-carboxylate |
| 54 | 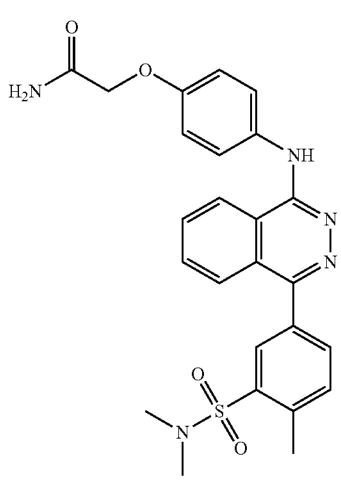 [SMILES: Cc1ccc(-c2nnc(Nc3ccc(OCC(N)=O)cc3)c3ccccc23)cc1S(=O)(=O)N(C)C] | 2-[4-({4-[3-(dimethylsulfamoyl)-4-methylphenyl]phthalazin-1-yl}amino)phenoxy]acetamide |

TABLE 5-continued

Chemical names and structures of tested compounds

| Entry No. | Structure | Chemical name |
|---|---|---|
| 55 | 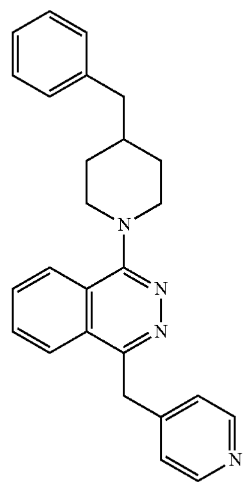 [SMILES: c1ccc(CC2CCN(c3nnc(Cc4ccncc4)c4ccccc34)CC2)cc1] | 1-(4-benzylpiperidin-1-yl)-4-(pyridin-4-ylmethyl)phthalazine |
| 56 | 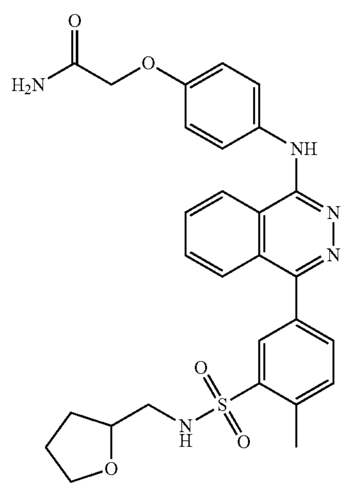 [SMILES: Cc1ccc(-c2nnc(Nc3ccc(OCC(N)=O)cc3)c3ccccc23)cc1S(=O)(=O)NCC1CCCO1] | 2-[4-[[4-[4-methyl-3-(oxolan-2-ylmethylsulfamoyl)phenyl]phthalazin-1-yl]amino]phenoxy]acetamide |
| 57a | 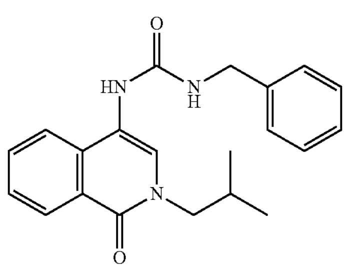 [SMILES: CC(C)Cn1cc(NC(=O)NCc2ccccc2)c2ccccc2c1=O] | 1-benzyl-3-[2-(2-methylpropyl)-1-oxoisoquinolin-4-yl]urea |
| 57 | 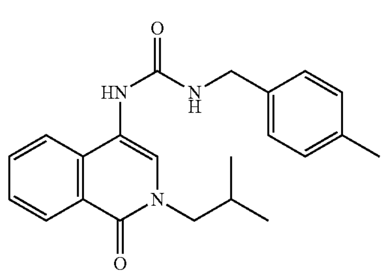 [SMILES: Cc1ccc(CNC(=O)Nc2cn(CC(C)C)c(=O)c3ccccc23)cc1] | 1-[(4-methylphenyl)methyl]-3-[2-(2-methylpropyl)-1-oxoisoquinolin-4-yl]urea |

TABLE 5-continued

Chemical names and structures of tested compounds

| Entry No. | Structure | Chemical name |
|---|---|---|
| 58 | 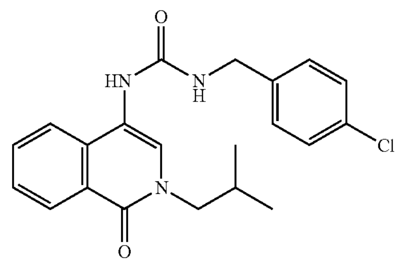 [SMILES: CC(C)Cn1cc(NC(=O)NCc2ccc(Cl)cc2)c2ccccc2c1=O] | 1-[(4-chlorophenyl)methyl]-3-[2-(2-methylpropyl)-1-oxoisoquinolin-4-yl]urea |
| 59 | 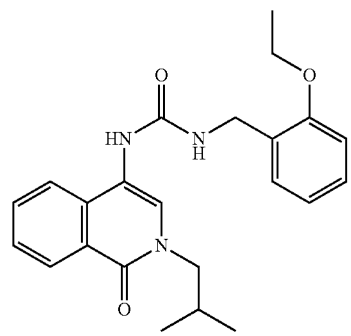 [SMILES: CCOc1ccccc1CNC(=O)Nc1cn(CC(C)C)c(=O)c2ccccc12] | 1-[(2-ethoxyphenyl)methyl]-3-[2-(2-methylpropyl)-1-oxoisoquinolin-4-yl]urea |
| 60a | 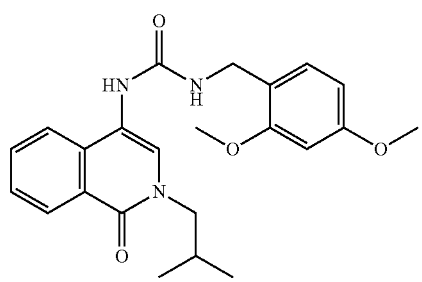 [SMILES: COc1ccc(CNC(=O)Nc2cn(CC(C)C)c(=O)c3ccccc23)c(OC)c1] | 1-[(2,4-dimethoxyphenyl)methyl]-3-[2-(2-methylpropyl)-1-oxoisoquinolin-4-yl]urea |
| 60 | 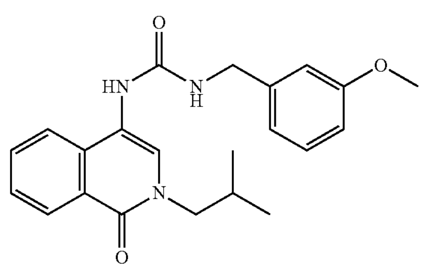 [SMILES: COc1cccc(CNC(=O)Nc2cn(CC(C)C)c(=O)c3ccccc23)c1] | 1-[(3-methoxyphenyl)methyl]-3-[2-(2-methylpropyl)-1-oxoisoquinolin-4-yl]urea |
| 61 | 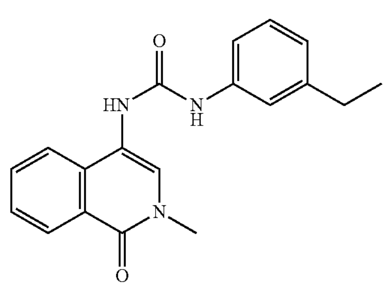 [SMILES: CCc1cccc(NC(=O)Nc2cn(C)c(=O)c3ccccc23)c1] | 1-(3-ethylphenyl)-3-(2-methyl-1-oxoisoquinolin-4-yl)urea |

TABLE 5-continued

Chemical names and structures of tested compounds

| Entry No. | Structure | Chemical name |
|---|---|---|
| 62 | 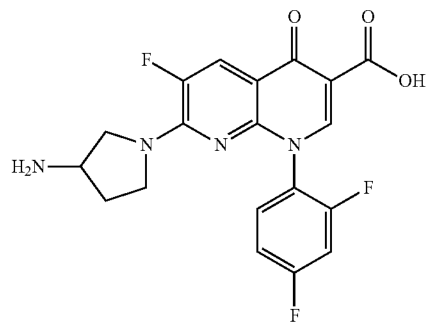 [SMILES: NC1CCN(c2nc3c(cc2F)c(=O)c(C(=O)O)cn3-c2ccc(F)cc2F)C1] | 7-(3-aminopyrrolidin-1-yl)-1-(2,4-difluorophenyl)-6-fluoro-4-oxo-1,4-dihydro-1,8-naphthyridine-3-carboxylic acid |
| 63 | 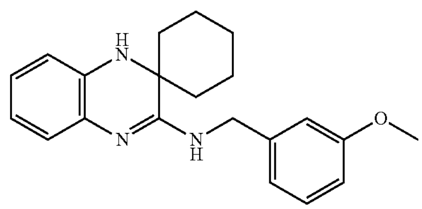 [SMILES: COc1cccc(CNC2=Nc3ccccc3NC23CCCCC3)c1] | N-[(3-methoxyphenyl)methyl]spiro[4H-quinoxaline-3,1'-cyclohexane]-2-amine |
| 64 | 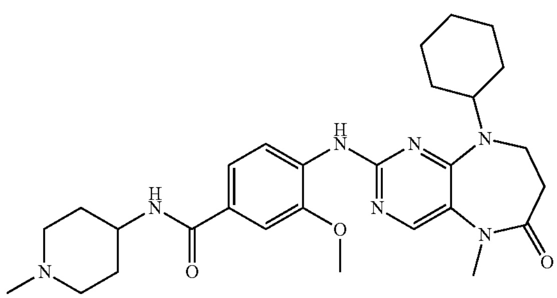 [SMILES: COc1cc(C(=O)NC2CCN(C)CC2)ccc1Nc1ncc2c(n1)N(C1CCCCC1)CCC(=O)N2C] | 4-[(9-cyclohexyl-5-methyl-6-oxo-7,8-dihydropyrimido[4,5-b][1,4]diazepin-2-yl)amino]-3-methoxy-N-(1-methylpiperidin-4-yl)benzamide |
| 65 | 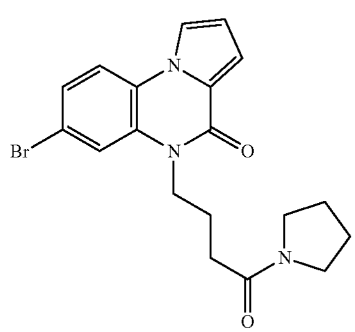 [SMILES: O=C(CCCn1c(=O)c2cccn2c2ccc(Br)cc21)N1CCCC1] | 7-bromo-5-(4-oxo-4-pyrrolidin-1-ylbutyl)pyrrolo[1,2-a]quinoxalin-4-one |
| 66 | 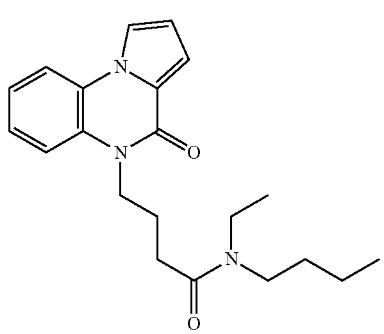 [SMILES: CCCCN(CC)C(=O)CCCn1c(=O)c2cccn2c2ccccc21] | N-butyl-N-ethyl-4-(4-oxopyrrolo[1,2-a]quinoxalin-5-yl)butanamide |

TABLE 5-continued

Chemical names and structures of tested compounds

| Entry No. | Structure | Chemical name |
|---|---|---|
| 67 | 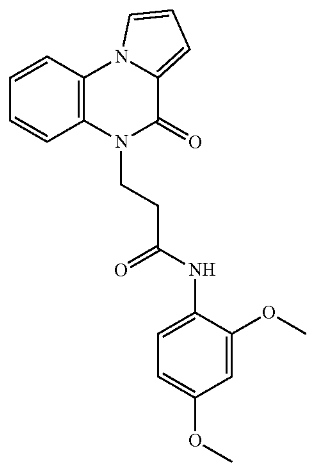 [SMILES: COc1ccc(NC(=O)CCn2c(=O)c3cccn3c3ccccc32)c(OC)c1] | N-(2,4-dimethoxyphenyl)-3-(4-oxopyrrolo[1,2-a]quinoxalin-5-yl)propanamide |
| 68 | 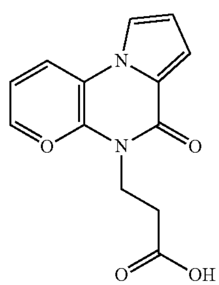 | 3-{7-Oxo-2.8.10-triazatricyclo[7.4.0.02,6]trideca-1(13),3,5,9,11-pentaen-8-yl}propionic acid |
| 69 | 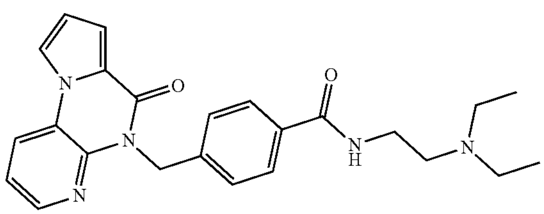 [SMILES: CCN(CC)CCNC(=O)c1ccc(Cn2c(=O)c3cccn3c3cccnc32)cc1] | N-(2-(diethylamino)ethyl)-4-((6-oxopyrido[2,3-e]pyrrolo[1,2-a]pyrazin-5(6H)-yl)methyl)benzamide |
| 70 | 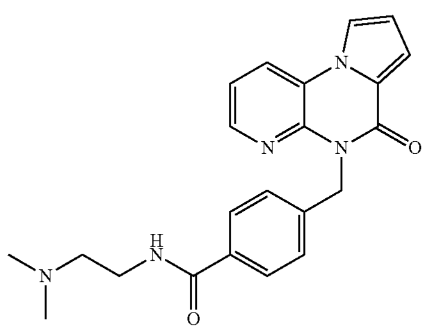 [SMILES: CN(C)CCNC(=O)c1ccc(Cn2c(=O)c3cccn3c3cccnc32)cc1] | N-[2-(dimethylamino)ethyl]-4-[(6-oxopyrido[2,3-e]pyrrolo[1,2-a]pyrazin-5(6H)-yl)methyl]benzamide |
| 71 | 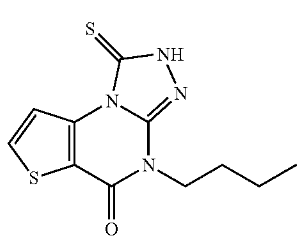 [SMILES: CCCCn1c(=O)c2sccc2n2c(=S)[nH]nc12] | 4-butyl-1-thioxo-2,4-dihydrothieno[2,3-e][1,2,4]triazolo[4,3-a]pyrimidin-5(1H)-one |

TABLE 5-continued

Chemical names and structures of tested compounds

| Entry No. | Structure | Chemical name |
|---|---|---|
| 72 | 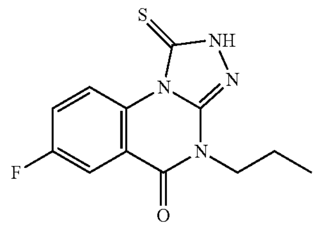 [SMILES: CCCn1c(=O)c2cc(F)ccc2n2c(=S)[nH]nc12] | 7-fluoro-4-propyl-1-thioxo-2,4-dihydro[1,2,4]triazolo[4,3-a]quinazolin-5(1H)-one |
| 73 | 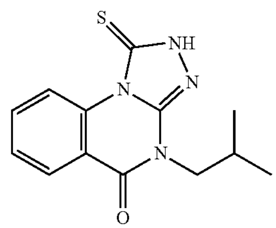 [SMILES: CC(C)Cn1c(=O)c2ccccc2n2c(=S)[nH]nc12] | 4-isobutyl-1-thioxo-2,4-dihydro[1,2,4]triazolo[4,3-a]quinazolin-5(1H)-one |
| 74 | 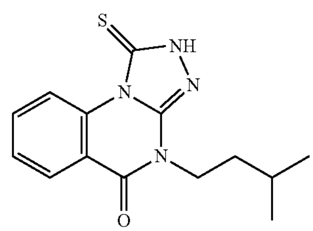 [SMILES: CC(C)CCn1c(=O)c2ccccc2n2c(=S)[nH]nc12] | 1-mercapto-4-(3-methylbutyl)[1,2,4]triazolo[4,3-a]quinazolin-5(4H)-one |
| 75 | 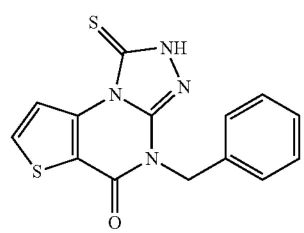 [SMILES: O=c1c2sccc2n2c(=S)[nH]nc2n1Cc1ccccc1] | 4-benzyl-1-thioxo-2,4-dihydrothieno[2,3-e][1,2,4]triazolo[4,3-a]pyrimidin-5(1H)-one |
| 76 | 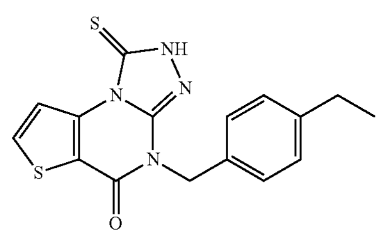 [SMILES: CCc1ccc(Cn2c(=O)c3sccc3n3c(=S)[nH]nc23)cc1] | 4-(4-ethylbenzyl)-1-thioxo-2,4-dihydrothieno[2,3-e][1,2,4]triazolo[4,3-a]pyrimidin-5(1H)-one |
| 77 | 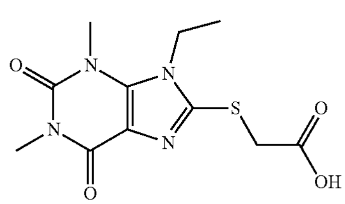 [SMILES: CCn1c(SCC(=O)O)nc2c(=O)n(C)c(=O)n(C)c21] | 2-(9-ethyl-1,3-dimethyl-2,6-dioxopurin-8-yl)sulfanylacetic acid |

TABLE 5-continued

Chemical names and structures of tested compounds

| Entry No. | Structure | Chemical name |
|---|---|---|
| 78 | 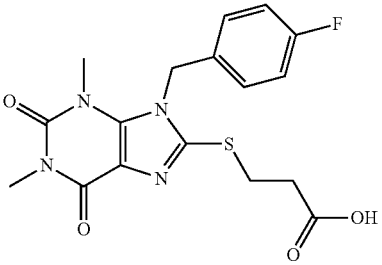 [SMILES: Cn1c(=O)c2nc(SCCC(=O)O)n(Cc3ccc(F)cc3)c2n(C)c1=O] | 3-{[9-(4-fluorobenzyl)-1,3-dimethyl-2,6-dioxo-2,3,6,9-tetrahydro-1H-purin-8-yl]sulfanyl}propanoic acid |
| 79 | 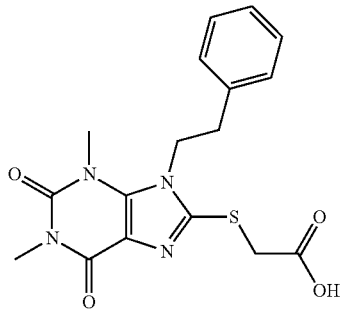 [SMILES: Cn1c(=O)c2nc(SCC(=O)O)n(CCc3ccccc3)c2n(C)c1=O] | 2-[1,3-dimethyl-2,6-dioxo-9-(2-phenylethyl)purin-8-yl]sulfanylacetic acid |
| 80 | 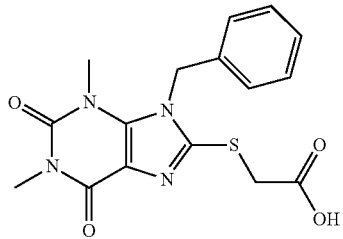 [SMILES: Cn1c(=O)c2nc(SCC(=O)O)n(Cc3ccccc3)c2n(C)c1=O] | 2-(9-benzyl-1,3-dimethyl-2,6-dioxopurin-8-yl)sulfanylacetic acid |
| 81 | 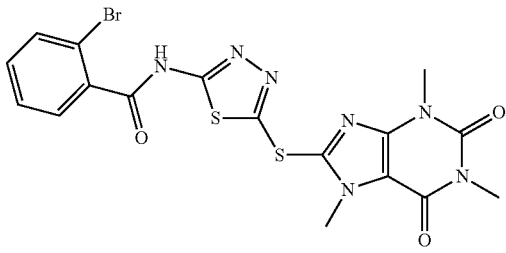 [SMILES: Cn1c(=O)c2c(nc(Sc3nnc(NC(=O)c4ccccc4Br)s3)n2C)n(C)c1=O] | 2-bromo-N-{5-[(1,3,7-trimethyl-2,6-dioxo-2,3,6,7-tetrahydro-1H-purin-8-yl)thiol-1,3,4-thiadiazol-2-yl}benzamide |
| 82 | 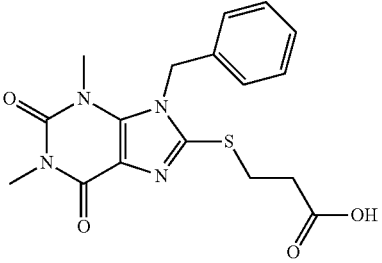 [SMILES: Cn1c(=O)c2nc(SCCC(=O)O)n(Cc3ccccc3)c2n(C)c1=O] | 3-(9-benzyl-1,3-dimethyl-2,6-dioxopurin-8-yl)sulfanylpropanoic acid |

TABLE 5-continued

Chemical names and structures of tested compounds

| Entry No. | Structure | Chemical name |
|---|---|---|
| 83 | 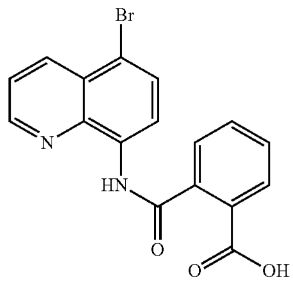 [SMILES: O=C(O)c1ccccc1C(=O)Nc1ccc(Br)c2cccnc12] | 2-[(5-bromoquinolin-8-yl)carbamoyl]benzoic acid |
| 84 | 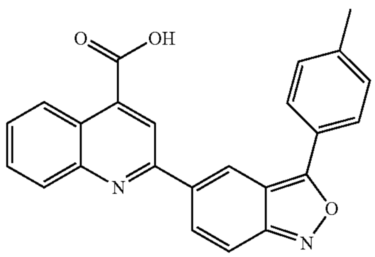 [SMILES: Cc1ccc(-c2onc3ccc(-c4cc(C(=O)O)c5ccccc5n4)cc23)cc1] | 2-[3-(4-methylphenyl)-2,1-benzoxazol-5-yl]quinoline-4-carboxylic acid |
| 85 | 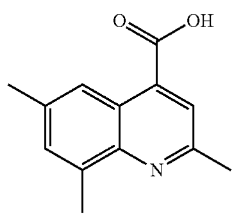 | 2,6,8-trimethylquinoline-4-carboxylic acid |
| 86 | 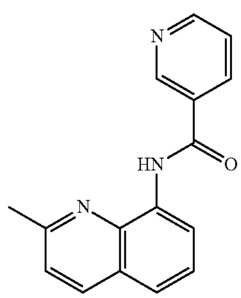 [SMILES: Cc1ccc2cccc(NC(=O)c3cccnc3)c2n1] | N-(2-methylquinolin-8-yl)nicotinamide |
| 87 | 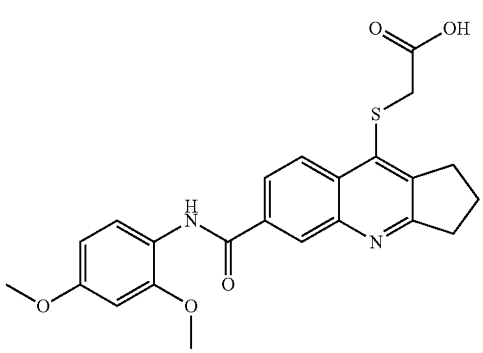 [SMILES: COc1ccc(NC(=O)c2ccc3c(SCC(=O)O)c4c(nc3c2)CCC4)c(OC)c1] | 2-[[6-[(2,4-dimethoxyphenyl)carbamoyl]-2,3-dihydro-1H-cyclopenta[b]quinolin-9-yl]sulfanyl]acetic acid |

TABLE 5-continued

Chemical names and structures of tested compounds

| Entry No. | Structure | Chemical name |
|---|---|---|
| 88 | 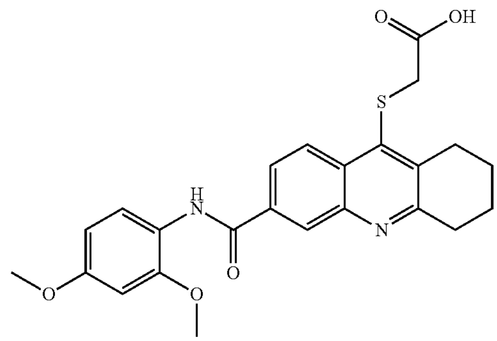 [SMILES: COc1ccc(NC(=O)c2ccc3c(SCC(=O)O)c4c(nc3c2)CCCC4)c(OC)c1] | [(6-{[(2,4-dimethoxyphenyl)amino]carbonyl}-1,2,3,4-tetrahydroacridin-9-yl)thio]acetic acid |
| 89 | 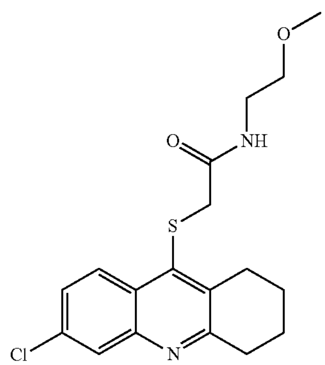 [SMILES: COCCNC(=O)CSc1c2c(nc3cc(Cl)ccc13)CCCC2] | 2-[(6-chloro-1,2,3,4-tetrahydroacridin-9-yl)sulfanyl]-N-(2-methoxyethyl)acetamide |
| 90 | 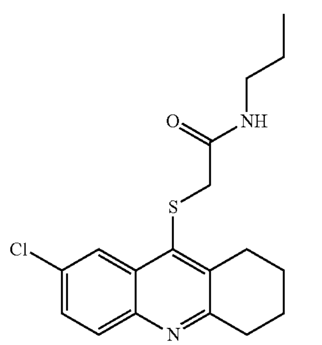 [SMILES: CCCNC(=O)CSc1c2c(nc3ccc(Cl)cc13)CCCC2] | 2-[(7-chloro-1,2,3,4-tetrahydroacridin-9-yl)sulfanyl]-N-propylacetamide |
| 91 | 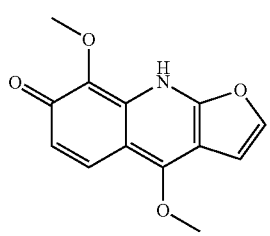 [SMILES: COc1c2[nH]c3occc3c(OC)c-2ccc1=O] | 4,8-dimethoxy-9H-furo[2,3-b]quinolin-7-one |
| 92 | 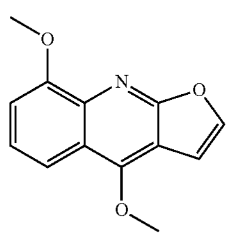 [SMILES: COc1c2ccoc2nc2c(OC)cccc12] | 4,8-dimethoxyfuro[2,3-b]quinoline |

TABLE 5-continued

Chemical names and structures of tested compounds

| Entry No. | Structure | Chemical name |
|---|---|---|
| 93 | 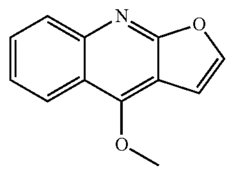 | 4-Methoxyfuro[2,3-b]quinoline |
| 94 | 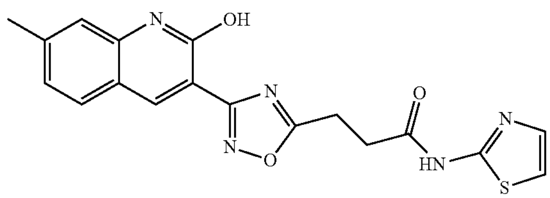 [SMILES: Cc1ccc2cc(-c3noc(CCC(=O)Nc4nccs4)n3)c(O)nc2c1] | 3-[3-(2-hydroxy-7-methylquinolin-3-yl)-1,2,4-oxadiazol-5-yl]-N-1,3-thiazol-2-ylpropanamide |
| 95 | 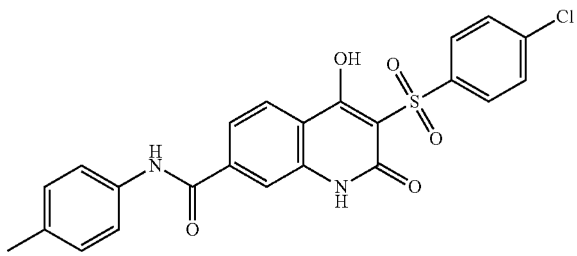 [SMILES: Cc1ccc(NC(=O)c2ccc3c(O)c(S(=O)(=O)c4ccc(Cl)cc4)c(=O)[nH]c3c2)cc1] | 3-(4-chlorophenyl)sulfonyl-4-hydroxy-N-(4-methylphenyl)-2-oxo-1H-quinoline-7-carboxamide |
| 96 | 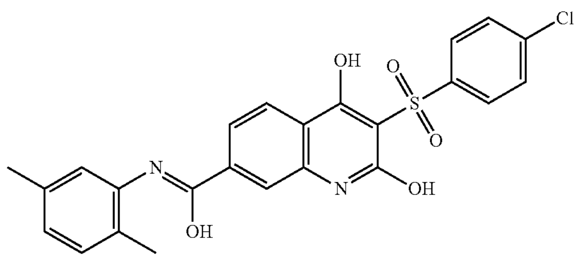 [SMILES: Cc1ccc(C)c(/N=C(\O)c2ccc3c(O)c(S(=O)(=O)c4ccc(Cl)cc4)c(O)nc3c2)c1] | (Z)-3-((4-chlorophenyl)sulfonyl)-N-(2,5-dimethylphenyl)-2,4-dihydroxyquinoline-7-carbimidic acid |
| 97 | 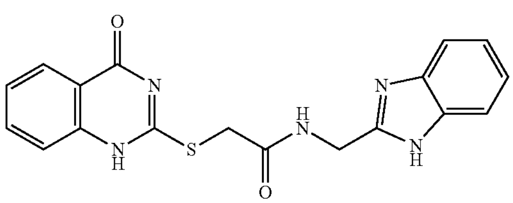 [SMILES: O=C(CSc1nc(=O)c2ccccc2[nH]1)NCc1nc2ccccc2[nH]1] | N-(1H-benzimidazol-2-ylmethyl)-2-[(4-oxo-1H-quinazolin-2-yl)sulfanyl]acetamide |
| 98 | 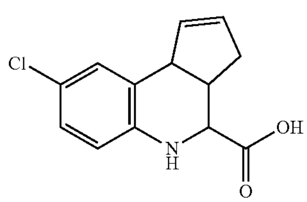 [SMILES: O=C(O)C1Nc2ccc(Cl)cc2C2C=CCC12] | 8-Chloro-3a,4,5,9b-tetrahydro-3H-cyclopenta[c]quinoline-4-carboxylic acid |
| 99 | 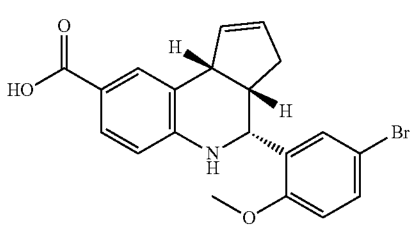 [SMILES: COc1ccc(Br)cc1[C@@H]1Nc2ccc(C(=O)O)cc2[C@@H]2C=CC[C@@H]21] | (3aS,4R,9bR)-4-(5-bromo-2-methoxyphenyl)-3a,4,5,9b-tetrahydro-3H-cyclopenta[c]quinoline-8-carboxylic acid |

TABLE 5-continued

Chemical names and structures of tested compounds

| Entry No. | Structure | Chemical name |
|---|---|---|
| 100 | 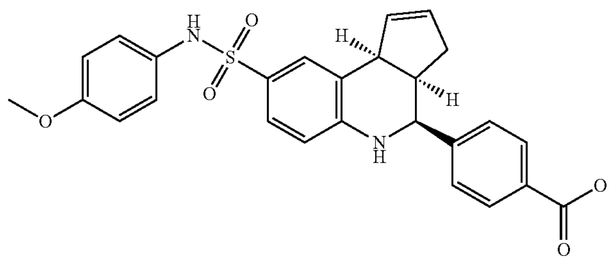 [SMILES: COc1ccc(NS(=O)(=O)c2ccc3c(c2)[C@H]2C=CC[C@H]2[C@@H](c2ccc(C(=O)O)cc2)N3)cc1] | 4-[(3aR,4S,9bS)-8-[(4-methoxyphenyl)sulfamoyl]-3a,4,5,9b-tetrahydro-3H-cyclopenta[c]quinolin-4-yl]benzoic acid |
| 101 | 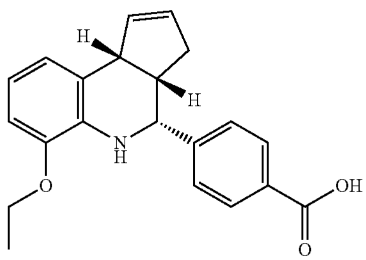 [SMILES: CCOc1cccc2c1N[C@@H](c1ccc(C(=O)O)cc1)[C@H]1CC=C[C@@H]21] | 4-[(3aS,4R,9bR)-6-ethoxy-3a,4,5,9b-tetrahydro-3H-cyclopenta[c]quinolin-4-yl]benzoic acid |
| 102 | 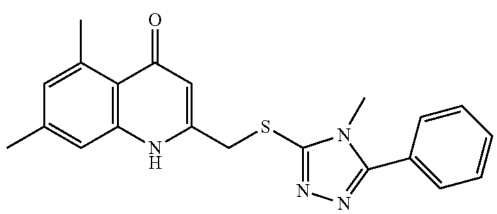 [SMILES: Cc1cc(C)c2c(=O)cc(CSc3nnc(-c4ccccc4)n3C)[nH]c2c1] | 5,7-dimethyl-2-[(4-methyl-5-phenyl-1,2,4-triazol-3-yl)sulfanylmethyl]-1H-quinolin-4-one |
| 103 | 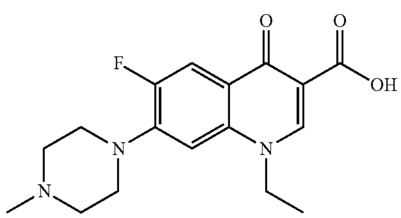 [SMILES: CCn1cc(C(=O)O)c(=O)c2cc(F)c(N3CCN(C)CC3)cc21] | 1-ethyl-6-fluoro-7-(4-methylpiperazin-1-yl)-4-oxo-1,4-dihydroquinoline-3-carboxylic acid |
| 104 | 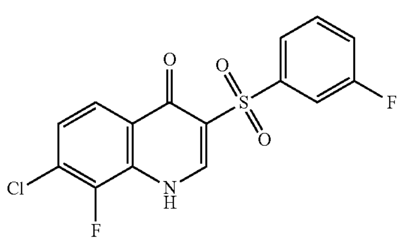 [SMILES: O=c1c(S(=O)(=O)c2cccc(F)c2)c[nH]c2c(F)c(Cl)ccc12] | 7-chloro-8-fluoro-3-(3-fluorophenyl)sulfonyl-1H-quinolin-4-one |
| 105 | 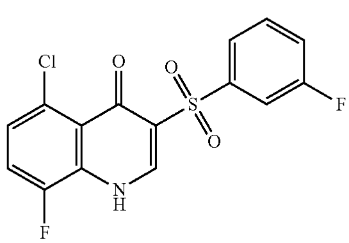 [SMILES: O=c1c(S(=O)(=O)c2cccc(F)c2)c[nH]c2c(F)ccc(Cl)c12] | 5-chloro-8-fluoro-3-(3-fluorophenyl)sulfonyl-1H-quinolin-4-one |

TABLE 5-continued

Chemical names and structures of tested compounds

| Entry No. | Structure | Chemical name |
|---|---|---|
| 106 | 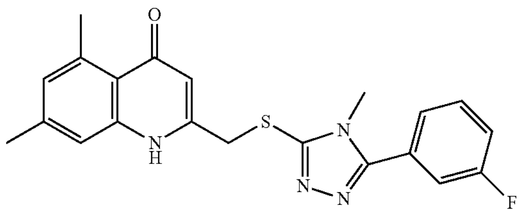 [SMILES: Cc1cc(C)c2c(=O)cc(CSc3nnc(-c4cccc(F)c4)n3C)[nH]c2c1] | 2-[[5-(3-fluorophenyl)-4-methyl-1,2,4-triazol-3-yl]sulfanylmethyl]-5,7-dimethyl-1H-quinolin-4-one |
| 107 | 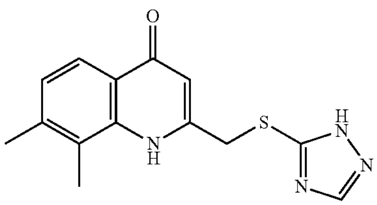 [SMILES: Cc1ccc2c(=O)cc(CSc3ncn[nH]3)[nH]c2c1C] | 7,8-dimethyl-2-(1H-1,2,4-triazol-5-ylsulfanylmethyl)-1H-quinolin-4-one |
| 108 | 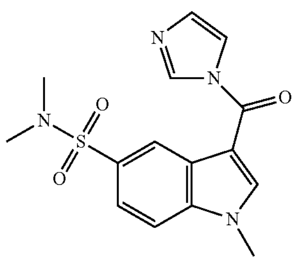 [SMILES: CN(C)S(=O)(=O)c1ccc2c(c1)c(C(=O)n1ccnc1)cn2C] | 3-(I-Imidazole-1-carbonyl)-N,N,1-trimethylindole-5-sulfonamide |
| 109 | 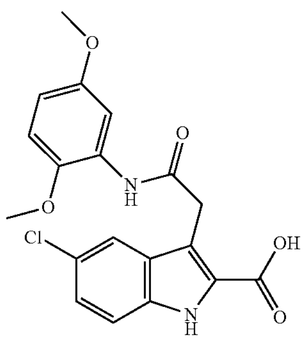 [SMILES: COc1ccc(OC)c(NC(=O)Cc2c(C(=O)O)[nH]c3ccc(Cl)cc23)c1] | 5-chloro-3-[2-(2,5-dimethoxyanilino)-2-oxoethyl]-1H-indole-2-carboxylic acid |
| 110 | 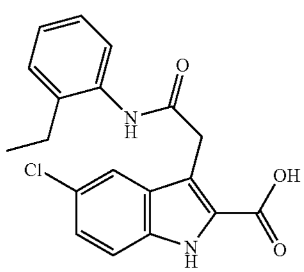 [SMILES: CCc1ccccc1NC(=O)Cc1c(C(=O)O)[nH]c2ccc(Cl)cc12] | 5-chloro-3-[2-(2-ethylanilino)-2-oxoethyl]-1H-indole-2-carboxylic acid |
| 111 | 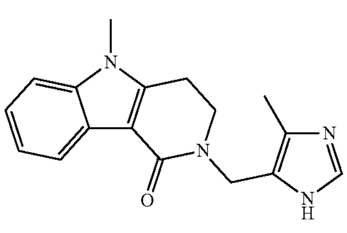 [SMILES: Cc1nc[nH]c1CN1CCc2c(c3ccccc3n2C)C1=O] | 5-methyl-2-((4-methyl-1H-imidazol-5-yl)methyl)-2,3,4,5-tetrahydro-1H-pyrido[4,3-b]indol-1-one |

TABLE 5-continued

Chemical names and structures of tested compounds

| Entry No. | Structure | Chemical name |
|---|---|---|
| 112 | 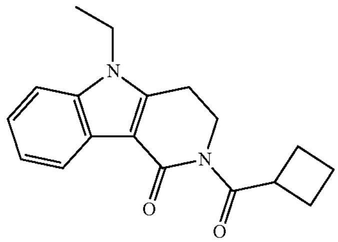 [SMILES: CCn1c2c(c3ccccc31)C(=O)N(C(=O)C1CCC1)CC2] | cyclobutyl-(5-ethyl-3,4-dihydro-1H-pyrido[4,3-b]indol-2-yl)methanone |
| 113 | 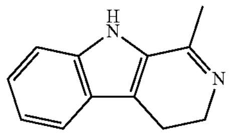 | 1-Methyl-4,9-dihydro-3H-beta-carboline |
| 114 | 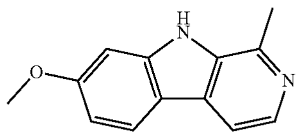 [SMILES: COc1ccc2c(c1)[nH]c1c(C)nccc12] | 7-Methoxy-1-methyl-9H-pyrido[3,4-b]indole |
| 115 | 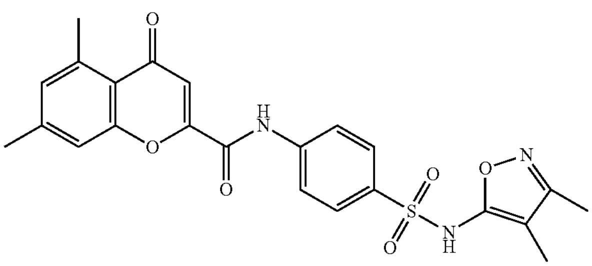 | N-[4-[(3,4-dimethyl-1,2-oxazol-5-yl)sulfamoyl]phenyl]-5,7-dimethyl-4-oxochromene-2-carboxamide |
| 116 | 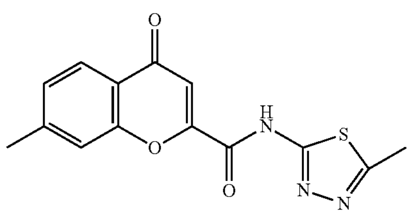 | 7-methyl-N-(5-methyl-1,3,4-thiadiazol-2-yl)-4-oxo-4H-chromene-2-carboxamide |
| 117 | 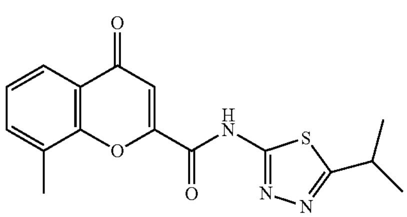 [SMILES: Cc1cccc2c(=O)cc(C(=O)Nc3nnc(C(C)C)s3)oc12] | 8-methyl-4-oxo-N-(5-propan-2-yl-1,3,4-thiadiazol-2-yl)chromene-2-carboxamide |
| 118 | 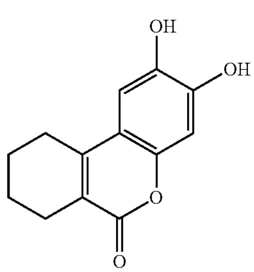 [SMILES: O=c1oc2cc(O)c(O)cc2c2c1CCCC2] | 2,3-dihydroxy-7,8,9,10-tetrahydro-6H-benzo[c]-chromen-6-one |

TABLE 5-continued

Chemical names and structures of tested compounds

| Entry No. | Structure | Chemical name |
|---|---|---|
| 119 | 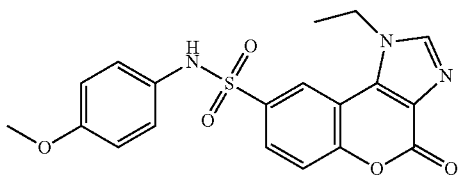 [SMILES: CCn1cnc2c(=O)oc3ccc(S(=O)(=O)Nc4ccc(OC)cc4)cc3c21] | 1-ethyl-N-(4-methoxyphenyl)-4-oxochromeno[3,4-d]imidazole-8-sulfonamide |
| 120 | 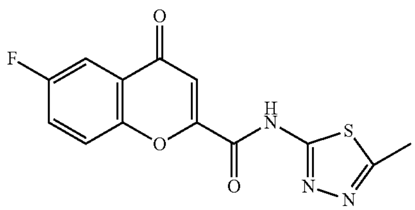 [SMILES: Cc1nnc(NC(=O)c2cc(=O)c3cc(F)ccc3o2)s1] | 6-fluoro-N-(5-methyl-1,3,4-thiadiazol-2-yl)-4-oxo-4H-chromene-2-carboxamide |
| 121 | 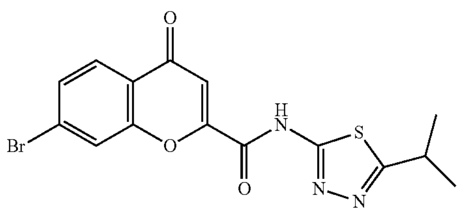 [SMILES: CC(C)c1nnc(NC(=O)c2cc(=O)c3ccc(Br)cc3o2)s1] | 7-bromo-4-oxo-N-(5-propan-2-yl-1,3,4-thiadiazol-2-yl)chromene-2-carboxamide |
| 122 | 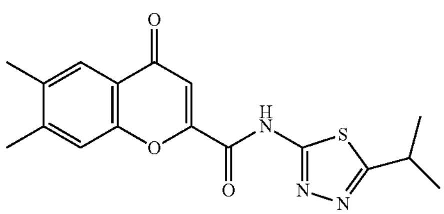 [SMILES: Cc1cc2oc(C(=O)Nc3nnc(C(C)C)s3)cc(=O)c2cc1C] | 6,7-dimethyl-4-oxo-N-(5-propan-2-yl-1,3,4-thiadiazol-2-yl)chromene-2-carboxamide |
| 123 | 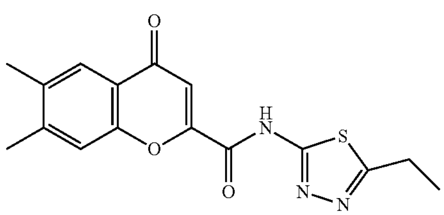 [SMILES: CCc1nnc(NC(=O)c2cc(=O)c3cc(C)c(C)cc3o2)s1] | N-(5-ethyl-1,3,4-thiadiazol-2-yl)-6,7-dimethyl-4-oxo-4H-chromene-2-carboxamide |
| 124 | 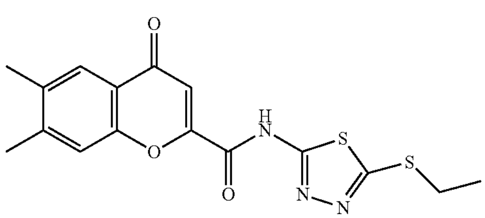 [SMILES: CCSc1nnc(NC(=O)c2cc(=O)c3cc(C)c(C)cc3o2)s1] | N-(5-ethylsulfanyl-1,3,4-thiadiazol-2-yl)-6,7-dimethyl-4-oxochromene-2-carboxamide |
| 125 | 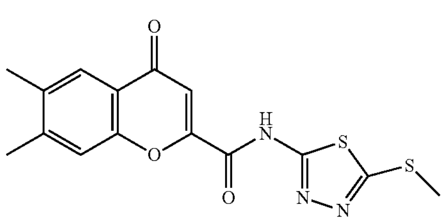 | 6,7-dimethyl-N-[5-(methylsulfanyl)-1,3,4-thiadiazol-2-yl]-4-oxo-4H-chromene-2-carboxamide |

TABLE 5-continued

Chemical names and structures of tested compounds

| Entry No. | Structure | Chemical name |
|---|---|---|
| 126 | 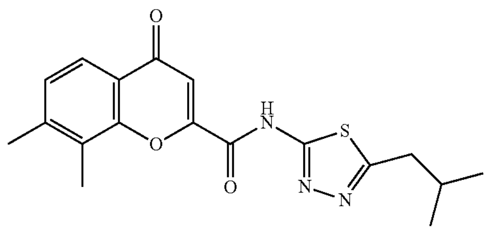 [SMILES: Cc1ccc2c(=O)cc(C(=O)Nc3nnc(CC(C)C)s3)oc2c1C] | 7,8-dimethyl-N-[5-(2-methylpropyl)-1,3,4-thiadiazol-2-yl]-4-oxochromene-2-carboxamide |
| 127 | 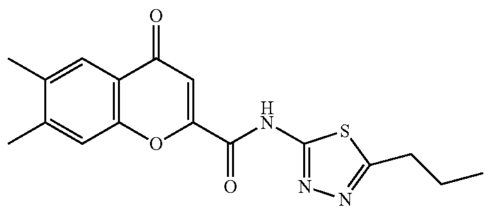 [SMILES: CCCc1nnc(NC(=O)c2cc(=O)c3cc(C)c(C)cc3o2)s1] | 6,7-dimethyl-4-oxo-N-(5-propyl-1,3,4-thiadiazol-2-yl)-4H-chromene-2-carboxamide |
| 128 | 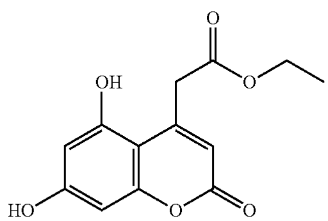 [SMILES: CCOC(=O)Cc1cc(=O)oc2cc(O)cc(O)c12] | Ethyl (5,7-dihydroxy-2-oxo-2H-chromen-4-yl)acetate |
| 129 | 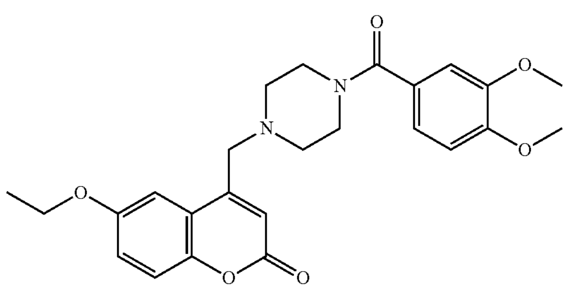 [SMILES: CCOc1ccc2oc(=O)cc(CN3CCN(C(=O)c4ccc(OC)c(OC)c4)CC3)c2c1] | 4-[[4-(3,4-dimethoxybenzoyl)piperazin-1-yl]methyl]-6-ethoxychromen-2-one |
| 130 | 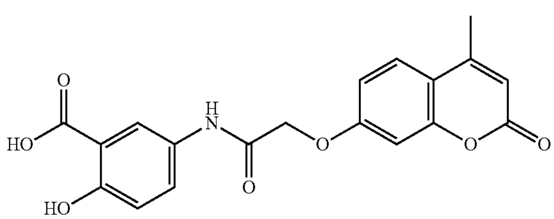 [SMILES: Cc1cc(=O)oc2cc(OCC(=O)Nc3ccc(O)c(C(=O)O)c3)ccc12] | 2-hydroxy-5-[[2-(4-methyl-2-oxochromen-7-yl)oxyacetyl]amino]benzoic acid |
| 131 | 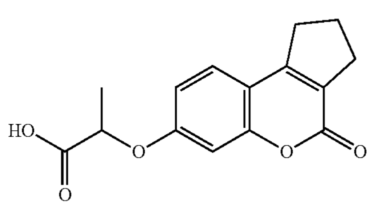 [SMILES: CC(Oc1ccc2c3c(c(=O)oc2c1)CCC3)C(=O)O] | 2-[(4-Oxo-1,2,3,4-tetrahydrocyclopenta[c]chromen-7-yl)oxy]propanoic acid |
| 132 | 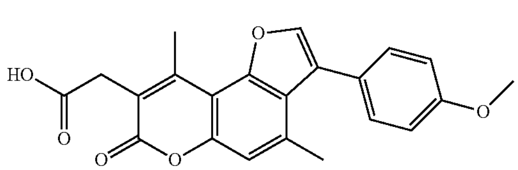 [SMILES: COc1ccc(-c2coc3c2c(C)cc2oc(=O)c(CC(=O)O)c(C)c23)cc1] | [3-(4-methoxyphenyl)-4,9-dimethyl-7-oxo-7H-furo[2,3-f]chromen-8-yl]acetic acid |

TABLE 5-continued

Chemical names and structures of tested compounds

| Entry No. | Structure | Chemical name |
|---|---|---|
| 133 | 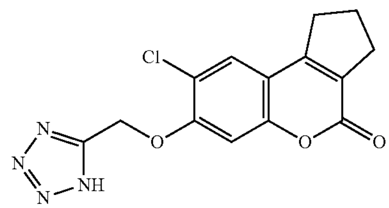 [SMILES: O=c1oc2cc(OCc3nnn[nH]3)c(Cl)cc2c2c1CCC2] | 8-chloro-7-(1H-tetrazol-5-ylmethoxy)-2,3-dihydrocyclopenta[c]chromen-4(1H)-one |
| 134 | 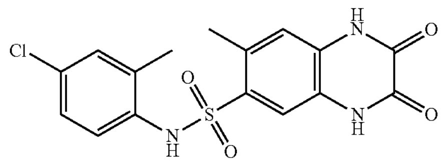 [SMILES: Cc1cc(Cl)ccc1NS(=O)(=O)c1cc2[nH]c(=O)c(=O)[nH]c2cc1C] | N-(4-chloro-2-methylphenyl)-7-methyl-2,3-dioxo-1,4-dihydroquinoxaline-6-sulfonamide |
| 135 | 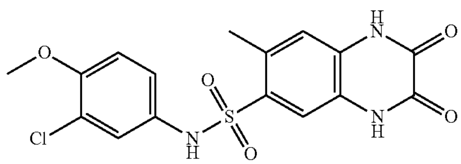 [SMILES: COc1ccc(NS(=O)(=O)c2cc3[nH]c(=O)c(=O)[nH]c3cc2C)cc1Cl] | N-(3-chloro-4-methoxyphenyl)-7-methyl-2,3-dioxo-1,4-dihydroquinoxaline-6-sulfonamide |
| 136 | 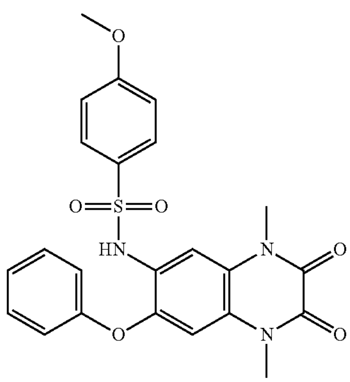 [SMILES: COc1ccc(S(=O)(=O)Nc2cc3c(cc2Oc2ccccc2)n(C)c(=O)c(=O)n3C)cc1] | N-(1,4-dimethyl-2,3-dioxo-7-phenoxy-1,2,3,4-tetrahydroquinoxalin-6-yl)-4-methoxybenzenesulfonamide |
| 137 | 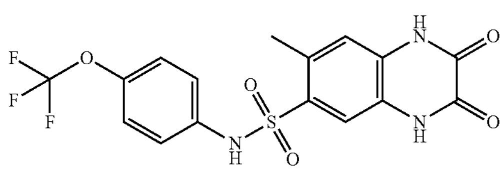 [SMILES: Cc1cc2[nH]c(=O)c(=O)[nH]c2cc1S(=O)(=O)Nc1ccc(OC(F)(F)F)cc1] | 7-methyl-2,3-dioxo-N-[4-(trifluoromethoxy)phenyl]-1,4-dihydroquinoxaline-6-sulfonamide |
| 138 | 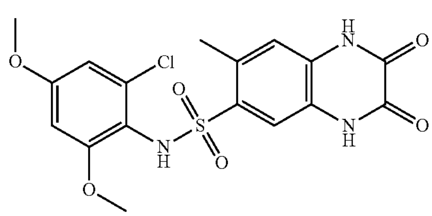 [SMILES: COc1cc(Cl)c(NS(=O)(=O)c2cc3[nH]c(=O)c(=O)[nH]c3cc2C)c(OC)c1] | N-(2-chloro-4,6-dimethoxyphenyl)-7-methyl-2,3-dioxo-1,4-dihydroquinoxaline-6-sulfonamide |
| 139 | 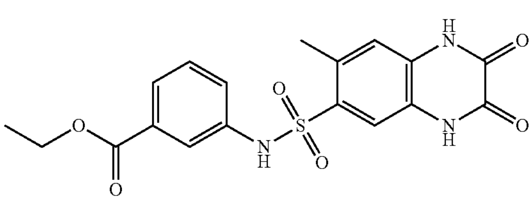 [SMILES: CCOC(=O)c1cccc(NS(=O)(=O)c2cc3[nH]c(=O)c(=O)[nH]c3cc2C)c1] | ethyl 3-[(7-methyl-2,3-dioxo-1,4-dihydroquinoxalin-6-yl)sulfonylamino]benzoate |

TABLE 5-continued

Chemical names and structures of tested compounds

| Entry No. | Structure | Chemical name |
|---|---|---|
| 140 | 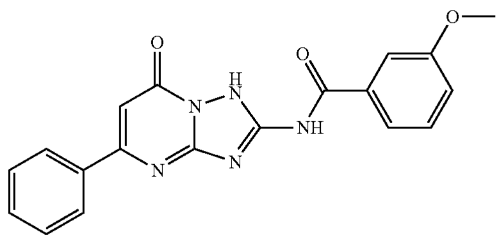 [SMILES: COc1cccc(C(=O)Nc2nc3nc(-c4ccccc4)cc(=O)n3[nH]2)c1] | 3-methoxy-N-(7-oxo-5-phenyl-1H-[1,2,4]triazolo[1,5-a]pyrimidin-2-yl)benzamide |
| 141 | 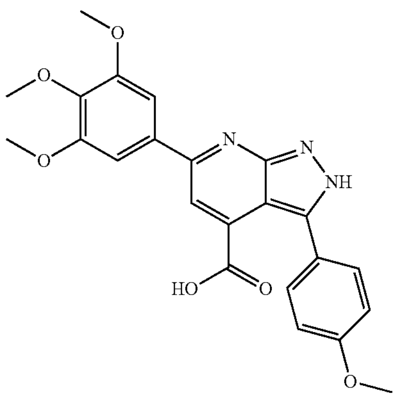 | 3-(4-methoxyphenyl)-6-(3,4,5-trimethoxyphenyl)-2H-pyrazolo[3,4-b]pyridine-4-carboxylic acid |
| 142 | 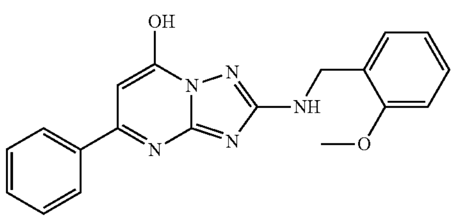 [SMILES: COc1ccccc1CNc1nc2nc(-c3ccccc3)cc(O)n2n1] | N-(7-hydroxy-5-phenyl-[1,2,4]triazolo[1,5-a]pyrimidin-2-yl)-2-methoxybenzamide |
| 143 | 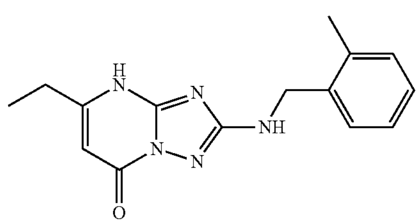 [SMILES: CCc1cc(=O)n2nc(NCc3ccccc3C)nc2[nH]1] | 5-ethyl-2-[(2-methylbenzyl)amino][1,2,4]triazolo[1,5-a]pyrimidin-7(4H)-one |
| 144 | 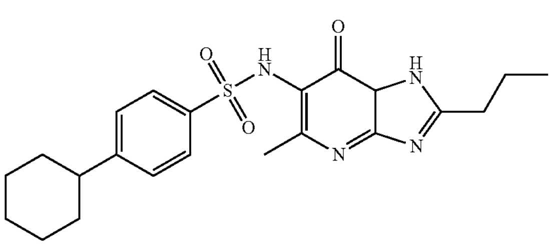 [SMILES: CCCC1=NC2=NC(C)=C(NS(=O)(=O)c3ccc(C4CCCCC4)cc3)C(=O)C2N1] | 4-cyclohexyl-N-(5-methyl-7-oxo-2-propyl-1H-[1,2,4]triazolo[1,5-a]pyrimidin-6-yl)benzenesulfonamide |

TABLE 5-continued

Chemical names and structures of tested compounds

| Entry No. | Structure | Chemical name |
|---|---|---|
| 145 | 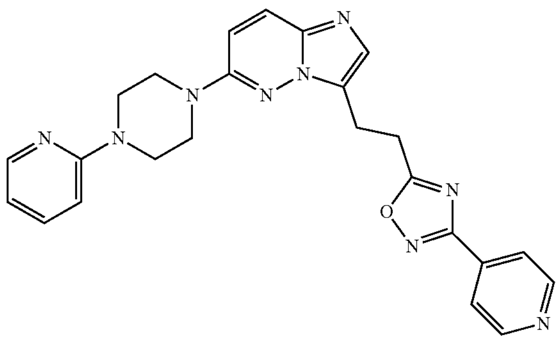 [SMILES: c1ccc(N2CCN(c3ccc4ncc(CCc5nc(-c6ccncc6)no5)n4n3)CC2)nc1] | 5-(2-(6-(4-(pyridin-2-yl)piperazin-1-yl)-[1,2,4]triazolo[4,3-b]pyridazin-3-yl)ethyl)-3-(pyridin-4-yl)-1,2,4-oxadiazole |
| 146 | 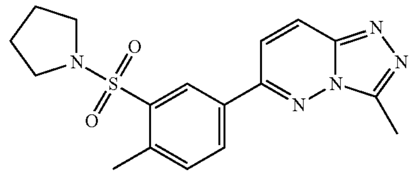 [SMILES: Cc1ccc(-c2ccc3nnc(C)n3n2)cc1S(=O)(=O)N1CCCC1] | 3-methyl-6-(4-methyl-3-pyrrolidin-1-ylsulfonylphenyl)-[1,2,4]triazolo[4,3-b]pyridazine |
| 147 | 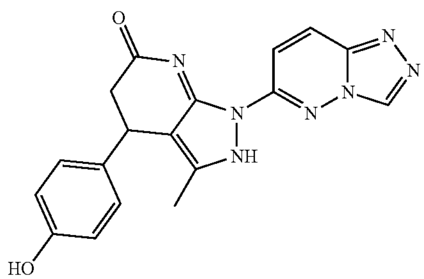 [SMILES: CC1=C2C(=NC(=O)CC2c2ccc(O)cc2)N(c2ccc3nncn3n2)N1] | 4-(4-hydroxyphenyl)-3-methyl-1-([1,2,4]triazolo[4,3-b]pyridazin-6-yl)-4,5-dihydro-2H-pyrazolo[3,4-b]pyridin-6-one |
| 148 | 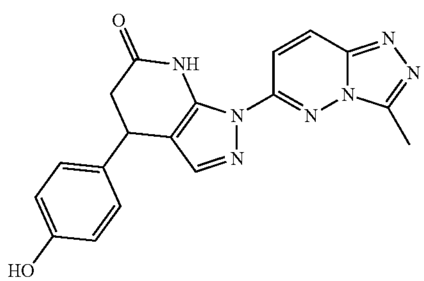 [SMILES: Cc1nnc2ccc(-n3ncc4c3NC(=O)CC4c3ccc(O)cc3)nn12] | 4-(4-hydroxyphenyl)-1-(3-methyl[1,2,4]triazolo[4,3-b]pyridazin-6-yl)-1,4,5,7-tetrahydro-6H-pyrazolo[3,4-b]pyridin-6-one |
| 149 | 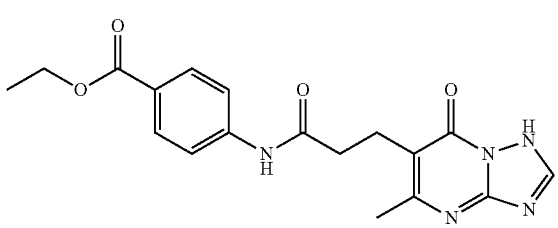 [SMILES: CCOC(=O)c1ccc(NC(=O)CCc2c(C)nc3nc[nH]n3c2=O)cc1] | ethyl 4-[3-(5-methyl-7-oxo-1H-[1,2,4]triazolo[1,5-a]pyrimidin-6-yl)propanoylamino]benzoate |
| 150 | 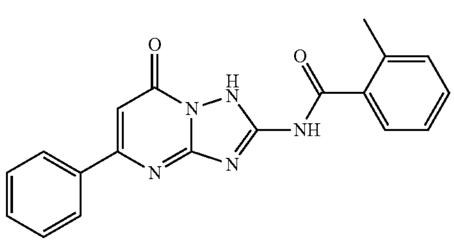 [SMILES: Cc1ccccc1C(=O)Nc1nc2nc(-c3ccccc3)cc(=O)n2[nH]1] | 2-methyl-N-(7-oxo-5-phenyl-1H-[1,2,4]triazolo[1,5-a]pyrimidin-2-yl)benzamide |

TABLE 5-continued

Chemical names and structures of tested compounds

| Entry No. | Structure | Chemical name |
|---|---|---|
| 151 | 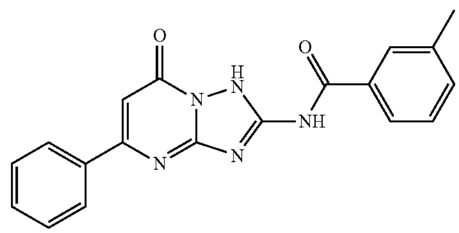 [SMILES: Cc1cccc(C(=O)Nc2nc3nc(-c4ccccc4)cc(=O)n3[nH]2)c1] | 3-methyl-N-(7-oxo-5-phenyl-1H-[1,2,4]triazolo[1,5-a]pyrimidin-2-yl)benzamide |
| 152 | 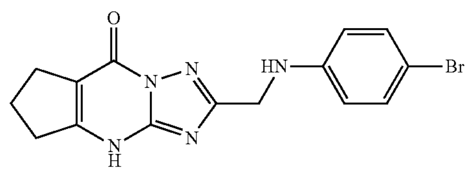 [SMILES: O=c1c2c([nH]c3nc(CNc4ccc(Br)cc4)nn13)CCC2] | 2-{[(4-bromophenyl)amino]methyl}-4,5,6,7-tetrahydro-8H-cyclopenta[d][1,2,4]triazolo[1,5-a]pyrimidin-8-one |
| 153 | 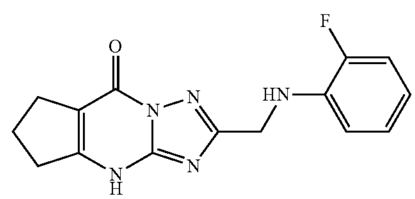 [SMILES: O=c1c2c([nH]c3nc(CNc4ccccc4F)nn13)CCC2] | 2-{[(2-fluorophenyl)amino]methyl}-4,5,6,7-tetrahydro-8H-cyclopenta[d][1,2,4]triazolo[1,5-a]pyrimidin-8-one |
| 154 | 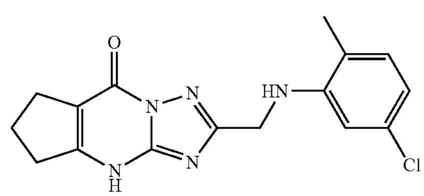 [SMILES: Cc1ccc(Cl)cc1NCc1nc2[nH]c3c(c(=O)n2n1)CCC3] | 2-{[(5-chloro-2-methylphenyl)amino]methyl}-4,5,6,7-tetrahydro-8H-cyclopenta[d][1,2,4]triazolo[1,5-a]pyrimidin-8-one |
| 155 | 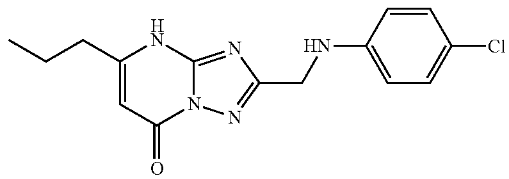 [SMILES: CCCc1cc(=O)n2nc(CNc3ccc(Cl)cc3)nc2[nH]1] | 2-{[(4-chlorophenyl)amino]methyl}-5-propyl[1,2,4]triazolo[1,5-a]pyrimidin-7(4H)-one |
| 156 | 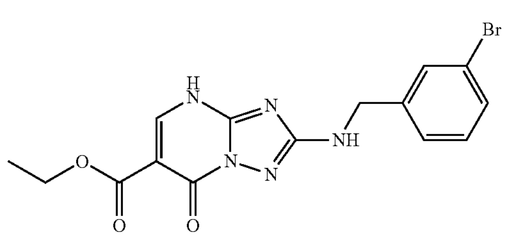 [SMILES: CCOC(=O)c1c[nH]c2nc(NCc3cccc(Br)c3)nn2c1=O] | ethyl 2-[(3-bromophenyl)methylamino]-7-oxo-1H-[1,2,4]triazolo[1,5-a]pyrimidine-6-carboxylate |

TABLE 5-continued

Chemical names and structures of tested compounds

| Entry No. | Structure | Chemical name |
|---|---|---|
| 157 | 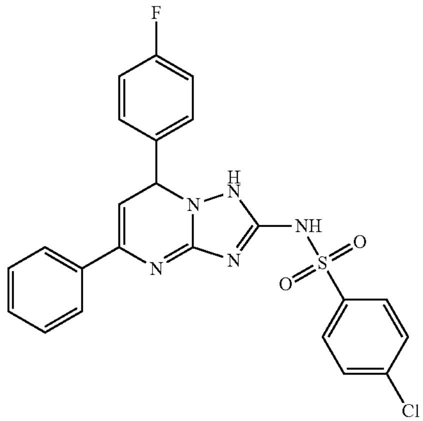 [SMILES: O=S(=O)(NC1=NC2=NC(c3ccccc3)=CC(c3ccc(F)cc3)N2N1)c1ccc(Cl)cc1] | 4-chloro-N-[7-(4-fluorophenyl)-5-phenyl-1,7-dihydro-[1,2,4]triazolo[1,5-a]pyrimidin-2-yl]benzenesulfonamide |
| 158 | 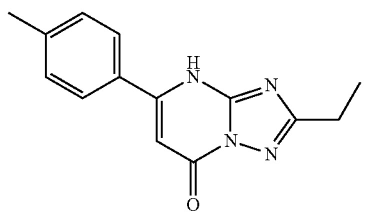 [SMILES: CCc1nc2[nH]c(-c3ccc(C)cc3)cc(=O)n2n1] | 2-ethyl-5-(4-methylphenyl)[1,2,4]triazolo[1,5-a]pyrimidin-7(4H)-one |
| 159 | 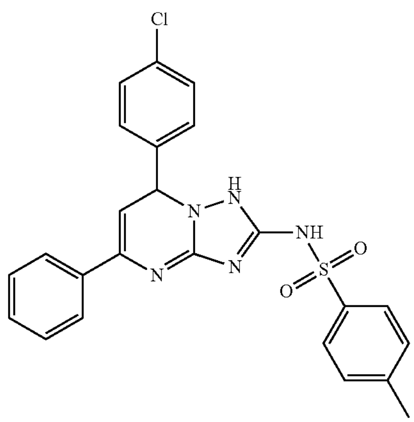 [SMILES: Cc1ccc(S(=O)(=O)NC2=NC3=NC(c4ccccc4)=CC(c4ccc(Cl)cc4)N3N2)cc1] | N-[7-(4-chlorophenyl)-5-phenyl-1,7-dihydro-[1,2,4]triazolo[1,5-a]pyrimidin-2-yl]-4-methylbenzenesulfonamide |
| 160 | 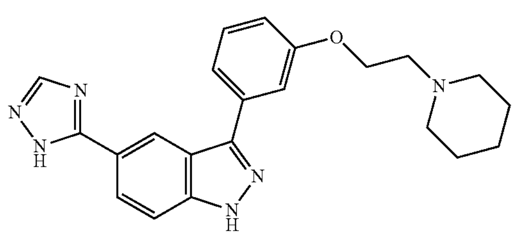 [SMILES: c1cc(OCCN2CCCCC2)cc(-c2n[nH]c3ccc(-c4ncn[nH]4)cc23)c1] | 3-[3-(2-piperidin-1-ylethoxy)phenyl]-5-(1H-1,2,4-triazol-5-yl)-1H-indazole |
| 161 | 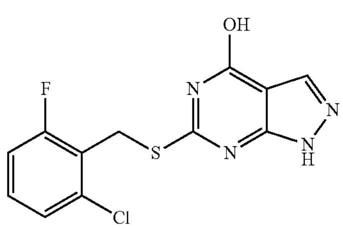 [SMILES: Oc1nc(SCc2c(F)cccc2Cl)nc2[nH]ncc12] | 2-[(2-chloro-6-fluorobenzyl)thio]-9H-purin-6-ol |

TABLE 5-continued

Chemical names and structures of tested compounds

| Entry No. | Structure | Chemical name |
|---|---|---|
| 162 | 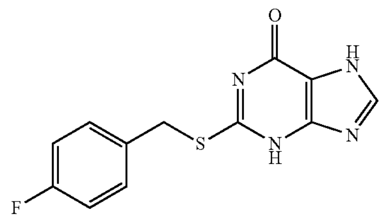 [SMILES: O=c1nc(SCc2ccc(F)cc2)[nH]c2nc[nH]c12] | 2-[(4-fluorophenyl)methylsulfanyl]-3,7-dihydropurin-6-one |
| 163 | 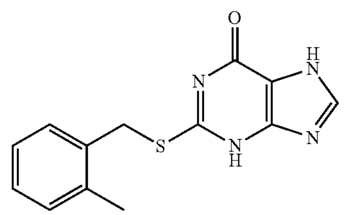 [SMILES: Cc1ccccc1CSc1nc(=O)c2[nH]cnc2[nH]1] | 2-[(2-methylphenyl)methylsulfanyl]-3,7-dihydropurin-6-one |
| 164 | 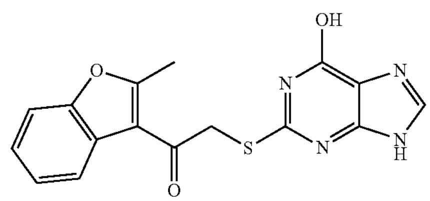 [SMILES: Cc1oc2ccccc2c1C(=O)CSc1nc(O)c2nc[nH]c2n1] | 2-[(6-hydroxy-9H-purin-2-yl)thio]-1-(2-methyl-1-benzofuran-3-yl)ethanone |
| 165 | 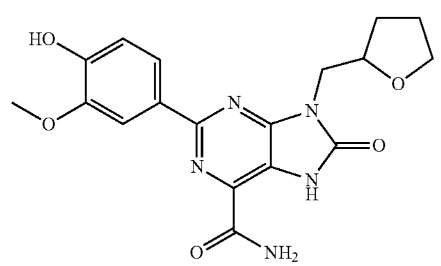 [SMILES: COc1cc(-c2nc(C(N)=O)c3[nH]c(=O)n(CC4CCCO4)c3n2)ccc1O] | 2-(4-hydroxy-3-methoxyphenyl)-8-oxo-9-(tetrahydrofuran-2-ylmethyl)-8,9-dihydro-7H-purine-6-carboxamide |
| 166 | 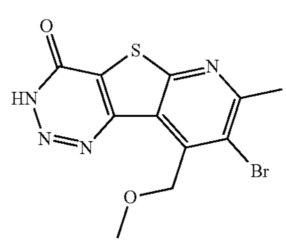 [SMILES: COCc1c(Br)c(C)nc2sc3c(=O)[nH]nnc3c12] | 8-bromo-9-(methoxymethyl)-7-methylpyrido[3',2':4,5]thieno[3,2-d][1,2,3]triazin-4(3H)-one |
| 167 | 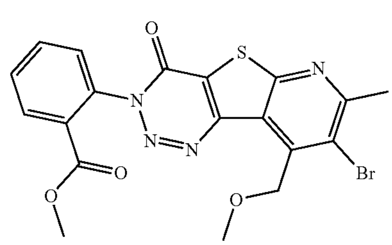 [SMILES: COCc1c(Br)c(C)nc2sc3c(=O)n(-c4ccccc4C(=O)OC)nnc3c12] | methyl 2-(8-bromo-9-(methoxymethyl)-7-methyl-4-oxopyrido[3',2':4,5]thieno[3,2-d][1,2,3]triazin-3(4H)-yl)benzoate |

TABLE 5-continued

Chemical names and structures of tested compounds

| Entry No. | Structure | Chemical name |
|---|---|---|
| 168 | 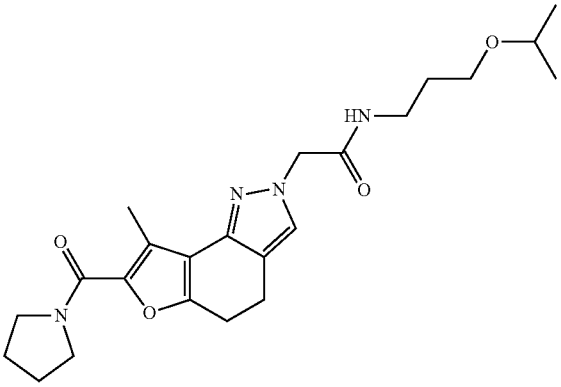 [SMILES: Cc1c(C(=O)N2CCCC2)oc2c1-c1nn(CC(=O)NCCCOC(C)C)cc1CC2] | 2-[8-methyl-7-(pyrrolidine-1-carbonyl)-4,5-dihydrofuro[2,3-g]indazol-2-yl]-N-(3-propan-2-yloxypropyl)acetamide |
| 169 | 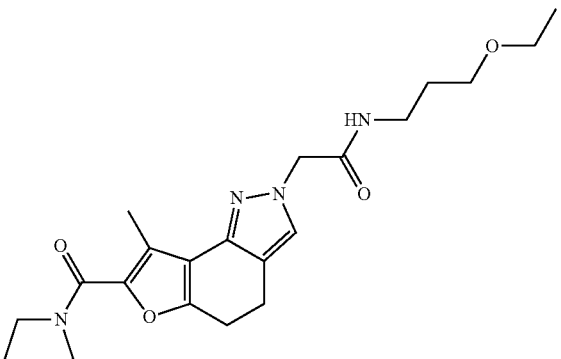 | N-(3-ethoxypropyl)-2-[8-methyl-7-(pyrrolidine-1-carbonyl)-4,5-dihydrofuro[2,3-g]indazol-2-yl]acetamide |
| 170 | 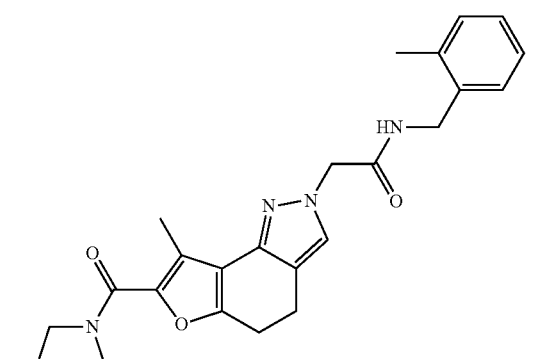 | N-[(2-methylphenyl)methyl]-2-[8-methyl-7-(pyrrolidine-1-carbonyl)-4,5-dihydrofuro[2,3-g]indazol-2-yl]acetamide |
| 171 | 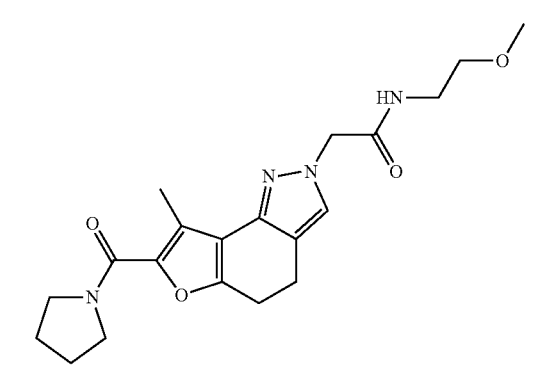 [SMILES: COCCNC(=O)Cn1cc2c(n1)-c1c(oc(C(=O)N3CCCC3)c1C)CC2] | N-(2-methoxyethyl)-2-[8-methyl-7-(pyrrolidine-1-carbonyl)-4,5-dihydrofuro[2,3-g]indazol-2-yl]acetamide |

TABLE 5-continued

Chemical names and structures of tested compounds

| Entry No. | Structure | Chemical name |
|---|---|---|
| 172 | 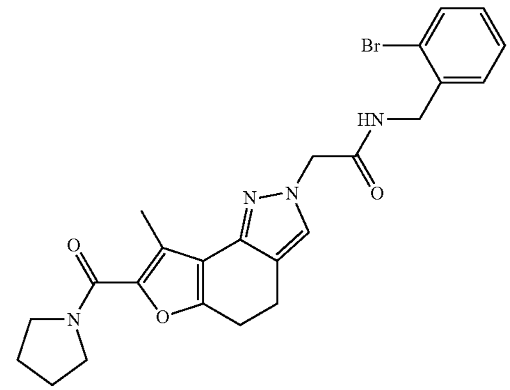 [SMILES: Cc1c(C(=O)N2CCCC2)oc2c1-c1nn(CC(=O)NCc3ccccc3Br)cc1CC2] | N-[(2-bromophenyl)methyl]-2-[8-methyl-7-(pyrrolidine-1-carbonyl)-4,5-dihydrofuro[2,3-g]indazol-2-yl]acetamide |
| 173 | 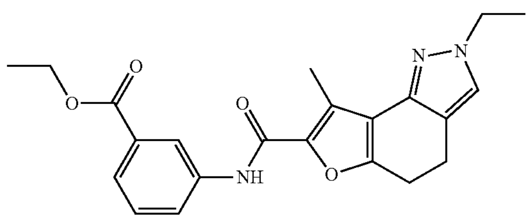 [SMILES: CCOC(=O)c1cccc(NC(=O)c2oc3c(c2C)-c2nn(CC)cc2CC3)c1] | ethyl 3-[(2-ethyl-8-methyl-4,5-dihydrofuro[2,3-g]indazole-7-carbonyl)amino]benzoate |
| 174 | 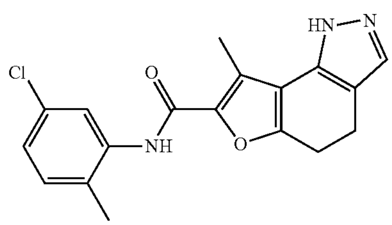 [SMILES: Cc1ccc(Cl)cc1NC(=O)c1oc2c(c1C)-c1[nH]ncc1CC2] | N-(5-chloro-2-methylphenyl)-8-methyl-4,5-dihydro-1H-furo[2,3-g]indazole-7-carboxamide |
| 175 | 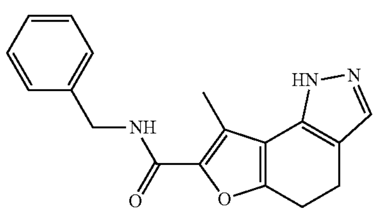 [SMILES: Cc1c(C(=O)NCc2ccccc2)oc2c1-c1[nH]ncc1CC2] | N-benzyl-8-methyl-4,5-dihydro-1H-furo[2,3-g]indazole-7-carboxamide |
| 176 | 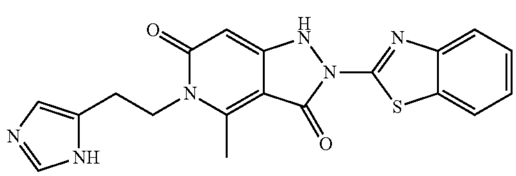 [SMILES: Cc1c2c(=O)n(-c3nc4ccccc4s3)[nH]c2cc(=O)n1CCc1cnc[nH]1] | 5-(2-(1H-imidazol-5-yl)ethyl)-2-(benzo[d]thiazol-2-yl)-4-methyl-1,2-dihydro-3H-pyrazolo[4,3-c]pyridine-3,6(5H)-dione |
| 177 | 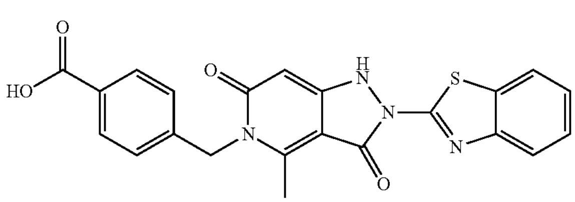 [SMILES: Cc1c2c(=O)n(-c3nc4ccccc4s3)[nH]c2cc(=O)n1Cc1ccc(C(=O)O)cc1] | 4-[[2-(1,3-benzothiazol-2-yl)-4-methyl-3,6-dioxo-1H-pyrazolo[4,3-c]pyridin-5-yl]methyl]benzoic acid |

TABLE 5-continued

Chemical names and structures of tested compounds

| Entry No. | Structure | Chemical name |
|---|---|---|
| 178 | 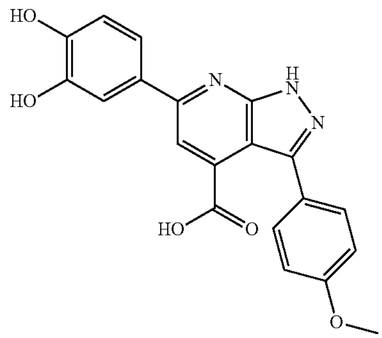 [SMILES: COc1ccc(-c2n[nH]c3nc(-c4ccc(O)c(O)c4)cc(C(=O)O)c23)cc1] | 6-(3,4-dihydroxyphenyl)-3-(4-methoxyphenyl)-1H-pyrazolo[3,4-b]pyridine-4-carboxylic acid |
| 179 | 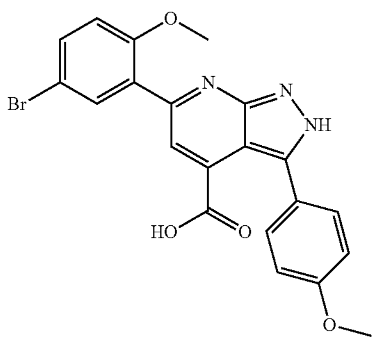 [SMILES: COc1ccc(-c2[nH]nc3nc(-c4cc(Br)ccc4OC)cc(C(=O)O)c23)cc1] | 6-(5-bromo-2-methoxyphenyl)-3-(4-methoxyphenyl)-2H-pyrazolo[3,4-b]pyridine-4-carboxylic acid |
| 180 | 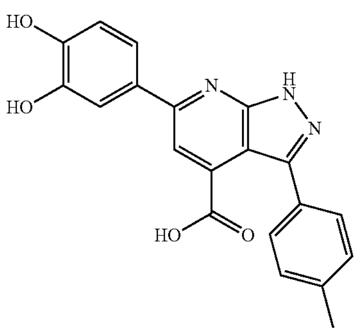 [SMILES: Cc1ccc(-c2n[nH]c3nc(-c4ccc(O)c(O)c4)cc(C(=O)O)c23)cc1] | 6-(3,4-dihydroxyphenyl)-3-(p-tolyl)-1H-pyrazolo[3,4-b]pyridine-4-carboxylic acid |
| 181 | 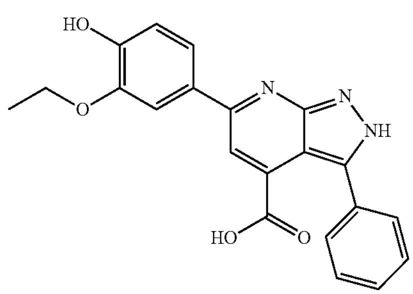 [SMILES: CCOc1cc(-c2cc(C(=O)O)c3c(-c4ccccc4)[nH]nc3n2)ccc1O] | 6-(3-ethoxy-4-hydroxyphenyl)-3-phenyl-2H-pyrazolo[3,4-b]pyridine-4-carboxylic acid |

TABLE 5-continued

Chemical names and structures of tested compounds

| Entry No. | Structure | Chemical name |
| --- | --- | --- |
| 182 | 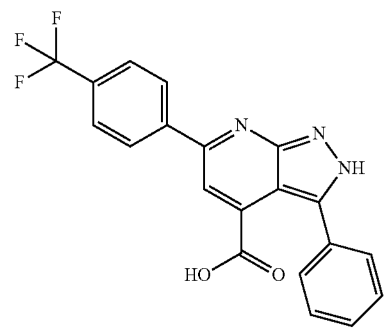 [SMILES: O=C(O)c1cc(-c2ccc(C(F)(F)F)cc2)nc2n[nH]c(-c3ccccc3)c12] | 3-phenyl-6-[4-(trifluoromethyl)phenyl]-2H-pyrazolo[3,4-b]pyridine-4-carboxylic acid |
| 183 | 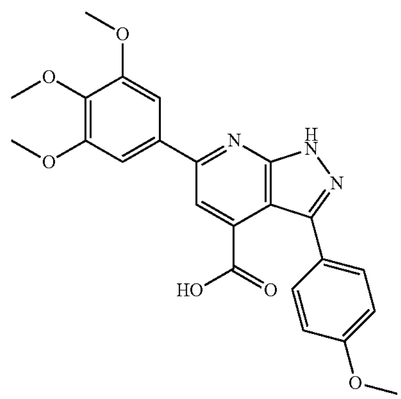 | 3-(4-methoxyphenyl)-6-(3,4,5-trimethoxyphenyl)-1H-pyrazolo[3,4-b]pyridine-4-carboxylic acid |
| 184 | 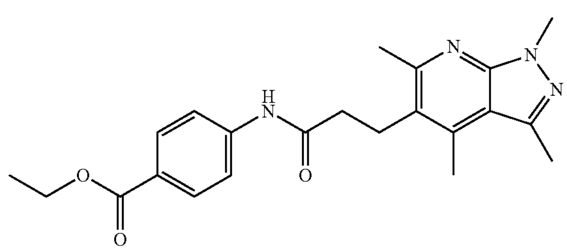 [SMILES: CCOC(=O)c1ccc(NC(=O)CCc2c(C)nc3c(c(C)nn3C)c2C)cc1] | ethyl 4-[3-(1,3,4,6-tetramethylpyrazolo[3,4-b]pyridin-5-yl)propanoylamino]benzoate |
| 185 | 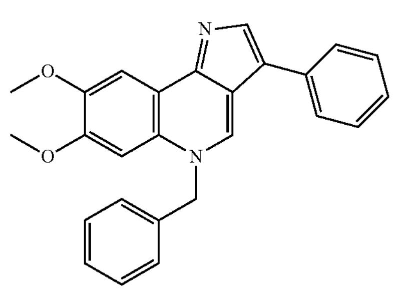 [SMILES: COc1cc2c3ncc(-c4ccccc4)c-3cn(Cc3ccccc3)c2cc1OC] | 5-benzyl-7,8-dimethoxy-3-phenyl-5H-pyrazolo[4,3-c]quinoline |
| 186 | 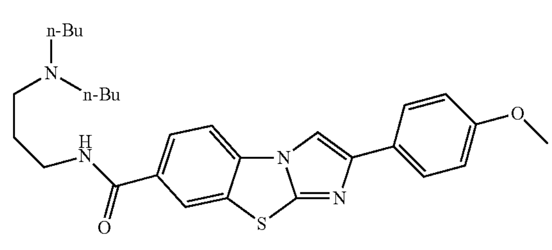 | N-[3-(dibutylamino)propyl]-2-(4-methoxyphenyl)imidazo[2,1-b][1,3]benzothiazole-7-carboxamide |

TABLE 5-continued

Chemical names and structures of tested compounds

| Entry No. | Structure | Chemical name |
|---|---|---|
| 187 | 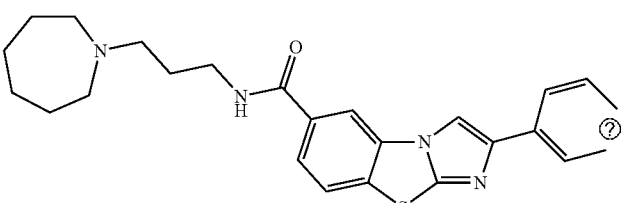 | N-[3-(azepan-1-yl)propyl]-2-(4-methylphenyl)imidazo[2,1-b][1,3]benzothiazole-6-carboxamide |
| 188 | 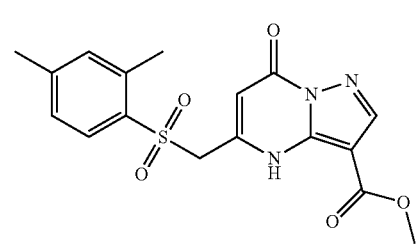 | Methyl 5-{[(2,4-dimethylphenyl)sulfonyl]methyl}-7-oxo-4,7-dihydropyrazolo[1,5-a]pyrimidine-3-carboxylate |
| 189 | 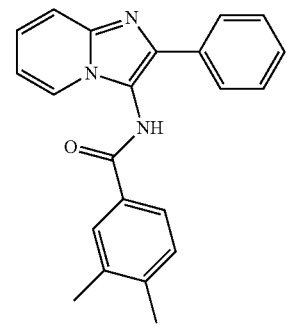 [SMILES: Cc1ccc(C(=O)Nc2c(-c3ccccc3)nc3ccccn23)cc1C] | 3,4-dimethyl-N-(2-phenylimidazo[1,2-a]pyridin-3-yl)benzamide |
| 190 | 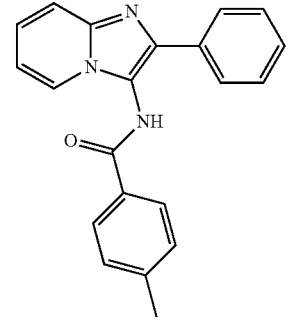 [SMILES: Cc1ccc(C(=O)Nc2c(-c3ccccc3)nc3ccccn23)cc1] | 4-methyl-N-(2-phenylimidazo[1,2-a]pyridin-3-yl)benzamide |
| 191 | 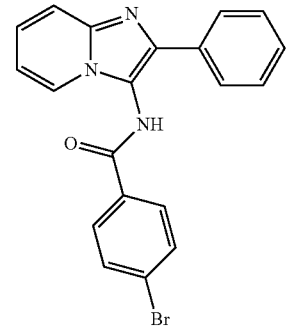 [SMILES: O=C(Nc1c(-c2ccccc2)nc2ccccn12)c1ccc(Br)cc1] | 4-bromo-N-(2-phenylimidazo[1,2-a]pyridin-3-yl)benzamide |

TABLE 5-continued

Chemical names and structures of tested compounds

| Entry No. | Structure | Chemical name |
|---|---|---|
| 192 | 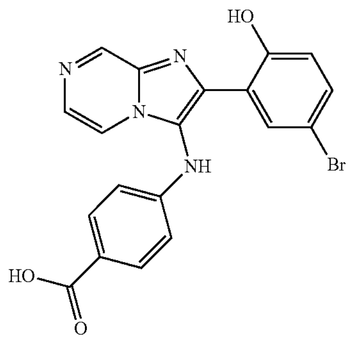 [SMILES: O=C(O)c1ccc(Nc2c(-c3cc(Br)ccc3O)nc3cnccn23)cc1] | 4-{[2-(5-bromo-2-hydroxyphenyl)imidazo[1,2-a]pyrazin-3-yl]amino}benzoic acid |
| 193 | 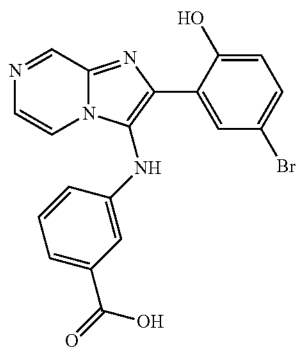 [SMILES: O=C(O)c1cccc(Nc2c(-c3cc(Br)ccc3O)nc3cnccn23)c1] | 3-{[2-(5-bromo-2-hydroxyphenyl)imidazo[1,2-a]pyrazin-3-yl]amino}benzoic acid |
| 194 | 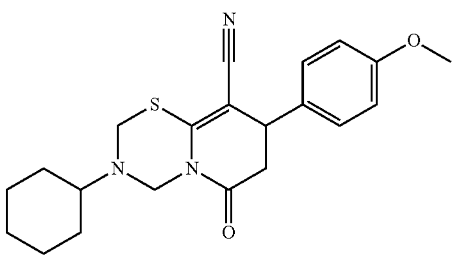 [SMILES: COc1ccc(C2CC(=O)N3CN(C4CCCCC4)CSC3=C2C#N)cc1] | 3-cyclohexyl-8-(4-methoxyphenyl)-6-oxo-3,4,7,8-tetrahydro-2H,6H-pyrido[2,1-b][1,3,5]thiadiazine-9-carbonitrile |
| 195 | 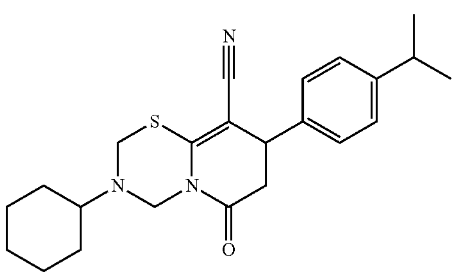 [SMILES: CC(C)c1ccc(C2CC(=O)N3CN(C4CCCCC4)CSC3=C2C#N)cc1] | 3-cyclohexyl-6-oxo-8-(4-propan-2-ylphenyl)-2,4,7,8-tetrahydropyrido[2,1-b][1,3,5]thiadiazine-9-carbonitrile |
| 196 | 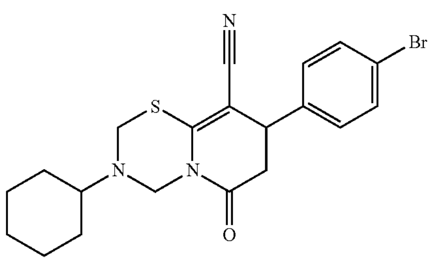 [SMILES: N#CC1=C2SCN(C3CCCCC3)CN2C(=O)CC1c1ccc(Br)cc1] | 8-(4-bromophenyl)-3-cyclohexyl-6-oxo-3,4,7,8-tetrahydro-2H,6H-pyrido[2,1-b][1,3,5]thiadiazine-9-carbonitrile |

TABLE 5-continued

Chemical names and structures of tested compounds

| Entry No. | Structure | Chemical name |
|---|---|---|
| 197 | 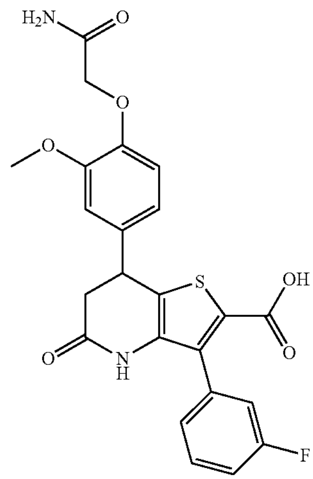 [SMILES: COc1cc(C2CC(=O)Nc3c2sc(C(=O)O)c3-c2cccc(F)c2)ccc1OCC(N)=O] | 7-[4-(2-amino-2-oxoethoxy)-3-methoxyphenyl]-3-(3-fluorophenyl)-5-oxo-4,5,6,7-tetrahydrothieno[3,2-b]pyridine-2-carboxylic acid |
| 198 | 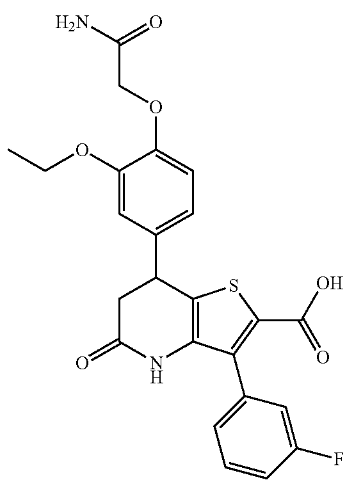 [SMILES: CCOc1cc(C2CC(=O)Nc3c2sc(C(=O)O)c3-c2cccc(F)c2)ccc1OCC(N)=O] | 7-[4-(2-amino-2-oxoethoxy)-3-ethoxyphenyl]-3-(3-fluorophenyl)-5-oxo-4,5,6,7-tetrahydrothieno[3,2-b]pyridine-2-carboxylic acid |
| 199 | 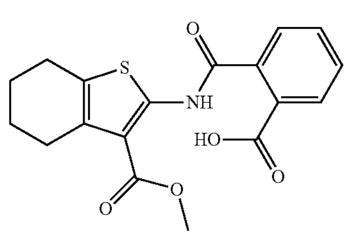 [SMILES: COC(=O)c1c(NC(=O)c2ccccc2C(=O)O)sc2c1CCCC2] | 2-({[3-(methoxycarbonyl)-4,5,6,7-tetrahydro-1-benzothien-2-yl]amino}carbonyl)benzoic acid |
| 200 | 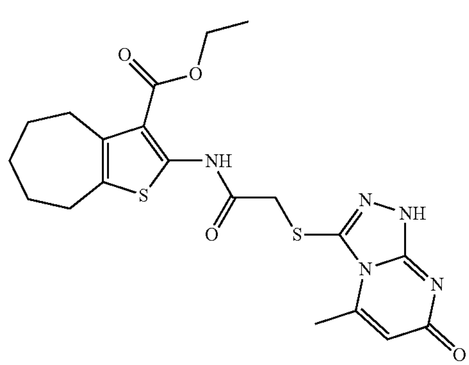 [SMILES: CCOC(=O)c1c(NC(=O)CSc2n[nH]c3nc(=O)cc(C)n23)sc2c1CCCCC2] | ethyl 2-[[2-[(5-methyl-7-oxo-1H-[1,2,4]triazolo[4,3-a]pyrimidin-3-yl)sulfanyl]acetyl]amino]-5,6,7,8-tetrahydro-4H-cyclohepta[b]thiophene-3-carboxylate |

TABLE 5-continued

Chemical names and structures of tested compounds

| Entry No. | Structure | Chemical name |
|---|---|---|
| 201 | 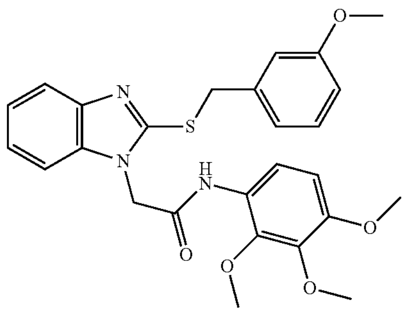 [SMILES: COc1cccc(CSc2nc3ccccc3n2CC(=O)Nc2ccc(OC)c(OC)c2OC)c1] | 2-[2-[(3-methoxyphenyl)methylsulfanyl]imidazo[4,5-c]pyridin-3-yl]-N-(2,3,4-trimethoxyphenyl)acetamide |
| 202 | 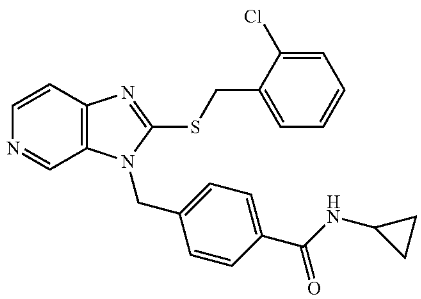 [SMILES: O=C(NC1CC1)c1ccc(Cn2c(SCc3ccccc3Cl)nc3ccncc32)cc1] | 4-({2-[(2-chlorobenzyl)thio]-3H-imidazo[4,5-c]pyridin-3-yl]methyl)-N-cyclopropylbenzamide |
| 203 | 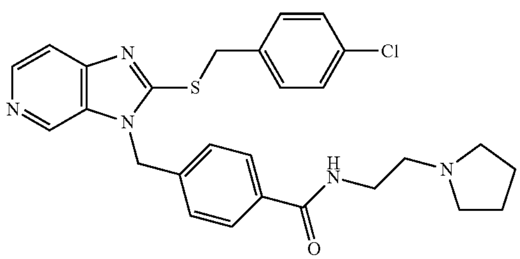 [SMILES: O=C(NCCN1CCCC1)c1ccc(Cn2c(SCc3ccc(Cl)cc3)nc3ccncc32)cc1] | 4-({2-[(4-chlorobenzyl)thio]-3H-imidazo[4,5-c]pyridin-3-yl}methyl)-N-(2-pyrrolidin-1-ylethyl)benzamide |
| 204 | 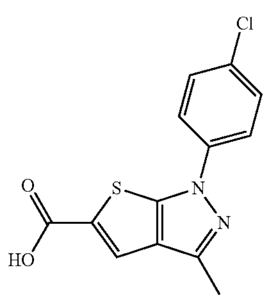 [SMILES: Cc1nn(-c2ccc(Cl)cc2)c2sc(C(=O)O)cc12] | 1-(4-Chloro-phenyl)-3-methyl-1H-thieno[2,3-c]pyrazole-5-carboxylic acid |
| 205 | 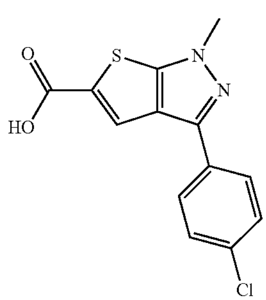 [SMILES: Cn1nc(-c2ccc(Cl)cc2)c2cc(C(=O)O)sc21] | 3-(4-chlorophenyl)-1-methylthieno[2,3-c]pyrazole-5-carboxylic acid |

TABLE 5-continued

Chemical names and structures of tested compounds

| Entry No. | Structure | Chemical name |
|---|---|---|
| 206 | 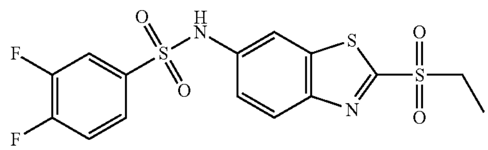 [SMILES: CCS(=O)(=O)c1nc2ccc(NS(=O)(=O)c3ccc(F)c(F)c3)cc2s1] | N-(2-(ethylsulfonyl)benzo[d]thiazol-6-yl)-3,4-difluorobenzenesulfonamide |
| 207 | 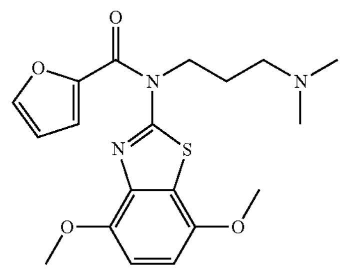 [SMILES: COc1ccc(OC)c2sc(N(CCCN(C)C)C(=O)c3ccco3)nc12] | N-(4,7-dimethoxy-1,3-benzothiazol-2-yl)-N-[3-(dimethylamino)propyl]furan-2-carboxamide |
| 208 | 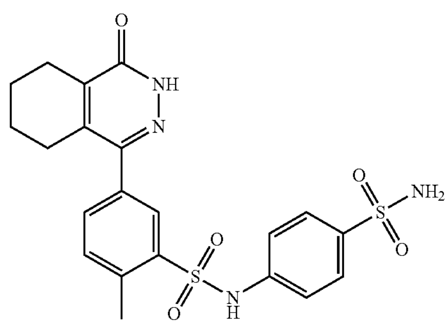 [SMILES: Cc1ccc(-c2n[nH]c(=O)c3c2CCCC3)cc1S(=O)(=O)Nc1ccc(S(N)(=O)=O)cc1] | N-[4-(aminosulfonyl)phenyl]-2-methyl-5-(4-oxo-3,4,5,6,7,8-hexahydrophthalazin-1-yl)benzenesulfonamide |
| 209 | 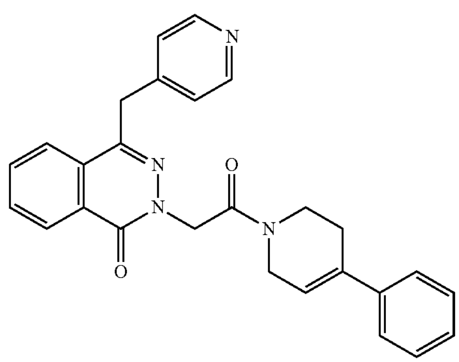 [SMILES: O=C(Cn1nc(Cc2ccncc2)c2ccccc2c1=O)N1CC=C(c2ccccc2)CC1] | 2-[2-oxo-2-(4-phenyl-3,6-dihydropyridin-1(2H)-yl)ethyl]-4-(pyridin-4-ylmethyl)phthalazin-1(2H)-one |
| 210 | 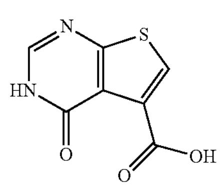 [SMILES: O=C(O)c1csc2nc[nH]c(=O)c12] | 4-Oxo-3,4-dihydrothieno[2,3-d]pyrimidine-5-carboxylic acid |
| 211 | 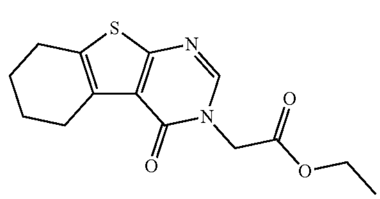 [SMILES: CCOC(=O)Cn1cnc2sc3c(c2c1=O)CCCC3] | Ethyl (4-oxo-5,6,7,8-tetrahydro[1]benzothieno[2,3-d]pyrimidin-3(4H)-yl)acetate |

TABLE 5-continued

Chemical names and structures of tested compounds

| Entry No. | Structure | Chemical name |
|---|---|---|
| 212 | 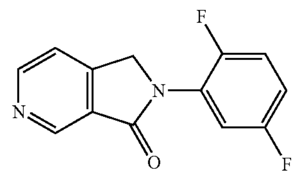 [SMILES: O=C1c2cnccc2CN1c1cc(F)ccc1F] | 2-(2,5-difluorophenyl)-1H-pyrrolo[3,4-c]pyridin-3-one |
| 213 | 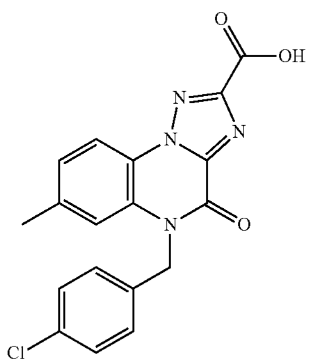 [SMILES: Cc1ccc2c(c1)n(Cc1ccc(Cl)cc1)c(=O)c1nc(C(=O)O)nn12] | 5-(4-chlorobenzyl)-7-methyl-4-oxo-4,5-dihydro[1,2,4]triazolo[1,5-a]quinoxaline-2-carboxylic acid |
| 214 | 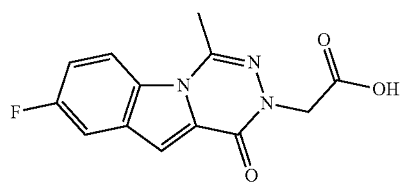 [SMILES: Cc1nn(CC(=O)O)c(=O)c2cc3cc(F)ccc3n12] | 2-(8-fluoro-4-methyl-1-oxo-[1,2,4]triazino[4,5-a]indol-2-yl)acetic acid |
| 215 | 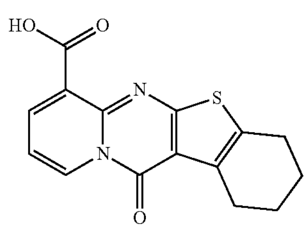 [SMILES: O=C(O)c1cccn2c(=O)c3c4c(sc3nc12)CCCC4] | 12-oxo-1,2,3,4-tetrahydro-12H-[1]benzothieno[2,3-d]pyrido[1,2-a]pyrimidine-7-carboxylic acid |
| 216 | 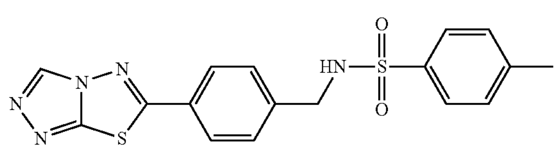 [SMILES: Cc1ccc(S(=O)(=O)NCc2ccc(-c3nn4cnnc4s3)cc2)cc1] | 4-methyl-N-[[4-([1,2,4]triazolo[3,4-b][1,3,4]thiadiazol-6-yl)phenyl]methyl]benzenesulfonamide |
| 217 | 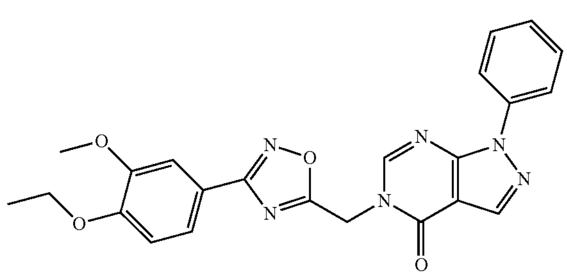 [SMILES: CCOc1ccc(-c2noc(Cn3cnc4c(cnn4-c4ccccc4)c3=O)n2)cc1OC] | 5-[[3-(4-ethoxy-3-methoxyphenyl)-1,2,4-oxadiazol-5-yl]methyl]-1-phenylpyrazolo[3,4-d]pyrimidin-4-one |

TABLE 5-continued

Chemical names and structures of tested compounds

| Entry No. | Structure | Chemical name |
|---|---|---|
| 218 | 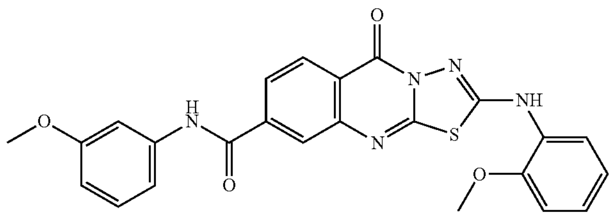 [SMILES: COc1cccc(NC(=O)c2ccc3c(=O)n4nc(Nc5ccccc5OC)sc4nc3c2)c1] | 2-(2-methoxyanilino)-N-(3-methoxyphenyl)-5-oxo-[1,3,4]thiadiazolo[2,3-b]quinazoline-8-carboxamide |
| 219 | 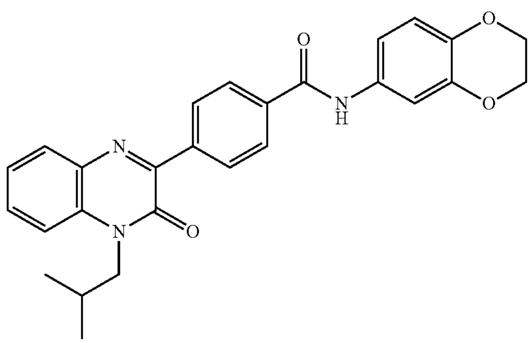 [SMILES: CC(C)Cn1c(=O)c(-c2ccc(C(=O)Nc3ccc4c(c3)OCCO4)cc2)nc2ccccc21] | N-(2,3-dihydro-1,4-benzodioxin-6-yl)-4-[4-(2-methylpropyl)-3-oxoquinoxalin-2-yl]benzamide |
| 220 | 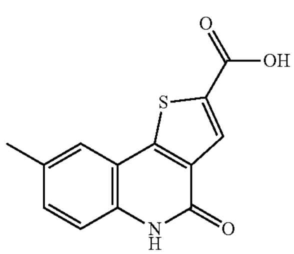 [SMILES: Cc1ccc2[nH]c(=O)c3cc(C(=O)O)sc3c2c1] | 8-methyl-4-oxo-5H-thieno[3,2-c]quinoline-2-carboxylic acid |
| 221 | 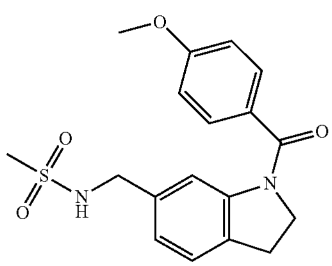 [SMILES: COc1ccc(C(=O)N2CCc3ccc(CNS(C)(=O)=O)cc32)cc1] | N-[[1-(4-methoxybenzoyl)-2,3-dihydroindol-6-yl]methyl]methanesulfonamide |
| 222 | 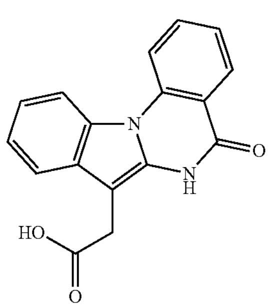 [SMILES: O=C(O)Cc1c2ccccc2n2c1[nH]c(=O)c1ccccc12] | 2-(5-oxo-6H-indolo[1,2-a]quinazolin-7-yl)acetic acid |

TABLE 5-continued

Chemical names and structures of tested compounds

| Entry No. | Structure | Chemical name |
|---|---|---|
| 223 | 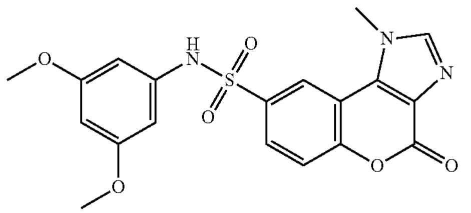 [SMILES: COc1cc(NS(=O)(=O)c2ccc3oc(=O)c4ncn(C)c4c3c2)cc(OC)c1] | N-(3,5-dimethoxyphenyl)-1-methyl-4-oxochromeno[3,4-d]imidazole-8-sulfonamide |
| 224 | 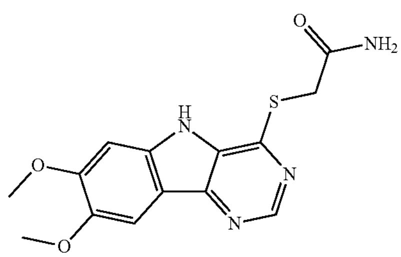 [SMILES: COc1cc2[nH]c3c(SCC(N)=O)ncnc3c2cc1OC] | 2-[(7,8-dimethoxy-5H-pyrimido[5,4-b]indol-4-yl)sulfanyl]acetamide |
| 225 | 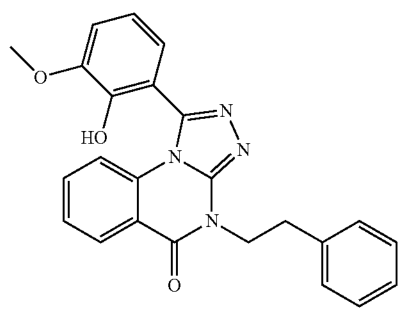 [SMILES: COc1cccc(-c2nnc3n(CCc4ccccc4)c(=O)c4ccccc4n23)c1O] | (1Z)-1-(5-methoxy-6-oxocyclohexa-2,4-dien-1-ylidene)-4-(2-phenylethyl)-2H-[1,2,4]triazolo[4,3-a]quinazolin-5-one |
| 226 | 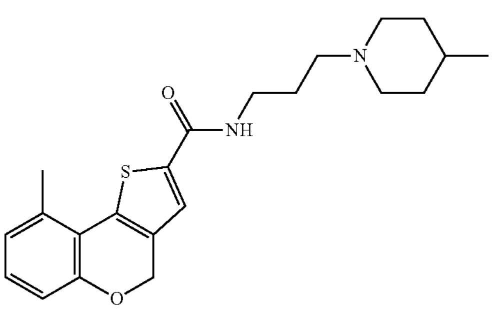 [SMILES: Cc1cccc2c1-c1sc(C(=O)NCCCN3CCC(C)CC3)cc1CO2] | 9-methyl-N-[3-(4-methylpiperidin-1-yl)propyl]-4H-thieno[3,2-c]chromene-2-carboxamide |
| 227 | 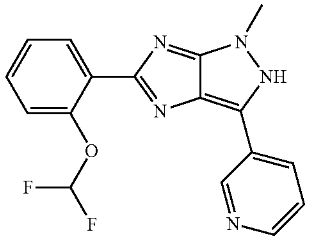 [SMILES: Cn1[nH]c(-c2cccnc2)c2nc(-c3ccccc3OC(F)F)nc1-2] | 5-[2-(difluoromethoxy)phenyl]-1-methyl-3-pyridin-3-yl-2H-imidazo[4,5-c]pyrazole |

TABLE 5-continued

Chemical names and structures of tested compounds

| Entry No. | Structure | Chemical name |
|---|---|---|
| 228 | 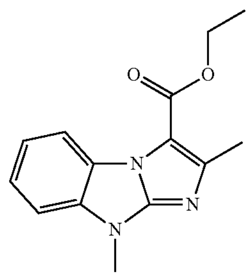 [SMILES: CCOC(=O)c1c(C)nc2n(C)c3ccccc3n12] | ethyl 2,9-dimethyl-9H-benzo[d]imidazo[1,2-a]imidazole-3-carboxylate |
| 229 | 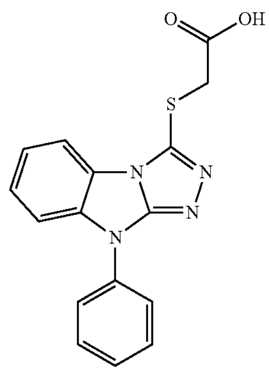 [SMILES: O=C(O)CSc1nnc2n(-c3ccccc3)c3ccccc3n12] | [(9-Phenyl-9H-[1,2,4]triazolo[4,3-a]benzimidazol-3-yl)thio]acetic acid |
| 230 | 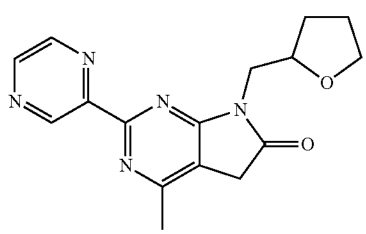 [SMILES: Cc1nc(-c2cnccn2)nc2c1CC(=O)N2CC1CCCO1] | 4-methyl-2-(2-pyrazinyl)-7-(tetrahydro-2-furanylmethyl)-5,7-dihydro-6H-pyrrolo[2,3-d]pyrimidin-6-one |
| 231 | 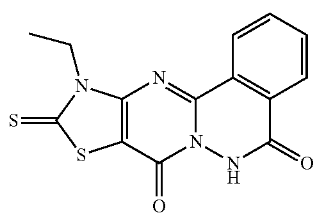 [SMILES: CCn1c(=S)sc2c(=O)n3[nH]c(=O)c4ccccc4c3nc21] | 11-ethyl-10-thioxo-10,11-dihydro-6H-[1,3]thiazolo[4',5':4,5]pyrimido[2,1-a]phthalazine-5,8-dione |
| 232 | 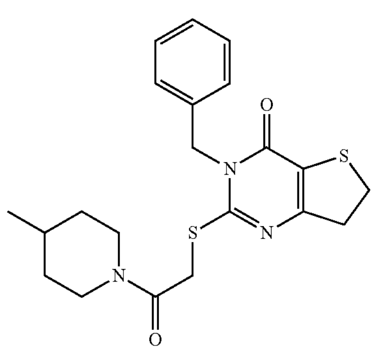 [SMILES: CC1CCN(C(=O)CSc2nc3c(c(=O)n2Cc2ccccc2)SCC3)CC1] | 3-benzyl-2-((2-(4-methylpiperidin-1-yl)-2-oxoethyl)thio)-6,7-dihydrothieno[3,2-d]pyrimidin-4(3H)-one |

TABLE 5-continued

Chemical names and structures of tested compounds

| Entry No. | Structure | Chemical name |
|---|---|---|
| 233 | 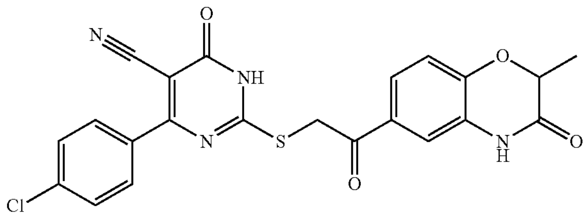 [SMILES: CC1Oc2ccc(C(=O)CSc3nc(-c4ccc(Cl)cc4)c(C#N)c(=O)[nH]3)cc2NC1=O] | 4-(4-chlorophenyl)-2-{[2-(2-methyl-3-oxo-3,4-dihydro-2H-1,4-benzoxazin-6-yl)-2-oxoethyl]sulfanyl}-6-oxo-1,6-dihydro-5-pyrimidinecarbonitrile |
| 234 | 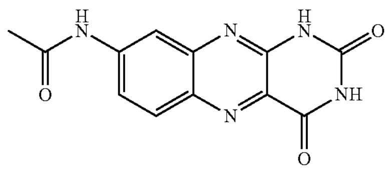 [SMILES: CC(=O)Nc1ccc2nc3c(=O)[nH]c(=O)[nH]c3nc2c1] | N-(2,4-dioxo-1H-benzo[g]pteridin-8-yl)acetamide |
| 235 | 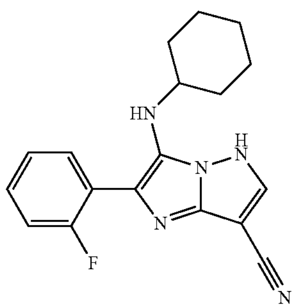 [SMILES: N#Cc1c[nH]n2c(NC3CCCCC3)c(-c3ccccc3F)nc12] | 3-(cyclohexylamino)-2-(2-fluorophenyl)-5H-imidazo[1,2-b]pyrazole-7-carbonitrile |
| 236 | 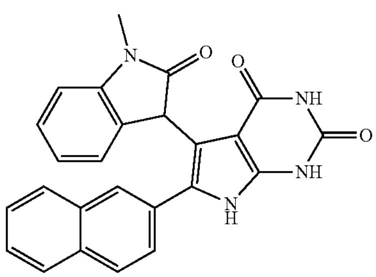 [SMILES: CN1C(=O)C(c2c(-c3ccc4ccccc4c3)[nH]c3[nH]c(=O)[nH]c(=O)c23)c2ccccc21] | 5-(1-methyl-2-oxo-2,3-dihydro-1H-indol-3-yl)-6-(2-naphthyl)-1H-pyrrolo[2,3-d]pyrimidine-2,4(3H,7H)-dione |
| 237 | 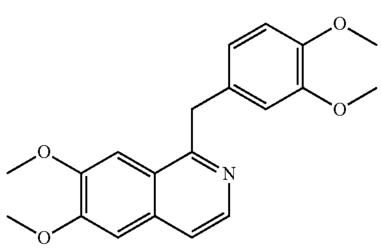 | 1-(3,4-dimethoxybenzyl)-6,7-dimethoxyisoquinoline |
| 238 | 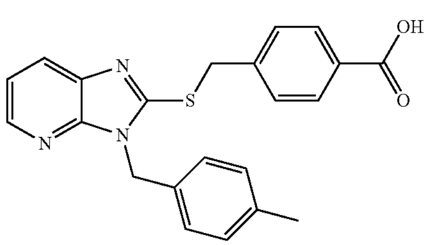 [SMILES: Cc1ccc(Cn2c(SCc3ccc(C(=O)O)cc3)nc3cccnc32)cc1] | 4-[[3-[(4-methylphenyl)methyl]imidazo[4,5-b]pyridin-2-yl]sulfanylmethyl]benzoic acid |

TABLE 5-continued

Chemical names and structures of tested compounds

| Entry No. | Structure | Chemical name |
|---|---|---|
| 239 | 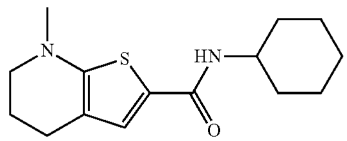 [SMILES: CN1CCCc2cc(C(=O)NC3CCCCC3)sc21] | N~2~cyclohexyl-7-methyl-4,5,6,7-tetrahydrothieno[2,3-b]pyridine-2-carboxamide |
| 240 | 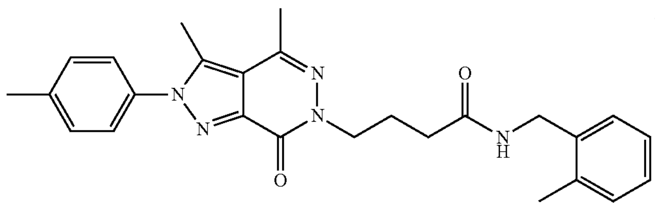 [SMILES: Cc1ccc(-n2nc3c(=O)n(CCCC(=O)NCc4ccccc4C)nc(C)c3c2C)cc1] | 4-[3,4-dimethyl-2-(4-methylphenyl)-7-oxopyrazolo[3,4-d]pyridazin-6-yl]-N-[(2-methylphenyl)methyl]butanamide |
| 241 | 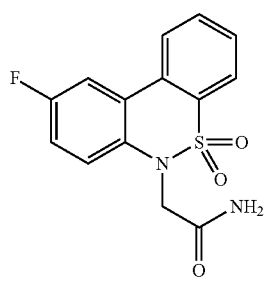 [SMILES: NC(=O)CN1c2ccc(F)cc2-c2ccccc2S1(=O)=O] | 2-(9-fluoro-5,5-dioxido-6H-dibenzo[c,e][1,2]thiazin-6-yl)acetamide |
| 242 | 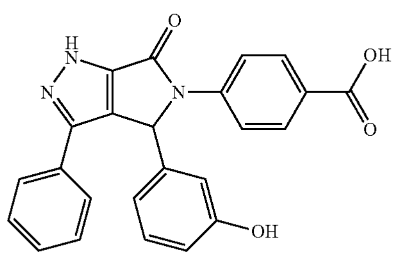 [SMILES: O=C(O)c1ccc(N2C(=O)c3[nH]nc(-c4ccccc4)c3C2c2cccc(O)c2)cc1] | 4-[4-(3-hydroxyphenyl)-6-oxo-3-phenyl-1,4-dihydropyrrolo[3,4-c]pyrazol-5-yl]benzoic acid |
| 243 | 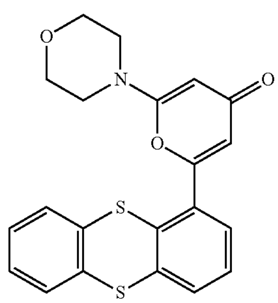 [SMILES: O=c1cc(-c2cccc3c2Sc2ccccc2S3)oc(N2CCOCC2)c1] | 2-morpholin-4-yl-6-thianthren-1-ylpyran-4-one |
| 244 | 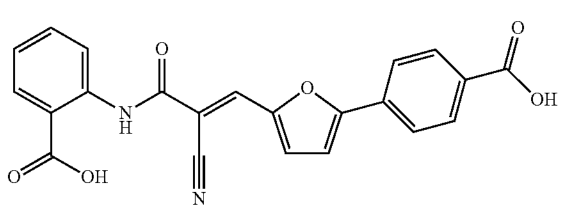 [SMILES: N#C/C(=C\c1ccc(-c2ccc(C(=O)O)cc2)o1)C(=O)Nc1ccccc1C(=O)O] | 2-[[(E)-3-[5-(4-carboxyphenyl)furan-2-yl]-2-cyanoprop-2-enoyl]amino]benzoic acid |

TABLE 5-continued

Chemical names and structures of tested compounds

| Entry No. | Structure | Chemical name |
|---|---|---|
| 245 | 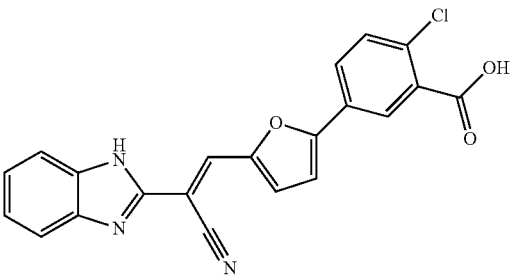 [SMILES: N#C/C(=C\c1ccc(-c2ccc(Cl)c(C(=O)O)c2)o1)c1nc2ccccc2[nH]1] | 5-[5-[(E)-2-(1H-benzimidazol-2-yl)-2-cyanoethenyl]furan-2-yl]-2-chlorobenzoic acid |

Example 11

Figure 14:
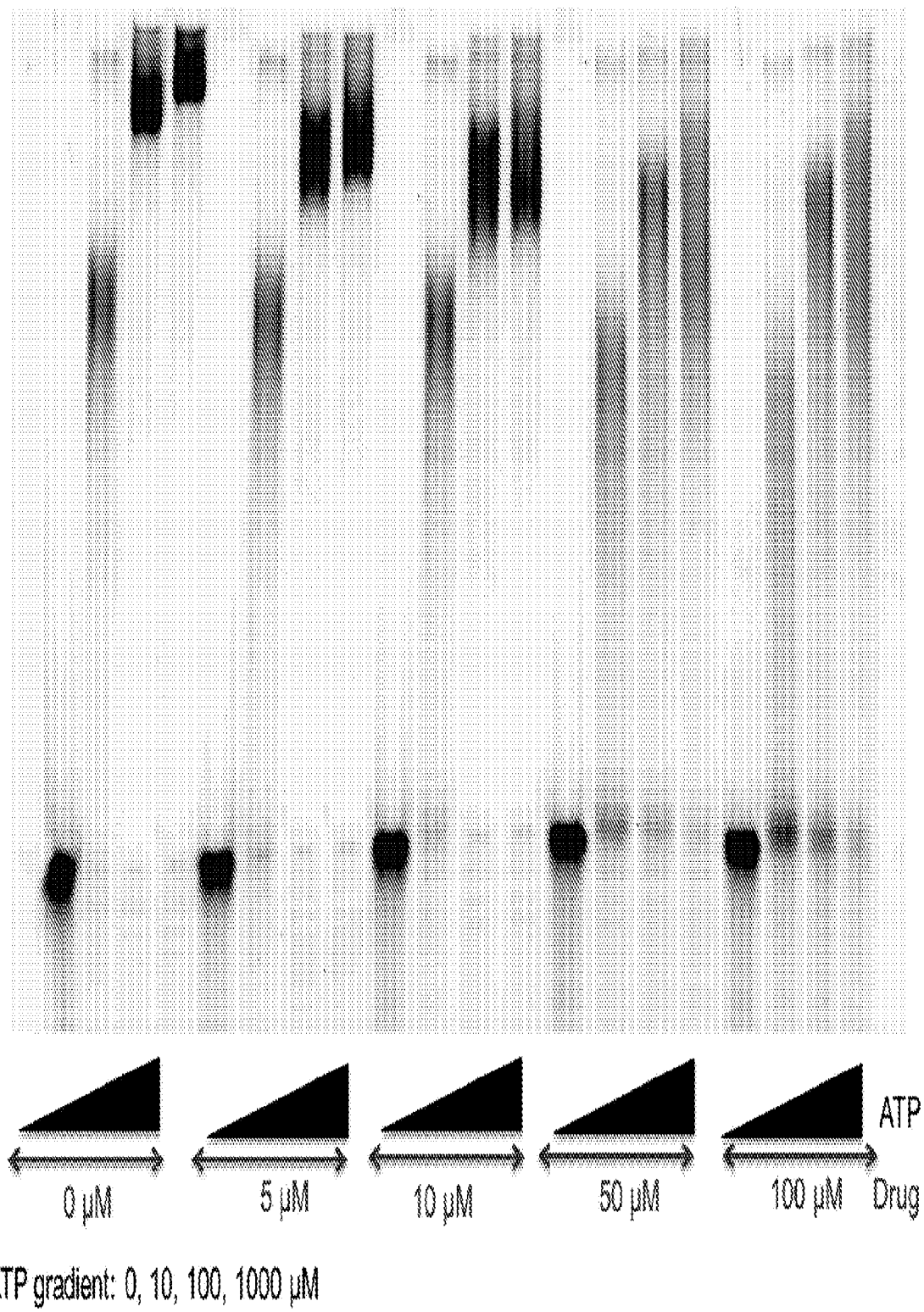
FIG. 14 shows the results of dose response of 2-[[3-ethoxycarbonyl-6-(trifluoromethoxy) quinolin-4-yl]amino]benzoic acid (Table 5, Entry 1) vs ATP in the PAPD5 oligonucleotide extension assay.
Figure 15:
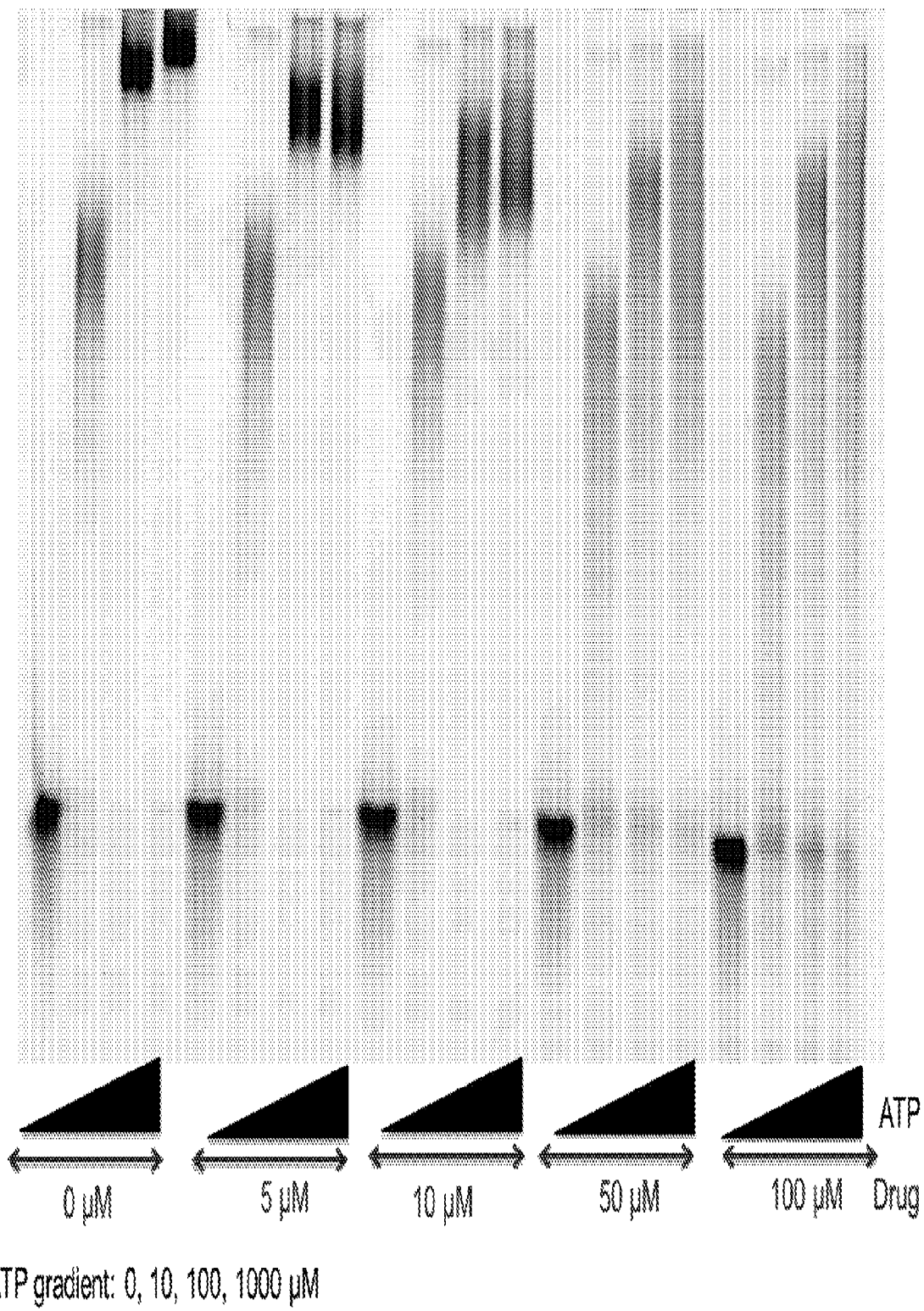
FIG. 15 shows the results of dose response of 1-[3-(3,4-dimethylbenzoyl)-6-ethylquinolin-4-yl]piperidine-4-carboxamide (Table 5, Entry 2) vs ATP in the PAPD5 oligonucleotide extension assay.
Figure 16:
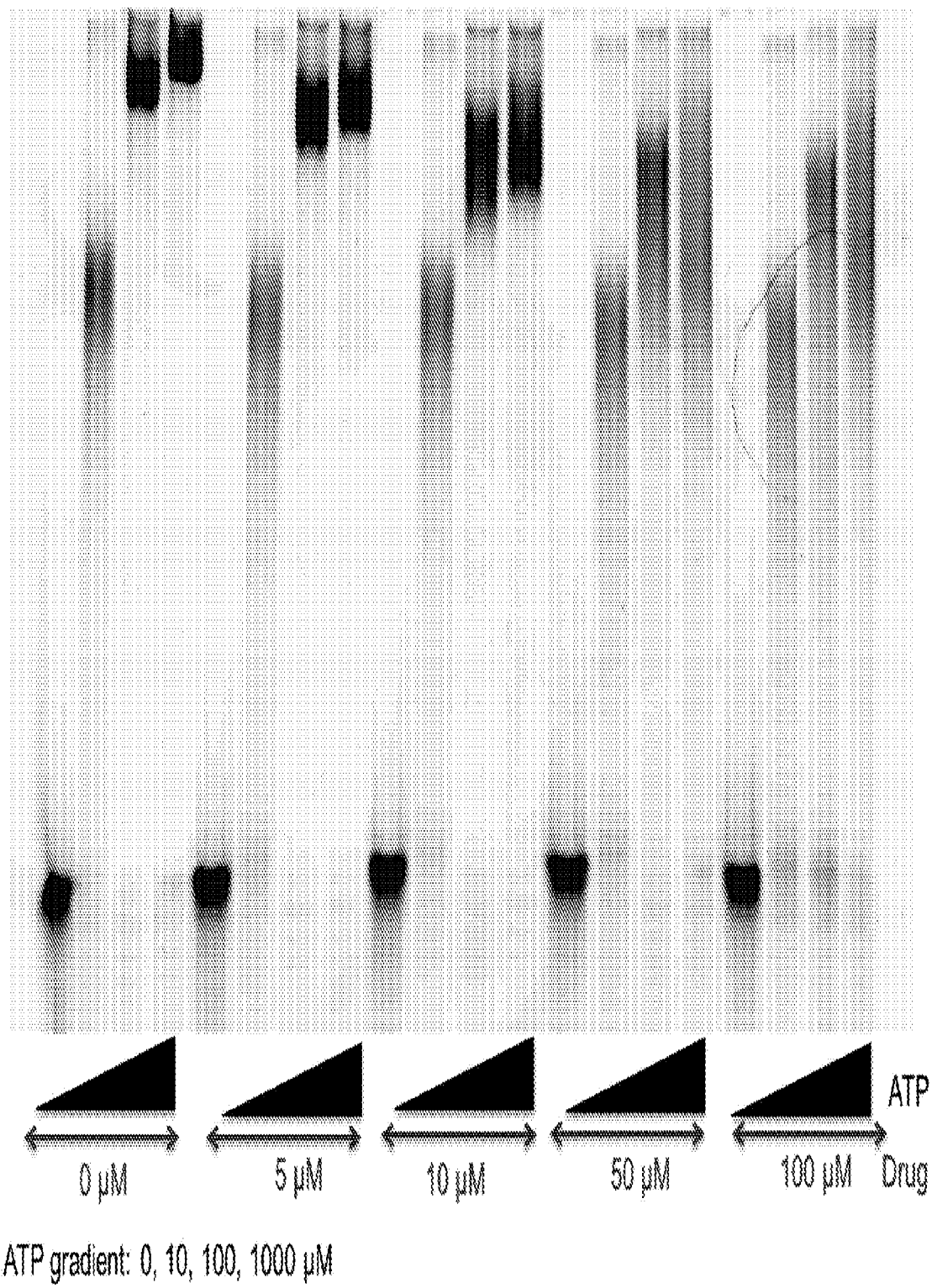
FIG. 16 shows the results of dose response of 2-[[(E)-3-[5-(4-carboxyphenyl) furan-2-yl]-2-cyanoprop-2-enoyl] amino]benzoic acid (Table 5, Entry 244) vs ATP in the PAPD5 oligonucleotide extension assay.

FIGS. 14, 15, and 16 show images of gels demonstrating results of dose response of compound corresponding to entry 1 in Table 5 (FIG. 6), compound corresponding to entry 2 in Table 5 (FIG. 7), and compound corresponding to entry 244 in Table 5 (FIG. 8) vs ATP in the PAPD5 oligonucleotide extension assay. Each compound tested in the assay was tested at 0 µM, 5 µM, 10 µM, 50 µM, and 100 µM. At each concentration, each compound was tested at 0 µM, 10 µM, 100 µM, and 1000 µM concentration of ATP. The assay shows that the tested compounds are active at less than 10 µM concentration.

Example 12

Figure 17:
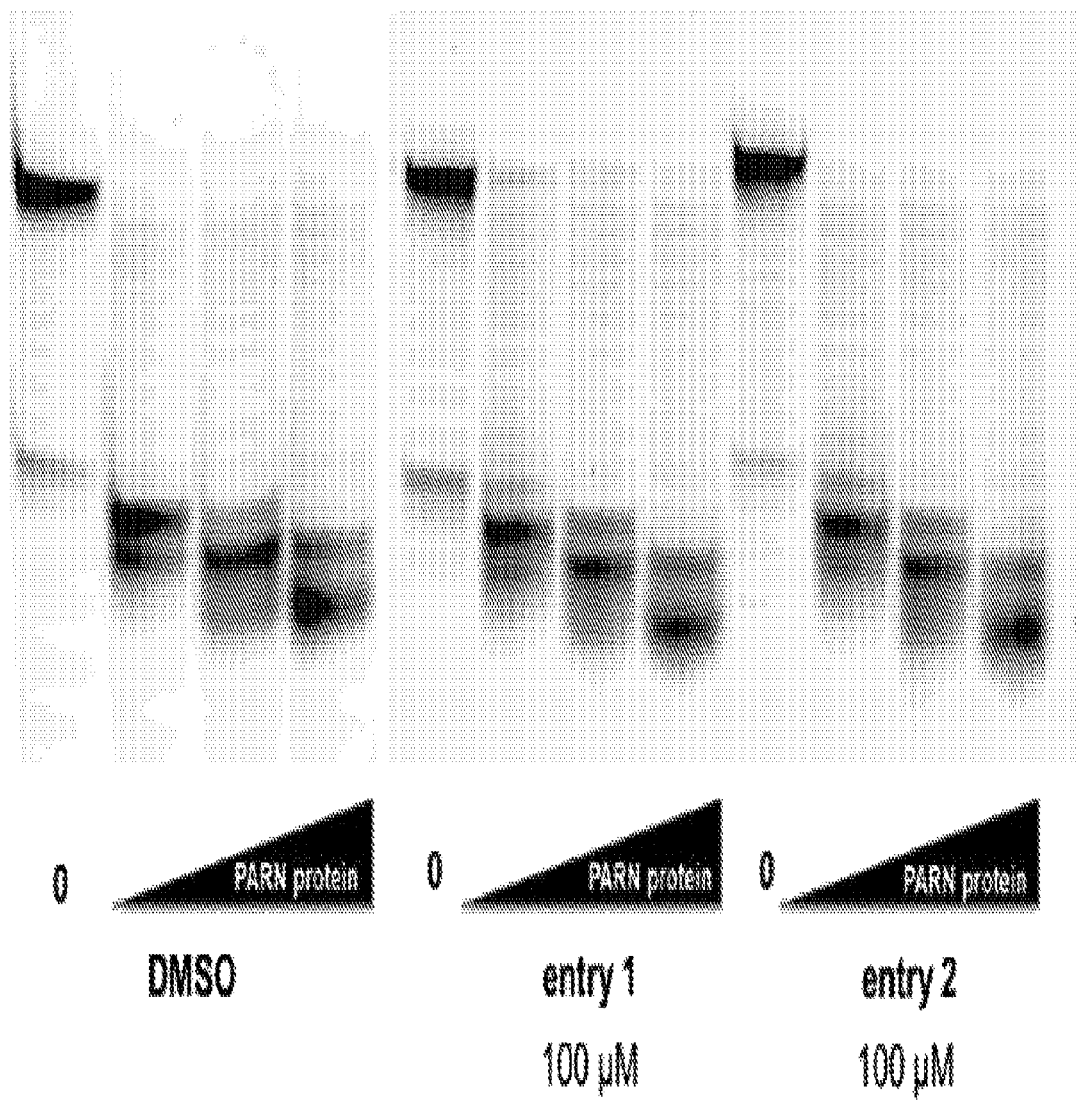
FIG. 17 shows that (2-[[3-ethoxycarbonyl-6-(trifluoromethoxy) quinolin-4-yl]amino]benzoic acid) (Table 5, Entry 1) and (1-[3-(3,4-dimethylbenzoyl)-6-ethylquinolin-4-yl]piperidine-4-carboxamide) (Table 5, Entry 2) do not inhibit PARN exonuclease.
Figure 18:
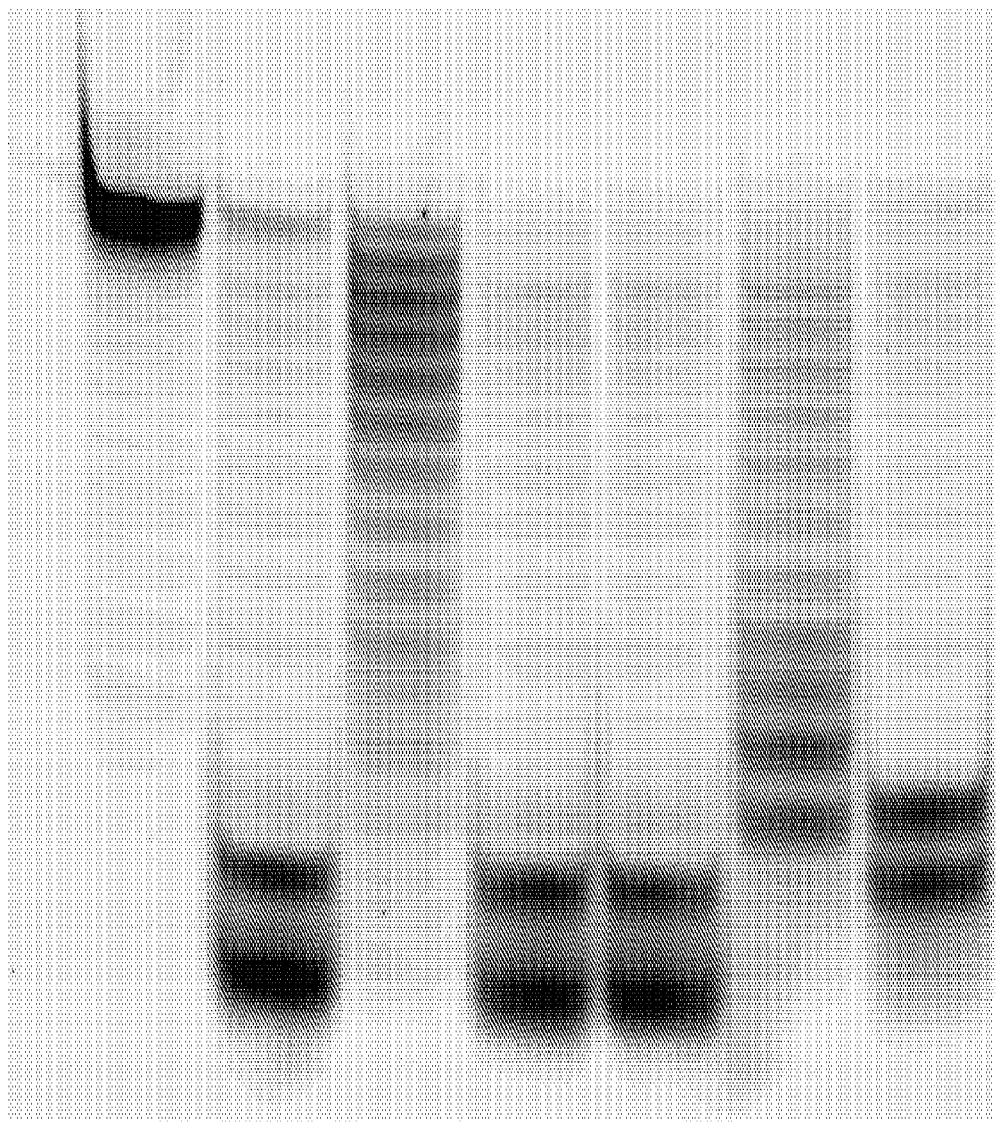
FIG. 18 shows results of counter-screen to identify compounds that do not inhibit PARN exonuclease (compounds corresponding to entries 1 and 2, Table 5).

FIGS. 17 and 18 show that compounds corresponding to entries 1 and 2 in Table 5 do not inhibit PARN. Although PARN and PAPD5 have opposing functions in TERC maturation and stabilization, PARN and PAPD5 are structurally related, and so molecules that inhibit one enzyme may inhibit the other. The tested compounds inhibit PAPD5 but do not inhibit PARN.

FIG. 19 shows validating the tested compounds for further development, (a) and (b) show interrogation of TERC 3' end maturation, which correlates completely with prior genetic data and TERC stabilization, TERC levels and telomere restoration. At 10 UM and 100 µM, in PARN-deficient human cells, compound corresponding to entry 1 in table 1 shows restoration of TERC maturation that is similar to that achieved by PAPD5 knockdown (panel B). Panel (a) shows strategy for 3' rapid amplification of cDNA ends (RACE). Panel (b) shows agarose gel electrophoresis of 3' RACE TERC products from HEK 293 cells transduced with lentivirus encoding shRNA against PAPD5, PARN or luciferase (ctrl). The expected amplicons representing mature TERC versus extended forms are indicated (arrows). Panel (c) shows dose-responsive restoration of TERC 3' end processing by the putative PAPD5 inhibitor (2-[[3-ethoxy-carbonyl-6-(trifluoromethoxy) quinolin-4-yl]amino]benzoic acid) (Table 5, entry 1). HEK 293 with stable shRNA-mediated knockdown of PARN were treated for 7 days with the Table 5, entry 1 compound.

Example 13

Figure 20:
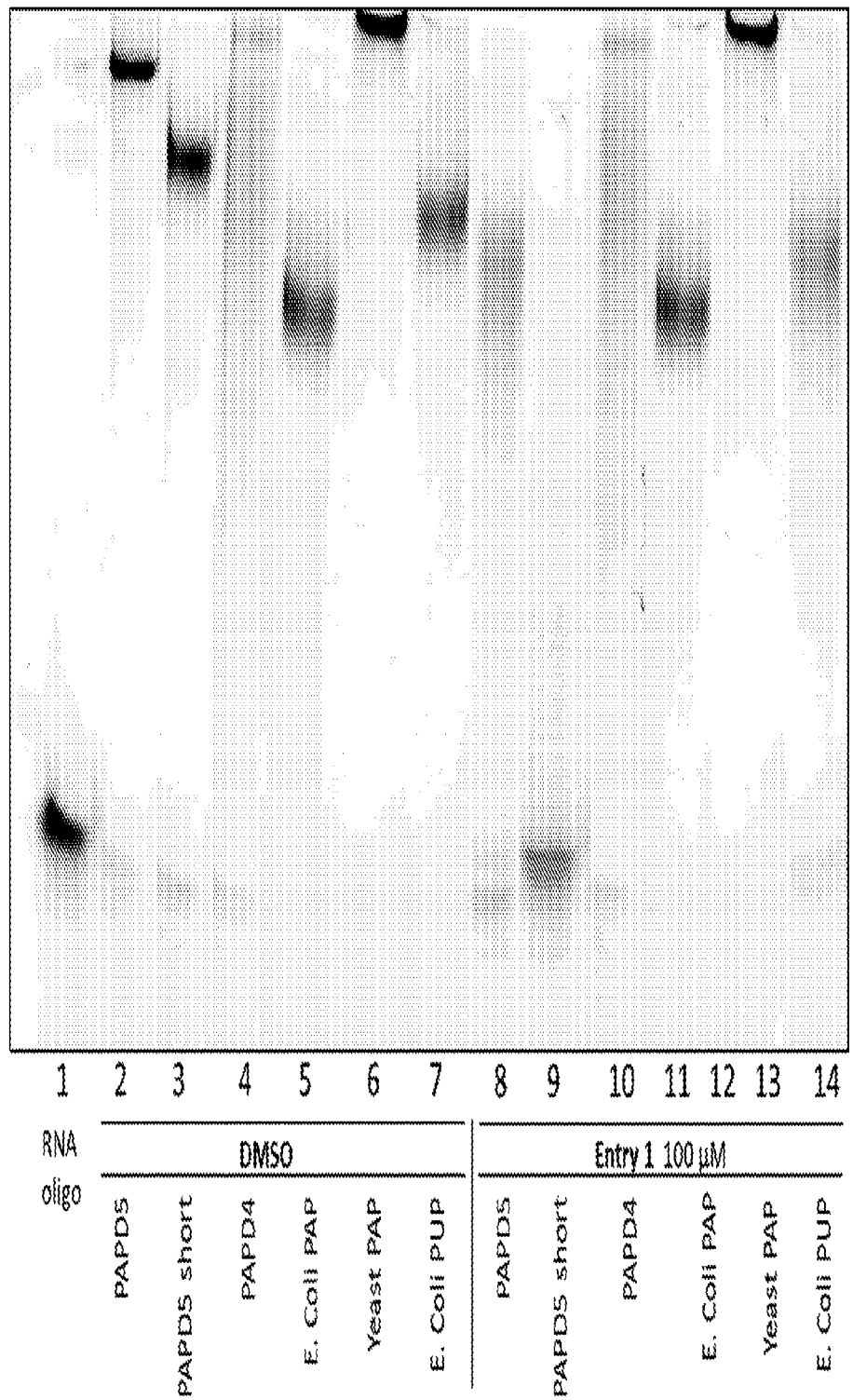
FIG. 20 shows specificity of compound 2-[[3-ethoxycarbonyl-6-(trifluoromethoxy) quinolin-4-yl]amino]benzoic acid (Table 5, Entry 1) for PAPD5 inhibition in oligo extension assay, compared to four other polynucleotide polymerases.

FIG. 19 shows specificity of compound corresponding to entry 1 in Table 5 for PAPD5 inhibition in oligo extension assay, compared to four other polynucleotide polymerases. Referring to FIG. 20, specific inhibition of PAPD5 (compare lanes 2 and 8) and "PAPD5 short" (compare lanes 3 and 9) by Entry 1, as opposed to PAPD4, E. Coli PAP, Yeast PAP, and E. Coli PUP.

PAPD5 short: Active truncation mutant of human PAPD5
PAPD4: human non-canonical poly(A) polymerase
E. Coli PAP: E. Coli canonical poly(A) polymerase
Yeast PAP: Yeast canonical poly(A) polymerase
E. Coli PUP: E. Coli canonical poly(U) polymerase—can use UTP or ATP as substrate

Example 15

The compounds described herein are specific and selective inhibitors of PAPD5. For example, the PAPD5 inhibitors of the present disclosure do not inhibit PARN or other polynucleotide polymerases.

Figure 21:
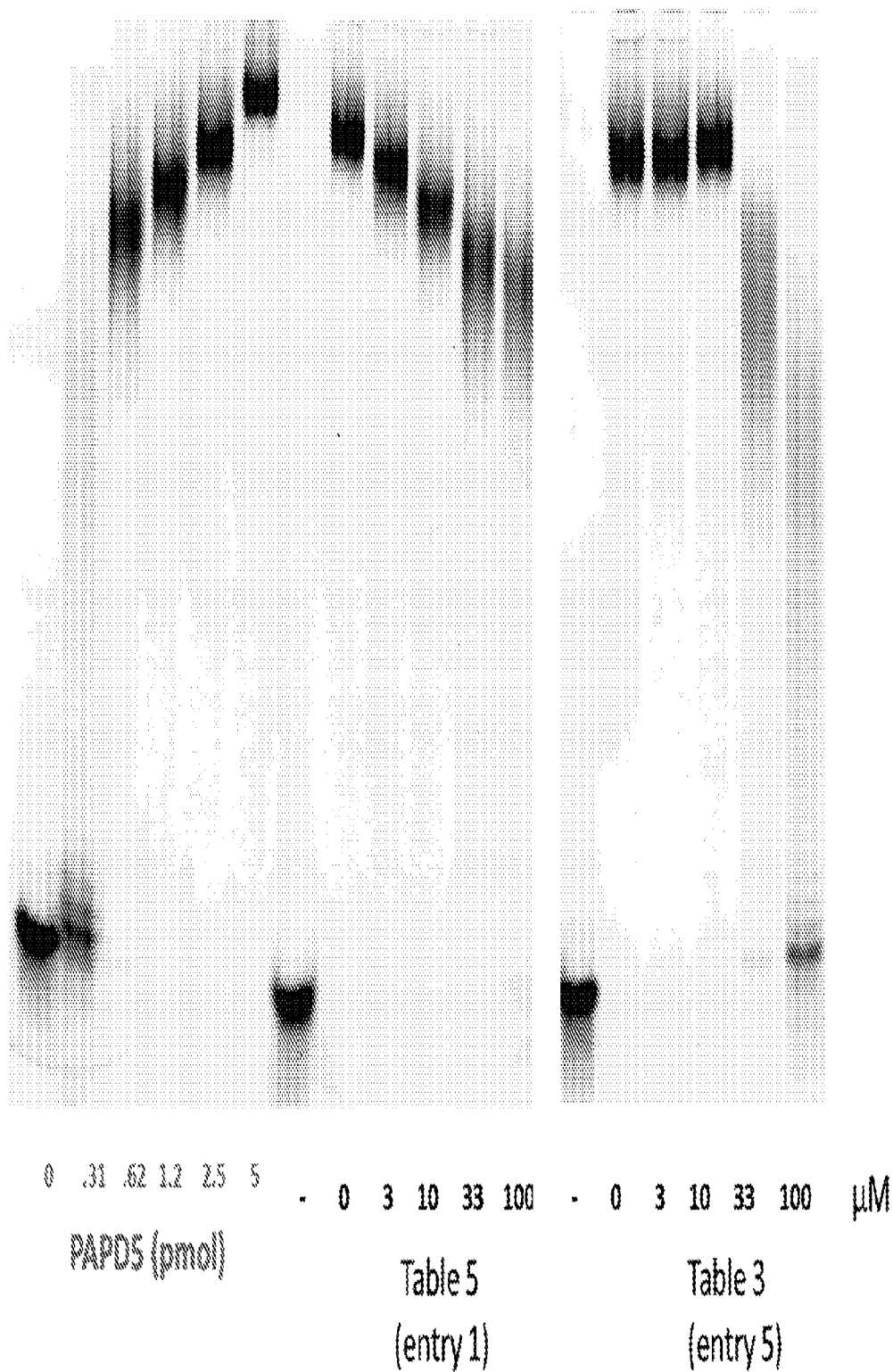
FIG. 21 shows inhibition of rPAPD5 in vitro by compound of table 5 (entry 1) and table 3 (entry 5).
Figure 22:
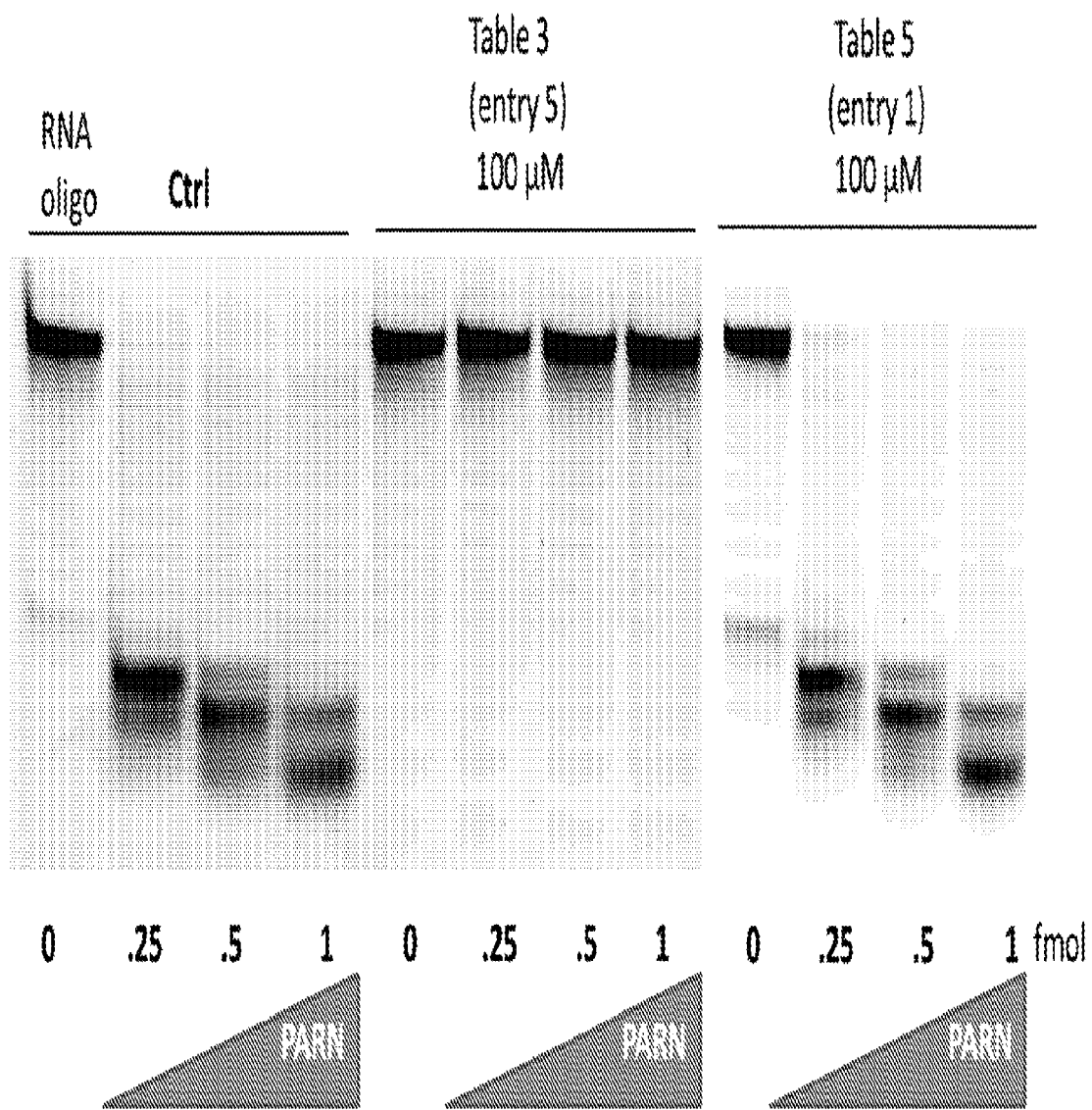
FIG. 22 shows that compound of table 3 (entry 5) inhibits PARN exonuclease whereas compound of table 5 (entry 1) does not inhibit PARN.
Figure 23:
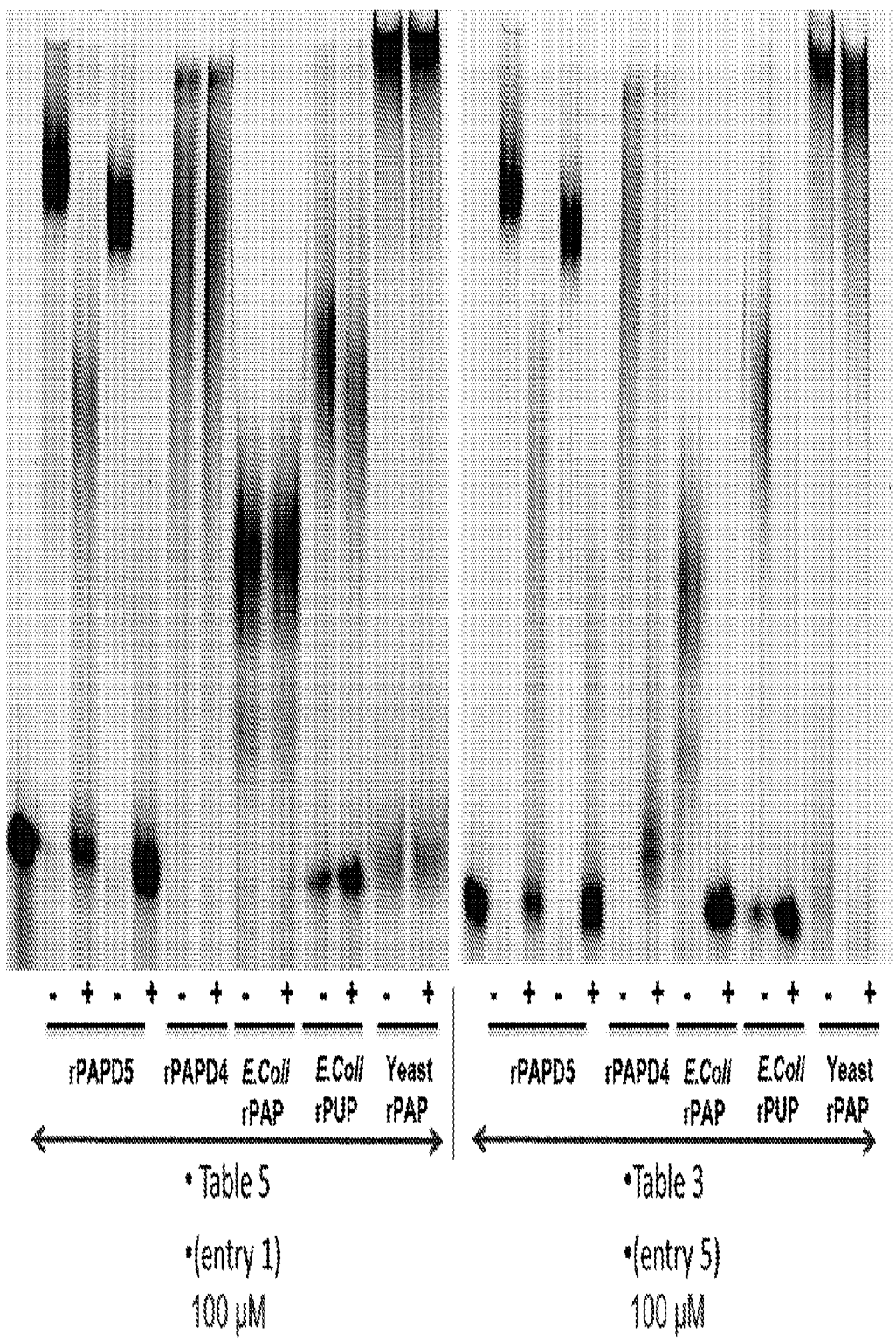
FIG. 23 shows that compound of table 3 (entry 5) inhibits multiple polynucleotide polymerases, whereas compound of table 5 (entry 1) is specific to PAPD5.
Figure 25:
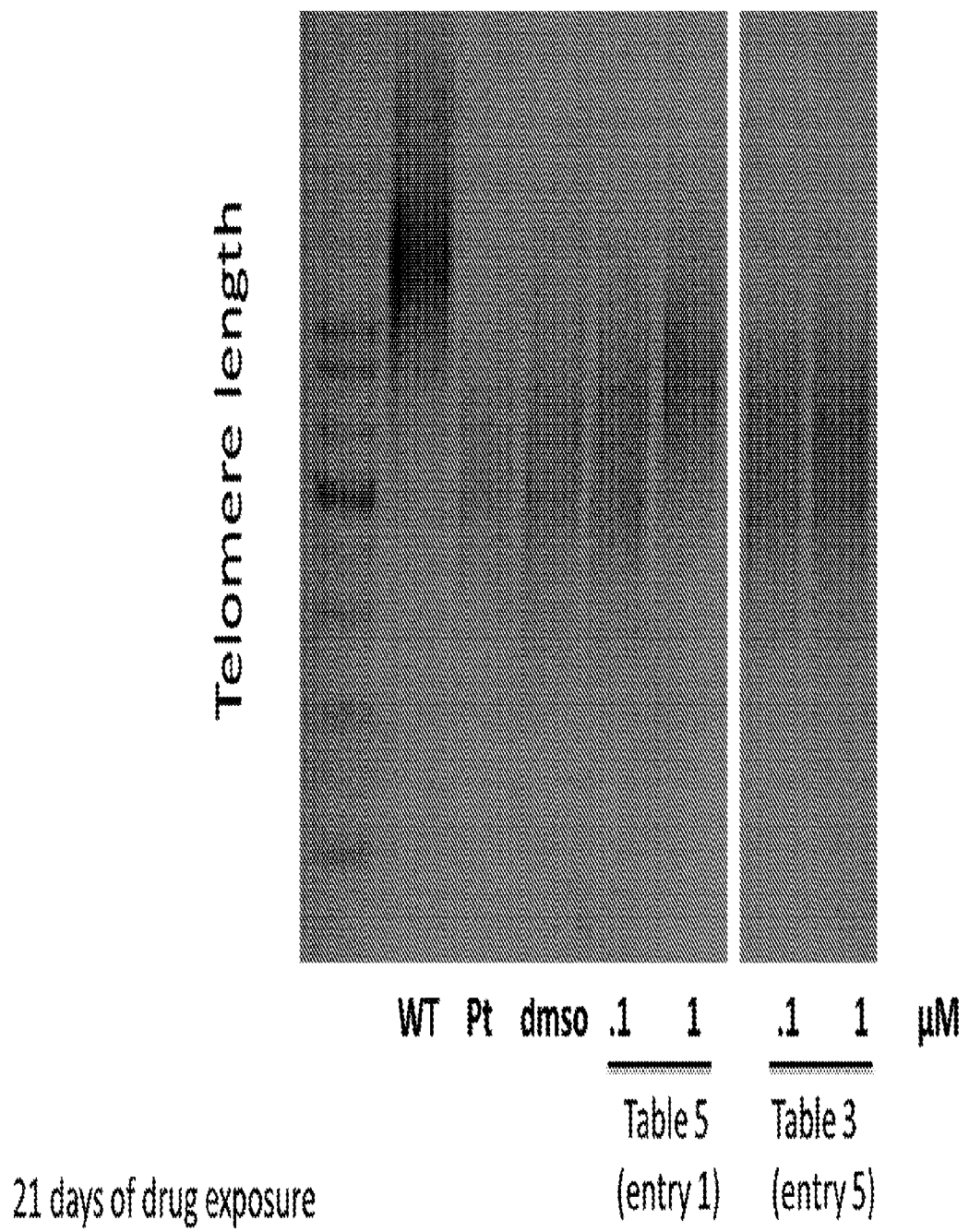
FIG. 25 shows that the compound of table 5 (entry 1) restores telomere length in DC patient iPS cells whereas the compound of table 3 (entry 5) does not.

FIG. 21 shows inhibitory activity of compounds of Table 5 (entry 1) and of Table 3 (entry 5) against PAPD5; while FIG. 22 shows specificity for PAPD5 compared to PARN and FIG. 23 shows specificity for PAPD5 compared to other polynucleotide polymerases. Relative effects on TERC RNA 3' end processing are shown in FIG. 24. Relative effects on telomere length in patient iPSCs are shown in FIG. 25.

Other Embodiments

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A method of treating a disease or condition selected from: a disorder associated with telomere or telomerase dysfunction, a degenerative disorder associated with aging, a pre-leukemic or pre-cancerous condition, a neurodevelopmental disorder, and an acquired or genetic disease or condition associated with alterations in RNA, the method comprising administering to a subject in need thereof a therapeutically effective amount of a compound of Formula (II-IIb):

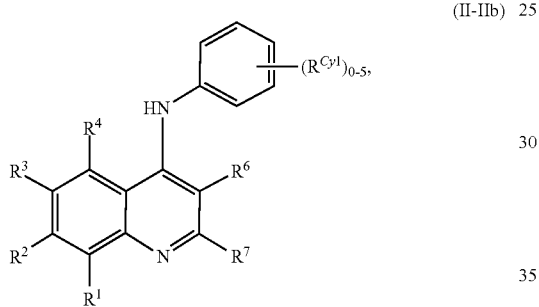

(II-IIb)

or a pharmaceutically acceptable salt thereof, wherein:

$R^2$, $R^4$, $R^6$, and $R^7$ are each independently selected from H, $C_{1-6}$ alkyl, $OR^{a1}$, $C(O)OR^{a1}$, $C(O)R^{b1}$, $NR^{c1}R^{d1}$, and $NR^{c1}C(O)R^{b1}$;

$R^1$ is selected from H, $C_{1-6}$ alkyl, $C(O)OR^{a1}$, $C(O)R^{b1}$, $NR^{c1}R^{d1}$, and $NR^{c1}C(O)R^{b1}$;

$R^3$ is selected from H, $C_{1-6}$ alkyl, $OR^{a1}$, $C(O)R^{b1}$, $NR^{c1}R^{d1}$, and $NR^{c1}C(O)R^{b1}$;

each $R^{Cy1}$ is independently selected from $C_{1-6}$ alkyl, $C(O)OR^{a4}$, $OR^{a4}$, $C(O)R^{b4}$, and halo;

$R^{a1}$, $R^{b1}$, $R^{b4}$, $R^{c1}$, and $R^{d1}$ are each independently selected from $C_{1-6}$ alkyl, and $C_{1-4}$ haloalkyl; and $R^{a4}$ is selected from H, $C_{1-6}$ alkyl, and $C_{1-4}$ haloalkyl.

2. The method of claim 1, wherein the compound of Formula (II-IIb) is selected from any one of the following compounds, or a pharmaceutically acceptable salt thereof:

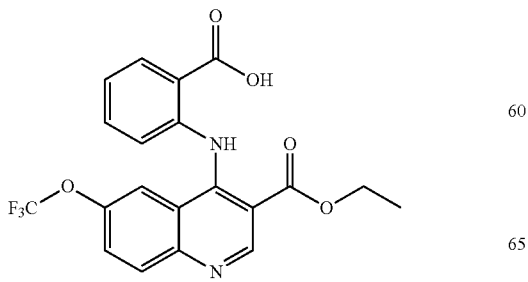

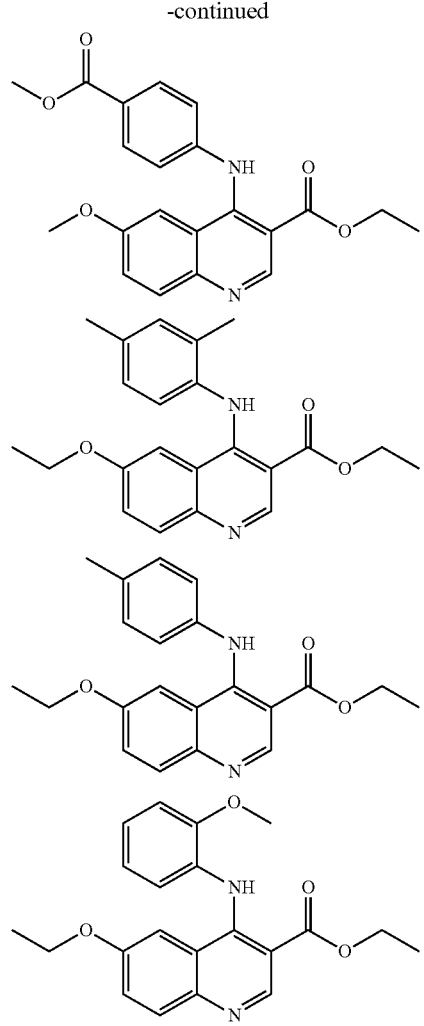

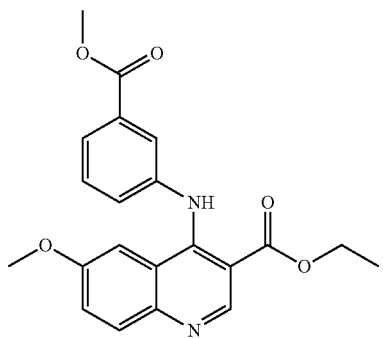

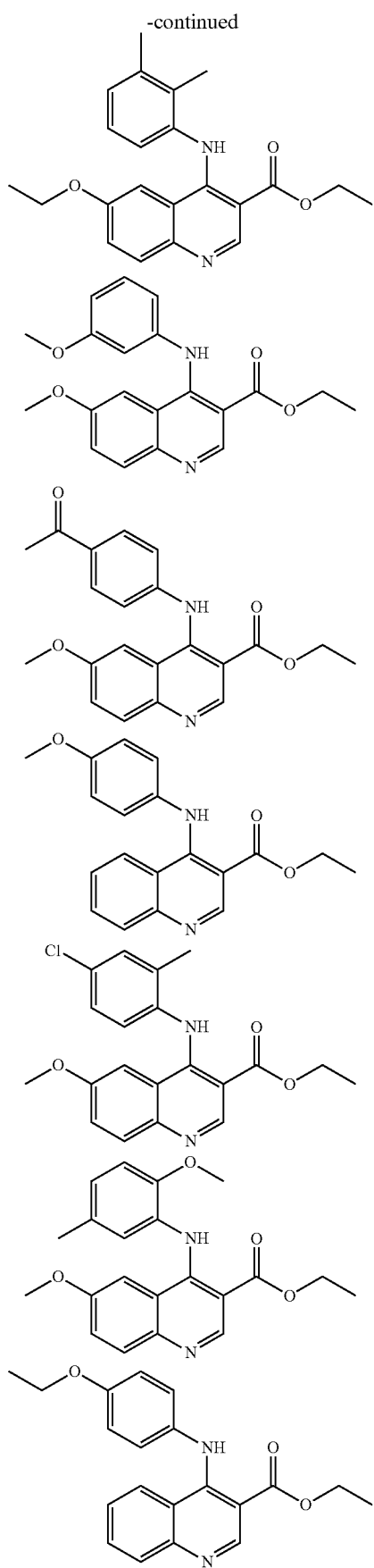
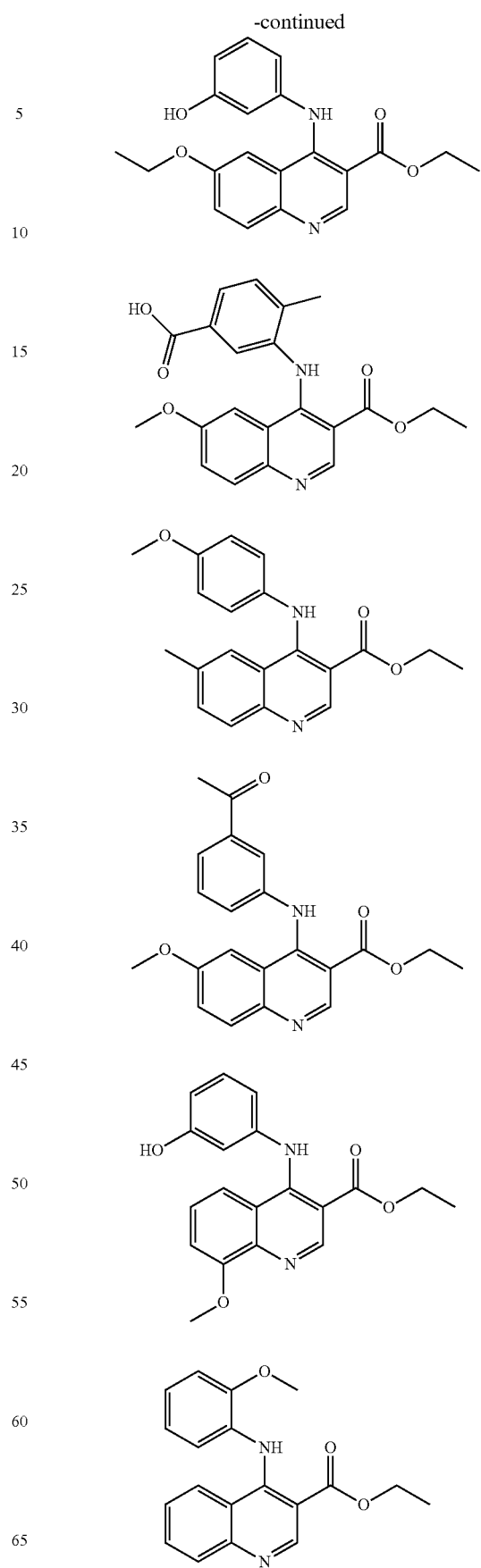

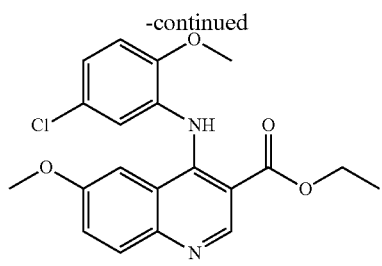

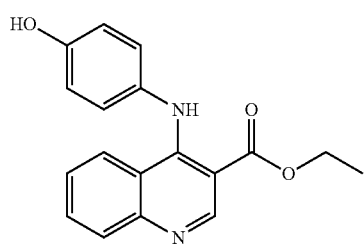

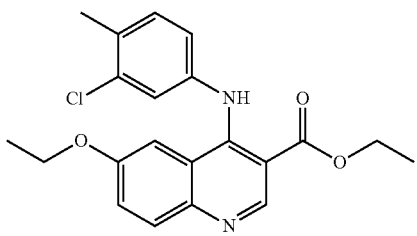

3. The method of claim 1, wherein the disease or condition is the disorder associated with telomere or telomerase dysfunction selected from dyskeratosis congenita, aplastic anemia, pulmonary fibrosis, myelodysplastic syndrome, idiopathic pulmonary fibrosis, hematological disorder, and hepatic fibrosis.

4. The method of claim 3, wherein the disorder associated with telomere or telomerase dysfunction is dyskeratosis congenita.

5. The method of claim 1, wherein the disease or condition is the neurodevelopmental disorder which is pontocerebellar hypoplasia.

6. The method of claim 2, wherein the disease or condition is the disorder associated with telomere or telomerase dysfunction selected from dyskeratosis congenita, aplastic anemia, pulmonary fibrosis, myelodysplastic syndrome, idiopathic pulmonary fibrosis, hematological disorder, and hepatic fibrosis.

7. The method of claim 6, wherein the disorder associated with telomere or telomerase dysfunction is dyskeratosis congenita.

8. The method of claim 2, wherein the disease or condition is the neurodevelopmental disorder which is pontocerebellar hypoplasia.

9. The method of claim 1, wherein the compound of Formula (II-IIb) has formula:

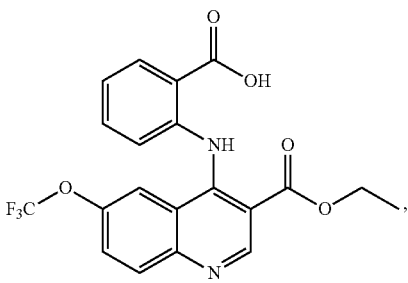 [SMILES: CCOC(=O)c1cnc2ccc(OC(F)(F)F)cc2c1Nc1ccccc1C(=O)O]

or a pharmaceutically acceptable salt thereof.

10. The method of claim 9, wherein the disease or condition is the disorder associated with telomere or telomerase dysfunction selected from dyskeratosis congenita, aplastic anemia, pulmonary fibrosis, myelodysplastic syndrome, idiopathic pulmonary fibrosis, hematological disorder, and hepatic fibrosis.

11. The method of claim 9, wherein the disease or condition is the neurodevelopmental disorder which is pontocerebellar hypoplasia.

12. A method of treating dyskeratosis congenita, the method comprising administering to a subject in need thereof a therapeutically effective amount of a compound of formula:

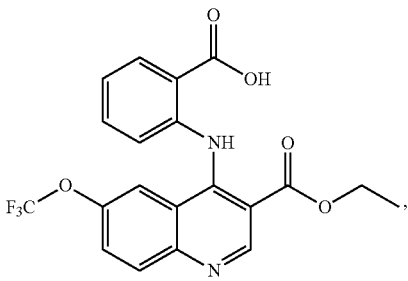

or a pharmaceutically acceptable salt thereof.

13. The method of claim 1, wherein:

$R^3$ is selected from $C_{1-6}$ alkoxy and $C_{1-4}$ haloalkoxy;

$R^1$ is selected from H and $C_{1-6}$ alkyl;

$R^2$, $R^4$, and $R^7$ are each H;

$R^6$ is $C(O)OR^{a1}$; and $R^{a1}$ is $C_{1-6}$ alkyl.

14. A method of treating a disease or condition selected from: a disorder associated with telomere or telomerase dysfunction, a disorder associated with aging, a pre-leukemic or pre-cancerous condition, a neurodevelopmental disorder, and an acquired or genetic disease or condition associated with alterations in RNA, the method comprising administering to a subject in need thereof a therapeutically effective amount of a compound of formula:

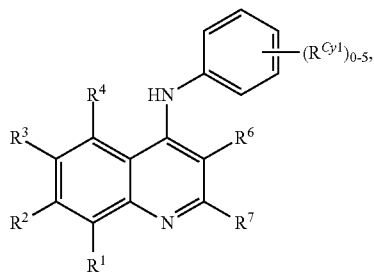

or a pharmaceutically acceptable salt thereof, wherein:

$R^2$, $R^3$, $R^4$, $R^6$, and $R^7$ are each independently selected from H, halo $Cy^1$, $C_{1-6}$ alkyl, $OR^{a1}$, $SR^{a1}$, $C(O)OR^{a1}$, $C(O)NR^{c1}R^{d1}$, $NR^{c1}C(O)R^{b1}$, $NR^{c1}R^{d1}$, $S(O)_2R^{b1}$ and $C(O)R^{b1}$;

$R^1$ is selected from $OR^{a1}$ and $SR^{a1}$;

each $Cy^1$ is independently selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy1}$;

each $R^{Cy1}$ is independently selected from $C(O)OR^{a4}$, $OR^{a4}$, $C(O)R^{b4}$, and halo;

$R^{a1}$, $R^{b1}$, $R^{b4}$, $R^{c1}$, and $R^{d1}$ are each independently selected from $C_{1-6}$ alkyl, and $C_{1-4}$ haloalkyl; and $R^{a4}$ is selected from H, $C_{1-6}$ alkyl, and $C_{1-4}$ haloalkyl.

15. The method of claim 14, wherein the disease or condition is the disorder associated with telomere or telomerase dysfunction selected from dyskeratosis congenita, aplastic anemia, pulmonary fibrosis, myelodysplastic syndrome, idiopathic pulmonary fibrosis, hematological disorder, and hepatic fibrosis.

16. The method of claim 14, wherein the compound is selected from any one of the following compounds, or a pharmaceutically acceptable salt thereof:

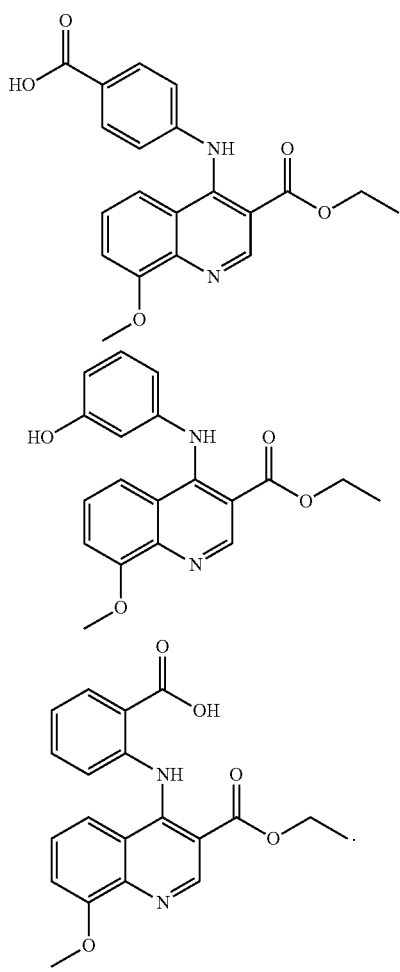

* * * * *